(12) United States Patent
Fleetham et al.

(10) Patent No.: US 11,925,105 B2
(45) Date of Patent: Mar. 5, 2024

(54) ORGANIC ELECTROLUMINESCENT MATERIALS AND DEVICES

(71) Applicant: Universal Display Corporation, Ewing, NJ (US)

(72) Inventors: Tyler Fleetham, Newtown, PA (US); Hsiao-Fan Chen, Lawrence Township, NJ (US); Jerald Feldman, Cherry Hill, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 358 days.

(21) Appl. No.: 16/988,003

(22) Filed: Aug. 7, 2020

(65) Prior Publication Data

US 2021/0066622 A1  Mar. 4, 2021

Related U.S. Application Data

(60) Provisional application No. 62/891,623, filed on Aug. 26, 2019.

(51) Int. Cl.
*H10K 85/30* (2023.01)
*H05B 33/00* (2006.01)
*C07D 401/14* (2006.01)
*H10K 50/11* (2023.01)
*H10K 101/10* (2023.01)

(52) U.S. Cl.
CPC ......... *H10K 85/346* (2023.02); *C07D 401/14* (2013.01); *H05B 33/00* (2013.01); *H10K 50/11* (2023.02); *H10K 2101/10* (2023.02)

(58) Field of Classification Search
CPC .................................................. H01L 51/0087
See application file for complete search history.

(56) References Cited

U.S. PATENT DOCUMENTS

| | | | |
|---|---|---|---|
| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — William D Young
(74) *Attorney, Agent, or Firm* — DUANE MORRIS LLP

(57) ABSTRACT

Provided is a new composition of matter for phosphorescent emitters containing a chelating ligand including five or more fused carbocyclic or heterocyclic rings that form two bonds to a metal forming a 7-membered chelate. This fused ring structure provides added rigidity to the molecule for enhanced stability in an OLED device and improve photophysical properties.

17 Claims, 2 Drawing Sheets

(56) References Cited

U.S. PATENT DOCUMENTS

| | | |
|---|---|---|
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 10,340,467 B2 | 7/2019 | Choi et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2017/0183367 A1* | 6/2017 | Metz ............... C09K 11/06 |
| 2018/0337350 A1* | 11/2018 | Li ................... C07F 15/0086 |
| 2019/0036055 A1 | 1/2019 | Lin |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 5707818 | 4/2015 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

(56) References Cited

OTHER PUBLICATIONS

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4''-Tri(N-carbazolyl)triphenylamine (TCTA) and 4,4',4''-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5''-Bis (dimesitylboryl)-2,2'5',2''-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based On Silole Derivatives And Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N∧C∧N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes Of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Xia, Dao-Cheng et al., "Crystal structure of bis([3,2-c]isoquinolin-5-amine)benzofuro[6,5-b]furancadmium(II) dichloride, Cd(C24H12N4O2)CI2" Z. Kristallogr. NCS 225 (2010) 563-564 / DOI 10.152/ncrs.2010.0246.

* cited by examiner

ORGANIC ELECTROLUMINESCENT MATERIALS AND DEVICES

CROSS-REFERENCE TO RELATED APPLICATIONS

This application claims priority under 35 U.S.C. § 119(e) to U.S. Provisional Application No. 62/891,623, filed on Aug. 26, 2019, the entire contents of which are incorporated herein by reference.

FIELD

The present disclosure generally relates to organometallic compounds and formulations and their various uses including as emitters in devices such as organic light emitting diodes and related electronic devices.

BACKGROUND

Opto-electronic devices that make use of organic materials are becoming increasingly desirable for various reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials.

OLEDs make use of thin organic films that emit light when voltage is applied across the device. OLEDs are becoming an increasingly interesting technology for use in applications such as flat panel displays, illumination, and backlighting.

One application for phosphorescent emissive molecules is a full color display. Industry standards for such a display call for pixels adapted to emit particular colors, referred to as "saturated" colors. In particular, these standards call for saturated red, green, and blue pixels. Alternatively, the OLED can be designed to emit white light. In conventional liquid crystal displays emission from a white backlight is filtered using absorption filters to produce red, green and blue emission. The same technique can also be used with OLEDs. The white OLED can be either a single emissive layer (EML) device or a stack structure. Color may be measured using CIE coordinates, which are well known to the art.

SUMMARY

This disclosure provides a new composition of matter for phosphorescent emitters containing a chelating ligand comprised of five or more fused cathocyclic or heterocyclic rings. The five or more fused rings form two bonds to a metal forming a 7-membered chelate. This fused ring structure provides added rigidity to the molecule for enhanced stability in an OLED device and improved photophysical properties.

In one aspect, the present disclosure provides a compound having a fragment with at least five rings fused next to each other consecutively wherein the fragment has at least two atoms coordinated to a metal.

In another aspect, the present disclosure provides a compound comprising a ligand $L_A$ of Formula I

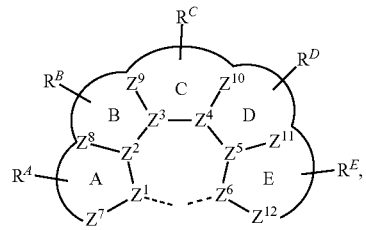

wherein: rings A, B, C, D, and E are each independently a 5-membered or 6-membered carbocyclic or heterocyclic ring; $Z^1$-$Z^{12}$ are each independently C or N; $R^A$, $R^B$, $R^C$, $R^D$, and $R^E$ each independently represents zero, mono, or up to a maximum allowed substitutions to its associated ring; $R^A$, $R^B$, $R^C$, $R^D$, and $R^E$ are each independently a hydrogen or a substituent selected from the group consisting of deuterium, halide, alkyl, cycloalkyl, fluorinated alkyl, heteroalkyl, alkylalkyl, alkoxy, aryloxy, amino, silyl, boryl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and two substituents can be joined or fused together to form a ring, wherein the ligand $L_A$ is complexed to a metal M selected from the group consisting of Ir, Rh, Re, Ru, Os, Pt, Pd, Au, Ag, and Cu; wherein M can be coordinated to other ligands; and wherein the ligand $L_A$ can be linked with other ligands to form a tridentate, tetradentate, pentadentate, or hexadentate ligand.

In another aspect, the present disclosure provides a formulation comprising a compound having a fragment with at least five rings fused next to each other consecutively wherein the fragment has at least two atoms coordinated to a metal.

In yet another aspect, the present disclosure provides a formulation comprising a compound of Formula I described herein.

In yet another aspect, the present disclosure provides an OLED having an organic layer comprising a compound having a fragment with at least five rings fused next to each other consecutively wherein the fragment has at least two atoms coordinated to a metal.

In yet another aspect, the present disclosure provides an OLED having an organic layer comprising the compound of Formula I described herein.

In yet another aspect, the present disclosure provides a consumer product comprising an OLED having an organic layer comprising a compound having a fragment with at least five rings fused next to each other consecutively wherein the fragment has at least two atoms coordinated to a metal.

In yet another aspect, the present disclosure provides a consumer product comprising an OLED with an organic layer comprising the compound of Formula I described herein.

In yet another aspect, the present disclosure provides an OLED device comprising an emitter wherein the device emits a luminescent radiation at room temperature when a voltage is applied across the device, wherein the luminescent radiation comprises a first radiation component emitted from the emitter, and wherein the first radiation component has a full width at half maximum equal or less than 15 nm.

DETAILED DESCRIPTION

A. Terminology

Figure 1:
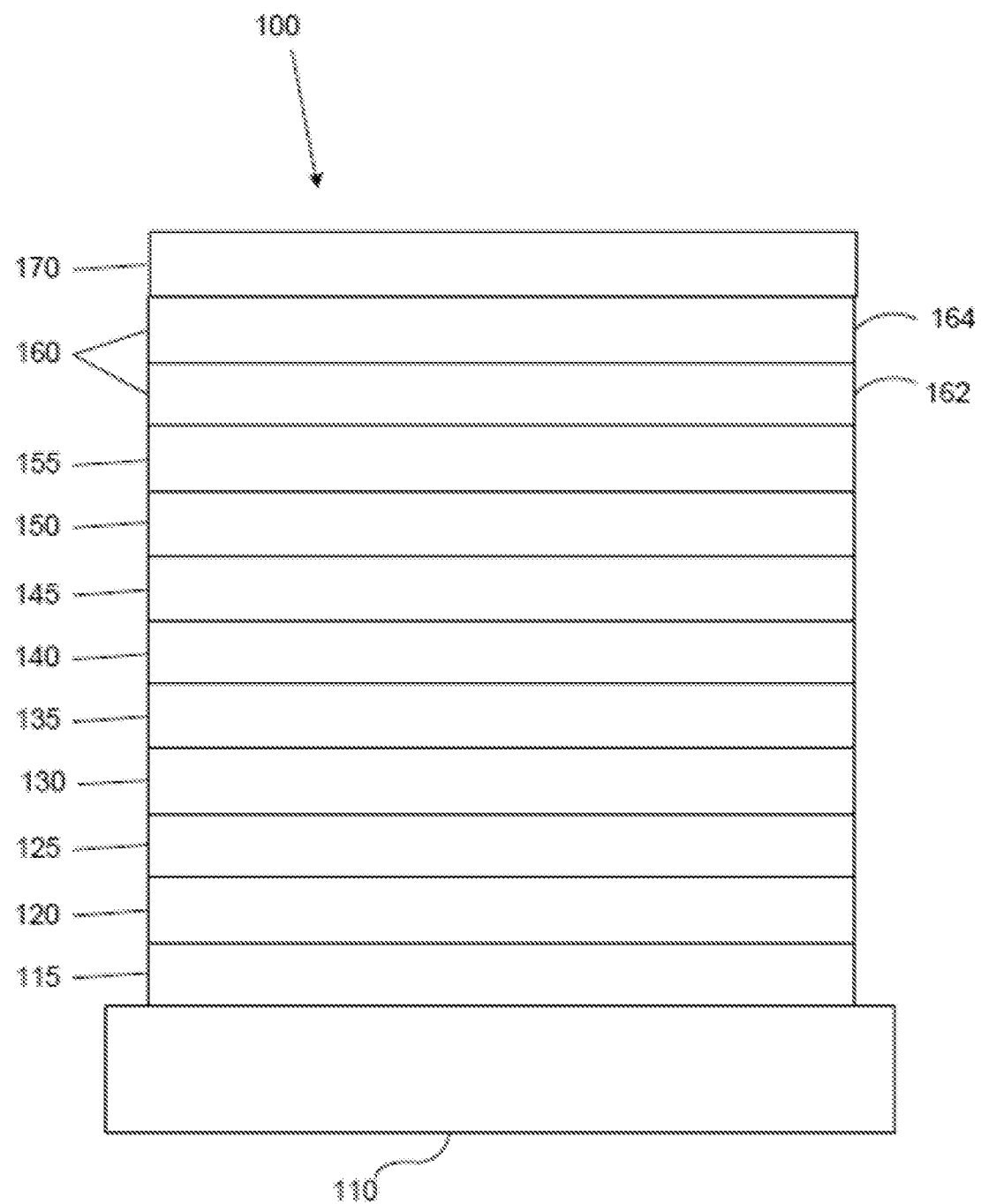
FIG. 1 shows an organic light emitting device.

Unless otherwise specified, the below terms used herein are defined as follows:

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

The terms "halo," "halogen," and "halide" are used interchangeably and refer to fluorine, chlorine, bromine, and iodine.

The term "acyl" refers to a substituted carbonyl radical (C(O)—$R_s$).

The term "ester" refers to a substituted oxycarbonyl (—O—C(O)—$R_s$ or —C(O)—O—$R_s$) radical.

The term "ether" refers to an —$OR_s$ radical.

The terms "sulfanyl" or "thio-ether" are used interchangeably and refer to a —$SR_s$ radical.

The term "sulfinyl" refers to a —S(O)—$R_s$ radical.

The term "sulfonyl" refers to a —$SO_2$—$R_s$ radical.

The term "phosphino" refers to a —$P(R_s)_3$ radical, wherein each $R_s$ can be same or different.

The term "silyl" refers to a —$Si(R_s)_3$ radical, wherein each $R_s$ can be same or different.

The term "boryl" refers to a —$B(R_s)_2$ radical or its Lewis adduct —$B(R_s)_3$ radical, wherein $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo [3.1.1]heptyl, spiro[4.5]decyl, spiro[5.5]undecyl, adamantyl, and the like. Additionally, the cycloalkyl group may be optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group may be optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group may be optionally substituted.

The term "alkynyl" refers to and includes both straight and branched chain alkyne radicals. Alkynyl groups are essentially alkyl groups that include at least one carbon-carbon triple bond in the alkyl chain. Preferred alkynyl groups are those containing two to fifteen carbon atoms. Additionally, the alkynyl group may be optionally substituted.

The terms "aralkyl" or "arylalkyl" are used interchangeably and refer to an alkyl group that is substituted with an aryl group. Additionally, the aralkyl group may be optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the hetero-cyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, boryl, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, boryl, and combinations thereof.

In some instances, the more preferred general substituents are selected from the group consisting of deuterium, fluorine, alkyl, cycloalkyl, alkoxy, aryloxy, amino, silyl, boryl, aryl, heteroaryl, sulfanyl, and combinations thereof.

In yet other instances, the most preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents zero or no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[fh]quinoxaline and dibenzo[fh]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed. (Reviews)* 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2, 2' positions in a biphenyl, or 1, 8 position in a naphthalene, as long as they can form a stable fused ring system.

B. The Compounds of the Present Disclosure

In one aspect, the present disclosure provides a compound having a fragment with at least five rings fused next to each other consecutively wherein the fragment has at least two atoms coordinated to a metal.

In some embodiments, the compound can be a metal coordination compound comprising a ligand, wherein the ligand comprises a fragment having at least five rings fused next to each other consecutively in a row; and wherein the fragment has at least two atoms coordinated to a metal.

In some embodiments, the at least five rings can comprise two 5-membered rings and three 6-membered rings fused to each other consecutively.

In some embodiments, the at least five rings can comprise five aromatic rings fused next to each other consecutively.

In some embodiments, the fragment can comprise at least six rings fused next to each other consecutively.

In some embodiments, the fragment can comprise at least seven rings fused next to each other consecutively.

In another aspect, the present disclosure provides a ligand $L_A$ of Formula I

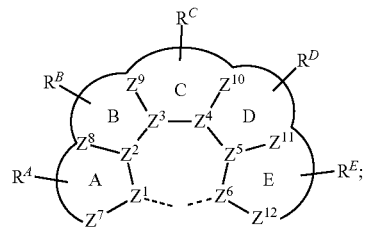

wherein: rings A, B, C, D, and E are each independently a 5-membered or 6-membered cathocyclic or heterocyclic ring; $Z^1$-$Z^{12}$ are each independently C or N; $R^A$, $R^B$, $R^C$, $R^D$, and $R^E$ each independently represents zero, mono, or up to a maximum allowed substitution to its associated ring; $R^A$, $R^B$, $R^C$, $R^D$, and $R^E$ are each independently a hydrogen or a substituent selected from the group consisting of the general substituents defined herein; two substituents can be joined or fused together to form a ring, wherein the ligand $L_A$ is complexed to a metal M selected from the group consisting of Ir, Rh, Re, Ru, Os, Pt, Pd, Au, Ag, and Cu; wherein M can be coordinated to other ligands; and wherein the ligand $L_A$ can be linked with other ligands to form a tridentate, tetradentate, pentadentate, or hexadentate ligand.

In some embodiments, $R^A$, $R^B$, $R^C$, $R^D$, and $R^E$ each can be independently a hydrogen or a substituent selected from the group consisting of the preferred general substituents defined herein.

In some embodiments, M can be Ir, Pt or Pd.

In some embodiments, the ligand $L_A$ can be bidentate.

In some embodiments, the ligand $L_A$ can be linked with other ligands to form a tetradentate ligand.

In some embodiments, ring A, ring C, and ring E can be 6-membered rings, and ring B and ring D can be 5-membered rings.

In some embodiments, ring A, ring C, and ring E can be 5-membered rings, and ring B and ring D can be 6-membered rings.

In some embodiments, ring A and ring E can be 5-membered rings, and ring B, ring C, and ring D can be 6-membered rings.

In some embodiments, ring A and ring E can be 6-membered rings, and ring B, ring C, and ring D can be 5-membered rings.

In some embodiments, ring A, ring B, ring D, and ring E can be 5-membered rings, and ring C can be a 6-membered ring.

In some embodiments, $Z^1$-$Z^{12}$ can be C.

In some embodiments, at least one of $Z^1$-$Z^{12}$ can be N.

In some embodiments, one of $Z^1$ and $Z^6$ can be N and the other can be C.

In some embodiments, $Z^1$ and $Z^6$ can be C.

In some embodiments, $Z^1$ and $Z^6$ can be N.

In some embodiments of $L_A$ of Formula I, the ligand $L_A$ can be selected from the group consisting of:
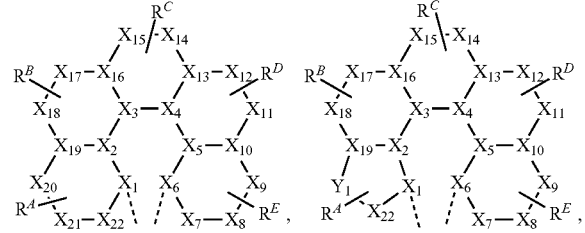
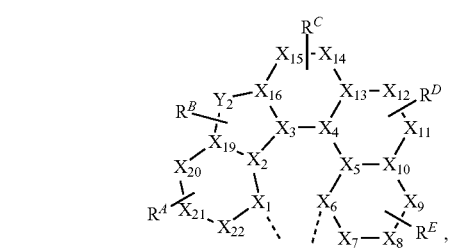
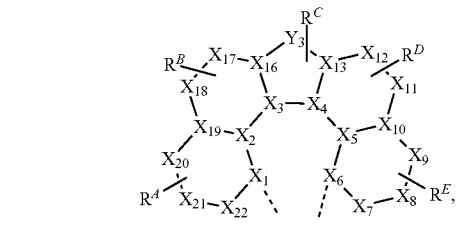
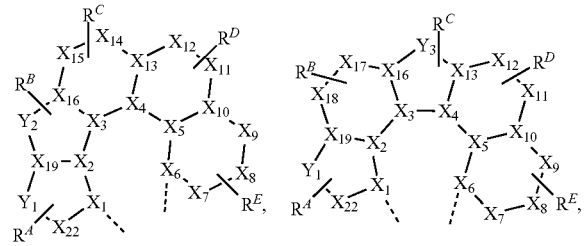
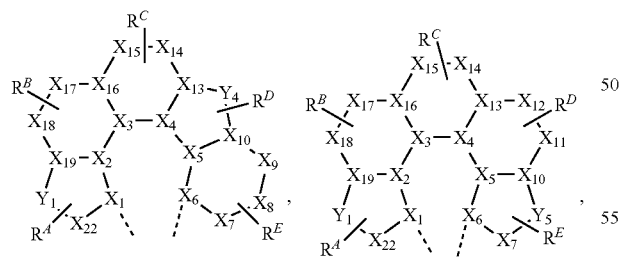
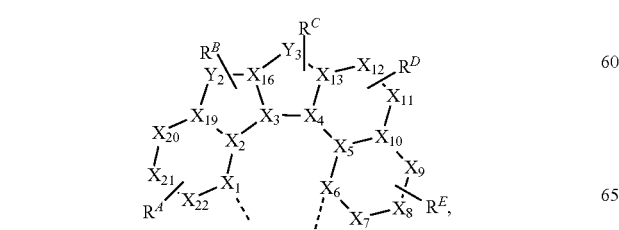
-continued
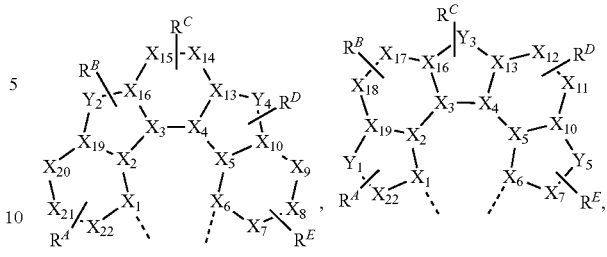
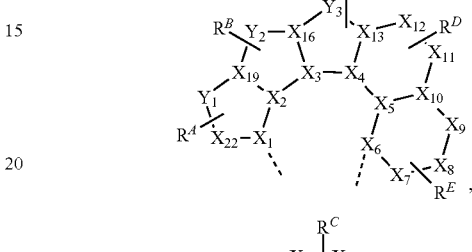
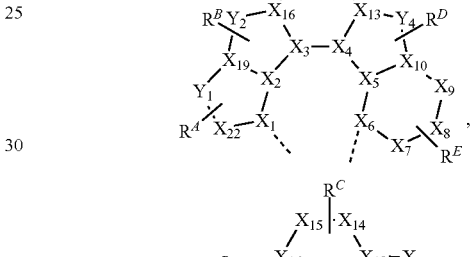

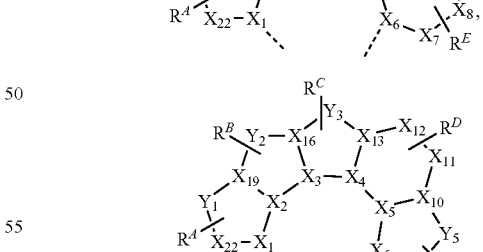
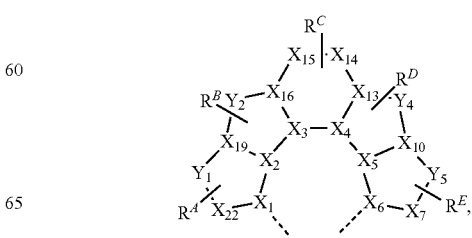

-continued

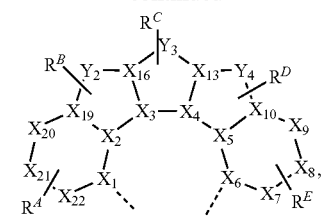

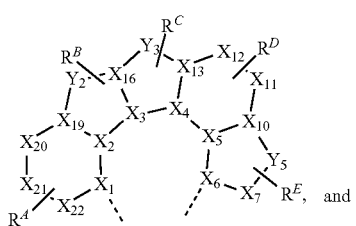

and

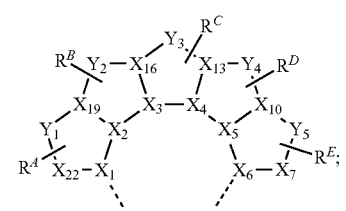

wherein each $X_1$-$X_{22}$ is independently selected from the group consisting of C and N; wherein no more than two N atoms are bond to one another; wherein each $Y_1$-$Y_5$ is selected from the group consisting of O, S, Se, NR, CRR', SiRR', GeRR', and BR; and wherein R and R' are each independently selected from the group consisting of hydrogen, deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, and combinations thereof.

In some embodiments of $L_A$ of Formula I, the ligand $L_A$ can be selected from the group consisting of the structures shown in LIST 1 below:

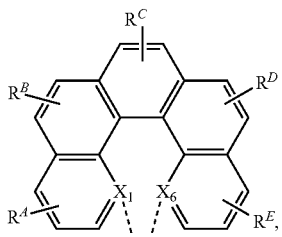

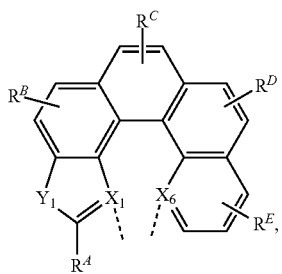

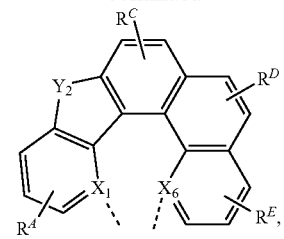

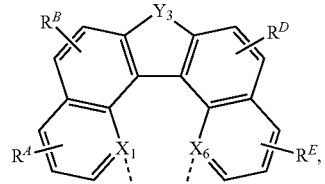

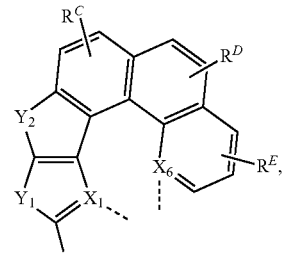

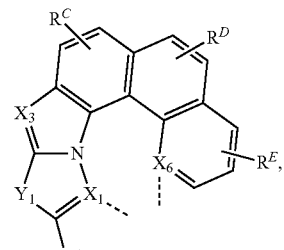

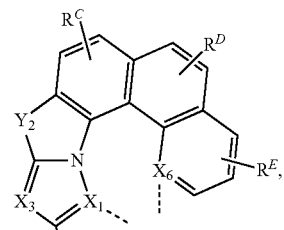

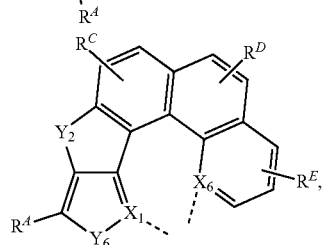

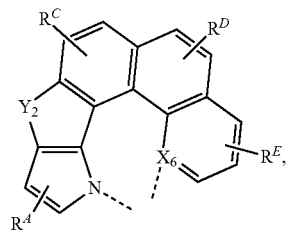

-continued
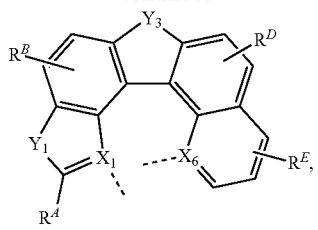
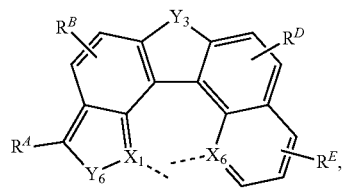
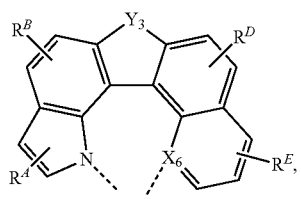
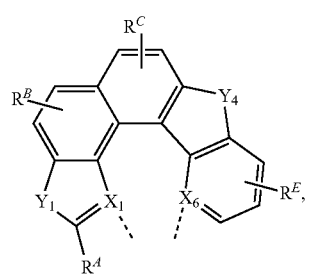
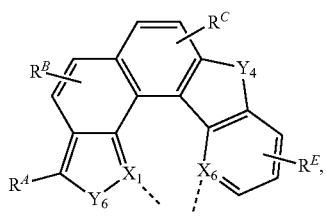
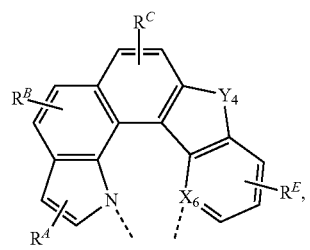
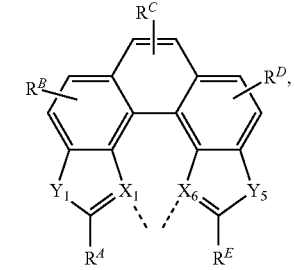
-continued
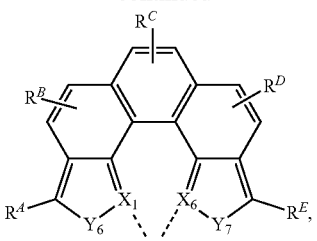
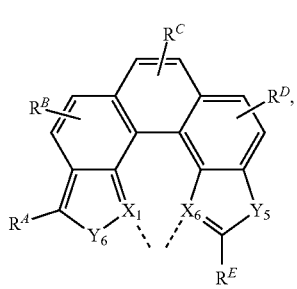
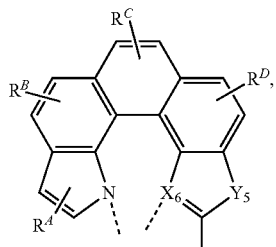
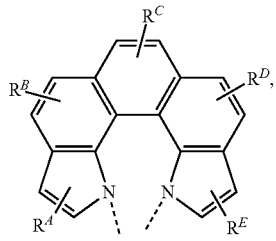
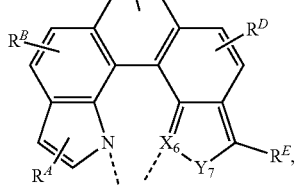
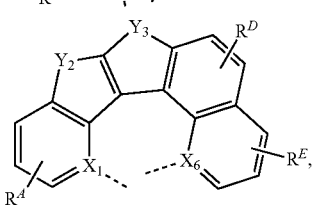
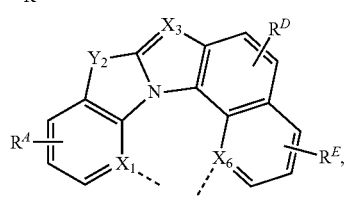

-continued
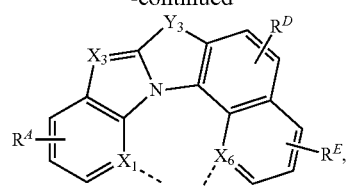
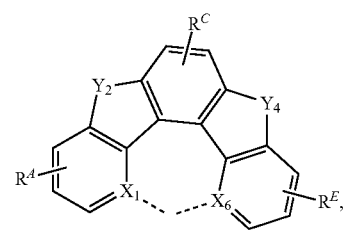
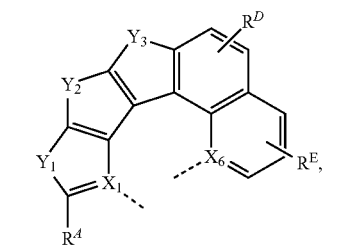
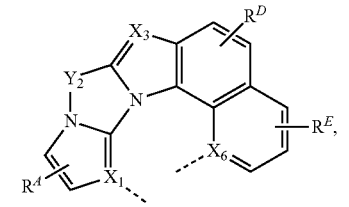
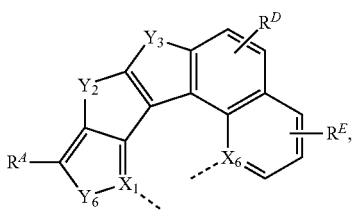
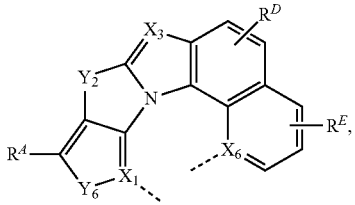
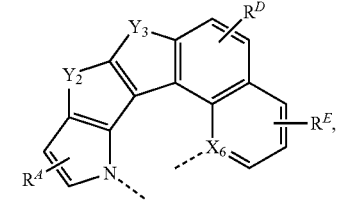
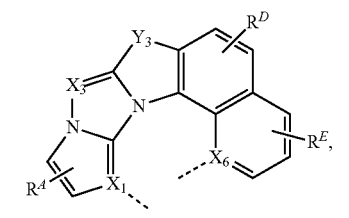
-continued
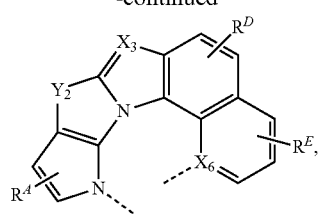
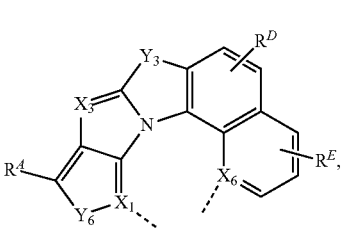
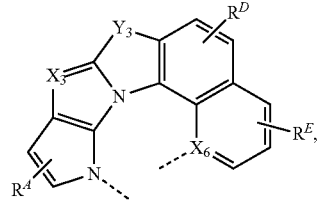
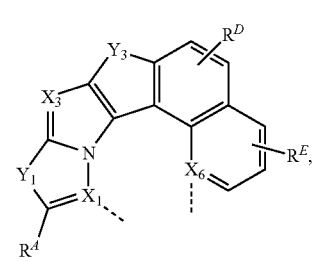
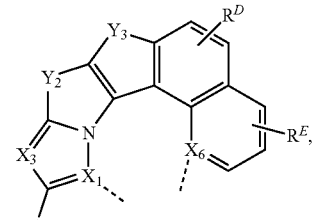
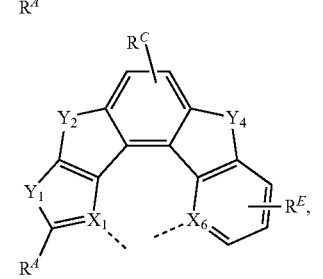
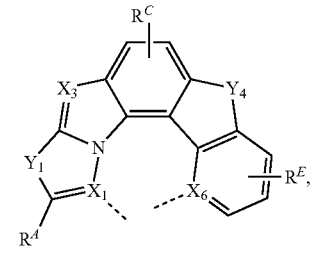

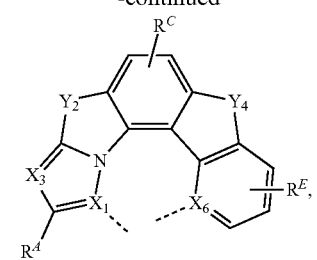
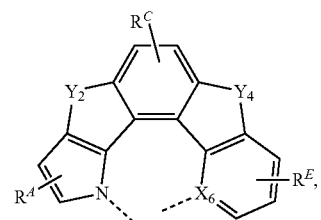
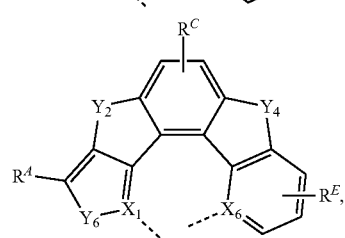
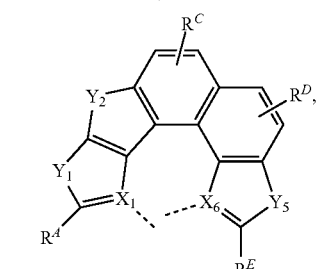
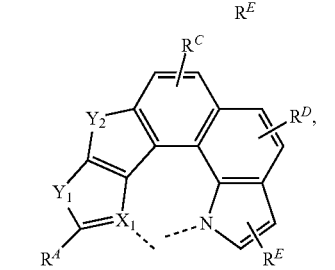
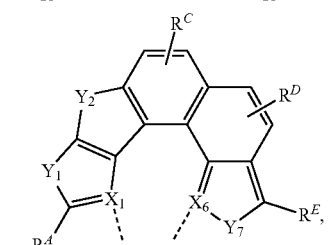
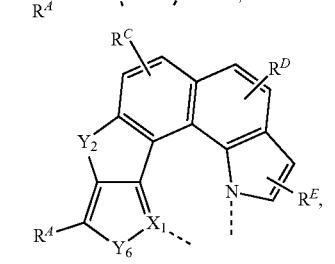
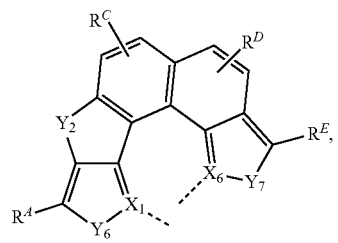
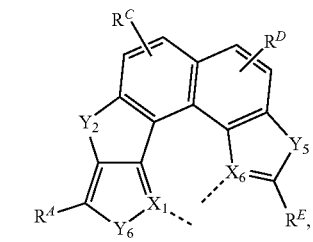
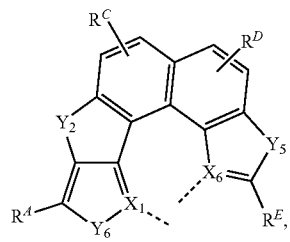
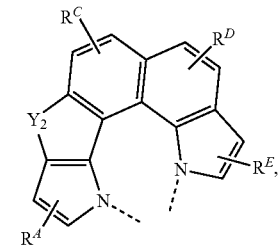
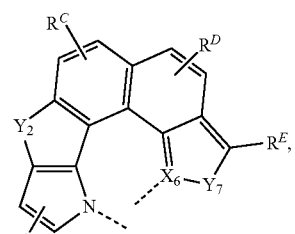
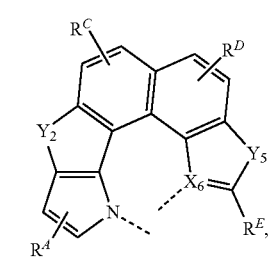
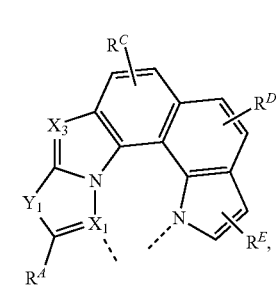

-continued
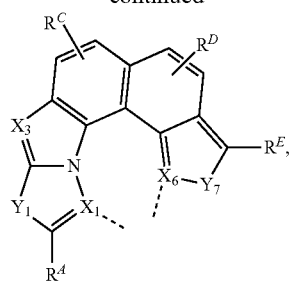
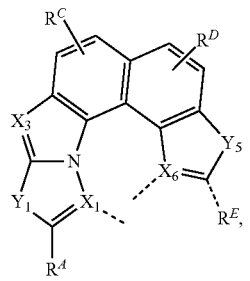
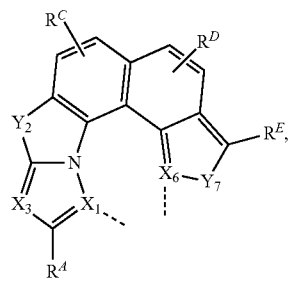
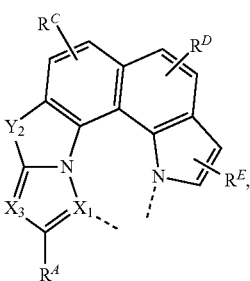
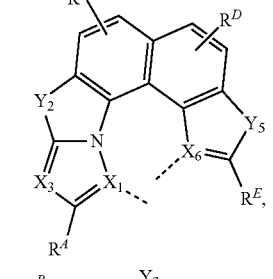
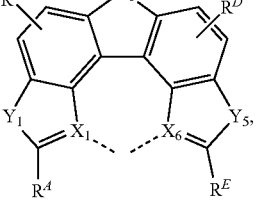
-continued
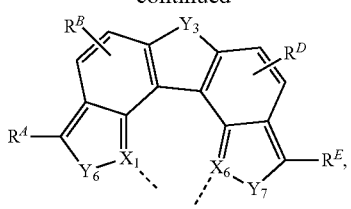
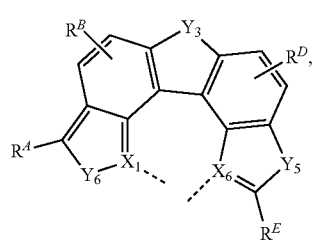
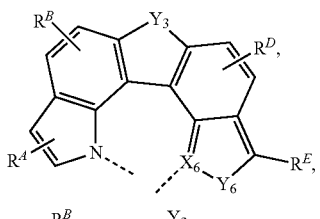
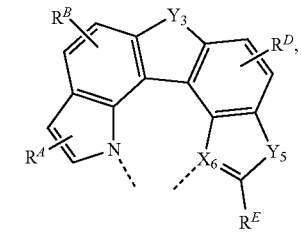
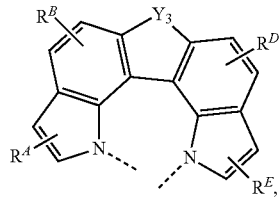
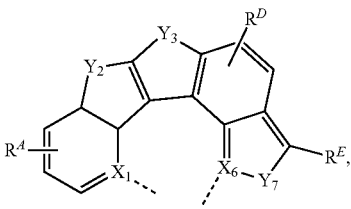
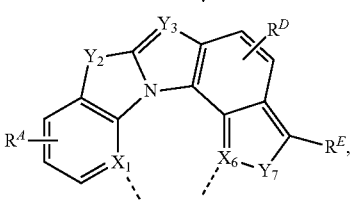
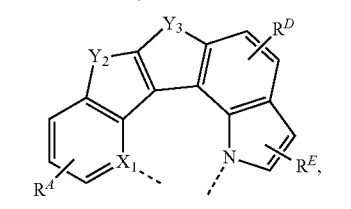

-continued
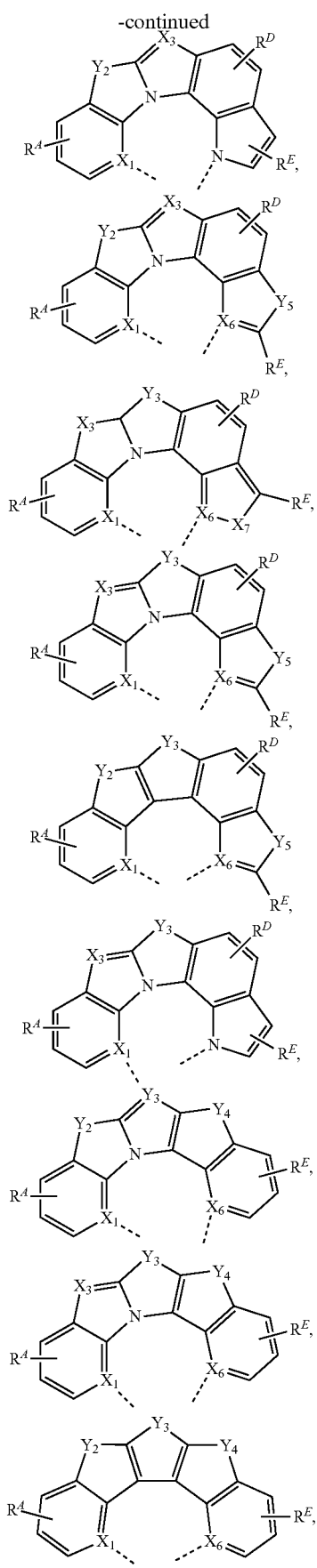
-continued
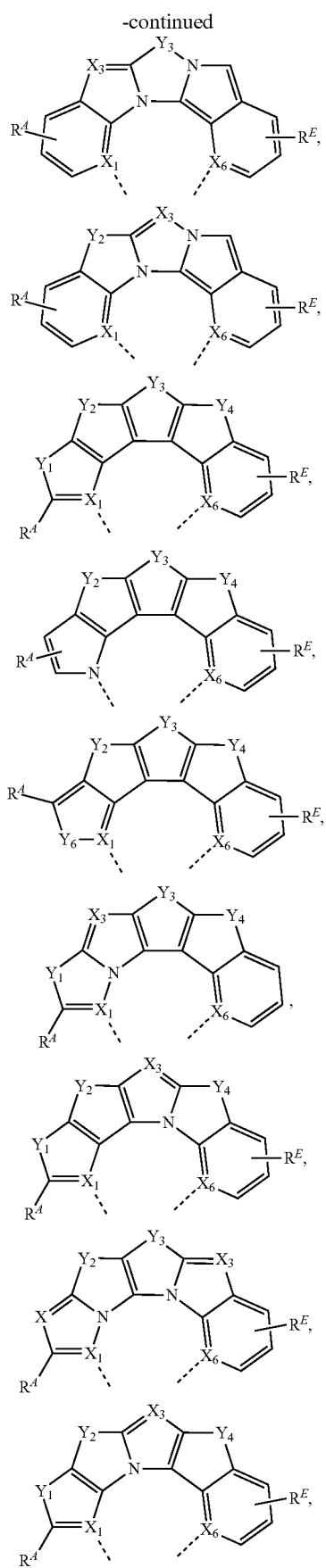

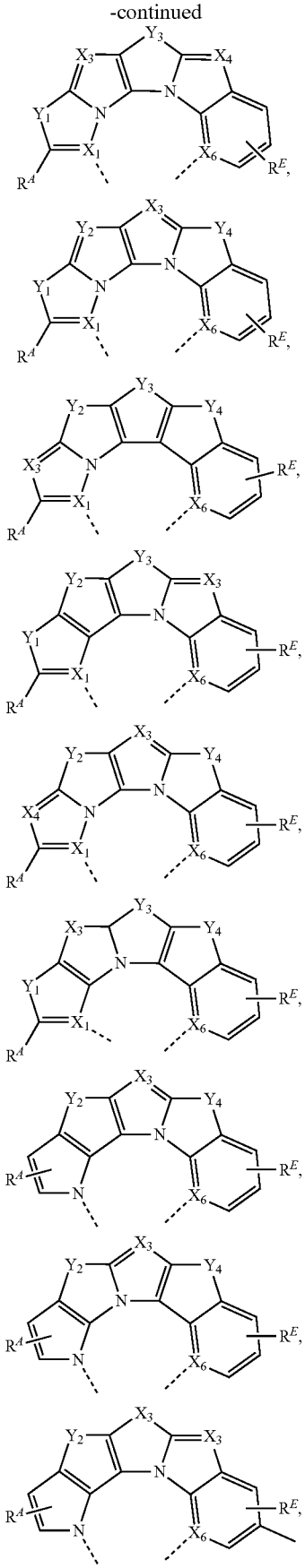
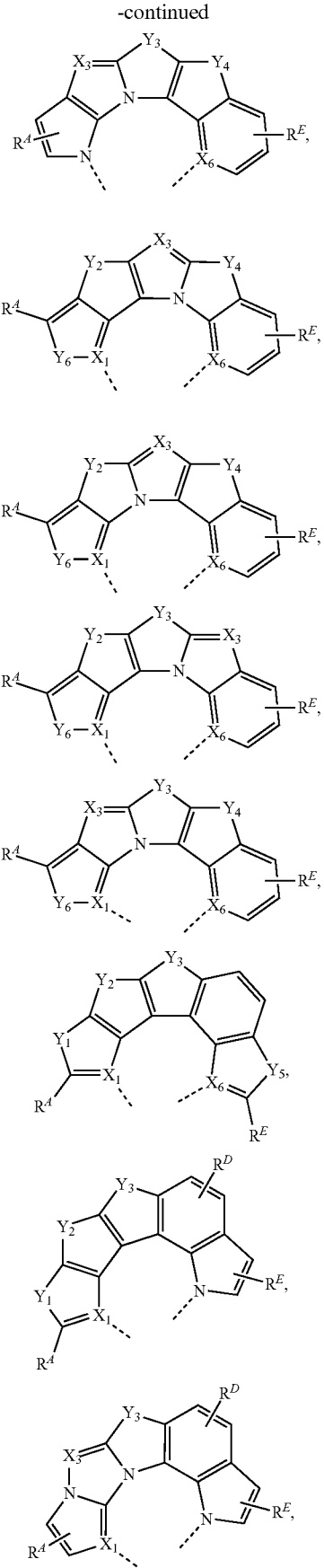

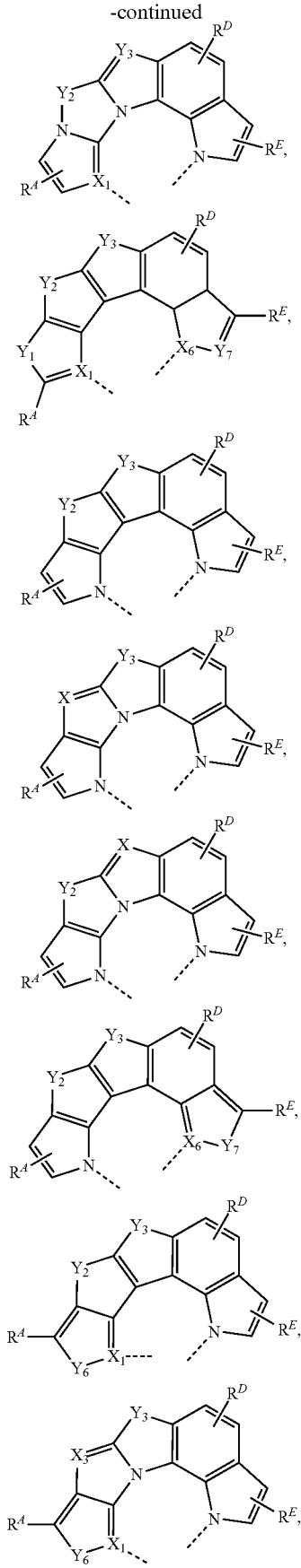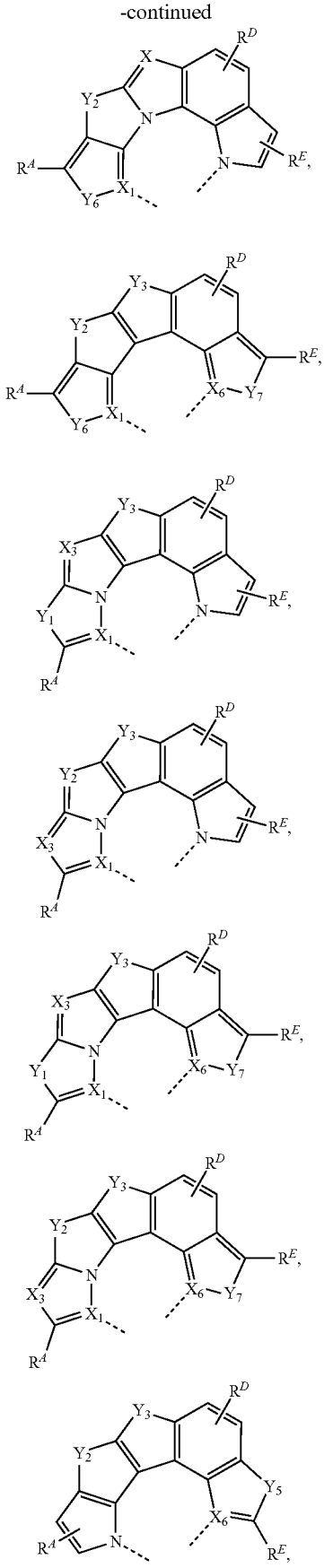

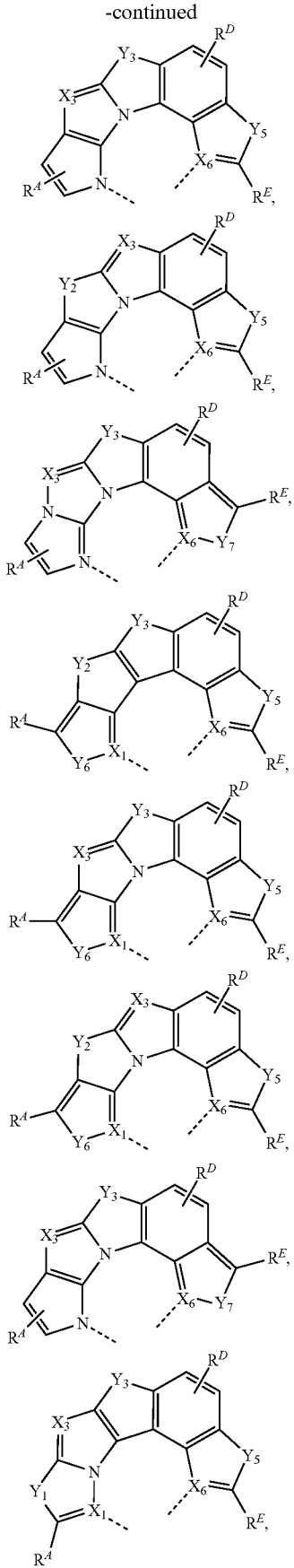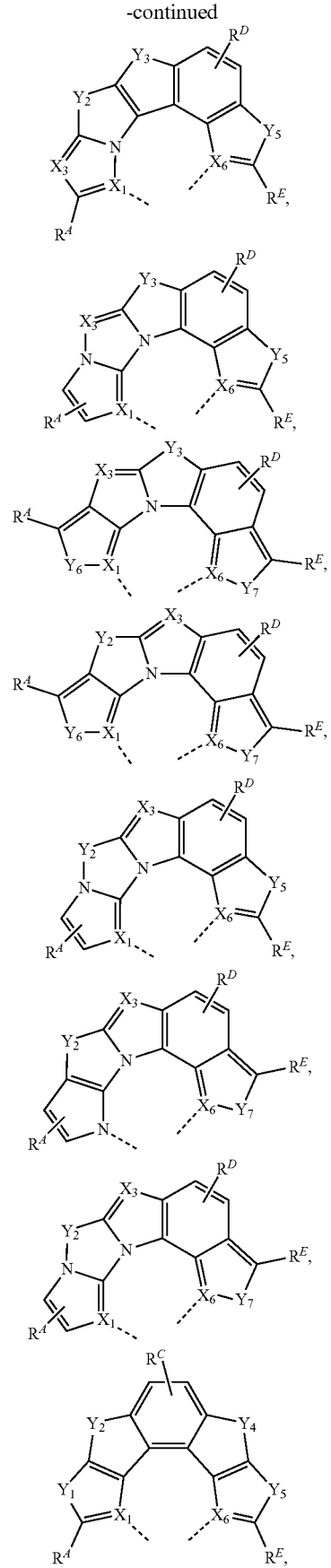

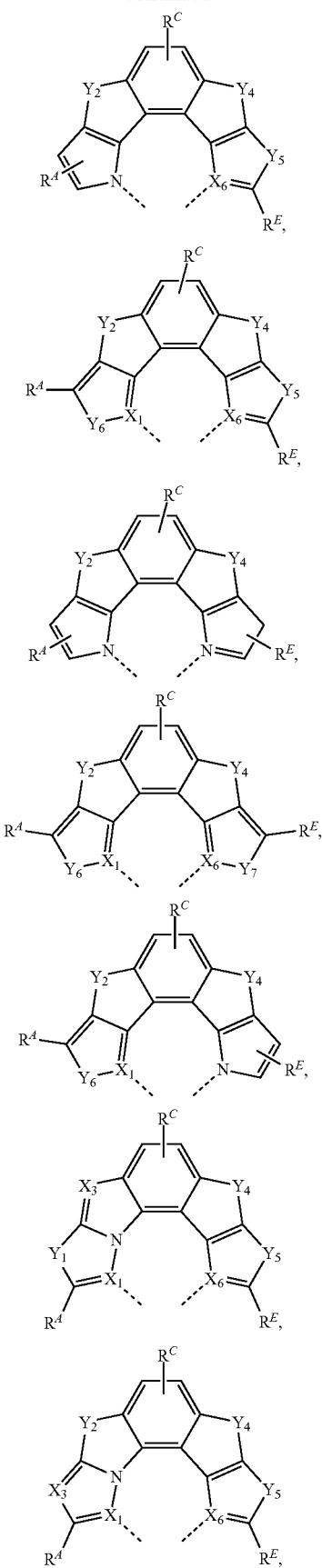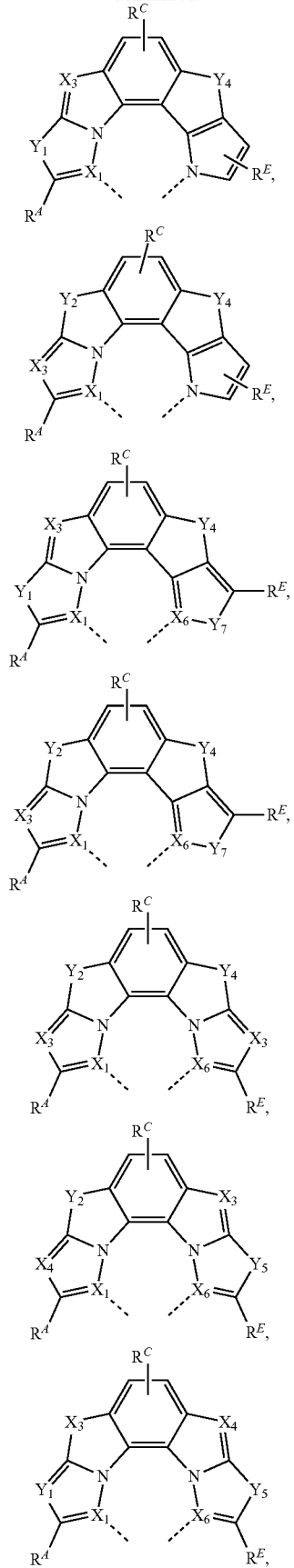

-continued

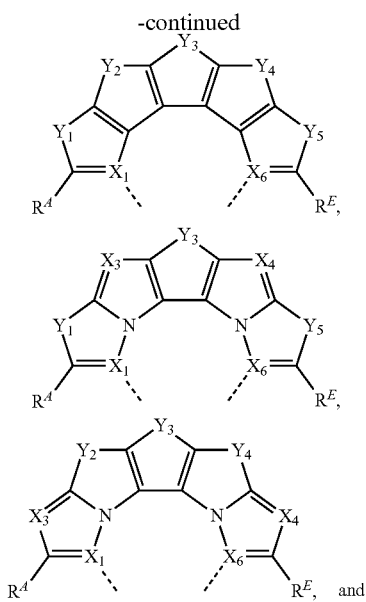

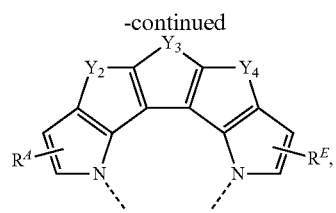

wherein each $X_1$-$X_6$ is independently selected from the group consisting of C and N; wherein no more than two N atoms are bond to one another; wherein each $Y_1$-$Y_7$ is selected from the group consisting of O, S, Se, NR, CRR', SiRR', GeRR', and BR; and wherein R and R' are each independently selected from the group consisting of hydrogen, deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, and combinations thereof.

In some embodiments, the ligand $L_A$ can be selected from the group consisting of the structures shown in LIST 2 below. It should be noted that the variables Yi and Yj used in LIST 2 and the subscripted variables $Y_1$-$Y_7$ used above are different set of variables.

LIST 2

| Name of ligand $L_A$ | Structure | i, j |
|---|---|---|
| $L_A$I-[(i)(j)] having the structure | 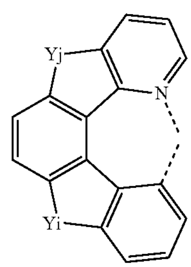 | wherein i and j are independently an integer from 1 to 30, and |
| $L_A$II-[(i)(j)(k)] having the structure | 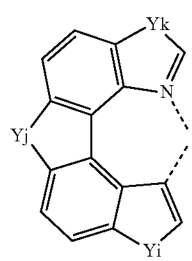 | wherein i, j, and k are independently an integer from 1 to 30, and |
| $L_A$III-[(i)(j)] having the structure | 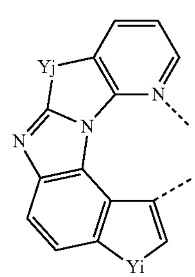 | Wherein i and j are independently an integer from 1 to 30, and |

LIST 2

| Name of ligand $L_A$ | Structure | i, j |
|---|---|---|
| $L_A$IV-[(i)] having the structure | | wherein i is an integer from 1 to 30, and |
| $L_A$V-[(i)(j)] having the structure | 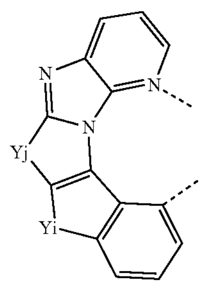 | wherein i and j are independently an integer from 1 to 30, and |
| $L_A$VI-[(i)(j)] having the structure | 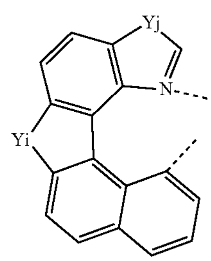 | wherein i and j are independently an integer from 1 to 30, and |
| $L_A$VII-[(i)] having the structure | 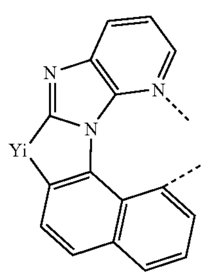 | wherein i is an integer from 1 to 30, and |
| $L_A$VIII-[(i)(j)] having the structure | 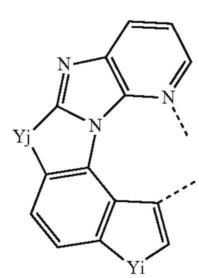 | wherein i and j are independently an integer from 1 to 30, and |

LIST 2

| Name of ligand $L_A$ | Structure | i, j |
|---|---|---|
| $L_A$IX-[(i)(j)] having the structure | (structure) | wherein i and j are independently an integer from 1 to 30, and |
| $L_A$X-[(i)(j)] having the structure | (structure) | wherein i and j are independently an integer from 1 to 30, and |
| $L_A$XI-[(i)(j)] having the structure | (structure) | wherein i and j are independently an from 1 to 30, and |
| $L_A$XII-[(i)] having the structure | (structure) | wherein i is an integer from 1 to 30, and |
| $L_A$XIII-[(i)(j)] having the structure | (structure) | wherein i and j are independently an integer from 1 to 30, and |

LIST 2

| Name of ligand $L_A$ | Structure | i, j |
|---|---|---|
| $L_A$XIV-[(i)(j)] having the structure | 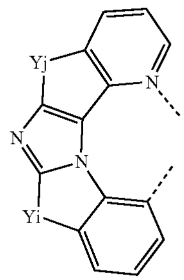 | wherein i, j, are independently an integer from 1 to 30, and |
| $L_A$XV-[(i)] having the structure | 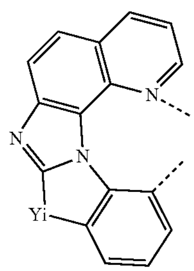 | wherein i is an integer from 1 to 30, and |
| $L_A$XVI-[(i)(j)] having the structure | 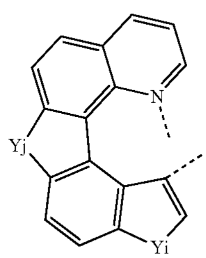 | wherein i is an integer from 1 to 30, and |
| $L_A$XVII-[(i)(j)] having the structure | 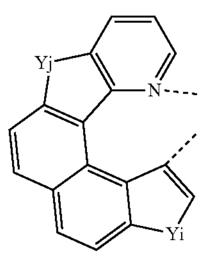 | wherein i and j are independently an integer from 1 to 30, and |
| $L_A$XVIII-[(i)(j)] having the structure | | wherein i and j are independently an integer from 1 to 30, and | wherein Y1 through Y30 have the structures defined below:
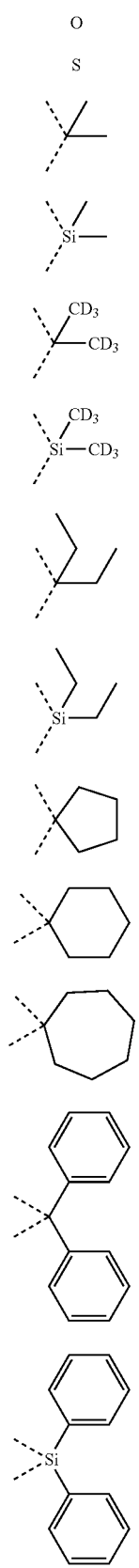
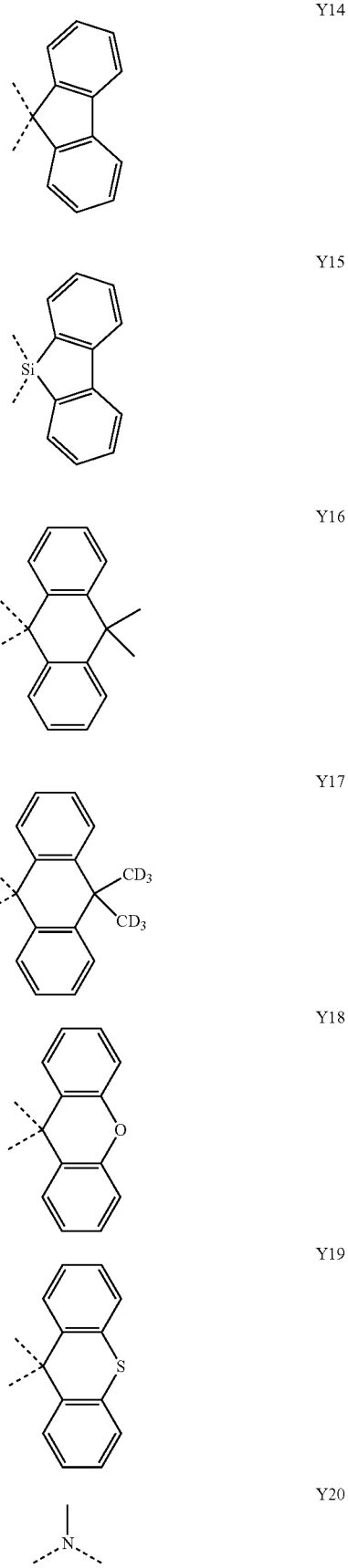

Y21 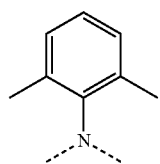
Y22 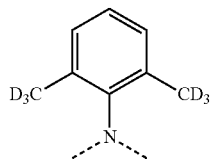
Y23 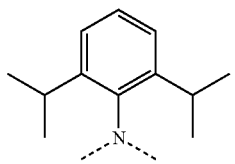
Y24 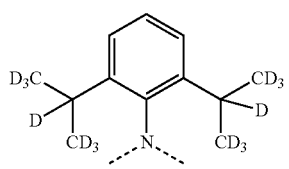
Y25 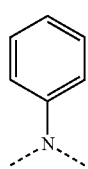
Y26 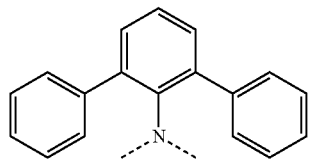
Y27 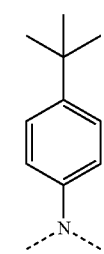
Y28 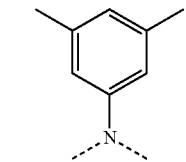
Y29 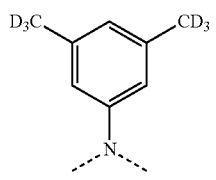
Y30 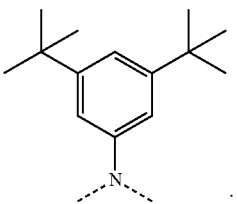
In some embodiments, the compound can have the formula $Ir(L_A)_3$, the formula $Ir(L_A)(L_B)_2$, the formula $Ir(L_A)_2(L_B)$, or the formula $Ir(L_A)_2(L_C)$, wherein:
$L_A$ is selected from the group consisting of the structures shown in LIST 2 above;
$L_B$ is selected from the group consisting of $L_{B1}$ through $L_{B468}$ as shown in LIST 3 below:
$L_{B1}$ 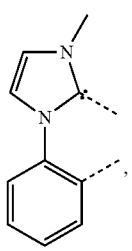
$L_{B2}$ 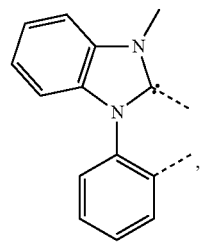
$L_{B3}$ 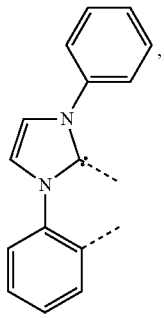
$L_{B4}$ 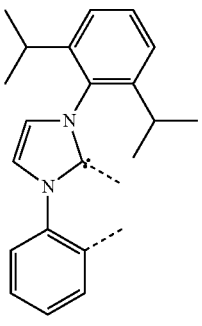

-continued
L_{B5}
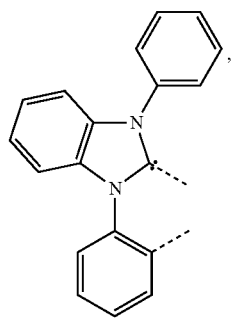
L_{B6}
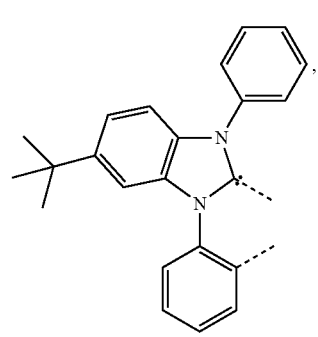
L_{B7}
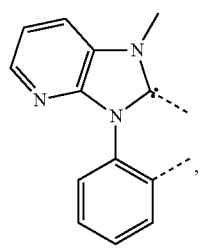
L_{B8}
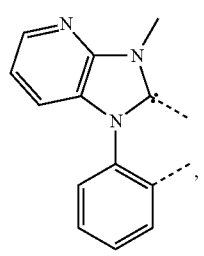
L_{B9}
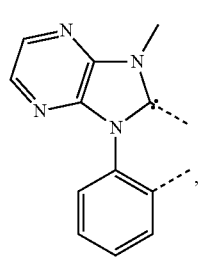
-continued
L_{B10}
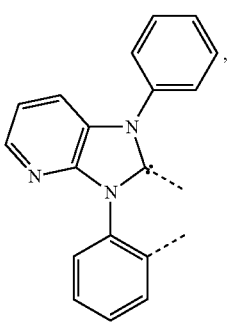
L_{B11}
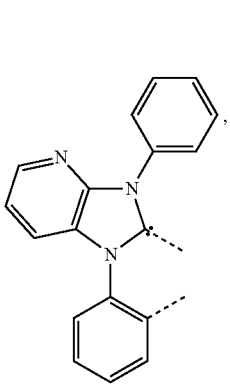
L_{B12}
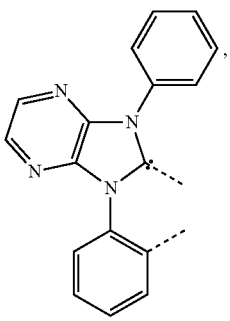
L_{B13}
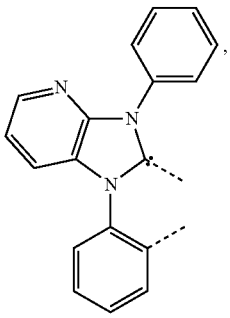
L_{B14}
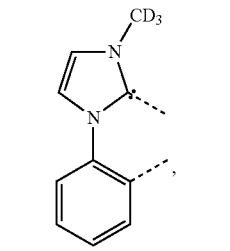

L_{B15}
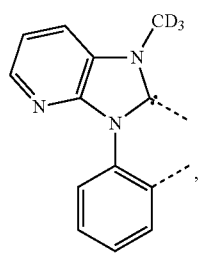
L_{B16}
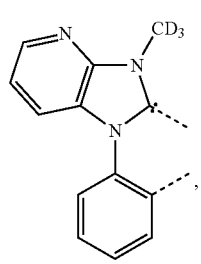
L_{B17}
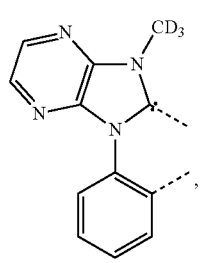
L_{B18}
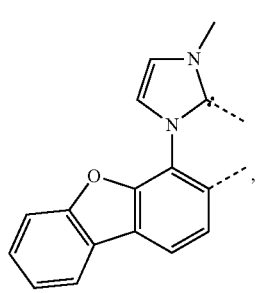
L_{B19}
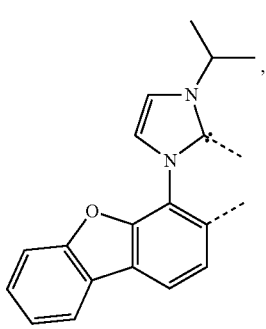
L_{B20}
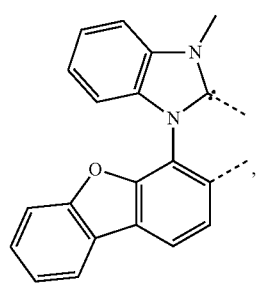
L_{B21}
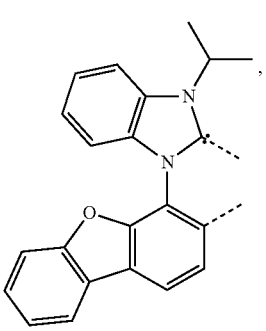
L_{B22}
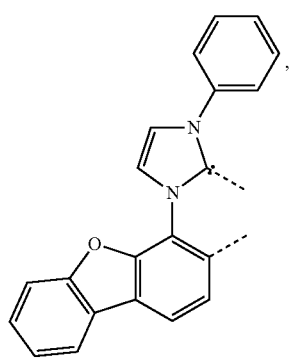
L_{B23}
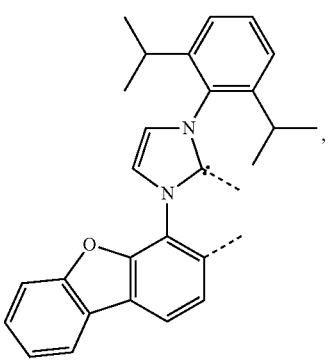

L$_{B24}$
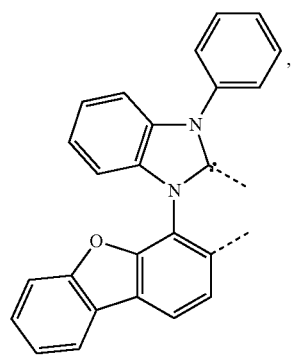
L$_{B25}$
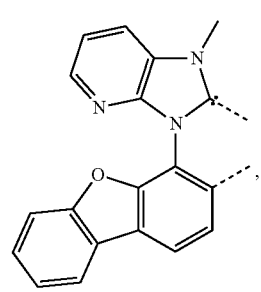
L$_{B26}$
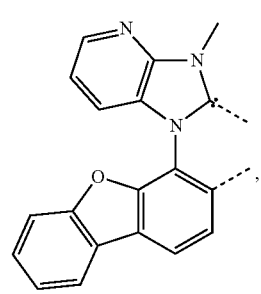
L$_{B27}$
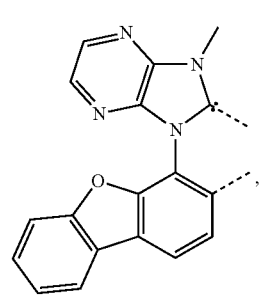
L$_{B28}$
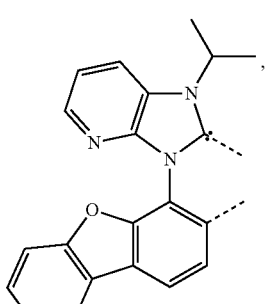
L$_{B29}$
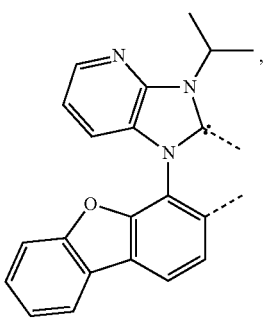
L$_{B30}$
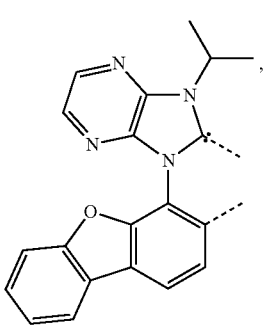
L$_{B31}$
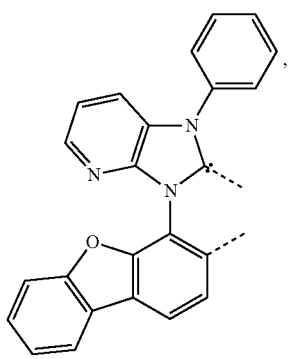
L$_{B32}$
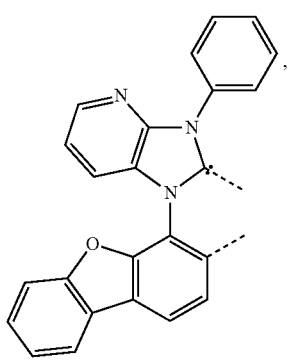

L_{B33}
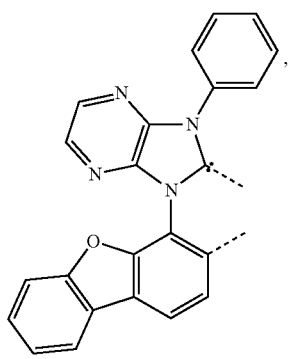
L_{B34}
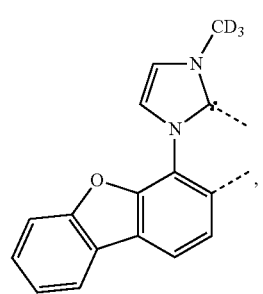
L_{B35}
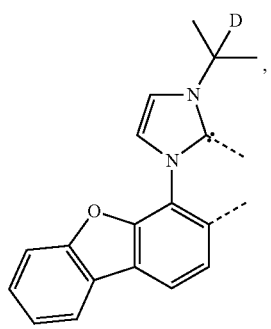
L_{B36}
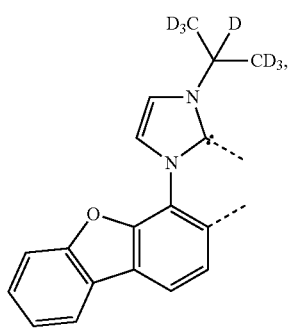
L_{B37}
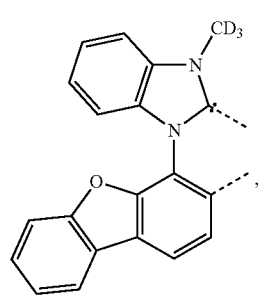
L_{B38}
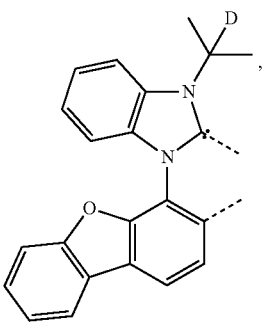
L_{B39}
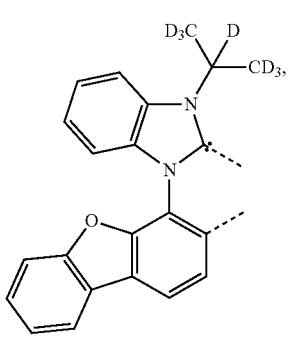
L_{B40}
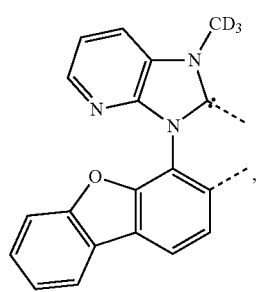
L_{B41}
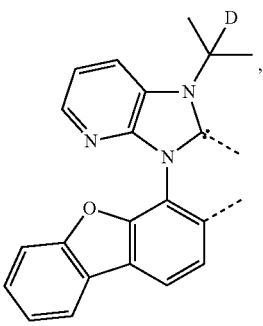
L_{B42}
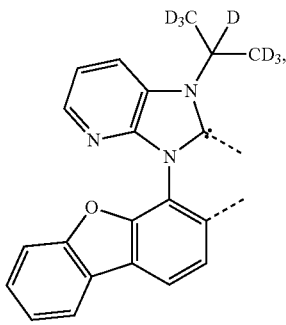

L<sub>B43</sub> 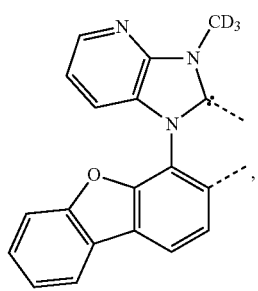
L<sub>B44</sub> 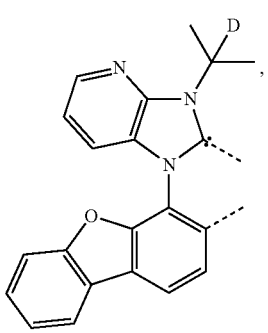
L<sub>B45</sub> 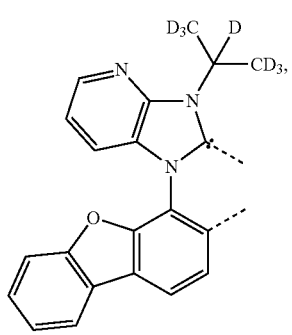
L<sub>B46</sub> 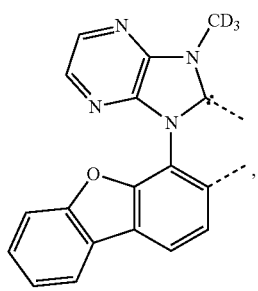
L<sub>B47</sub> 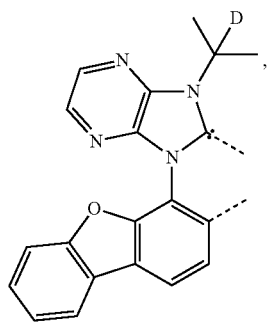
L<sub>B48</sub> 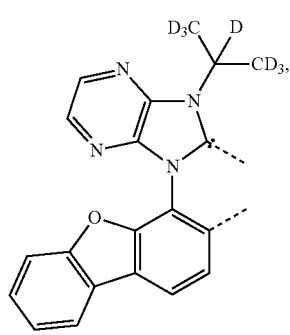
L<sub>B49</sub> 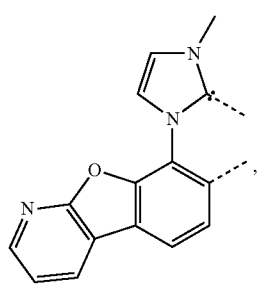
L<sub>B50</sub> 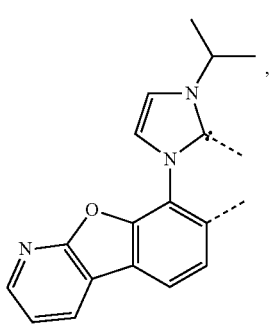
L<sub>B51</sub> 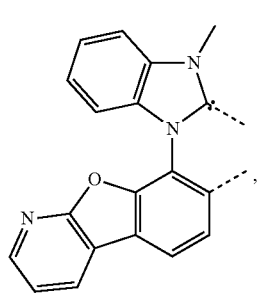
L<sub>B52</sub> 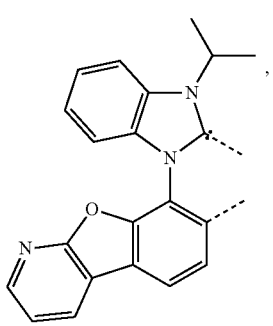

L_{B53}
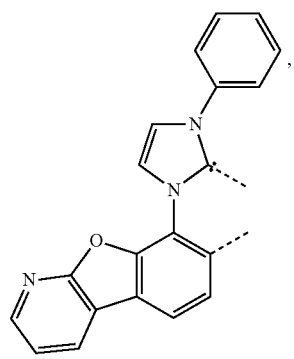
L_{B54}
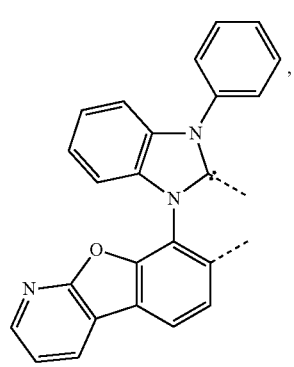
L_{B55}
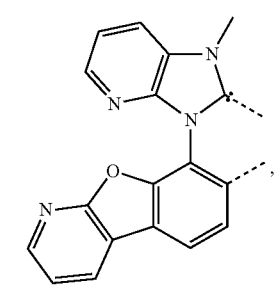
L_{B56}
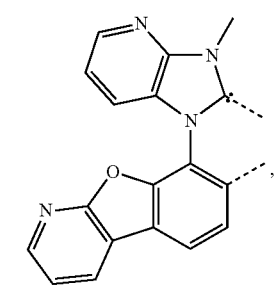
L_{B57}
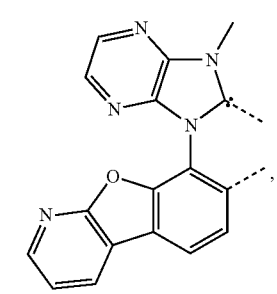
L_{B58}
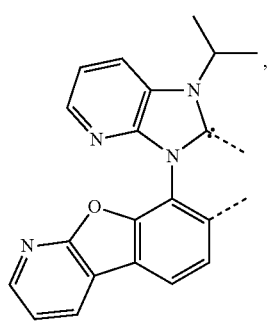
L_{B59}
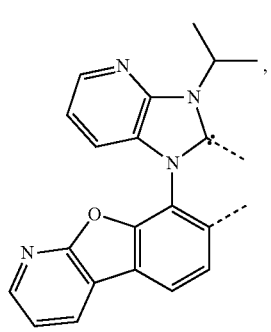
L_{B60}
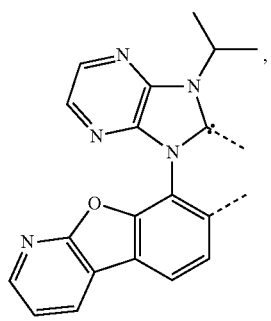
L_{B61}
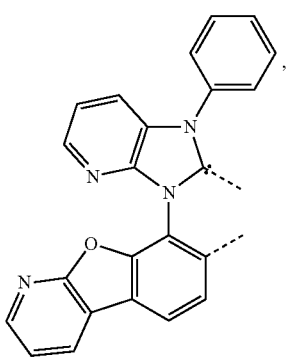

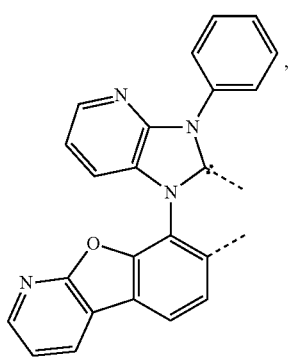 L_{B62}
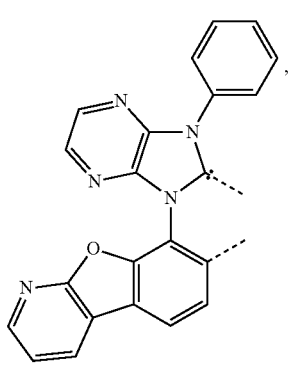 L_{B63}
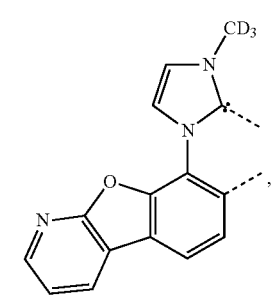 L_{B64}
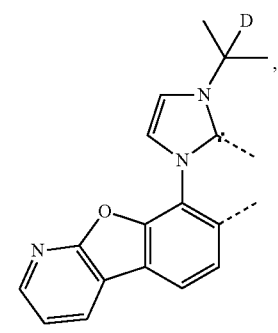 L_{B65}
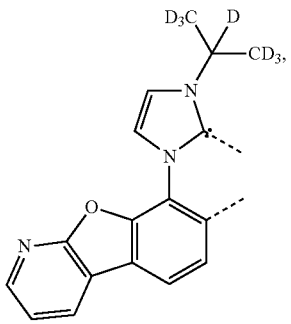 L_{B66}
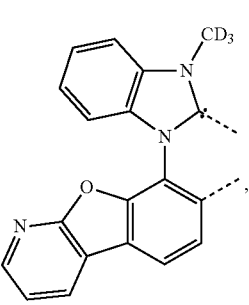 L_{B67}
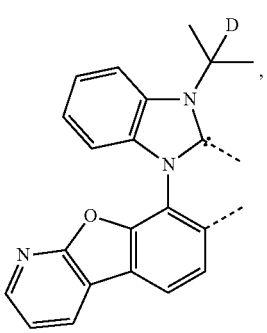 L_{B68}
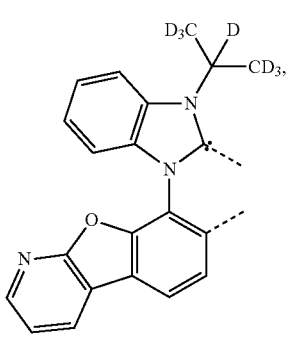 L_{B69}
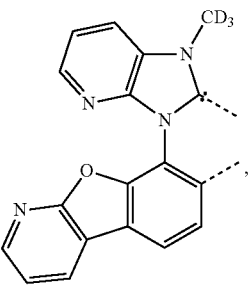 L_{B70}

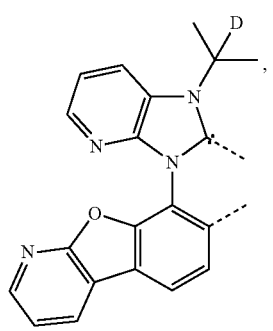 L_{B71}
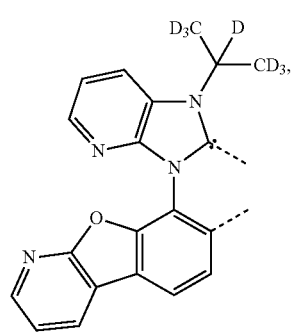 L_{B72}
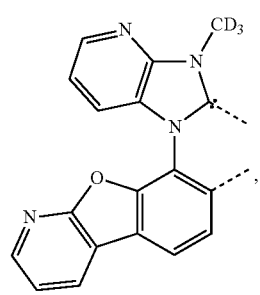 L_{B73}
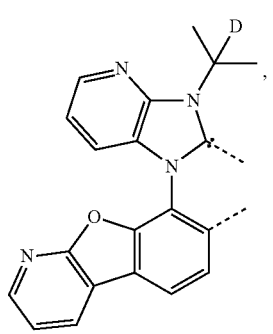 L_{B74}
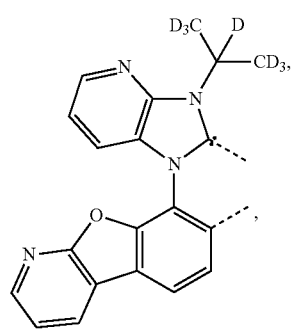 L_{B75}
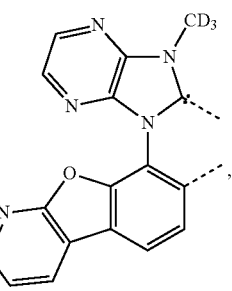 L_{B76}
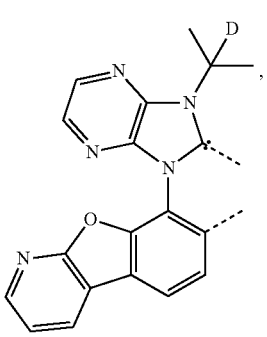 L_{B77}
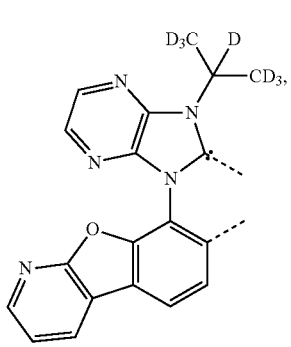 L_{B78}
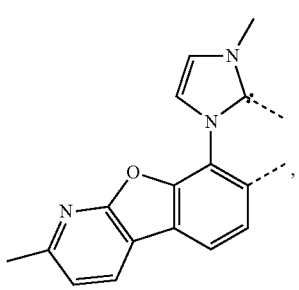 L_{B79}
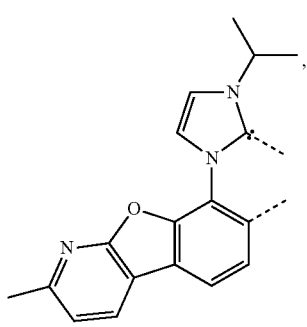 L_{B80}

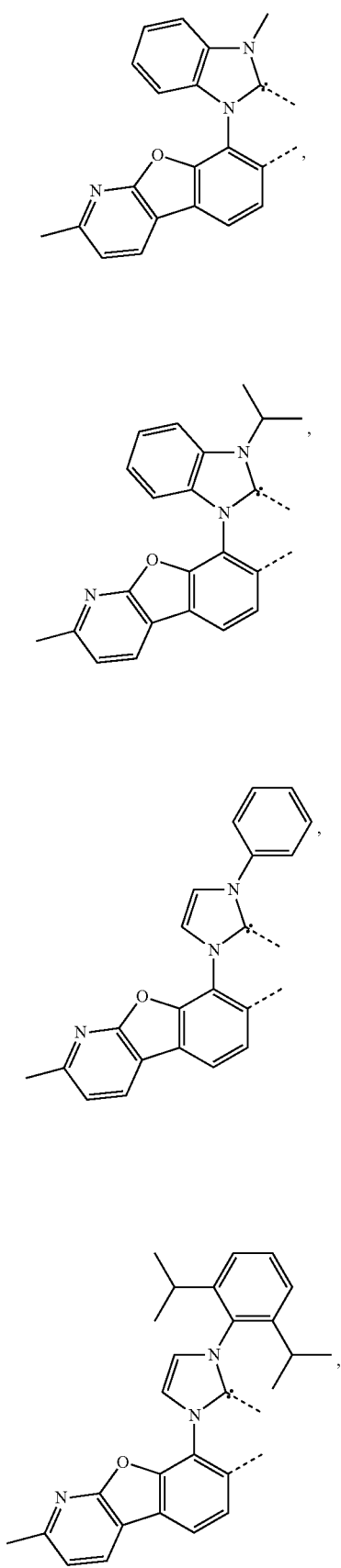
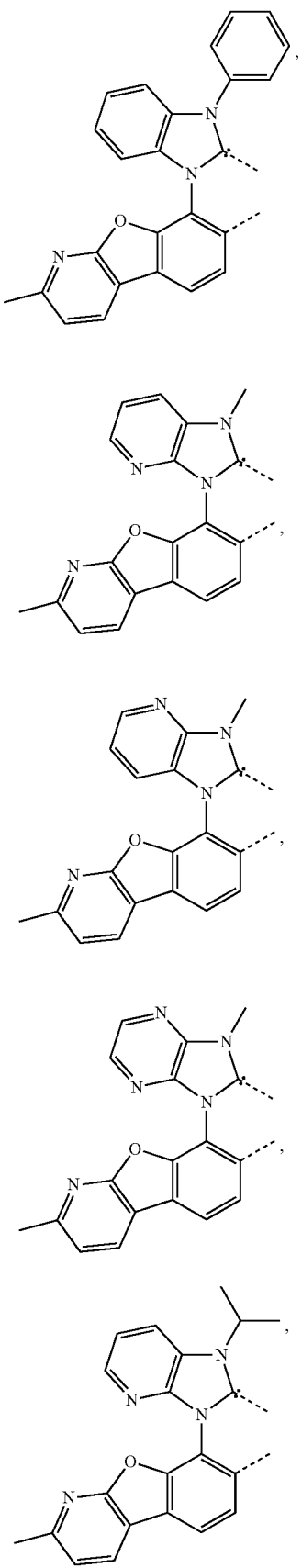

L<sub>B90</sub> 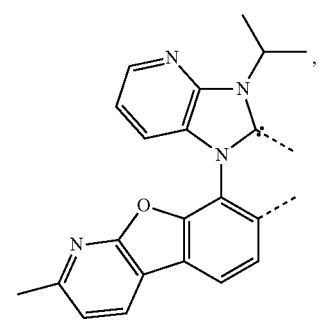
L<sub>B91</sub> 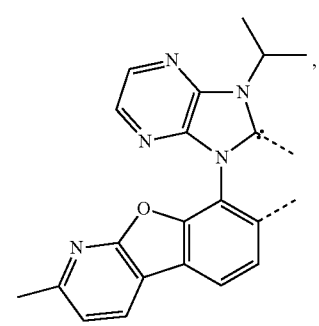
L<sub>B92</sub> 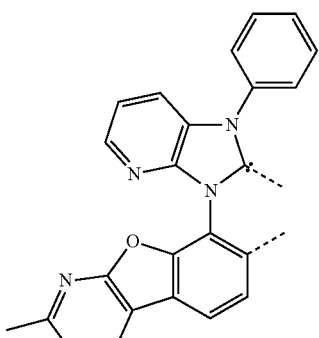
L<sub>B93</sub> 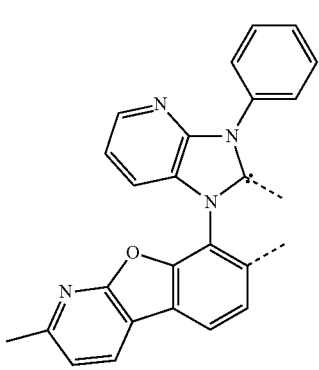
L<sub>B94</sub> 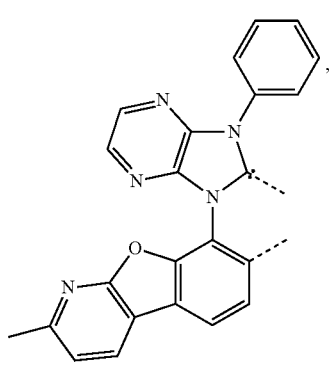
L<sub>B95</sub> 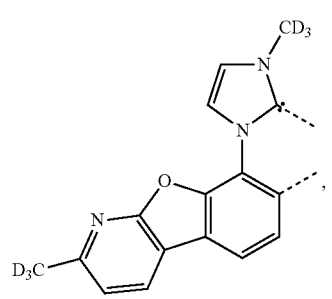
L<sub>B96</sub> 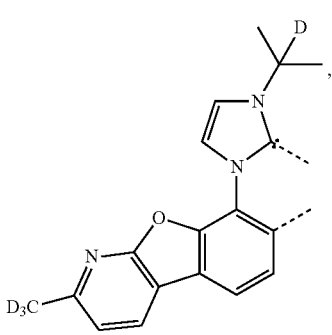
L<sub>B97</sub> 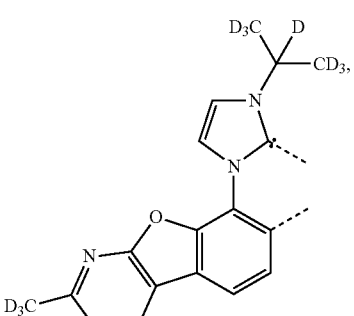
L<sub>B98</sub> 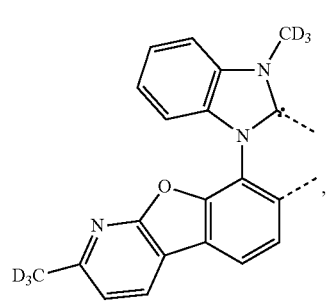

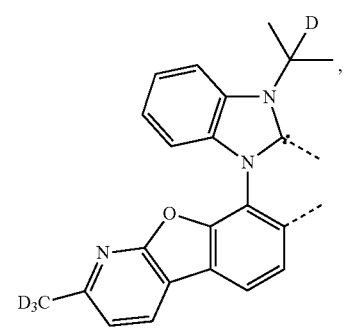 L_{B99}
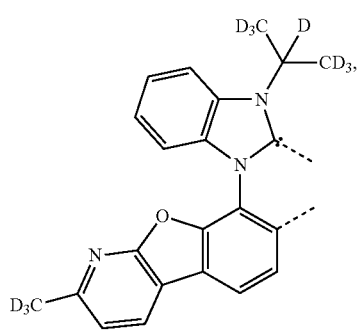 L_{B100}
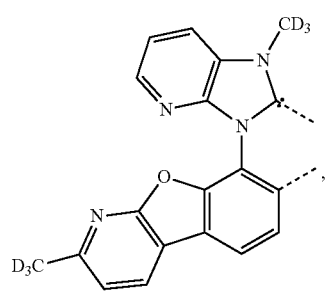 L_{B101}
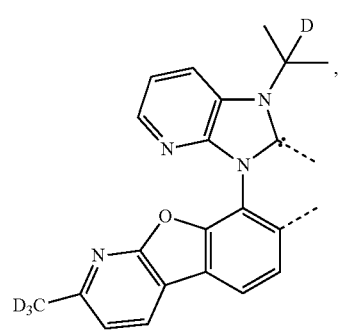 L_{B102}
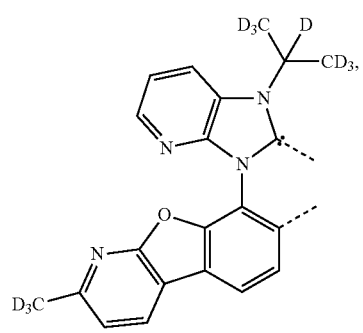 L_{B103}
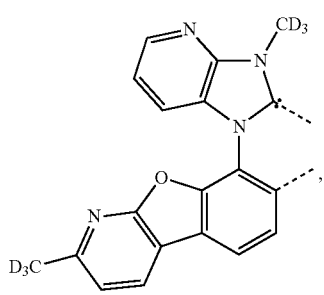 L_{B104}
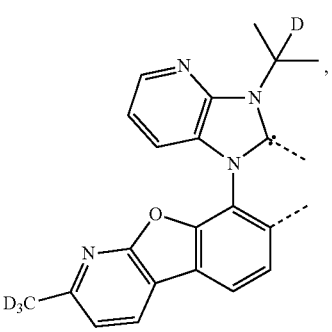 L_{B105}
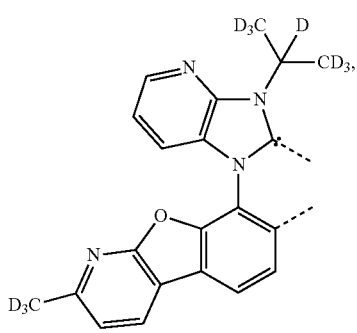 L_{B106}
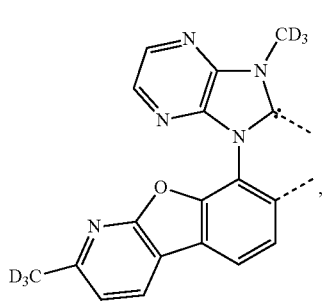 L_{B107}
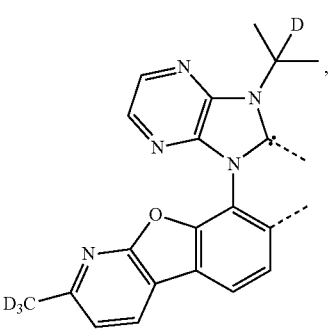 L_{B108}

-continued
L<sub>B109</sub>
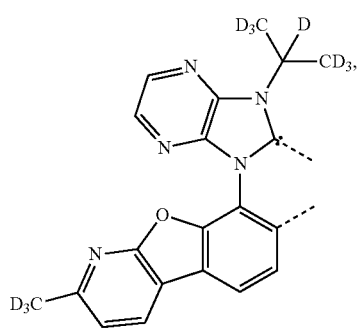
L<sub>B110</sub>
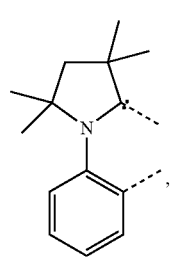
L<sub>B111</sub>
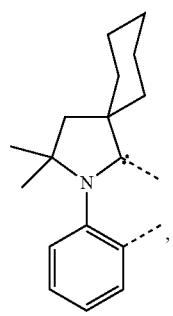
L<sub>B112</sub>
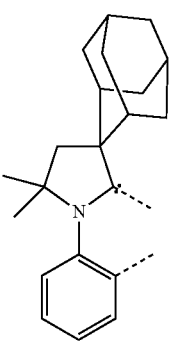
L<sub>B113</sub>
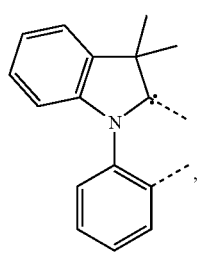
-continued
L<sub>B114</sub>
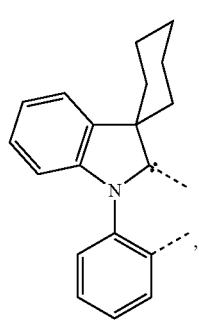
L<sub>B115</sub>
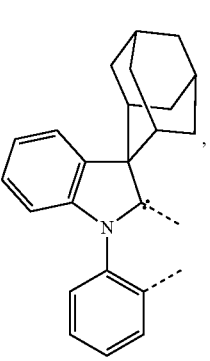
L<sub>B116</sub>
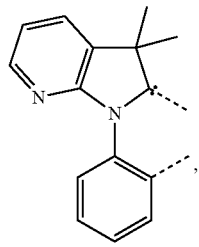
L<sub>B117</sub>
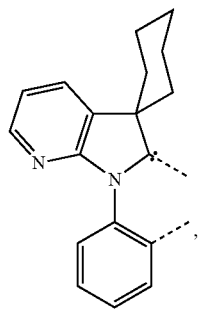
L<sub>B118</sub>
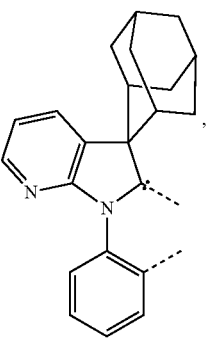

L<sub>B119</sub>
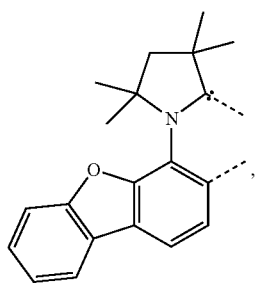
L<sub>B120</sub>
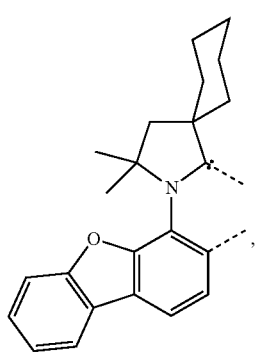
L<sub>B121</sub>
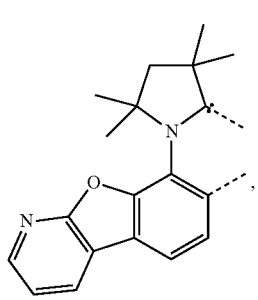
L<sub>B122</sub>
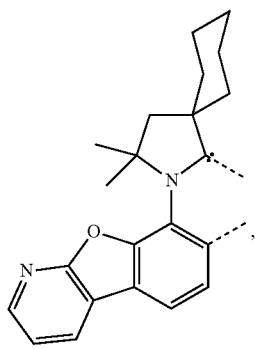
L<sub>B123</sub>
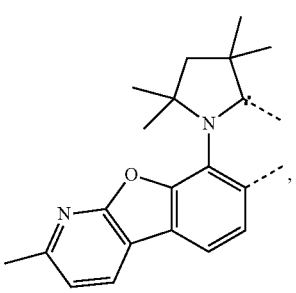
L<sub>B124</sub>
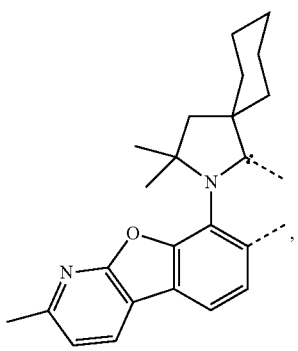
L<sub>B125</sub>
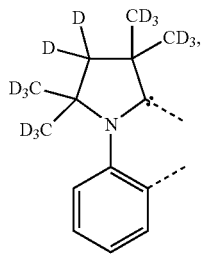
L<sub>B126</sub>
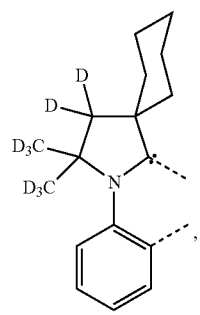
L<sub>B127</sub>
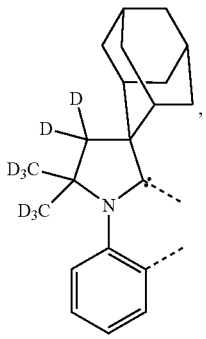
L<sub>B128</sub>
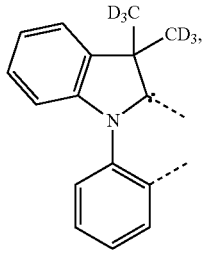

LB129 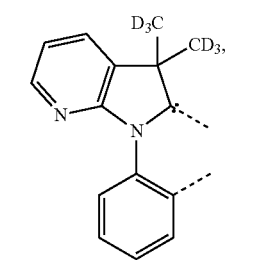
LB130 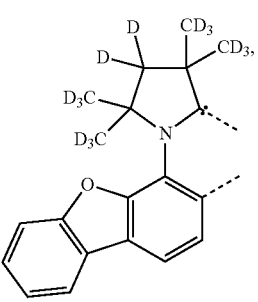
LB131 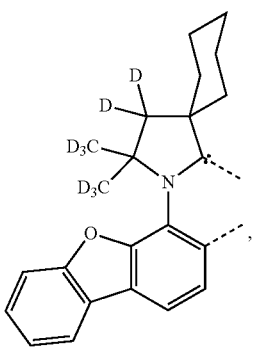
LB132 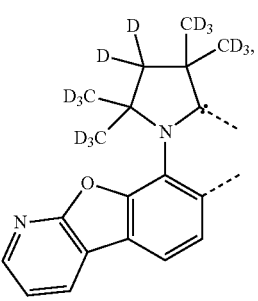
LB133 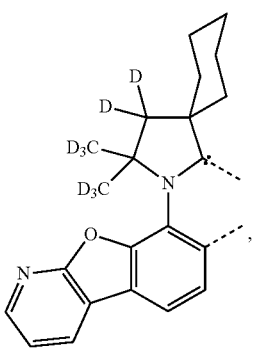
LB134 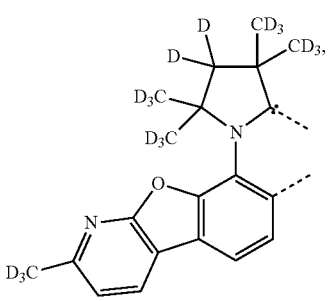
LB135 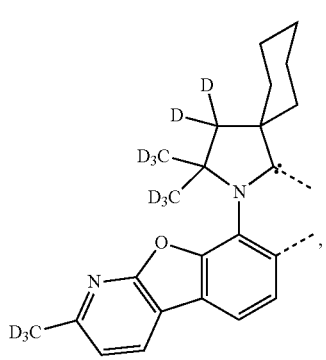
LB136 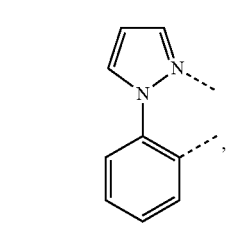
LB137 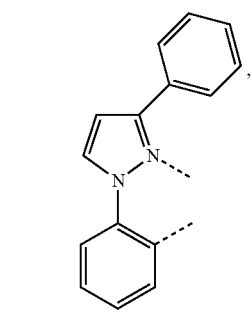
LB138 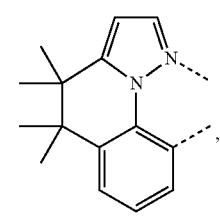

-continued
L<sub>B139</sub>
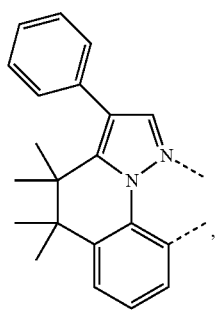
L<sub>B140</sub>
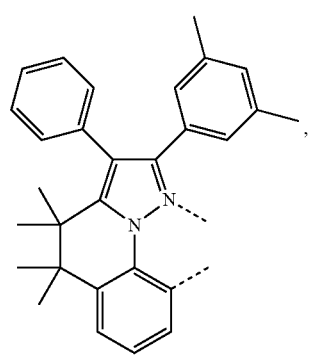
L<sub>B141</sub>
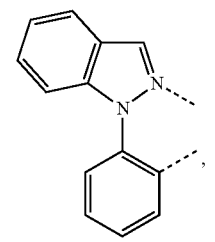
L<sub>B142</sub>
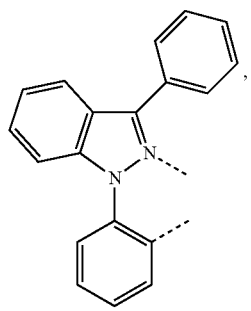
L<sub>B143</sub>
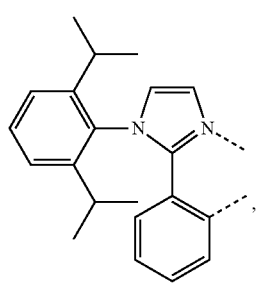
-continued
L<sub>B144</sub>
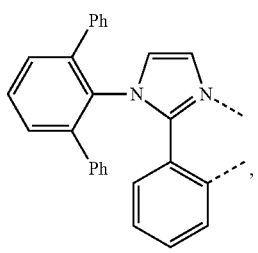
L<sub>B145</sub>
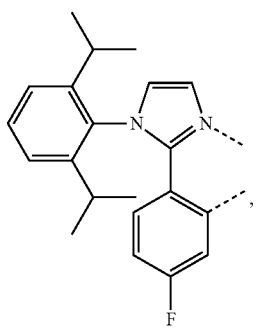
L<sub>B146</sub>
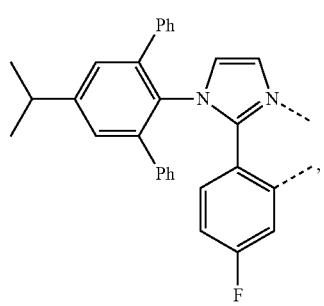
L<sub>B147</sub>
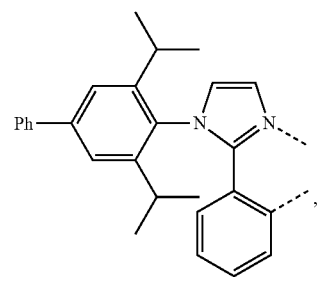
L<sub>B148</sub>
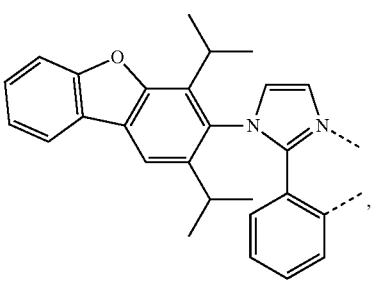

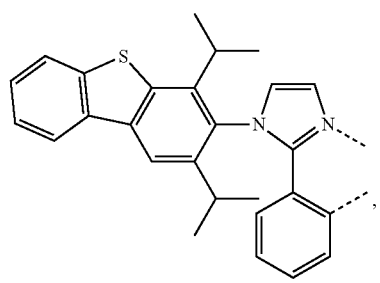
L_{B149}
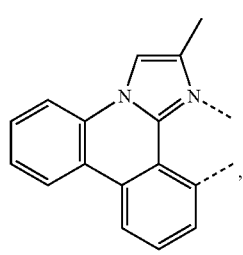
L_{B150}
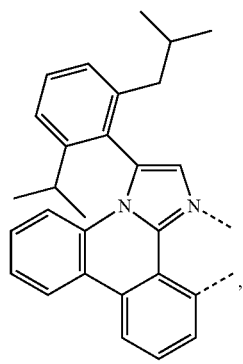
L_{B151}
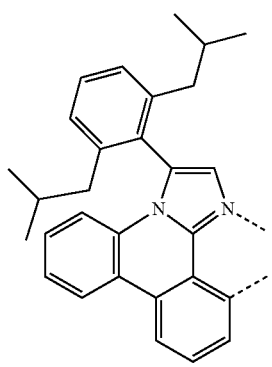
L_{B152}
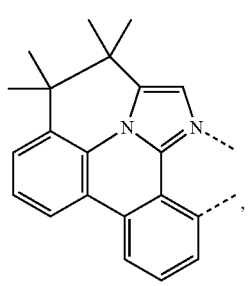
L_{B153}
L_{B154}
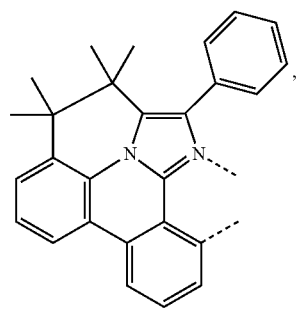
L_{B155}
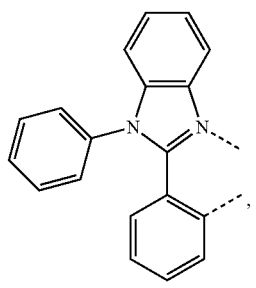
L_{B156}
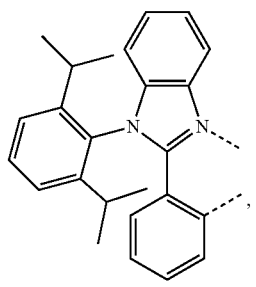
L_{B157}
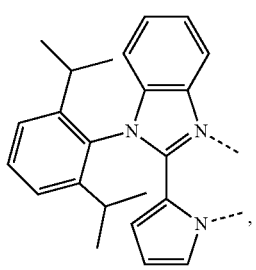
L_{B158}

-continued
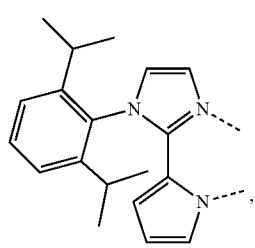 L<sub>B159</sub>
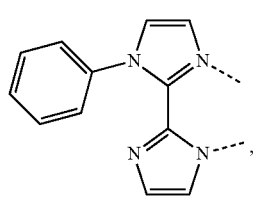 L<sub>B160</sub>
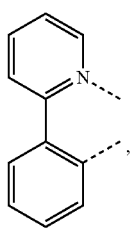 L<sub>B161</sub>
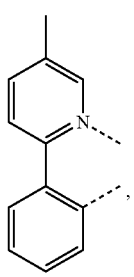 L<sub>B162</sub>
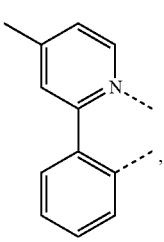 L<sub>B163</sub>
 L<sub>B164</sub>
-continued
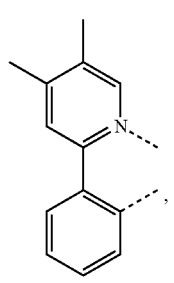 L<sub>B165</sub>
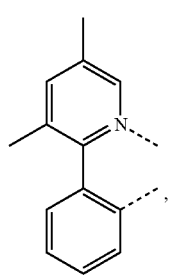 L<sub>B166</sub>
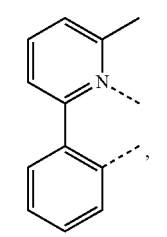 L<sub>B167</sub>
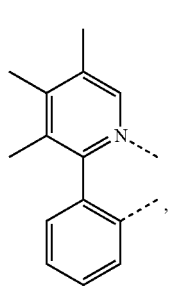 L<sub>B168</sub>
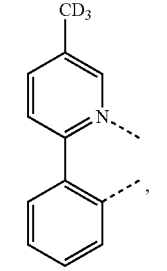 L<sub>B169</sub>
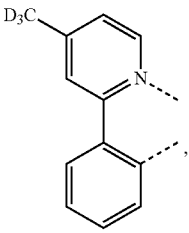 L<sub>B170</sub>

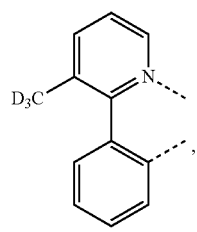 L_{B171}
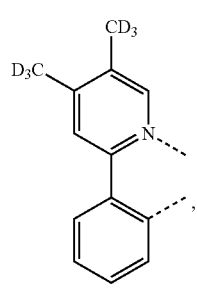 L_{B172}
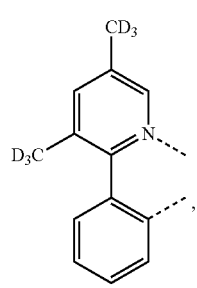 L_{B173}
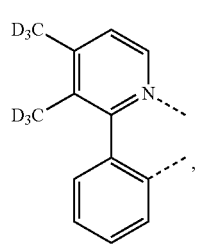 L_{B174}
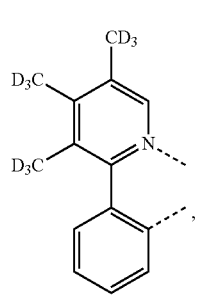 L_{B175}
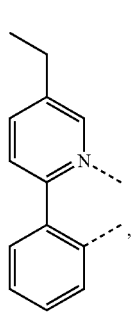 L_{B176}
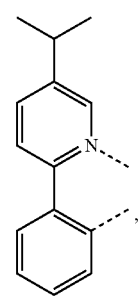 L_{B177}
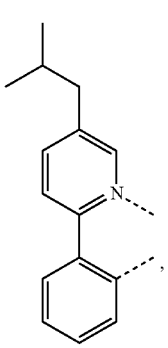 L_{B178}
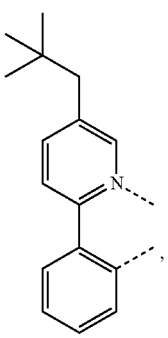 L_{B179}
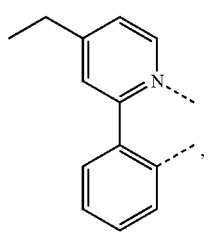 L_{B180}
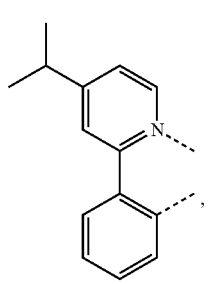 L_{B181}

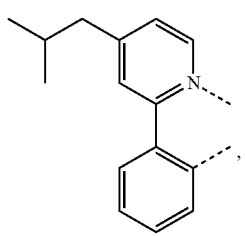 L_{B182}
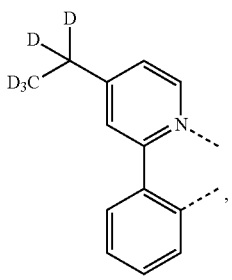 L_{B187}
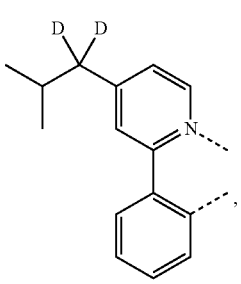 L_{B183}
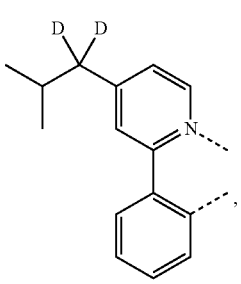 L_{B188}
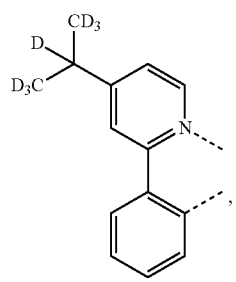 L_{B184}
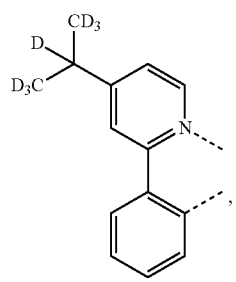 L_{B189}
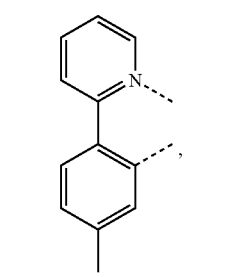 L_{B185}
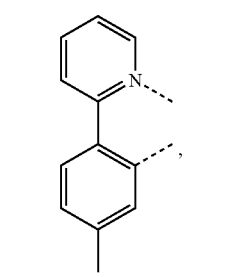 L_{B190}
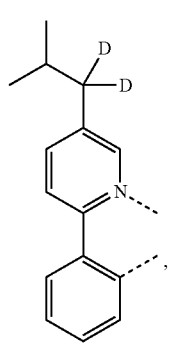 L_{B186}
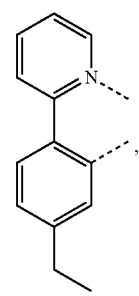 L_{B191}

L_{B192} 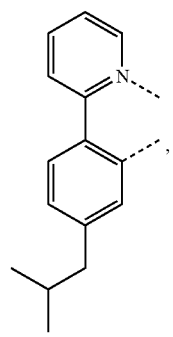
L_{B193} 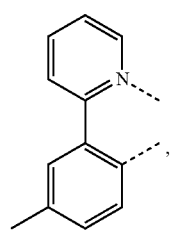
L_{B194} 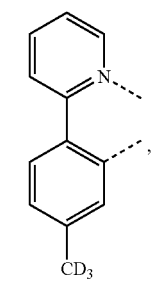
L_{B195} 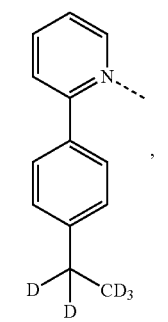
L_{B196} 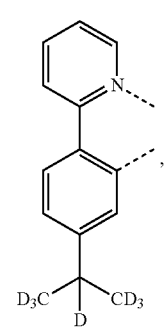
L_{B197} 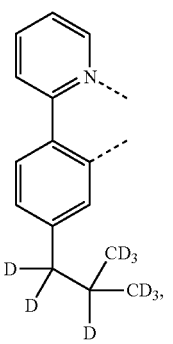
L_{B198} 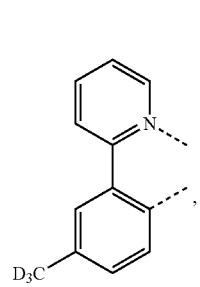
L_{B199} 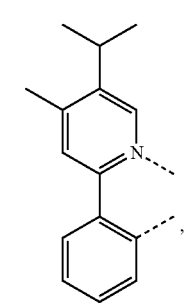
L_{B200} 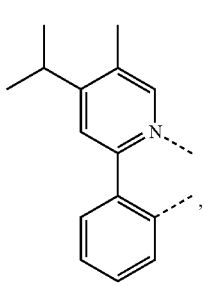
L_{B201} 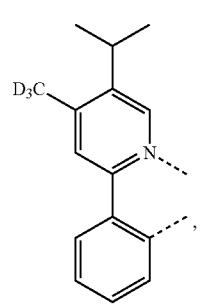

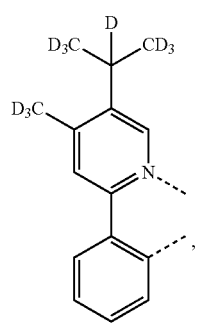 L$_{B202}$
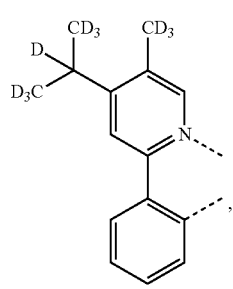 L$_{B203}$
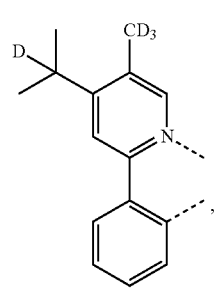 L$_{B204}$
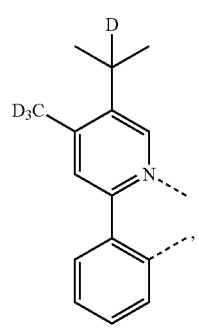 L$_{B205}$
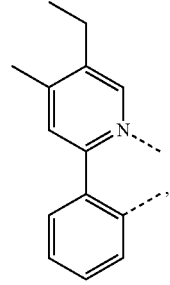 L$_{B206}$
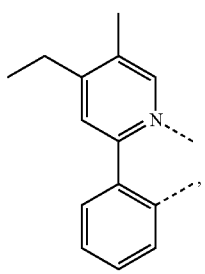 L$_{B207}$
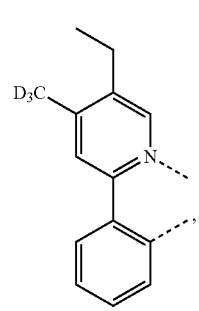 L$_{B208}$
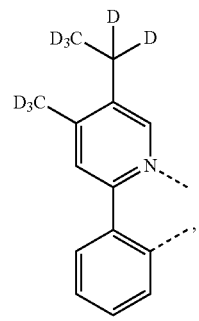 L$_{B209}$
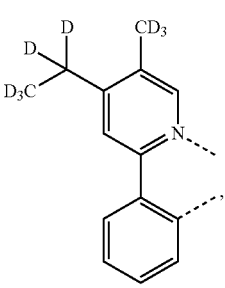 L$_{B210}$
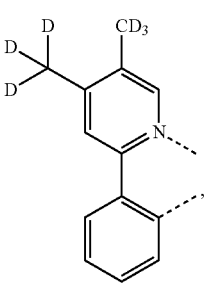 L$_{B211}$ L_{B212}
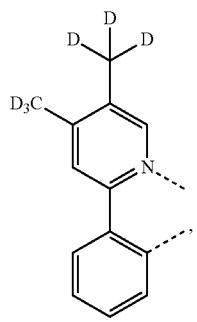
L_{B213}
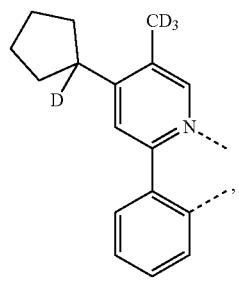
L_{B214}
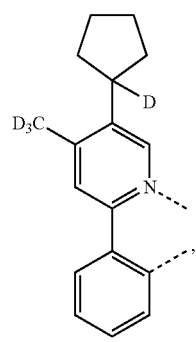
L_{B215}
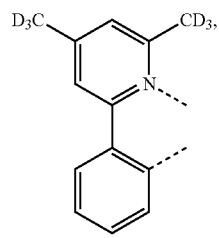
L_{B216}
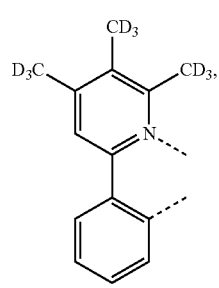
L_{B217}
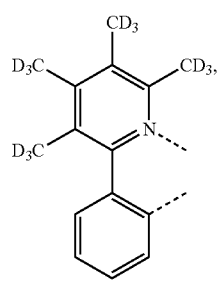
L_{B218}
L_{B219}
L_{B220}
L_{B221}

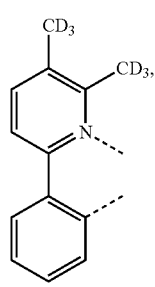 L_{B222}
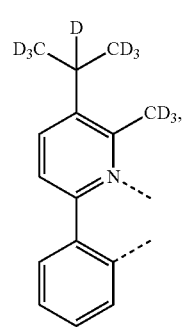 L_{B223}
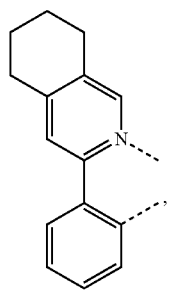 L_{B224}
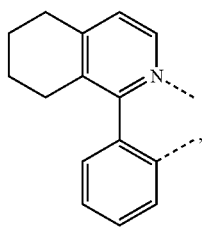 L_{B225}
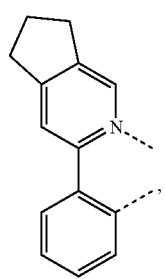 L_{B226}
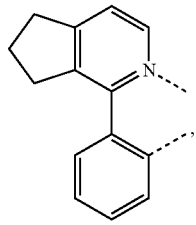 L_{B227}
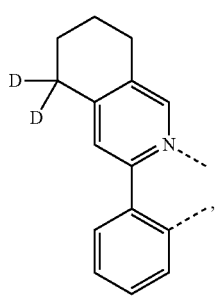 L_{B228}
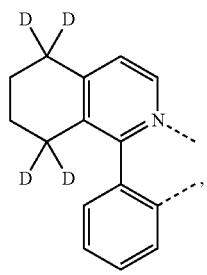 L_{B229}
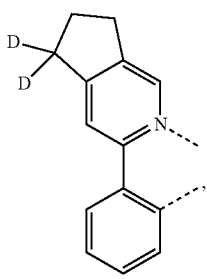 L_{B230}
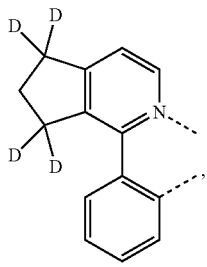 L_{B231}

-continued
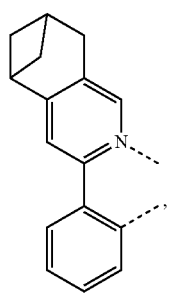 L_{B232}
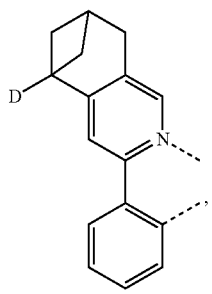 L_{B233}
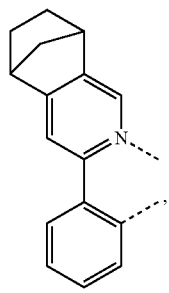 L_{B234}
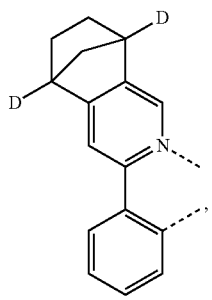 L_{B235}
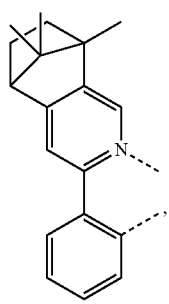 L_{B236}
-continued
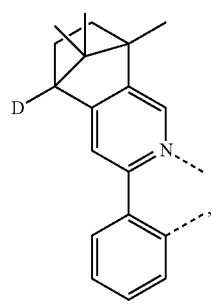 L_{B237}
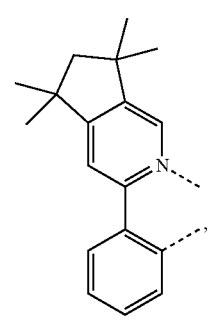 L_{B238}
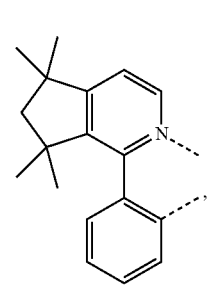 L_{B239}
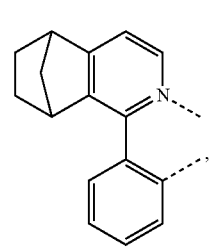 L_{B240}
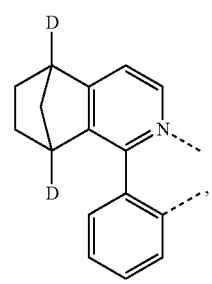 L_{B241}

L<sub>B242</sub>
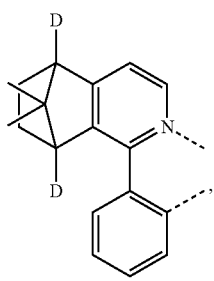
L<sub>B243</sub>
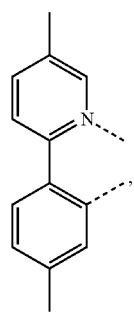
L<sub>B244</sub>
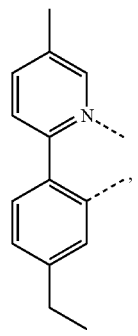
L<sub>B245</sub>
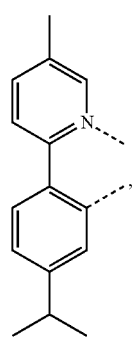
L<sub>B246</sub>
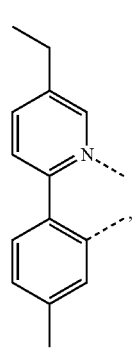
L<sub>B247</sub>
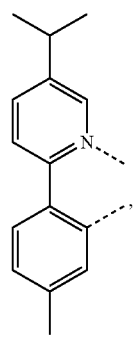
L<sub>B248</sub>
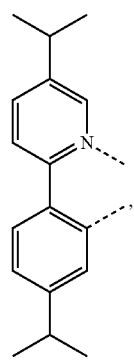
L<sub>B249</sub>
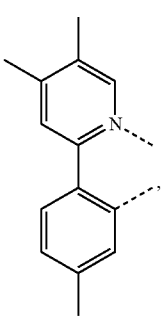
L<sub>B250</sub>
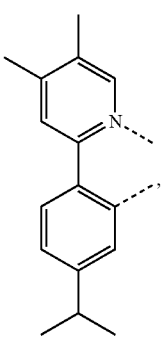

93
-continued
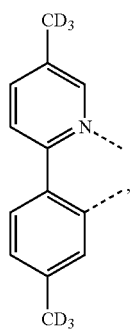
L_{B251}
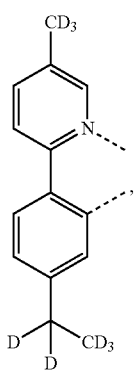
L_{B252}
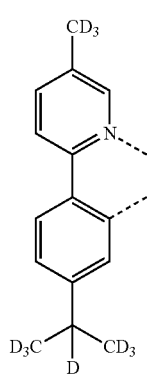
L_{B253}
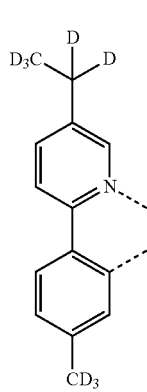
L_{B254}
94
-continued
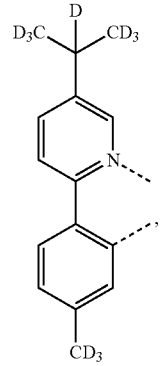
L_{B255}
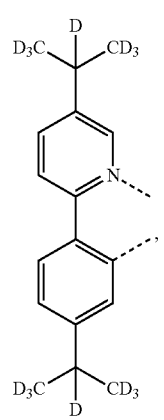
L_{B256}
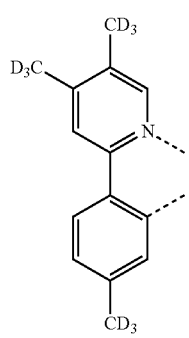
L_{B257}
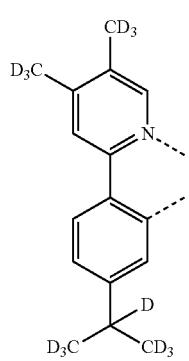
L_{B258}

L_{B259}
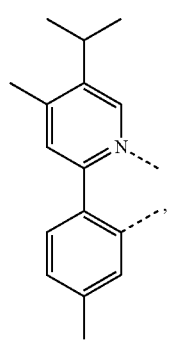
L_{B260}
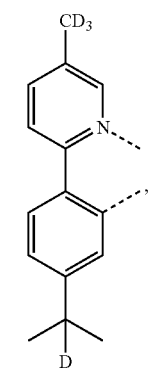
L_{B261}
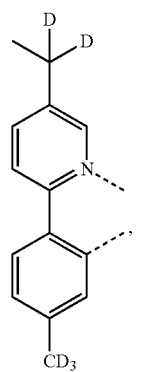
L_{B262}
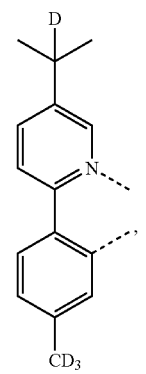
L_{B263}
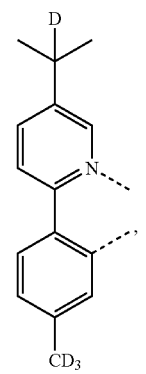
L_{B264}
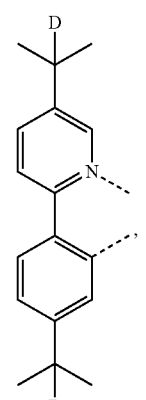
L_{B265}
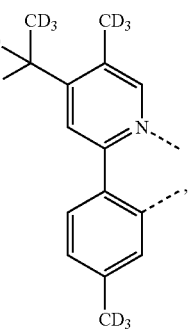
L_{B266}
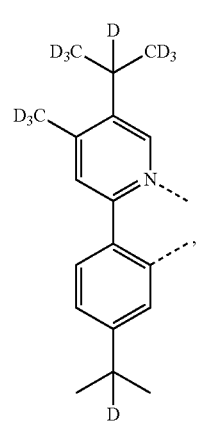

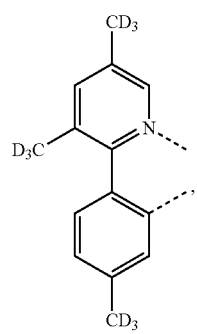
L<sub>B267</sub>
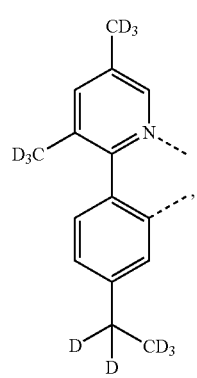
L<sub>B268</sub>
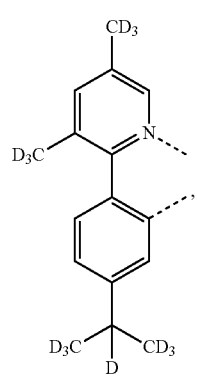
L<sub>B269</sub>
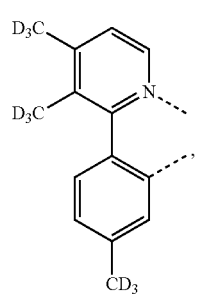
L<sub>B270</sub>
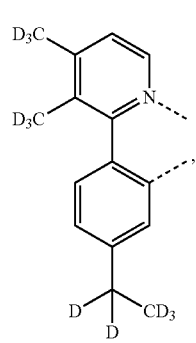
L<sub>B271</sub>
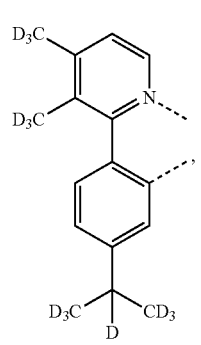
L<sub>B272</sub>
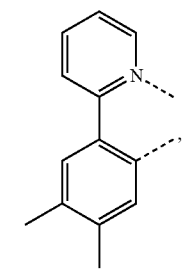
L<sub>B273</sub>
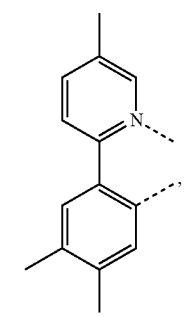
L<sub>B274</sub>
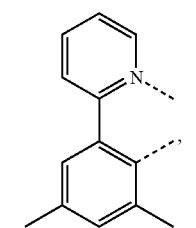
L<sub>B275</sub>

-continued
L_{B276}
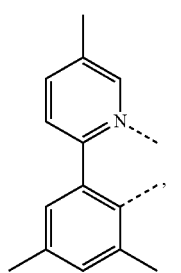
L_{B277}
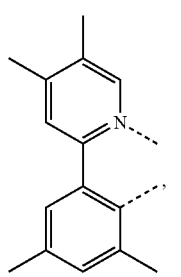
L_{B278}
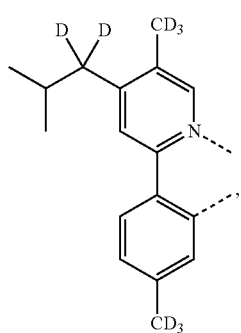
L_{B279}
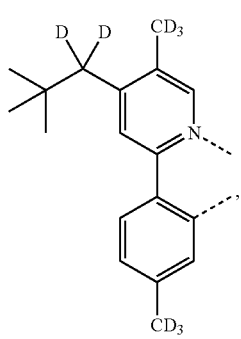
L_{B280}
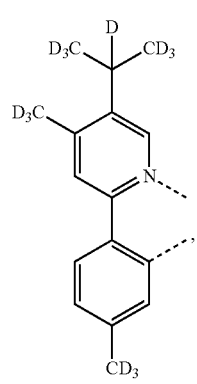
-continued
L_{B281}
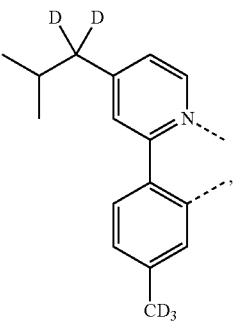
L_{B282}
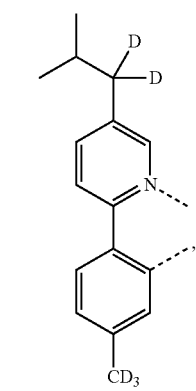
L_{B283}
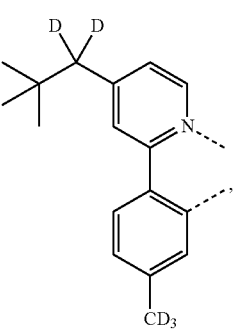
L_{B284}
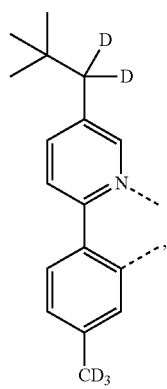

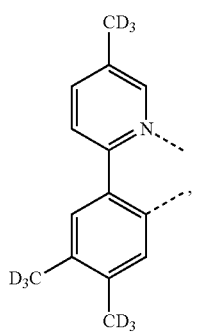 L_B285
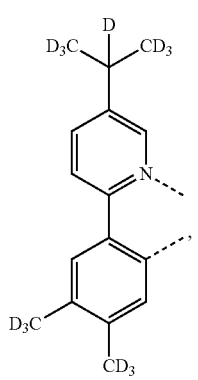 L_B286
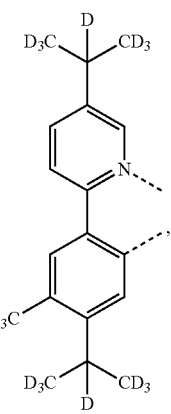 L_B287
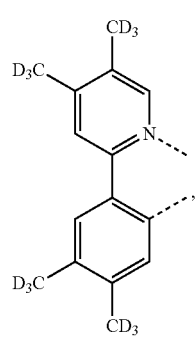 L_B288
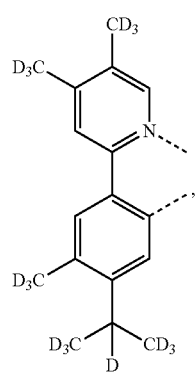 L_B289
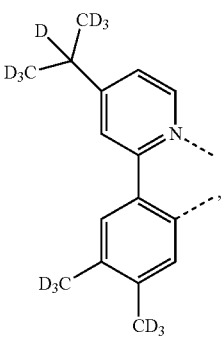 L_B290
L_B291
L_B292

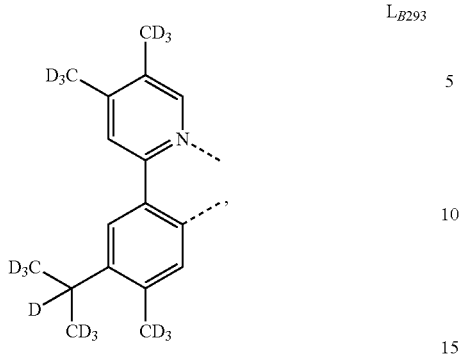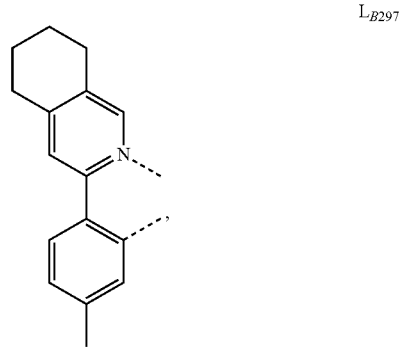

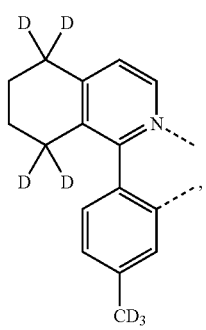 L_{B302}
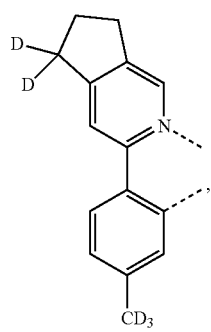 L_{B303}
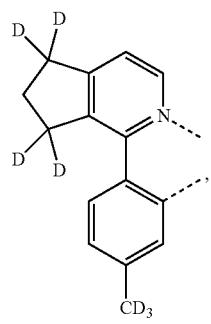 L_{B304}
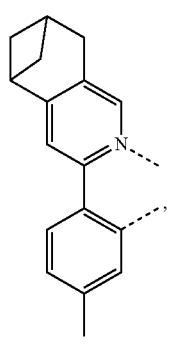 L_{B305}
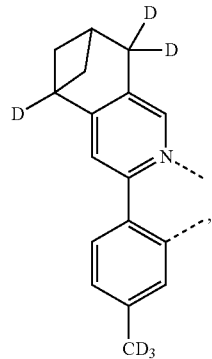 L_{B306}
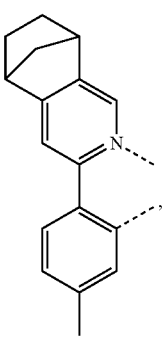 L_{B307}
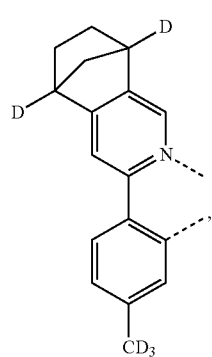 L_{B308}
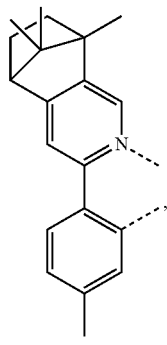 L_{B309}

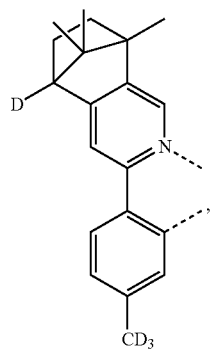
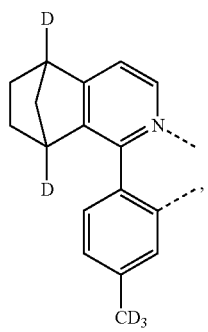

| | | |
|---|---|---|
| 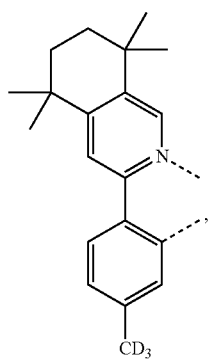 | L<sub>B318</sub> | 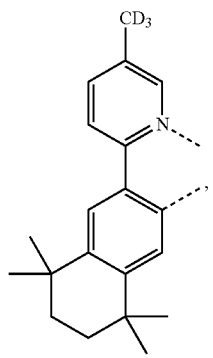 L<sub>B322</sub> |
| 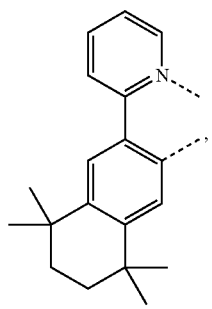 | L<sub>B319</sub> | 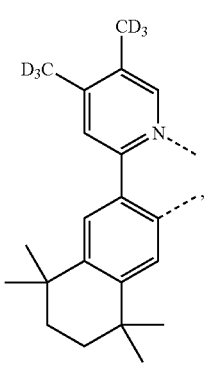 L<sub>B323</sub> |
| 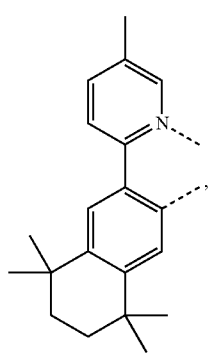 | L<sub>B320</sub> | 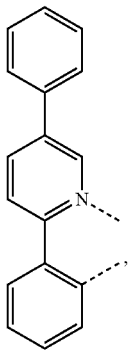 L<sub>B324</sub> |
| 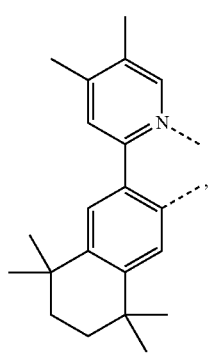 | L<sub>B321</sub> | 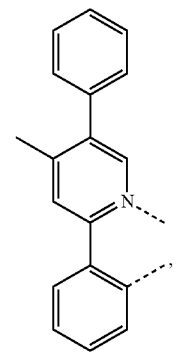 L<sub>B325</sub> |

L<sub>B326</sub>
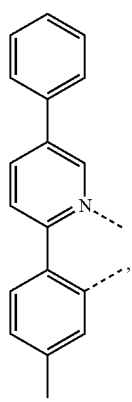
L<sub>B327</sub>
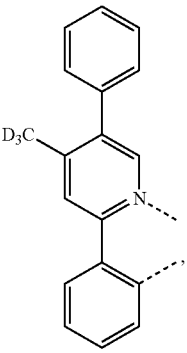
L<sub>B328</sub>
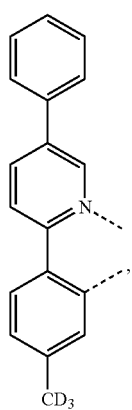
L<sub>B329</sub>
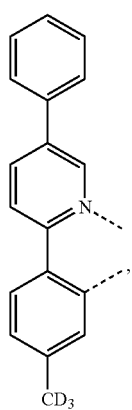
L<sub>B330</sub>
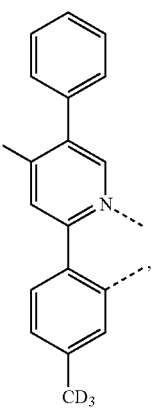
L<sub>B331</sub>
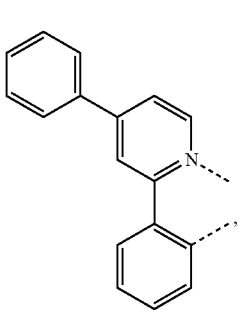
L<sub>B332</sub>
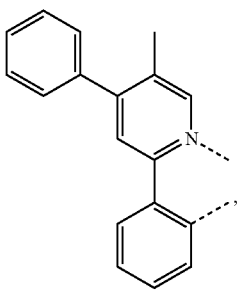
L<sub>B333</sub>
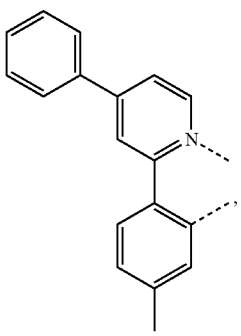

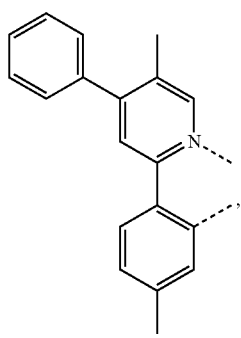 L<sub>B334</sub>
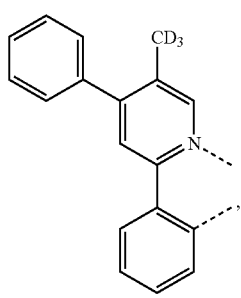 L$_{B335}$
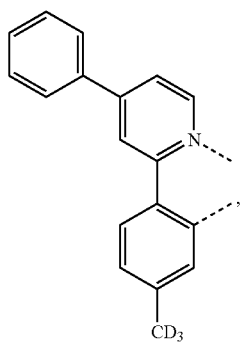 L$_{B336}$
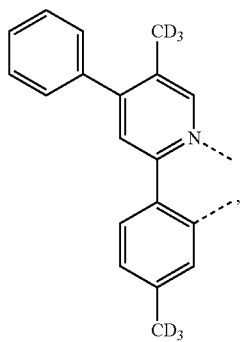 L$_{B337}$
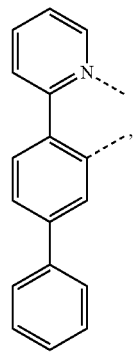 L$_{B338}$
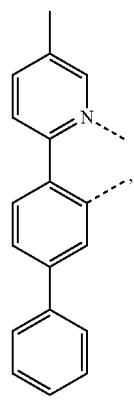 L$_{B339}$
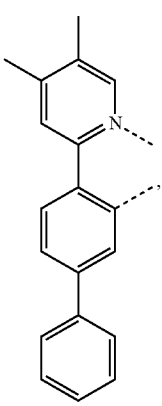 L$_{B340}$
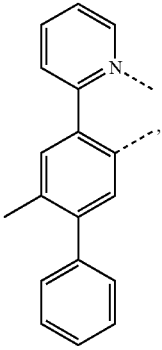 L$_{B341}$ L<sub>B342</sub>
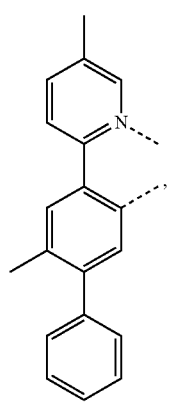
L<sub>B343</sub>
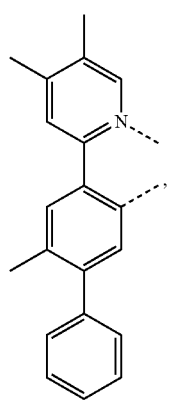
L<sub>B344</sub>
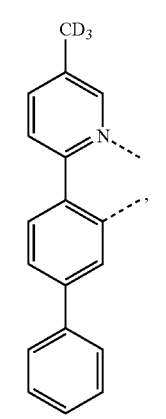
L<sub>B345</sub>
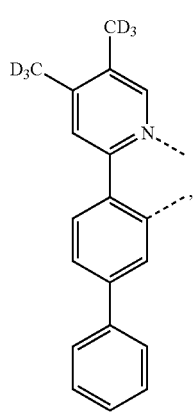
L<sub>B346</sub>
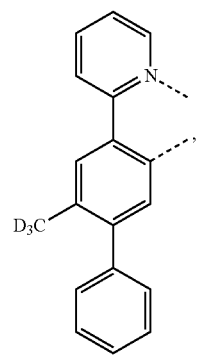
L<sub>B347</sub>
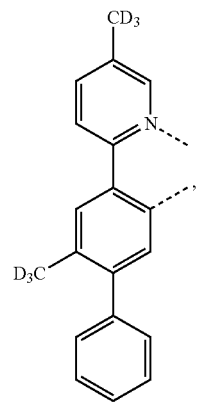
L<sub>B348</sub>
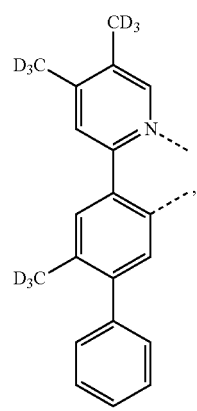
L<sub>B349</sub>
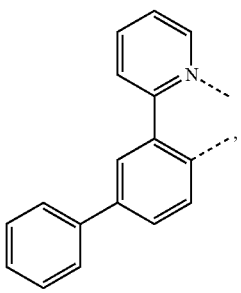

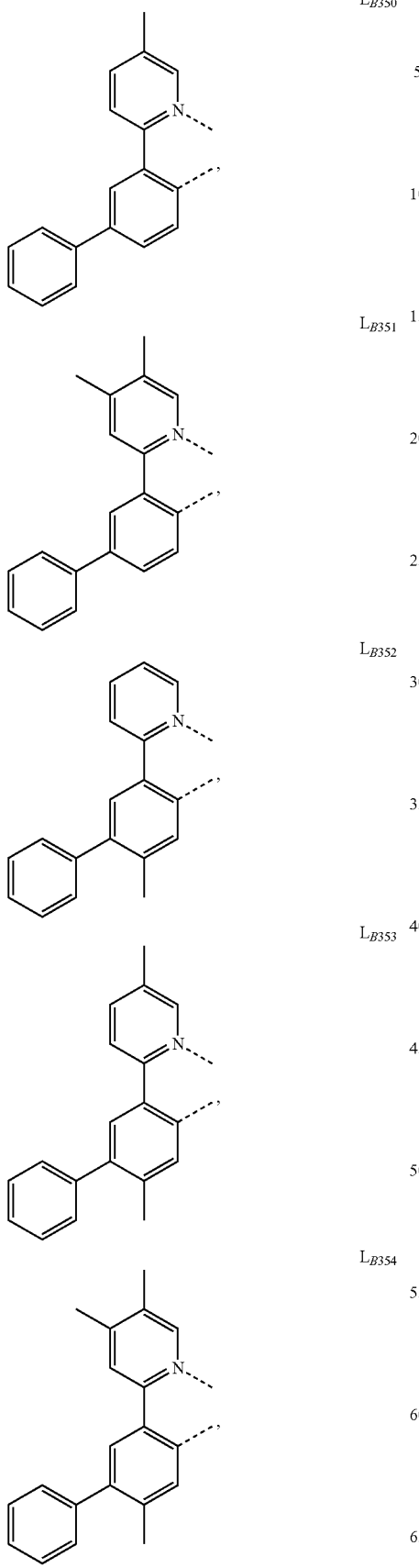
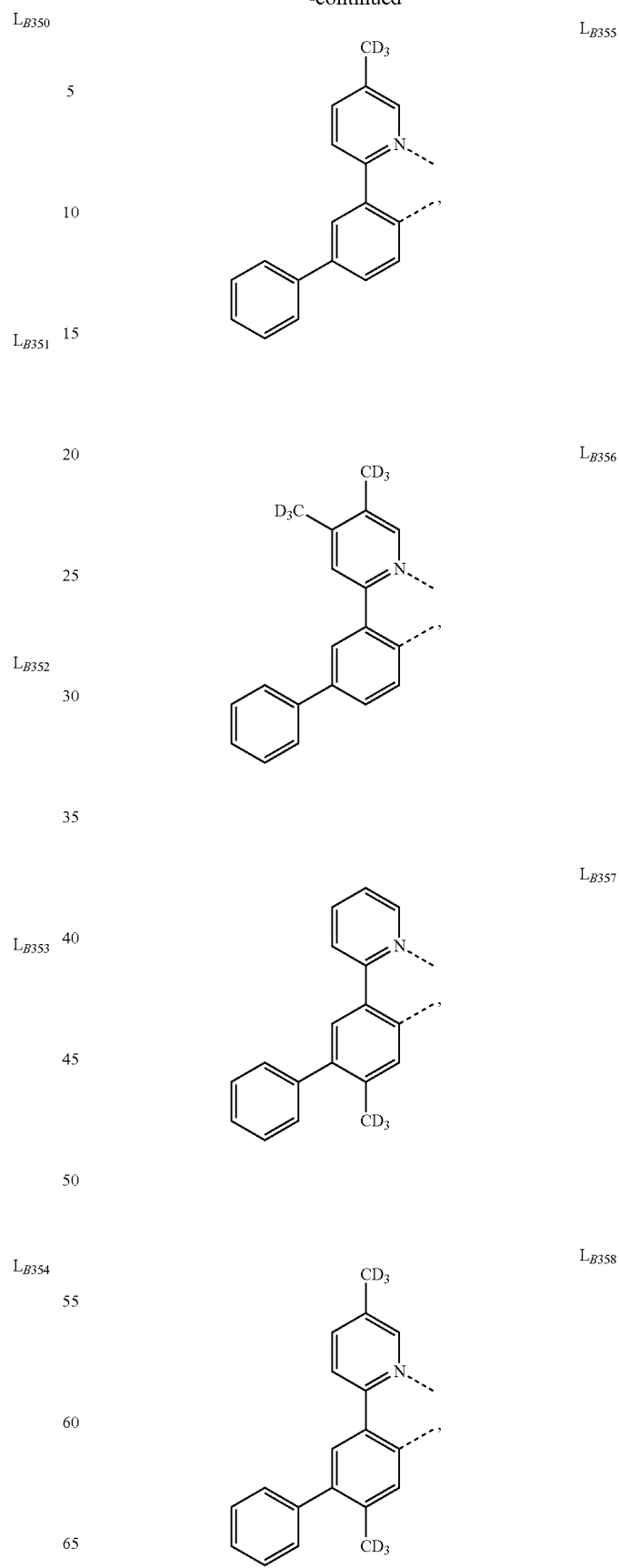

L$_{B359}$ 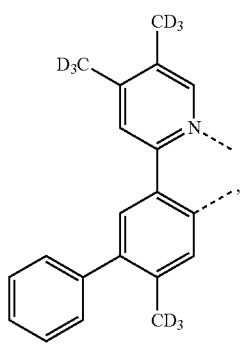
L$_{B360}$
L$_{B361}$
L$_{B362}$
L$_{B363}$
L$_{B364}$ 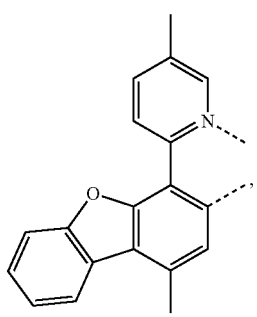
L$_{B365}$ 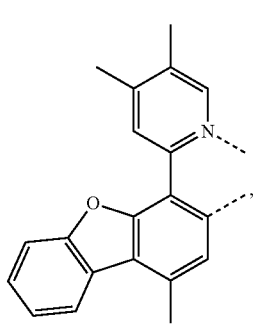
L$_{B366}$ 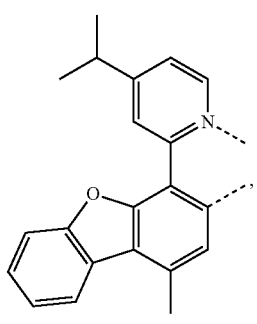
L$_{B367}$ 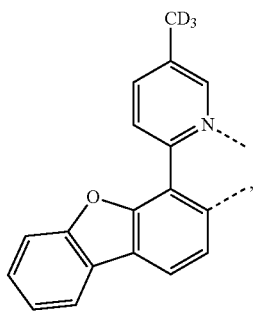
L$_{B368}$ 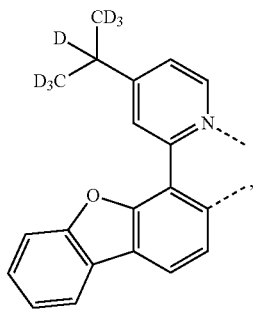

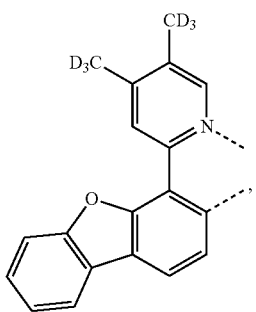
L<sub>B369</sub>
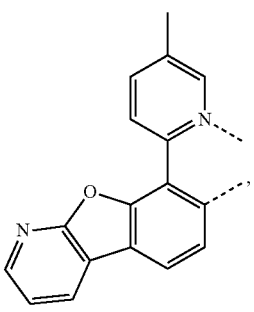
L<sub>B374</sub>
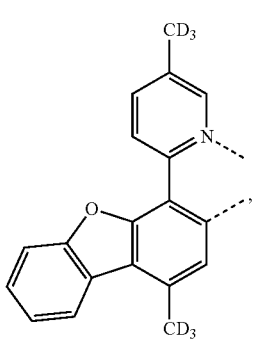
L<sub>B370</sub>
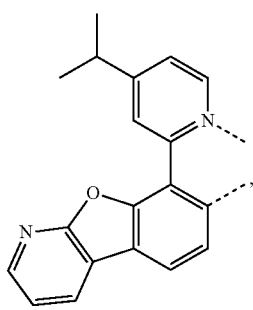
L<sub>B375</sub>
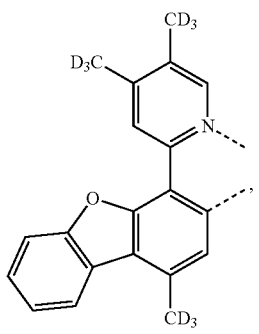
L<sub>B371</sub>
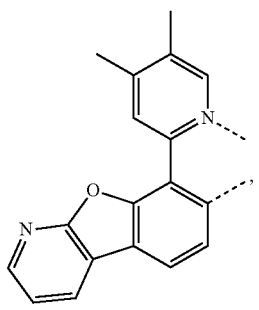
L<sub>B376</sub>
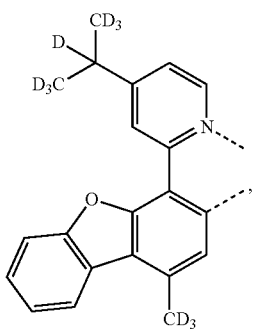
L<sub>B372</sub>
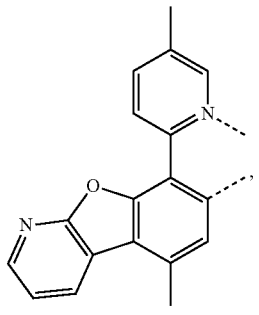
L<sub>B377</sub>
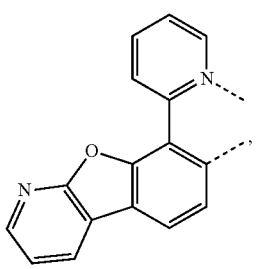
L<sub>B373</sub>
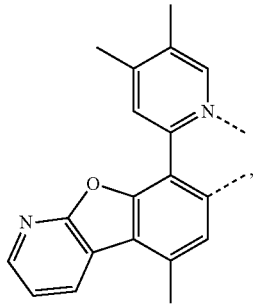
L<sub>B378</sub>

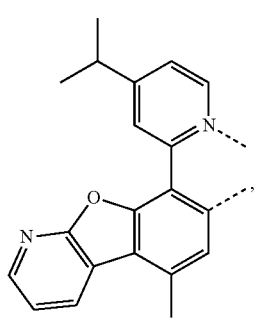
L<sub>B</sub>379
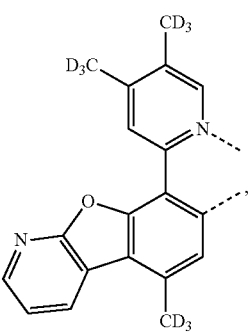
L<sub>B</sub>384
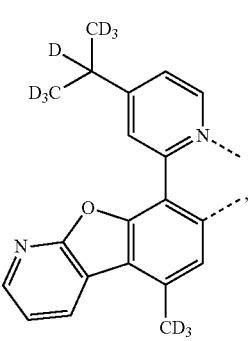
L<sub>B</sub>385
L<sub>B</sub>380
L<sub>B</sub>381
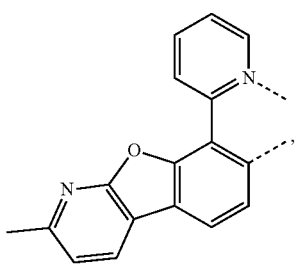
L<sub>B</sub>386
L<sub>B</sub>382
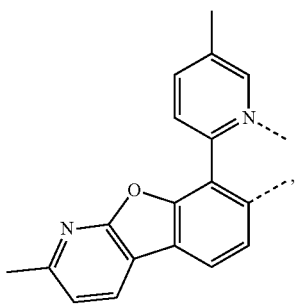
L<sub>B</sub>387
L<sub>B</sub>383
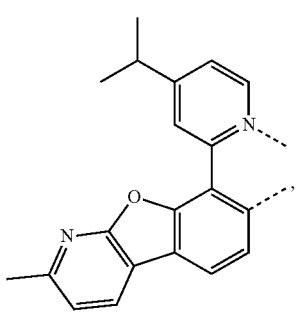
L<sub>B</sub>388

L<sub>B389</sub>
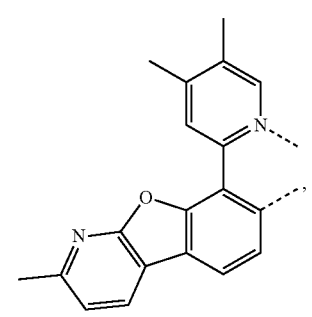
L<sub>B390</sub>
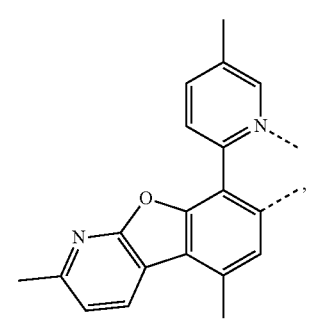
L<sub>B391</sub>
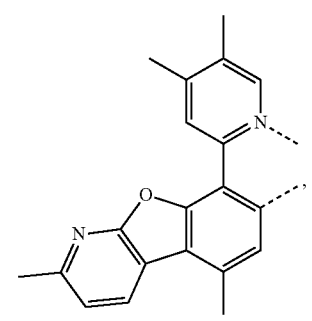
L<sub>B392</sub>
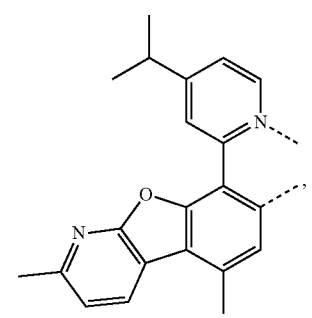
L<sub>B393</sub>
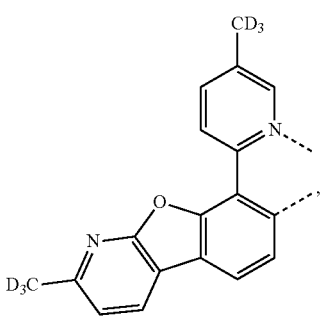
L<sub>B394</sub>
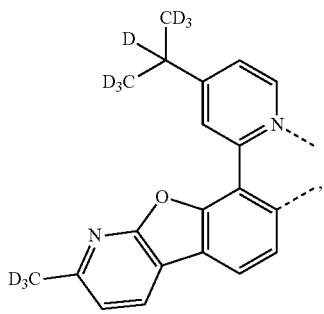
L<sub>B395</sub>
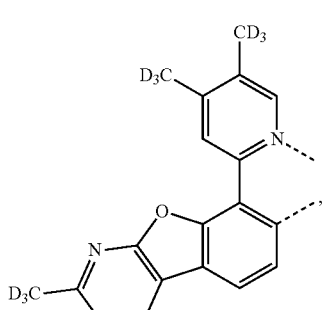
L<sub>B396</sub>
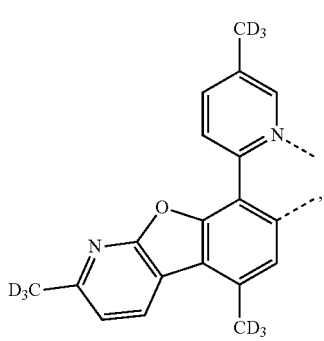
L<sub>B397</sub>
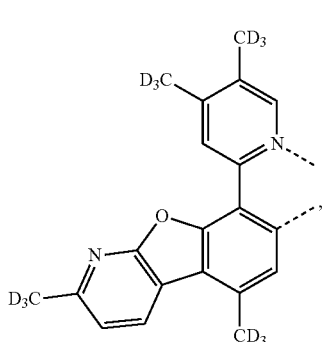
L<sub>B398</sub>
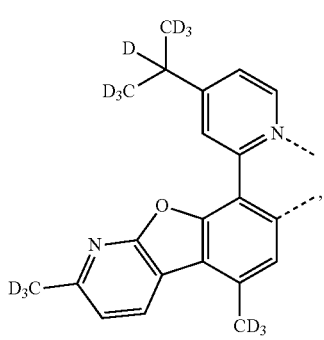

L<sub>B399</sub>
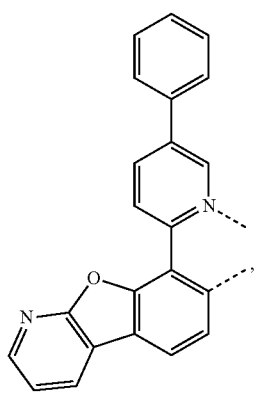
L<sub>B400</sub>
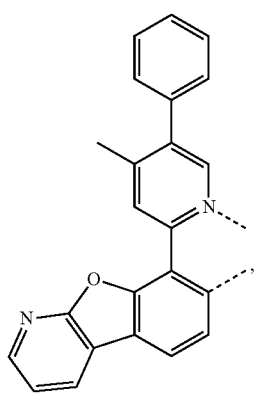
L<sub>B401</sub>
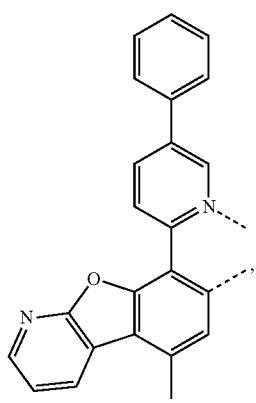
L<sub>B402</sub>
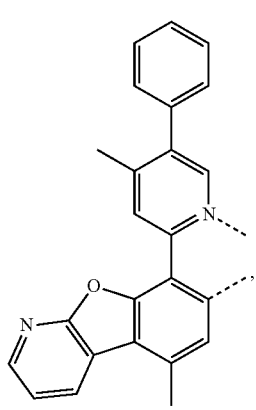
L<sub>B403</sub>
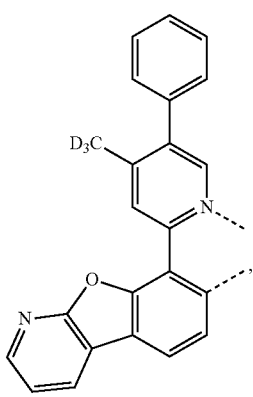
L<sub>B404</sub>
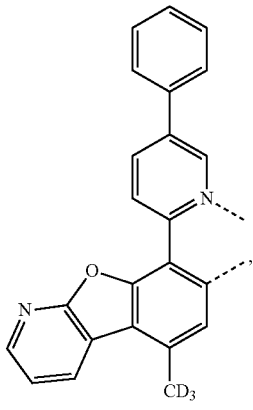
L<sub>B405</sub>
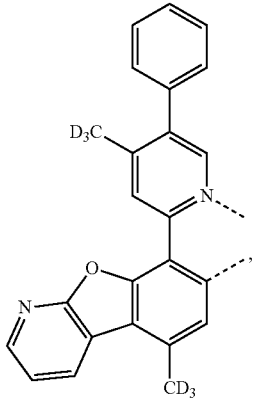
L<sub>B406</sub>
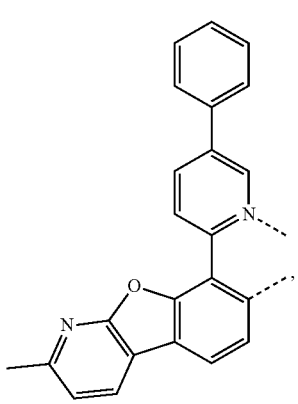

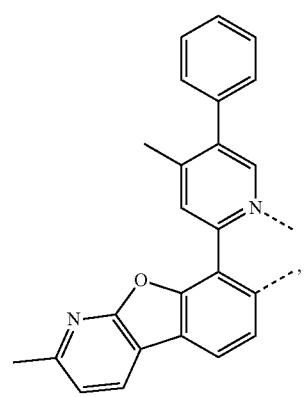
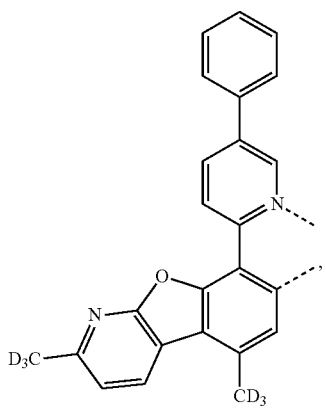
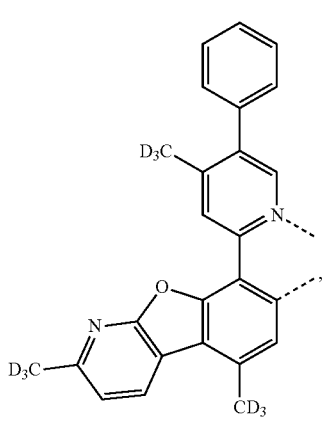
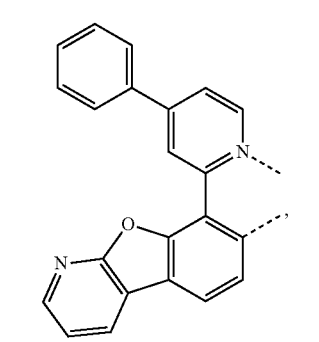
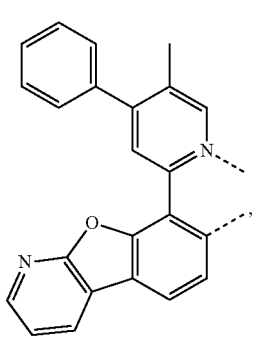

L<sub>B415</sub>
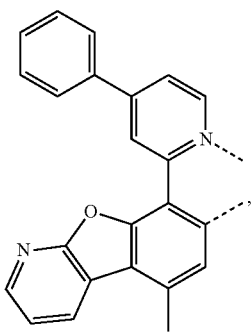
L<sub>B416</sub>
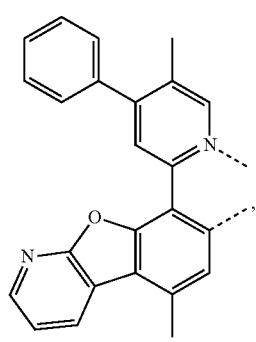
L<sub>B417</sub>
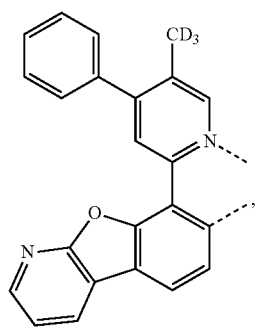
L<sub>B418</sub>
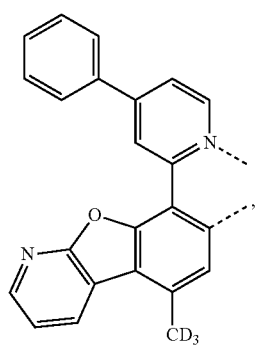
L<sub>B419</sub>
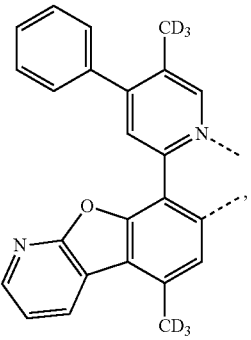
L<sub>B420</sub>
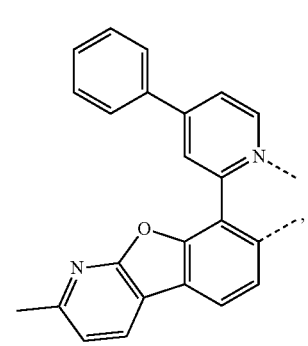
L<sub>B421</sub>
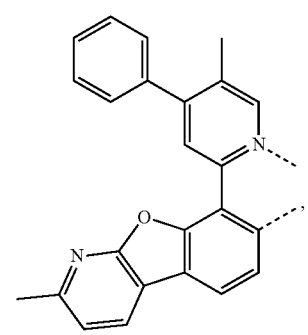
L<sub>B422</sub>
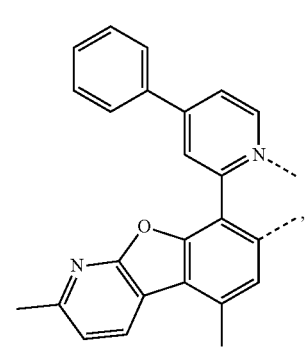

L<sub>B423</sub>
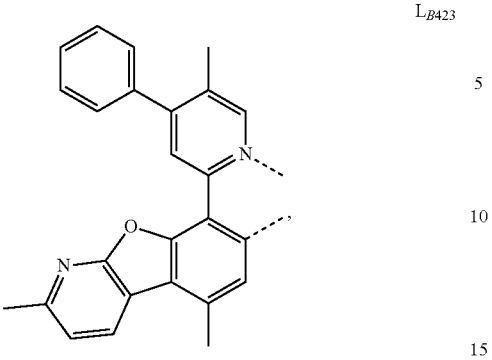
L<sub>B424</sub>
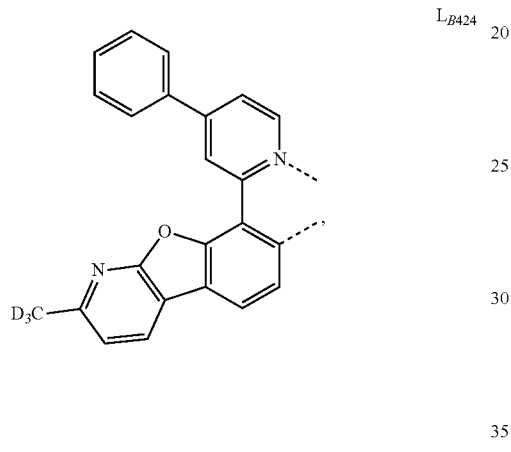
L<sub>B425</sub>
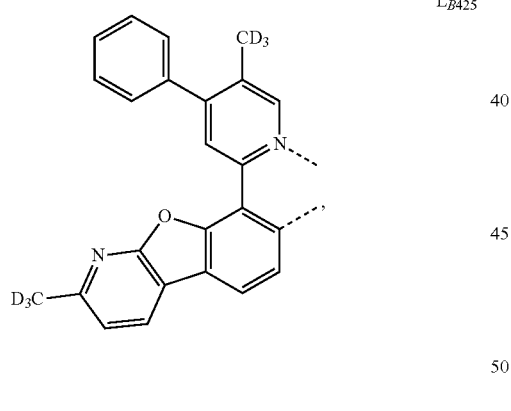
L<sub>B426</sub>
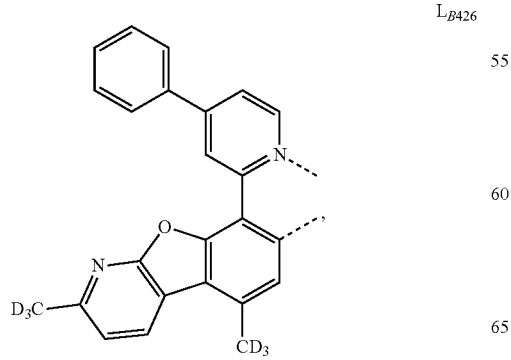
L<sub>B427</sub>
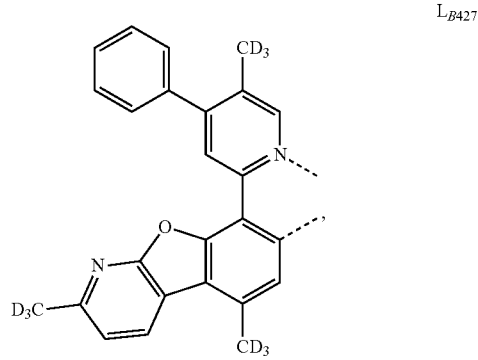
L<sub>B428</sub>
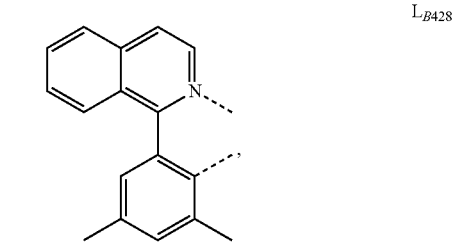
L<sub>B429</sub>
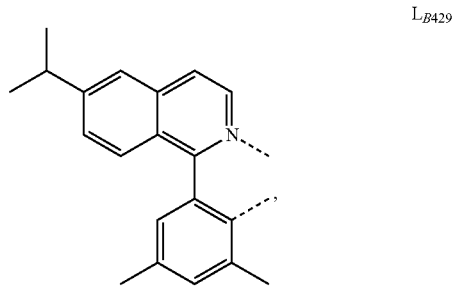
L<sub>B430</sub>
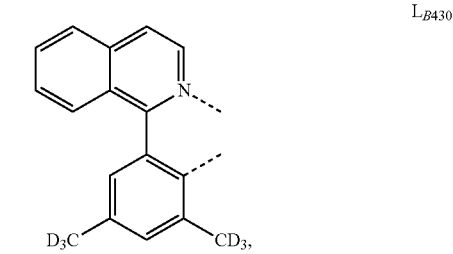
L<sub>B431</sub>
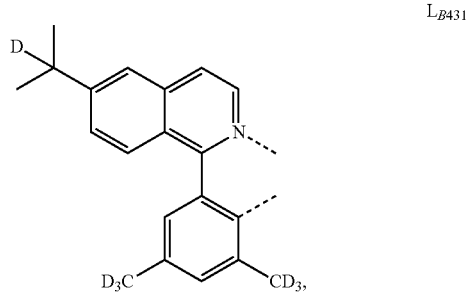

$L_{B432}$ $L_{B433}$ $L_{B434}$ $L_{B435}$ $L_{B436}$ $L_{B437}$ $L_{B438}$ $L_{B439}$ $L_{B440}$ $L_{B441}$

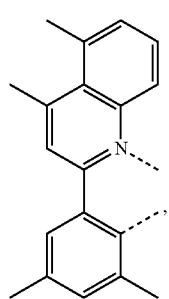 L_{B442}
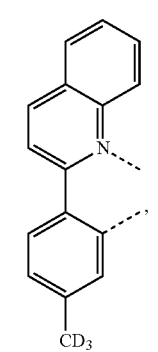 L_{B443}
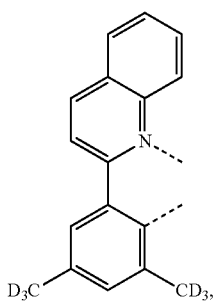 L_{B444}
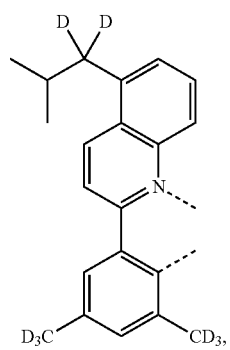 L_{B445}
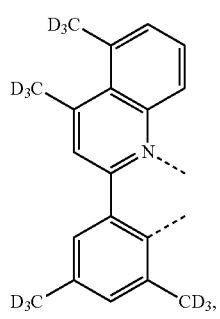 L_{B446}
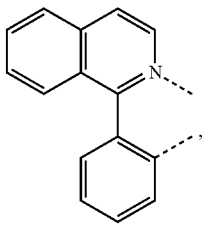 L_{B447}
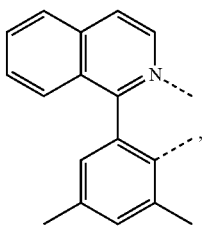 L_{B448}
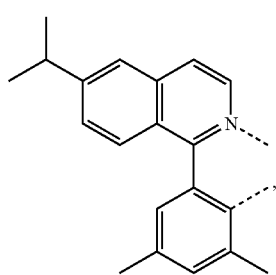 L_{B449}
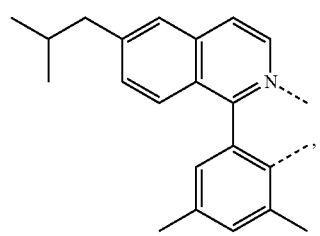 L_{B450}
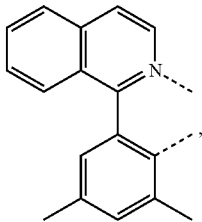 L_{B451}
L_{B452}

L_{B453}
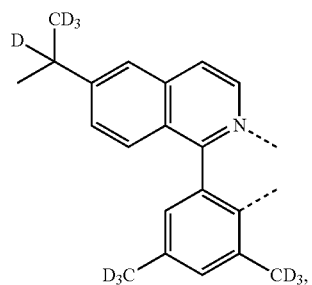
L_{B454}
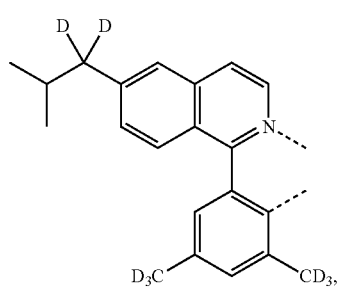
L_{B455}
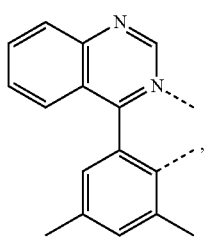
L_{B456}
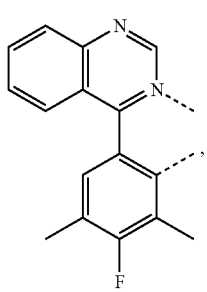
L_{B457}
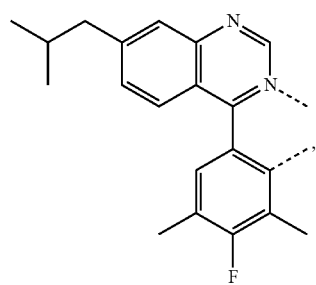
L_{B458}
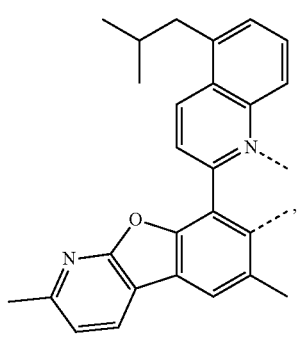
L_{B459}
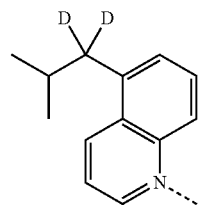
L_{B460}
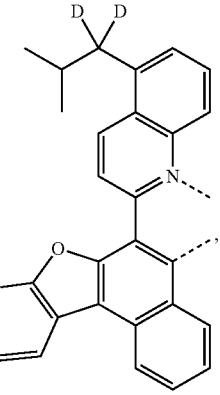
L_{B461}
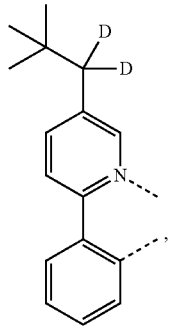

L*B*462
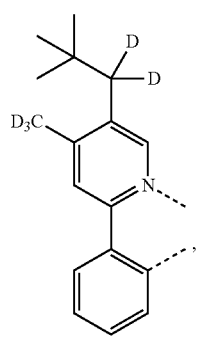
L*B*463
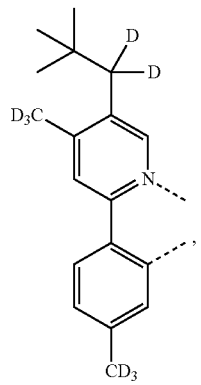
L*B*464
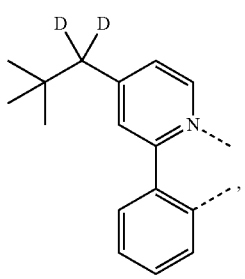
L*B*465
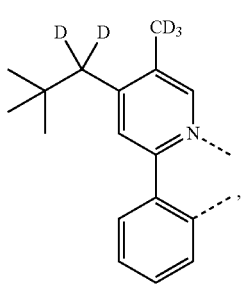
L*B*466
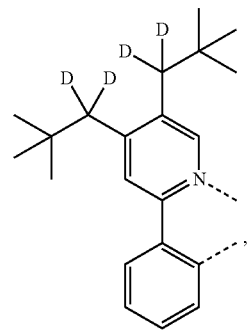
L*B*467
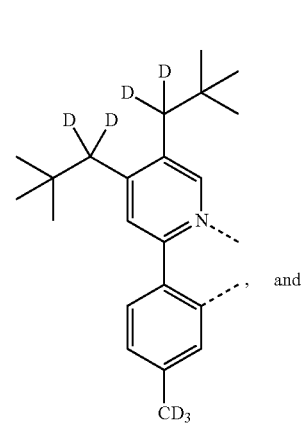
, and
L*B*468
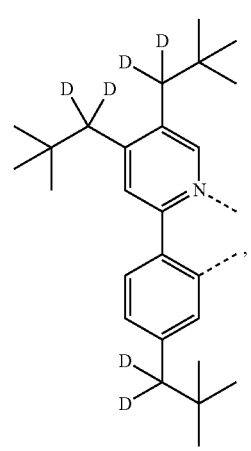
and
L*C* is selected from the group consisting of L*C*1 through L*C*1260 based on a structure of Formula X
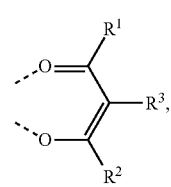

wherein for each of the ligands $L_{C1}$ through $L_{C1260}$, $R^1$, $R^2$, and $R^3$ are defined in LIST 4 below:

| Ligand | $R^1$ | $R^2$ | $R^3$ | Ligand | $R^1$ | $R^2$ | $R^3$ | Ligand | $R^1$ | $R^2$ | $R^3$ |
|---|---|---|---|---|---|---|---|---|---|---|---|
| $L_{C1}$ | $R^{D1}$ | $R^{D1}$ | H | $L_{C421}$ | $R^{D26}$ | $R^{D21}$ | H | $L_{C841}$ | $R^{D7}$ | $R^{D14}$ | $R^{D1}$ |
| $L_{C2}$ | $R^{D2}$ | $R^{D2}$ | H | $L_{C422}$ | $R^{D26}$ | $R^{D23}$ | H | $L_{C842}$ | $R^{D7}$ | $R^{D15}$ | $R^{D1}$ |
| $L_{C3}$ | $R^{D3}$ | $R^{D3}$ | H | $L_{C423}$ | $R^{D26}$ | $R^{D24}$ | H | $L_{C843}$ | $R^{D7}$ | $R^{D16}$ | $R^{D1}$ |
| $L_{C4}$ | $R^{D4}$ | $R^{D4}$ | H | $L_{C424}$ | $R^{D26}$ | $R^{D25}$ | H | $L_{C844}$ | $R^{D7}$ | $R^{D17}$ | $R^{D1}$ |
| $L_{C5}$ | $R^{D5}$ | $R^{D5}$ | H | $L_{C425}$ | $R^{D26}$ | $R^{D27}$ | H | $L_{C845}$ | $R^{D7}$ | $R^{D18}$ | $R^{D1}$ |
| $L_{C6}$ | $R^{D6}$ | $R^{D6}$ | H | $L_{C426}$ | $R^{D26}$ | $R^{D28}$ | H | $L_{C846}$ | $R^{D7}$ | $R^{D19}$ | $R^{D1}$ |
| $L_{C7}$ | $R^{D7}$ | $R^{D7}$ | H | $L_{C427}$ | $R^{D26}$ | $R^{D29}$ | H | $L_{C847}$ | $R^{D7}$ | $R^{D20}$ | $R^{D1}$ |
| $L_{C8}$ | $R^{D8}$ | $R^{D8}$ | H | $L_{C428}$ | $R^{D26}$ | $R^{D30}$ | H | $L_{C848}$ | $R^{D7}$ | $R^{D21}$ | $R^{D1}$ |
| $L_{C9}$ | $R^{D9}$ | $R^{D9}$ | H | $L_{C429}$ | $R^{D26}$ | $R^{D31}$ | H | $L_{C849}$ | $R^{D7}$ | $R^{D22}$ | $R^{D1}$ |
| $L_{C10}$ | $R^{D10}$ | $R^{D10}$ | H | $L_{C430}$ | $R^{D26}$ | $R^{D32}$ | H | $L_{C850}$ | $R^{D7}$ | $R^{D23}$ | $R^{D1}$ |
| $L_{C11}$ | $R^{D11}$ | $R^{D11}$ | H | $L_{C431}$ | $R^{D26}$ | $R^{D33}$ | H | $L_{C851}$ | $R^{D7}$ | $R^{D24}$ | $R^{D1}$ |
| $L_{C12}$ | $R^{D12}$ | $R^{D12}$ | H | $L_{C432}$ | $R^{D26}$ | $R^{D34}$ | H | $L_{C852}$ | $R^{D7}$ | $R^{D25}$ | $R^{D1}$ |
| $L_{C13}$ | $R^{D13}$ | $R^{D13}$ | H | $L_{C433}$ | $R^{D26}$ | $R^{D35}$ | H | $L_{C853}$ | $R^{D7}$ | $R^{D26}$ | $R^{D1}$ |
| $L_{C14}$ | $R^{D14}$ | $R^{D14}$ | H | $L_{C434}$ | $R^{D26}$ | $R^{D40}$ | H | $L_{C854}$ | $R^{D7}$ | $R^{D27}$ | $R^{D1}$ |
| $L_{C15}$ | $R^{D15}$ | $R^{D15}$ | H | $L_{C435}$ | $R^{D26}$ | $R^{D41}$ | H | $L_{C855}$ | $R^{D7}$ | $R^{D28}$ | $R^{D1}$ |
| $L_{C16}$ | $R^{D16}$ | $R^{D16}$ | H | $L_{C436}$ | $R^{D26}$ | $R^{D42}$ | H | $L_{C856}$ | $R^{D7}$ | $R^{D29}$ | $R^{D1}$ |
| $L_{C17}$ | $R^{D17}$ | $R^{D17}$ | H | $L_{C437}$ | $R^{D26}$ | $R^{D64}$ | H | $L_{C857}$ | $R^{D7}$ | $R^{D30}$ | $R^{D1}$ |
| $L_{C18}$ | $R^{D18}$ | $R^{D18}$ | H | $L_{C438}$ | $R^{D26}$ | $R^{D66}$ | H | $L_{C858}$ | $R^{D7}$ | $R^{D31}$ | $R^{D1}$ |
| $L_{C19}$ | $R^{D19}$ | $R^{D19}$ | H | $L_{C439}$ | $R^{D26}$ | $R^{D68}$ | H | $L_{C859}$ | $R^{D7}$ | $R^{D32}$ | $R^{D1}$ |
| $L_{C20}$ | $R^{D20}$ | $R^{D20}$ | H | $L_{C440}$ | $R^{D26}$ | $R^{D76}$ | H | $L_{C860}$ | $R^{D7}$ | $R^{D33}$ | $R^{D1}$ |
| $L_{C21}$ | $R^{D21}$ | $R^{D21}$ | H | $L_{C441}$ | $R^{D35}$ | $R^{D5}$ | H | $L_{C861}$ | $R^{D7}$ | $R^{D34}$ | $R^{D1}$ |
| $L_{C22}$ | $R^{D22}$ | $R^{D22}$ | H | $L_{C442}$ | $R^{D35}$ | $R^{D6}$ | H | $L_{C862}$ | $R^{D7}$ | $R^{D35}$ | $R^{D1}$ |
| $L_{C23}$ | $R^{D23}$ | $R^{D23}$ | H | $L_{C443}$ | $R^{D35}$ | $R^{D9}$ | H | $L_{C863}$ | $R^{D7}$ | $R^{D40}$ | $R^{D1}$ |
| $L_{C24}$ | $R^{D24}$ | $R^{D24}$ | H | $L_{C444}$ | $R^{D35}$ | $R^{D10}$ | H | $L_{C864}$ | $R^{D7}$ | $R^{D41}$ | $R^{D1}$ |
| $L_{C25}$ | $R^{D25}$ | $R^{D25}$ | H | $L_{C445}$ | $R^{D35}$ | $R^{D12}$ | H | $L_{C865}$ | $R^{D7}$ | $R^{D42}$ | $R^{D1}$ |
| $L_{C26}$ | $R^{D26}$ | $R^{D26}$ | H | $L_{C446}$ | $R^{D35}$ | $R^{D15}$ | H | $L_{C866}$ | $R^{D7}$ | $R^{D64}$ | $R^{D1}$ |
| $L_{C27}$ | $R^{D27}$ | $R^{D27}$ | H | $L_{C447}$ | $R^{D35}$ | $R^{D16}$ | H | $L_{C867}$ | $R^{D7}$ | $R^{D66}$ | $R^{D1}$ |
| $L_{C28}$ | $R^{D28}$ | $R^{D28}$ | H | $L_{C448}$ | $R^{D35}$ | $R^{D17}$ | H | $L_{C868}$ | $R^{D7}$ | $R^{D68}$ | $R^{D1}$ |
| $L_{C29}$ | $R^{D29}$ | $R^{D29}$ | H | $L_{C449}$ | $R^{D35}$ | $R^{D18}$ | H | $L_{C869}$ | $R^{D7}$ | $R^{D76}$ | $R^{D1}$ |
| $L_{C30}$ | $R^{D30}$ | $R^{D30}$ | H | $L_{C450}$ | $R^{D35}$ | $R^{D19}$ | H | $L_{C870}$ | $R^{D8}$ | $R^{D5}$ | $R^{D1}$ |
| $L_{C31}$ | $R^{D31}$ | $R^{D31}$ | H | $L_{C451}$ | $R^{D35}$ | $R^{D20}$ | H | $L_{C871}$ | $R^{D8}$ | $R^{D6}$ | $R^{D1}$ |
| $L_{C32}$ | $R^{D32}$ | $R^{D32}$ | H | $L_{C452}$ | $R^{D35}$ | $R^{D21}$ | H | $L_{C872}$ | $R^{D8}$ | $R^{D9}$ | $R^{D1}$ |
| $L_{C33}$ | $R^{D33}$ | $R^{D33}$ | H | $L_{C453}$ | $R^{D35}$ | $R^{D23}$ | H | $L_{C873}$ | $R^{D8}$ | $R^{D10}$ | $R^{D1}$ |
| $L_{C34}$ | $R^{D34}$ | $R^{D34}$ | H | $L_{C454}$ | $R^{D35}$ | $R^{D24}$ | H | $L_{C874}$ | $R^{D8}$ | $R^{D11}$ | $R^{D1}$ |
| $L_{C35}$ | $R^{D35}$ | $R^{D35}$ | H | $L_{C455}$ | $R^{D35}$ | $R^{D25}$ | H | $L_{C875}$ | $R^{D8}$ | $R^{D12}$ | $R^{D1}$ |
| $L_{C36}$ | $R^{D40}$ | $R^{D40}$ | H | $L_{C456}$ | $R^{D35}$ | $R^{D27}$ | H | $L_{C876}$ | $R^{D8}$ | $R^{D13}$ | $R^{D1}$ |
| $L_{C37}$ | $R^{D41}$ | $R^{D41}$ | H | $L_{C457}$ | $R^{D35}$ | $R^{D28}$ | H | $L_{C877}$ | $R^{D8}$ | $R^{D14}$ | $R^{D1}$ |
| $L_{C38}$ | $R^{D42}$ | $R^{D42}$ | H | $L_{C458}$ | $R^{D35}$ | $R^{D29}$ | H | $L_{C878}$ | $R^{D8}$ | $R^{D15}$ | $R^{D1}$ |
| $L_{C39}$ | $R^{D64}$ | $R^{D64}$ | H | $L_{C459}$ | $R^{D35}$ | $R^{D30}$ | H | $L_{C879}$ | $R^{D8}$ | $R^{D16}$ | $R^{D1}$ |
| $L_{C40}$ | $R^{D66}$ | $R^{D66}$ | H | $L_{C460}$ | $R^{D35}$ | $R^{D31}$ | H | $L_{C880}$ | $R^{D8}$ | $R^{D17}$ | $R^{D1}$ |
| $L_{C41}$ | $R^{D68}$ | $R^{D68}$ | H | $L_{C461}$ | $R^{D35}$ | $R^{D32}$ | H | $L_{C881}$ | $R^{D8}$ | $R^{D18}$ | $R^{D1}$ |
| $L_{C42}$ | $R^{D76}$ | $R^{D76}$ | H | $L_{C462}$ | $R^{D35}$ | $R^{D33}$ | H | $L_{C882}$ | $R^{D8}$ | $R^{D19}$ | $R^{D1}$ |
| $L_{C43}$ | $R^{D1}$ | $R^{D2}$ | H | $L_{C463}$ | $R^{D35}$ | $R^{D34}$ | H | $L_{C883}$ | $R^{D8}$ | $R^{D20}$ | $R^{D1}$ |
| $L_{C44}$ | $R^{D1}$ | $R^{D3}$ | H | $L_{C464}$ | $R^{D35}$ | $R^{D40}$ | H | $L_{C884}$ | $R^{D8}$ | $R^{D21}$ | $R^{D1}$ |
| $L_{C45}$ | $R^{D1}$ | $R^{D4}$ | H | $L_{C465}$ | $R^{D35}$ | $R^{D41}$ | H | $L_{C885}$ | $R^{D8}$ | $R^{D22}$ | $R^{D1}$ |
| $L_{C46}$ | $R^{D1}$ | $R^{D5}$ | H | $L_{C466}$ | $R^{D35}$ | $R^{D42}$ | H | $L_{C886}$ | $R^{D8}$ | $R^{D23}$ | $R^{D1}$ |
| $L_{C47}$ | $R^{D1}$ | $R^{D6}$ | H | $L_{C467}$ | $R^{D35}$ | $R^{D64}$ | H | $L_{C887}$ | $R^{D8}$ | $R^{D24}$ | $R^{D1}$ |
| $L_{C48}$ | $R^{D1}$ | $R^{D7}$ | H | $L_{C468}$ | $R^{D35}$ | $R^{D66}$ | H | $L_{C888}$ | $R^{D8}$ | $R^{D25}$ | $R^{D1}$ |
| $L_{C49}$ | $R^{D1}$ | $R^{D8}$ | H | $L_{C469}$ | $R^{D35}$ | $R^{D68}$ | H | $L_{C889}$ | $R^{D8}$ | $R^{D26}$ | $R^{D1}$ |
| $L_{C50}$ | $R^{D1}$ | $R^{D9}$ | H | $L_{C470}$ | $R^{D35}$ | $R^{D76}$ | H | $L_{C890}$ | $R^{D8}$ | $R^{D27}$ | $R^{D1}$ |
| $L_{C51}$ | $R^{D1}$ | $R^{D10}$ | H | $L_{C471}$ | $R^{D40}$ | $R^{D5}$ | H | $L_{C891}$ | $R^{D8}$ | $R^{D28}$ | $R^{D1}$ |
| $L_{C52}$ | $R^{D1}$ | $R^{D11}$ | H | $L_{C472}$ | $R^{D40}$ | $R^{D6}$ | H | $L_{C892}$ | $R^{D8}$ | $R^{D29}$ | $R^{D1}$ |
| $L_{C53}$ | $R^{D1}$ | $R^{D12}$ | H | $L_{C473}$ | $R^{D40}$ | $R^{D9}$ | H | $L_{C893}$ | $R^{D8}$ | $R^{D30}$ | $R^{D1}$ |
| $L_{C54}$ | $R^{D1}$ | $R^{D13}$ | H | $L_{C474}$ | $R^{D40}$ | $R^{D10}$ | H | $L_{C894}$ | $R^{D8}$ | $R^{D31}$ | $R^{D1}$ |
| $L_{C55}$ | $R^{D1}$ | $R^{D14}$ | H | $L_{C475}$ | $R^{D40}$ | $R^{D12}$ | H | $L_{C895}$ | $R^{D8}$ | $R^{D32}$ | $R^{D1}$ |
| $L_{C56}$ | $R^{D1}$ | $R^{D15}$ | H | $L_{C476}$ | $R^{D40}$ | $R^{D15}$ | H | $L_{C896}$ | $R^{D8}$ | $R^{D33}$ | $R^{D1}$ |
| $L_{C57}$ | $R^{D1}$ | $R^{D16}$ | H | $L_{C477}$ | $R^{D40}$ | $R^{D16}$ | H | $L_{C897}$ | $R^{D8}$ | $R^{D34}$ | $R^{D1}$ |
| $L_{C58}$ | $R^{D1}$ | $R^{D17}$ | H | $L_{C478}$ | $R^{D40}$ | $R^{D17}$ | H | $L_{C898}$ | $R^{D8}$ | $R^{D35}$ | $R^{D1}$ |
| $L_{C59}$ | $R^{D1}$ | $R^{D18}$ | H | $L_{C479}$ | $R^{D40}$ | $R^{D18}$ | H | $L_{C899}$ | $R^{D8}$ | $R^{D40}$ | $R^{D1}$ |
| $L_{C60}$ | $R^{D1}$ | $R^{D19}$ | H | $L_{C480}$ | $R^{D40}$ | $R^{D19}$ | H | $L_{C900}$ | $R^{D8}$ | $R^{D41}$ | $R^{D1}$ |
| $L_{C61}$ | $R^{D1}$ | $R^{D20}$ | H | $L_{C481}$ | $R^{D40}$ | $R^{D20}$ | H | $L_{C901}$ | $R^{D8}$ | $R^{D42}$ | $R^{D1}$ |
| $L_{C62}$ | $R^{D1}$ | $R^{D21}$ | H | $L_{C482}$ | $R^{D40}$ | $R^{D21}$ | H | $L_{C902}$ | $R^{D8}$ | $R^{D64}$ | $R^{D1}$ |
| $L_{C63}$ | $R^{D1}$ | $R^{D22}$ | H | $L_{C483}$ | $R^{D40}$ | $R^{D23}$ | H | $L_{C903}$ | $R^{D8}$ | $R^{D66}$ | $R^{D1}$ |
| $L_{C64}$ | $R^{D1}$ | $R^{D23}$ | H | $L_{C484}$ | $R^{D40}$ | $R^{D24}$ | H | $L_{C904}$ | $R^{D8}$ | $R^{D68}$ | $R^{D1}$ |
| $L_{C65}$ | $R^{D1}$ | $R^{D24}$ | H | $L_{C485}$ | $R^{D40}$ | $R^{D25}$ | H | $L_{C905}$ | $R^{D8}$ | $R^{D76}$ | $R^{D1}$ |
| $L_{C66}$ | $R^{D1}$ | $R^{D25}$ | H | $L_{C486}$ | $R^{D40}$ | $R^{D27}$ | H | $L_{C906}$ | $R^{D11}$ | $R^{D5}$ | $R^{D1}$ |
| $L_{C67}$ | $R^{D1}$ | $R^{D26}$ | H | $L_{C487}$ | $R^{D40}$ | $R^{D28}$ | H | $L_{C907}$ | $R^{D11}$ | $R^{D6}$ | $R^{D1}$ |
| $L_{C68}$ | $R^{D1}$ | $R^{D27}$ | H | $L_{C488}$ | $R^{D40}$ | $R^{D29}$ | H | $L_{C908}$ | $R^{D11}$ | $R^{D9}$ | $R^{D1}$ |
| $L_{C69}$ | $R^{D1}$ | $R^{D28}$ | H | $L_{C489}$ | $R^{D40}$ | $R^{D30}$ | H | $L_{C909}$ | $R^{D11}$ | $R^{D10}$ | $R^{D1}$ |
| $L_{C70}$ | $R^{D1}$ | $R^{D29}$ | H | $L_{C490}$ | $R^{D40}$ | $R^{D31}$ | H | $L_{C910}$ | $R^{D11}$ | $R^{D12}$ | $R^{D1}$ |
| $L_{C71}$ | $R^{D1}$ | $R^{D30}$ | H | $L_{C491}$ | $R^{D40}$ | $R^{D32}$ | H | $L_{C911}$ | $R^{D11}$ | $R^{D13}$ | $R^{D1}$ |
| $L_{C72}$ | $R^{D1}$ | $R^{D31}$ | H | $L_{C492}$ | $R^{D40}$ | $R^{D33}$ | H | $L_{C912}$ | $R^{D11}$ | $R^{D14}$ | $R^{D1}$ |
| $L_{C73}$ | $R^{D1}$ | $R^{D32}$ | H | $L_{C493}$ | $R^{D40}$ | $R^{D34}$ | H | $L_{C913}$ | $R^{D11}$ | $R^{D15}$ | $R^{D1}$ |
| $L_{C74}$ | $R^{D1}$ | $R^{D33}$ | H | $L_{C494}$ | $R^{D40}$ | $R^{D41}$ | H | $L_{C914}$ | $R^{D11}$ | $R^{D16}$ | $R^{D1}$ |
| $L_{C75}$ | $R^{D1}$ | $R^{D34}$ | H | $L_{C495}$ | $R^{D40}$ | $R^{D42}$ | H | $L_{C915}$ | $R^{D11}$ | $R^{D17}$ | $R^{D1}$ |
| $L_{C76}$ | $R^{D1}$ | $R^{D35}$ | H | $L_{C496}$ | $R^{D40}$ | $R^{D64}$ | H | $L_{C916}$ | $R^{D11}$ | $R^{D18}$ | $R^{D1}$ |

| Ligand | $R^1$ | $R^2$ | $R^3$ | Ligand | $R^1$ | $R^2$ | $R^3$ | Ligand | $R^1$ | $R^2$ | $R^3$ |
|---|---|---|---|---|---|---|---|---|---|---|---|
| $L_{C77}$ | $R^{D1}$ | $R^{D40}$ | H | $L_{C497}$ | $R^{D40}$ | $R^{D66}$ | H | $L_{C917}$ | $R^{D11}$ | $R^{D19}$ | $R^{D1}$ |
| $L_{C78}$ | $R^{D1}$ | $R^{D41}$ | H | $L_{C498}$ | $R^{D40}$ | $R^{D68}$ | H | $L_{C918}$ | $R^{D11}$ | $R^{D20}$ | $R^{D1}$ |
| $L_{C79}$ | $R^{D1}$ | $R^{D42}$ | H | $L_{C499}$ | $R^{D40}$ | $R^{D76}$ | H | $L_{C919}$ | $R^{D11}$ | $R^{D21}$ | $R^{D1}$ |
| $L_{C80}$ | $R^{D1}$ | $R^{D64}$ | H | $L_{C500}$ | $R^{D41}$ | $R^{D5}$ | H | $L_{C920}$ | $R^{D11}$ | $R^{D22}$ | $R^{D1}$ |
| $L_{C81}$ | $R^{D1}$ | $R^{D66}$ | H | $L_{C501}$ | $R^{D41}$ | $R^{D6}$ | H | $L_{C921}$ | $R^{D11}$ | $R^{D23}$ | $R^{D1}$ |
| $L_{C82}$ | $R^{D1}$ | $R^{D68}$ | H | $L_{C502}$ | $R^{D41}$ | $R^{D9}$ | H | $L_{C922}$ | $R^{D11}$ | $R^{D24}$ | $R^{D1}$ |
| $L_{C83}$ | $R^{D1}$ | $R^{D76}$ | H | $L_{C503}$ | $R^{D41}$ | $R^{D10}$ | H | $L_{C923}$ | $R^{D11}$ | $R^{D25}$ | $R^{D1}$ |
| $L_{C84}$ | $R^{D2}$ | $R^{D1}$ | H | $L_{C504}$ | $R^{D41}$ | $R^{D12}$ | H | $L_{C924}$ | $R^{D11}$ | $R^{D26}$ | $R^{D1}$ |
| $L_{C85}$ | $R^{D2}$ | $R^{D3}$ | H | $L_{C505}$ | $R^{D41}$ | $R^{D15}$ | H | $L_{C925}$ | $R^{D11}$ | $R^{D27}$ | $R^{D1}$ |
| $L_{C86}$ | $R^{D2}$ | $R^{D4}$ | H | $L_{C506}$ | $R^{D41}$ | $R^{D16}$ | H | $L_{C926}$ | $R^{D11}$ | $R^{D28}$ | $R^{D1}$ |
| $L_{C87}$ | $R^{D2}$ | $R^{D5}$ | H | $L_{C507}$ | $R^{D41}$ | $R^{D17}$ | H | $L_{C927}$ | $R^{D11}$ | $R^{D29}$ | $R^{D1}$ |
| $L_{C88}$ | $R^{D2}$ | $R^{D6}$ | H | $L_{C508}$ | $R^{D41}$ | $R^{D18}$ | H | $L_{C928}$ | $R^{D11}$ | $R^{D30}$ | $R^{D1}$ |
| $L_{C89}$ | $R^{D2}$ | $R^{D7}$ | H | $L_{C509}$ | $R^{D41}$ | $R^{D19}$ | H | $L_{C929}$ | $R^{D11}$ | $R^{D31}$ | $R^{D1}$ |
| $L_{C90}$ | $R^{D2}$ | $R^{D8}$ | H | $L_{C510}$ | $R^{D41}$ | $R^{D20}$ | H | $L_{C930}$ | $R^{D11}$ | $R^{D32}$ | $R^{D1}$ |
| $L_{C91}$ | $R^{D2}$ | $R^{D9}$ | H | $L_{C511}$ | $R^{D41}$ | $R^{D21}$ | H | $L_{C931}$ | $R^{D11}$ | $R^{D33}$ | $R^{D1}$ |
| $L_{C92}$ | $R^{D2}$ | $R^{D10}$ | H | $L_{C512}$ | $R^{D41}$ | $R^{D23}$ | H | $L_{C932}$ | $R^{D11}$ | $R^{D34}$ | $R^{D1}$ |
| $L_{C93}$ | $R^{D2}$ | $R^{D11}$ | H | $L_{C513}$ | $R^{D41}$ | $R^{D24}$ | H | $L_{C933}$ | $R^{D11}$ | $R^{D35}$ | $R^{D1}$ |
| $L_{C94}$ | $R^{D2}$ | $R^{D12}$ | H | $L_{C514}$ | $R^{D41}$ | $R^{D25}$ | H | $L_{C934}$ | $R^{D11}$ | $R^{D40}$ | $R^{D1}$ |
| $L_{C95}$ | $R^{D2}$ | $R^{D13}$ | H | $L_{C515}$ | $R^{D41}$ | $R^{D27}$ | H | $L_{C935}$ | $R^{D11}$ | $R^{D41}$ | $R^{D1}$ |
| $L_{C96}$ | $R^{D2}$ | $R^{D14}$ | H | $L_{C516}$ | $R^{D41}$ | $R^{D28}$ | H | $L_{C936}$ | $R^{D11}$ | $R^{D42}$ | $R^{D1}$ |
| $L_{C97}$ | $R^{D2}$ | $R^{D15}$ | H | $L_{C517}$ | $R^{D41}$ | $R^{D29}$ | H | $L_{C937}$ | $R^{D11}$ | $R^{D64}$ | $R^{D1}$ |
| $L_{C98}$ | $R^{D2}$ | $R^{D16}$ | H | $L_{C518}$ | $R^{D41}$ | $R^{D30}$ | H | $L_{C938}$ | $R^{D11}$ | $R^{D66}$ | $R^{D1}$ |
| $L_{C99}$ | $R^{D2}$ | $R^{D17}$ | H | $L_{C519}$ | $R^{D41}$ | $R^{D31}$ | H | $L_{C939}$ | $R^{D11}$ | $R^{D68}$ | $R^{D1}$ |
| $L_{C100}$ | $R^{D2}$ | $R^{D18}$ | H | $L_{C520}$ | $R^{D41}$ | $R^{D32}$ | H | $L_{C940}$ | $R^{D11}$ | $R^{D76}$ | $R^{D1}$ |
| $L_{C101}$ | $R^{D2}$ | $R^{D19}$ | H | $L_{C521}$ | $R^{D41}$ | $R^{D33}$ | H | $L_{C941}$ | $R^{D13}$ | $R^{D5}$ | $R^{D1}$ |
| $L_{C102}$ | $R^{D2}$ | $R^{D20}$ | H | $L_{C522}$ | $R^{D41}$ | $R^{D34}$ | H | $L_{C942}$ | $R^{D13}$ | $R^{D6}$ | $R^{D1}$ |
| $L_{C103}$ | $R^{D2}$ | $R^{D21}$ | H | $L_{C523}$ | $R^{D41}$ | $R^{D42}$ | H | $L_{C943}$ | $R^{D13}$ | $R^{D9}$ | $R^{D1}$ |
| $L_{C104}$ | $R^{D2}$ | $R^{D22}$ | H | $L_{C524}$ | $R^{D41}$ | $R^{D64}$ | H | $L_{C944}$ | $R^{D13}$ | $R^{D10}$ | $R^{D1}$ |
| $L_{C105}$ | $R^{D2}$ | $R^{D23}$ | H | $L_{C525}$ | $R^{D41}$ | $R^{D66}$ | H | $L_{C945}$ | $R^{D13}$ | $R^{D12}$ | $R^{D1}$ |
| $L_{C106}$ | $R^{D2}$ | $R^{D24}$ | H | $L_{C526}$ | $R^{D41}$ | $R^{D68}$ | H | $L_{C946}$ | $R^{D13}$ | $R^{D14}$ | $R^{D1}$ |
| $L_{C107}$ | $R^{D2}$ | $R^{D25}$ | H | $L_{C527}$ | $R^{D41}$ | $R^{D76}$ | H | $L_{C947}$ | $R^{D13}$ | $R^{D15}$ | $R^{D1}$ |
| $L_{C108}$ | $R^{D2}$ | $R^{D26}$ | H | $L_{C528}$ | $R^{D64}$ | $R^{D5}$ | H | $L_{C948}$ | $R^{D13}$ | $R^{D16}$ | $R^{D1}$ |
| $L_{C109}$ | $R^{D2}$ | $R^{D27}$ | H | $L_{C529}$ | $R^{D64}$ | $R^{D6}$ | H | $L_{C949}$ | $R^{D13}$ | $R^{D17}$ | $R^{D1}$ |
| $L_{C110}$ | $R^{D2}$ | $R^{D28}$ | H | $L_{C530}$ | $R^{D64}$ | $R^{D9}$ | H | $L_{C950}$ | $R^{D13}$ | $R^{D18}$ | $R^{D1}$ |
| $L_{C111}$ | $R^{D2}$ | $R^{D29}$ | H | $L_{C531}$ | $R^{D64}$ | $R^{D10}$ | H | $L_{C951}$ | $R^{D13}$ | $R^{D19}$ | $R^{D1}$ |
| $L_{C112}$ | $R^{D2}$ | $R^{D30}$ | H | $L_{C532}$ | $R^{D64}$ | $R^{D12}$ | H | $L_{C952}$ | $R^{D13}$ | $R^{D20}$ | $R^{D1}$ |
| $L_{C113}$ | $R^{D2}$ | $R^{D31}$ | H | $L_{C533}$ | $R^{D64}$ | $R^{D15}$ | H | $L_{C953}$ | $R^{D13}$ | $R^{D21}$ | $R^{D1}$ |
| $L_{C114}$ | $R^{D2}$ | $R^{D32}$ | H | $L_{C534}$ | $R^{D64}$ | $R^{D16}$ | H | $L_{C954}$ | $R^{D13}$ | $R^{D22}$ | $R^{D1}$ |
| $L_{C115}$ | $R^{D2}$ | $R^{D33}$ | H | $L_{C535}$ | $R^{D64}$ | $R^{D17}$ | H | $L_{C955}$ | $R^{D13}$ | $R^{D23}$ | $R^{D1}$ |
| $L_{C116}$ | $R^{D2}$ | $R^{D34}$ | H | $L_{C536}$ | $R^{D64}$ | $R^{D18}$ | H | $L_{C956}$ | $R^{D13}$ | $R^{D24}$ | $R^{D1}$ |
| $L_{C117}$ | $R^{D2}$ | $R^{D35}$ | H | $L_{C537}$ | $R^{D64}$ | $R^{D19}$ | H | $L_{C957}$ | $R^{D13}$ | $R^{D25}$ | $R^{D1}$ |
| $L_{C118}$ | $R^{D2}$ | $R^{D40}$ | H | $L_{C538}$ | $R^{D64}$ | $R^{D20}$ | H | $L_{C958}$ | $R^{D13}$ | $R^{D26}$ | $R^{D1}$ |
| $L_{C119}$ | $R^{D2}$ | $R^{D41}$ | H | $L_{C539}$ | $R^{D64}$ | $R^{D21}$ | H | $L_{C959}$ | $R^{D13}$ | $R^{D27}$ | $R^{D1}$ |
| $L_{C120}$ | $R^{D2}$ | $R^{D42}$ | H | $L_{C540}$ | $R^{D64}$ | $R^{D23}$ | H | $L_{C960}$ | $R^{D13}$ | $R^{D28}$ | $R^{D1}$ |
| $L_{C121}$ | $R^{D2}$ | $R^{D64}$ | H | $L_{C541}$ | $R^{D64}$ | $R^{D24}$ | H | $L_{C961}$ | $R^{D13}$ | $R^{D29}$ | $R^{D1}$ |
| $L_{C122}$ | $R^{D2}$ | $R^{D66}$ | H | $L_{C542}$ | $R^{D64}$ | $R^{D25}$ | H | $L_{C962}$ | $R^{D13}$ | $R^{D30}$ | $R^{D1}$ |
| $L_{C123}$ | $R^{D2}$ | $R^{D68}$ | H | $L_{C543}$ | $R^{D64}$ | $R^{D27}$ | H | $L_{C963}$ | $R^{D13}$ | $R^{D31}$ | $R^{D1}$ |
| $L_{C124}$ | $R^{D2}$ | $R^{D76}$ | H | $L_{C544}$ | $R^{D64}$ | $R^{D28}$ | H | $L_{C964}$ | $R^{D13}$ | $R^{D32}$ | $R^{D1}$ |
| $L_{C125}$ | $R^{D3}$ | $R^{D4}$ | H | $L_{C545}$ | $R^{D64}$ | $R^{D29}$ | H | $L_{C965}$ | $R^{D13}$ | $R^{D33}$ | $R^{D1}$ |
| $L_{C126}$ | $R^{D3}$ | $R^{D5}$ | H | $L_{C546}$ | $R^{D64}$ | $R^{D30}$ | H | $L_{C966}$ | $R^{D13}$ | $R^{D34}$ | $R^{D1}$ |
| $L_{C127}$ | $R^{D3}$ | $R^{D6}$ | H | $L_{C547}$ | $R^{D64}$ | $R^{D31}$ | H | $L_{C967}$ | $R^{D13}$ | $R^{D35}$ | $R^{D1}$ |
| $L_{C128}$ | $R^{D3}$ | $R^{D7}$ | H | $L_{C548}$ | $R^{D64}$ | $R^{D32}$ | H | $L_{C968}$ | $R^{D13}$ | $R^{D40}$ | $R^{D1}$ |
| $L_{C129}$ | $R^{D3}$ | $R^{D8}$ | H | $L_{C549}$ | $R^{D64}$ | $R^{D33}$ | H | $L_{C969}$ | $R^{D13}$ | $R^{D41}$ | $R^{D1}$ |
| $L_{C130}$ | $R^{D3}$ | $R^{D9}$ | H | $L_{C550}$ | $R^{D64}$ | $R^{D34}$ | H | $L_{C970}$ | $R^{D13}$ | $R^{D42}$ | $R^{D1}$ |
| $L_{C131}$ | $R^{D3}$ | $R^{D10}$ | H | $L_{C551}$ | $R^{D64}$ | $R^{D42}$ | H | $L_{C971}$ | $R^{D13}$ | $R^{D64}$ | $R^{D1}$ |
| $L_{C132}$ | $R^{D3}$ | $R^{D11}$ | H | $L_{C552}$ | $R^{D64}$ | $R^{D64}$ | H | $L_{C972}$ | $R^{D13}$ | $R^{D66}$ | $R^{D1}$ |
| $L_{C133}$ | $R^{D3}$ | $R^{D12}$ | H | $L_{C553}$ | $R^{D64}$ | $R^{D66}$ | H | $L_{C973}$ | $R^{D13}$ | $R^{D68}$ | $R^{D1}$ |
| $L_{C134}$ | $R^{D3}$ | $R^{D13}$ | H | $L_{C554}$ | $R^{D64}$ | $R^{D68}$ | H | $L_{C974}$ | $R^{D13}$ | $R^{D76}$ | $R^{D1}$ |
| $L_{C135}$ | $R^{D3}$ | $R^{D14}$ | H | $L_{C555}$ | $R^{D64}$ | $R^{D76}$ | H | $L_{C975}$ | $R^{D14}$ | $R^{D5}$ | $R^{D1}$ |
| $L_{C136}$ | $R^{D3}$ | $R^{D15}$ | H | $L_{C556}$ | $R^{D66}$ | $R^{D5}$ | H | $L_{C976}$ | $R^{D14}$ | $R^{D6}$ | $R^{D1}$ |
| $L_{C137}$ | $R^{D3}$ | $R^{D16}$ | H | $L_{C557}$ | $R^{D66}$ | $R^{D6}$ | H | $L_{C977}$ | $R^{D14}$ | $R^{D9}$ | $R^{D1}$ |
| $L_{C138}$ | $R^{D3}$ | $R^{D17}$ | H | $L_{C558}$ | $R^{D66}$ | $R^{D9}$ | H | $L_{C978}$ | $R^{D14}$ | $R^{D10}$ | $R^{D1}$ |
| $L_{C139}$ | $R^{D3}$ | $R^{D18}$ | H | $L_{C559}$ | $R^{D66}$ | $R^{D10}$ | H | $L_{C979}$ | $R^{D14}$ | $R^{D12}$ | $R^{D1}$ |
| $L_{C140}$ | $R^{D3}$ | $R^{D19}$ | H | $L_{C560}$ | $R^{D66}$ | $R^{D12}$ | H | $L_{C980}$ | $R^{D14}$ | $R^{D15}$ | $R^{D1}$ |
| $L_{C141}$ | $R^{D3}$ | $R^{D20}$ | H | $L_{C561}$ | $R^{D66}$ | $R^{D15}$ | H | $L_{C981}$ | $R^{D14}$ | $R^{D16}$ | $R^{D1}$ |
| $L_{C142}$ | $R^{D3}$ | $R^{D21}$ | H | $L_{C562}$ | $R^{D66}$ | $R^{D16}$ | H | $L_{C982}$ | $R^{D14}$ | $R^{D17}$ | $R^{D1}$ |
| $L_{C143}$ | $R^{D3}$ | $R^{D22}$ | H | $L_{C563}$ | $R^{D66}$ | $R^{D17}$ | H | $L_{C983}$ | $R^{D14}$ | $R^{D18}$ | $R^{D1}$ |
| $L_{C144}$ | $R^{D3}$ | $R^{D23}$ | H | $L_{C564}$ | $R^{D66}$ | $R^{D18}$ | H | $L_{C984}$ | $R^{D14}$ | $R^{D19}$ | $R^{D1}$ |
| $L_{C145}$ | $R^{D3}$ | $R^{D24}$ | H | $L_{C565}$ | $R^{D66}$ | $R^{D19}$ | H | $L_{C985}$ | $R^{D14}$ | $R^{D20}$ | $R^{D1}$ |
| $L_{C146}$ | $R^{D3}$ | $R^{D25}$ | H | $L_{C566}$ | $R^{D66}$ | $R^{D20}$ | H | $L_{C986}$ | $R^{D14}$ | $R^{D21}$ | $R^{D1}$ |
| $L_{C147}$ | $R^{D3}$ | $R^{D26}$ | H | $L_{C567}$ | $R^{D66}$ | $R^{D21}$ | H | $L_{C987}$ | $R^{D14}$ | $R^{D22}$ | $R^{D1}$ |
| $L_{C148}$ | $R^{D3}$ | $R^{D27}$ | H | $L_{C568}$ | $R^{D66}$ | $R^{D23}$ | H | $L_{C988}$ | $R^{D14}$ | $R^{D23}$ | $R^{D1}$ |
| $L_{C149}$ | $R^{D3}$ | $R^{D28}$ | H | $L_{C569}$ | $R^{D66}$ | $R^{D24}$ | H | $L_{C989}$ | $R^{D14}$ | $R^{D24}$ | $R^{D1}$ |
| $L_{C150}$ | $R^{D3}$ | $R^{D29}$ | H | $L_{C570}$ | $R^{D66}$ | $R^{D25}$ | H | $L_{C990}$ | $R^{D14}$ | $R^{D25}$ | $R^{D1}$ |
| $L_{C151}$ | $R^{D3}$ | $R^{D30}$ | H | $L_{C571}$ | $R^{D66}$ | $R^{D27}$ | H | $L_{C991}$ | $R^{D14}$ | $R^{D26}$ | $R^{D1}$ |
| $L_{C152}$ | $R^{D3}$ | $R^{D31}$ | H | $L_{C572}$ | $R^{D66}$ | $R^{D28}$ | H | $L_{C992}$ | $R^{D14}$ | $R^{D27}$ | $R^{D1}$ |
| $L_{C153}$ | $R^{D3}$ | $R^{D32}$ | H | $L_{C573}$ | $R^{D66}$ | $R^{D29}$ | H | $L_{C993}$ | $R^{D14}$ | $R^{D28}$ | $R^{D1}$ |

-continued

| Ligand | R¹ | R² | R³ | Ligand | R¹ | R² | R³ | Ligand | R¹ | R² | R³ |
|---|---|---|---|---|---|---|---|---|---|---|---|
| $L_{C154}$ | $R^{D3}$ | $R^{D33}$ | H | $L_{C574}$ | $R^{D66}$ | $R^{D30}$ | H | $L_{C994}$ | $R^{D14}$ | $R^{D29}$ | $R^{D1}$ |
| $L_{C155}$ | $R^{D3}$ | $R^{D34}$ | H | $L_{C575}$ | $R^{D66}$ | $R^{D31}$ | H | $L_{C995}$ | $R^{D14}$ | $R^{D30}$ | $R^{D1}$ |
| $L_{C156}$ | $R^{D3}$ | $R^{D35}$ | H | $L_{C576}$ | $R^{D66}$ | $R^{D32}$ | H | $L_{C996}$ | $R^{D14}$ | $R^{D31}$ | $R^{D1}$ |
| $L_{C157}$ | $R^{D3}$ | $R^{D40}$ | H | $L_{C577}$ | $R^{D66}$ | $R^{D33}$ | H | $L_{C997}$ | $R^{D14}$ | $R^{D32}$ | $R^{D1}$ |
| $L_{C158}$ | $R^{D3}$ | $R^{D41}$ | H | $L_{C578}$ | $R^{D66}$ | $R^{D34}$ | H | $L_{C998}$ | $R^{D14}$ | $R^{D33}$ | $R^{D1}$ |
| $L_{C159}$ | $R^{D3}$ | $R^{D42}$ | H | $L_{C579}$ | $R^{D66}$ | $R^{D42}$ | H | $L_{C999}$ | $R^{D14}$ | $R^{D34}$ | $R^{D1}$ |
| $L_{C160}$ | $R^{D3}$ | $R^{D64}$ | H | $L_{C580}$ | $R^{D66}$ | $R^{D68}$ | H | $L_{C1000}$ | $R^{D14}$ | $R^{D35}$ | $R^{D1}$ |
| $L_{C161}$ | $R^{D3}$ | $R^{D66}$ | H | $L_{C581}$ | $R^{D66}$ | $R^{D76}$ | H | $L_{C1001}$ | $R^{D14}$ | $R^{D40}$ | $R^{D1}$ |
| $L_{C162}$ | $R^{D3}$ | $R^{D68}$ | H | $L_{C582}$ | $R^{D68}$ | $R^{D5}$ | H | $L_{C1002}$ | $R^{D14}$ | $R^{D41}$ | $R^{D1}$ |
| $L_{C163}$ | $R^{D3}$ | $R^{D76}$ | H | $L_{C583}$ | $R^{D68}$ | $R^{D6}$ | H | $L_{C1003}$ | $R^{D14}$ | $R^{D42}$ | $R^{D1}$ |
| $L_{C164}$ | $R^{D4}$ | $R^{D5}$ | H | $L_{C584}$ | $R^{D68}$ | $R^{D9}$ | H | $L_{C1004}$ | $R^{D14}$ | $R^{D64}$ | $R^{D1}$ |
| $L_{C165}$ | $R^{D4}$ | $R^{D6}$ | H | $L_{C585}$ | $R^{D68}$ | $R^{D10}$ | H | $L_{C1005}$ | $R^{D14}$ | $R^{D66}$ | $R^{D1}$ |
| $L_{C166}$ | $R^{D4}$ | $R^{D7}$ | H | $L_{C586}$ | $R^{D68}$ | $R^{D12}$ | H | $L_{C1006}$ | $R^{D14}$ | $R^{D68}$ | $R^{D1}$ |
| $L_{C167}$ | $R^{D4}$ | $R^{D8}$ | H | $L_{C587}$ | $R^{D68}$ | $R^{D15}$ | H | $L_{C1007}$ | $R^{D14}$ | $R^{D76}$ | $R^{D1}$ |
| $L_{C168}$ | $R^{D4}$ | $R^{D9}$ | H | $L_{C588}$ | $R^{D68}$ | $R^{D16}$ | H | $L_{C1008}$ | $R^{D22}$ | $R^{D5}$ | $R^{D1}$ |
| $L_{C169}$ | $R^{D4}$ | $R^{D10}$ | H | $L_{C589}$ | $R^{D68}$ | $R^{D17}$ | H | $L_{C1009}$ | $R^{D22}$ | $R^{D6}$ | $R^{D1}$ |
| $L_{C170}$ | $R^{D4}$ | $R^{D11}$ | H | $L_{C590}$ | $R^{D68}$ | $R^{D18}$ | H | $L_{C1010}$ | $R^{D22}$ | $R^{D9}$ | $R^{D1}$ |
| $L_{C171}$ | $R^{D4}$ | $R^{D12}$ | H | $L_{C591}$ | $R^{D68}$ | $R^{D19}$ | H | $L_{C1011}$ | $R^{D22}$ | $R^{D10}$ | $R^{D1}$ |
| $L_{C172}$ | $R^{D4}$ | $R^{D13}$ | H | $L_{C592}$ | $R^{D68}$ | $R^{D20}$ | H | $L_{C1012}$ | $R^{D22}$ | $R^{D12}$ | $R^{D1}$ |
| $L_{C173}$ | $R^{D4}$ | $R^{D14}$ | H | $L_{C593}$ | $R^{D68}$ | $R^{D21}$ | H | $L_{C1013}$ | $R^{D22}$ | $R^{D15}$ | $R^{D1}$ |
| $L_{C174}$ | $R^{D4}$ | $R^{D15}$ | H | $L_{C594}$ | $R^{D68}$ | $R^{D23}$ | H | $L_{C1014}$ | $R^{D22}$ | $R^{D16}$ | $R^{D1}$ |
| $L_{C175}$ | $R^{D4}$ | $R^{D16}$ | H | $L_{C595}$ | $R^{D68}$ | $R^{D24}$ | H | $L_{C1015}$ | $R^{D22}$ | $R^{D17}$ | $R^{D1}$ |
| $L_{C176}$ | $R^{D4}$ | $R^{D17}$ | H | $L_{C596}$ | $R^{D68}$ | $R^{D25}$ | H | $L_{C1016}$ | $R^{D22}$ | $R^{D18}$ | $R^{D1}$ |
| $L_{C177}$ | $R^{D4}$ | $R^{D18}$ | H | $L_{C597}$ | $R^{D68}$ | $R^{D27}$ | H | $L_{C1017}$ | $R^{D22}$ | $R^{D19}$ | $R^{D1}$ |
| $L_{C178}$ | $R^{D4}$ | $R^{D19}$ | H | $L_{C598}$ | $R^{D68}$ | $R^{D28}$ | H | $L_{C1018}$ | $R^{D22}$ | $R^{D20}$ | $R^{D1}$ |
| $L_{C179}$ | $R^{D4}$ | $R^{D20}$ | H | $L_{C599}$ | $R^{D68}$ | $R^{D29}$ | H | $L_{C1019}$ | $R^{D22}$ | $R^{D21}$ | $R^{D1}$ |
| $L_{C180}$ | $R^{D4}$ | $R^{D21}$ | H | $L_{C600}$ | $R^{D68}$ | $R^{D30}$ | H | $L_{C1020}$ | $R^{D22}$ | $R^{D23}$ | $R^{D1}$ |
| $L_{C181}$ | $R^{D4}$ | $R^{D22}$ | H | $L_{C601}$ | $R^{D68}$ | $R^{D31}$ | H | $L_{C1021}$ | $R^{D22}$ | $R^{D24}$ | $R^{D1}$ |
| $L_{C182}$ | $R^{D4}$ | $R^{D23}$ | H | $L_{C602}$ | $R^{D68}$ | $R^{D32}$ | H | $L_{C1022}$ | $R^{D22}$ | $R^{D25}$ | $R^{D1}$ |
| $L_{C183}$ | $R^{D4}$ | $R^{D24}$ | H | $L_{C603}$ | $R^{D68}$ | $R^{D33}$ | H | $L_{C1023}$ | $R^{D22}$ | $R^{D26}$ | $R^{D1}$ |
| $L_{C184}$ | $R^{D4}$ | $R^{D25}$ | H | $L_{C604}$ | $R^{D68}$ | $R^{D34}$ | H | $L_{C1024}$ | $R^{D22}$ | $R^{D27}$ | $R^{D1}$ |
| $L_{C185}$ | $R^{D4}$ | $R^{D26}$ | H | $L_{C605}$ | $R^{D68}$ | $R^{D42}$ | H | $L_{C1025}$ | $R^{D22}$ | $R^{D28}$ | $R^{D1}$ |
| $L_{C186}$ | $R^{D4}$ | $R^{D27}$ | H | $L_{C606}$ | $R^{D68}$ | $R^{D76}$ | H | $L_{C1026}$ | $R^{D22}$ | $R^{D29}$ | $R^{D1}$ |
| $L_{C187}$ | $R^{D4}$ | $R^{D28}$ | H | $L_{C607}$ | $R^{D76}$ | $R^{D5}$ | H | $L_{C1027}$ | $R^{D22}$ | $R^{D30}$ | $R^{D1}$ |
| $L_{C188}$ | $R^{D4}$ | $R^{D29}$ | H | $L_{C608}$ | $R^{D76}$ | $R^{D6}$ | H | $L_{C1028}$ | $R^{D22}$ | $R^{D31}$ | $R^{D1}$ |
| $L_{C189}$ | $R^{D4}$ | $R^{D30}$ | H | $L_{C609}$ | $R^{D76}$ | $R^{D9}$ | H | $L_{C1029}$ | $R^{D22}$ | $R^{D32}$ | $R^{D1}$ |
| $L_{C190}$ | $R^{D4}$ | $R^{D31}$ | H | $L_{C610}$ | $R^{D76}$ | $R^{D10}$ | H | $L_{C1030}$ | $R^{D22}$ | $R^{D33}$ | $R^{D1}$ |
| $L_{C191}$ | $R^{D4}$ | $R^{D32}$ | H | $L_{C611}$ | $R^{D76}$ | $R^{D12}$ | H | $L_{C1031}$ | $R^{D22}$ | $R^{D34}$ | $R^{D1}$ |
| $L_{C192}$ | $R^{D4}$ | $R^{D33}$ | H | $L_{C612}$ | $R^{D76}$ | $R^{D15}$ | H | $L_{C1032}$ | $R^{D22}$ | $R^{D35}$ | $R^{D1}$ |
| $L_{C193}$ | $R^{D4}$ | $R^{D34}$ | H | $L_{C613}$ | $R^{D76}$ | $R^{D16}$ | H | $L_{C1033}$ | $R^{D22}$ | $R^{D40}$ | $R^{D1}$ |
| $L_{C194}$ | $R^{D4}$ | $R^{D35}$ | H | $L_{C614}$ | $R^{D76}$ | $R^{D17}$ | H | $L_{C1034}$ | $R^{D22}$ | $R^{D41}$ | $R^{D1}$ |
| $L_{C195}$ | $R^{D4}$ | $R^{D40}$ | H | $L_{C615}$ | $R^{D76}$ | $R^{D18}$ | H | $L_{C1035}$ | $R^{D22}$ | $R^{D42}$ | $R^{D1}$ |
| $L_{C196}$ | $R^{D4}$ | $R^{D41}$ | H | $L_{C616}$ | $R^{D76}$ | $R^{D19}$ | H | $L_{C1036}$ | $R^{D22}$ | $R^{D64}$ | $R^{D1}$ |
| $L_{C197}$ | $R^{D4}$ | $R^{D42}$ | H | $L_{C617}$ | $R^{D76}$ | $R^{D20}$ | H | $L_{C1037}$ | $R^{D22}$ | $R^{D66}$ | $R^{D1}$ |
| $L_{C198}$ | $R^{D4}$ | $R^{D64}$ | H | $L_{C618}$ | $R^{D76}$ | $R^{D21}$ | H | $L_{C1038}$ | $R^{D22}$ | $R^{D68}$ | $R^{D1}$ |
| $L_{C199}$ | $R^{D4}$ | $R^{D66}$ | H | $L_{C619}$ | $R^{D76}$ | $R^{D23}$ | H | $L_{C1039}$ | $R^{D22}$ | $R^{D76}$ | $R^{D1}$ |
| $L_{C200}$ | $R^{D4}$ | $R^{D68}$ | H | $L_{C620}$ | $R^{D76}$ | $R^{D24}$ | H | $L_{C1040}$ | $R^{D26}$ | $R^{D5}$ | $R^{D1}$ |
| $L_{C201}$ | $R^{D4}$ | $R^{D76}$ | H | $L_{C621}$ | $R^{D76}$ | $R^{D25}$ | H | $L_{C1041}$ | $R^{D26}$ | $R^{D6}$ | $R^{D1}$ |
| $L_{C202}$ | $R^{D4}$ | $R^{D1}$ | H | $L_{C622}$ | $R^{D76}$ | $R^{D27}$ | H | $L_{C1042}$ | $R^{D26}$ | $R^{D9}$ | $R^{D1}$ |
| $L_{C203}$ | $R^{D7}$ | $R^{D5}$ | H | $L_{C623}$ | $R^{D76}$ | $R^{D28}$ | H | $L_{C1043}$ | $R^{D26}$ | $R^{D10}$ | $R^{D1}$ |
| $L_{C204}$ | $R^{D7}$ | $R^{D6}$ | H | $L_{C624}$ | $R^{D76}$ | $R^{D29}$ | H | $L_{C1044}$ | $R^{D26}$ | $R^{D12}$ | $R^{D1}$ |
| $L_{C205}$ | $R^{D7}$ | $R^{D8}$ | H | $L_{C625}$ | $R^{D76}$ | $R^{D30}$ | H | $L_{C1045}$ | $R^{D26}$ | $R^{D15}$ | $R^{D1}$ |
| $L_{C206}$ | $R^{D7}$ | $R^{D9}$ | H | $L_{C626}$ | $R^{D76}$ | $R^{D31}$ | H | $L_{C1046}$ | $R^{D26}$ | $R^{D16}$ | $R^{D1}$ |
| $L_{C207}$ | $R^{D7}$ | $R^{D10}$ | H | $L_{C627}$ | $R^{D76}$ | $R^{D32}$ | H | $L_{C1047}$ | $R^{D26}$ | $R^{D17}$ | $R^{D1}$ |
| $L_{C208}$ | $R^{D7}$ | $R^{D11}$ | H | $L_{C628}$ | $R^{D76}$ | $R^{D33}$ | H | $L_{C1048}$ | $R^{D26}$ | $R^{D18}$ | $R^{D1}$ |
| $L_{C209}$ | $R^{D7}$ | $R^{D12}$ | H | $L_{C629}$ | $R^{D76}$ | $R^{D34}$ | H | $L_{C1049}$ | $R^{D26}$ | $R^{D19}$ | $R^{D1}$ |
| $L_{C210}$ | $R^{D7}$ | $R^{D13}$ | H | $L_{C630}$ | $R^{D76}$ | $R^{D42}$ | H | $L_{C1050}$ | $R^{D26}$ | $R^{D20}$ | $R^{D1}$ |
| $L_{C211}$ | $R^{D7}$ | $R^{D14}$ | H | $L_{C631}$ | $R^{D1}$ | $R^{D1}$ | $R^{D1}$ | $L_{C1051}$ | $R^{D26}$ | $R^{D21}$ | $R^{D1}$ |
| $L_{C212}$ | $R^{D7}$ | $R^{D15}$ | H | $L_{C632}$ | $R^{D2}$ | $R^{D2}$ | $R^{D1}$ | $L_{C1052}$ | $R^{D26}$ | $R^{D23}$ | $R^{D1}$ |
| $L_{C213}$ | $R^{D7}$ | $R^{D16}$ | H | $L_{C633}$ | $R^{D3}$ | $R^{D3}$ | $R^{D1}$ | $L_{C1053}$ | $R^{D26}$ | $R^{D24}$ | $R^{D1}$ |
| $L_{C214}$ | $R^{D7}$ | $R^{D17}$ | H | $L_{C634}$ | $R^{D4}$ | $R^{D4}$ | $R^{D1}$ | $L_{C1054}$ | $R^{D26}$ | $R^{D25}$ | $R^{D1}$ |
| $L_{C215}$ | $R^{D7}$ | $R^{D18}$ | H | $L_{C635}$ | $R^{D5}$ | $R^{D5}$ | $R^{D1}$ | $L_{C1055}$ | $R^{D26}$ | $R^{D27}$ | $R^{D1}$ |
| $L_{C216}$ | $R^{D7}$ | $R^{D19}$ | H | $L_{C636}$ | $R^{D6}$ | $R^{D6}$ | $R^{D1}$ | $L_{C1056}$ | $R^{D26}$ | $R^{D28}$ | $R^{D1}$ |
| $L_{C217}$ | $R^{D7}$ | $R^{D20}$ | H | $L_{C637}$ | $R^{D7}$ | $R^{D7}$ | $R^{D1}$ | $L_{C1057}$ | $R^{D26}$ | $R^{D29}$ | $R^{D1}$ |
| $L_{C218}$ | $R^{D7}$ | $R^{D21}$ | H | $L_{C638}$ | $R^{D8}$ | $R^{D8}$ | $R^{D1}$ | $L_{C1058}$ | $R^{D26}$ | $R^{D30}$ | $R^{D1}$ |
| $L_{C219}$ | $R^{D7}$ | $R^{D22}$ | H | $L_{C639}$ | $R^{D9}$ | $R^{D9}$ | $R^{D1}$ | $L_{C1059}$ | $R^{D26}$ | $R^{D31}$ | $R^{D1}$ |
| $L_{C220}$ | $R^{D7}$ | $R^{D23}$ | H | $L_{C640}$ | $R^{D10}$ | $R^{D10}$ | $R^{D1}$ | $L_{C1060}$ | $R^{D26}$ | $R^{D32}$ | $R^{D1}$ |
| $L_{C221}$ | $R^{D7}$ | $R^{D24}$ | H | $L_{C641}$ | $R^{D11}$ | $R^{D11}$ | $R^{D1}$ | $L_{C1061}$ | $R^{D26}$ | $R^{D33}$ | $R^{D1}$ |
| $L_{C222}$ | $R^{D7}$ | $R^{D25}$ | H | $L_{C642}$ | $R^{D12}$ | $R^{D12}$ | $R^{D1}$ | $L_{C1062}$ | $R^{D26}$ | $R^{D34}$ | $R^{D1}$ |
| $L_{C223}$ | $R^{D7}$ | $R^{D26}$ | H | $L_{C643}$ | $R^{D13}$ | $R^{D13}$ | $R^{D1}$ | $L_{C1063}$ | $R^{D26}$ | $R^{D35}$ | $R^{D1}$ |
| $L_{C224}$ | $R^{D7}$ | $R^{D27}$ | H | $L_{C644}$ | $R^{D14}$ | $R^{D14}$ | $R^{D1}$ | $L_{C1064}$ | $R^{D26}$ | $R^{D40}$ | $R^{D1}$ |
| $L_{C225}$ | $R^{D7}$ | $R^{D28}$ | H | $L_{C645}$ | $R^{D15}$ | $R^{D15}$ | $R^{D1}$ | $L_{C1065}$ | $R^{D26}$ | $R^{D41}$ | $R^{D1}$ |
| $L_{C226}$ | $R^{D7}$ | $R^{D29}$ | H | $L_{C646}$ | $R^{D16}$ | $R^{D16}$ | $R^{D1}$ | $L_{C1066}$ | $R^{D26}$ | $R^{D42}$ | $R^{D1}$ |
| $L_{C227}$ | $R^{D7}$ | $R^{D30}$ | H | $L_{C647}$ | $R^{D17}$ | $R^{D17}$ | $R^{D1}$ | $L_{C1067}$ | $R^{D26}$ | $R^{D64}$ | $R^{D1}$ |
| $L_{C228}$ | $R^{D7}$ | $R^{D31}$ | H | $L_{C648}$ | $R^{D18}$ | $R^{D18}$ | $R^{D1}$ | $L_{C1068}$ | $R^{D26}$ | $R^{D66}$ | $R^{D1}$ |
| $L_{C229}$ | $R^{D7}$ | $R^{D32}$ | H | $L_{C649}$ | $R^{D19}$ | $R^{D19}$ | $R^{D1}$ | $L_{C1069}$ | $R^{D26}$ | $R^{D68}$ | $R^{D1}$ |
| $L_{C230}$ | $R^{D7}$ | $R^{D33}$ | H | $L_{C650}$ | $R^{D20}$ | $R^{D20}$ | $R^{D1}$ | $L_{C1070}$ | $R^{D26}$ | $R^{D76}$ | $R^{D1}$ |

-continued

| Ligand | R¹ | R² | R³ | Ligand | R¹ | R² | R³ | Ligand | R¹ | R² | R³ |
|---|---|---|---|---|---|---|---|---|---|---|---|
| $L_{C231}$ | $R^{D7}$ | $R^{D34}$ | H | $L_{C651}$ | $R^{D21}$ | $R^{D21}$ | $R^{D1}$ | $L_{C1071}$ | $R^{D35}$ | $R^{D5}$ | $R^{D1}$ |
| $L_{C232}$ | $R^{D7}$ | $R^{D35}$ | H | $L_{C652}$ | $R^{D22}$ | $R^{D22}$ | $R^{D1}$ | $L_{C1072}$ | $R^{D35}$ | $R^{D6}$ | $R^{D1}$ |
| $L_{C233}$ | $R^{D7}$ | $R^{D40}$ | H | $L_{C653}$ | $R^{D23}$ | $R^{D23}$ | $R^{D1}$ | $L_{C1073}$ | $R^{D35}$ | $R^{D9}$ | $R^{D1}$ |
| $L_{C234}$ | $R^{D7}$ | $R^{D41}$ | H | $L_{C654}$ | $R^{D24}$ | $R^{D24}$ | $R^{D1}$ | $L_{C1074}$ | $R^{D35}$ | $R^{D10}$ | $R^{D1}$ |
| $L_{C235}$ | $R^{D7}$ | $R^{D42}$ | H | $L_{C655}$ | $R^{D25}$ | $R^{D25}$ | $R^{D1}$ | $L_{C1075}$ | $R^{D35}$ | $R^{D12}$ | $R^{D1}$ |
| $L_{C236}$ | $R^{D7}$ | $R^{D64}$ | H | $L_{C656}$ | $R^{D26}$ | $R^{D26}$ | $R^{D1}$ | $L_{C1076}$ | $R^{D35}$ | $R^{D15}$ | $R^{D1}$ |
| $L_{C237}$ | $R^{D7}$ | $R^{D66}$ | H | $L_{C657}$ | $R^{D27}$ | $R^{D27}$ | $R^{D1}$ | $L_{C1077}$ | $R^{D35}$ | $R^{D16}$ | $R^{D1}$ |
| $L_{C238}$ | $R^{D7}$ | $R^{D68}$ | H | $L_{C658}$ | $R^{D28}$ | $R^{D28}$ | $R^{D1}$ | $L_{C1078}$ | $R^{D35}$ | $R^{D17}$ | $R^{D1}$ |
| $L_{C239}$ | $R^{D7}$ | $R^{D76}$ | H | $L_{C659}$ | $R^{D29}$ | $R^{D29}$ | $R^{D1}$ | $L_{C1079}$ | $R^{D35}$ | $R^{D18}$ | $R^{D1}$ |
| $L_{C240}$ | $R^{D8}$ | $R^{D5}$ | H | $L_{C660}$ | $R^{D30}$ | $R^{D30}$ | $R^{D1}$ | $L_{C1080}$ | $R^{D35}$ | $R^{D19}$ | $R^{D1}$ |
| $L_{C241}$ | $R^{D8}$ | $R^{D6}$ | H | $L_{C661}$ | $R^{D31}$ | $R^{D31}$ | $R^{D1}$ | $L_{C1081}$ | $R^{D35}$ | $R^{D20}$ | $R^{D1}$ |
| $L_{C242}$ | $R^{D8}$ | $R^{D9}$ | H | $L_{C662}$ | $R^{D32}$ | $R^{D32}$ | $R^{D1}$ | $L_{C1082}$ | $R^{D35}$ | $R^{D21}$ | $R^{D1}$ |
| $L_{C243}$ | $R^{D8}$ | $R^{D10}$ | H | $L_{C663}$ | $R^{D33}$ | $R^{D33}$ | $R^{D1}$ | $L_{C1083}$ | $R^{D35}$ | $R^{D23}$ | $R^{D1}$ |
| $L_{C244}$ | $R^{D8}$ | $R^{D11}$ | H | $L_{C664}$ | $R^{D34}$ | $R^{D34}$ | $R^{D1}$ | $L_{C1084}$ | $R^{D35}$ | $R^{D24}$ | $R^{D1}$ |
| $L_{C245}$ | $R^{D8}$ | $R^{D12}$ | H | $L_{C665}$ | $R^{D35}$ | $R^{D35}$ | $R^{D1}$ | $L_{C1085}$ | $R^{D35}$ | $R^{D25}$ | $R^{D1}$ |
| $L_{C246}$ | $R^{D8}$ | $R^{D13}$ | H | $L_{C666}$ | $R^{D40}$ | $R^{D40}$ | $R^{D1}$ | $L_{C1086}$ | $R^{D35}$ | $R^{D27}$ | $R^{D1}$ |
| $L_{C247}$ | $R^{D8}$ | $R^{D14}$ | H | $L_{C667}$ | $R^{D41}$ | $R^{D41}$ | $R^{D1}$ | $L_{C1087}$ | $R^{D35}$ | $R^{D28}$ | $R^{D1}$ |
| $L_{C248}$ | $R^{D8}$ | $R^{D15}$ | H | $L_{C668}$ | $R^{D42}$ | $R^{D42}$ | $R^{D1}$ | $L_{C1088}$ | $R^{D35}$ | $R^{D29}$ | $R^{D1}$ |
| $L_{C249}$ | $R^{D8}$ | $R^{D16}$ | H | $L_{C669}$ | $R^{D64}$ | $R^{D64}$ | $R^{D1}$ | $L_{C1089}$ | $R^{D35}$ | $R^{D30}$ | $R^{D1}$ |
| $L_{C250}$ | $R^{D8}$ | $R^{D17}$ | H | $L_{C670}$ | $R^{D66}$ | $R^{D66}$ | $R^{D1}$ | $L_{C1090}$ | $R^{D35}$ | $R^{D31}$ | $R^{D1}$ |
| $L_{C251}$ | $R^{D8}$ | $R^{D18}$ | H | $L_{C671}$ | $R^{D68}$ | $R^{D68}$ | $R^{D1}$ | $L_{C1091}$ | $R^{D35}$ | $R^{D32}$ | $R^{D1}$ |
| $L_{C252}$ | $R^{D8}$ | $R^{D19}$ | H | $L_{C672}$ | $R^{D76}$ | $R^{D76}$ | $R^{D1}$ | $L_{C1092}$ | $R^{D35}$ | $R^{D33}$ | $R^{D1}$ |
| $L_{C253}$ | $R^{D8}$ | $R^{D20}$ | H | $L_{C673}$ | $R^{D1}$ | $R^{D2}$ | $R^{D1}$ | $L_{C1093}$ | $R^{D35}$ | $R^{D34}$ | $R^{D1}$ |
| $L_{C254}$ | $R^{D8}$ | $R^{D21}$ | H | $L_{C674}$ | $R^{D1}$ | $R^{D3}$ | $R^{D1}$ | $L_{C1094}$ | $R^{D35}$ | $R^{D40}$ | $R^{D1}$ |
| $L_{C255}$ | $R^{D8}$ | $R^{D22}$ | H | $L_{C675}$ | $R^{D1}$ | $R^{D4}$ | $R^{D1}$ | $L_{C1095}$ | $R^{D35}$ | $R^{D41}$ | $R^{D1}$ |
| $L_{C256}$ | $R^{D8}$ | $R^{D23}$ | H | $L_{C676}$ | $R^{D1}$ | $R^{D5}$ | $R^{D1}$ | $L_{C1096}$ | $R^{D35}$ | $R^{D42}$ | $R^{D1}$ |
| $L_{C257}$ | $R^{D8}$ | $R^{D24}$ | H | $L_{C677}$ | $R^{D1}$ | $R^{D6}$ | $R^{D1}$ | $L_{C1097}$ | $R^{D35}$ | $R^{D64}$ | $R^{D1}$ |
| $L_{C258}$ | $R^{D8}$ | $R^{D25}$ | H | $L_{C678}$ | $R^{D1}$ | $R^{D7}$ | $R^{D1}$ | $L_{C1098}$ | $R^{D35}$ | $R^{D66}$ | $R^{D1}$ |
| $L_{C259}$ | $R^{D8}$ | $R^{D26}$ | H | $L_{C679}$ | $R^{D1}$ | $R^{D8}$ | $R^{D1}$ | $L_{C1099}$ | $R^{D35}$ | $R^{D68}$ | $R^{D1}$ |
| $L_{C260}$ | $R^{D8}$ | $R^{D27}$ | H | $L_{C680}$ | $R^{D1}$ | $R^{D9}$ | $R^{D1}$ | $L_{C1100}$ | $R^{D35}$ | $R^{D76}$ | $R^{D1}$ |
| $L_{C261}$ | $R^{D8}$ | $R^{D28}$ | H | $L_{C681}$ | $R^{D1}$ | $R^{D10}$ | $R^{D1}$ | $L_{C1101}$ | $R^{D40}$ | $R^{D5}$ | $R^{D1}$ |
| $L_{C262}$ | $R^{D8}$ | $R^{D29}$ | H | $L_{C682}$ | $R^{D1}$ | $R^{D11}$ | $R^{D1}$ | $L_{C1102}$ | $R^{D40}$ | $R^{D6}$ | $R^{D1}$ |
| $L_{C263}$ | $R^{D8}$ | $R^{D30}$ | H | $L_{C683}$ | $R^{D1}$ | $R^{D12}$ | $R^{D1}$ | $L_{C1103}$ | $R^{D40}$ | $R^{D9}$ | $R^{D1}$ |
| $L_{C264}$ | $R^{D8}$ | $R^{D31}$ | H | $L_{C684}$ | $R^{D1}$ | $R^{D13}$ | $R^{D1}$ | $L_{C1104}$ | $R^{D40}$ | $R^{D10}$ | $R^{D1}$ |
| $L_{C265}$ | $R^{D8}$ | $R^{D32}$ | H | $L_{C685}$ | $R^{D1}$ | $R^{D14}$ | $R^{D1}$ | $L_{C1105}$ | $R^{D40}$ | $R^{D12}$ | $R^{D1}$ |
| $L_{C266}$ | $R^{D8}$ | $R^{D33}$ | H | $L_{C686}$ | $R^{D1}$ | $R^{D15}$ | $R^{D1}$ | $L_{C1106}$ | $R^{D40}$ | $R^{D15}$ | $R^{D1}$ |
| $L_{C267}$ | $R^{D8}$ | $R^{D34}$ | H | $L_{C687}$ | $R^{D1}$ | $R^{D16}$ | $R^{D1}$ | $L_{C1107}$ | $R^{D40}$ | $R^{D16}$ | $R^{D1}$ |
| $L_{C268}$ | $R^{D8}$ | $R^{D35}$ | H | $L_{C688}$ | $R^{D1}$ | $R^{D17}$ | $R^{D1}$ | $L_{C1108}$ | $R^{D40}$ | $R^{D17}$ | $R^{D1}$ |
| $L_{C269}$ | $R^{D8}$ | $R^{D40}$ | H | $L_{C689}$ | $R^{D1}$ | $R^{D18}$ | $R^{D1}$ | $L_{C1109}$ | $R^{D40}$ | $R^{D18}$ | $R^{D1}$ |
| $L_{C270}$ | $R^{D8}$ | $R^{D41}$ | H | $L_{C690}$ | $R^{D1}$ | $R^{D19}$ | $R^{D1}$ | $L_{C1110}$ | $R^{D40}$ | $R^{D19}$ | $R^{D1}$ |
| $L_{C271}$ | $R^{D8}$ | $R^{D42}$ | H | $L_{C691}$ | $R^{D1}$ | $R^{D20}$ | $R^{D1}$ | $L_{C1111}$ | $R^{D40}$ | $R^{D20}$ | $R^{D1}$ |
| $L_{C272}$ | $R^{D8}$ | $R^{D64}$ | H | $L_{C692}$ | $R^{D1}$ | $R^{D21}$ | $R^{D1}$ | $L_{C1112}$ | $R^{D40}$ | $R^{D21}$ | $R^{D1}$ |
| $L_{C273}$ | $R^{D8}$ | $R^{D66}$ | H | $L_{C693}$ | $R^{D1}$ | $R^{D22}$ | $R^{D1}$ | $L_{C1113}$ | $R^{D40}$ | $R^{D23}$ | $R^{D1}$ |
| $L_{C274}$ | $R^{D8}$ | $R^{D68}$ | H | $L_{C694}$ | $R^{D1}$ | $R^{D23}$ | $R^{D1}$ | $L_{C1114}$ | $R^{D40}$ | $R^{D24}$ | $R^{D1}$ |
| $L_{C275}$ | $R^{D8}$ | $R^{D76}$ | H | $L_{C695}$ | $R^{D1}$ | $R^{D24}$ | $R^{D1}$ | $L_{C1115}$ | $R^{D40}$ | $R^{D25}$ | $R^{D1}$ |
| $L_{C276}$ | $R^{D11}$ | $R^{D5}$ | H | $L_{C696}$ | $R^{D1}$ | $R^{D25}$ | $R^{D1}$ | $L_{C1116}$ | $R^{D40}$ | $R^{D27}$ | $R^{D1}$ |
| $L_{C277}$ | $R^{D11}$ | $R^{D6}$ | H | $L_{C697}$ | $R^{D1}$ | $R^{D26}$ | $R^{D1}$ | $L_{C1117}$ | $R^{D40}$ | $R^{D28}$ | $R^{D1}$ |
| $L_{C278}$ | $R^{D11}$ | $R^{D9}$ | H | $L_{C698}$ | $R^{D1}$ | $R^{D27}$ | $R^{D1}$ | $L_{C1118}$ | $R^{D40}$ | $R^{D29}$ | $R^{D1}$ |
| $L_{C279}$ | $R^{D11}$ | $R^{D10}$ | H | $L_{C699}$ | $R^{D1}$ | $R^{D28}$ | $R^{D1}$ | $L_{C1119}$ | $R^{D40}$ | $R^{D30}$ | $R^{D1}$ |
| $L_{C280}$ | $R^{D11}$ | $R^{D12}$ | H | $L_{C700}$ | $R^{D1}$ | $R^{D29}$ | $R^{D1}$ | $L_{C1120}$ | $R^{D40}$ | $R^{D31}$ | $R^{D1}$ |
| $L_{C281}$ | $R^{D11}$ | $R^{D13}$ | H | $L_{C701}$ | $R^{D1}$ | $R^{D30}$ | $R^{D1}$ | $L_{C1121}$ | $R^{D40}$ | $R^{D32}$ | $R^{D1}$ |
| $L_{C282}$ | $R^{D11}$ | $R^{D14}$ | H | $L_{C702}$ | $R^{D1}$ | $R^{D31}$ | $R^{D1}$ | $L_{C1122}$ | $R^{D40}$ | $R^{D33}$ | $R^{D1}$ |
| $L_{C283}$ | $R^{D11}$ | $R^{D15}$ | H | $L_{C703}$ | $R^{D1}$ | $R^{D32}$ | $R^{D1}$ | $L_{C1123}$ | $R^{D40}$ | $R^{D34}$ | $R^{D1}$ |
| $L_{C284}$ | $R^{D11}$ | $R^{D16}$ | H | $L_{C704}$ | $R^{D1}$ | $R^{D33}$ | $R^{D1}$ | $L_{C1124}$ | $R^{D40}$ | $R^{D41}$ | $R^{D1}$ |
| $L_{C285}$ | $R^{D11}$ | $R^{D17}$ | H | $L_{C705}$ | $R^{D1}$ | $R^{D34}$ | $R^{D1}$ | $L_{C1125}$ | $R^{D40}$ | $R^{D42}$ | $R^{D1}$ |
| $L_{C286}$ | $R^{D11}$ | $R^{D18}$ | H | $L_{C706}$ | $R^{D1}$ | $R^{D35}$ | $R^{D1}$ | $L_{C1126}$ | $R^{D40}$ | $R^{D64}$ | $R^{D1}$ |
| $L_{C287}$ | $R^{D11}$ | $R^{D19}$ | H | $L_{C707}$ | $R^{D1}$ | $R^{D40}$ | $R^{D1}$ | $L_{C1127}$ | $R^{D40}$ | $R^{D66}$ | $R^{D1}$ |
| $L_{C288}$ | $R^{D11}$ | $R^{D20}$ | H | $L_{C708}$ | $R^{D1}$ | $R^{D41}$ | $R^{D1}$ | $L_{C1128}$ | $R^{D40}$ | $R^{D68}$ | $R^{D1}$ |
| $L_{C289}$ | $R^{D11}$ | $R^{D21}$ | H | $L_{C709}$ | $R^{D1}$ | $R^{D42}$ | $R^{D1}$ | $L_{C1129}$ | $R^{D40}$ | $R^{D76}$ | $R^{D1}$ |
| $L_{C290}$ | $R^{D11}$ | $R^{D22}$ | H | $L_{C710}$ | $R^{D1}$ | $R^{D64}$ | $R^{D1}$ | $L_{C1130}$ | $R^{D41}$ | $R^{D5}$ | $R^{D1}$ |
| $L_{C291}$ | $R^{D11}$ | $R^{D23}$ | H | $L_{C711}$ | $R^{D1}$ | $R^{D66}$ | $R^{D1}$ | $L_{C1131}$ | $R^{D41}$ | $R^{D6}$ | $R^{D1}$ |
| $L_{C292}$ | $R^{D11}$ | $R^{D24}$ | H | $L_{C712}$ | $R^{D1}$ | $R^{D68}$ | $R^{D1}$ | $L_{C1132}$ | $R^{D41}$ | $R^{D9}$ | $R^{D1}$ |
| $L_{C293}$ | $R^{D11}$ | $R^{D25}$ | H | $L_{C713}$ | $R^{D1}$ | $R^{D76}$ | $R^{D1}$ | $L_{C1133}$ | $R^{D41}$ | $R^{D10}$ | $R^{D1}$ |
| $L_{C294}$ | $R^{D11}$ | $R^{D26}$ | H | $L_{C714}$ | $R^{D2}$ | $R^{D1}$ | $R^{D1}$ | $L_{C1134}$ | $R^{D41}$ | $R^{D12}$ | $R^{D1}$ |
| $L_{C295}$ | $R^{D11}$ | $R^{D27}$ | H | $L_{C715}$ | $R^{D2}$ | $R^{D3}$ | $R^{D1}$ | $L_{C1135}$ | $R^{D41}$ | $R^{D15}$ | $R^{D1}$ |
| $L_{C296}$ | $R^{D11}$ | $R^{D28}$ | H | $L_{C716}$ | $R^{D2}$ | $R^{D4}$ | $R^{D1}$ | $L_{C1136}$ | $R^{D41}$ | $R^{D16}$ | $R^{D1}$ |
| $L_{C297}$ | $R^{D11}$ | $R^{D29}$ | H | $L_{C717}$ | $R^{D2}$ | $R^{D5}$ | $R^{D1}$ | $L_{C1137}$ | $R^{D41}$ | $R^{D17}$ | $R^{D1}$ |
| $L_{C298}$ | $R^{D11}$ | $R^{D30}$ | H | $L_{C718}$ | $R^{D2}$ | $R^{D6}$ | $R^{D1}$ | $L_{C1138}$ | $R^{D41}$ | $R^{D18}$ | $R^{D1}$ |
| $L_{C299}$ | $R^{D11}$ | $R^{D31}$ | H | $L_{C719}$ | $R^{D2}$ | $R^{D7}$ | $R^{D1}$ | $L_{C1139}$ | $R^{D41}$ | $R^{D19}$ | $R^{D1}$ |
| $L_{C300}$ | $R^{D11}$ | $R^{D32}$ | H | $L_{C720}$ | $R^{D2}$ | $R^{D8}$ | $R^{D1}$ | $L_{C1140}$ | $R^{D41}$ | $R^{D20}$ | $R^{D1}$ |
| $L_{C301}$ | $R^{D11}$ | $R^{D33}$ | H | $L_{C721}$ | $R^{D2}$ | $R^{D9}$ | $R^{D1}$ | $L_{C1141}$ | $R^{D41}$ | $R^{D21}$ | $R^{D1}$ |
| $L_{C302}$ | $R^{D11}$ | $R^{D34}$ | H | $L_{C722}$ | $R^{D2}$ | $R^{D10}$ | $R^{D1}$ | $L_{C1142}$ | $R^{D41}$ | $R^{D23}$ | $R^{D1}$ |
| $L_{C303}$ | $R^{D11}$ | $R^{D35}$ | H | $L_{C723}$ | $R^{D2}$ | $R^{D11}$ | $R^{D1}$ | $L_{C1143}$ | $R^{D41}$ | $R^{D24}$ | $R^{D1}$ |
| $L_{C304}$ | $R^{D11}$ | $R^{D40}$ | H | $L_{C724}$ | $R^{D2}$ | $R^{D12}$ | $R^{D1}$ | $L_{C1144}$ | $R^{D41}$ | $R^{D25}$ | $R^{D1}$ |
| $L_{C305}$ | $R^{D11}$ | $R^{D41}$ | H | $L_{C725}$ | $R^{D2}$ | $R^{D13}$ | $R^{D1}$ | $L_{C1145}$ | $R^{D41}$ | $R^{D27}$ | $R^{D1}$ |
| $L_{C306}$ | $R^{D11}$ | $R^{D42}$ | H | $L_{C726}$ | $R^{D2}$ | $R^{D14}$ | $R^{D1}$ | $L_{C1146}$ | $R^{D41}$ | $R^{D28}$ | $R^{D1}$ |
| $L_{C307}$ | $R^{D11}$ | $R^{D64}$ | H | $L_{C727}$ | $R^{D2}$ | $R^{D15}$ | $R^{D1}$ | $L_{C1147}$ | $R^{D41}$ | $R^{D29}$ | $R^{D1}$ |

-continued

| Ligand | R¹ | R² | R³ | Ligand | R¹ | R² | R³ | Ligand | R¹ | R² | R³ |
|---|---|---|---|---|---|---|---|---|---|---|---|
| $L_{C308}$ | $R^{D11}$ | $R^{D66}$ | H | $L_{C728}$ | $R^{D2}$ | $R^{D16}$ | $R^{D1}$ | $L_{C1148}$ | $R^{D41}$ | $R^{D30}$ | $R^{D1}$ |
| $L_{C309}$ | $R^{D11}$ | $R^{D68}$ | H | $L_{C729}$ | $R^{D2}$ | $R^{D17}$ | $R^{D1}$ | $L_{C1149}$ | $R^{D41}$ | $R^{D31}$ | $R^{D1}$ |
| $L_{C310}$ | $R^{D11}$ | $R^{D76}$ | H | $L_{C730}$ | $R^{D2}$ | $R^{D18}$ | $R^{D1}$ | $L_{C1150}$ | $R^{D41}$ | $R^{D32}$ | $R^{D1}$ |
| $L_{C311}$ | $R^{D13}$ | $R^{D5}$ | H | $L_{C731}$ | $R^{D2}$ | $R^{D19}$ | $R^{D1}$ | $L_{C1151}$ | $R^{D41}$ | $R^{D33}$ | $R^{D1}$ |
| $L_{C312}$ | $R^{D13}$ | $R^{D6}$ | H | $L_{C732}$ | $R^{D2}$ | $R^{D20}$ | $R^{D1}$ | $L_{C1152}$ | $R^{D41}$ | $R^{D34}$ | $R^{D1}$ |
| $L_{C313}$ | $R^{D13}$ | $R^{D9}$ | H | $L_{C733}$ | $R^{D2}$ | $R^{D21}$ | $R^{D1}$ | $L_{C1153}$ | $R^{D41}$ | $R^{D42}$ | $R^{D1}$ |
| $L_{C314}$ | $R^{D13}$ | $R^{D10}$ | H | $L_{C734}$ | $R^{D2}$ | $R^{D22}$ | $R^{D1}$ | $L_{C1154}$ | $R^{D41}$ | $R^{D64}$ | $R^{D1}$ |
| $L_{C315}$ | $R^{D13}$ | $R^{D12}$ | H | $L_{C735}$ | $R^{D2}$ | $R^{D23}$ | $R^{D1}$ | $L_{C1155}$ | $R^{D41}$ | $R^{D66}$ | $R^{D1}$ |
| $L_{C316}$ | $R^{D13}$ | $R^{D14}$ | H | $L_{C736}$ | $R^{D2}$ | $R^{D24}$ | $R^{D1}$ | $L_{C1156}$ | $R^{D41}$ | $R^{D68}$ | $R^{D1}$ |
| $L_{C317}$ | $R^{D13}$ | $R^{D15}$ | H | $L_{C737}$ | $R^{D2}$ | $R^{D25}$ | $R^{D1}$ | $L_{C1157}$ | $R^{D41}$ | $R^{D76}$ | $R^{D1}$ |
| $L_{C318}$ | $R^{D13}$ | $R^{D16}$ | H | $L_{C738}$ | $R^{D2}$ | $R^{D26}$ | $R^{D1}$ | $L_{C1158}$ | $R^{D64}$ | $R^{D5}$ | $R^{D1}$ |
| $L_{C319}$ | $R^{D13}$ | $R^{D17}$ | H | $L_{C739}$ | $R^{D2}$ | $R^{D27}$ | $R^{D1}$ | $L_{C1159}$ | $R^{D64}$ | $R^{D6}$ | $R^{D1}$ |
| $L_{C320}$ | $R^{D13}$ | $R^{D18}$ | H | $L_{C740}$ | $R^{D2}$ | $R^{D28}$ | $R^{D1}$ | $L_{C1160}$ | $R^{D64}$ | $R^{D9}$ | $R^{D1}$ |
| $L_{C321}$ | $R^{D13}$ | $R^{D19}$ | H | $L_{C741}$ | $R^{D2}$ | $R^{D29}$ | $R^{D1}$ | $L_{C1161}$ | $R^{D64}$ | $R^{D10}$ | $R^{D1}$ |
| $L_{C322}$ | $R^{D13}$ | $R^{D20}$ | H | $L_{C742}$ | $R^{D2}$ | $R^{D30}$ | $R^{D1}$ | $L_{C1162}$ | $R^{D64}$ | $R^{D12}$ | $R^{D1}$ |
| $L_{C323}$ | $R^{D13}$ | $R^{D21}$ | H | $L_{C743}$ | $R^{D2}$ | $R^{D31}$ | $R^{D1}$ | $L_{C1163}$ | $R^{D64}$ | $R^{D15}$ | $R^{D1}$ |
| $L_{C324}$ | $R^{D13}$ | $R^{D22}$ | H | $L_{C744}$ | $R^{D2}$ | $R^{D32}$ | $R^{D1}$ | $L_{C1164}$ | $R^{D64}$ | $R^{D16}$ | $R^{D1}$ |
| $L_{C325}$ | $R^{D13}$ | $R^{D23}$ | H | $L_{C745}$ | $R^{D2}$ | $R^{D33}$ | $R^{D1}$ | $L_{C1165}$ | $R^{D64}$ | $R^{D17}$ | $R^{D1}$ |
| $L_{C326}$ | $R^{D13}$ | $R^{D24}$ | H | $L_{C746}$ | $R^{D2}$ | $R^{D34}$ | $R^{D1}$ | $L_{C1166}$ | $R^{D64}$ | $R^{D18}$ | $R^{D1}$ |
| $L_{C327}$ | $R^{D13}$ | $R^{D25}$ | H | $L_{C747}$ | $R^{D2}$ | $R^{D35}$ | $R^{D1}$ | $L_{C1167}$ | $R^{D64}$ | $R^{D19}$ | $R^{D1}$ |
| $L_{C328}$ | $R^{D13}$ | $R^{D26}$ | H | $L_{C748}$ | $R^{D2}$ | $R^{D40}$ | $R^{D1}$ | $L_{C1168}$ | $R^{D64}$ | $R^{D20}$ | $R^{D1}$ |
| $L_{C329}$ | $R^{D13}$ | $R^{D27}$ | H | $L_{C749}$ | $R^{D2}$ | $R^{D41}$ | $R^{D1}$ | $L_{C1169}$ | $R^{D64}$ | $R^{D21}$ | $R^{D1}$ |
| $L_{C330}$ | $R^{D13}$ | $R^{D28}$ | H | $L_{C750}$ | $R^{D2}$ | $R^{D42}$ | $R^{D1}$ | $L_{C1170}$ | $R^{D64}$ | $R^{D23}$ | $R^{D1}$ |
| $L_{C331}$ | $R^{D13}$ | $R^{D29}$ | H | $L_{C751}$ | $R^{D2}$ | $R^{D64}$ | $R^{D1}$ | $L_{C1171}$ | $R^{D64}$ | $R^{D24}$ | $R^{D1}$ |
| $L_{C332}$ | $R^{D13}$ | $R^{D30}$ | H | $L_{C752}$ | $R^{D2}$ | $R^{D66}$ | $R^{D1}$ | $L_{C1172}$ | $R^{D64}$ | $R^{D25}$ | $R^{D1}$ |
| $L_{C333}$ | $R^{D13}$ | $R^{D31}$ | H | $L_{C753}$ | $R^{D2}$ | $R^{D68}$ | $R^{D1}$ | $L_{C1173}$ | $R^{D64}$ | $R^{D27}$ | $R^{D1}$ |
| $L_{C334}$ | $R^{D13}$ | $R^{D32}$ | H | $L_{C754}$ | $R^{D2}$ | $R^{D76}$ | $R^{D1}$ | $L_{C1174}$ | $R^{D64}$ | $R^{D28}$ | $R^{D1}$ |
| $L_{C335}$ | $R^{D13}$ | $R^{D33}$ | H | $L_{C755}$ | $R^{D3}$ | $R^{D4}$ | $R^{D1}$ | $L_{C1175}$ | $R^{D64}$ | $R^{D29}$ | $R^{D1}$ |
| $L_{C336}$ | $R^{D13}$ | $R^{D34}$ | H | $L_{C756}$ | $R^{D3}$ | $R^{D5}$ | $R^{D1}$ | $L_{C1176}$ | $R^{D64}$ | $R^{D30}$ | $R^{D1}$ |
| $L_{C337}$ | $R^{D13}$ | $R^{D35}$ | H | $L_{C757}$ | $R^{D3}$ | $R^{D6}$ | $R^{D1}$ | $L_{C1177}$ | $R^{D64}$ | $R^{D31}$ | $R^{D1}$ |
| $L_{C338}$ | $R^{D13}$ | $R^{D40}$ | H | $L_{C758}$ | $R^{D3}$ | $R^{D7}$ | $R^{D1}$ | $L_{C1178}$ | $R^{D64}$ | $R^{D32}$ | $R^{D1}$ |
| $L_{C339}$ | $R^{D13}$ | $R^{D41}$ | H | $L_{C759}$ | $R^{D3}$ | $R^{D8}$ | $R^{D1}$ | $L_{C1179}$ | $R^{D64}$ | $R^{D33}$ | $R^{D1}$ |
| $L_{C340}$ | $R^{D13}$ | $R^{D42}$ | H | $L_{C760}$ | $R^{D3}$ | $R^{D9}$ | $R^{D1}$ | $L_{C1180}$ | $R^{D64}$ | $R^{D34}$ | $R^{D1}$ |
| $L_{C341}$ | $R^{D13}$ | $R^{D64}$ | H | $L_{C761}$ | $R^{D3}$ | $R^{D10}$ | $R^{D1}$ | $L_{C1181}$ | $R^{D64}$ | $R^{D42}$ | $R^{D1}$ |
| $L_{C342}$ | $R^{D13}$ | $R^{D66}$ | H | $L_{C762}$ | $R^{D3}$ | $R^{D11}$ | $R^{D1}$ | $L_{C1182}$ | $R^{D64}$ | $R^{D64}$ | $R^{D1}$ |
| $L_{C343}$ | $R^{D13}$ | $R^{D68}$ | H | $L_{C763}$ | $R^{D3}$ | $R^{D12}$ | $R^{D1}$ | $L_{C1183}$ | $R^{D64}$ | $R^{D66}$ | $R^{D1}$ |
| $L_{C344}$ | $R^{D13}$ | $R^{D76}$ | H | $L_{C764}$ | $R^{D3}$ | $R^{D13}$ | $R^{D1}$ | $L_{C1184}$ | $R^{D64}$ | $R^{D68}$ | $R^{D1}$ |
| $L_{C345}$ | $R^{D14}$ | $R^{D5}$ | H | $L_{C765}$ | $R^{D3}$ | $R^{D14}$ | $R^{D1}$ | $L_{C1185}$ | $R^{D64}$ | $R^{D76}$ | $R^{D1}$ |
| $L_{C346}$ | $R^{D14}$ | $R^{D6}$ | H | $L_{C766}$ | $R^{D3}$ | $R^{D15}$ | $R^{D1}$ | $L_{C1186}$ | $R^{D66}$ | $R^{D5}$ | $R^{D1}$ |
| $L_{C347}$ | $R^{D14}$ | $R^{D9}$ | H | $L_{C767}$ | $R^{D3}$ | $R^{D16}$ | $R^{D1}$ | $L_{C1187}$ | $R^{D66}$ | $R^{D6}$ | $R^{D1}$ |
| $L_{C348}$ | $R^{D14}$ | $R^{D10}$ | H | $L_{C768}$ | $R^{D3}$ | $R^{D17}$ | $R^{D1}$ | $L_{C1188}$ | $R^{D66}$ | $R^{D9}$ | $R^{D1}$ |
| $L_{C349}$ | $R^{D14}$ | $R^{D12}$ | H | $L_{C769}$ | $R^{D3}$ | $R^{D18}$ | $R^{D1}$ | $L_{C1189}$ | $R^{D66}$ | $R^{D10}$ | $R^{D1}$ |
| $L_{C350}$ | $R^{D14}$ | $R^{D15}$ | H | $L_{C770}$ | $R^{D3}$ | $R^{D19}$ | $R^{D1}$ | $L_{C1190}$ | $R^{D66}$ | $R^{D12}$ | $R^{D1}$ |
| $L_{C351}$ | $R^{D14}$ | $R^{D16}$ | H | $L_{C771}$ | $R^{D3}$ | $R^{D20}$ | $R^{D1}$ | $L_{C1191}$ | $R^{D66}$ | $R^{D15}$ | $R^{D1}$ |
| $L_{C352}$ | $R^{D14}$ | $R^{D17}$ | H | $L_{C772}$ | $R^{D3}$ | $R^{D21}$ | $R^{D1}$ | $L_{C1192}$ | $R^{D66}$ | $R^{D16}$ | $R^{D1}$ |
| $L_{C353}$ | $R^{D14}$ | $R^{D18}$ | H | $L_{C773}$ | $R^{D3}$ | $R^{D22}$ | $R^{D1}$ | $L_{C1193}$ | $R^{D66}$ | $R^{D17}$ | $R^{D1}$ |
| $L_{C354}$ | $R^{D14}$ | $R^{D19}$ | H | $L_{C774}$ | $R^{D3}$ | $R^{D23}$ | $R^{D1}$ | $L_{C1194}$ | $R^{D66}$ | $R^{D18}$ | $R^{D1}$ |
| $L_{C355}$ | $R^{D14}$ | $R^{D20}$ | H | $L_{C775}$ | $R^{D3}$ | $R^{D24}$ | $R^{D1}$ | $L_{C1195}$ | $R^{D66}$ | $R^{D19}$ | $R^{D1}$ |
| $L_{C356}$ | $R^{D14}$ | $R^{D21}$ | H | $L_{C776}$ | $R^{D3}$ | $R^{D25}$ | $R^{D1}$ | $L_{C1196}$ | $R^{D66}$ | $R^{D20}$ | $R^{D1}$ |
| $L_{C357}$ | $R^{D14}$ | $R^{D22}$ | H | $L_{C777}$ | $R^{D3}$ | $R^{D26}$ | $R^{D1}$ | $L_{C1197}$ | $R^{D66}$ | $R^{D21}$ | $R^{D1}$ |
| $L_{C358}$ | $R^{D14}$ | $R^{D23}$ | H | $L_{C778}$ | $R^{D3}$ | $R^{D27}$ | $R^{D1}$ | $L_{C1198}$ | $R^{D66}$ | $R^{D23}$ | $R^{D1}$ |
| $L_{C359}$ | $R^{D14}$ | $R^{D24}$ | H | $L_{C779}$ | $R^{D3}$ | $R^{D28}$ | $R^{D1}$ | $L_{C1199}$ | $R^{D66}$ | $R^{D24}$ | $R^{D1}$ |
| $L_{C360}$ | $R^{D14}$ | $R^{D25}$ | H | $L_{C780}$ | $R^{D3}$ | $R^{D29}$ | $R^{D1}$ | $L_{C1200}$ | $R^{D66}$ | $R^{D25}$ | $R^{D1}$ |
| $L_{C361}$ | $R^{D14}$ | $R^{D26}$ | H | $L_{C781}$ | $R^{D3}$ | $R^{D30}$ | $R^{D1}$ | $L_{C1201}$ | $R^{D66}$ | $R^{D27}$ | $R^{D1}$ |
| $L_{C362}$ | $R^{D14}$ | $R^{D27}$ | H | $L_{C782}$ | $R^{D3}$ | $R^{D31}$ | $R^{D1}$ | $L_{C1202}$ | $R^{D66}$ | $R^{D28}$ | $R^{D1}$ |
| $L_{C363}$ | $R^{D14}$ | $R^{D28}$ | H | $L_{C783}$ | $R^{D3}$ | $R^{D32}$ | $R^{D1}$ | $L_{C1203}$ | $R^{D66}$ | $R^{D29}$ | $R^{D1}$ |
| $L_{C364}$ | $R^{D14}$ | $R^{D29}$ | H | $L_{C784}$ | $R^{D3}$ | $R^{D33}$ | $R^{D1}$ | $L_{C1204}$ | $R^{D66}$ | $R^{D30}$ | $R^{D1}$ |
| $L_{C365}$ | $R^{D14}$ | $R^{D30}$ | H | $L_{C785}$ | $R^{D3}$ | $R^{D34}$ | $R^{D1}$ | $L_{C1205}$ | $R^{D66}$ | $R^{D31}$ | $R^{D1}$ |
| $L_{C366}$ | $R^{D14}$ | $R^{D31}$ | H | $L_{C786}$ | $R^{D3}$ | $R^{D35}$ | $R^{D1}$ | $L_{C1206}$ | $R^{D66}$ | $R^{D32}$ | $R^{D1}$ |
| $L_{C367}$ | $R^{D14}$ | $R^{D32}$ | H | $L_{C787}$ | $R^{D3}$ | $R^{D40}$ | $R^{D1}$ | $L_{C1207}$ | $R^{D66}$ | $R^{D33}$ | $R^{D1}$ |
| $L_{C368}$ | $R^{D14}$ | $R^{D33}$ | H | $L_{C788}$ | $R^{D3}$ | $R^{D41}$ | $R^{D1}$ | $L_{C1208}$ | $R^{D66}$ | $R^{D34}$ | $R^{D1}$ |
| $L_{C369}$ | $R^{D14}$ | $R^{D34}$ | H | $L_{C789}$ | $R^{D3}$ | $R^{D42}$ | $R^{D1}$ | $L_{C1209}$ | $R^{D66}$ | $R^{D42}$ | $R^{D1}$ |
| $L_{C370}$ | $R^{D14}$ | $R^{D35}$ | H | $L_{C790}$ | $R^{D3}$ | $R^{D64}$ | $R^{D1}$ | $L_{C1210}$ | $R^{D66}$ | $R^{D68}$ | $R^{D1}$ |
| $L_{C371}$ | $R^{D14}$ | $R^{D40}$ | H | $L_{C791}$ | $R^{D3}$ | $R^{D66}$ | $R^{D1}$ | $L_{C1211}$ | $R^{D66}$ | $R^{D76}$ | $R^{D1}$ |
| $L_{C372}$ | $R^{D14}$ | $R^{D41}$ | H | $L_{C792}$ | $R^{D3}$ | $R^{D68}$ | $R^{D1}$ | $L_{C1212}$ | $R^{D68}$ | $R^{D5}$ | $R^{D1}$ |
| $L_{C373}$ | $R^{D14}$ | $R^{D42}$ | H | $L_{C793}$ | $R^{D3}$ | $R^{D76}$ | $R^{D1}$ | $L_{C1213}$ | $R^{D68}$ | $R^{D6}$ | $R^{D1}$ |
| $L_{C374}$ | $R^{D14}$ | $R^{D64}$ | H | $L_{C794}$ | $R^{D4}$ | $R^{D5}$ | $R^{D1}$ | $L_{C1214}$ | $R^{D68}$ | $R^{D9}$ | $R^{D1}$ |
| $L_{C375}$ | $R^{D14}$ | $R^{D66}$ | H | $L_{C795}$ | $R^{D4}$ | $R^{D6}$ | $R^{D1}$ | $L_{C1215}$ | $R^{D68}$ | $R^{D10}$ | $R^{D1}$ |
| $L_{C376}$ | $R^{D14}$ | $R^{D68}$ | H | $L_{C796}$ | $R^{D4}$ | $R^{D7}$ | $R^{D1}$ | $L_{C1216}$ | $R^{D68}$ | $R^{D12}$ | $R^{D1}$ |
| $L_{C377}$ | $R^{D14}$ | $R^{D76}$ | H | $L_{C797}$ | $R^{D4}$ | $R^{D8}$ | $R^{D1}$ | $L_{C1217}$ | $R^{D68}$ | $R^{D15}$ | $R^{D1}$ |
| $L_{C378}$ | $R^{D22}$ | $R^{D5}$ | H | $L_{C798}$ | $R^{D4}$ | $R^{D9}$ | $R^{D1}$ | $L_{C1218}$ | $R^{D68}$ | $R^{D16}$ | $R^{D1}$ |
| $L_{C379}$ | $R^{D22}$ | $R^{D6}$ | H | $L_{C799}$ | $R^{D4}$ | $R^{D10}$ | $R^{D1}$ | $L_{C1219}$ | $R^{D68}$ | $R^{D17}$ | $R^{D1}$ |
| $L_{C380}$ | $R^{D22}$ | $R^{D9}$ | H | $L_{C800}$ | $R^{D4}$ | $R^{D11}$ | $R^{D1}$ | $L_{C1220}$ | $R^{D68}$ | $R^{D18}$ | $R^{D1}$ |
| $L_{C381}$ | $R^{D22}$ | $R^{D10}$ | H | $L_{C801}$ | $R^{D4}$ | $R^{D12}$ | $R^{D1}$ | $L_{C1221}$ | $R^{D68}$ | $R^{D19}$ | $R^{D1}$ |
| $L_{C382}$ | $R^{D22}$ | $R^{D12}$ | H | $L_{C802}$ | $R^{D4}$ | $R^{D13}$ | $R^{D1}$ | $L_{C1222}$ | $R^{D68}$ | $R^{D20}$ | $R^{D1}$ |
| $L_{C383}$ | $R^{D22}$ | $R^{D15}$ | H | $L_{C803}$ | $R^{D4}$ | $R^{D14}$ | $R^{D1}$ | $L_{C1223}$ | $R^{D68}$ | $R^{D21}$ | $R^{D1}$ |
| $L_{C384}$ | $R^{D22}$ | $R^{D16}$ | H | $L_{C804}$ | $R^{D4}$ | $R^{D15}$ | $R^{D1}$ | $L_{C1224}$ | $R^{D68}$ | $R^{D23}$ | $R^{D1}$ |

-continued

| Ligand | R¹ | R² | R³ | Ligand | R¹ | R² | R³ | Ligand | R¹ | R² | R³ |
|---|---|---|---|---|---|---|---|---|---|---|---|
| $L_{C385}$ | $R^{D22}$ | $R^{D17}$ | H | $L_{C805}$ | $R^{D4}$ | $R^{D16}$ | $R^{D1}$ | $L_{C1225}$ | $R^{D68}$ | $R^{D24}$ | $R^{D1}$ |
| $L_{C386}$ | $R^{D22}$ | $R^{D18}$ | H | $L_{C806}$ | $R^{D4}$ | $R^{D17}$ | $R^{D1}$ | $L_{C1226}$ | $R^{D68}$ | $R^{D25}$ | $R^{D1}$ |
| $L_{C387}$ | $R^{D22}$ | $R^{D19}$ | H | $L_{C807}$ | $R^{D4}$ | $R^{D18}$ | $R^{D1}$ | $L_{C1227}$ | $R^{D68}$ | $R^{D27}$ | $R^{D1}$ |
| $L_{C388}$ | $R^{D22}$ | $R^{D20}$ | H | $L_{C808}$ | $R^{D4}$ | $R^{D19}$ | $R^{D1}$ | $L_{C1228}$ | $R^{D68}$ | $R^{D28}$ | $R^{D1}$ |
| $L_{C389}$ | $R^{D22}$ | $R^{D21}$ | H | $L_{C809}$ | $R^{D4}$ | $R^{D20}$ | $R^{D1}$ | $L_{C1229}$ | $R^{D68}$ | $R^{D29}$ | $R^{D1}$ |
| $L_{C390}$ | $R^{D22}$ | $R^{D23}$ | H | $L_{C810}$ | $R^{D4}$ | $R^{D21}$ | $R^{D1}$ | $L_{C1230}$ | $R^{D68}$ | $R^{D30}$ | $R^{D1}$ |
| $L_{C391}$ | $R^{D22}$ | $R^{D24}$ | H | $L_{C811}$ | $R^{D4}$ | $R^{D22}$ | $R^{D1}$ | $L_{C1231}$ | $R^{D68}$ | $R^{D31}$ | $R^{D1}$ |
| $L_{C392}$ | $R^{D22}$ | $R^{D25}$ | H | $L_{C812}$ | $R^{D4}$ | $R^{D23}$ | $R^{D1}$ | $L_{C1232}$ | $R^{D68}$ | $R^{D32}$ | $R^{D1}$ |
| $L_{C393}$ | $R^{D22}$ | $R^{D26}$ | H | $L_{C813}$ | $R^{D4}$ | $R^{D24}$ | $R^{D1}$ | $L_{C1233}$ | $R^{D68}$ | $R^{D33}$ | $R^{D1}$ |
| $L_{C394}$ | $R^{D22}$ | $R^{D27}$ | H | $L_{C814}$ | $R^{D4}$ | $R^{D25}$ | $R^{D1}$ | $L_{C1234}$ | $R^{D68}$ | $R^{D34}$ | $R^{D1}$ |
| $L_{C395}$ | $R^{D22}$ | $R^{D28}$ | H | $L_{C815}$ | $R^{D4}$ | $R^{D26}$ | $R^{D1}$ | $L_{C1235}$ | $R^{D68}$ | $R^{D42}$ | $R^{D1}$ |
| $L_{C396}$ | $R^{D22}$ | $R^{D29}$ | H | $L_{C816}$ | $R^{D4}$ | $R^{D27}$ | $R^{D1}$ | $L_{C1236}$ | $R^{D68}$ | $R^{D76}$ | $R^{D1}$ |
| $L_{C397}$ | $R^{D22}$ | $R^{D30}$ | H | $L_{C817}$ | $R^{D4}$ | $R^{D28}$ | $R^{D1}$ | $L_{C1237}$ | $R^{D76}$ | $R^{D5}$ | $R^{D1}$ |
| $L_{C398}$ | $R^{D22}$ | $R^{D31}$ | H | $L_{C818}$ | $R^{D4}$ | $R^{D29}$ | $R^{D1}$ | $L_{C1238}$ | $R^{D76}$ | $R^{D6}$ | $R^{D1}$ |
| $L_{C399}$ | $R^{D22}$ | $R^{D32}$ | H | $L_{C819}$ | $R^{D4}$ | $R^{D30}$ | $R^{D1}$ | $L_{C1239}$ | $R^{D76}$ | $R^{D9}$ | $R^{D1}$ |
| $L_{C400}$ | $R^{D22}$ | $R^{D33}$ | H | $L_{C820}$ | $R^{D4}$ | $R^{D31}$ | $R^{D1}$ | $L_{C1240}$ | $R^{D76}$ | $R^{D10}$ | $R^{D1}$ |
| $L_{C401}$ | $R^{D22}$ | $R^{D34}$ | H | $L_{C821}$ | $R^{D4}$ | $R^{D32}$ | $R^{D1}$ | $L_{C1241}$ | $R^{D76}$ | $R^{D12}$ | $R^{D1}$ |
| $L_{C402}$ | $R^{D22}$ | $R^{D35}$ | H | $L_{C822}$ | $R^{D4}$ | $R^{D33}$ | $R^{D1}$ | $L_{C1242}$ | $R^{D76}$ | $R^{D15}$ | $R^{D1}$ |
| $L_{C403}$ | $R^{D22}$ | $R^{D40}$ | H | $L_{C823}$ | $R^{D4}$ | $R^{D34}$ | $R^{D1}$ | $L_{C1243}$ | $R^{D76}$ | $R^{D16}$ | $R^{D1}$ |
| $L_{C404}$ | $R^{D22}$ | $R^{D41}$ | H | $L_{C824}$ | $R^{D4}$ | $R^{D35}$ | $R^{D1}$ | $L_{C1244}$ | $R^{D76}$ | $R^{D17}$ | $R^{D1}$ |
| $L_{C405}$ | $R^{D22}$ | $R^{D42}$ | H | $L_{C825}$ | $R^{D4}$ | $R^{D40}$ | $R^{D1}$ | $L_{C1245}$ | $R^{D76}$ | $R^{D18}$ | $R^{D1}$ |
| $L_{C406}$ | $R^{D22}$ | $R^{D64}$ | H | $L_{C826}$ | $R^{D4}$ | $R^{D41}$ | $R^{D1}$ | $L_{C1246}$ | $R^{D76}$ | $R^{D19}$ | $R^{D1}$ |
| $L_{C407}$ | $R^{D22}$ | $R^{D66}$ | H | $L_{C827}$ | $R^{D4}$ | $R^{D42}$ | $R^{D1}$ | $L_{C1247}$ | $R^{D76}$ | $R^{D20}$ | $R^{D1}$ |
| $L_{C408}$ | $R^{D22}$ | $R^{D68}$ | H | $L_{C828}$ | $R^{D4}$ | $R^{D64}$ | $R^{D1}$ | $L_{C1248}$ | $R^{D76}$ | $R^{D21}$ | $R^{D1}$ |
| $L_{C409}$ | $R^{D22}$ | $R^{D76}$ | H | $L_{C829}$ | $R^{D4}$ | $R^{D66}$ | $R^{D1}$ | $L_{C1249}$ | $R^{D76}$ | $R^{D23}$ | $R^{D1}$ |
| $L_{C410}$ | $RD^{26}$ | $R^{D5}$ | H | $L_{C830}$ | $R^{D4}$ | $R^{D68}$ | $R^{D1}$ | $L_{C1250}$ | $R^{D76}$ | $R^{D24}$ | $R^{D1}$ |
| $L_{C411}$ | $RD^{26}$ | $R^{D6}$ | H | $L_{C831}$ | $R^{D4}$ | $R^{D76}$ | $R^{D1}$ | $L_{C1251}$ | $R^{D76}$ | $R^{D25}$ | $R^{D1}$ |
| $L_{C412}$ | $RD^{26}$ | $R^{D9}$ | H | $L_{C832}$ | $R^{D4}$ | $R^{D1}$ | $R^{D1}$ | $L_{C1252}$ | $R^{D76}$ | $R^{D27}$ | $R^{D1}$ |
| $L_{C413}$ | $RD^{26}$ | $R^{D10}$ | H | $L_{C833}$ | $R^{D7}$ | $R^{D5}$ | $R^{D1}$ | $L_{C1253}$ | $R^{D76}$ | $R^{D28}$ | $R^{D1}$ |
| $L_{C414}$ | $RD^{26}$ | $R^{D12}$ | H | $L_{C834}$ | $R^{D7}$ | $R^{D6}$ | $R^{D1}$ | $L_{C1254}$ | $R^{D76}$ | $R^{D29}$ | $R^{D1}$ |
| $L_{C415}$ | $RD^{26}$ | $R^{D15}$ | H | $L_{C835}$ | $R^{D7}$ | $R^{D8}$ | $R^{D1}$ | $L_{C1255}$ | $R^{D76}$ | $R^{D30}$ | $R^{D1}$ |
| $L_{C416}$ | $RD^{26}$ | $R^{D16}$ | H | $L_{C836}$ | $R^{D7}$ | $R^{D9}$ | $R^{D1}$ | $L_{C1256}$ | $R^{D76}$ | $R^{D31}$ | $R^{D1}$ |
| $L_{C417}$ | $RD^{26}$ | $R^{D17}$ | H | $L_{C837}$ | $R^{D7}$ | $R^{D10}$ | $R^{D1}$ | $L_{C1257}$ | $R^{D76}$ | $R^{D32}$ | $R^{D1}$ |
| $L_{C418}$ | $RD^{26}$ | $R^{D18}$ | H | $L_{C838}$ | $R^{D7}$ | $R^{D11}$ | $R^{D1}$ | $L_{C1258}$ | $R^{D76}$ | $R^{D33}$ | $R^{D1}$ |
| $L_{C419}$ | $RD^{26}$ | $R^{D19}$ | H | $L_{C839}$ | $R^{D7}$ | $R^{D12}$ | $R^{D1}$ | $L_{C1259}$ | $R^{D76}$ | $R^{D34}$ | $R^{D1}$ |
| $L_{C420}$ | $RD^{26}$ | $R^{D20}$ | H | $L_{C840}$ | $R^{D7}$ | $R^{D13}$ | $R^{D1}$ | $L_{C1260}$ | $R^{D76}$ | $R^{D42}$ | $R^{D1}$ | wherein $R^{D1}$ to $R^{D21}$ have the following structures:

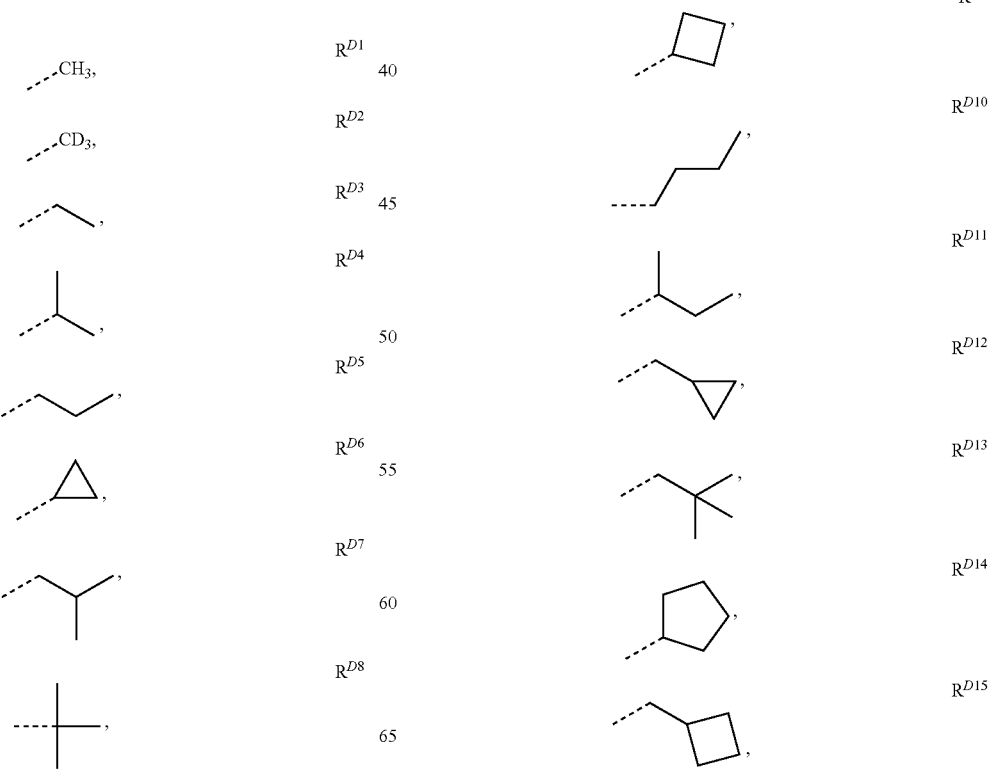

-continued
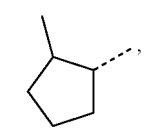
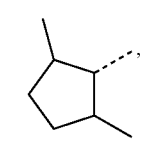
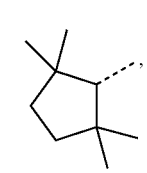
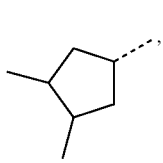
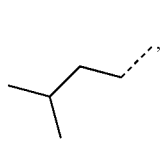
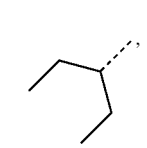
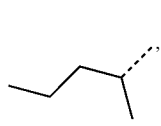
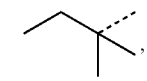
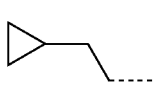
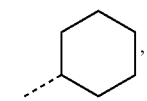
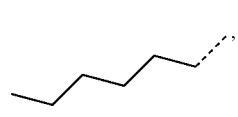
-continued
$R^{D16}$
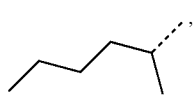
$R^{D17}$
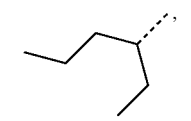
$R^{D18}$
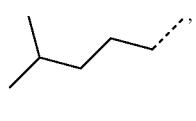
$R^{D19}$
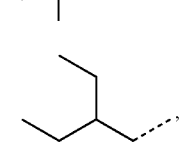
$R^{D20}$
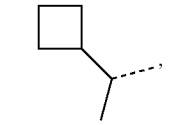
$R^{D21}$
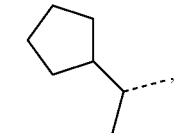
$R^{D22}$
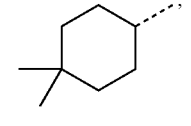
$R^{D23}$
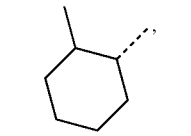
$R^{D24}$
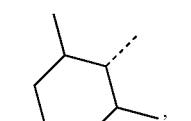
$R^{D25}$
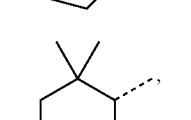
$R^{D26}$
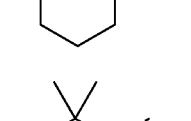
$R^{D27}$
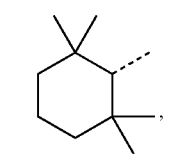
$R^{D28}$
$R^{D29}$
$R^{D30}$
$R^{D31}$
$R^{D32}$
$R^{D33}$
$R^{D34}$
$R^{D35}$
$R^{D36}$
$R^{D37}$
$R^{D38}$
$R^{D39}$

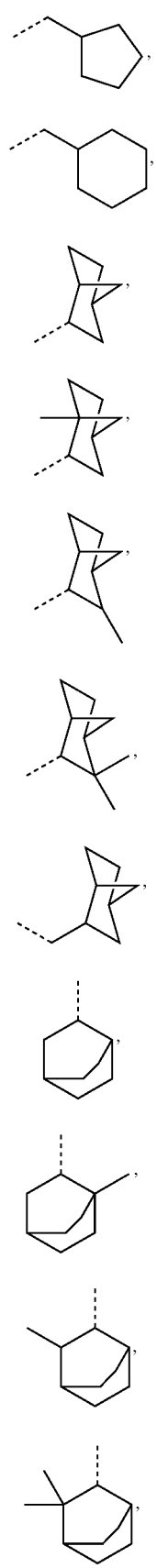
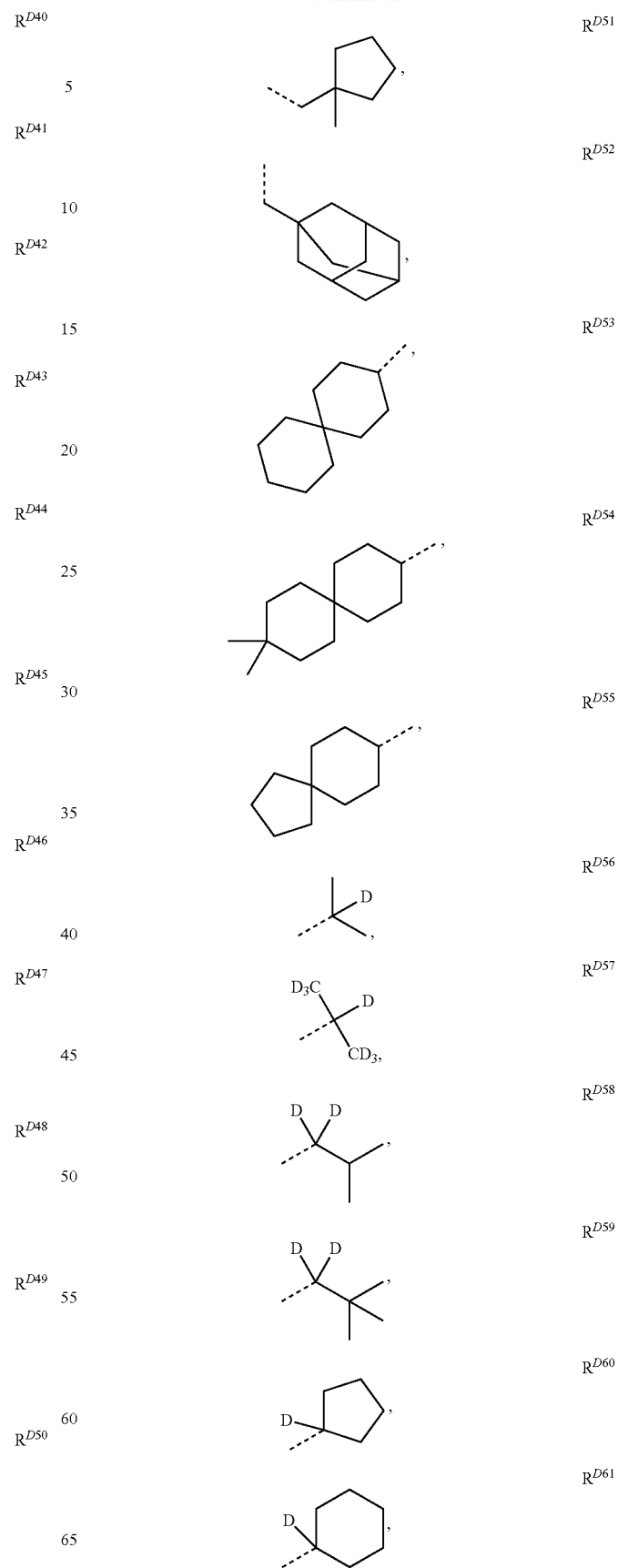

-continued

R^{D62} 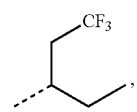

R^{D62} 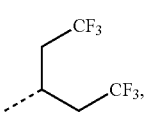

R^{D63} ----CF₃,

R^{D64} 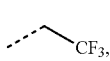

R^{D65} 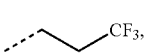

R^{D66} 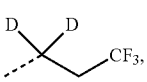

R^{D67} 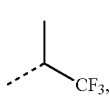

R^{D68} 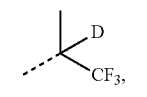

R^{D69} 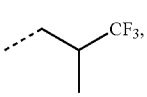

R^{D70} 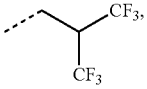

R^{D71} 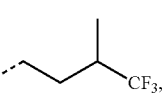

-continued

R^{D72} 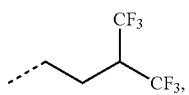

R^{D73} 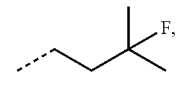

R^{D74} 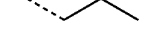

R^{D75} 

R^{D76} 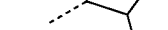

R^{D77} 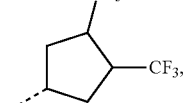

R^{D78} 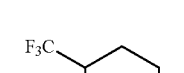

R^{D79} 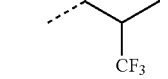

R^{D80} 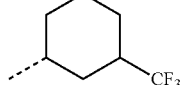

R^{D81} 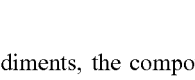

In some embodiments, the compound can have the formula Pt(L$_A$) or the formula Pd(L$_A$), wherein the ligand L$_A$ can be selected from the group consisting of the structures defined in LIST 5 below:

| Name of ligand L$_A$ | Structure | i, j, l, k |
|---|---|---|
| L$_A$XIX-[(i)(j)(k)(l)] having the structure | 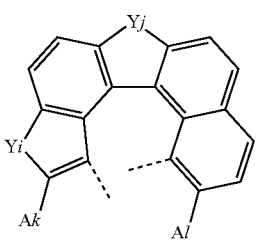 | wherein i and j are independently an integer from 1 to 30, and k and l are independently an integer from 1 to 200, and |

| Name of ligand L$_A$ | Structure | i, j, l, k |
|---|---|---|
| L$_A$XX-[(i)(j)(k)(l)] having the structure | 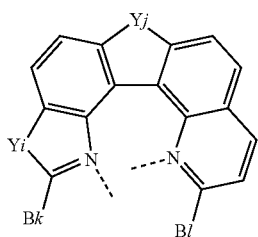 | wherein i and j are independently an integer from 1 to 30, and k and l are independently an integer from 1 to 50, and |
| L$_A$XXI-[(i)(j)(k)(l)] having the structure | 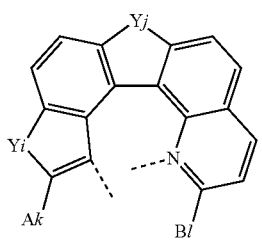 | wherein i and j are independently an integer from 1 to 30, k is an integer from 1 to 200, and l is an integer from 1 to 50, and |
| L$_A$XXII-[(i)(j)Bk)(l)] having the structure | 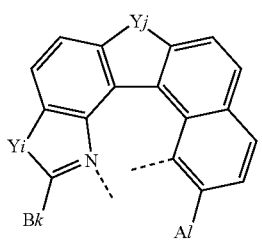 | wherein i and j are independently an integer from 1 to 30, k is an integer from 1 to 50, and l is an integer from 1 to 200, and |
| L$_A$XXIII-[(i)(j)(k)(l)] having the structure | 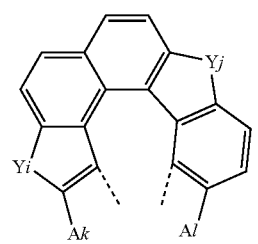 | wherein i and j are independently an integer from 1 to 30, and k and l are independently an integer from 1 to 200, and |
| L$_A$XXIV-[(i)(j)(k)(l)] having the structure | 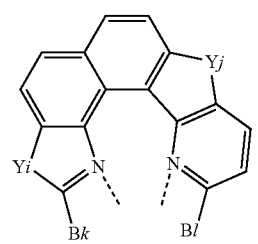 | wherein i and j are independently an integer from 1 to 30, and k and l are independently an integer from 1 to 50, and |
| L$_A$XXV-[(i)(j)(k)(l)] having the structure | 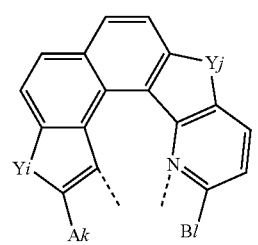 | wherein i and j are independently an integer from 1 to 30, k is an integer from 1 to 200, and l is an integer from 1 to 50, and |

| Name of ligand $L_A$ | Structure | i, j, l, k |
|---|---|---|
| $L_A$XXVI-[(i)(j)(k)(l)] having the structure | 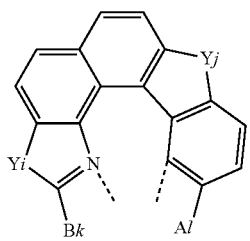 | wherein i and j are independently an integer from 1 to 30, k is an integer from 1 to 50, and l is an integer from 1 to 200, and |
| $L_A$XXVII-[(i)(j)(k)(l)] having the structure | 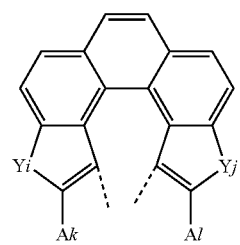 | wherein i and j are independently an integer from 1 to 30, and k and l are independently an integer from 1 to 200, and |
| $L_A$XXVIII-[(i)(j)(k)(l)] having the structure | 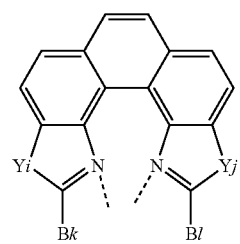 | wherein i and j are independently an integer from 1 to 30, and k and l are independently an integer from 1 to 50, and |
| $L_A$XXIX-[(i)(j)(k)(l)] having the structure | 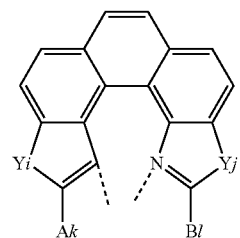 | wherein i and j are independently an integer from 1 to 30, k is an integer from 1 to 200, and l is an integer from 1 to 50, and |
| $L_A$XXX-[(i)(k)(l)] having the structure | 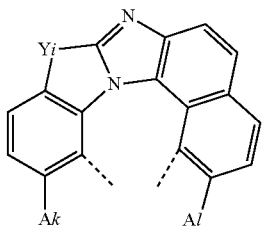 | wherein i is an integer from 1 to 30, and k and l are independently an integer from 1 to 200, and |
| $L_A$XXXI-[(i)(k)(l)] having the structure | 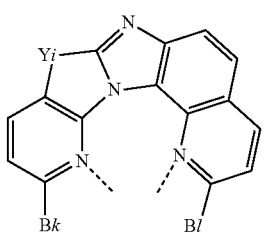 | wherein i is an integer from 1 to 30, and k and l are independently an integer from 1 to 50, and |

| Name of ligand $L_A$ | Structure | i, j, l, k |
|---|---|---|
| $L_A$XXXII-[(i)(k)(l)] having the structure | 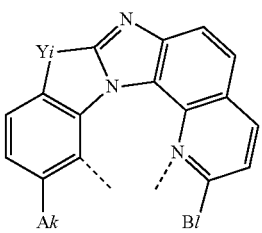 | wherein i is an integer from 1 to 30, k is an integer from 1 to 200, and l is an integer from 1 to 50, and |
| $L_A$XXXIII-[(i)(k)(l)] having the structure | 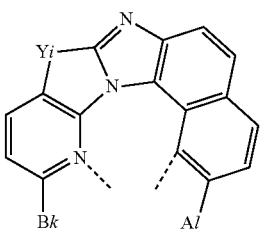 | wherein i is an integer from 1 to 30, k is an integer from 1 to 50, and l is an integer from 1 to 200, and |
| $L_A$XXXIV-[(i)(k)(l)] having the structure | 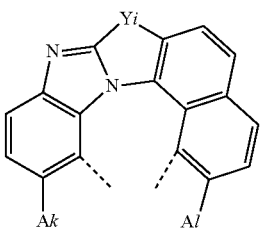 | wherein i is an integer from 1 to 30, and k and l are independently an integer from 1 to 200, and |
| $L_A$XXXV-[(i)(k)(l)] having the structure | 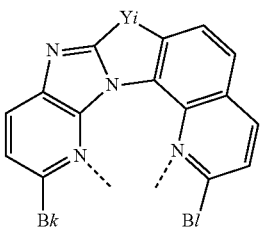 | wherein i is an integer from 1 to 30, and k and l are independently an integer from 1 to 50, and |
| $L_A$XXXVI-[(i)(k)(l)] having the structure | 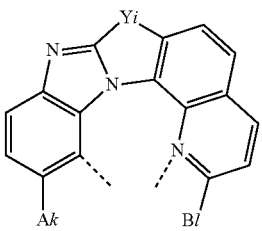 | wherein i is an integer from 1 to 30, k is an integer from 1 to 200, and l is an integer from 1 to 50, and |
| $L_A$XXXVII-[(i)(k)(l)] having the structure | 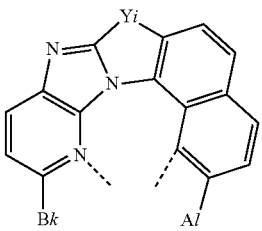 | wherein i is an integer from 1 to 30, k is an integer from 1 to 50, and l is an integer from 1 to 200 and |

| Name of ligand $L_A$ | Structure | i, j, l, k |
|---|---|---|
| $L_A$XXXVIII-[(i)(j)(k)(l)] having the structure | 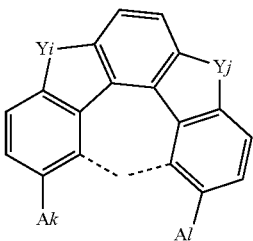 | wherein i and j are independently an integer from 1 to 30, and k and l are independently an integer from 1 to 200, and |
| $L_A$XXXIX-[(i)(j)(k)(l)] having the structure | 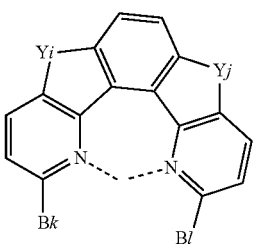 | wherein i and j are independently an integer from 1 to 30, and k and l are independently an integer from 1 to 50, and |
| $L_A$XL-[(i)(j)(k)(l)] having the structure | 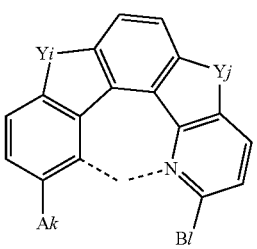 | wherein i and j are independently an integer from 1 to 30, k is an integer from 1 to 200, and l is an integer from 1 to 50, and |
| $L_A$XLI-[(i)(j)(k)(l)(m)] having the structure | 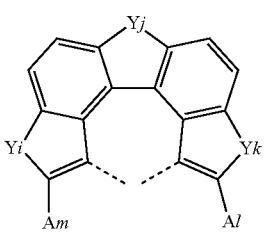 | wherein i, j, and k are independently an integer from 1 to 30, l and m are independently an integer from 1 to 200, and |
| $L_A$XLII-[(i)(j)(k)(l)(m)] having the structure | 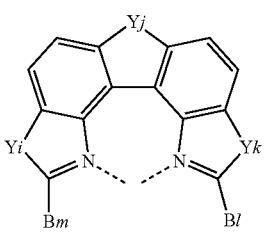 | wherein i, j, and k are independently an integer from 1 to 30, and l and m are independently an integer from 1 to 50, and |
| $L_A$XLIII-[(i)(j)(k)(l)(m)] having the structure | 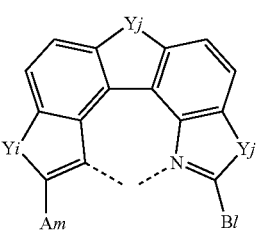 | wherein i, j, and k are independently an integer from 1 to 30, and l is an integer from 1 to 50, and m is an integer from 1 to 200, and |

-continued

| Name of ligand $L_A$ | Structure | i, j, l, k |
|---|---|---|
| $L_A$XLIV-[(i)(j)(k)(l)] having the structure | 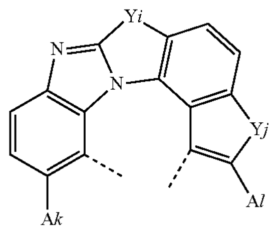 | wherein i and j are independently an integer from 1 to 30, and k and l are independently an integer from 1 to 200, and |
| $L_A$XLV-[(i)(j)(k)(l)] having the structure | 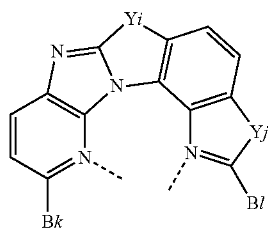 | wherein i and j are independently an integer from 1 to 30, and k and l are independently an integer from 1 to 50, and |
| $L_A$XLVI-[(i)(j)(k)(l)] having the structure | 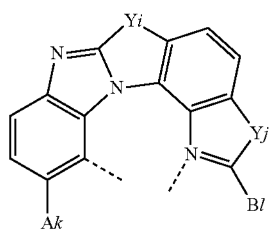 | wherein i and j are independently an integer from 1 to 30, k is an integer from 1 to 200, and l is an integer from 1 to 50, and |
| $L_A$XLVII-[(i)(j)(k)(l)] having the structure | 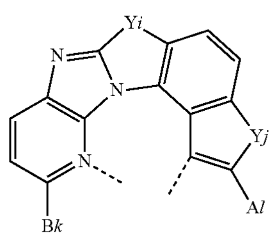 | wherein i and j are independently an integer from 1 to 30, k is an integer from 1 to 50, and l is an integer from 1 to 200, and |
| $L_A$XLVIII-[(i)(j)(k)(l)] having the structure | 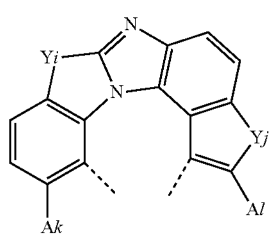 | wherein i and j are independently an integer from 1 to 30, and k and l are independently an integer from 1 to 200, and |
| $L_A$XLIX-[(i)(j)(k)(l)] having the structure | 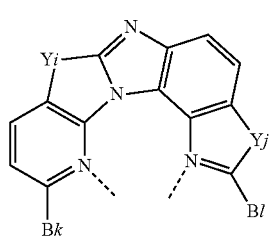 | wherein i and j are independently an integer from 1 to 30, and k and l are independently an integer from 1 to 50, and |

-continued

| Name of ligand $L_A$ | Structure | i, j, l, k |
|---|---|---|
| $L_A$L-[(i)(j)(k)(l)] having the structure | 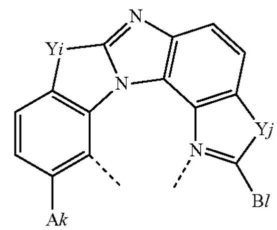 | wherein i and j are independently an integer from 1 to 30, k is an integer from 1 to 200, and l is an integer from 1 to 50, and |
| $L_A$LI-[(i)(j)(k)(l)] having the structure | 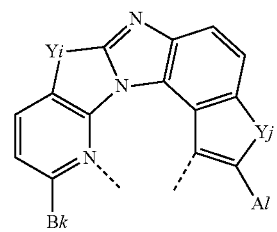 | wherein i and j are independently an integer from 1 to 30, k is an integer from 1 to 50, and l is an integer from 1 to 200, and |
| $L_A$LII-[(i)(j)(k)(l)] having the structure | 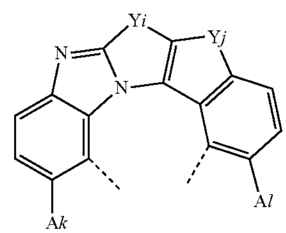 | wherein i and j are independently an integer from 1 to 30, and k and l are independently an integer from 1 to 200, and |
| $L_A$LIII-[(i)(j)(k)(l)] having the structure | 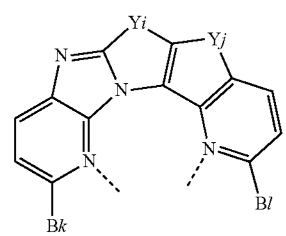 | wherein i and j are independently an integer from 1 to 30, and k and l are independently an integer from 1 to 50, and |
| $L_A$LIV-[(i)(j)(k)(l)] having the structure | 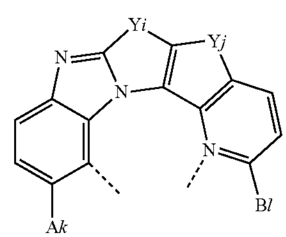 | wherein i and j are independently an integer from 1 to 30, k is an integer from 1 to 200, and l is an integer from 1 to 50, and |
| $L_A$LV-[(i)(j)(k)(l)] having the structure | 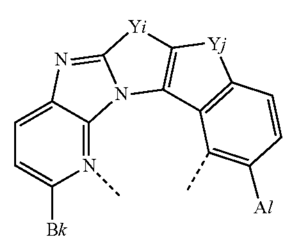 | wherein i and j are independently an integer from 1 to 30, k is an integer from 1 to 50, and l is an integer from 1 to 200, and |

| Name of ligand $L_A$ | Structure | i, j, l, k |
|---|---|---|
| $L_A$LVI-[(i)(j)(k)(l)] having the structure | 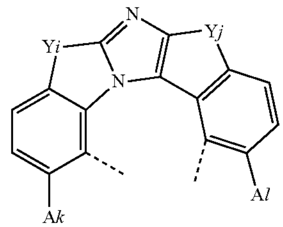 | wherein i and j are independently an integer from 1 to 30, and k and l are independently an integer from 1 to 200, and |
| $L_A$LVII-[(i)(j)(k)(l)] having the structure | 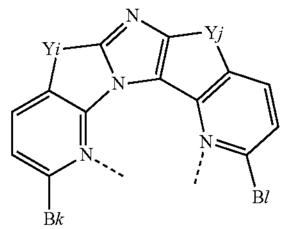 | wherein i and j are independently an integer from 1 to 30, and k and l are an integer from 1 to 50, and |
| $L_A$LVIII-[(i)(j)(k)(l)] having the structure | 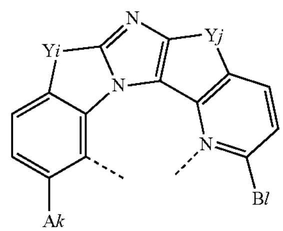 | wherein i and j are independently an integer from 1 to 30, k is an integer from 1 to 200, and l is an integer from 1 to 50, and |
| $L_A$LIX-[(i)(j)(k)(l)] having the structure | | wherein i and j are independently an integer from 1 to 30, k is an integer from 1 to 50, and l is an integer from 1 to 200, and | wherein the structures of Y1 to Y30 are as described above and the structures of A1 to A200 are defined as follows:

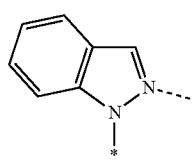
A1

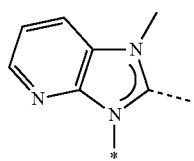
A2

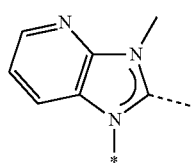
A3

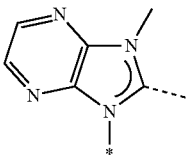
A4

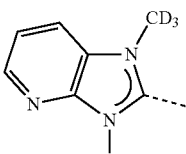
A5

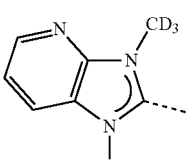
A6

| | |
|---|---|
| 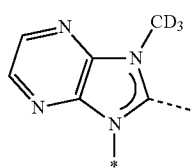 A7 | 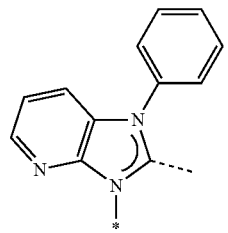 A16 |
| 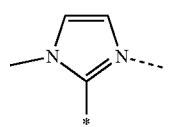 A8 | 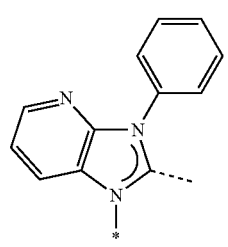 A17 |
| 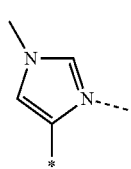 A9 | 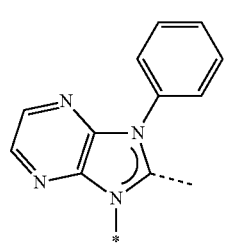 A18 |
| 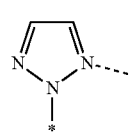 A10 | 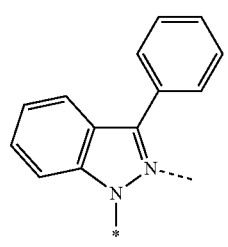 A19 |
| 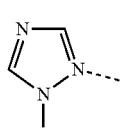 A11 | 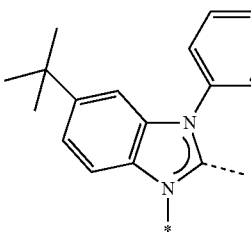 A20 |
| 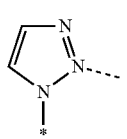 A12 | 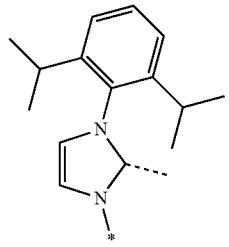 A21 |
| 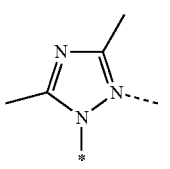 A13 | |
| 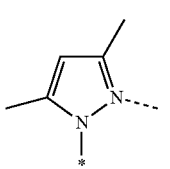 A14 | |
| 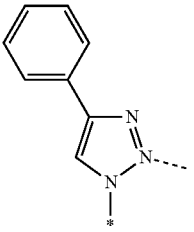 A15 | |

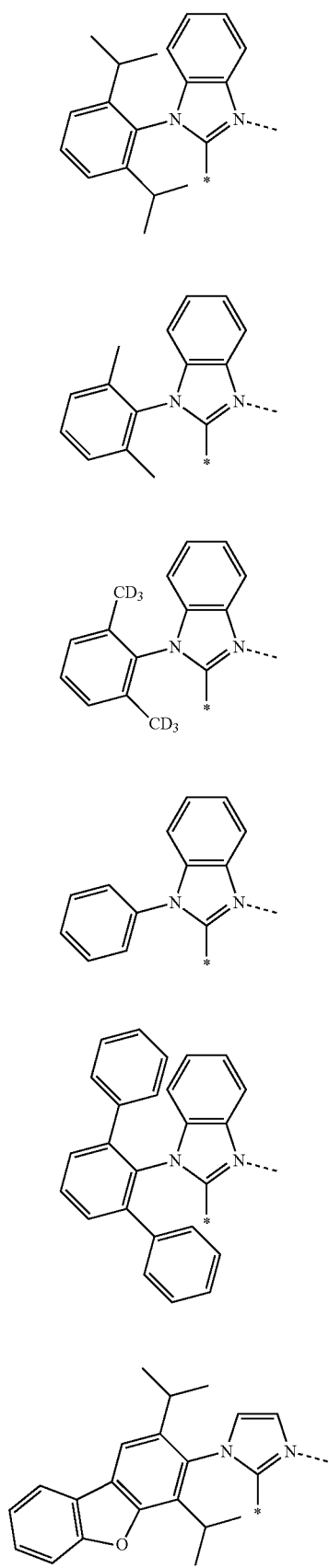
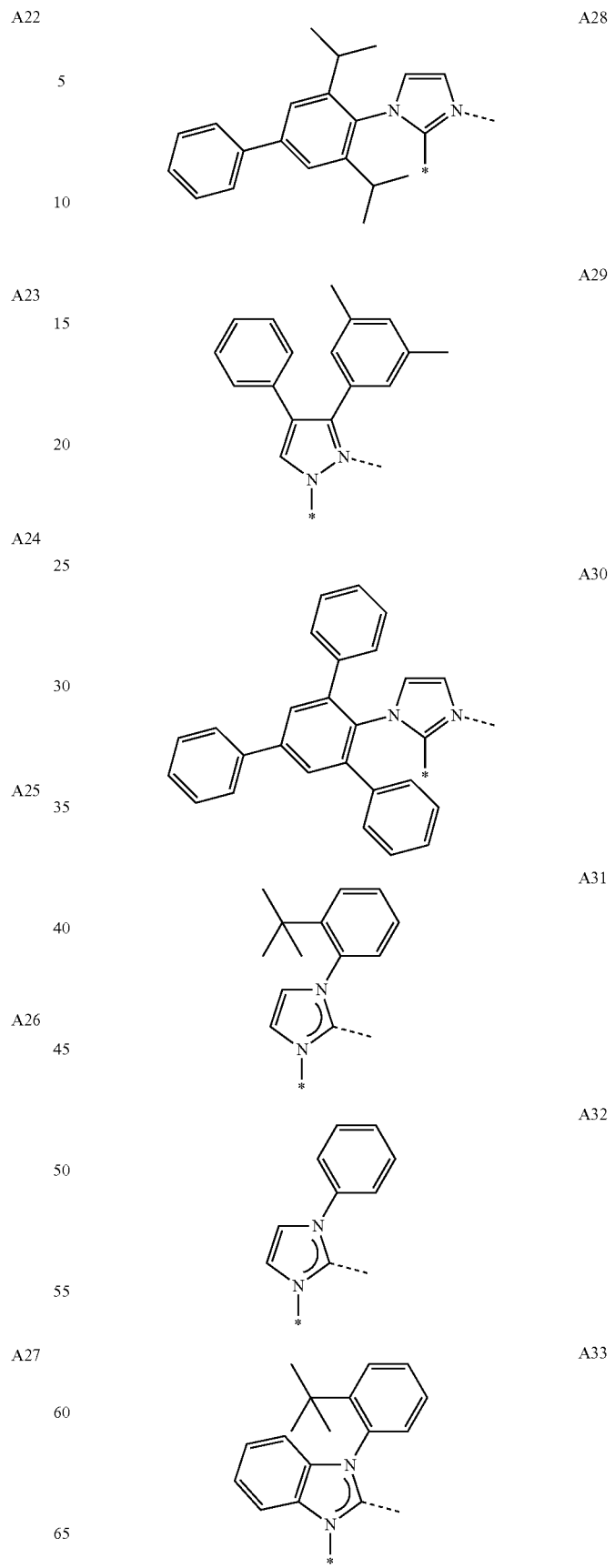

| | |
|---|---|
| 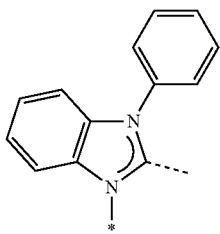 A34 | 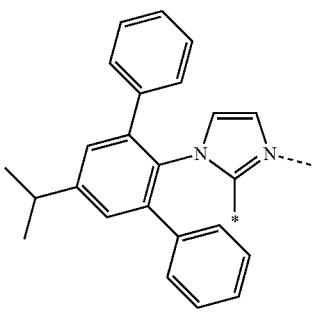 A41 |
| 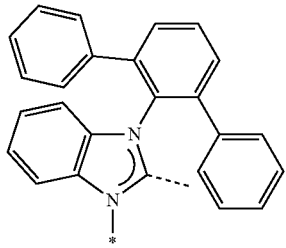 A35 | 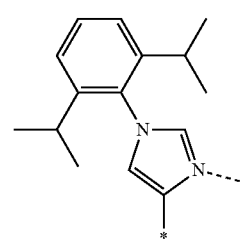 A42 |
| 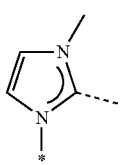 A36 | 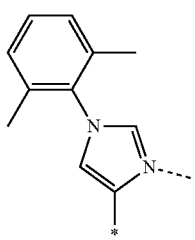 A43 |
| 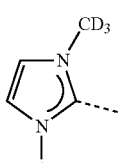 A37 | 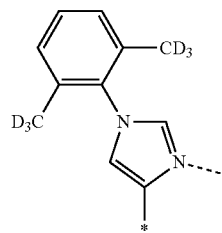 A44 |
| 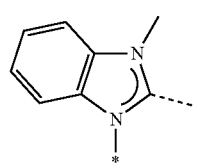 A38 | 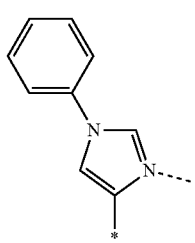 A45 |
| 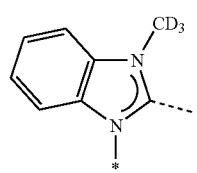 A39 | 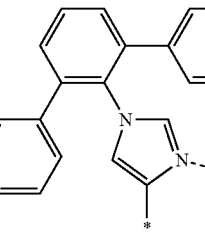 A46 |
| 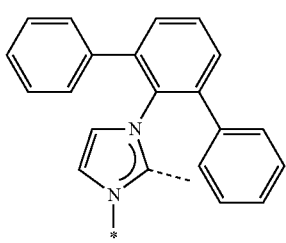 A40 | |

| | |
|---|---|
| 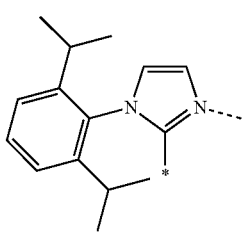 A47 | 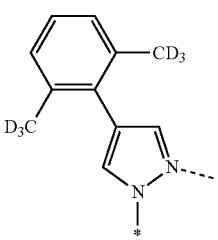 A54 |
| 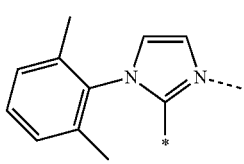 A48 | 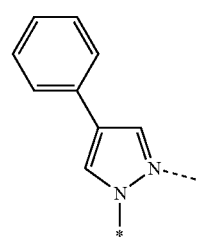 A55 |
| 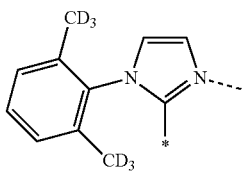 A49 | 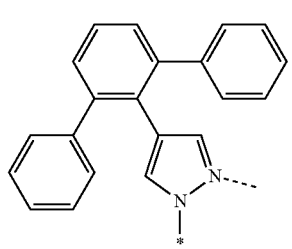 A56 |
| 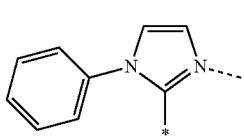 A50 | |
| 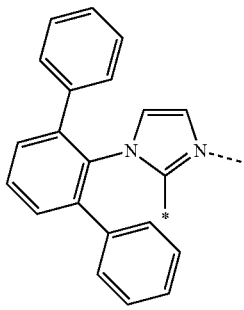 A51 | 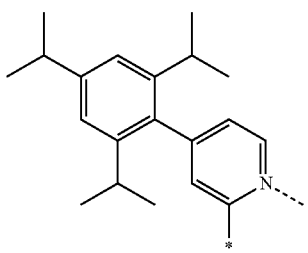 A57 |
| 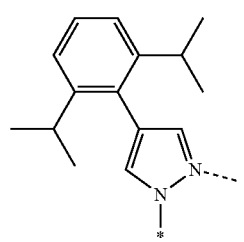 A52 | 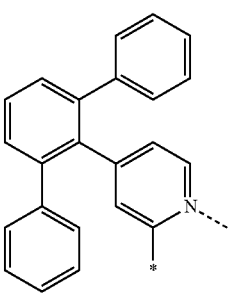 A58 |
| 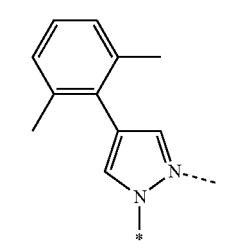 A53 | 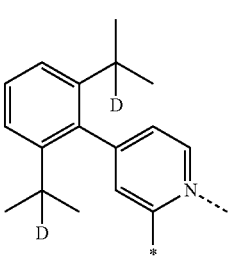 A59 |

A60 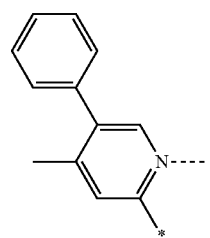
A61 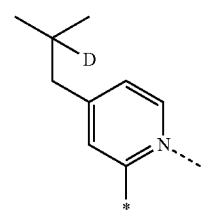
A62 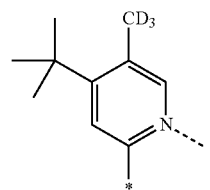
A63 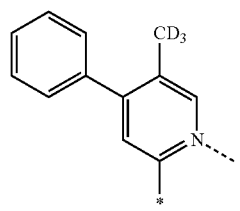
A64 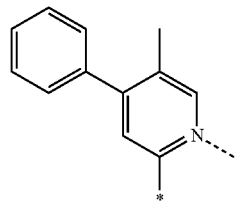
A65 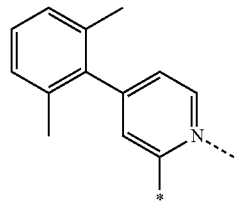
A66 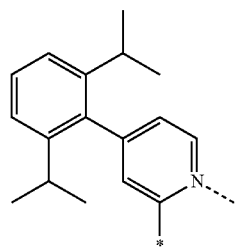
A67 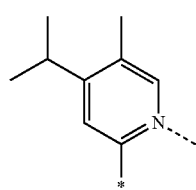
A68 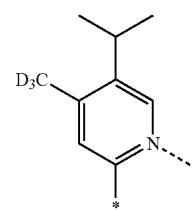
A69 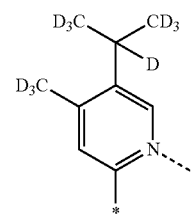
A70 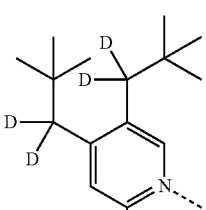
A71 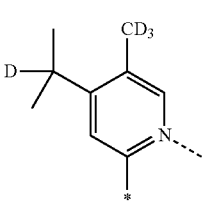
A72 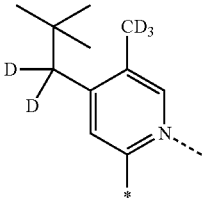
A73 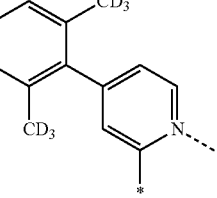

-continued
| | |
|---|---|
| 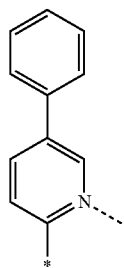 | A74 |
| 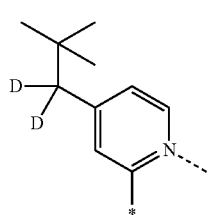 | A75 |
| 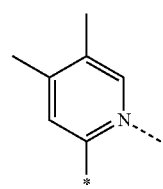 | A76 |
| 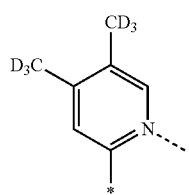 | A77 |
| 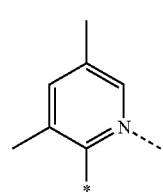 | A78 |
| 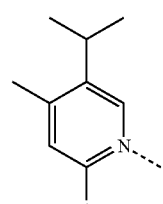 | A79 |
| 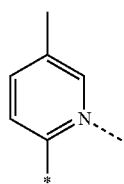 | A80 |
-continued
| | |
|---|---|
| 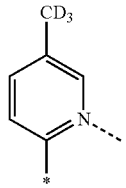 | A81 |
| 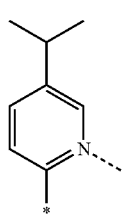 | A82 |
| 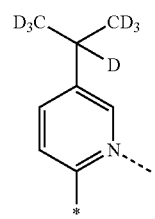 | A83 |
| 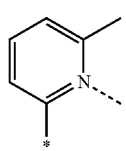 | A84 |
| 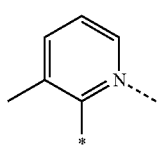 | A85 |
| 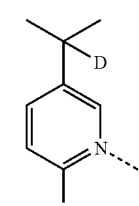 | A86 |
| 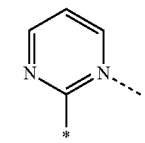 | A87 |
| | A88 |

| 187 -continued | | 188 -continued | |
|---|---|---|---|
| 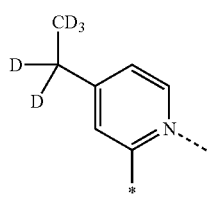 | A89 | 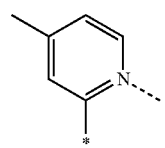 | A97 |
| 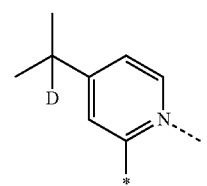 | A90 | 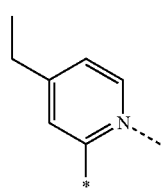 | A98 |
| 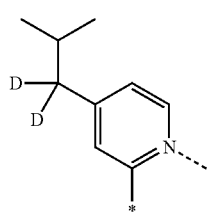 | A91 | 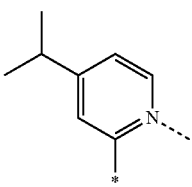 | A99 |
| 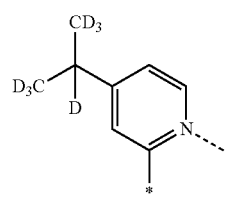 | A92 | 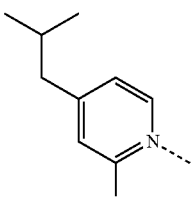 | A100 |
| 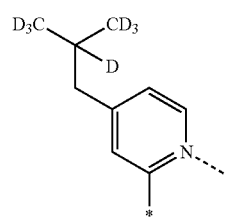 | A93 | 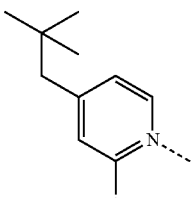 | A101 |
| 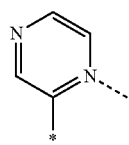 | A94 | 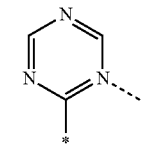 | A102 |
| 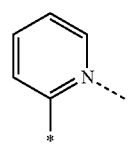 | A95 | 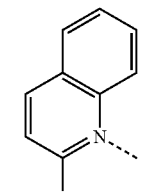 | A103 |
| 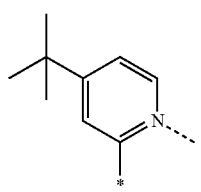 | A96 | 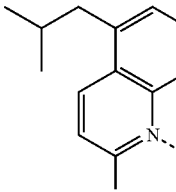 | A104 |

-continued
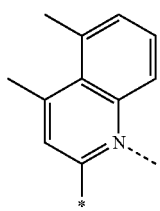
A105
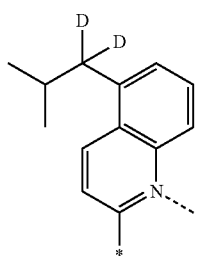
A106
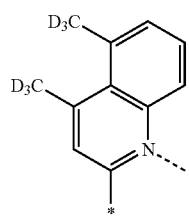
A107
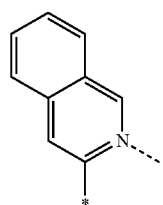
A108
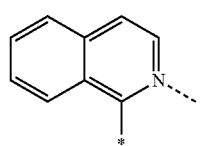
A109
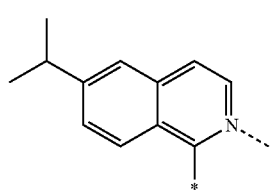
A110
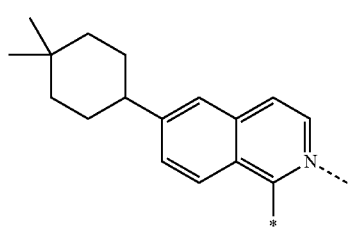
A111
-continued
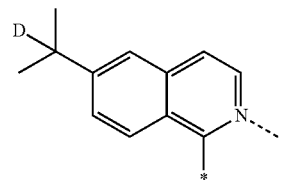
A112
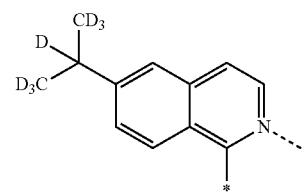
A113
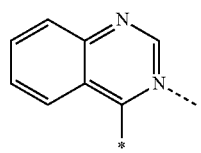
A114
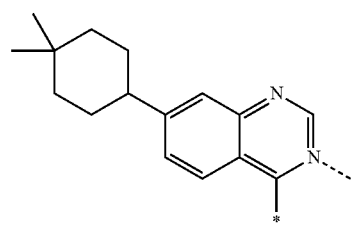
A115
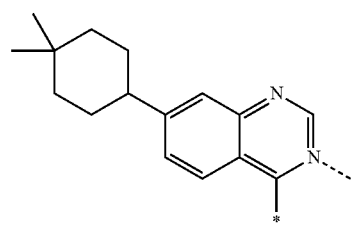
A116
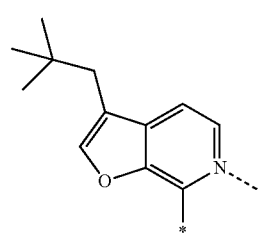
A117
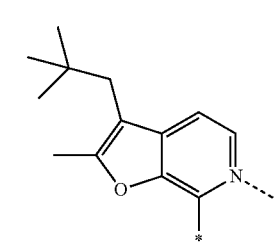
A118
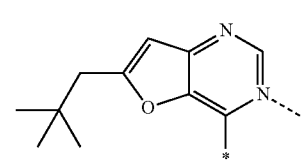
A119

-continued
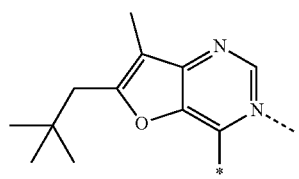
A120
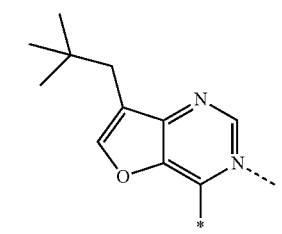
A121
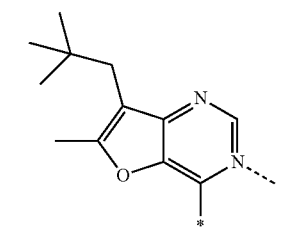
A122
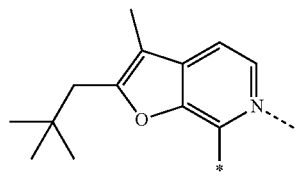
A123
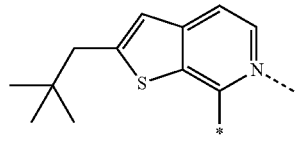
A124
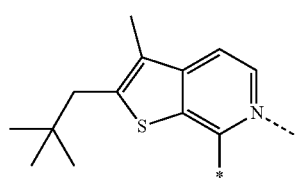
A125
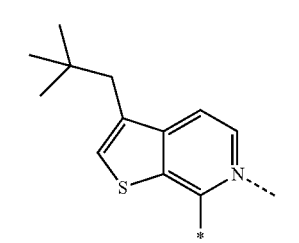
A126
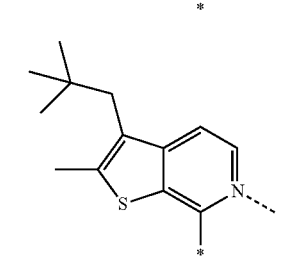
A127
-continued
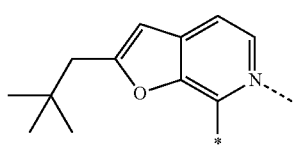
A128
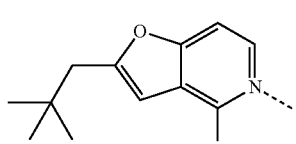
A129
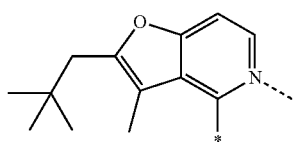
A130
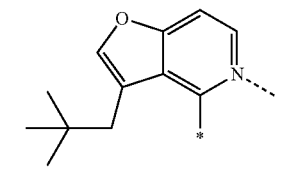
A131
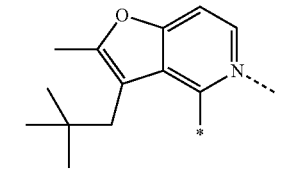
A132
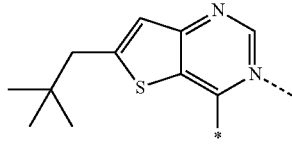
A133
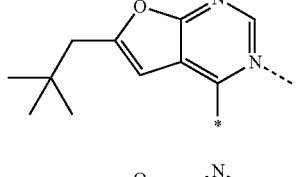
A134
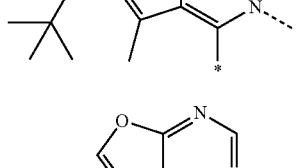
A135
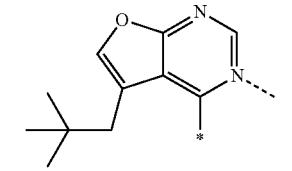
A136

-continued
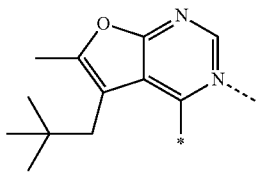 A137
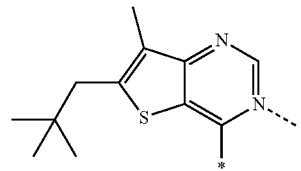 A138
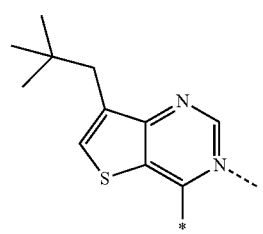 A139
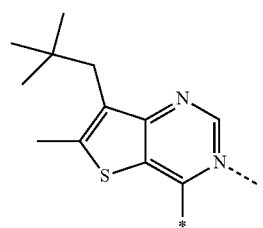 A140
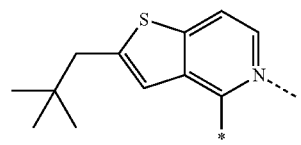 A141
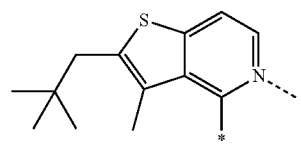 A142
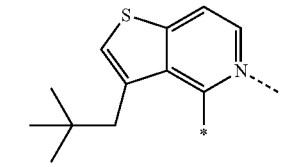 A143
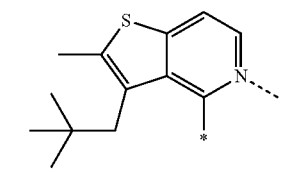 A144
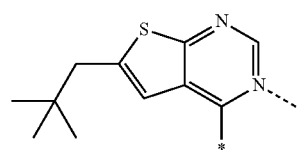 A145
-continued
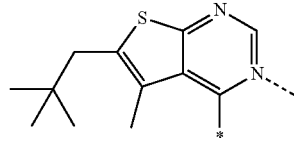 A146
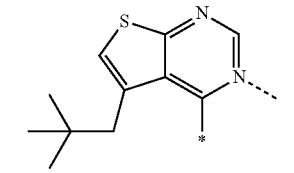 A147
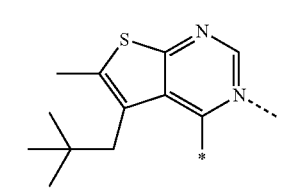 A148
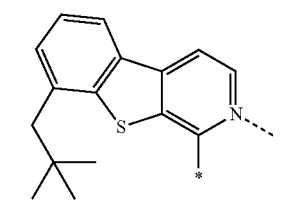 A149
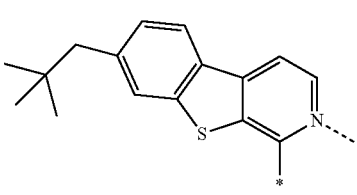 A150
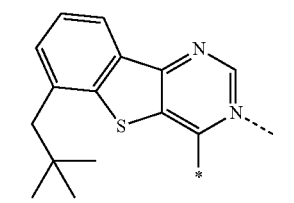 A151
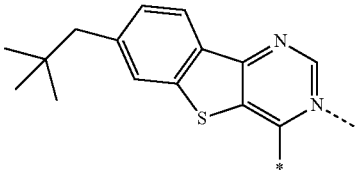 A152
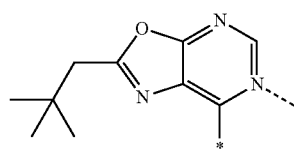 A153

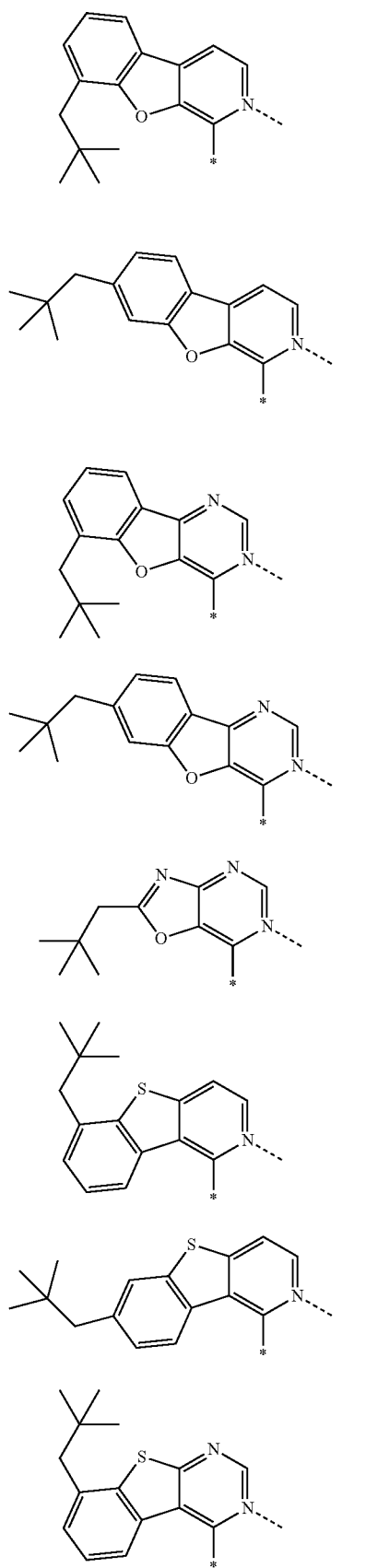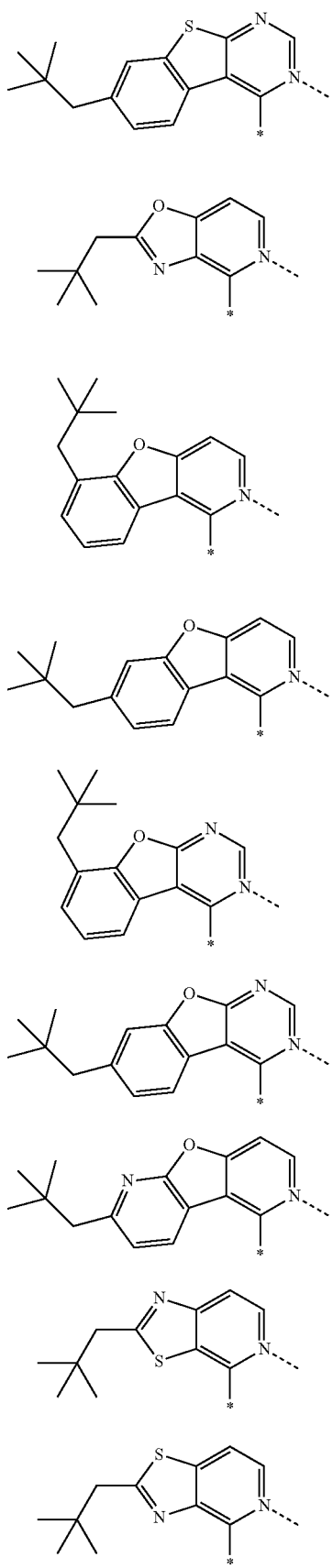

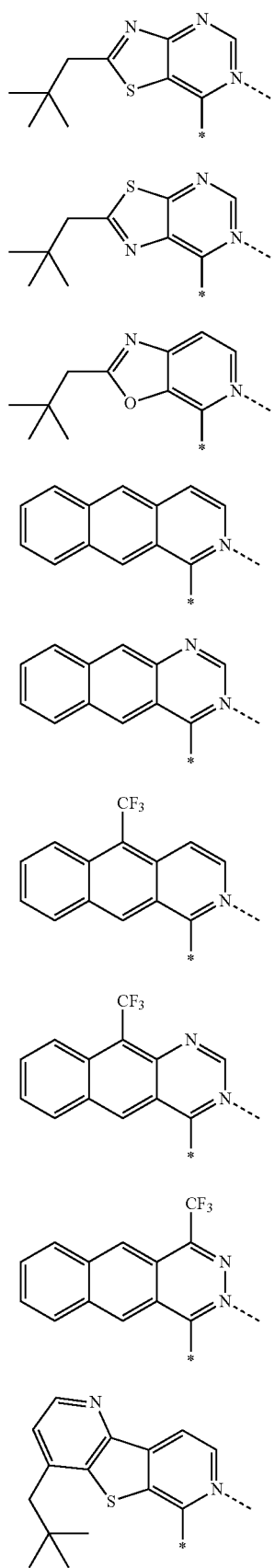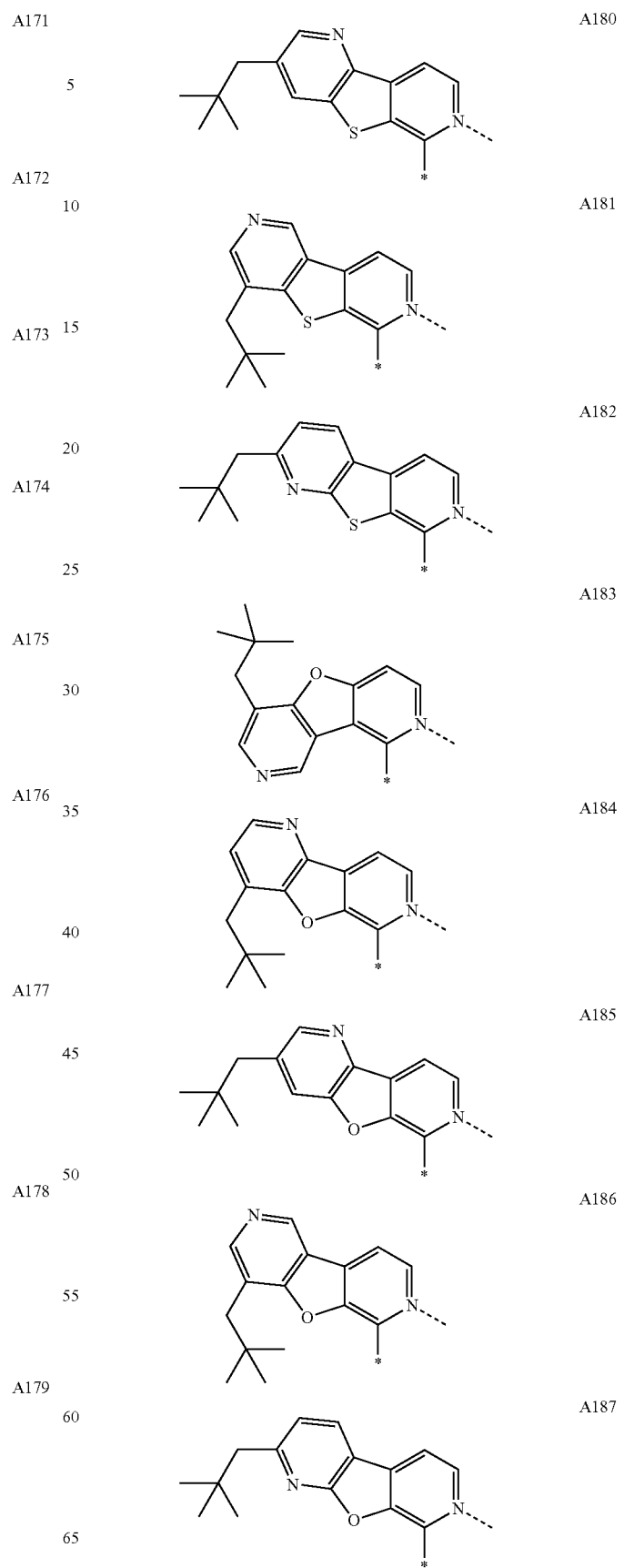

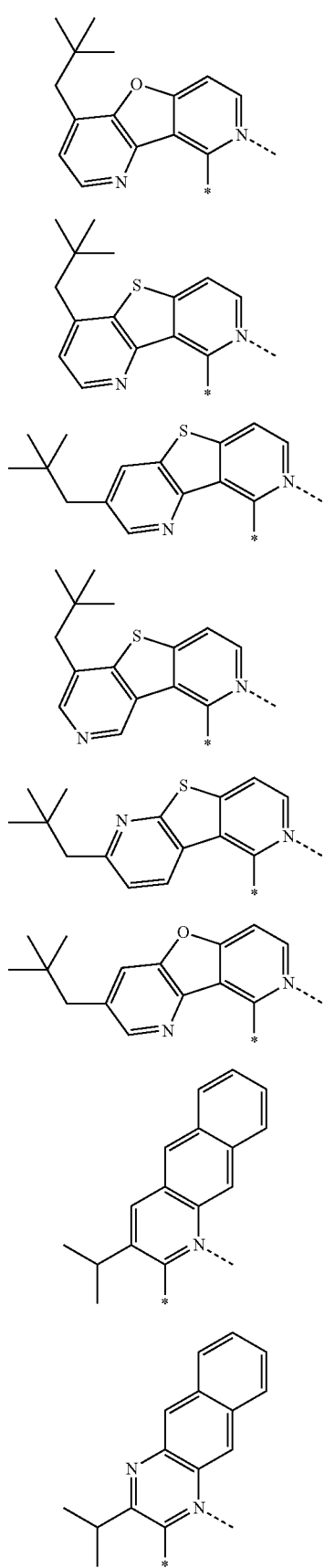
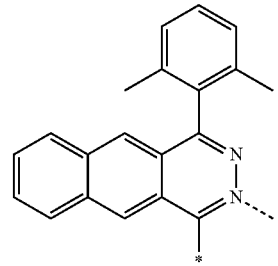
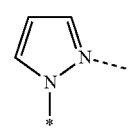
wherein the structures of B1 to B50 are as shown below:
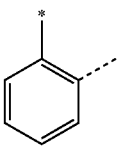
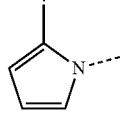

201
-continued
B4
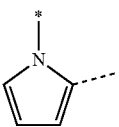
B5
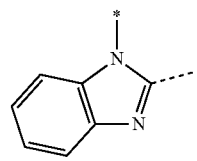
B6
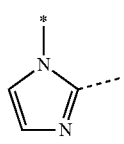
B7
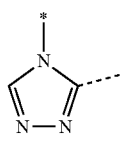
B8
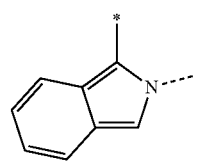
B9
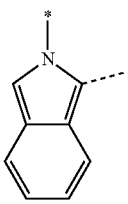
B10
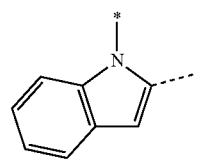
B11
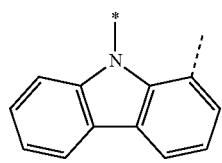
B12
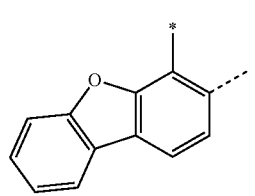
202
-continued
B13
B14
B15
B16
B17
B18
B19

203
-continued
B20 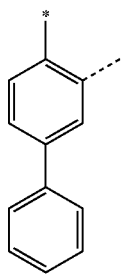
B21 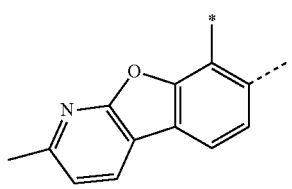
B22 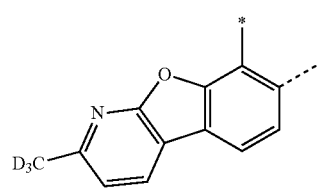
B23 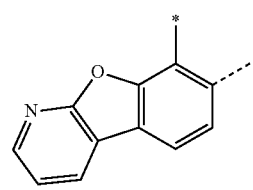
B24 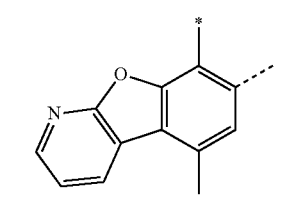
B25 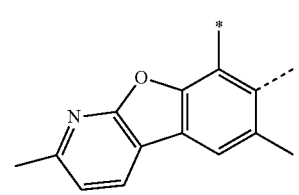
B26 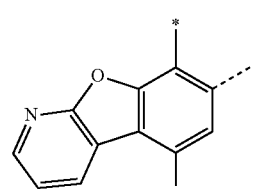
B27 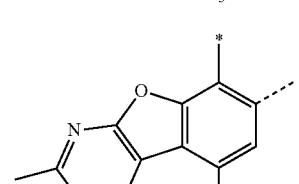
204
-continued
B28 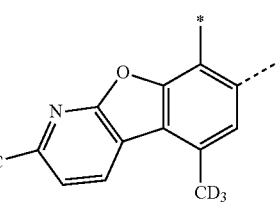
B29 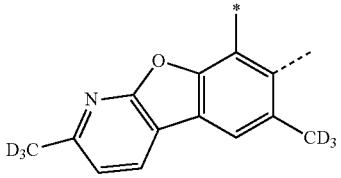
B30 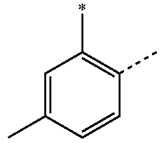
B31 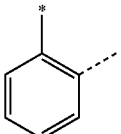
B32 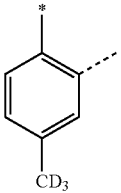
B33 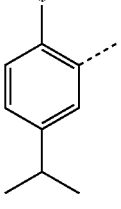
B34 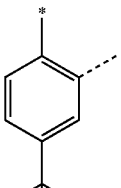
B35 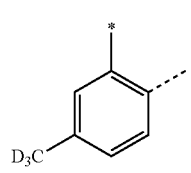

-continued
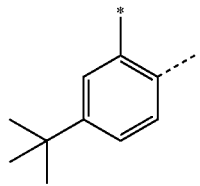
B36
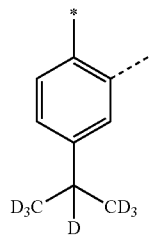
B37
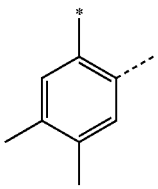
B38
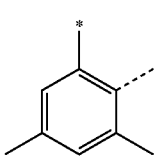
B39
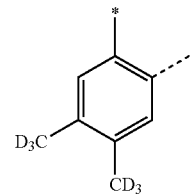
B40
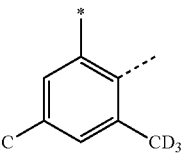
B41
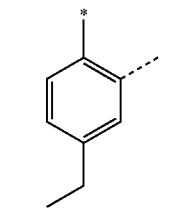
B42
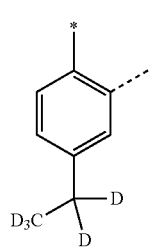
B43
-continued
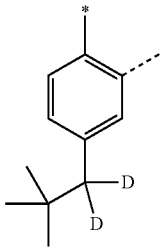
B44
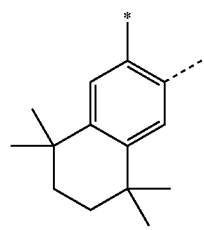
B45
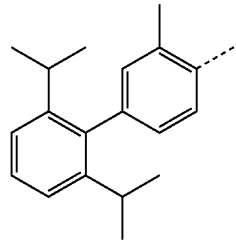
B46
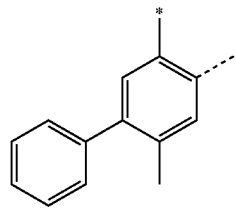
B47
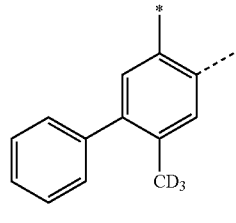
B48
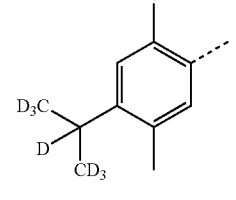
B49
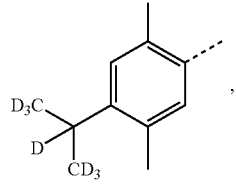
B50 wherein in the structures of A1 to A200, and B1 to B50, * represents the point of attachment to $L_A$ and the dashed line represents the coordination bond to Pt or Pd.

In some embodiments, the compound can have the formula Au($L_A$), wherein the ligand $L_A$ can be selected from the group consisting of the structures shown in LIST 6 below:

| Name of ligand $L_A$ | Structure | i, j, l, k |
|---|---|---|
| $L_A$LX-[(i)(j)(k)(l)] having the structure | 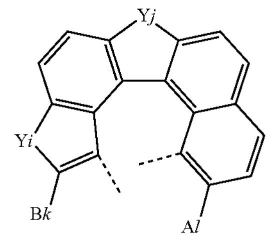 | wherein i and j are independently an integer from 1 to 30, and k and l are independently an integer from 1 to 200, and |
| $L_A$LXI-[(i)(j)(k)(l)] having the structure | 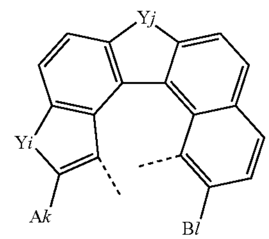 | wherein i and j are independently an integer from 1 to 30, and k and l are independently an integer from 1 to 50, and |
| $L_A$LXII-[(i)(j)(k)(l)] having the structure | 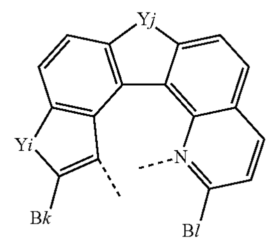 | wherein i and j are independently an integer from 1 to 30, k is an integer from 1 to 200, and l is an integer from 1 to 50, and |
| $L_A$LXIII-[(i)(j)(k)(l)] having the structure | 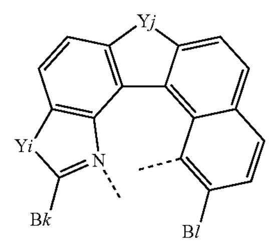 | wherein i and j are independently an integer from 1 to 30, k is an integer from 1 to 50, and l is an integer from 1 to 200, and |
| $L_A$LXIV-[(i)(j)(k)(l)] having the structure | 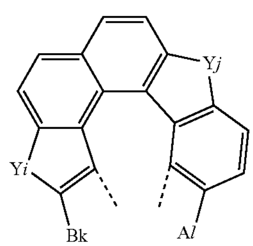 | wherein i and j are independently an integer from 1 to 30, and k and l are independently an integer from 1 to 200, and |
| $L_A$LXV-[(i)(j)(k)(l)] having the structure | 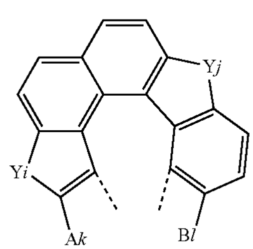 | wherein i and j are independently an integer from 1 to 30, and k and l are independently an integer from 1 to 50, and |

| Name of ligand L$_A$ | Structure | i, j, l, k |
|---|---|---|
| L$_A$LXVI-[(i)(j)(k)(l)] having the structure | 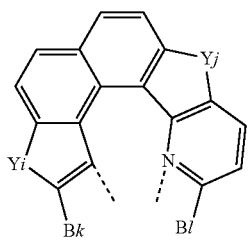 | wherein i and j are independently an integer from 1 to 30, k is an integer from 1 to 200, and l is an integer from 1 to 50, and |
| L$_A$LXVII-[(i)(j)(k)(l)] having the structure | 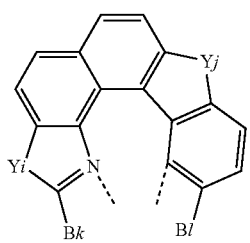 | wherein i and j are independently an integer from 1 to 30, k is an integer from 1 to 50, and l is an integer from 1 to 200, and |
| L$_A$LXVIII-[(i)(j)(k)(l)] having the structure | 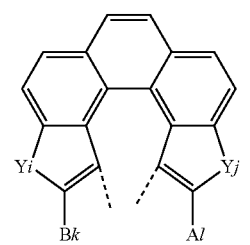 | wherein i and j are independently an integer from 1 to 30, and k and l are independently an integer from 1 to 200, and |
| L$_A$LXIX-[(i)(j)(k)(l)] having the structure | 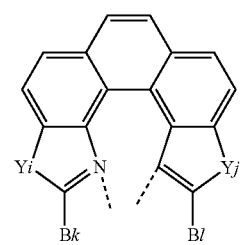 | wherein i and j are independently an integer from 1 to 30, and k and l are independently an integer from 1 to 50, and |
| L$_A$LXX-[(i)(k)(l)] having the structure | 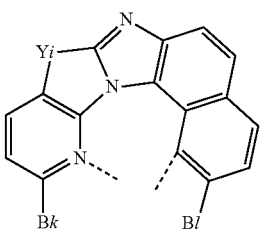 | wherein i is an integer from 1 to 30, and k and l are independently an integer from 1 to 200, and |
| L$_A$LXXI-[(i)(k)(l)] having the structure | 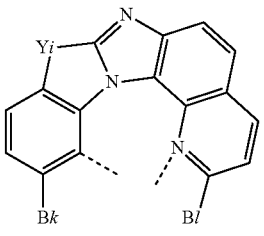 | wherein i is an integer from 1 to 30, and k and l are independently an integer from 1 to 50, and |

| Name of ligand $L_A$ | Structure | i, j, l, k |
|---|---|---|
| $L_A$LXXII-[(i)(k)(l)] having the structure | 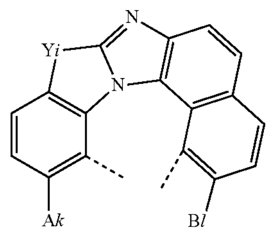 | wherein i is an integer from 1 to 30, k is an integer from 1 to 200, and l is an integer from 1 to 50, and |
| $L_A$LXXIII-[(i)(k)(l)] having the structure | 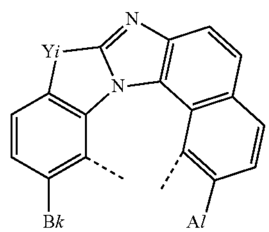 | wherein i is an integer from 1 to 30, k is an integer from 1 to 50, and l is an integer from 1 to 200, and |
| $L_A$LXXIV-[(i)(k)(l)] having the structure | 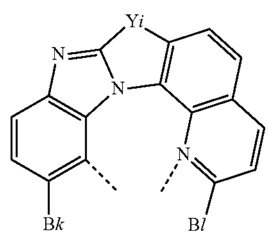 | wherein i is an integer from 1 to 30, and k and l are independently an integer from 1 to 200, and |
| $L_A$LXXV-[(i)(k)(l)] having the structure | 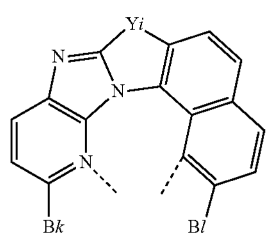 | wherein i is an integer from 1 to 30, and k and l are independently an integer from 1 to 50, and |
| $L_A$LXXVI-[(i)(k)(l)] having the structure | 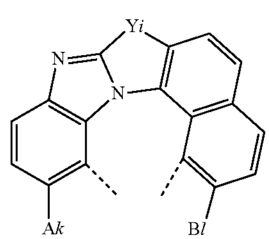 | wherein i is an integer from 1 to 30, k is an integer from 1 to 200, and l is an integer from 1 to 50, and |
| $L_A$LXXVII-[(i)(k)(l)] having the structure | 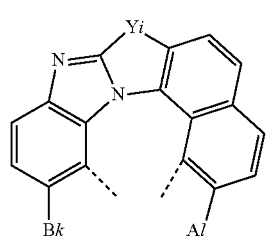 | wherein i is an integer from 1 to 30, k is an integer from 1 to 50, and l is an integer from 1 to 200, and |

| Name of ligand $L_A$ | Structure | i, j, l, k |
|---|---|---|
| $L_A$LXXVIII-[(i)(j)(k)(l)] having the structure | 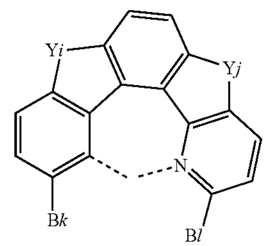 | wherein i and j are independently an integer from 1 to 30, and k and l are independently an integer from 1 to 200, and |
| $L_A$LXXIX-[(i)(j)(k)(l)] having the structure | 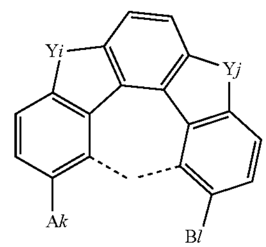 | wherein i and j are independently an integer from 1 to 30, k is an integer from 1 to 200, and l is an integer from 1 to 50, and |
| $L_A$LXXX-[(i)(j)(k)(l)(m)] having the structure | 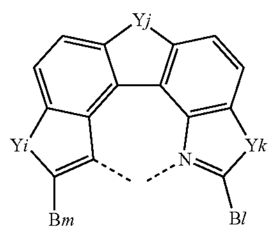 | wherein i, j, and k are independently an integer from 1 to 30, and l and m are independently an integer from 1 to 50, and |
| $L_A$LXXXI-[(i)(j)(k)(l)(m)] having the structure | 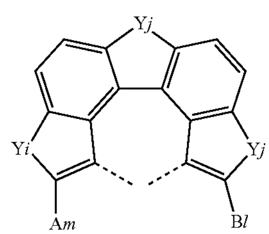 | wherein i, j, and k are independently an integer from 1 to 30, l is an integer from 1 to 50, and m is an integer from 1 to 200, and |
| $L_A$LXXXII-[(i)(j)(k)(l)] having the structure | 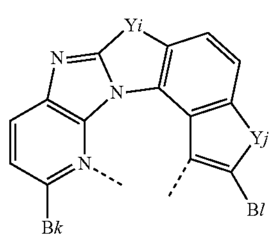 | wherein I and j are independently an integer from 1 to 30, and k and l are independently an integer from 1 to 200, and |
| $L_A$LXXXIII-[(i)(j)(k)(l)] having the structure | 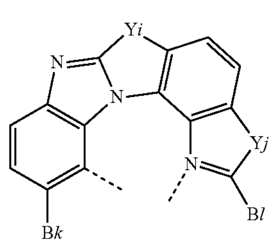 | wherein i and j are independently an integer from 1 to 30, and k and l are independently an integer from 1 to 50, |

| Name of ligand $L_A$ | Structure | i, j, l, k |
|---|---|---|
| $L_A$LXXXIV-[(i)(j)(k)(l)] having the structure | 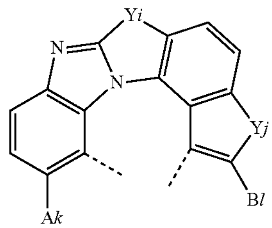 | wherein i and j are independently an integer from 1 to 30, k is an integer from 1 to 200, and l is an integer from 1 to 50, and |
| $L_A$LXXXV-[(i)(j)(k)(l)] having the structure | 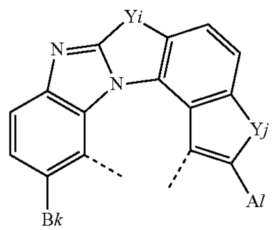 | wherein i and j are independently an integer from 1 to 30, k is an integer from 1 to 50, and l is an integer from 1 to 200, and |
| $L_A$LXXXVI-[(i)(j)(k)(l)] having the structure | 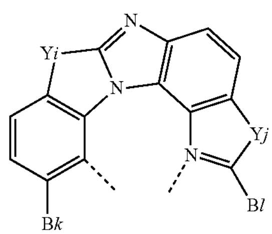 | wherein i and j are independently an integer from 1 to 30, and k and l are independently an integer from 1 to 200, and |
| $L_A$LXXXVII-[(i)(j)(k)(l)] having the structure | 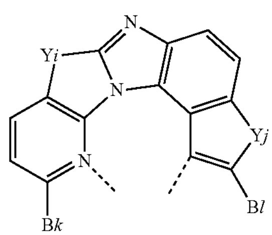 | wherein i and j are independently an integer from 1 to 30, and k and l are independently an integer from 1 to 50, and |
| $L_A$LXXXVIII-[(i)(j)(k)(l)] having the structure | 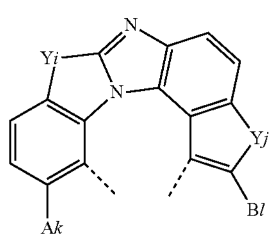 | wherein i and j are independently an integer from 1 to 30, k is an integer from 1 to 200, and l is an integer from 1 to 50, and |
| $L_A$LXXXIX-[(i)(j)(k)(l)] having the structure | 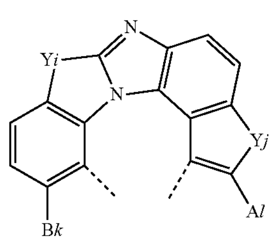 | wherein i and j are independently an integer from 1 to 30, k is an integer from 1 to 50, and l is an integer from 1 to 200, and |

-continued

| Name of ligand $L_A$ | Structure | i, j, l, k |
|---|---|---|
| $L_4$LXL-[(i)(j)(k)(l)] having the structure | | wherein i and j are independently an integer from 1 to 30, and k and l are independently an integer from 1 to 200, and |
| $L_4$LXLI-[(i)(j)(k)(l)] having the structure | | wherein i and j are independently an integer from 1 to 30, and k and l are independently an integer from 1 to 50, and |
| $L_4$LXLII-[(i)(j)(k)(l)] having the structure | | wherein i and j are independently an integer from 1 to 30, k is an integer from 1 to 200, and l is an integer from 1 to 50, and |
| $L_4$LXLIII-[(i)(j)(k)(l)] having the structure | | wherein i and j are independently an integer from 1 to 30, k is an integer from 1 to 50, and l is an integer from 1 to 200, and |
| $L_4$LXLIV-[(i)(j)(k)(l)] having the structure | | wherein i and j are independently an integer from 1 to 30, and k and l are independently an integer from 1 to 200, and |
| $L_4$LXLV-[(i)(j)(k)(l)] having the structure | | wherein i and j are independently an integer from 1 to 30, and k and l are independently an integer from 1 to 50, and |

| Name of ligand $L_A$ | Structure | i, j, l, k |
|---|---|---|
| $L_A$LXLVI-[(i)(j)(k)(l)] having the structure | 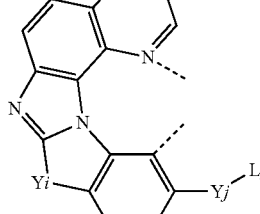 | wherein i and j are independently an integer from 1 to 30, k is an integer from 1 to 200, and l is an integer from 1 to 50, and |
| $L_A$LXLVII-[(i)(j)(k)(l)] having the structure | 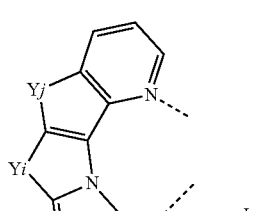 | wherein i and j are independently an integer from 1 to 30, k is an integer from 1 to 50, and l is an integer from 1 to 200, and | wherein Y1 to Y30, A1 to A200, and B1 to B50 have the structures as defined herein.

In some embodiments, the compound can have the formula $Pt(L_C)(L_{C'})$ or the formula $Pt(L_C)(L_B)$, wherein $L_C$ and $L_{C'}$ are selected from the group consisting of the structures shown in LIST 7 below:

| Name of ligands $L_C$ and $L_{C'}$ | Structure of Ligand $L_C$ and $L_{C'}$ | i, j, k, l |
|---|---|---|
| $L_C$I-[(i)(j)] having the structure | 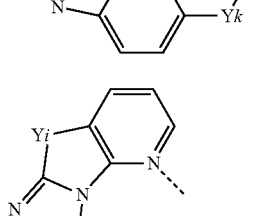 | wherein i and j are independently an integer from 1 to 30, and |
| $L_C$II-[(i)(j)(k)] having the structure | | wherein i, j and k are independently an integer from 1 to 30, and |
| $L_C$III-[(i)(j)] having the structure | | wherein i and j are independently an integer from 1 to 30, and |

-continued

| Name of ligands L$_C$ and L$_{C'}$ | Structure of Ligand L$_C$ and L$_{C'}$ | i, j, k, l |
|---|---|---|
| L$_C$IV-[(i)(j)(k)] having the structure | | wherein i, j, and k are independently an integer from 1 to 30, and |
| L$_C$V-[(i)(j)(k)] having the structure | | wherein i, j, and k are independently an integer from 1 to 30, and |
| L$_C$VI-[(i)(j)(k)] having the structure | | wherein i, j, and k are independently an integer from 1 to 30, and |
| L$_C$VII-[(i)(j)(k)] having the structure | | wherein i, j, and k are independently an integer from 1 to 30, and |
| L$_C$VIII-[(i)(j)(k)] having the structure | | wherein i, j, and k are independently an integer from 1 to 30, and |

| Name of ligands $L_C$ and $L_{C'}$ | Structure of Ligand $L_C$ and $L_{C'}$ | i, j, k, l |
|---|---|---|
| $L_C$IX-[(i)(j)(k)] having the structure | | wherein i, j, and k are independently an integer from 1 to 30, and |
| $L_C$X-[(i)(j)(k)] having the structure | | wherein i, j, and k are independently an integer from 1 to 30, and |
| $L_C$XI-[(i)(j)(k)] having the structure | | wherein i, j, and k are independently an integer from 1 to 30, and |
| $L_C$XII-[(i)(j)(k)(l)] having the structure | | wherein i, j, k, and l are independently an integer from 1 to 30, and |
| $L_C$XIII-[(i)(j)(k)] having the structure | | wherein i, j, and k are independently an integer from 1 to 30, and |

-continued

| Name of ligands $L_C$ and $L_{C'}$ | Structure of Ligand $L_C$ and $L_{C'}$ | i, j, k, l |
|---|---|---|
| $L_C$XIV-[(i)(j)] having the structure | | wherein i and j are independently an integer from 1 to 30, and |
| $L_C$XV-[(i)(j)] having the structure | | wherein i and j are independently an integer from 1 to 30, and |
| $L_C$XVI-[(i)(j)(k)] having the structure | | wherein i, j, and k are independently an integer from 1 to 30, and | wherein Y1 to Y30 have the structures as defined herein; and
wherein $L_{By}$ have the structures defined in LIST 9 below:

| $L_{By}$ | Structure of $L_{By}$ | $Ar^1, Ar^2, Ar^3, R^1, R^2$ | y |
|---|---|---|---|
| where y is an integer from 1 to 9900, $L_{By}$ have the structure | | wherein for each y, $Ar^1$ = Ari and $R^1$ = Rk, wherein i is an integer from 1 to 30 and k is an integer from 1 to 330, and | wherein y = 330(i − 1) + k |
| where y is an integer from 9901 to 19800, $L_{By}$ have the structure | | wherein for each y, $Ar^1$ = Ari and $R^1$ = Rk, wherein i is an integer from 1 to 30 and k is an integer from 1 to 330, and | wherein y = 330(i − 1) + k + 9900 |

| $L_{By}$ | Structure of $L_{By}$ | $Ar^1, Ar^2, Ar^3, R^1, R^2$ | y |
|---|---|---|---|
| where y is an integer from 19801 to 29700, $L_{By}$ have the structure | | wherein for each y, $Ar^1$ = Ari and $R^1$ = Rk, wherein i is an integer from 1 to 30 and k is an integer from 1 to 330, and | wherein y = 330(i − 1) + k + 19800 |
| where y is an integer from 29701 to 39600, $L_{By}$ have the structure | | wherein for each y, $Ar^1$ = Ari and $R^1$ = Rk, wherein i is an integer from 1 to 30 and k is an integer from 1 to 330, and | wherein y = 330(i − 1) + k + 29700 |
| where y is an integer from 39601 to 49500, $L_{By}$ have the structure | | wherein for each y, $Ar^1$ = Ari and $R^1$ = Rk, wherein i is an integer from 1 to 30 and k is an integer from 1 to 330, and | wherein y = 330(i − 1) + k + 39600 |
| where y is an integer from 49501 to 59400, $L_{By}$ have the structure | | wherein for each y, $Ar^1$ = Ari and $R^1$ = Rk, wherein i is an integer from 1 to 30 and k is an integer from 1 to 330, and | wherein y = 330(i − 1) + k + 49500 |
| where y is an integer from 59401 to 69300, $L_{By}$ have the structure | | wherein for each y, $Ar^1$ = Ari and $R^1$ = Rk, wherein i is an integer from 1 to 30 and k is an integer from 1 to 330, and | wherein y = 330(i − 1) + k + 59400 |

| $L_{By}$ | Structure of $L_{By}$ | $Ar^1$, $Ar^2$, $Ar^3$, $R^1$, $R^2$ | y |
|---|---|---|---|
| where y is an integer from 69301 to 79200, $L_{By}$ have the structure | | wherein for each y, $Ar^1$ = Ari and $R^1$ = Rk, wherein i is an integer from 1 to 30 and k is an integer from 1 to 330, and | wherein y = 330(i − 1) + k + 69300 |
| where y is an integer from 79201 to 79530, $L_{By}$ have the structure | | wherein for each y, $R^1$ = Rk, wherein k is an integer from 1 to 330, and | wherein y = k + 79200 |
| where y is an integer from 79531 to 79860, $L_{By}$ have the structure | | wherein for each y, $R^1$ = Rk, wherein k is an integer from 1 to 330, and | wherein y = k + 79530 |
| where y is an integer from 79861 to 80190, $L_{By}$ have the structure | | wherein for each y, $R^1$ = Rk, wherein k is an integer from 1 to 330, and | wherein y = k + 79860 |
| where y is an integer from 80191 to 80520, $L_{By}$ have the structure | | wherein for each y, $R^1$ = Rk, wherein k is an integer from 1 to 330, and | wherein y = k + 80190 |

| $L_{By}$ | Structure of $L_{By}$ | $Ar^1, Ar^2, Ar^3, R^1, R^2$ | y |
|---|---|---|---|
| where y is an integer from 80521 to 81510, $L_{By}$ have the structure | 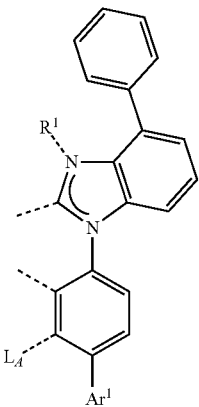 | wherein for each y, $AR^1$ = Ari and $R^1$ = Rk, wherein i is an integer from 1 to 30 and k is an integer from 1 to 330, and | wherein y = 330(i − 1) + k + 80520 |
| where y is an integer from 81511 to 82500, $L_{By}$ have the structure | 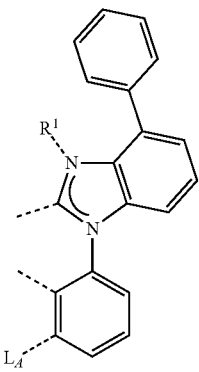 | wherein for each y, $R^1$ = Rk, wherein k is an integer from 1 to 330, and | wherein y = k + 81510 |
| where y is an integer from 82501 to 82830, $L_{By}$ have the structure | 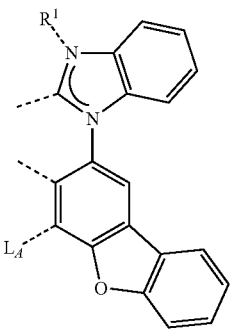 | wherein for each y, $R^1$ = Rk, wherein k is an integer from 1 to 330, and | wherein y = k + 82500 |
| where y is an integer from 82831 to 83160, $L_{By}$ have the structure | 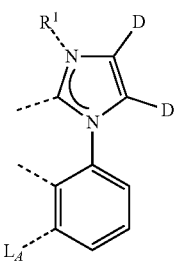 | wherein for each y, $R^1$ = Rk, wherein k is an integer from 1 to 330, and | wherein y = k + 82830 |

| L$_{By}$ | Structure of L$_{By}$ | Ar$^1$, Ar$^2$, Ar$^3$, R$^1$, R$^2$ | y |
|---|---|---|---|
| where y is an integer from 83161 to 84150, L$_{By}$ have the structure | (imidazole with R$^1$ on N, two D substituents, N connected to phenyl bearing L$_A$ and Ar$^1$) | wherein for each y, Ar$^1$ = Ari and R$^1$ = Rk, wherein i is an integer from 1 to 30 and k is an integer from 1 to 330, and | wherein y = 330(i − 1) + k + 83160 |
| where y is an integer from 84151 to 85140, L$_{By}$ have the structure | (imidazole with R$^1$ on N, two D substituents, N connected to phenyl bearing L$_A$ and Ar$^1$) | wherein for each y, Ar$^1$ = Ari and R$^1$ = Rk, wherein i is an integer from 1 to 30 and k is an integer from 1 to 330, and | wherein y = 330(i − 1) + k + 84150 |
| where y is an integer from 85141 to 85470, L$_{By}$ have the structure | (imidazole with R$^1$ on N, two D substituents, N connected to dibenzofuran bearing L$_A$) | wherein for each y, R$^1$ = Rk, wherein k is an integer from 1 to 330, and | wherein y = k + 85140 |
| where y is an integer from 85471 to 85800, L$_{By}$ have the structure | (imidazole with R$^1$ on N, two CD$_3$ substituents, N connected to phenyl bearing L$_A$) | wherein for each y, R$^1$ = Rk, wherein k is an integer from 1 to 330, and | wherein y = k + 85470 |
| where y is an integer from 85801 to 86790, L$_{By}$ have the structure | (imidazole with R$^1$ on N, two CD$_3$ substituents, N connected to phenyl bearing L$_A$ and Ar$^1$) | wherein for each y, Ar$^1$ = Ari and R$^1$ = Rk, wherein i is an integer from 1 to 30 and k is an integer from 1 to 330, and | wherein y = 330(i − 1) + k + 85800 |

| $L_{By}$ | Structure of $L_{By}$ | $Ar^1, Ar^2, Ar^3, R^1, R^2$ | y |
|---|---|---|---|
| where y is an integer from 86791 to 87780, $L_{By}$ have the structure | (structure: imidazole with $R^1$, two $CD_3$ groups, N-phenyl bearing $L_A$ and $Ar^1$) | wherein for each y, $Ar^1$ = Ari and $R^1$ = Rk, wherein i is an integer from 1 to 30 and k is an integer from 1 to 330, and | wherein y = 330(i − 1) + k + 86790 |
| where y is an integer from 87781 to 88110, $L_{By}$ have the structure | (structure: imidazole with $R^1$, two $CD_3$ groups, attached to dibenzofuran bearing $L_A$) | wherein for each y, $R^1$ = Rk, wherein k is an integer from 1 to 330, and | wherein y = k + 87780 |
| where y is an integer from 88111 to 88140, $L_{By}$ have the structure | (structure: pyridine with $Ar^2$, linked to carbazole bearing $L_A$) | wherein for each y, $Ar^2$ = Arj, wherein j is an integer from 1 to 30, and | wherein y = j + 88110 |
| where y is 88141, $L_{By}$ has the structure | (structure: pyridine linked to carbazole bearing $L_A$) | | |
| where y is an integer from 88142 to 89041, $L_{By}$ have the structure | (structure: pyridine with $Ar^2$, linked to carbazole bearing $L_A$ and $Ar^3$) | wherein for each y, $Ar^2$ = Arj and $Ar^3$ = Am, wherein j is an integer from 1 to 30 and m is an integer from 1 to 30, and | wherein y = 30(j − 1) + m + 88141 |

-continued

| $L_{By}$ | Structure of $L_{By}$ | $Ar^1, Ar^2, Ar^3, R^1, R^2$ | y |
|---|---|---|---|
| where y is an integer from 89042 to 89071, $L_{By}$ have the structure | | wherein for each y, $Ar^2$ = Arj, wherein j is an integer from 1 to 30, and | wherein y = j + 89041 |
| where y is an integer from 89072 to 89971, $L_{By}$ have the structure | | wherein for each y, $Ar^2$ = Arj and $Ar^3$ = Am, wherein j is an integer from 1 to 30 and m is an integer from 1 to 30, and | wherein y = 30(j − 1) + m + 89071 |
| where y is an integer from 89972 to 90001, $L_{By}$ have the structure | | wherein for each y, $Ar^2$ = Arj, wherein j is an integer from 1 to 30, and | wherein y = j + 89971 |
| where y is an integer from 90002 to 90031, $L_{By}$ have the structure | | wherein for each y, $Ar^2$ = Arj, wherein j is an integer from 1 to 30, and | wherein y = j + 90001 |
| where y is an integer from 90032 to 90931, $L_{By}$ have the structure | | wherein for each y, $Ar^2$ = Arj and $Ar^3$ = Arm, wherein j is an integer from 1 to 30 and m is an integer from 1 to 30, and | wherein y = 30(j − 1) + m + 90031 |

| $L_{By}$ | Structure of $L_{By}$ | $Ar^1, Ar^2, Ar^3, R^1, R^2$ | y |
|---|---|---|---|
| where y is an integer from 90932 to 91831, $L_{By}$ have the structure | [structure with Ar², Ar³, L_A on carbazole-pyridine] | wherein for each y, $Ar^2$ = Arj and $Ar^3$ = Arm, wherein j is an integer from 1 to 30 and m is an integer from 1 to 30, and | wherein y = 30(j − 1) + m + 90931 |
| where y is an integer from 91832 to 92731, $L_{By}$ have the structure | [structure with Ar², Ar³, L_A on carbazole-pyridine] | wherein for each y, $Ar^2$ = Arj and $Ar^3$ = Arm, wherein j is an integer from 1 to 30 and m is an integer from 1 to 30, and | wherein y = 30(j − 1) + m + 91831 |
| where y is an integer from 92732 to 92761, $L_{By}$ have the structure | [structure with Ar², L_A on carbazole-pyridine] | wherein for each y, $Ar^2$ = Arj, wherein j is an integer from 1 to 30, and | wherein y = j + 92731 |
| where y is an integer from 92762 to 93661, $L_{By}$ have the structure | [structure with Ar², Ar³, L_A on carbazole-pyridine] | wherein for each y, $Ar^2$ = Arj and $Ar^3$ = Arm, wherein j is an integer from 1 to 30 and m is an integer from 1 to 30, and | wherein y = 30(j − 1) + m + 92761 |
| where y is an integer from 92762 to 93691, $L_{By}$ have the structure | [structure with Ar², L_A on carbazole-pyridine] | wherein for each y, $Ar^2$ = Arj, wherein j is an integer from 1 to 30, and | wherein y = j + 92761 |

-continued

| $L_{By}$ | Structure of $L_{By}$ | $Ar^1, Ar^2, Ar^3, R^1, R^2$ | y |
|---|---|---|---|
| where y is an integer from 93692 to 94591, $L_{By}$ have the structure | (structure with Ar², Ar³, L_A on carbazole-pyridine) | wherein for each y, $Ar^2$ = Arj and $Ar^3$ = Arm, wherein j is an integer from 1 to 30 and m is an integer from 1 to 30, and | wherein y = 30(j − 1) + m + 93691 |
| where y is an integer from 94592 to 95491, $L_{By}$ have the structure | (structure with Ar², Ar³, L_A on carbazole-pyridine) | wherein for each y, $Ar^2$ = Arj and $Ar^3$ = Arm, wherein j is an integer from 1 to 30 and m is an integer from 1 to 30, and | wherein y = 30(j − 1) + m + 94591 |
| where y is 95492, $L_{By}$ has the structure | (structure with dimethylpyridine-carbazole, L_A) | | |
| where y is an integer from 95494 to 95522, $L_{By}$ have the structure | (structure with Ar², L_A on carbazole-dimethylpyridine) | wherein for each y, $Ar^2$ = Arj, wherein j is an integer from 1 to 30, and | wherein y = j + 95492 |
| where y is an integer from 95523 to 95552, $L_{By}$ have the structure | (structure with Ar², L_A on carbazole-dimethylpyridine) | wherein for each y, $Ar^2$ = Arj, wherein j is an integer from 1 to 30, and | wherein y = j + 95522 |

| $L_{By}$ | Structure of $L_{By}$ | $Ar^1$, $Ar^2$, $Ar^3$, $R^1$, $R^2$ | y |
|---|---|---|---|
| where y is an integer from 95553 to 95582, $L_{By}$ have the structure | | wherein for each y, $Ar^2$ = Arj, wherein j is an integer from 1 to 30, and | wherein y = j + 95552 |
| where y is an integer from 95583 to 95612, $L_{By}$ have the structure | | wherein for each y, $Ar^2$ = Arj, wherein j is an integer from 1 to 30, and | wherein y = j + 95582 |
| where y is 95613, $L_{By}$ has the structure | | | |
| where y is an integer from 95614 to 95643, $L_{By}$ have the structure | | wherein for each y, $Ar^2$ = Arj, wherein j is an integer from 1 to 30, and | wherein y = j + 95613 |
| where y is an integer from 95644 to 96543, $L_{By}$ have the structure | | wherein for each y, $Ar^2$ = Arj and $Ar^3$ = Am, wherein j is an integer from 1 to 30 and m is an integer from 1 to 30, and | wherein y = 30(j − 1) + m + 95643 |

| $L_{By}$ | Structure of $L_{By}$ | $Ar^1, Ar^2, Ar^3, R^1, R^2$ | y |
|---|---|---|---|
| where y is an integer from 96544 to 96573, $L_{By}$ have the structure | | wherein for each y, $Ar^2 =$ Arj, wherein j is an integer from 1 to 30, and | wherein y = j + 96543 |
| where y is an integer from 96574 to 97473, $L_{By}$ have the structure | | wherein for each y, $Ar^2 =$ Arj and $Ar^3 =$ Arm, wherein j is an integer from 1 to 30 and m is an integer from 1 to 30, and | wherein y = 30(j − 1) + m + 96573 |
| where y is an integer from 97474 to 97503, $L_{By}$ have the structure | | wherein for each y, $Ar^2 =$ Arj, wherein j is an integer from 1 to 30, and | wherein y = j + 97473 |
| where y is an integer from 97504 to 97533, $L_{By}$ have the structure | | wherein for each y, $Ar^2 =$ Arj, wherein j is an integer from 1 to 30, and | wherein y = j + 97503 |
| where y is an integer from 97534 to 98433, $L_{By}$ have the structure | | wherein for each y, $Ar^2 =$ Arj and $Ar^3 =$ Arm, wherein j is an integer from 1 to 30 and m is an integer from 1 to 30, and | wherein y = 30(j − 1) + m + 97533 |

-continued

| $L_{By}$ | Structure of $L_{By}$ | $Ar^1, Ar^2, Ar^3, R^1, R^2$ | y |
|---|---|---|---|
| where y is an integer from 98434 to 99333, $L_{By}$ have the structure | | wherein for each y, $Ar^2$ = Arj and $Ar^3$ = Arm, wherein j is an integer from 1 to 30 and m is an integer from 1 to 30, and | wherein y = 30(j − 1) + m + 98433 |
| where y is an integer from 99334 to 99363, $L_{By}$ have the structure | | wherein for each y, $Ar^2$ = Arj, wherein j is an integer from 1 to 30, and | wherein y = j + 99333 |
| where y is 99364, $L_{By}$ has the structure | | | |
| where y is an integer from 99365 to 99394, $L_{By}$ have the structure | | wherein for each y, $Ar^2$ = Arj, wherein j is an integer from 1 to 30, and | wherein y = j + 99364 |
| where y is 99395, $L_{By}$ has the structure | | | |
| where y is an integer from 99396 to 102395, $L_{By}$ have the structure | | wherein for each y, $Ar^2$ = Arj and $R^2$ = Rl, wherein j is an integer from 1 to 30 and l is an integer from 1 to 330, and | wherein y = 330(j − 1) + l + 99395 |

| $L_{By}$ | Structure of $L_{By}$ | $Ar^1, Ar^2, Ar^3, R^1, R^2$ | y |
|---|---|---|---|
| where y is an integer from 102396 to 102495, $L_{By}$ have the structure | (imidazole-phenyl structure with $R^2$, $L_A$) | wherein for each y, $R^2$ = Rl, wherein l is an integer from 1 to 330, and | wherein y = l + 102395 |
| where y is an integer from 102496 to 105495, $L_{By}$ have the structure | (Ar², R² substituted benzimidazole fused with gem-dimethyl cyclohexane and phenyl, $L_A$) | wherein for each y, $Ar^2$ = Arj and $R^2$ = Rl, wherein j is an integer from 1 to 30 and l is an integer from 1 to 330, and | wherein y = 330(j − 1) + l + 12215 |
| where y is an integer from 105496 to 105595, $L_{By}$ have the structure | (R² substituted benzimidazole fused with gem-dimethyl cyclohexane and phenyl, $L_A$) | wherein for each y, $R^2$ = Rl, wherein l is an integer from 1 to 330, and | wherein y = l + 105495 |
| where y is an integer from 105596 to 108595, $L_{By}$ have the structure | (Ar², R² imidazole-carbazole structure, $L_A$) | wherein $Ar^2$ = Arj and $R^2$ = Rl, wherein j is an integer from 1 to 30 and l is an integer from 1 to 330, and | wherein y = 330(j − 1) + l + 105595 |
| where y is an integer from 108596 to 108695, $L_{By}$ have the structure | (R² imidazole-carbazole structure, $L_A$) | wherein for each y, $R^2$ = Rl, wherein l is an integer from 1 to 330, and | wherein y = l + 108595 |
| where y is an integer from 108696 to 111695, $L_{By}$ have the structure | (Ar², R² imidazole-carbazole structure, $L_A$) | wherein for each y, $Ar^2$ = Arj and $R^2$ = Rl, wherein j is an integer from 1 to 30 and l is an integer from 1 to 330, and | wherein y = 330(j − 1) + l + 111695 |

| $L_{By}$ | Structure of $L_{By}$ | $Ar^1, Ar^2, Ar^3, R^1, R^2$ | y |
|---|---|---|---|
| where y is an integer from 111696 to 111795, $L_{By}$ have the structure | 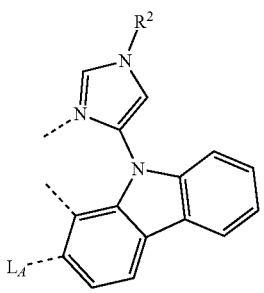 | wherein for each y, $R^2$ = Rl, wherein l is an integer from 1 to 330, and | wherein y = l + 111795 |
| where y is an integer from 111796 to 114795, $L_{By}$ have the structure | 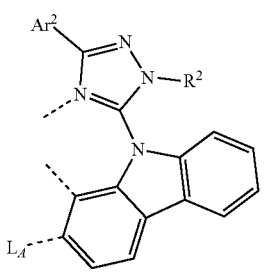 | wherein for each y, $Ar^2$ = Arj and $R^2$ = Rl, wherein j is an integer from 1 to 30 and l is an integer from 1 to 330, and | wherein y = 330(j − 1) + l + 111795 |
| where y is an integer from 114796 to 114895, $L_{By}$ have the structure | 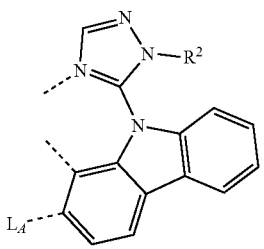 | wherein for each y, $R^2$ = Rl, wherein l is an integer from 1 to 330, and | wherein y = l + 114795 |
| where y is an integer from 114896 to 117895, $L_{By}$ have the structure | 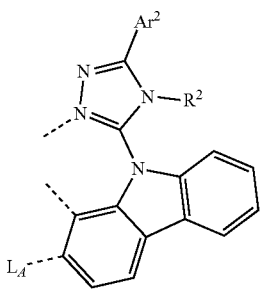 | wherein for each y, $Ar^2$ = Arj and $R^2$ = Rl, wherein j is an integer from 1 to 30 and l is an integer from 1 to 330, and | wherein y = 330(j − 1) + l + 114895 |
| where y is an integer from 117896 to 117995, $L_{By}$ have the structure | 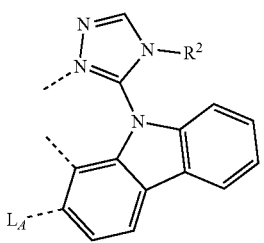 | wherein for each y, $R^2$ = Rl, wherein l is an integer from 1 to 330, and | wherein y = l + 117895 |

| $L_{By}$ | Structure of $L_{By}$ | $Ar^1, Ar^2, Ar^3, R^1, R^2$ | y |
|---|---|---|---|
| where y is an integer from 117996 to 120995, $L_{By}$ have the structure | | wherein for each y, $Ar^2$ = Arj and $R^2$ = Rl, wherein j is an integer from 1 to 30 and l is an integer from 1 to 330, and | wherein y = 330(j − 1) + l + 117995 |
| where y is an integer from 120996 to 121095, $L_{By}$ have the structure | | wherein for each y, $R^2$ = Rl, wherein l is an integer from 1 to 330, and | wherein y = l + 120995 |
| where y is an integer from 121096 to 121125, $L_{By}$ have the structure | | wherein for each y, $Ar^2$ = Arj, wherein j is an integer from 1 to 30, and | wherein y = j + 121095 |
| where y is 121126, $L_{By}$ has the structure | | | |
| where y is an integer from 121127 to 122026, $L_{By}$ have the structure | | wherein for each y, $Ar^2$ = Arj and $Ar^3$ = Arm, wherein j is an integer from 1 to 30 and m is an integer from 1 to 30, and | wherein y = 30(j − 1) + m + 121126 |

-continued

| $L_{By}$ | Structure of $L_{By}$ | $Ar^1, Ar^2, Ar^3, R^1, R^2$ | y |
|---|---|---|---|
| where y is an integer from 122027 to 122056, $L_{By}$ have the structure | (structure) | wherein for each y, $Ar^2$ = Arj, wherein j is an integer from 1 to 30, and | wherein y = j + 122026 |
| where y is an integer from 122057 to 122956, $L_{By}$ have the structure | (structure) | wherein for each y, $Ar^2$ = Arj and $Ar^3$ = Arm, wherein j is an integer from 1 to 30 and m is an integer from 1 to 30, and | wherein y = 30(j − 1) + m + 122056 |
| where y is an integer from 122957 to 122986, $L_{By}$ have the structure | (structure) | wherein for each y, $Ar^2$ = Arj, wherein j is an integer from 1 to 30, and | wherein y = j + 122956 |
| where y is an integer from 122987 to 123016, $L_{By}$ have the structure | (structure) | wherein for each y, $Ar^2$ = Arj, wherein j is an integer from 1 to 30, and | wherein y = j + 122986 |
| where y is 123017, $L_{By}$ has the structure | (structure) | | |

| $L_{By}$ | Structure of $L_{By}$ | $Ar^1, Ar^2, Ar^3, R^1, R^2$ | y |
|---|---|---|---|
| where y is an integer from 123018 to 223917, $L_{By}$ have the structure | (structure with D$_3$C-pyridine-carbazole, Ar$^2$, Ar$^3$, L$_A$) | wherein for each y, Ar$^2$ = Arj and Ar$^3$ = Arm, wherein j is an integer from 1 to 30 and m is an integer from 1 to 30, and | wherein y = 30(j − 1) + m + 123017 |
| where y is an integer from 223918 to 223947, $L_{By}$ have the structure | (structure with D$_3$C-pyridine-carbazole, Ar$^2$, L$_A$) | wherein for each y, Ar$^2$ = Arj, wherein j is an integer from 1 to 30, and | wherein y = j + 223917 |
| where y is an integer from 223948 to 224847, $L_{By}$ have the structure | (structure with D$_3$C-pyridine-carbazole, Ar$^2$, Ar$^3$, L$_A$) | wherein for each y, Ar$^2$ = Arj and Ar$^3$ = Arm, wherein j is an integer from 1 to 30 and m is an integer from 1 to 30, and | wherein y = 30(j − 1) + m + 223947 |
| where y is an integer from 2248487 to 224877, $L_{By}$ have the structure | (structure with D$_3$C-pyridine-carbazole, Ar$^2$, L$_A$) | wherein for each y, Ar$^2$ = Arj, wherein j is an integer from 1 to 30, and | wherein y = j + 224847 |
| where y is an integer from 224878 to 225777, $L_{By}$ have the structure | (structure with D-pyridine-carbazole, Ar$^2$, Ar$^3$, L$_A$) | wherein for each y, Ar$^2$ = Arj and Ar$^3$ = Arm, wherein j is an integer from 1 to 30 and m is an integer from 1 to 30, and | wherein y = 30(j − 1) + m + 224877 |

| $L_{By}$ | Structure of $L_{By}$ | $Ar^1$, $Ar^2$, $Ar^3$, $R^1$, $R^2$ | y |
|---|---|---|---|
| where y is an integer from 225778 to 225807, $L_{By}$ have the structure | | wherein for each y, $Ar^2$ = Arj, wherein j is an integer from 1 to 30, and | wherein y = j + 225777 |
| where y is an integer from 225808 to 226707, $L_{By}$ have the structure | | wherein for each y, $Ar^2$ = Arj and $Ar^3$ = Arm, wherein j is an integer from 1 to 30 and m is an integer from 1 to 30, and | wherein y = 30(j − 1) + m + 225807 |
| where y is an integer from 226708 to 226737, $L_{By}$ have the structure | | wherein for each y, $Ar^2$ = Arj, wherein j is an integer from 1 to 30, and | wherein y = j + 226707 |
| where y is an integer from 226738 to 227637, $L_{By}$ have the structure | | wherein for each y, $Ar^2$ = Arj and $Ar^3$ = Arm, wherein j is an integer from 1 to 30 and m is an integer from 1 to 30, and | wherein y = 30(j − 1) + m + 226737 |
| where y is an integer from 227638 to 227667, $L_{By}$ have the structure | | wherein for each y, $Ar^2$ = Arj, wherein j is an integer from 1 to 30, and | wherein y = j + 227637 |

-continued

| $L_{By}$ | Structure of $L_{By}$ | $Ar^1, Ar^2, Ar^3, R^1, R^2$ | y |
|---|---|---|---|
| where y is an integer from 227668 to 228567, $L_{By}$ have the structure | (structure with D$_3$C-pyridine, carbazole, Ar$^2$, Ar$^3$, $L_A$) | wherein for each y, Ar$^2$ = Arj and Ar$^3$ = Arm, wherein j is an integer from 1 to 30 and m is an integer from 1 to 30, and | wherein y = 30(j − 1) + m + 227667 |
| where y is an integer from 228568 to 228597, $L_{By}$ have the structure | (structure with D$_3$C-pyridine, carbazole, Ar$^2$, $L_A$) | wherein for each y, Ar$^2$ = Arj, wherein j is an integer from 1 to 30, and | wherein y = j + 228567 |
| where y is an integer from 228598 to 228627, $L_{By}$ have the structure | (structure with pyridine, Ar$^2$, carbazole fused with benzofuran, $L_A$) | wherein for each y, Ar$^2$ = Arj, wherein j is an integer from 1 to 30, and | wherein y = j + 228597 |
| where y is an integer from 228628 to 228657, $L_{By}$ have the structure | (structure with pyridine, Ar$^2$, carbazole fused with benzofuran, $L_A$) | wherein for each y, Ar$^2$ = Arj, wherein j is an integer from 1 to 30, and | wherein y = j + 228627 |

| $L_{By}$ | Structure of $L_{By}$ | $Ar^1, Ar^2, Ar^3, R^1, R^2$ | y |
|---|---|---|---|
| where y is an integer from 228658 to 228687, $L_{By}$ have the structure | | wherein for each y, $Ar^2$ = Arj, wherein j is an integer from 1 to 30, and | wherein y = j + 228657 |
| where y is an integer from 228688 to 228717, $L_{By}$ have the structure | | wherein for each y, $Ar^2$ = Arj, wherein j is an integer from 1 to 30, and | wherein y = j + 228787 |
| where y is an integer from 228718 to 228747, $L_{By}$ have the structure | | wherein for each y, $Ar^2$ = Arj, wherein j is an integer from 1 to 30, and | wherein y = j + 228717 |

-continued
| L$_{By}$ | Structure of L$_{By}$ | Ar$^1$, Ar$^2$, Ar$^3$, R$^1$, R$^2$ | y |
|---|---|---|---|
| where y is an integer from 228748 to 228777, L$_{By}$ have the structure | 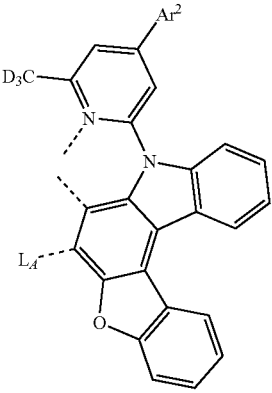 | wherein for each y, Ar$^2$ = Arj, wherein j is an integer from 1 to 30, and | wherein y = j + 228747 |
| where y is 228778, L$_{By}$ has the structure | 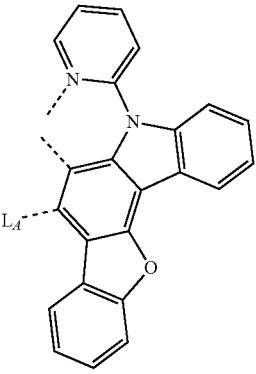 | | |
| where y is 228779, L$_{By}$ has the structure | 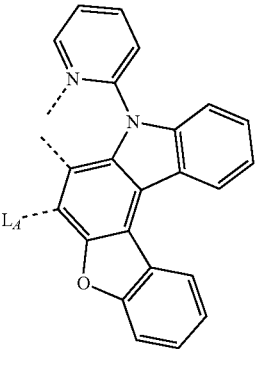 | | |
| where y is 228780, L$_{By}$ has the structure | 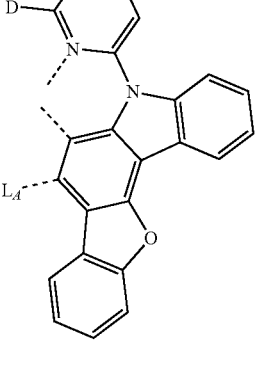 | | |

-continued
| L$_{By}$ | Structure of L$_{By}$ | Ar$^1$, Ar$^2$, Ar$^3$, R$^1$, R$^2$ | y |
|---|---|---|---|
| where y is 228781, L$_{By}$ has the structure | | | |
| where y is 228782, L$_{By}$ has the structure | | | |
| where y is 228783, L$_{By}$ has the structure | | | |
wherein Ar1 to Ar30 have the structures defined below:
Ar1
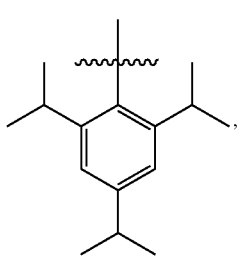
Ar2
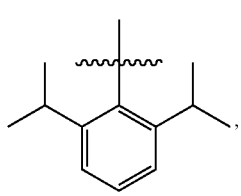
Ar3
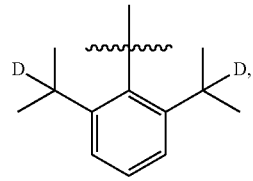

269
-continued
Ar4
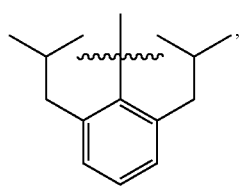
Ar5
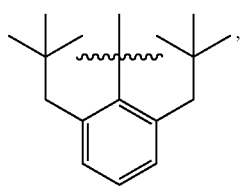
Ar6
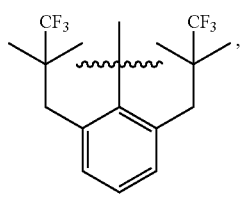
Ar7
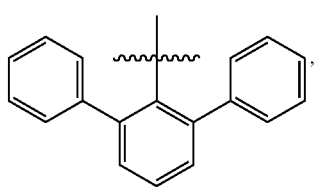
Ar8
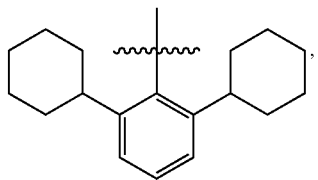
Ar9
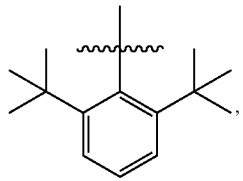
Ar10
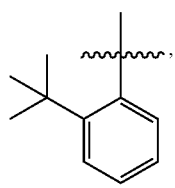
Ar11 Me,
Ar12 iPr,
Ar13 tBu,
270
-continued
Ar14
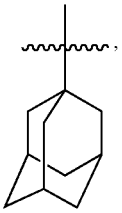
Ar15
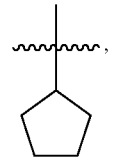
Ar16
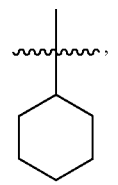
Ar17
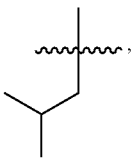
Ar18
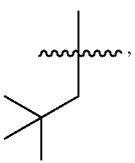
Ar19
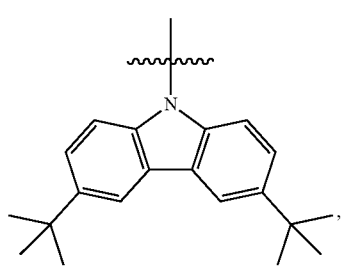
Ar20
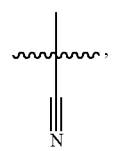
Ar21 $CD_3$,
Ar22
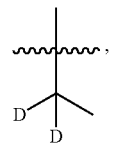

271
-continued
Ar23
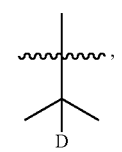
Ar24
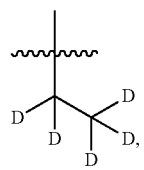
Ar25
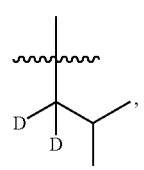
Ar26
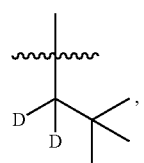
Ar27
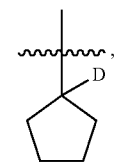
Ar28
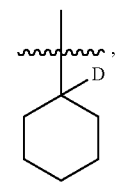
Ar29
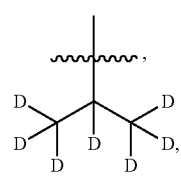
Ar30
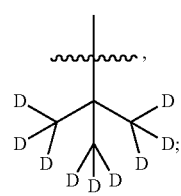
and wherein R1 to R330 have the structures defined in LIST 10 below:
R1
Me,
272
-continued
R2
iPr,
R3
tBu,
R4
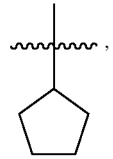
R5
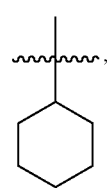
R6
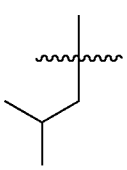
R7
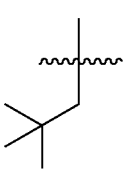
R8
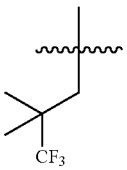
R9
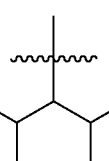
R10
CD$_3$,
R11
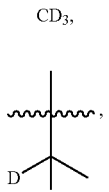
R12
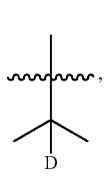

-continued
R13 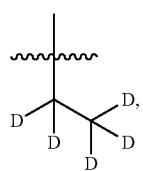
R14 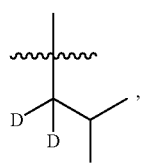
R15 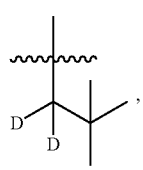
R16 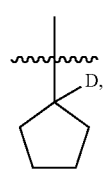
R17 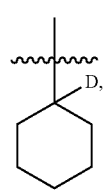
R18 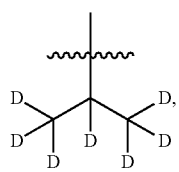
R19 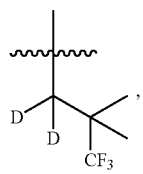
R20 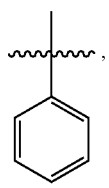
-continued
R21 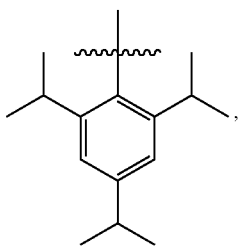
R22 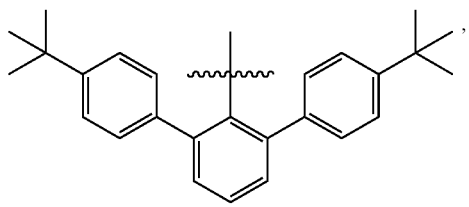
R23 
R24 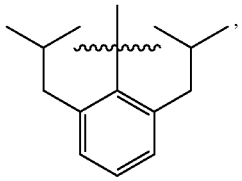
R25 
R26 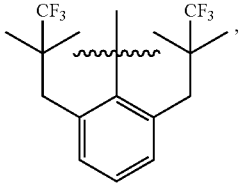
R27 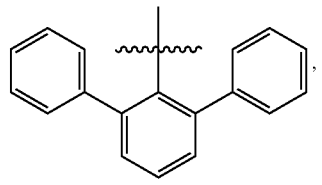
R28 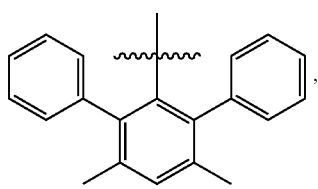

-continued
R29
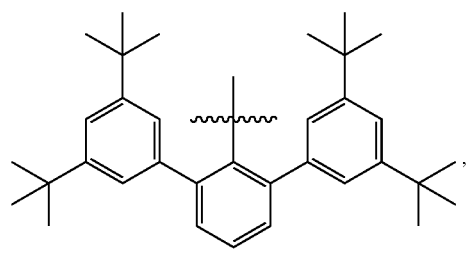
R30
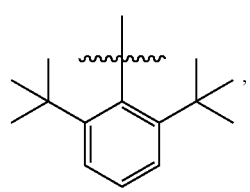
R31
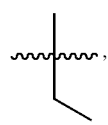
R32
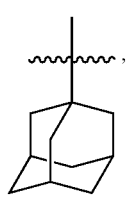
R33
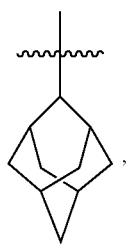
R34
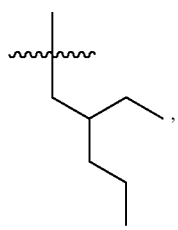
R35
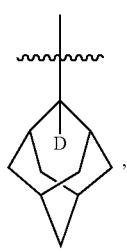
-continued
R36
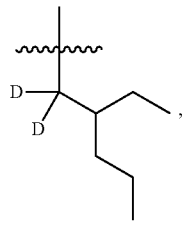
R37
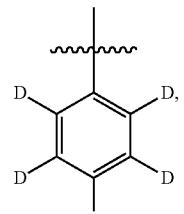
R38
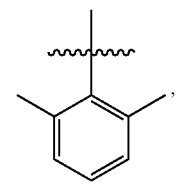
R39
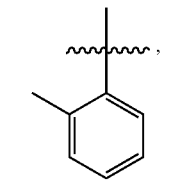
R40
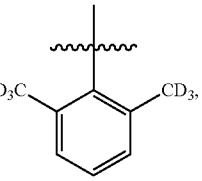
R41
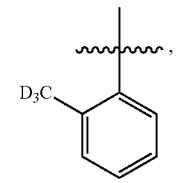
R42
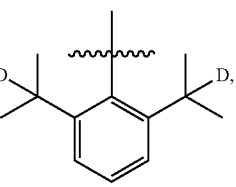
R43
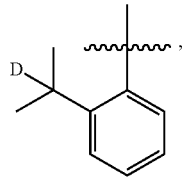

277
-continued
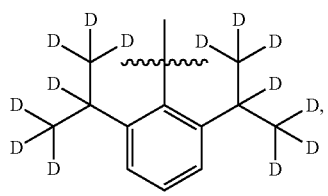
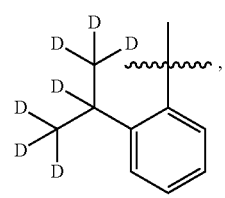
R45
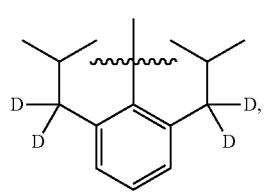
R46
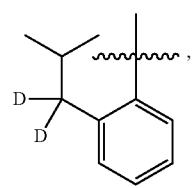
R47
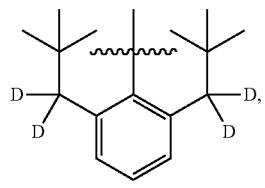
R48
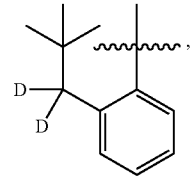
R49
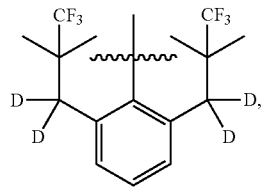
R50
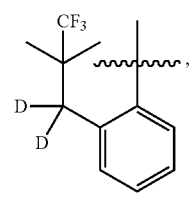
R51
278
-continued
R44
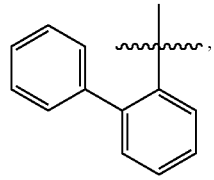
R52
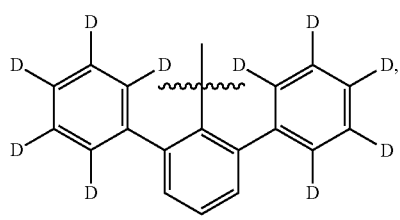
R53
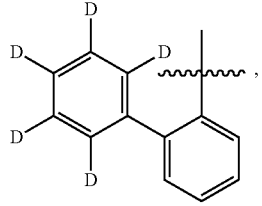
R54
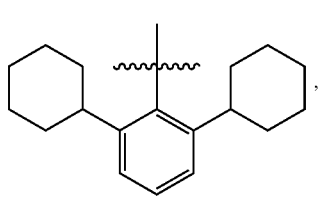
R55
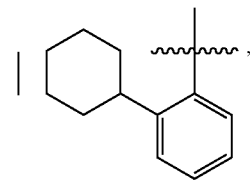
R56
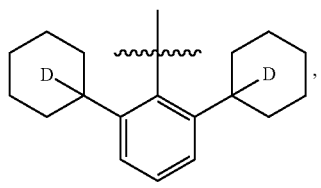
R57
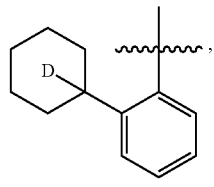
R58
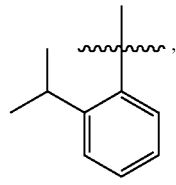
R59

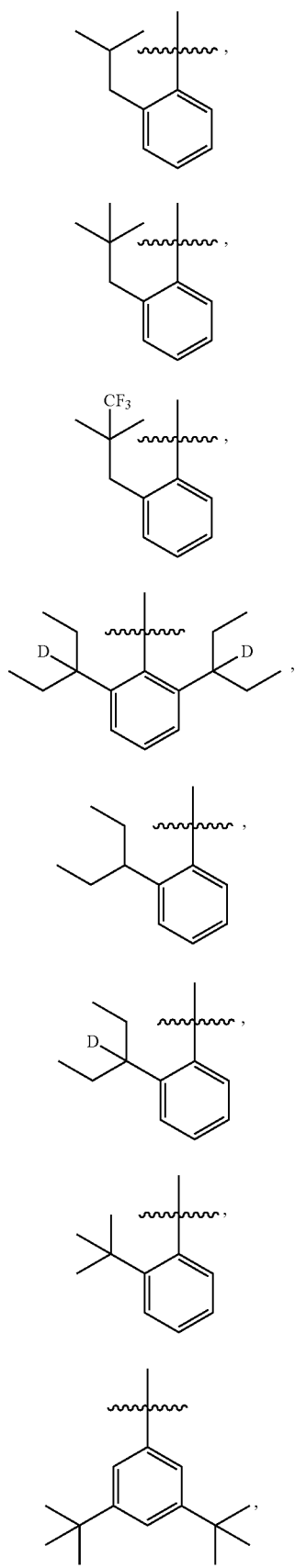
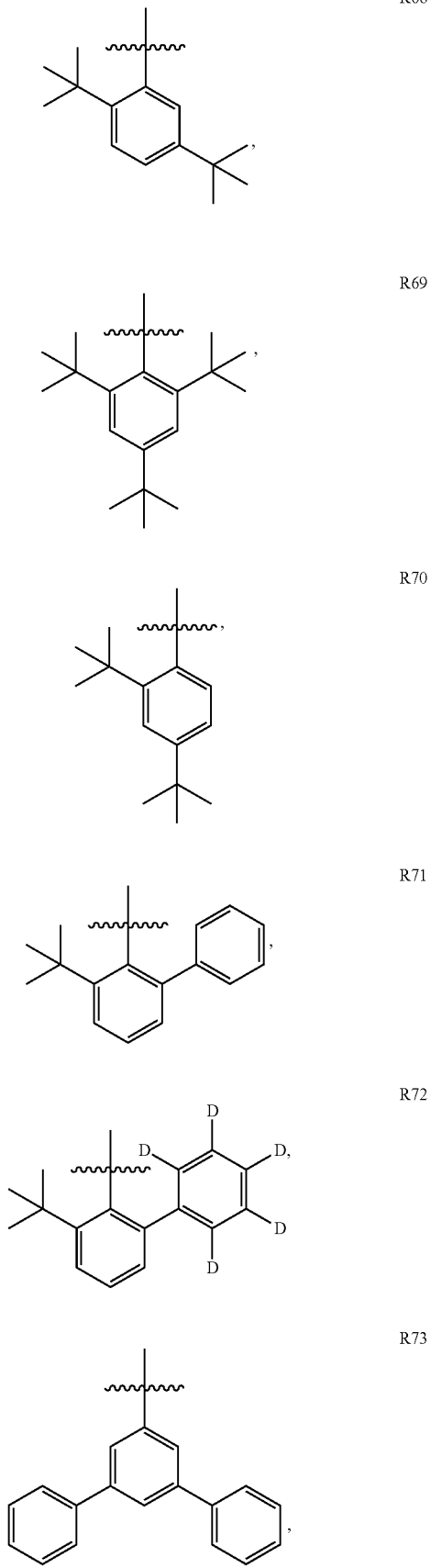

-continued
R74 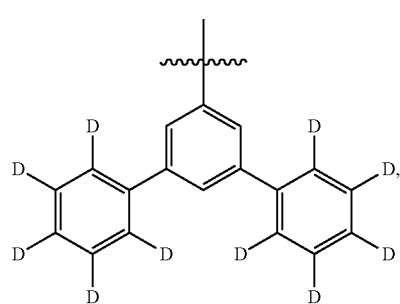
R75 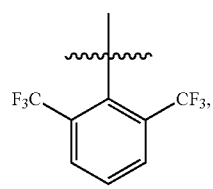
R76 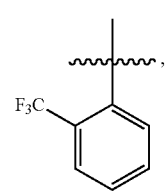
R77 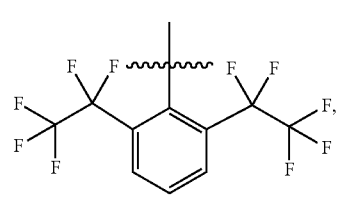
R78 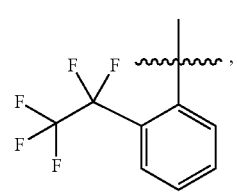
R79 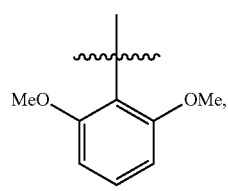
R80 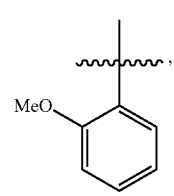
R81 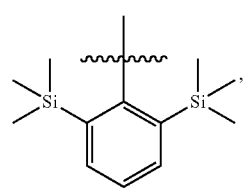
-continued
R82 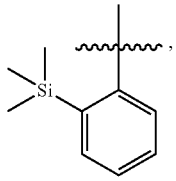
R83 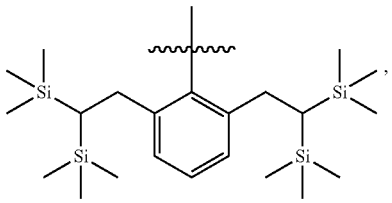
R84 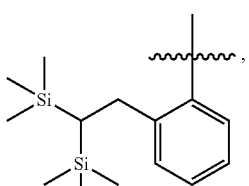
R85 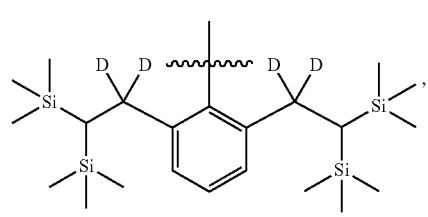
R86 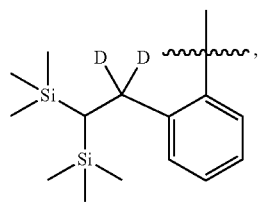
R87 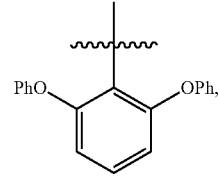
R88 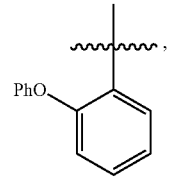
R89 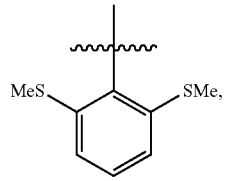

-continued

R90, R91, R92, R93, R94, R95, R96, R97, R98, R99, R100, R101, R102, R103, R104

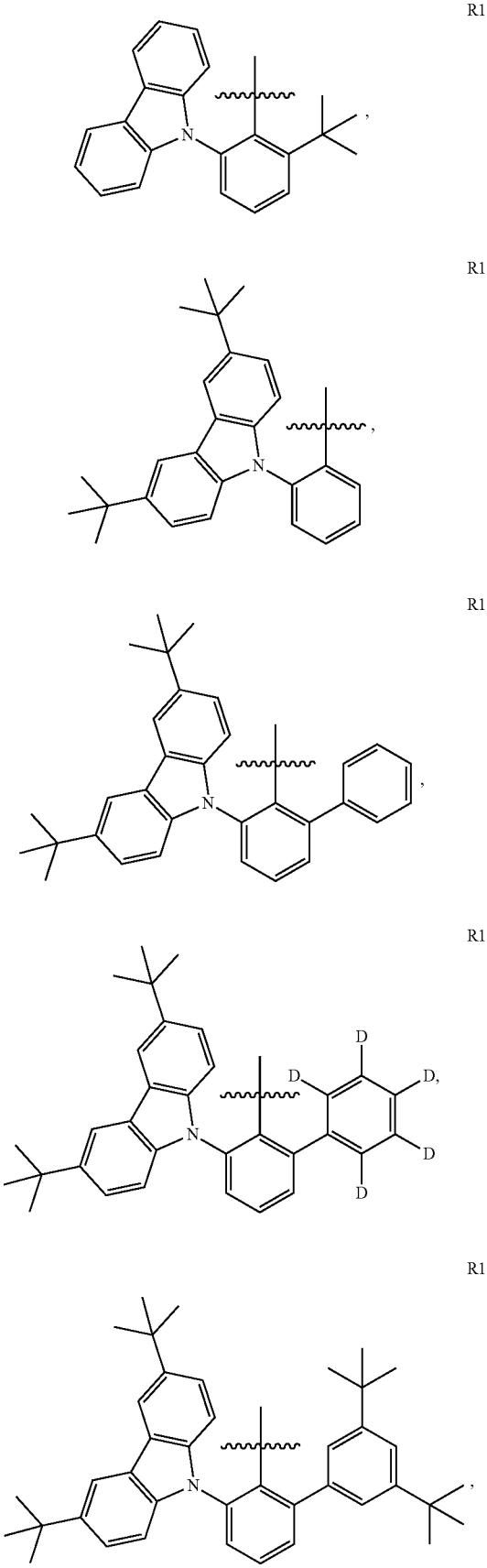
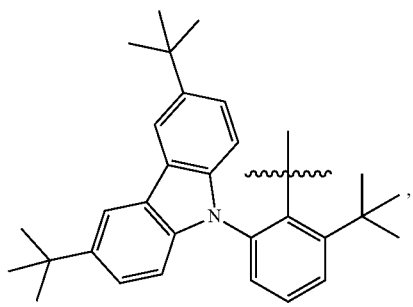
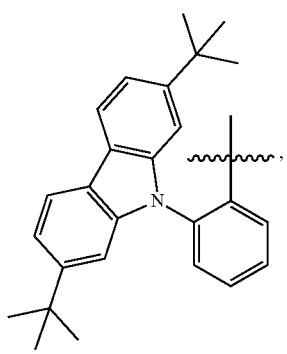
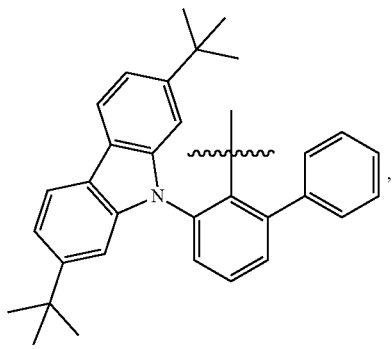
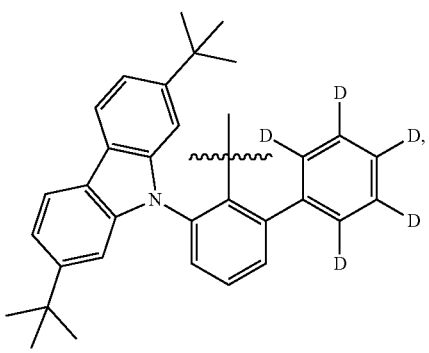

287
-continued
R114
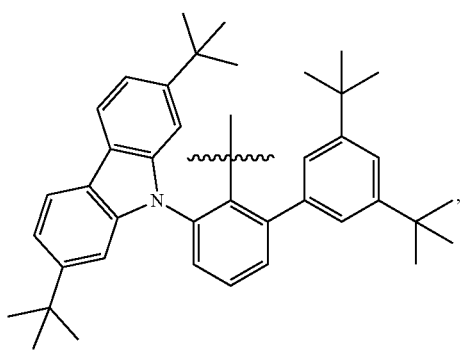
R115
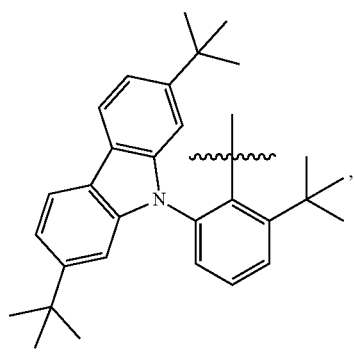
R116
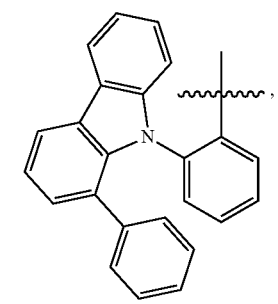
R117
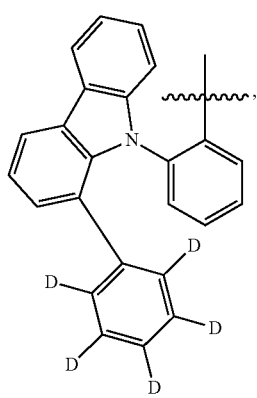
288
-continued
R118
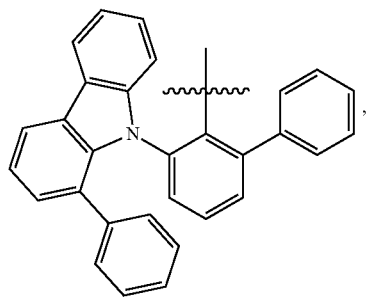
R119
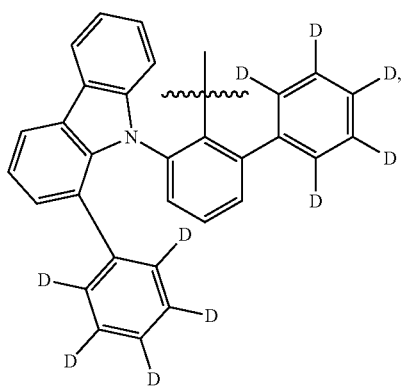
R120
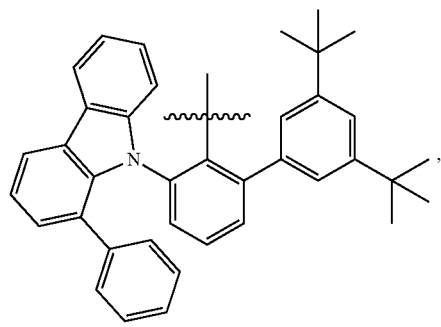
R121
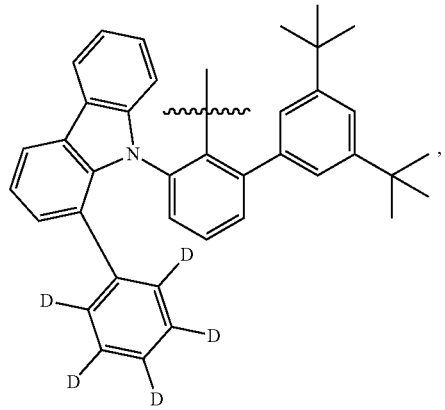

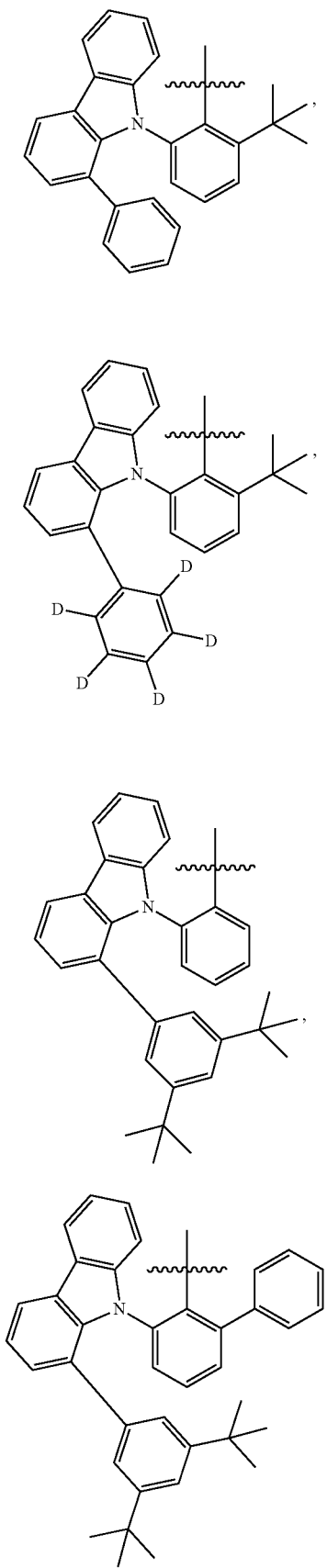
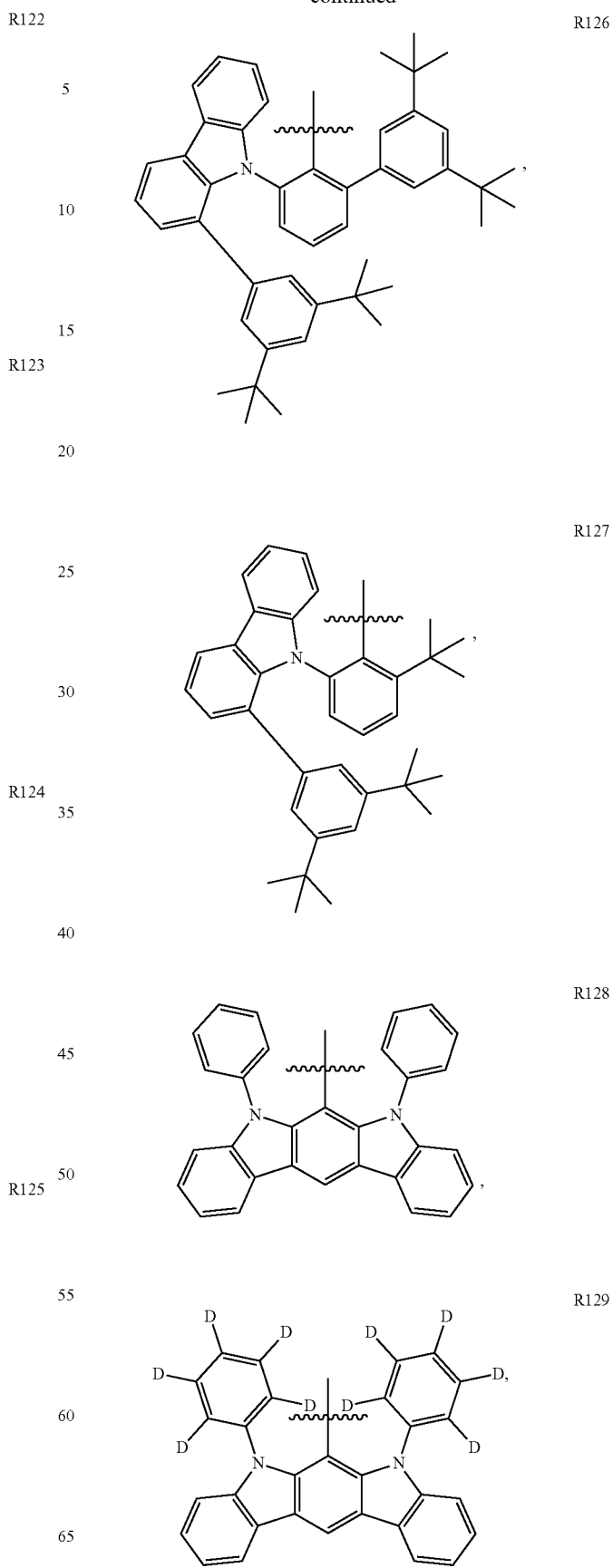

R130
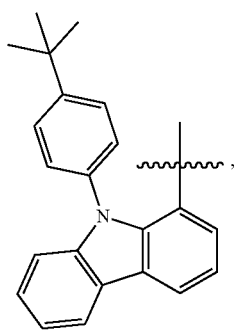
R131
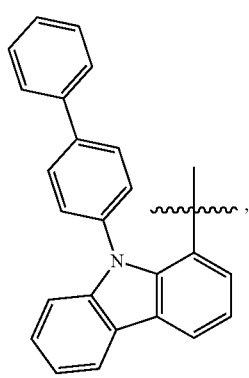
R132
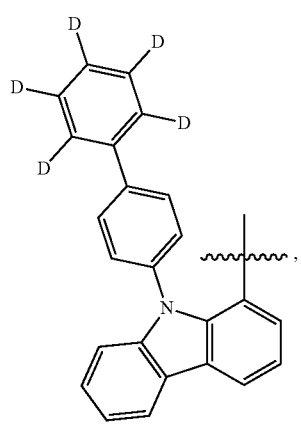
R133
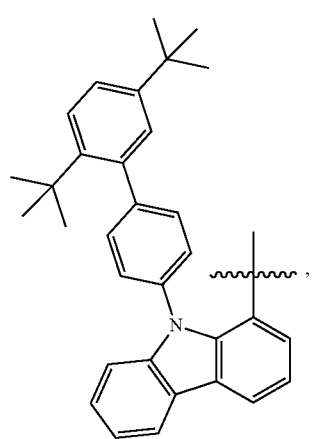
R134
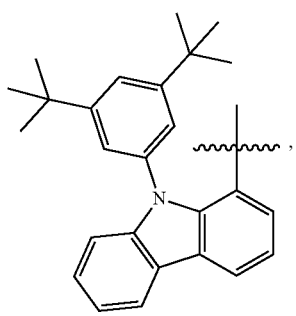
R135
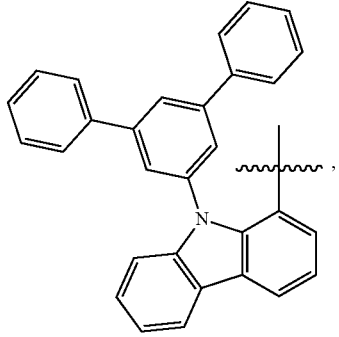
R136
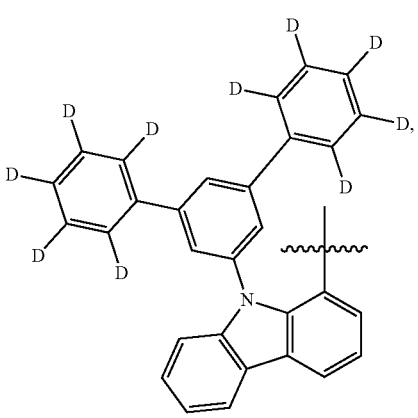
R137
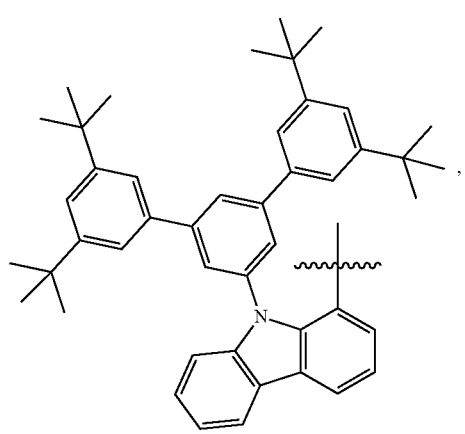

R138 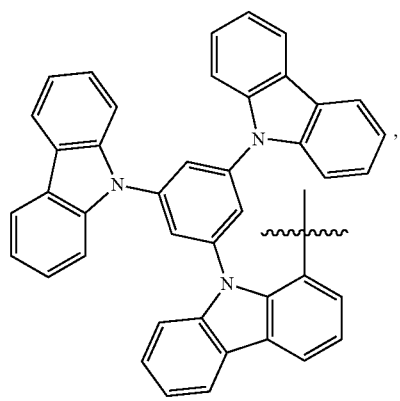
R139 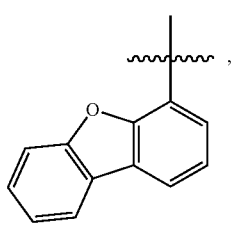
R140 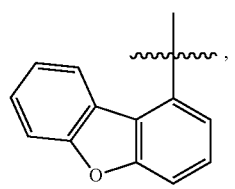
R141 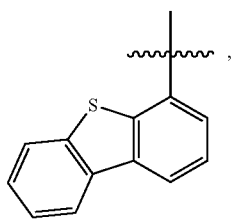
R142 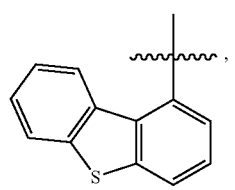
R143 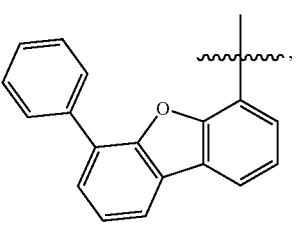
R144 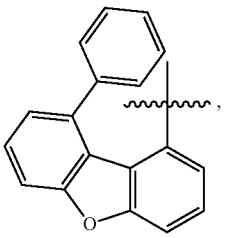
R145 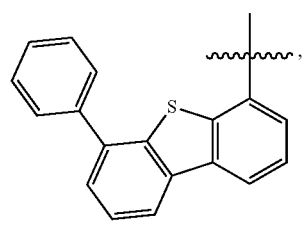
R146 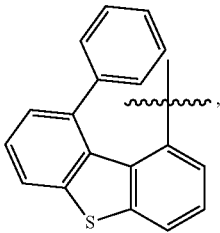
R147 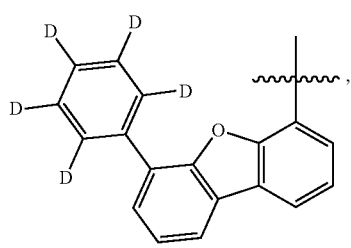
R148 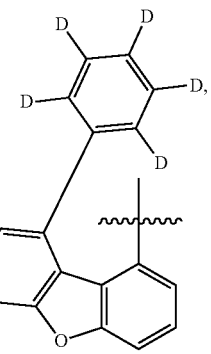
R149 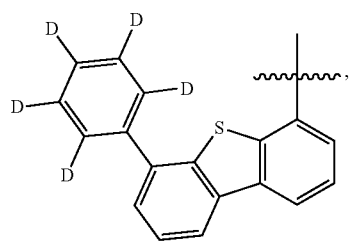

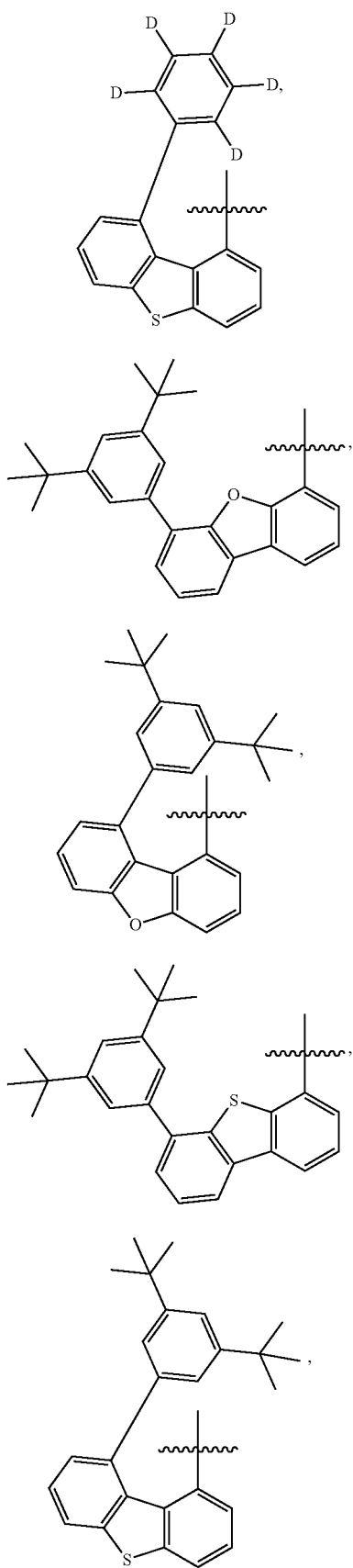
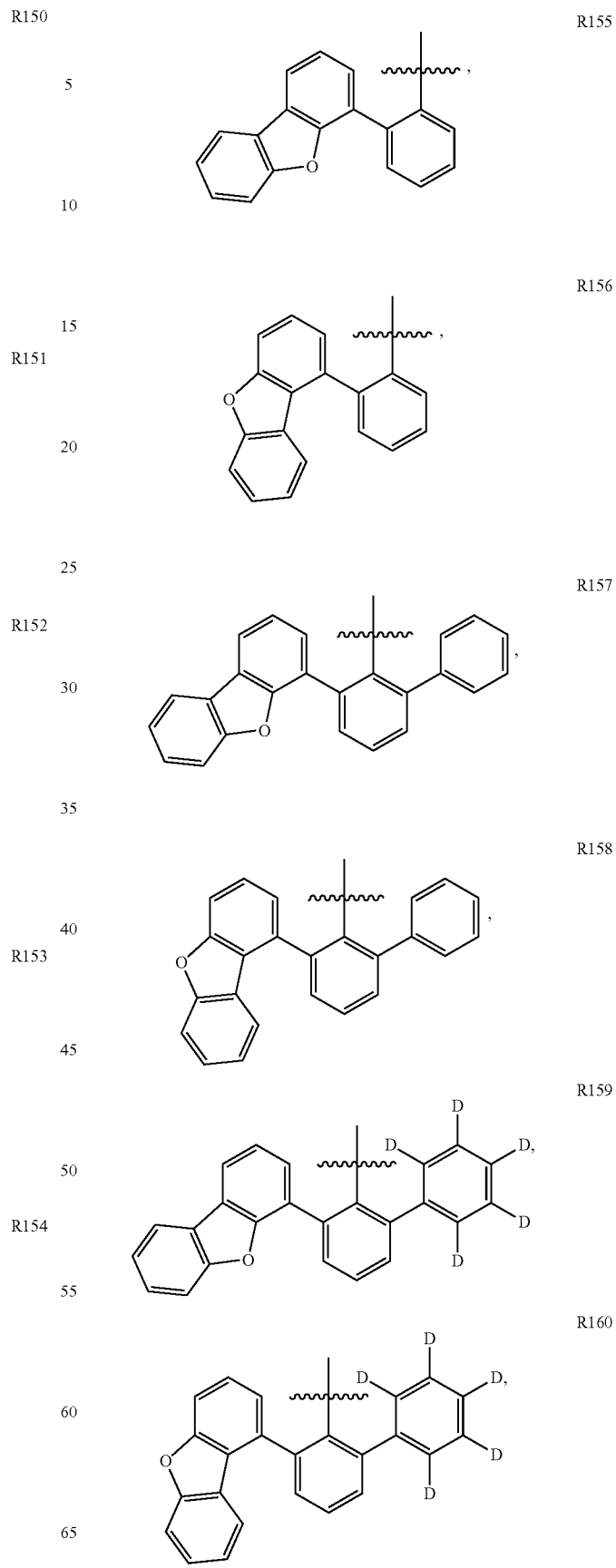

R161
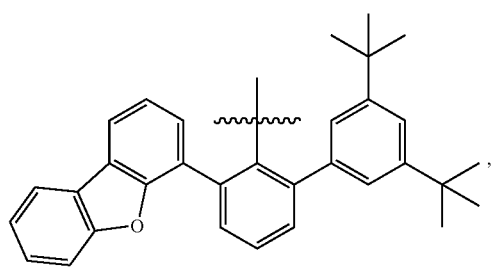
R162
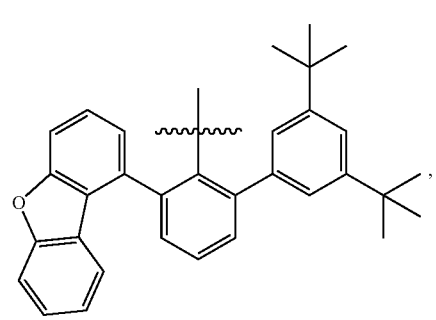
R163
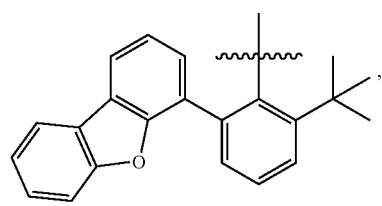
R164
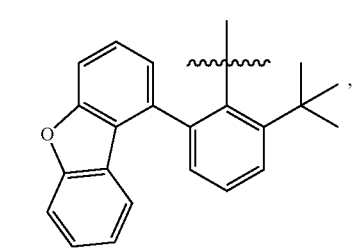
R165
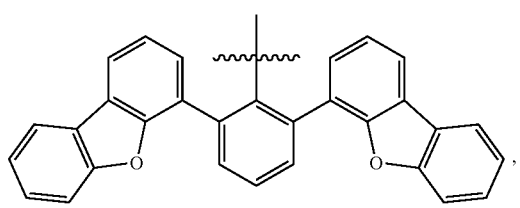
R166
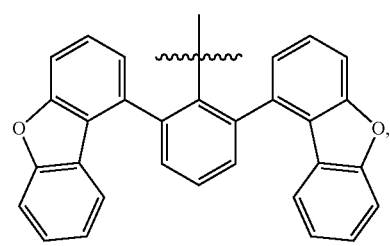
R167
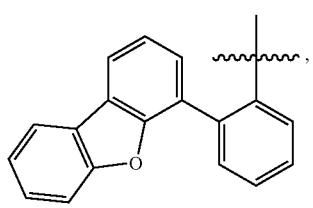
R168
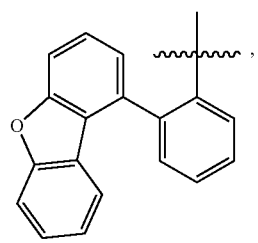
R169
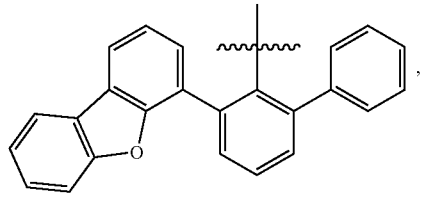
R170
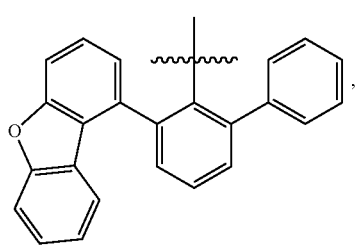
R171
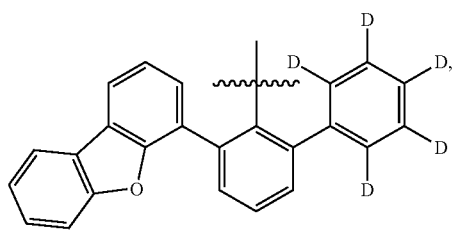
R172
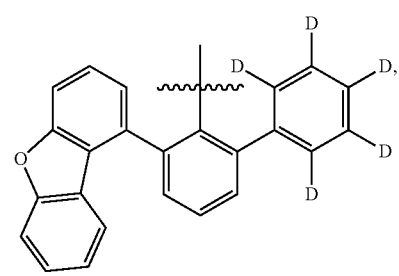

R173 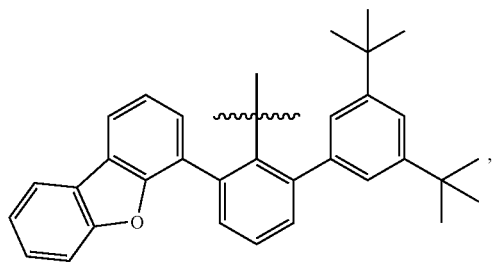
R174 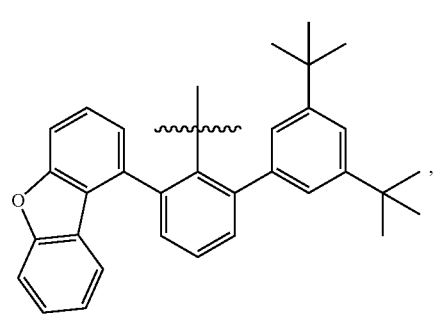
R175 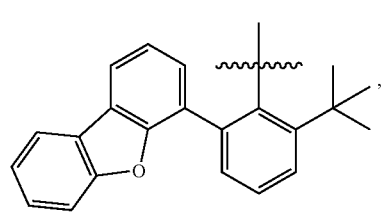
R176 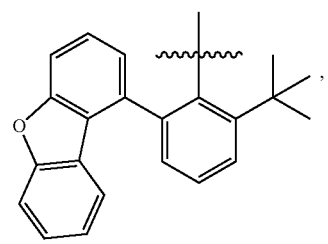
R177 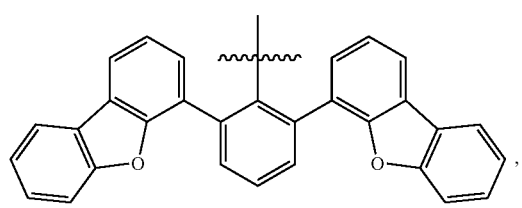
R178 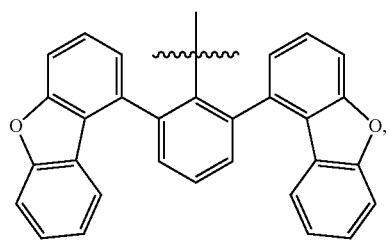
R179 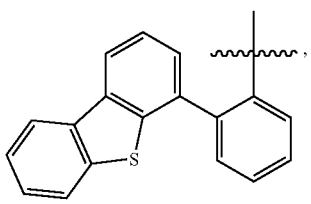
R180 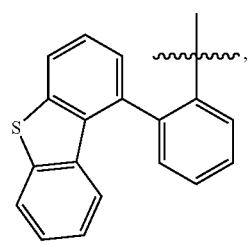
R181 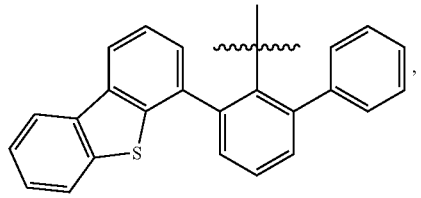
R182 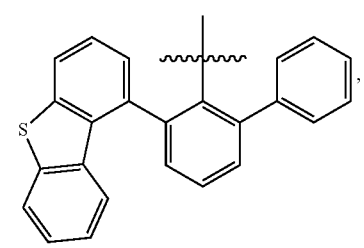
R183 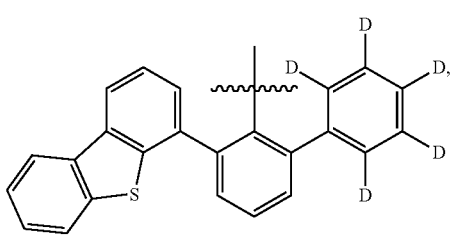
R184 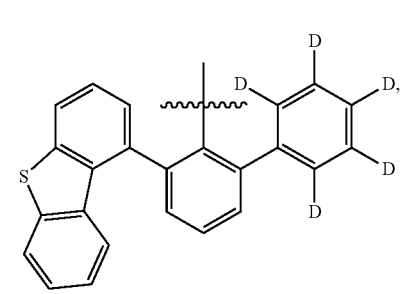

R185
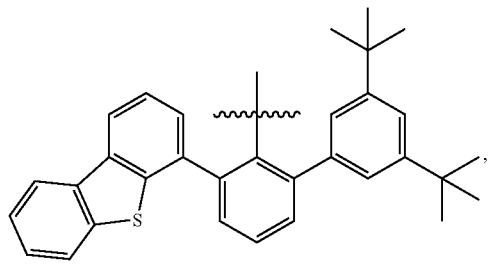
R191
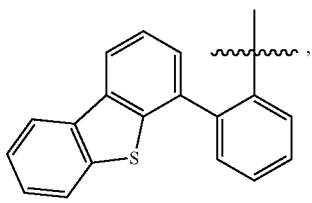
R186
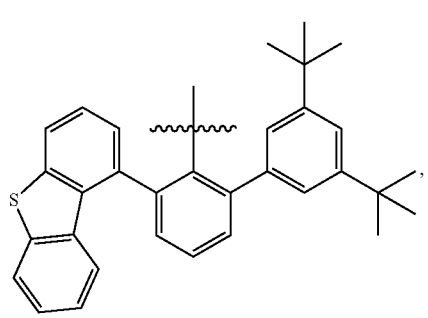
R192
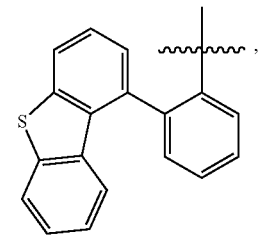
R187
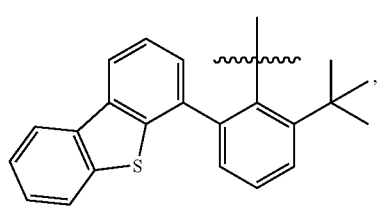
R193
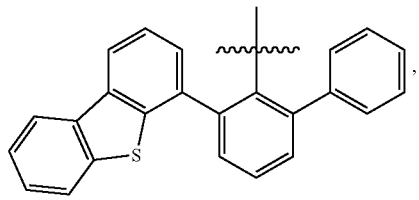
R188
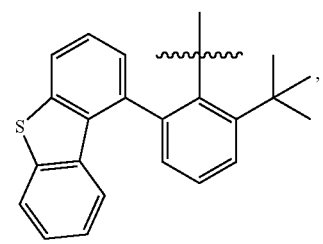
R194
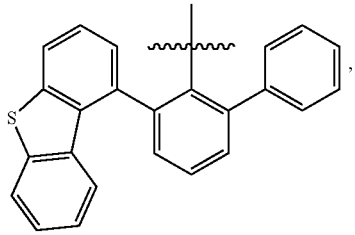
R189
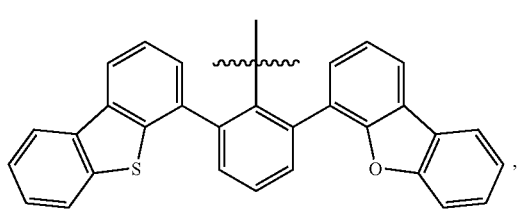
R195
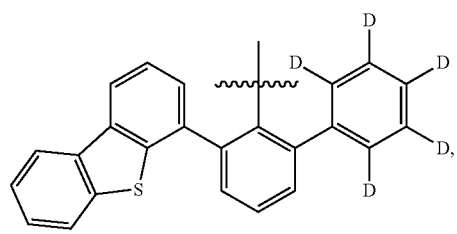
R190
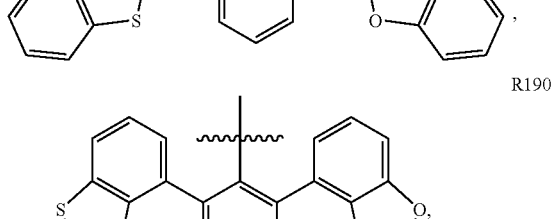
R196
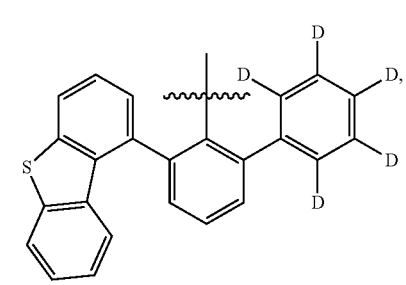

R197
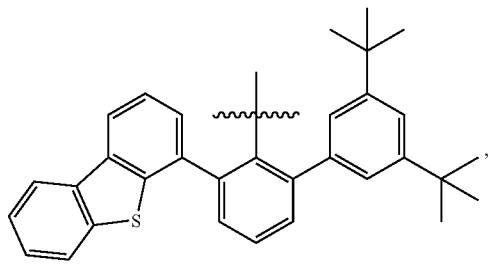
R198
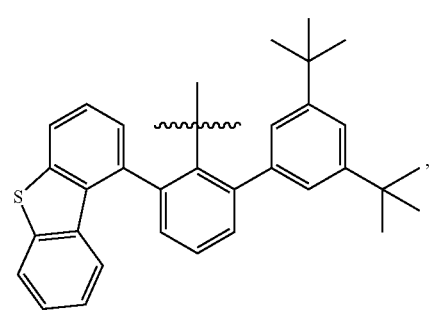
R199
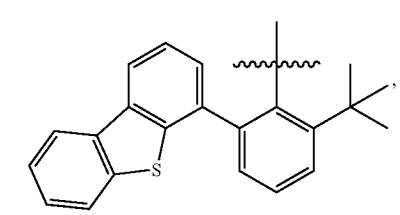
R200
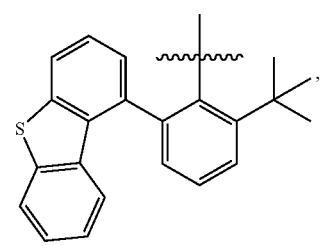
R201
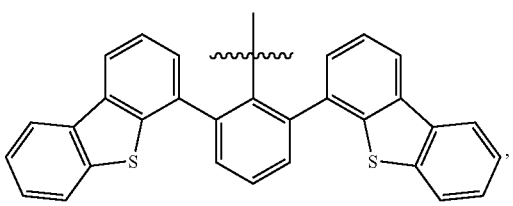
R202
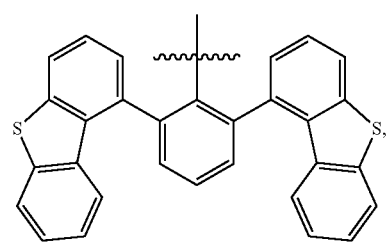
R203
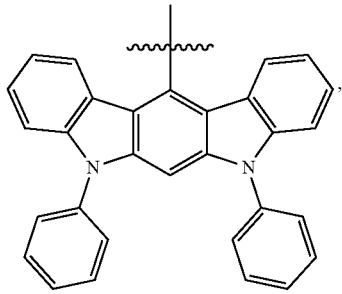
R204
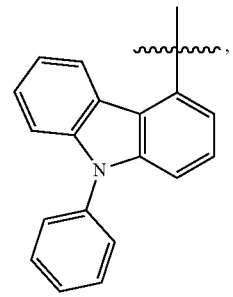
R205
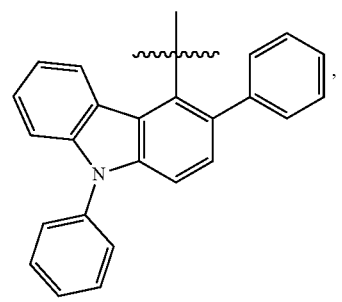
R206
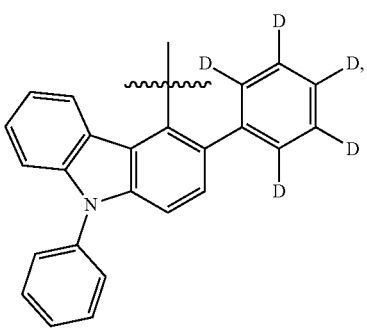
R207
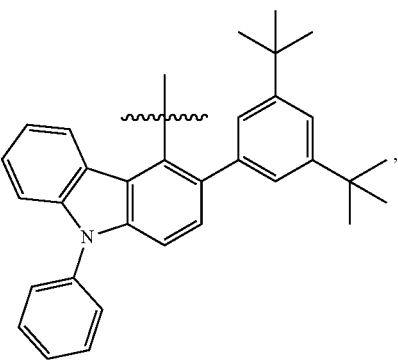

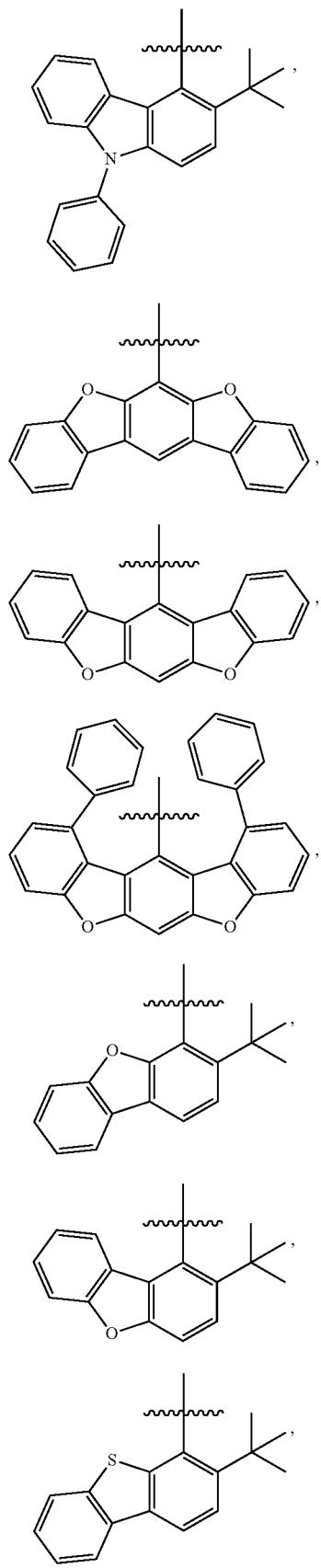
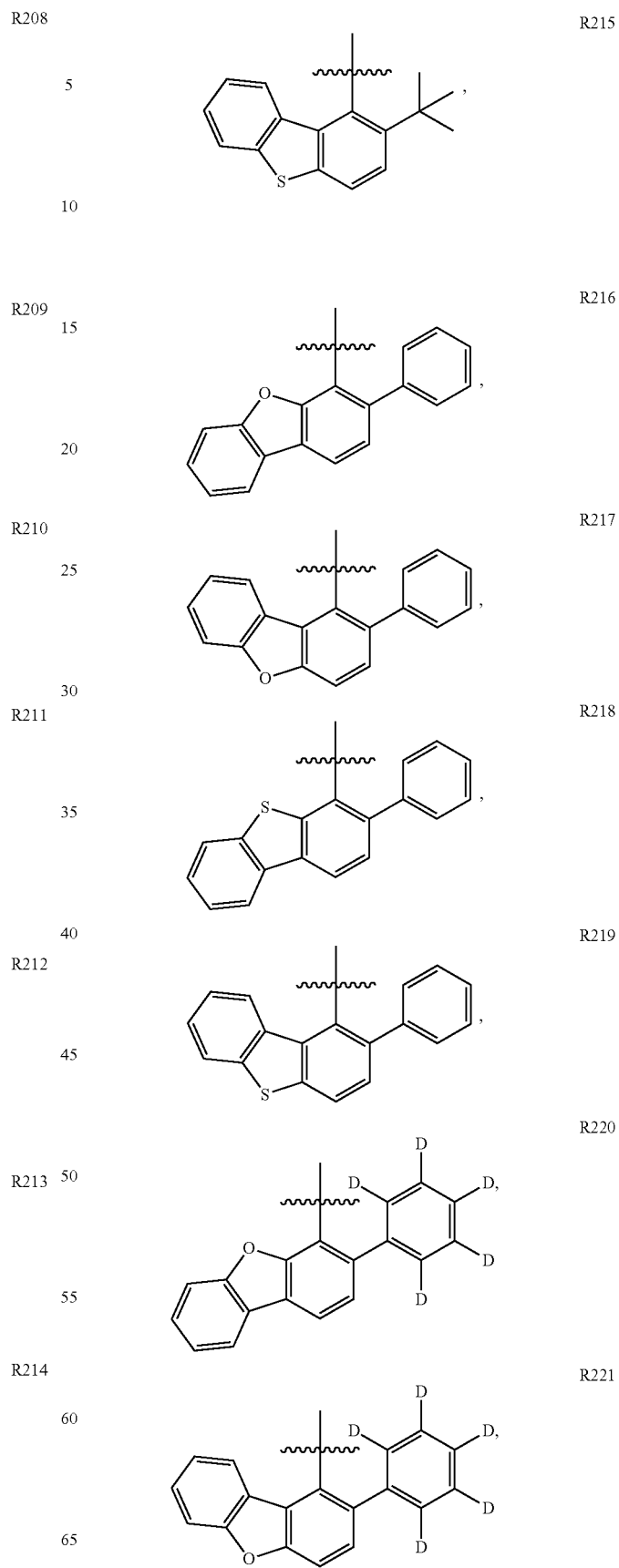

R222 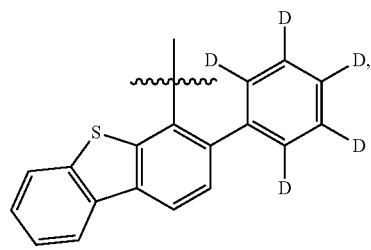
R223 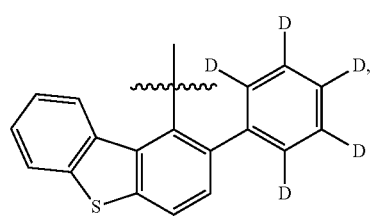
R224 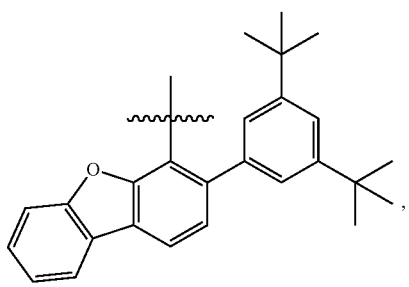
R225 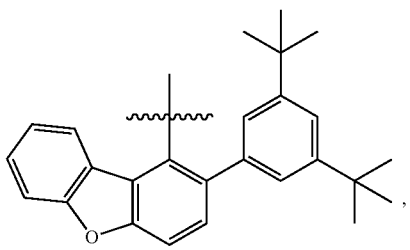
R226 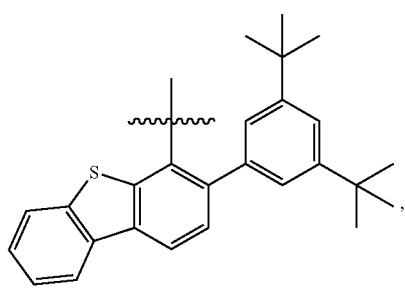
R227 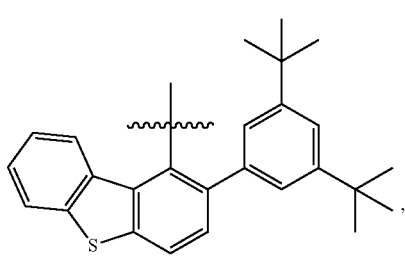
R228 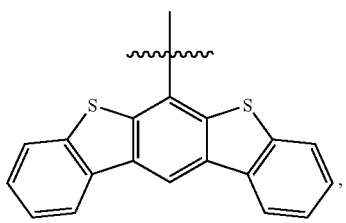
R229 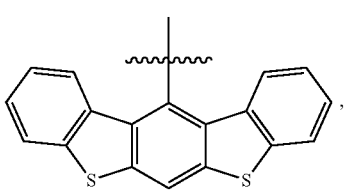
R230 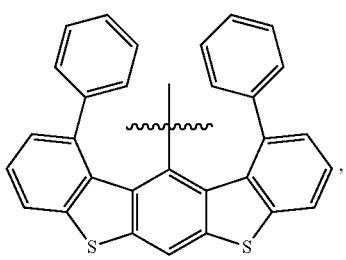
R231 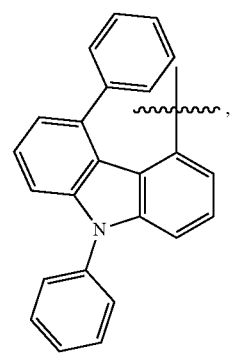
R232 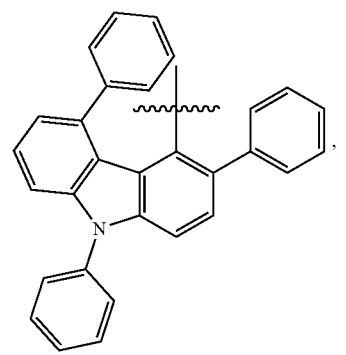

309
-continued
R233 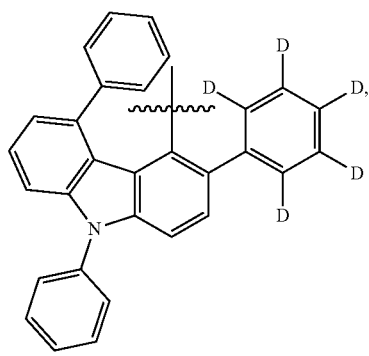
R234 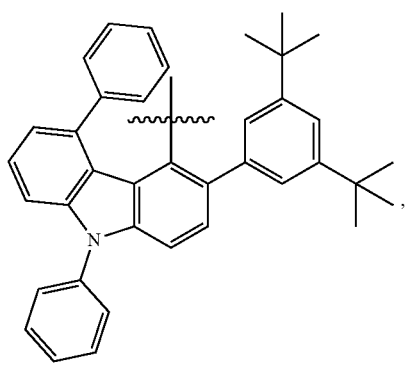
R235 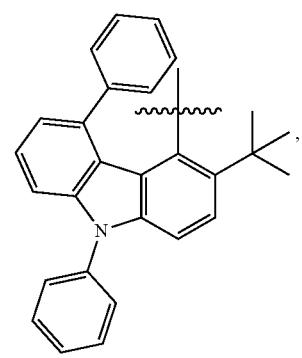
R236 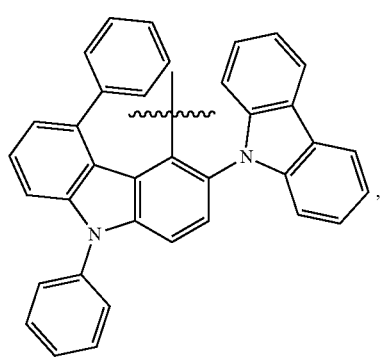
310
-continued
R237 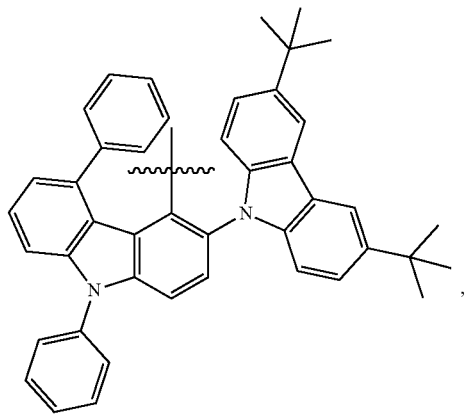
R238 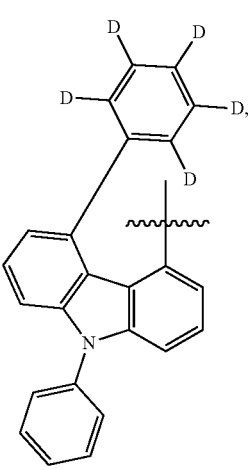
R239 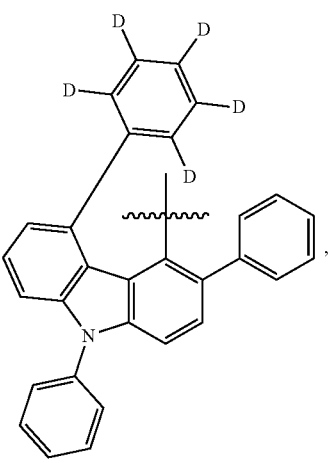

311
-continued
R240
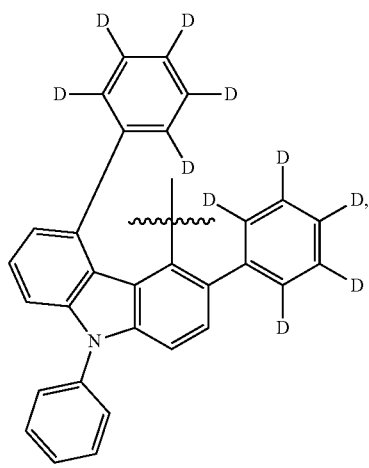
R241
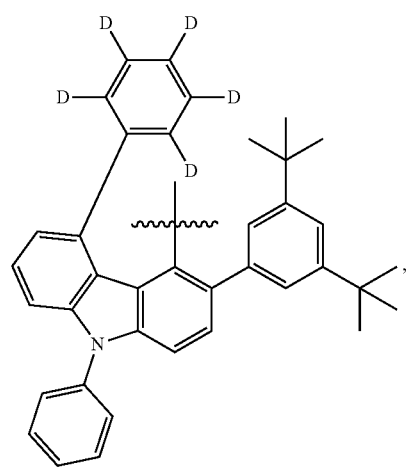
R242
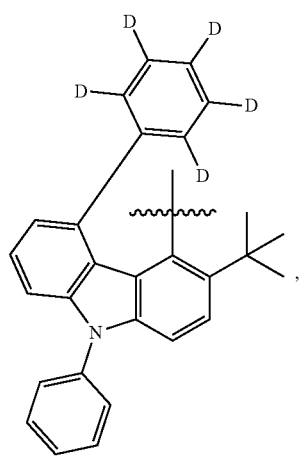
312
-continued
R243
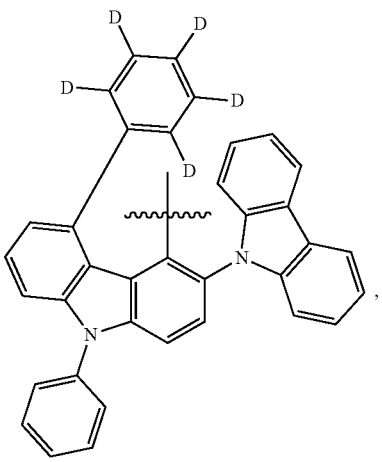
R244
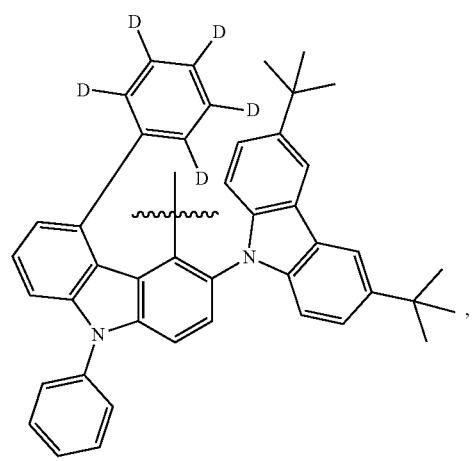
R245
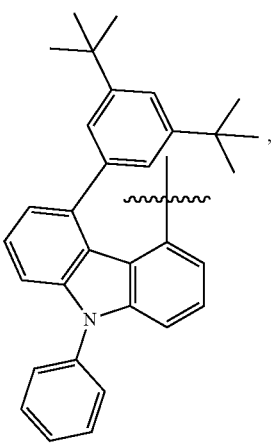

R246
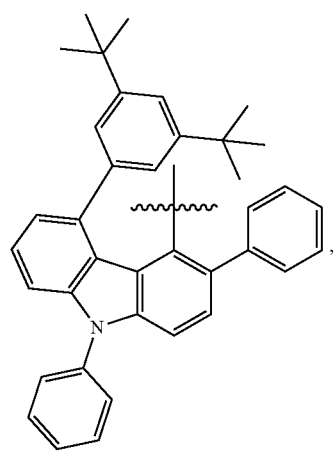
R249
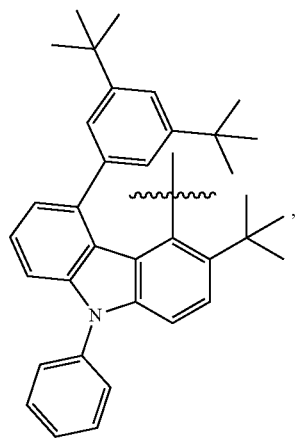
R247
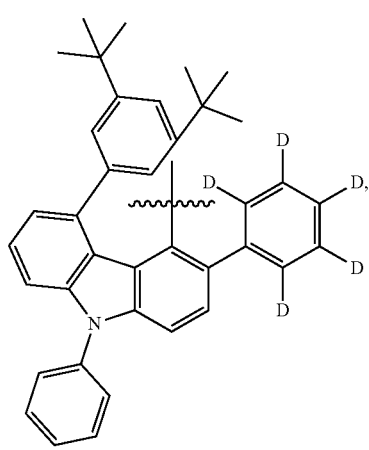
R250
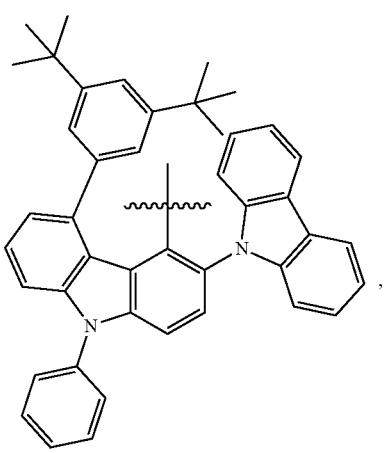
R248
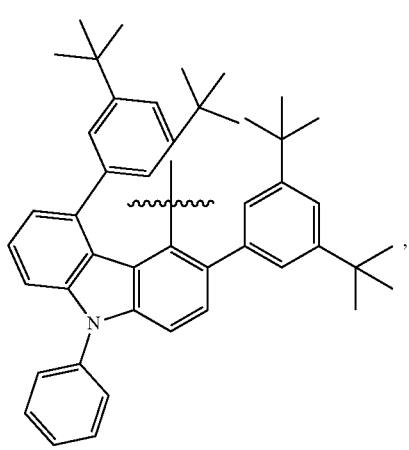
R251
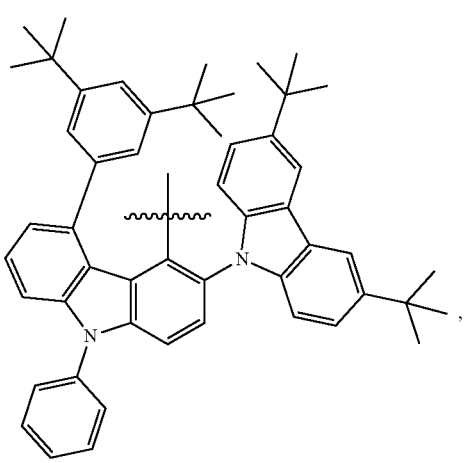

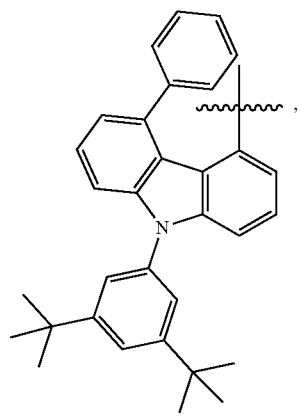
R252
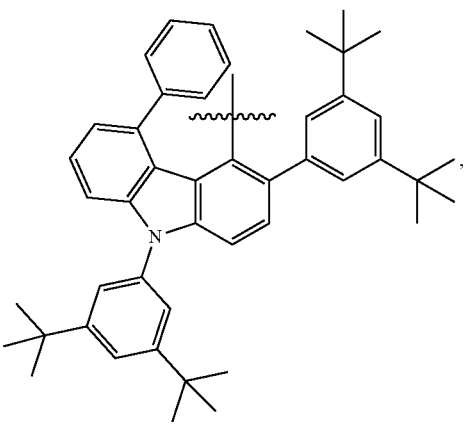
R255
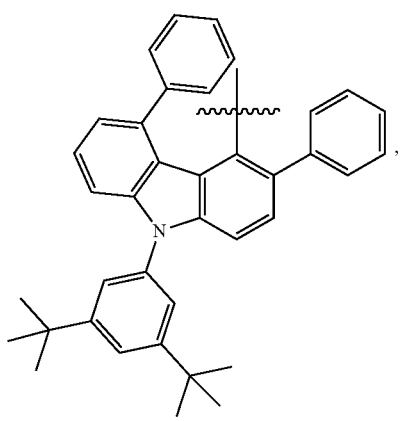
R253
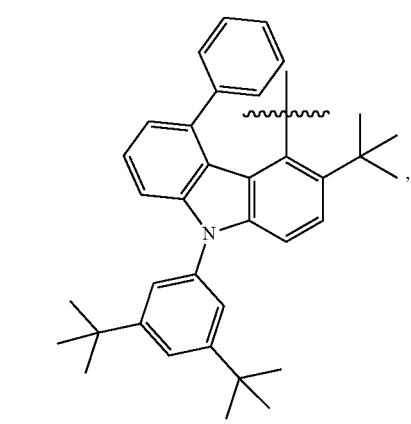
R256
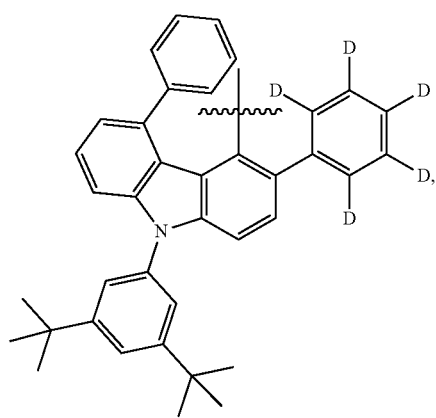
R254
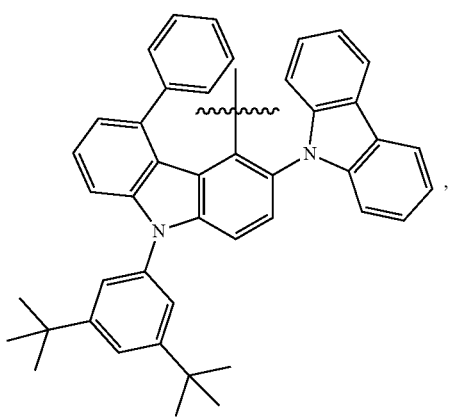
R257

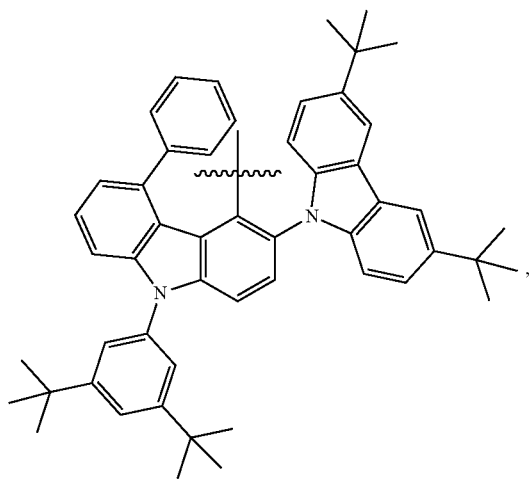
R258
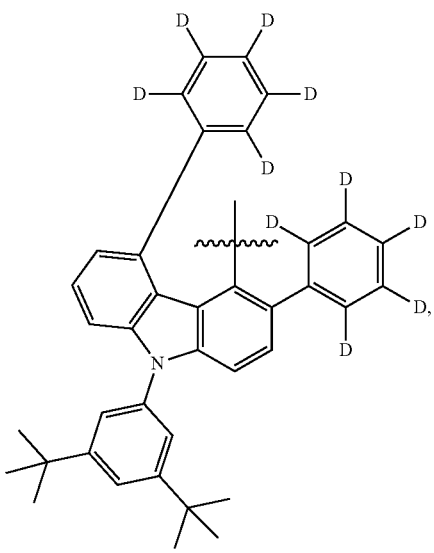
R261
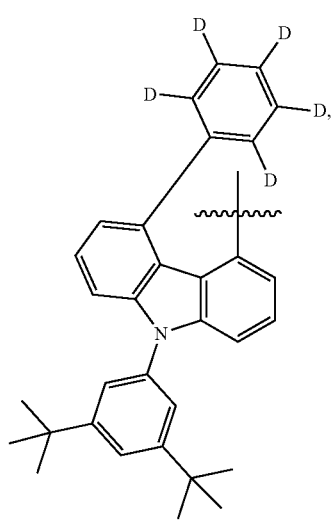
R259
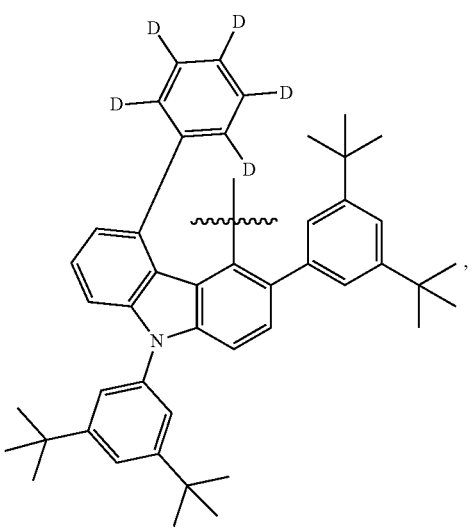
R262
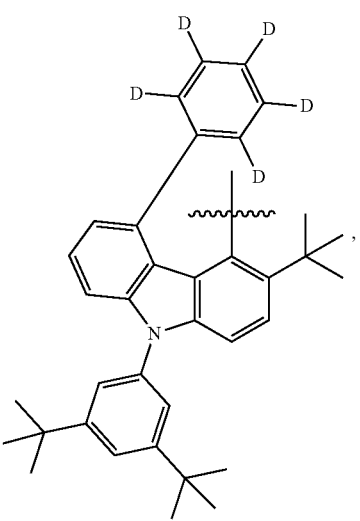
R260
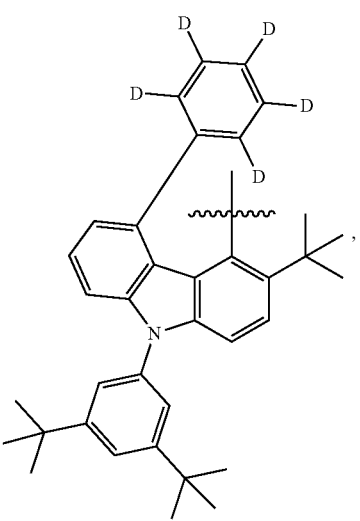
R263

R264
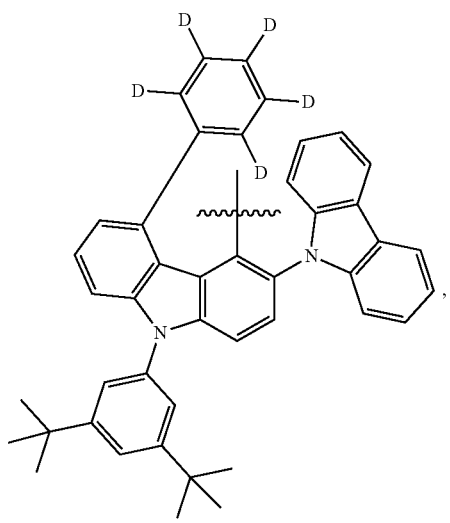
R265
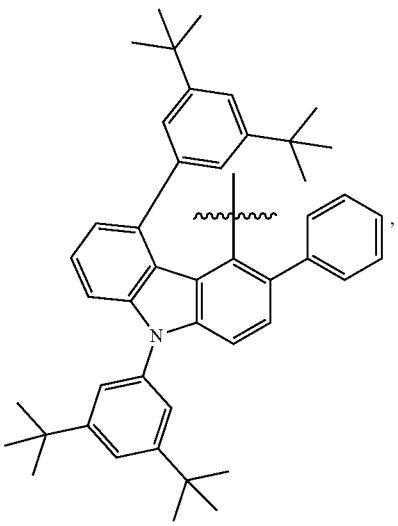
R266
R267
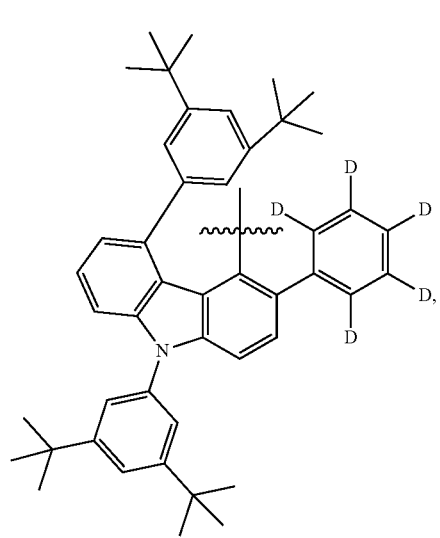
R268
R269
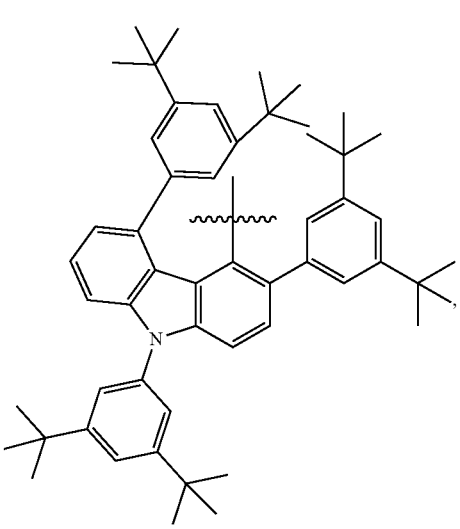

-continued
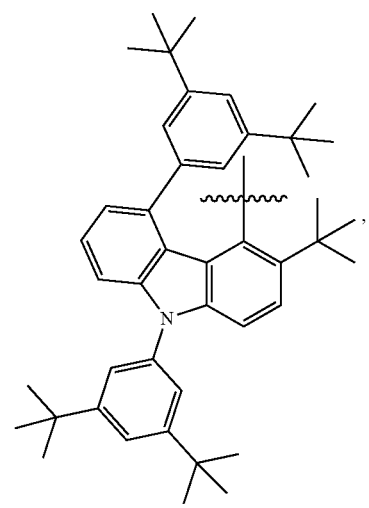
R270
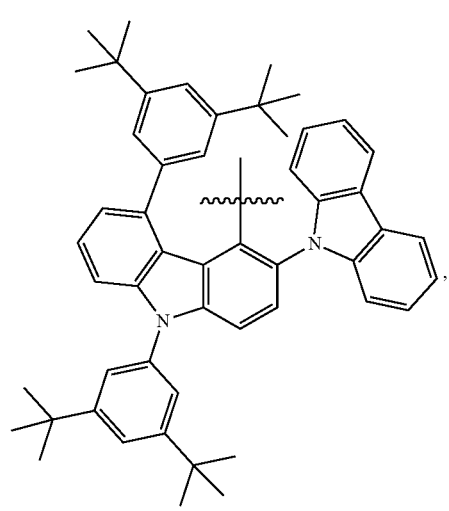
R271
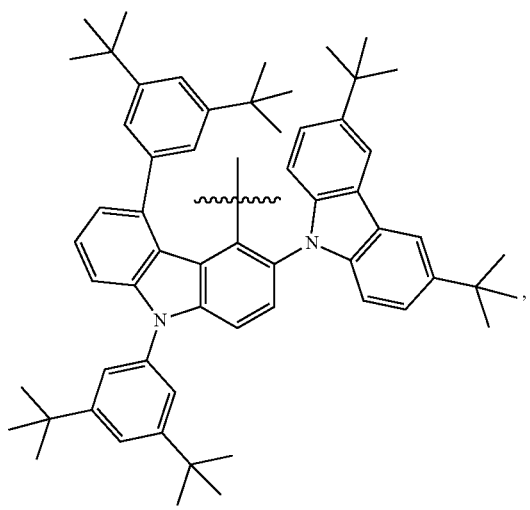
R272
-continued
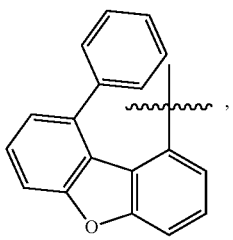
R273
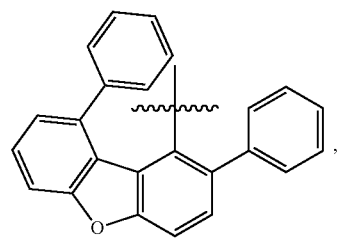
R274
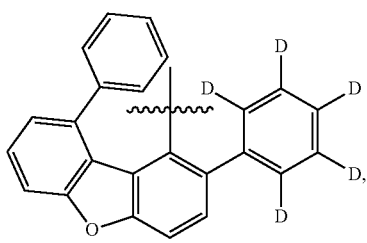
R275
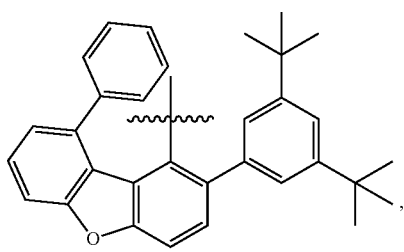
R276
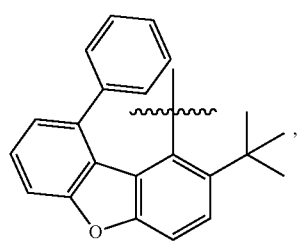
R277
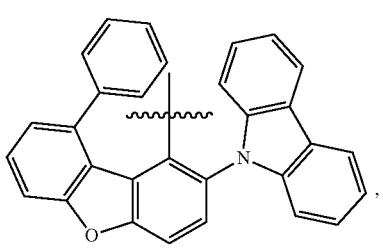
R278

-continued
R279
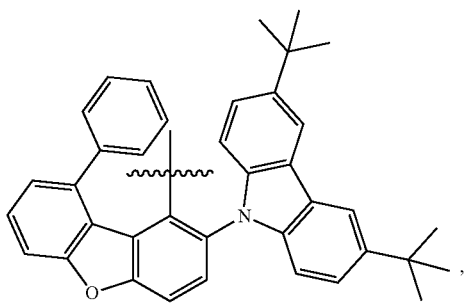
R280
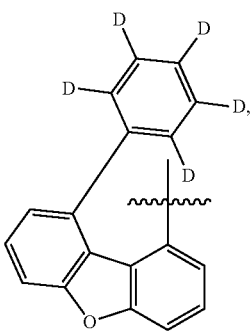
R281
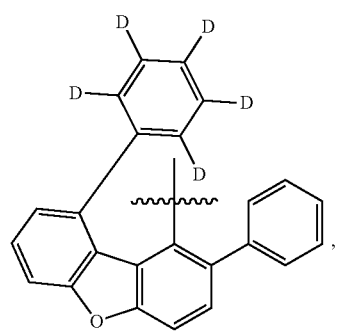
R282
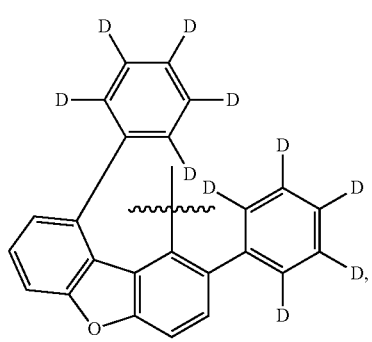
R283
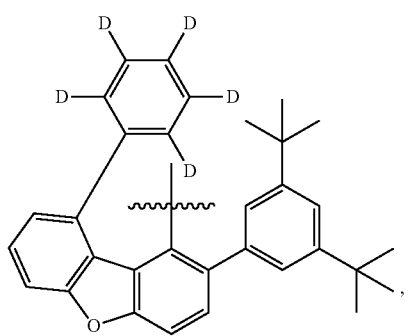
-continued
R284
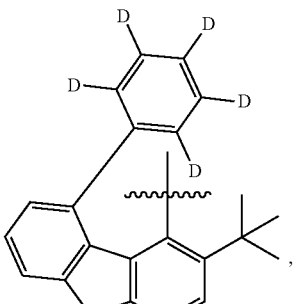
R285
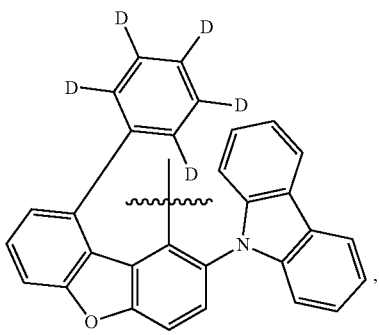
R286
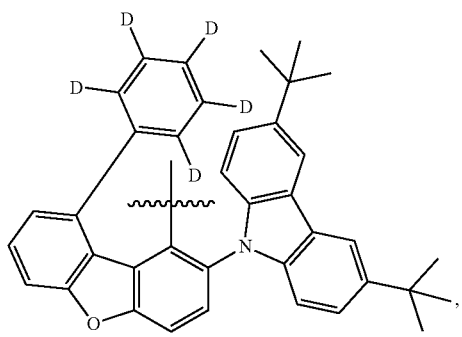
R287
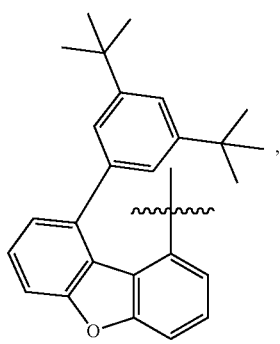

R288
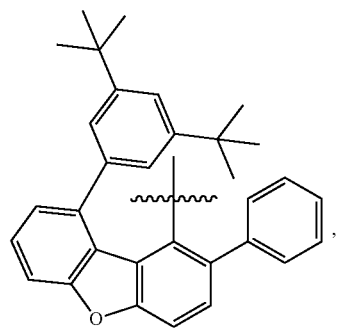
R289
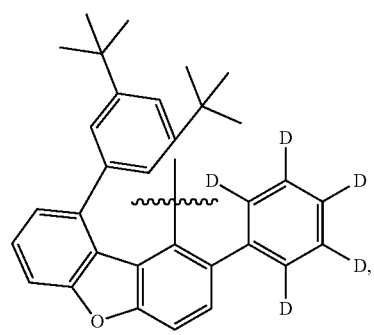
R290
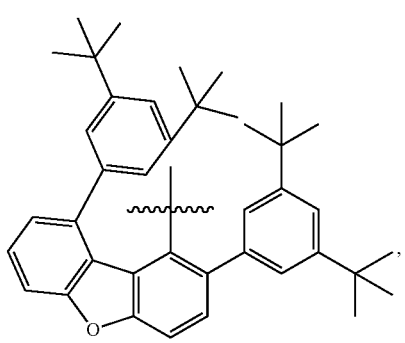
R291
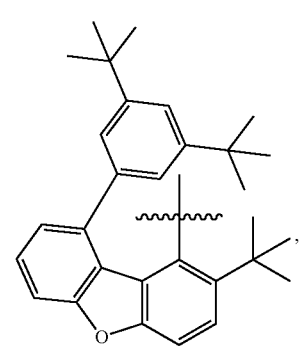
R292
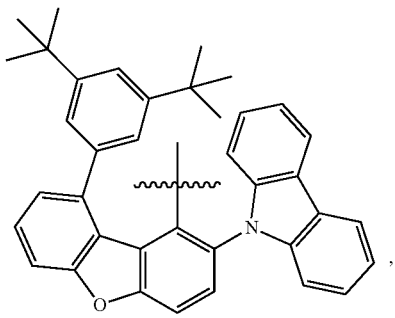
R293
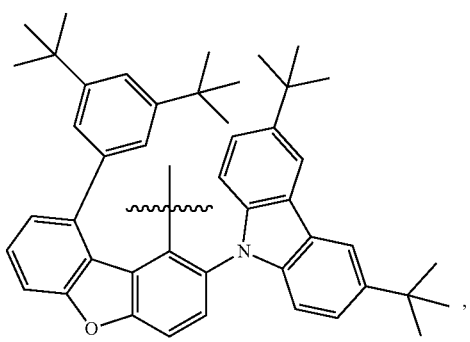
R294
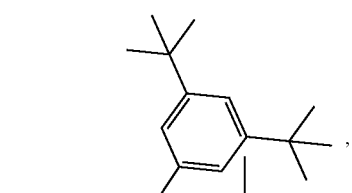
R295
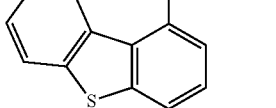
R296
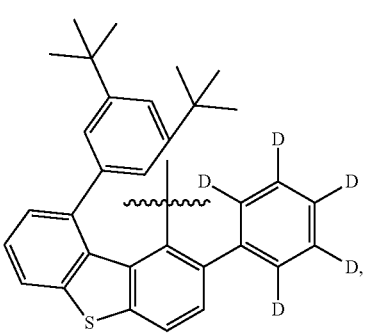

R297 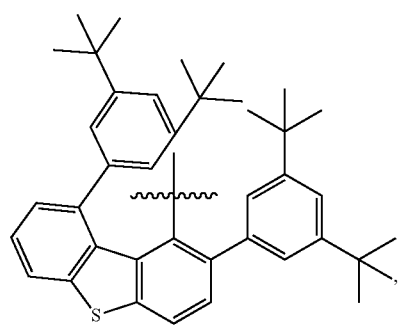
R298 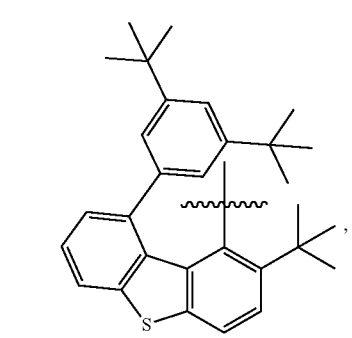
R299 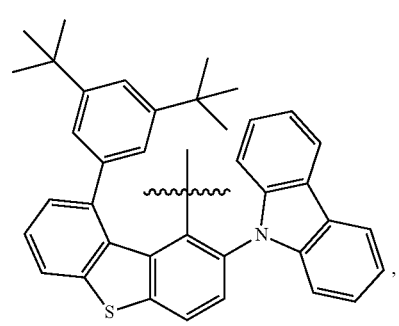
R300 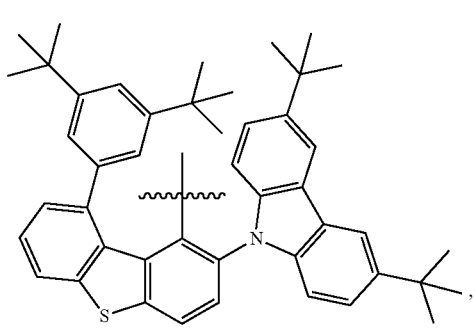
R301 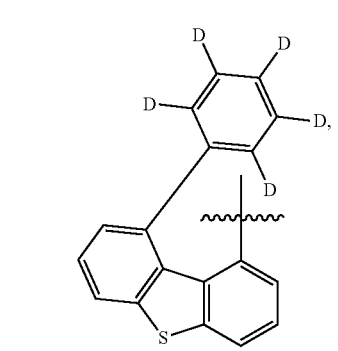
R302 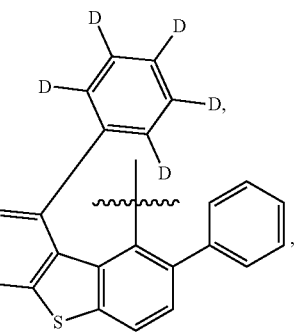
R303 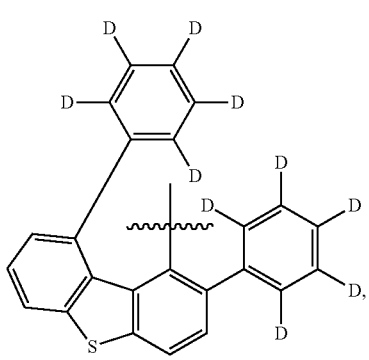
R304 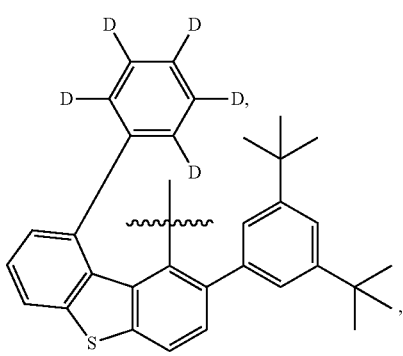
R305 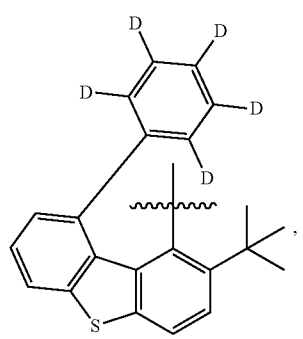

-continued
R306
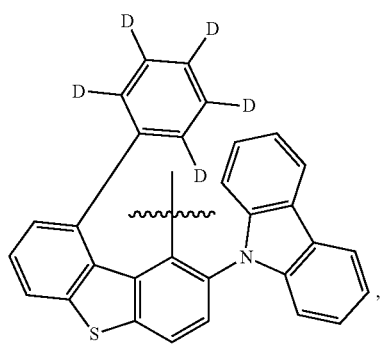
R307
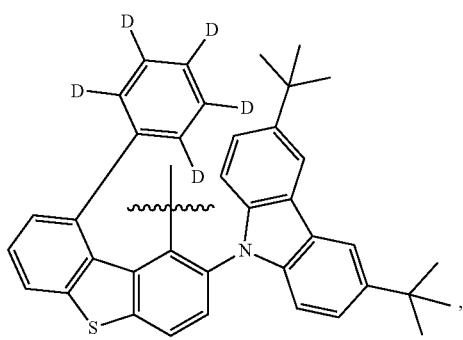
R308
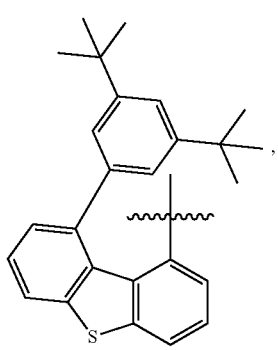
R309
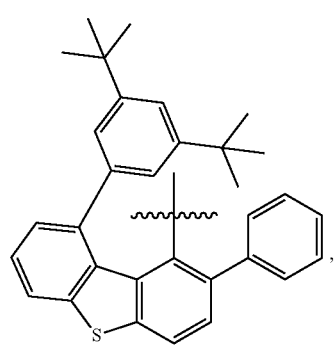
-continued
R310
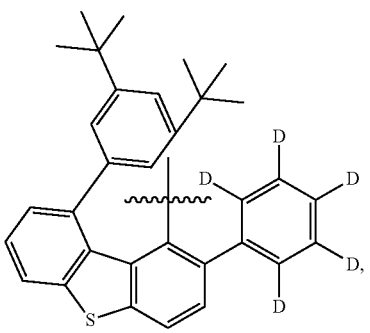
R311
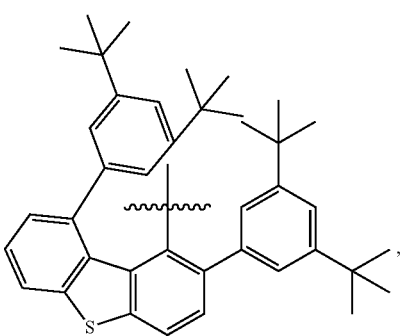
R312
R313
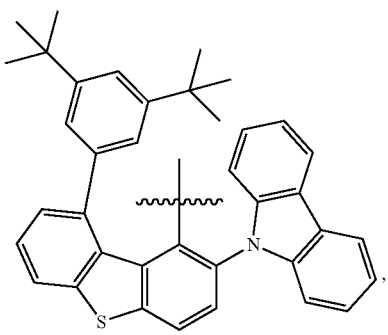

| R314 | R318 |
|---|---|
| 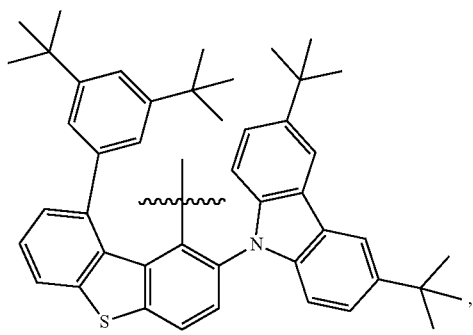 | 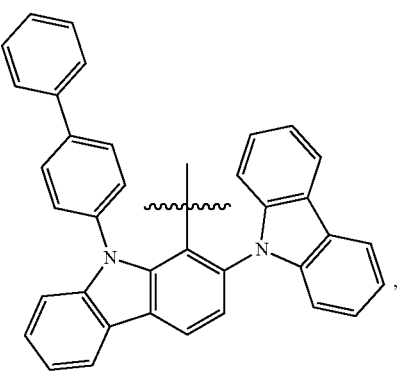 |
| R315 | R319 |
|---|---|
| 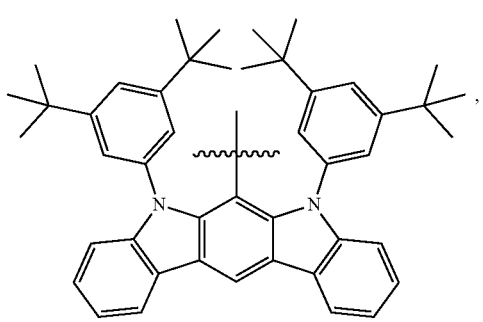 | 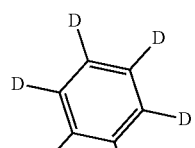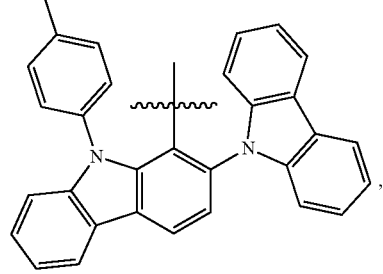 |
| R316 | R320 |
|---|---|
| 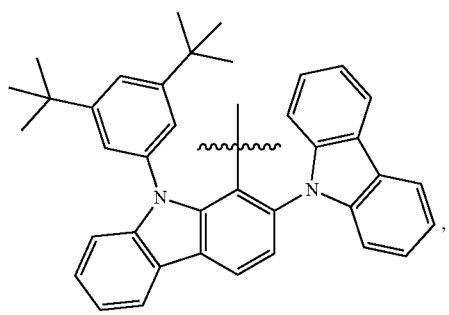 | 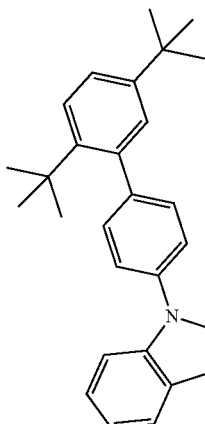 |
| R317 | R321 |
|---|---|
| 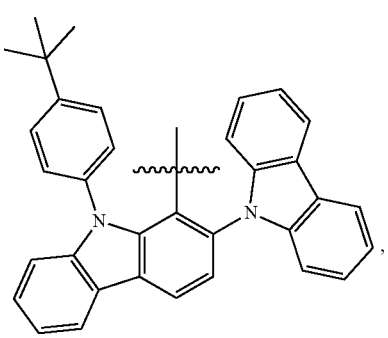 | 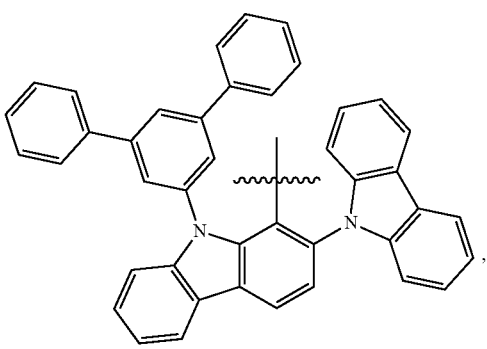 |

333
-continued
R322
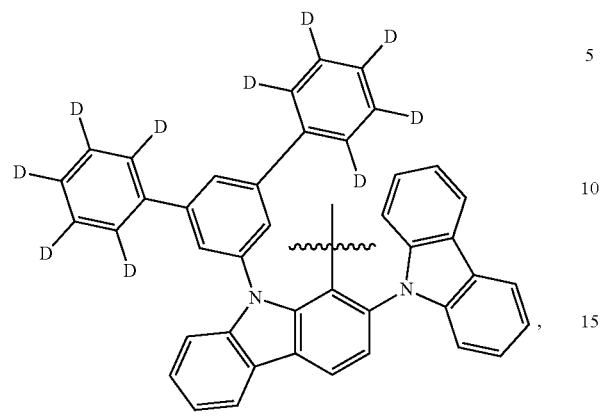
R323
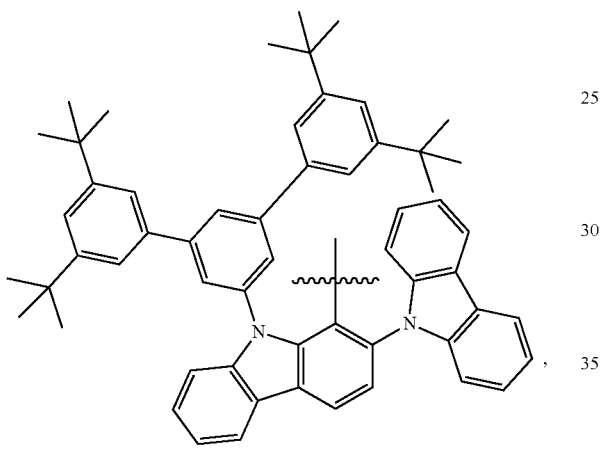
R324
R325
334
-continued
R326
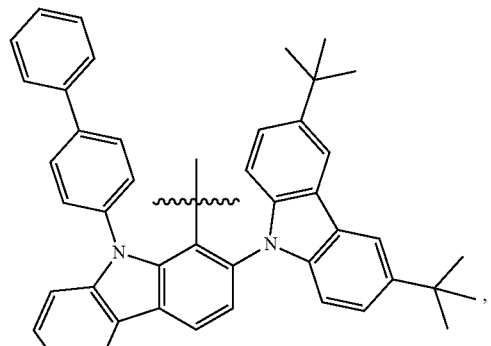
R327
R328
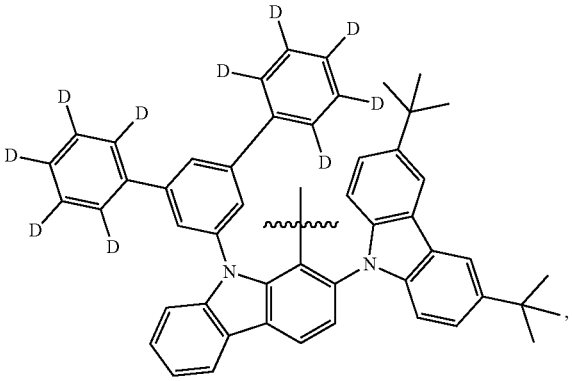
R329

-continued

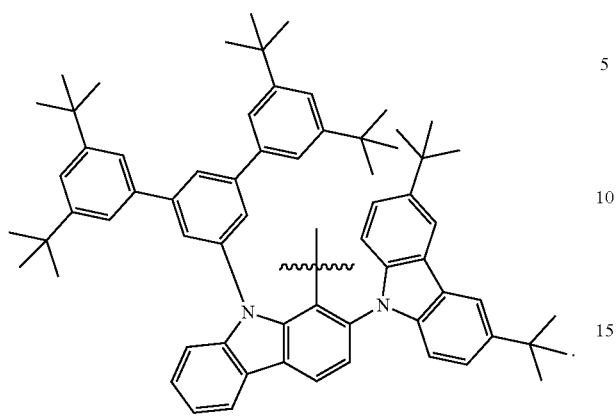

In some embodiments, the compound can comprise a ligand $L_A$ of Formula II

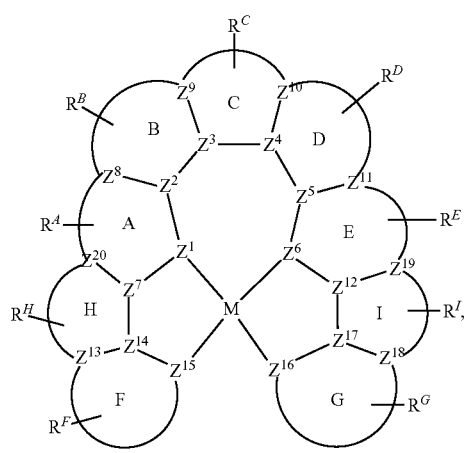

wherein rings H, I, F, and G are each independently a 5-membered or 6-membered cathocyclic or heterocyclic ring; $Z^{13}$-$Z^{20}$ are each independently C or N; $R^H$, $R^I$, $R^F$, and $R^G$ each independently represents zero, mono, or up to a maximum allowed substitutions to its associated ring; $R^H$, $R^I$, $R^F$, and $R^G$ are each independently selected from the group consisting of hydrogen or a substituent selected from a group consisting of the general substituents defined herein; M is Pt or Pd; and wherein rings A, B, C, D, and E are all defined the same as above for Formula I; $Z^1$-$Z^{12}$ are all defined the same as above for Formula I; and $R^A$, $R^B$, $R^C$, and $R^E$ are all defined the same as above for Formula I.

In some of the above embodiments, the compound can be selected from the group consisting of:

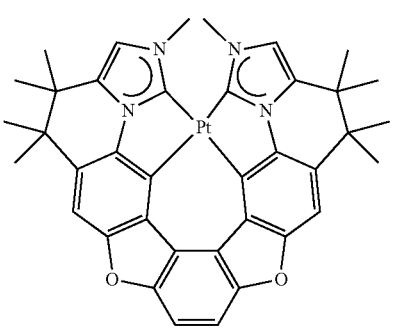

,

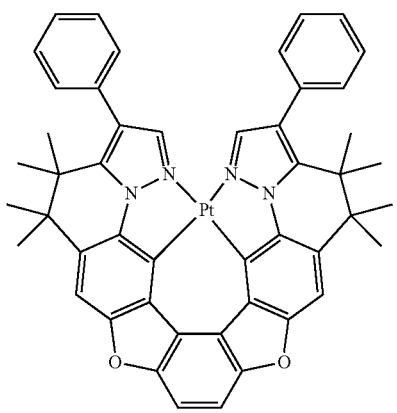

,

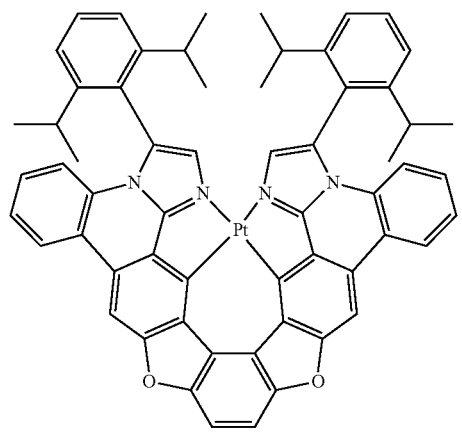

,

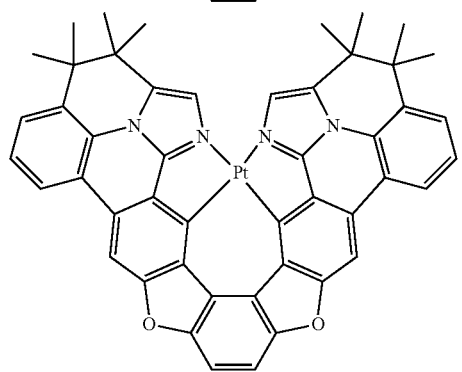

,

337
-continued
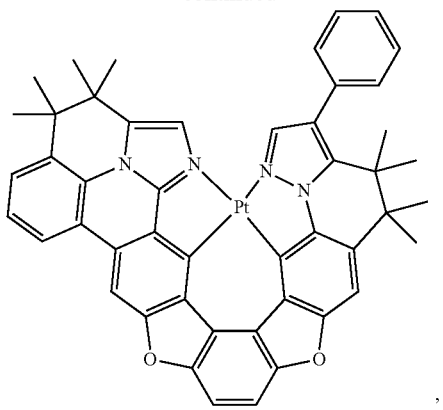
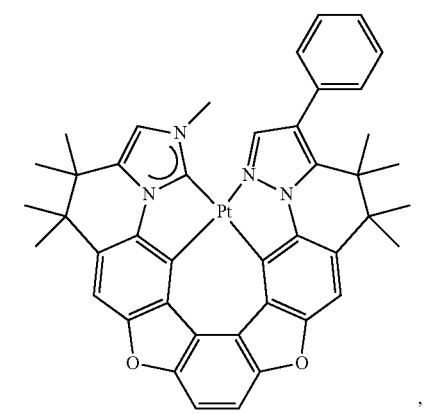
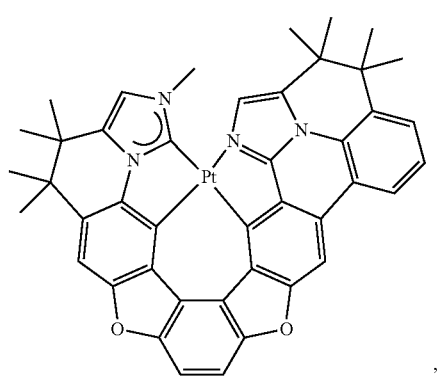
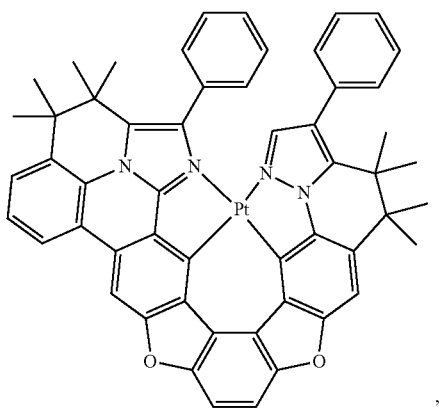
338
-continued
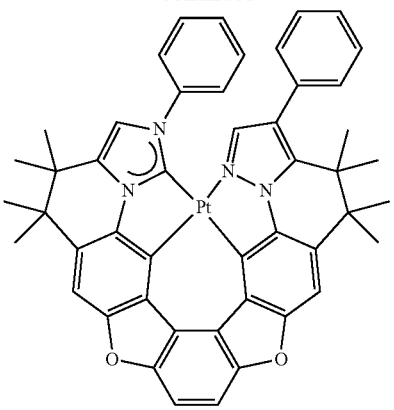
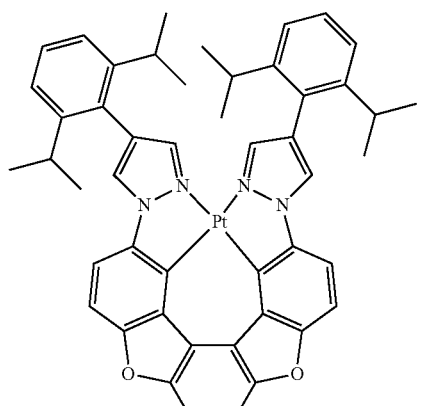
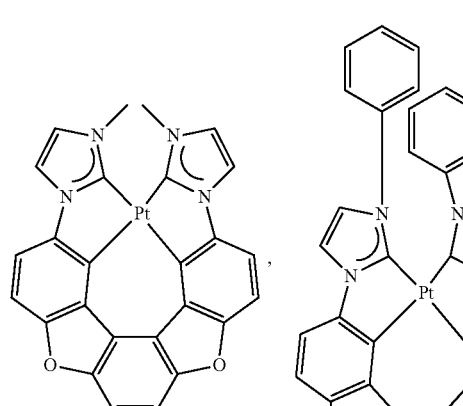
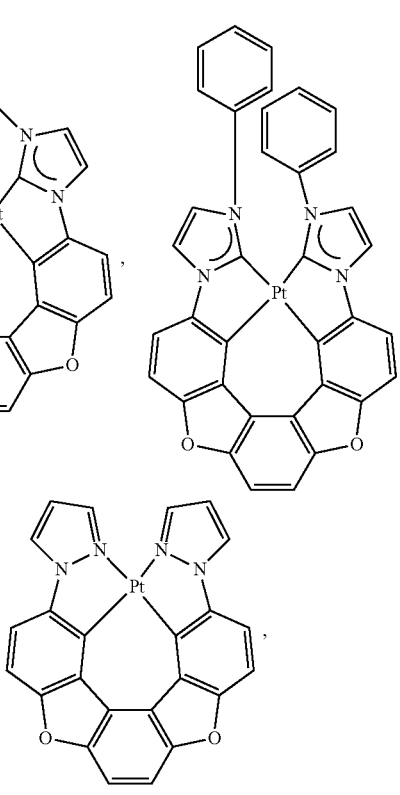

339
-continued
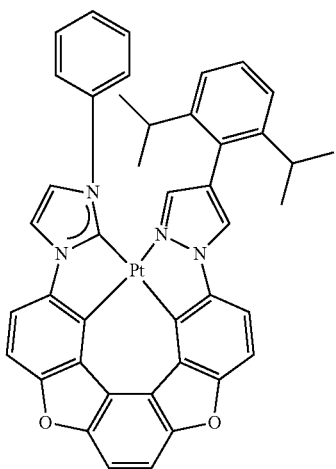
,
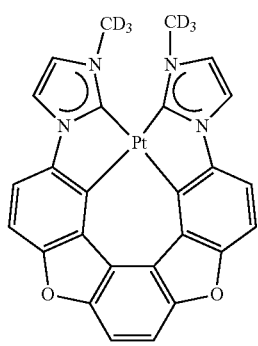
,
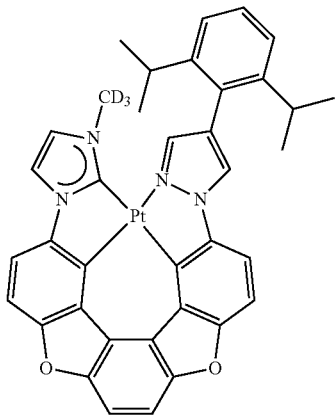
,
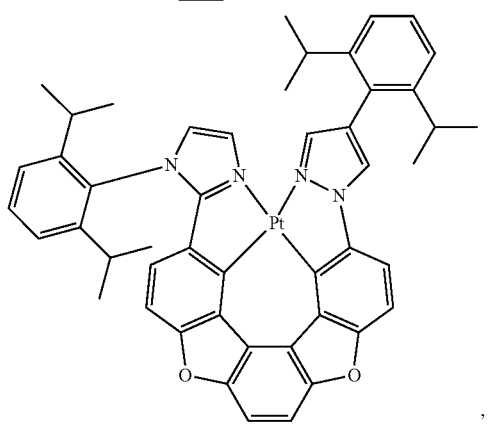
,
340
-continued
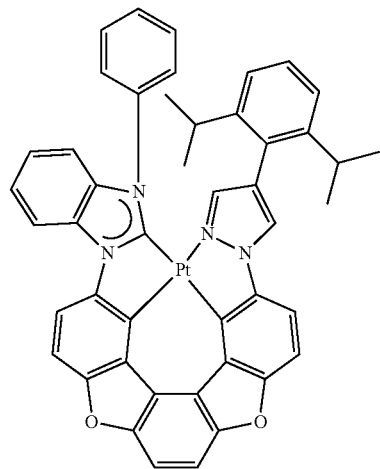
,
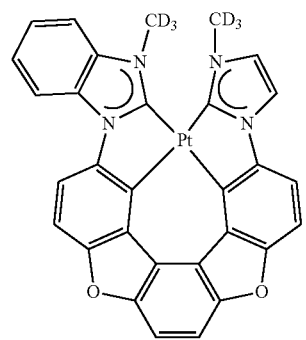
,
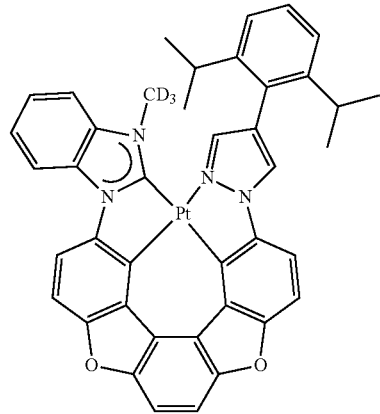
,
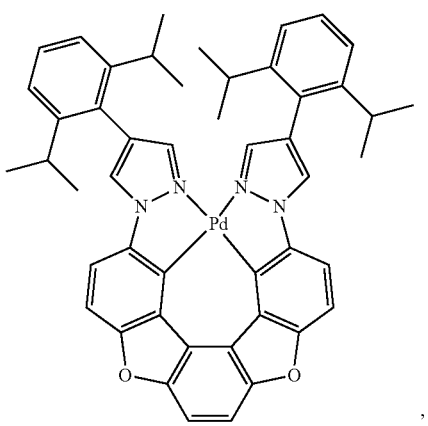
, 341
-continued
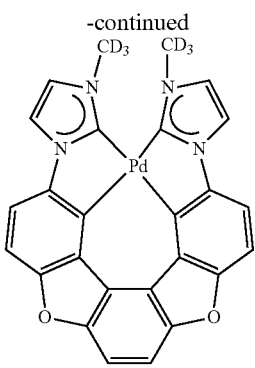
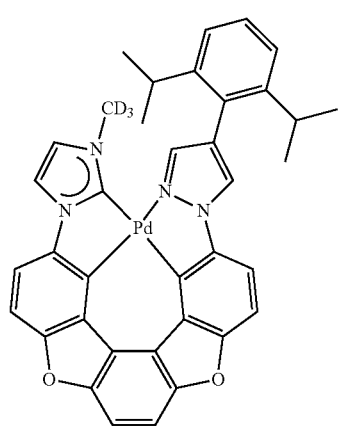
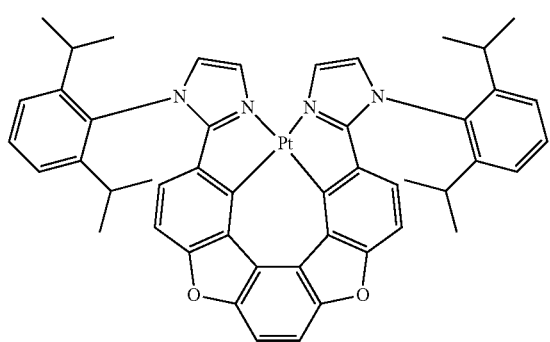
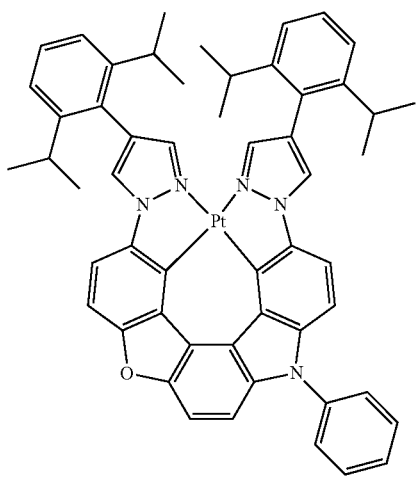
342
-continued
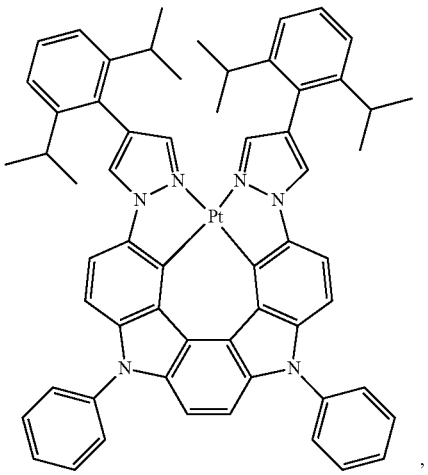
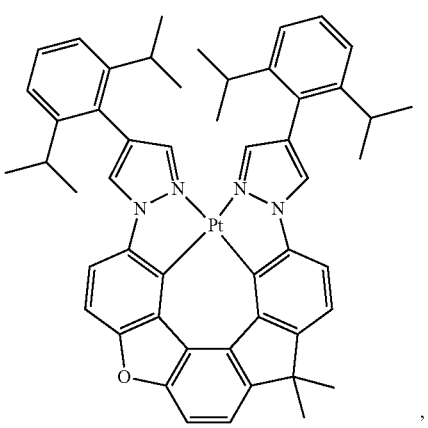
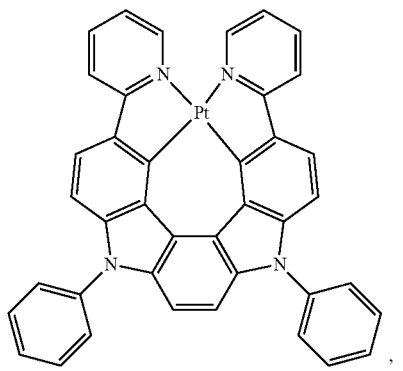
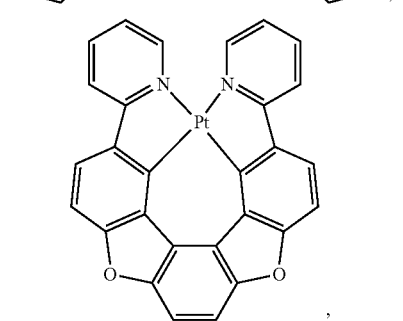

343
-continued
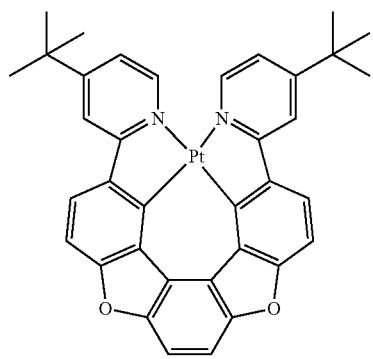
,
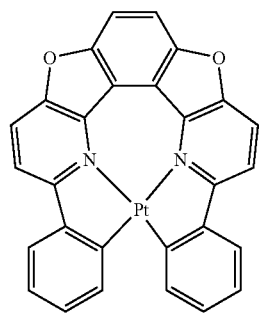
,
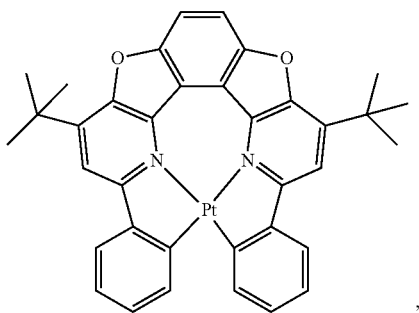
,
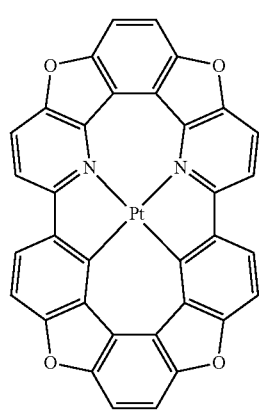
,
344
-continued
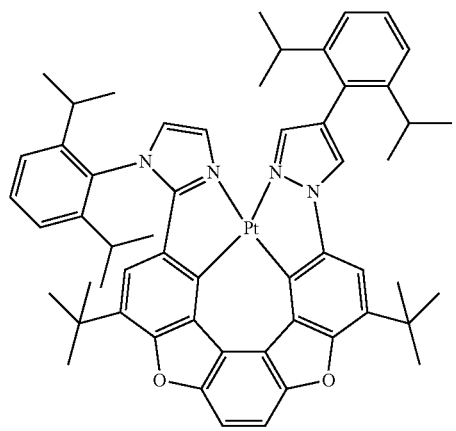
,
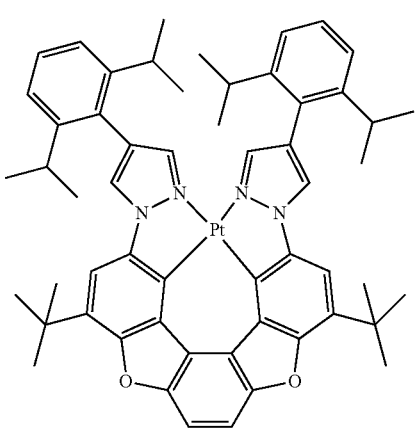
,
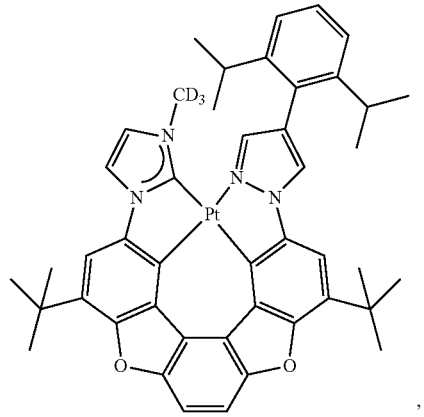
,
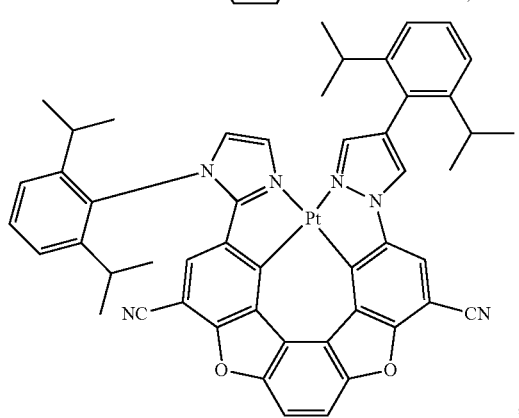
,

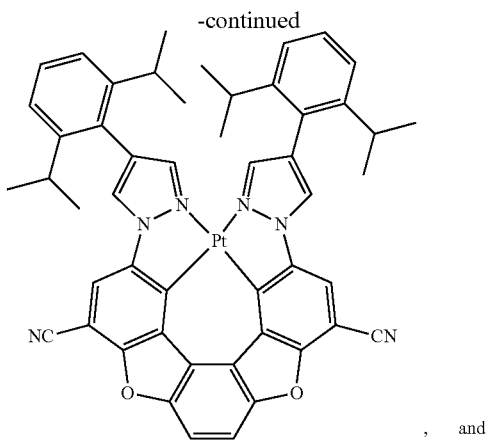

, and

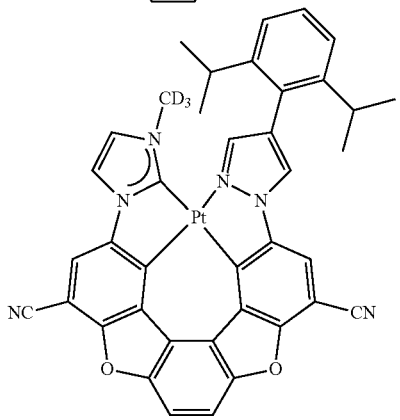

In some embodiments, the compounds as described herein emit light upon photoexcitation at room temperature, wherein the light emitted has an emission spectrum characterized by a peak emission wavelength $\lambda_{max}$ when measured at a concentration of 0.1 mM in a solution of 2-methyl tetrahydrofuran; and wherein the full width at half maximum of the emission at $\lambda_{max}$ that is equal to or less than 20 nm.

In some of the above embodiments, the full width at half maximum of the emission at $\lambda_{max}$ is equal to or less than 15 nm.

In some of the above embodiments, the full width at half maximum of the emission at $\lambda_{max}$ is equal to or less than 10 nm.

C. The OLEDs and the Devices of the Present Disclosure

In another aspect, the present disclosure also provides an OLED device comprising a first organic layer that contains a compound as disclosed in the above compounds section of the present disclosure.

In some embodiments, the OLED comprises an anode, a cathode, and a first organic layer disposed between the anode and the cathode. The first organic layer can comprise a compound having a fragment with at least five rings fused next to each other consecutively wherein the fragment has at least two atoms coordinated to a metal.

In some embodiments, the organic layer can comprise a metal coordination compound comprising a ligand, wherein the ligand comprises a fragment having at least five rings fused next to each other consecutively; and wherein the fragment has at least two atoms coordinated to a metal.

In some embodiments, the fragment is a ligand $L_A$ of Formula I

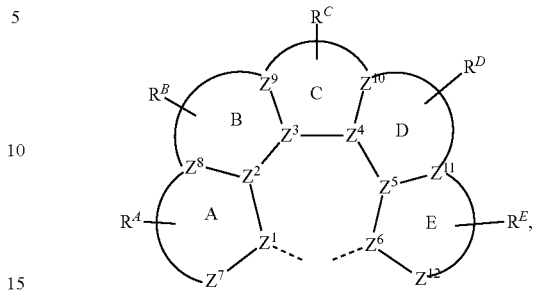

wherein rings A, B, C, D, and E are each independently a 5-membered or 6-membered carbocyclic or heterocyclic ring; $Z^1$-$Z^{12}$ are each independently C or N; $R^A$, $R^B$, $R^C$, $R^D$, and $R^E$ each independently represents zero, mono, or up to a maximum allowed substitutions to its associated ring; $R^A$, $R^B$, $R^C$, $R^D$, and $R^E$ are each independently a hydrogen or a substituent selected from the group consisting of the general substituents defined herein; and two substituents can be joined or fused together to form a ring, wherein the ligand $L_A$ is complexed to a metal M selected from the group consisting of Ir, Rh, Re, Ru, Os, Pt, Pd, Au, Ag, and Cu; wherein M can be coordinated to other ligands; wherein the ligand $L_A$ can be linked with other ligands to form a tridentate, tetradentate, pentadentate, or hexadentate ligand.

Also provided is an OLED comprising: an anode; a cathode; and an organic layer disposed between the anode and the cathode; wherein: the organic layer comprises a first compound as an emitter; the first compound is selected from the group consisting of phosphorescent emitter and delayed fluorescent emitter; the device emits a luminescent radiation at room temperature when a voltage is applied across the device; the luminescent radiation comprises a first radiation component emitted from the first compound; and the first radiation component has a full width at half maximum equal to or less than 15 nm.

In some embodiments, the organic layer may be an emissive layer and the compound as described herein may be an emissive dopant or a non-emissive dopant.

In some embodiments, the organic layer may further comprise a host, wherein the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡C$C_nH_{2n+1}$, $Ar_1$, $Ar_1$-$Ar_2$, $C_nH_{2n}$—$Ar_1$, or no substitution, wherein n is from 1 to 10; and wherein $Ar_1$ and $Ar_2$ are independently selected from the group consisting of benzene, biphenyl, naphthalene, triphenylene, carbazole, and heteroaromatic analogs thereof.

In some embodiments, the organic layer may further comprise a host, wherein host comprises at least one chemical group selected from the group consisting of triphenylene, carbazole, indolocarbazole, dibenzothiophene, dibenzofuran, dibenzoselenophene, 5,9-dioxa-13b-boranaphtho[3,2,1-de]anthracene, aza-triphenylene, aza-carbazole, aza-indolocarbazole, aza-dibenzothiophene, aza-dibenzofuran, aza-dibenzoselenophene, and aza-(5,9-dioxa-13b-bornnaphtho [3,2,1-de]anthracene).

In some embodiments, the host may be selected from the HOST Group consisting of:
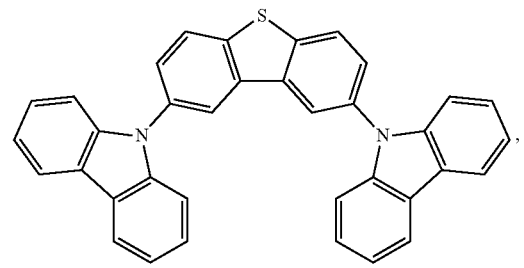
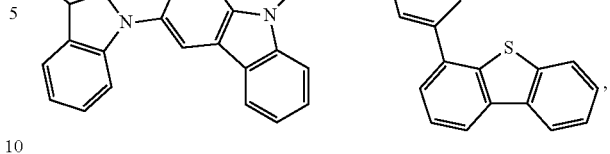
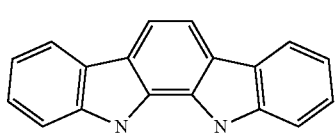
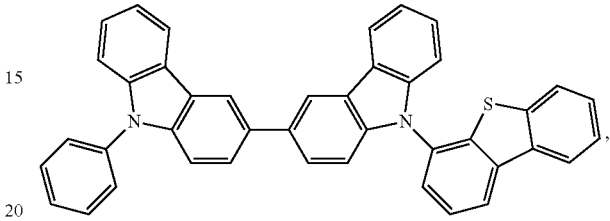
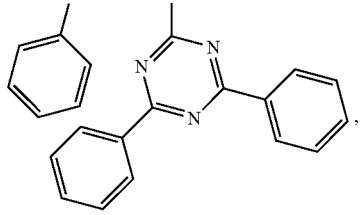
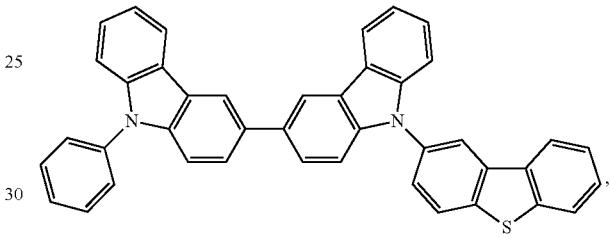
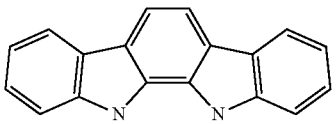
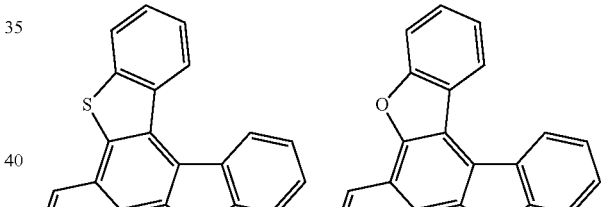
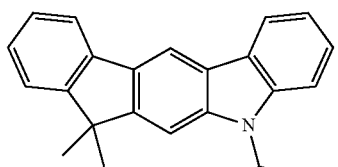
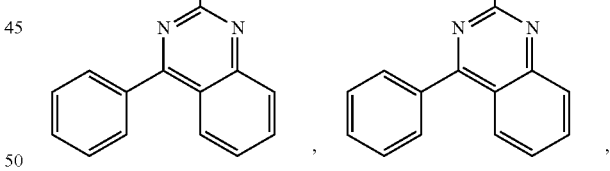
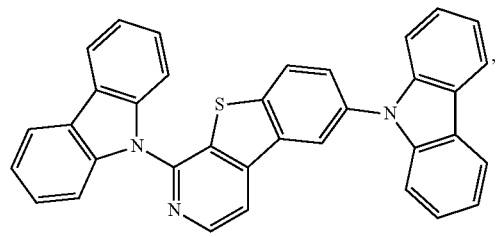
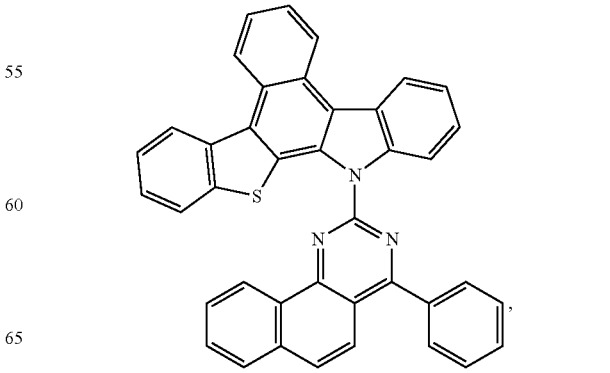

| 349 -continued | 350 -continued |
|---|---|
| 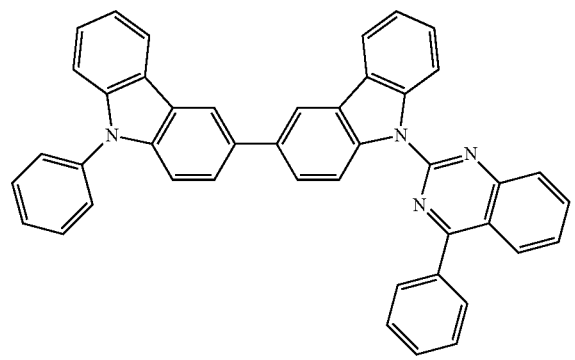 | 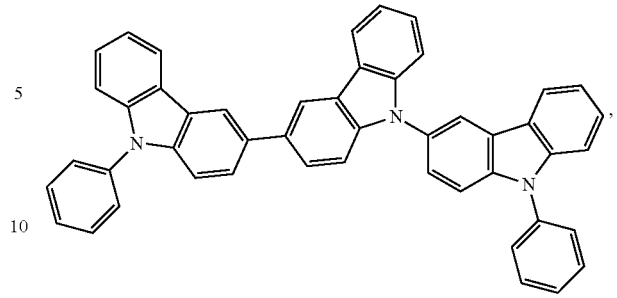 |
| 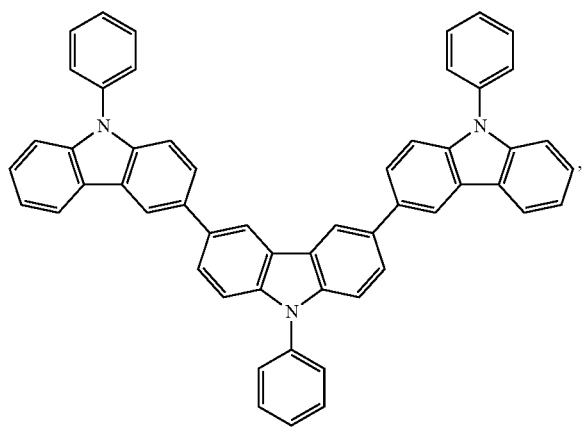 | 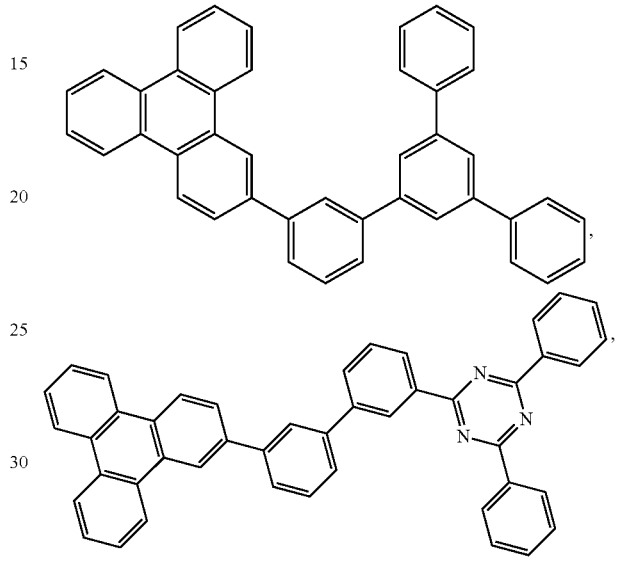 |
| 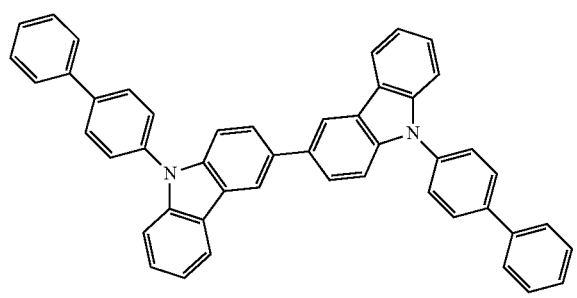 | 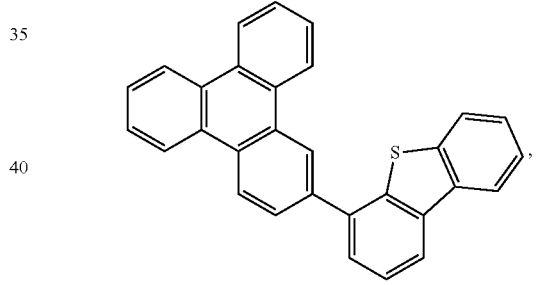 |
| 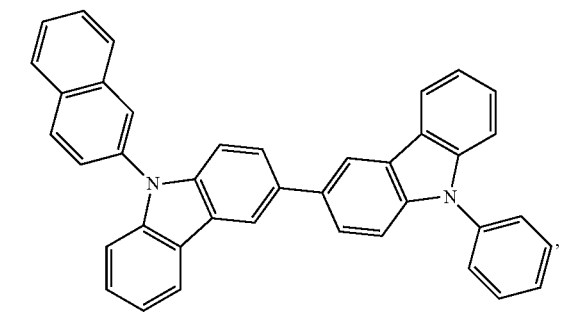 | 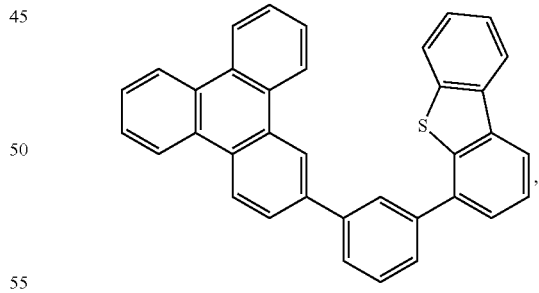 |
| 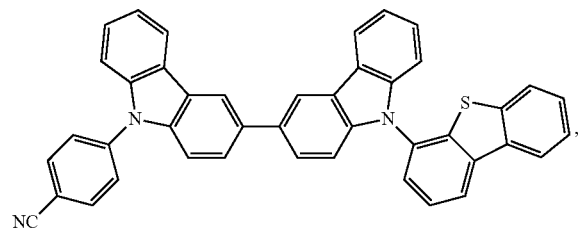 | 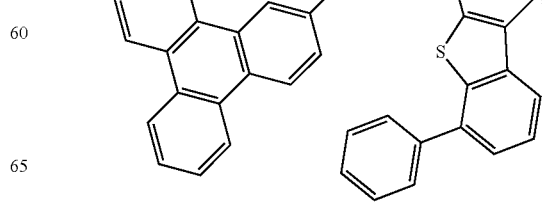 |

351
-continued

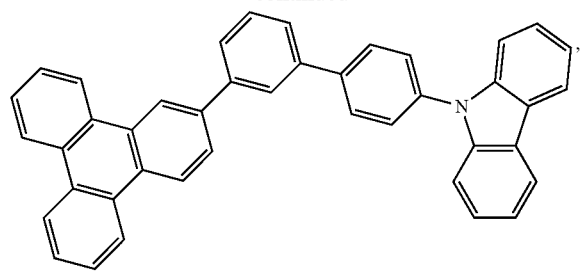

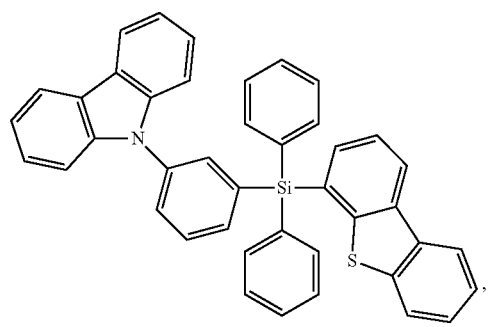

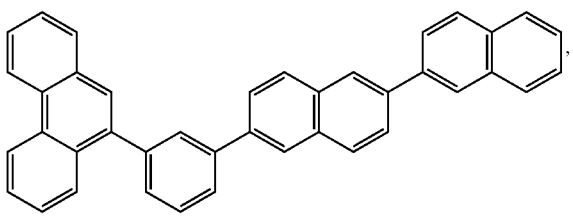

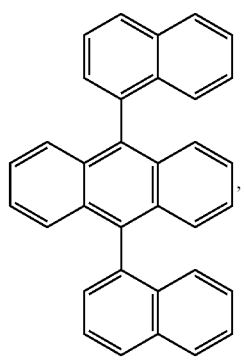

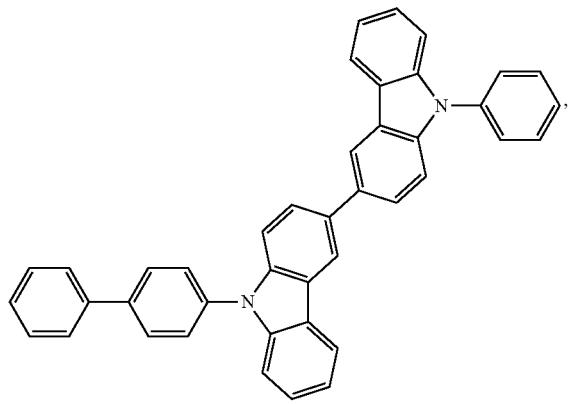

352
-continued

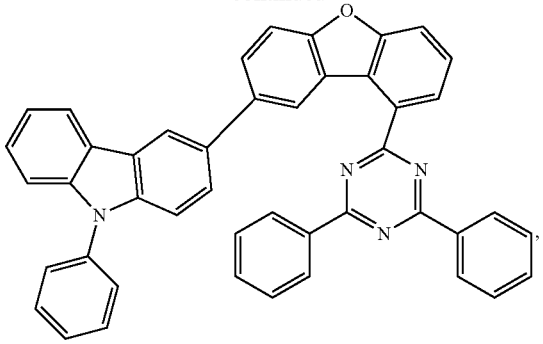

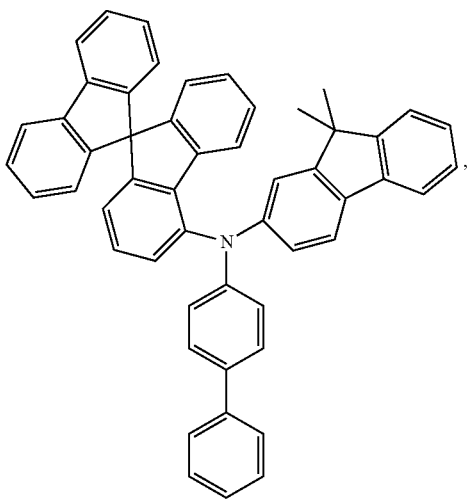

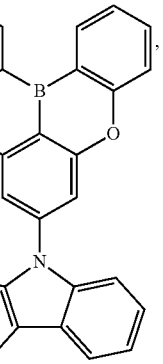

and combinations thereof.

In some embodiments, the organic layer may further comprise a host, wherein the host comprises a metal complex.

In some embodiments, the compound as described herein may be a sensitizer; wherein the device may further comprise an acceptor; and wherein the acceptor may be selected from the group consisting of fluorescent emitter, delayed fluorescence emitter, and combination thereof.

In yet another aspect, the OLED of the present disclosure may also comprise an emissive region containing a compound as disclosed in the above compounds section of the present disclosure.

In some embodiments, the emissive region can comprise a compound comprising a ligand $L_A$ of Formula I

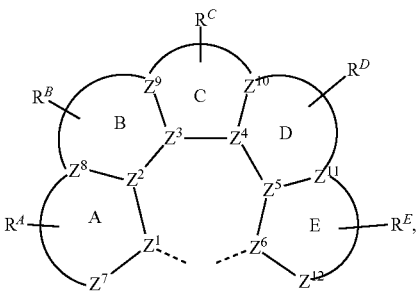

wherein rings A, B, C, D, and E are each independently a 5-membered or 6-membered carbocyclic or heterocyclic ring; $Z^1$-$Z^{12}$ are each independently C or N; $R^A$, $R^B$, $R^C$, $R^D$, and $R^E$ each independently represents zero, mono, or up to a maximum allowed substitutions to its associated ring; $R^A$, $R^B$, $R^C$, $R^D$, and $R^E$ are each independently a hydrogen or a substituent selected from the group consisting of the general substituents defined herein; and two substituents can be joined or fused together to form a ring, wherein the ligand $L_A$ is complexed to a metal M selected from the group consisting of Ir, Rh, Re, Ru, Os, Pt, Pd, Au, Ag, and Cu; wherein M can be coordinated to other ligands; wherein the ligand $L_A$ can be linked with other ligands to form a tridentate, tetradentate, pentadentate, or hexadentate ligand.

In some embodiments of the emissive region, the compound can be an emissive dopant or a non-emissive dopant. In some embodiments, the emissive region further comprises a host, wherein the host contains at least one group selected from the group consisting of metal complex, triphenylene, carbazole, dibenzothiophene, dibenzofuran, dibenzoselenophene, aza-triphenylene, aza-carbazole, aza-dibenzothiophene, aza-dibenzofuran, and aza-dibenzoselenophene. In some embodiments of the emissive region, the emissive region further comprises a host, wherein the host is selected from the Host Group defined above.

In yet another aspect, the present disclosure also provides a consumer product comprising an organic light-emitting device (OLED) having an anode; a cathode; and an organic layer disposed between the anode and the cathode, wherein the organic layer may comprise a compound as disclosed in the above compounds section of the present disclosure.

In some embodiments, the consumer product comprises an OLED having an anode; a cathode; and an organic layer disposed between the anode and the cathode, wherein the organic layer can comprise a compound having a fragment with at least five rings fused next to each other consecutively wherein the fragment has at least two atoms coordinated to a metal.

In some embodiments, the consumer product comprises an OLED having an anode; a cathode; and an organic layer disposed between the anode and the cathode, wherein the organic layer can comprise a compound comprising a ligand LA of Formula I as described herein.

In some embodiments, the consumer product can be one of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, a light therapy device, and a sign.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

Several OLED materials and configurations are described in U.S. Pat. Nos. 5,844,363, 6,303,238, and 5,707,745, which are incorporated herein by reference in their entirety.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
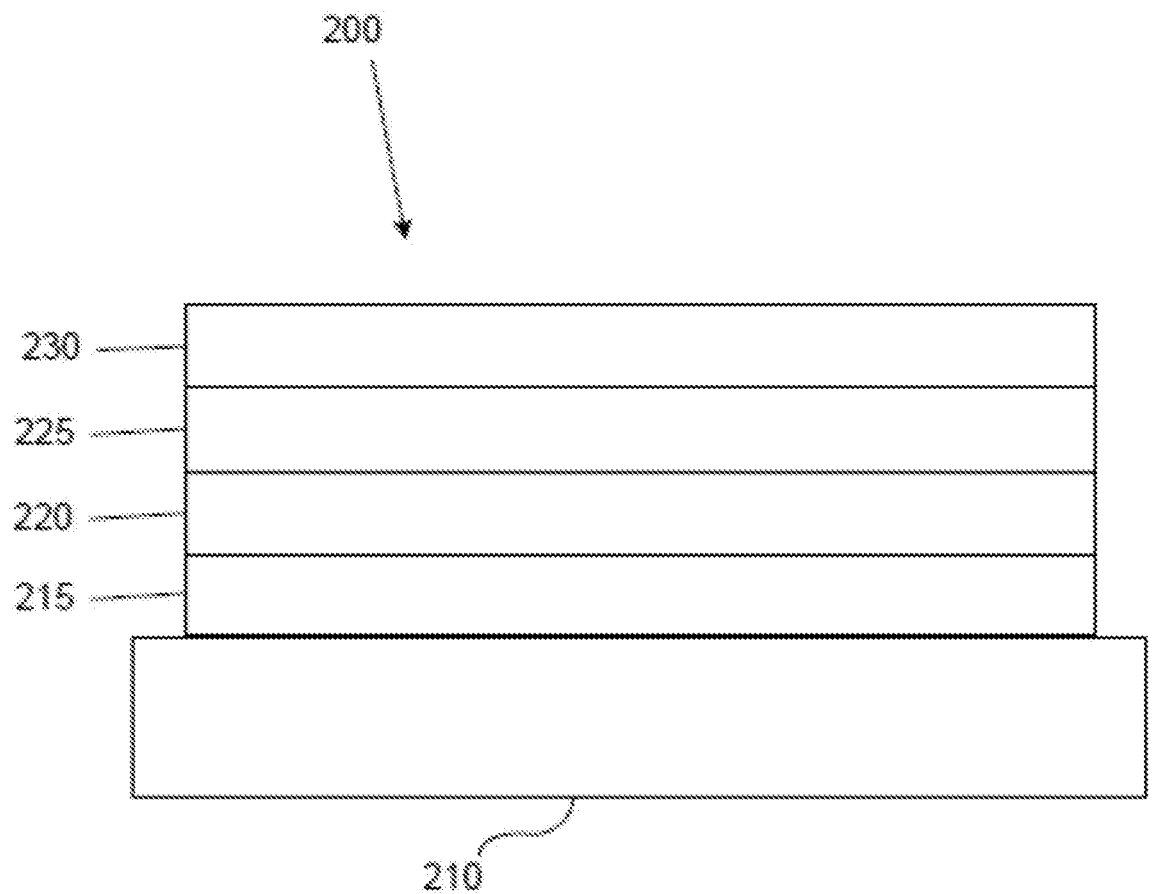
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the present disclosure may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons are a preferred range. Materials with asymmetric structures may have better solution processability than those having symmetric structures, because asymmetric materials may have a lower tendency to recrystallize Dendrimer substituents may be used to enhance the ability of small molecules to undergo solution processing.

Devices fabricated in accordance with embodiments of the present disclosure may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the present disclosure can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the present disclosure can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present disclosure, including passive matrix and active matrix. Many of the devices are intended for use in a temperature range comfortable to humans, such as 18 degrees C. to 30 degrees C., and more preferably at room temperature (20-25° C.), but could be used outside this temperature range, for example, from −40 degree C. to +80° C.

More details on OLEDs, and the definitions described above, can be found in U.S. Pat. No. 7,279,704, which is incorporated herein by reference in its entirety.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer. In some embodiments, the compound can be homoleptic (each ligand is the same). In some embodiments, the compound can be heteroleptic (at least one ligand is different from others). When there are more than one ligand coordinated to a metal, the ligands can all be the same in some embodiments. In some other embodiments, at least one ligand is different from the other ligands. In some embodiments, every ligand can be different from each other. This is also true in embodiments where a ligand being coordinated to a metal can be linked with other ligands being coordinated to that metal to form a tridentate, tetradentate, pentadentate, or hexadentate ligands Thus, where the coordinating ligands are being linked together, all of the ligands can be the same in some embodiments, and at least one of the ligands being linked can be different from the other ligand(s) in some other embodiments.

In some embodiments, the compound can be used as a phosphorescent sensitizer in an OLED where one or multiple layers in the OLED contains an acceptor in the form of one or more fluorescent and/or delayed fluorescence emitters. In some embodiments, the compound can be used as one component of an exciplex to be used as a sensitizer. As a phosphorescent sensitizer, the compound must be capable of energy transfer to the acceptor and the acceptor will emit the energy or further transfer energy to a final emitter. The acceptor concentrations can range from 0.001% to 100%. The acceptor could be in either the same layer as the phosphorescent sensitizer or in one or more different layers. In some embodiments, the acceptor is a TADF emitter. In some embodiments, the acceptor is a fluorescent emitter. In some embodiments, the emission can arise from any or all of the sensitizer, acceptor, and final emitter.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a "monovalent variant of a compound" refers to a moiety that is identical to the compound except that one hydrogen has been removed and replaced with a bond to the rest of the chemical structure. As used herein, a "polyvalent variant of a compound" refers to a moiety that is identical to the compound except that more than one hydrogen has been removed and replaced with a bond or bonds to the rest of the chemical structure. In the instance of a supramolecule, the inventive compound can also be incorporated into the supramolecule complex without covalent bonds.

D. Combination of the Compounds of the Present Disclosure With Other Materials The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

a) Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

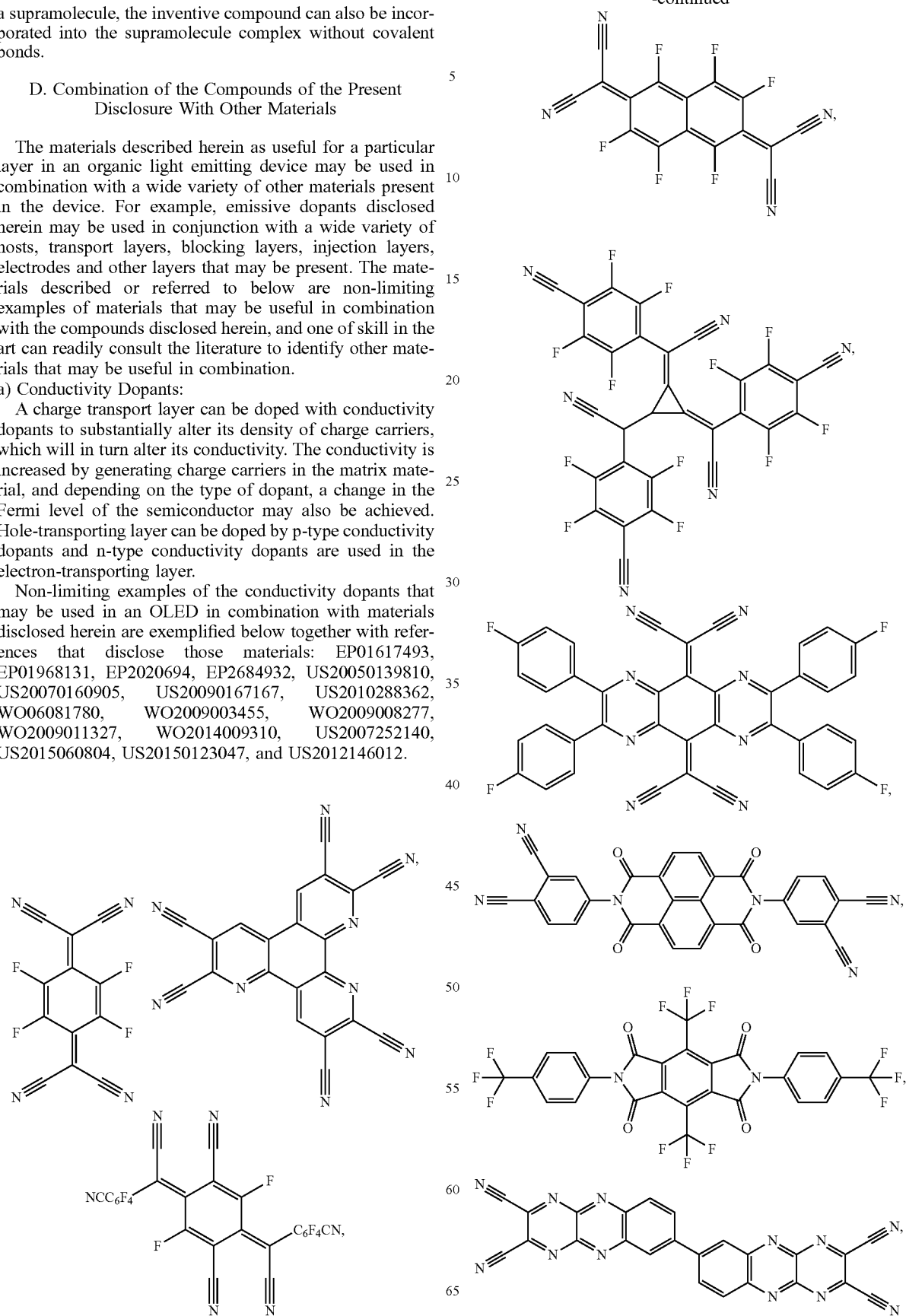

361
-continued

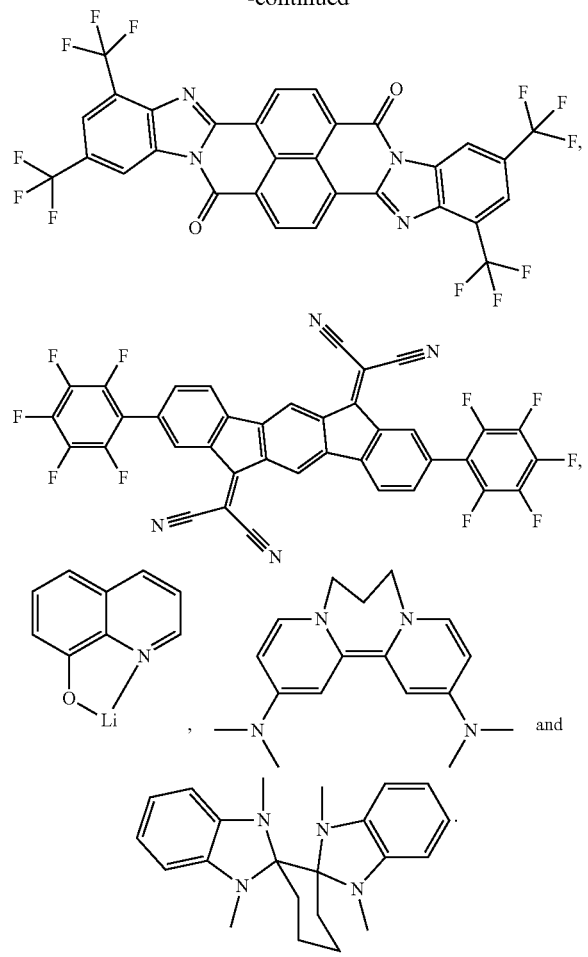

b) HIL/HTL:

A hole injecting/transporting material to be used in the present disclosure is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphoric acid and silane derivatives; a metal oxide derivative, such as $MoO_x$; a p-type semiconducting organic compound, such as 1,4,5, 8,9,12-Hexaazatriphenylenehexacarbonitrile; a metal complex, and a cross-linkable compounds.

Examples of aromatic amine derivatives used in HIL or HTL include, but not limit to the following general structures:

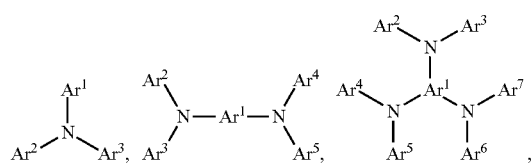

362
-continued

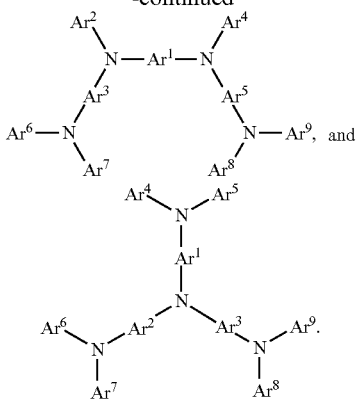

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroalyl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

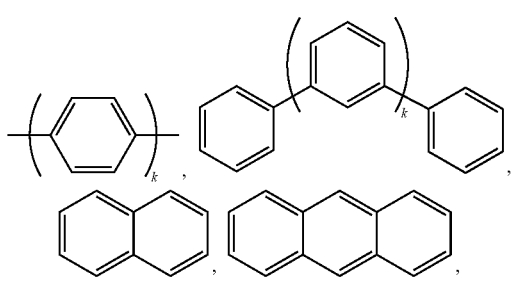

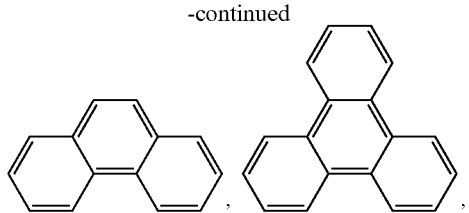

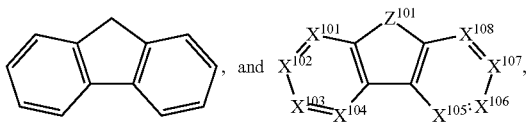

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

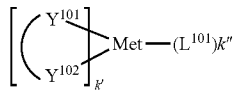

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a cathene ligand. In another aspect, Met is selected from Ir, Pt, Os, and Zn. In a further aspect, the metal complex has a smallest oxidation potential in solution vs. $Fc^+$/Fc couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Pat. No. 6,517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

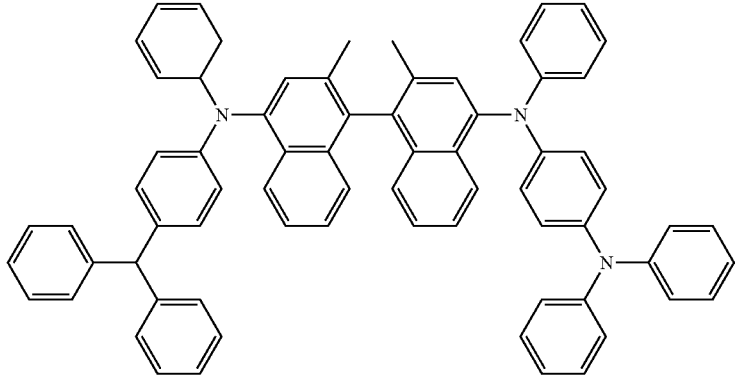

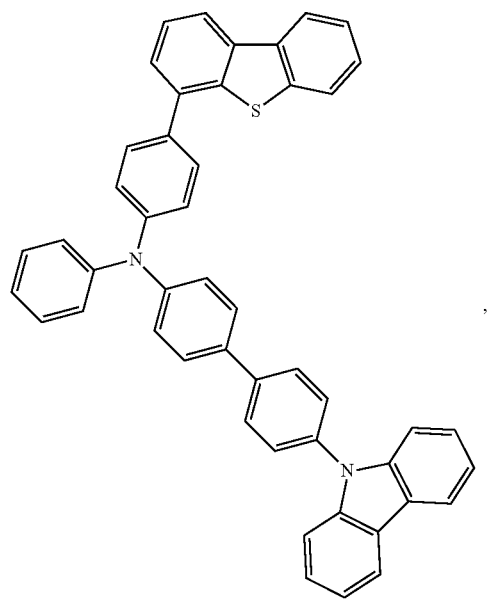
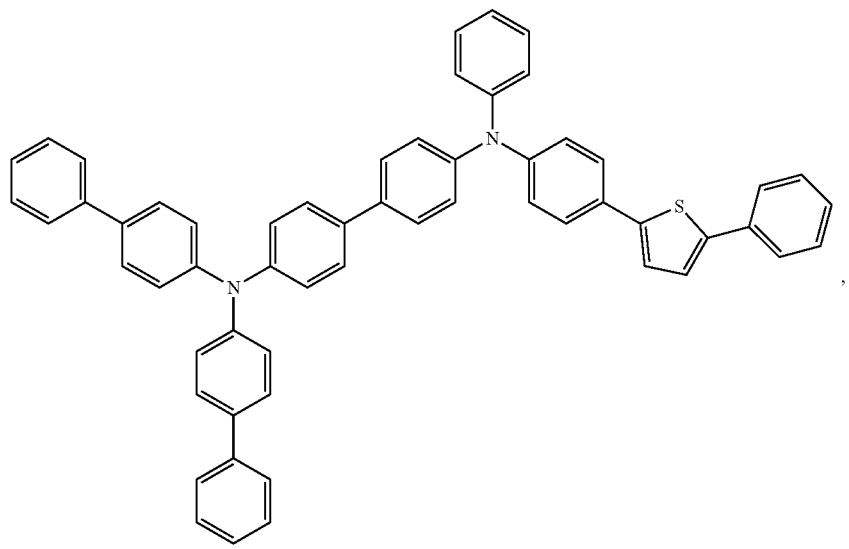
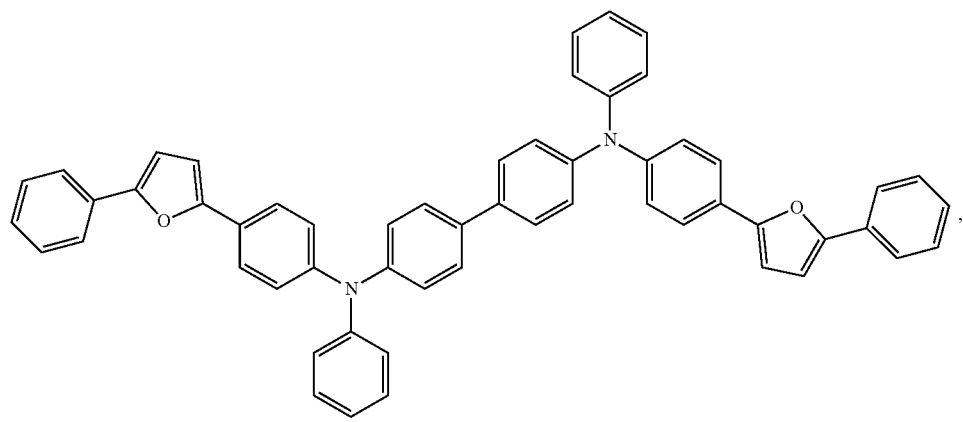

367 368
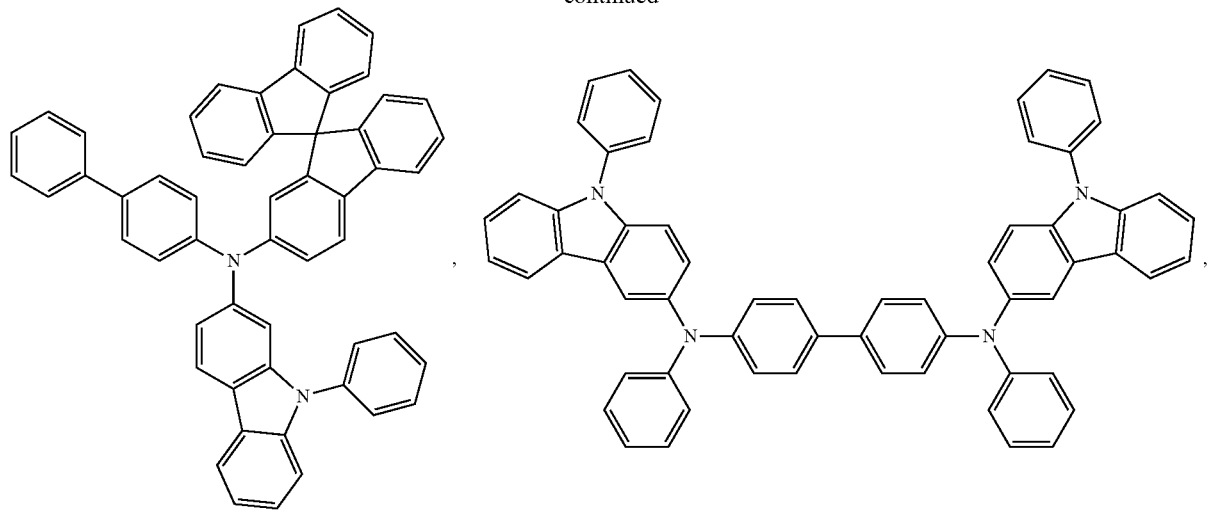
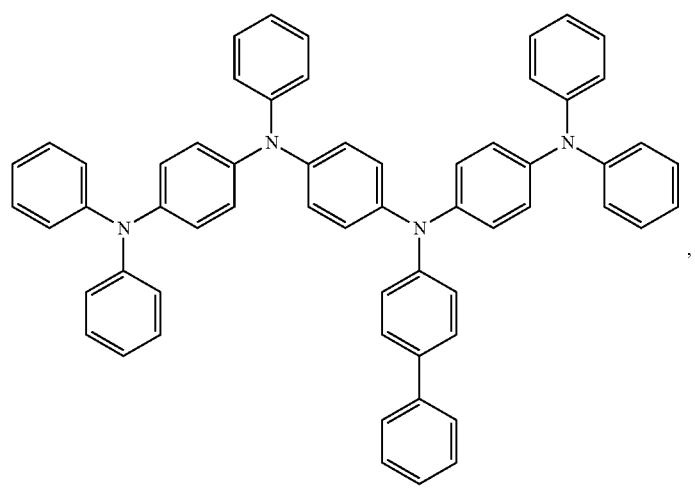
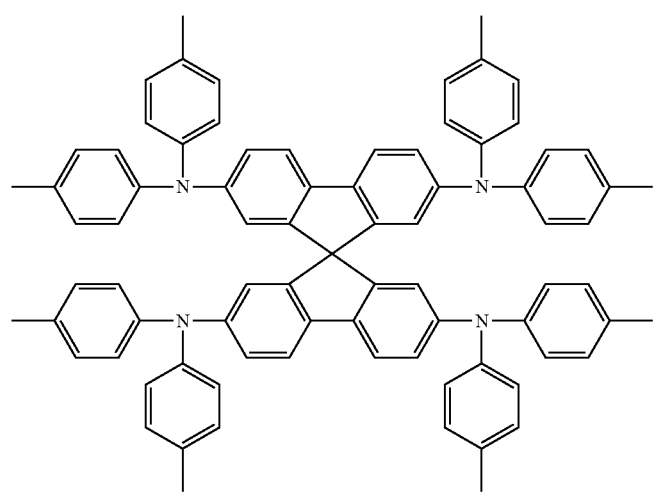

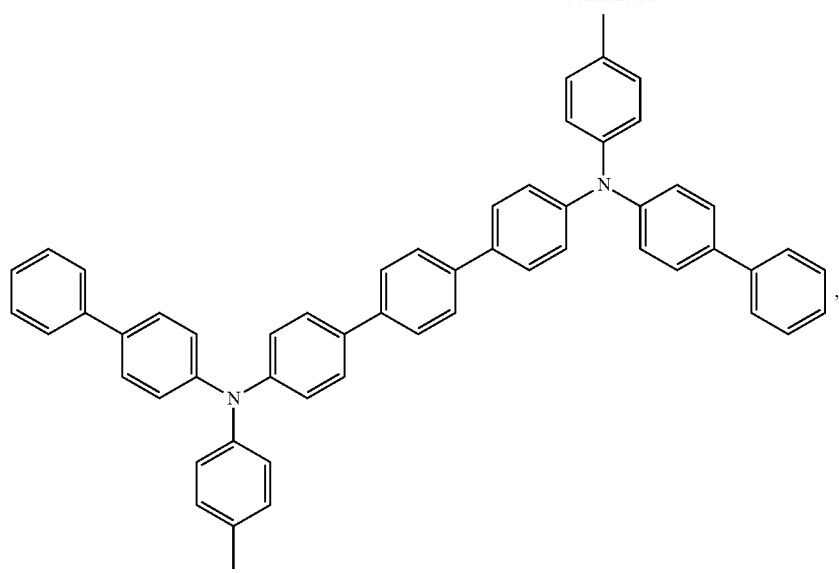
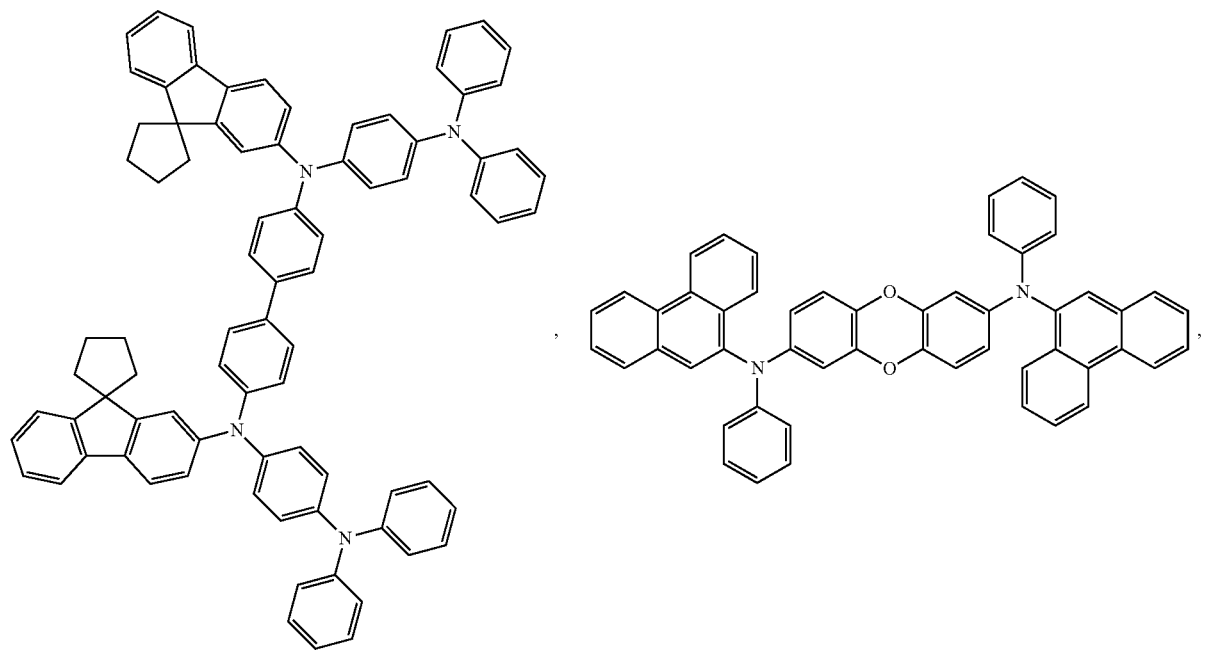
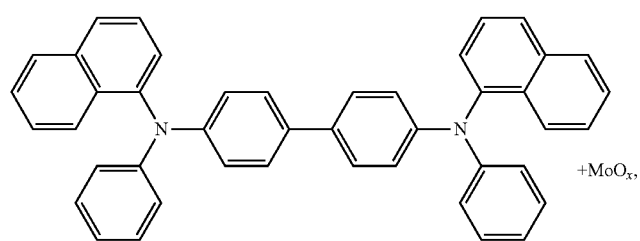

371
372
-continued
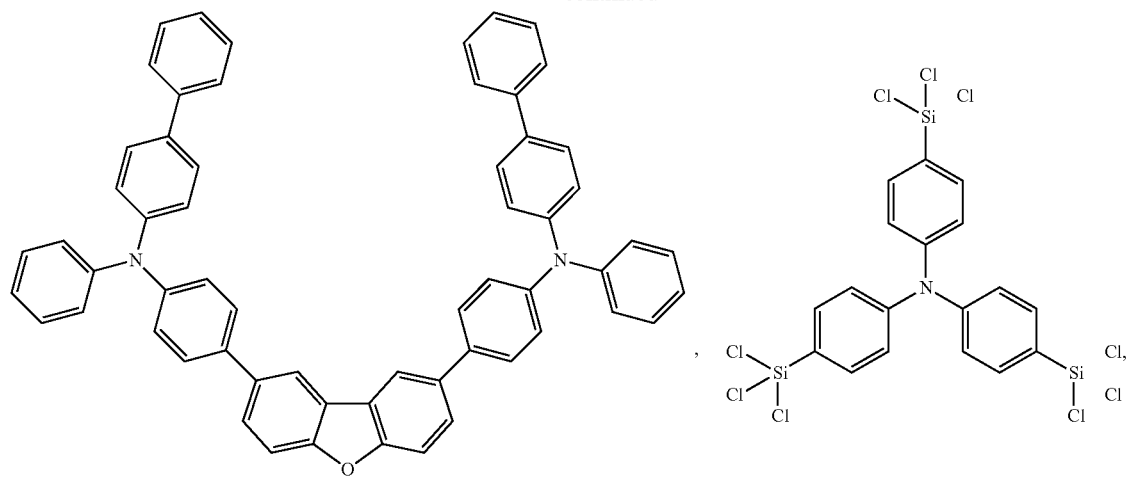
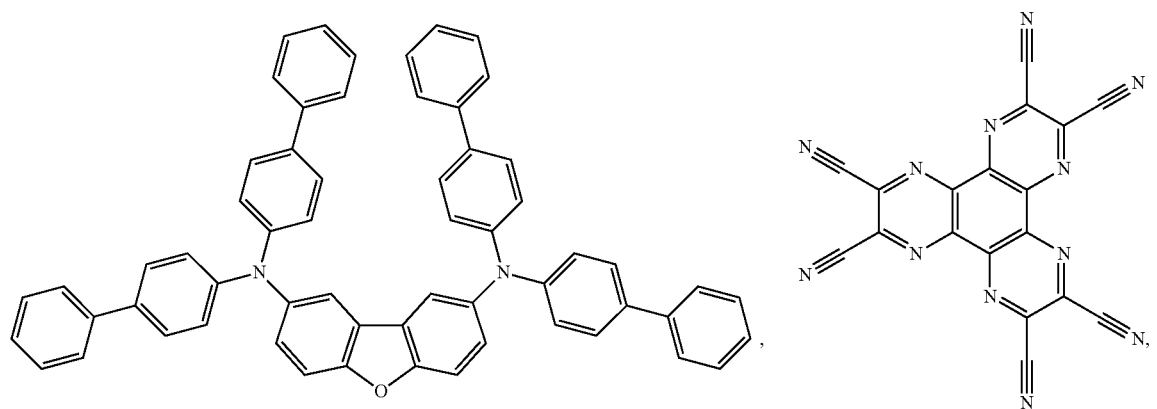
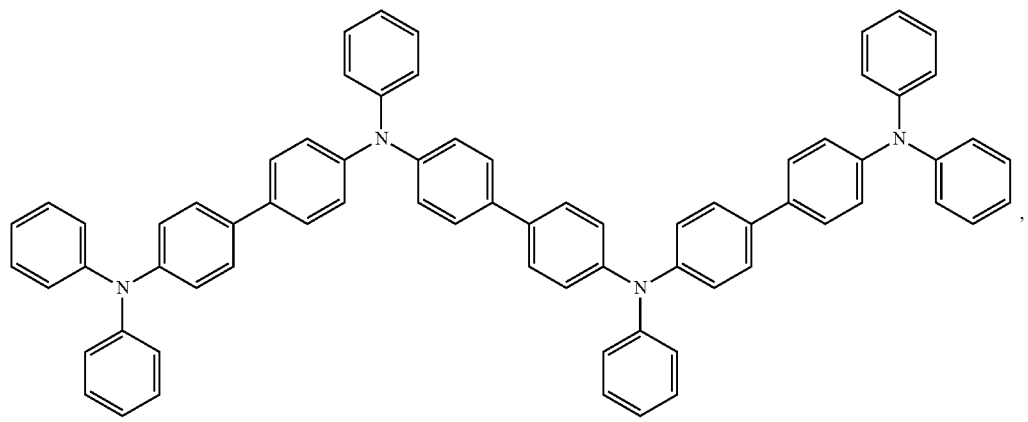

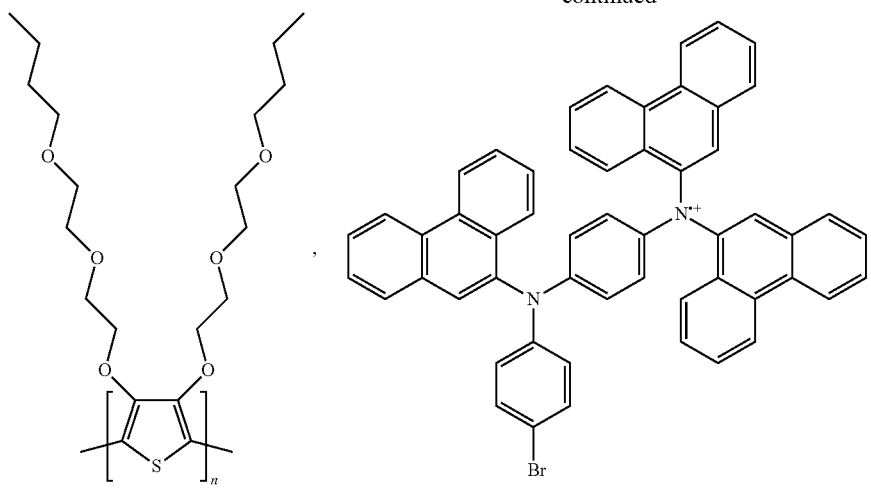
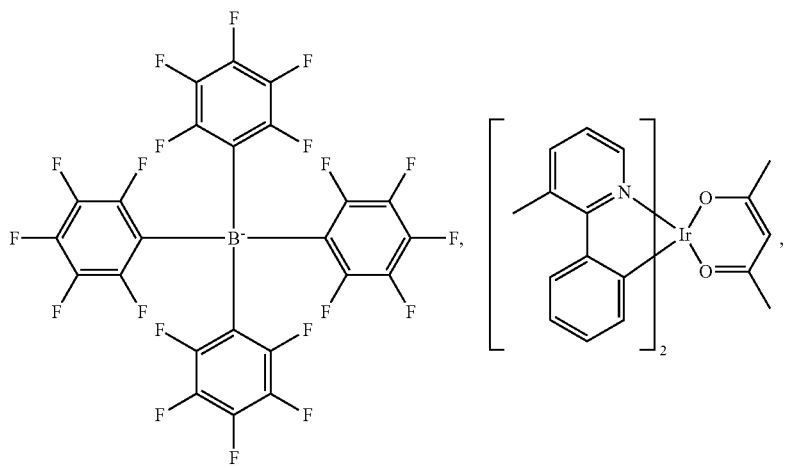
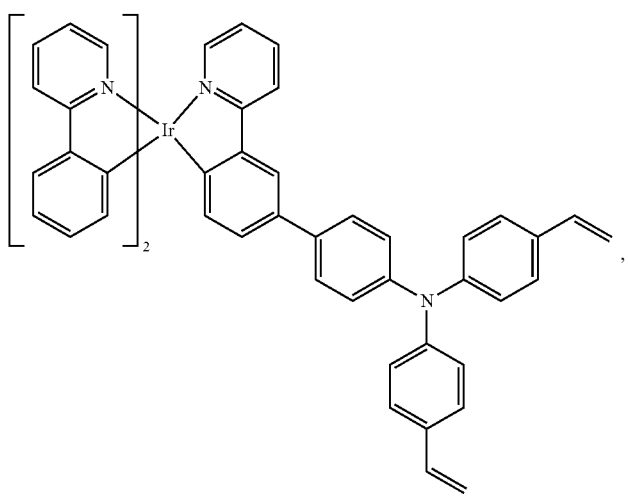

-continued
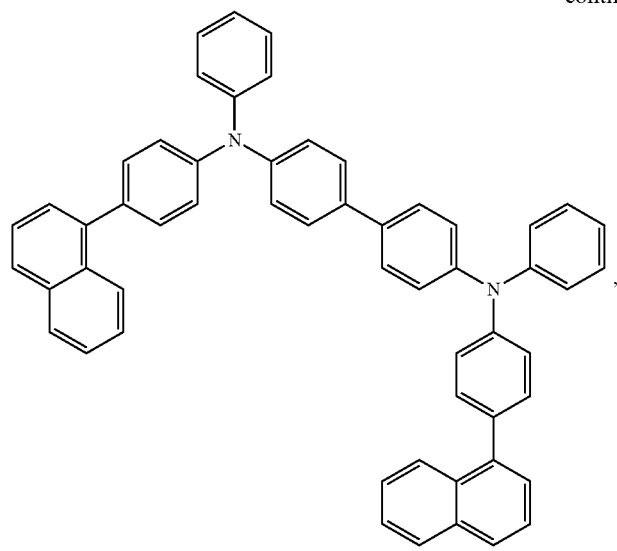
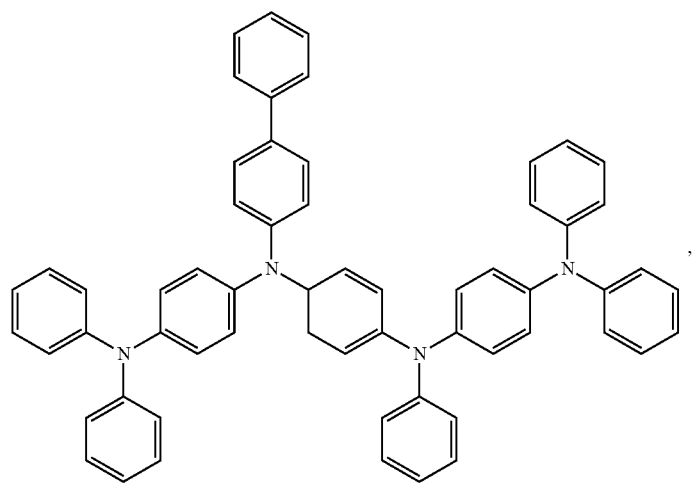
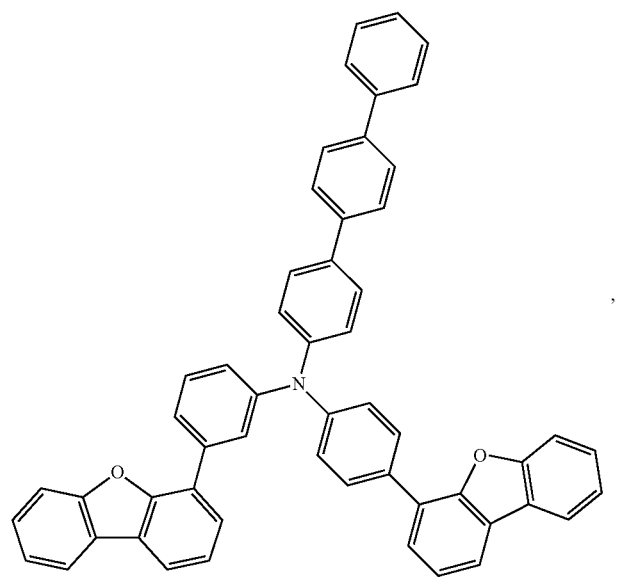

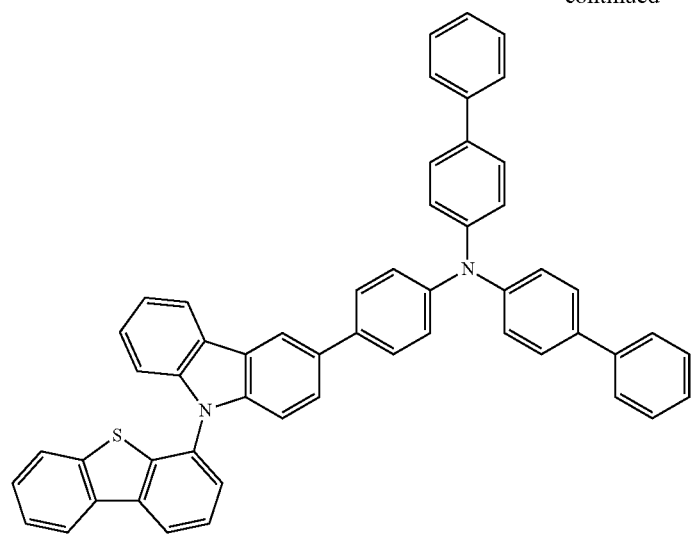
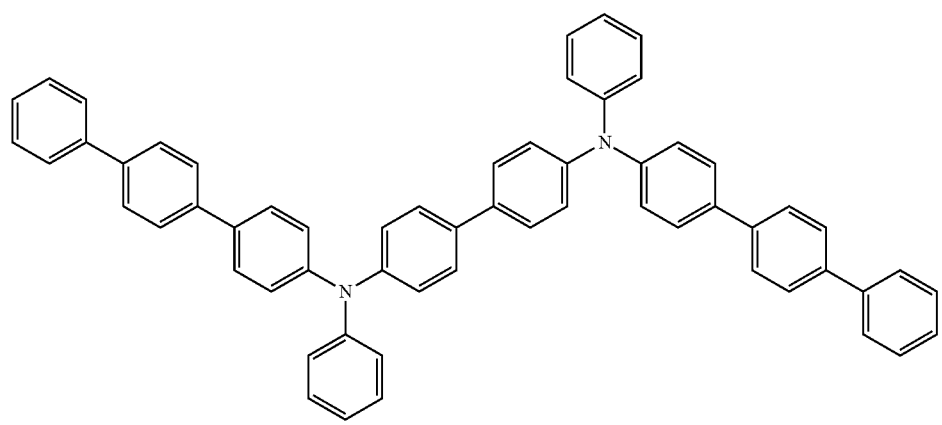
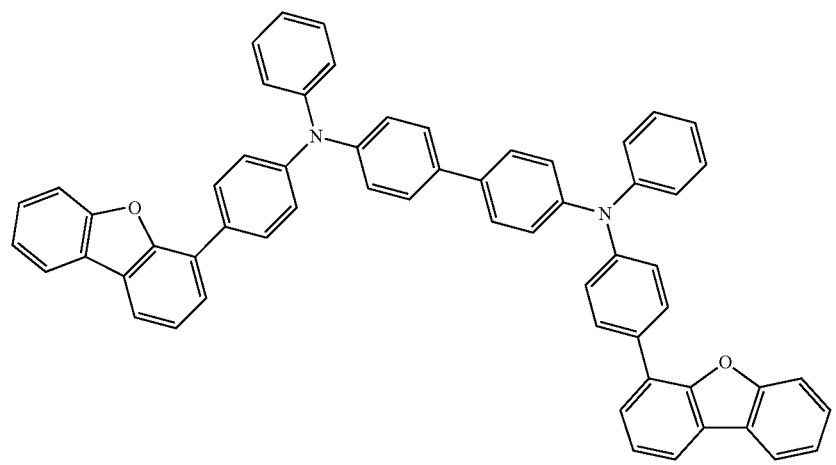

379
380
-continued
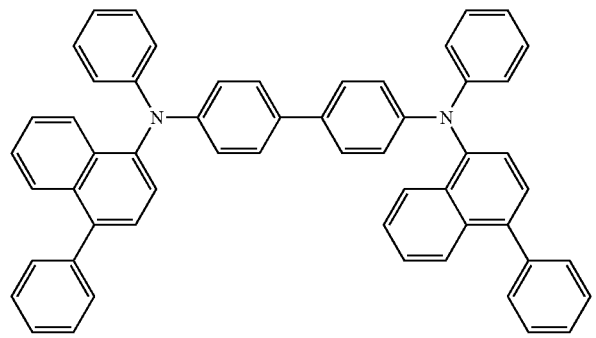
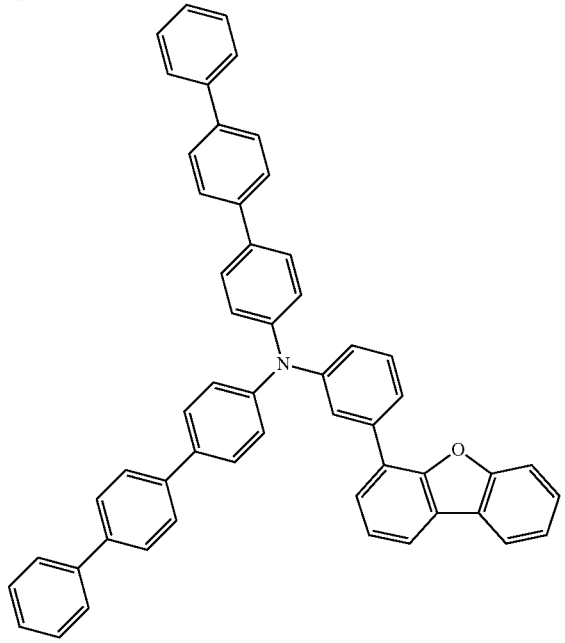
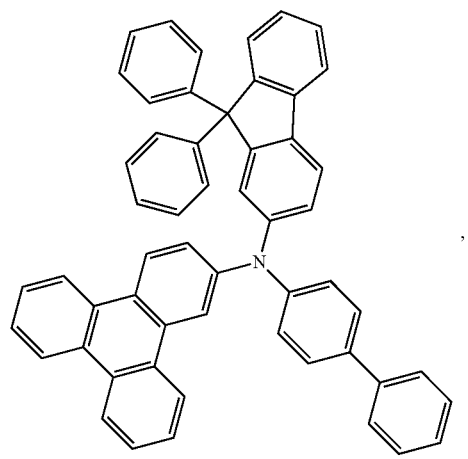
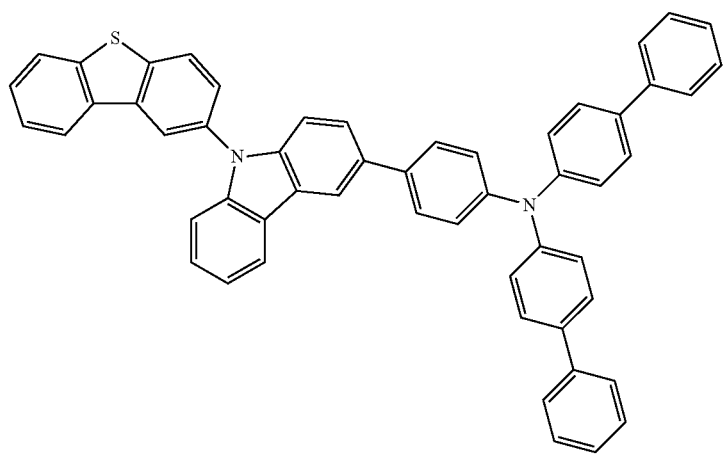
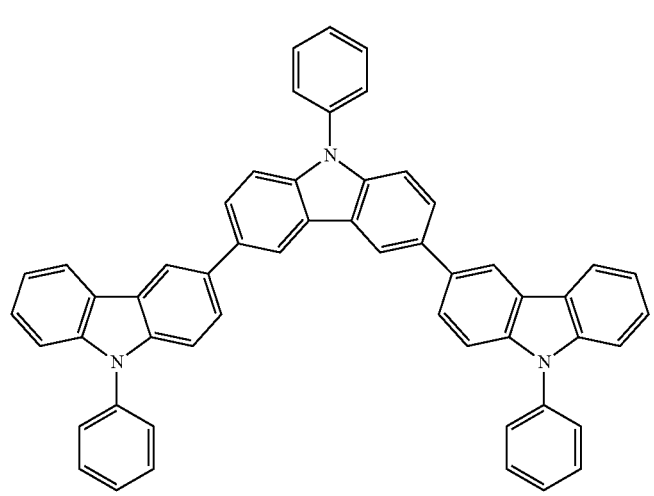
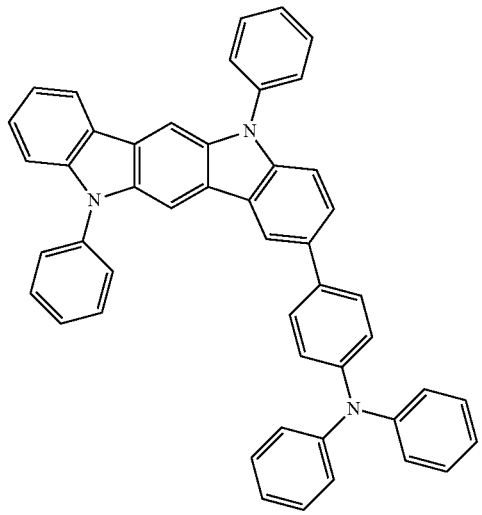

-continued
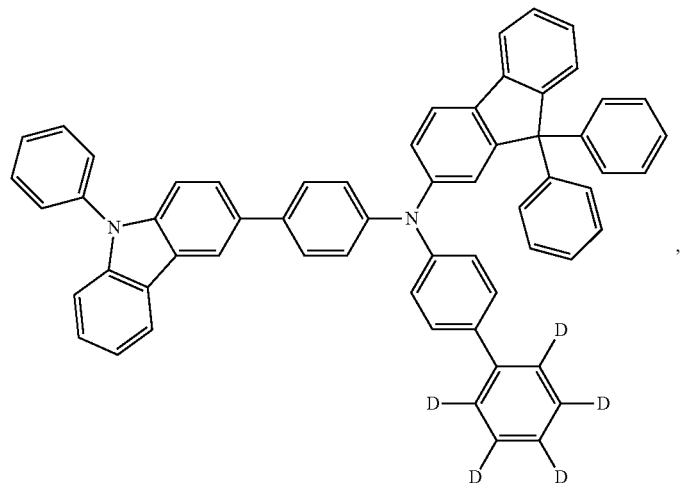
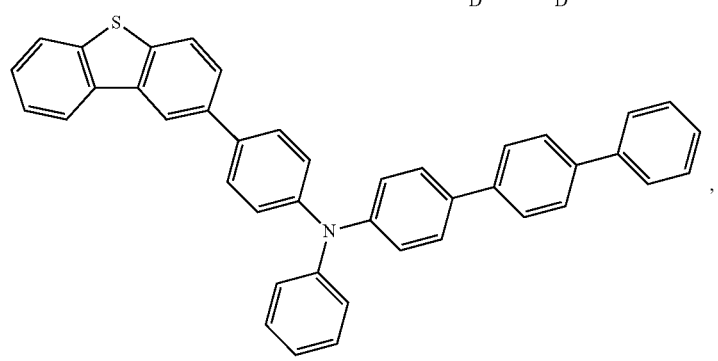
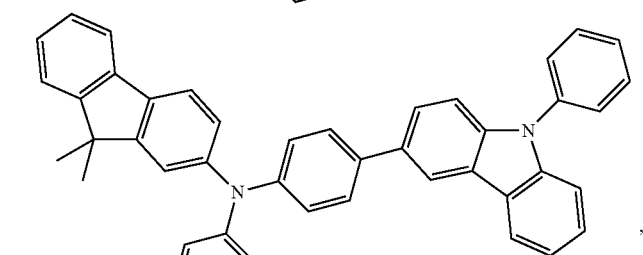
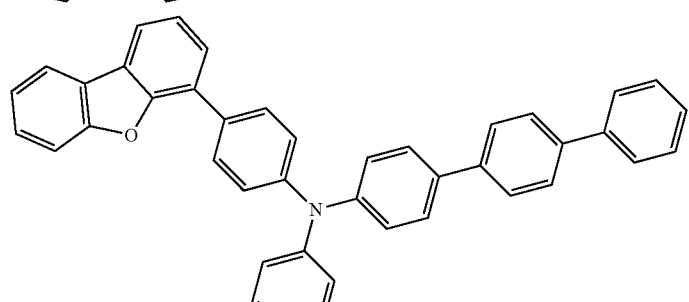
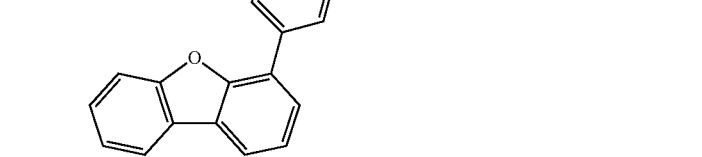

-continued
383 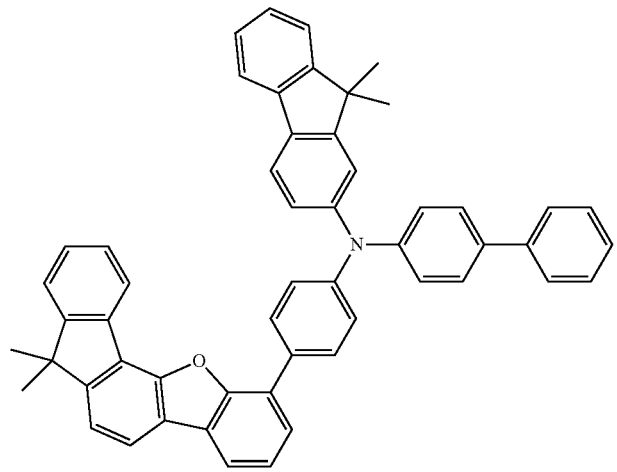
384 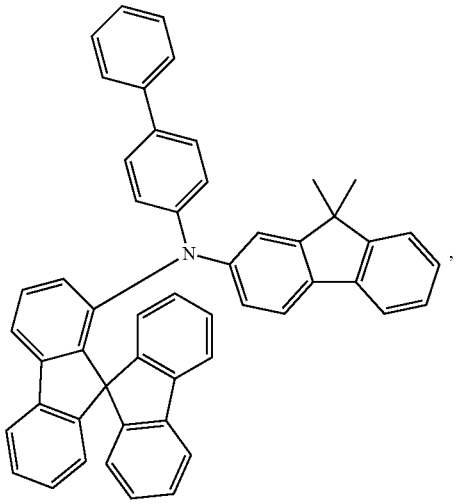
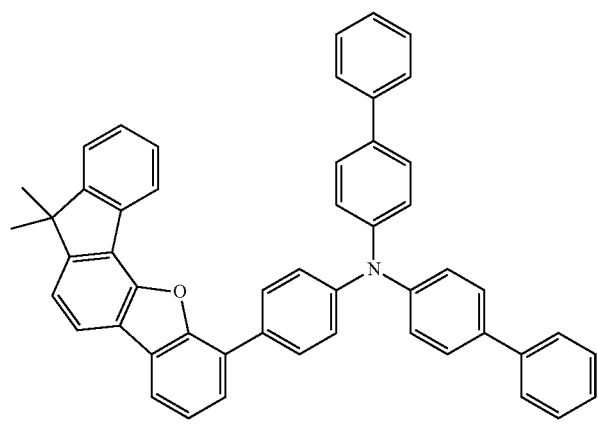
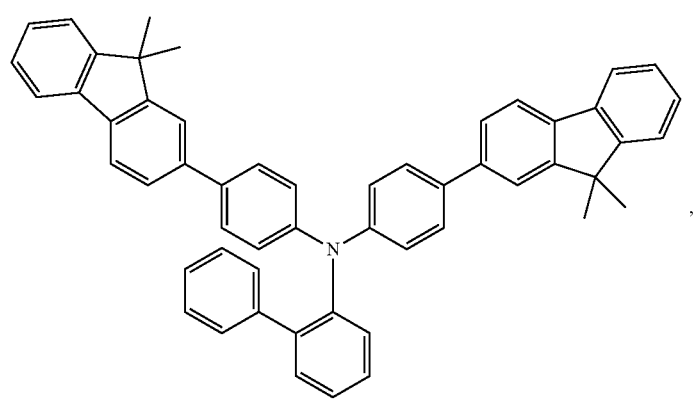

385 386
-continued
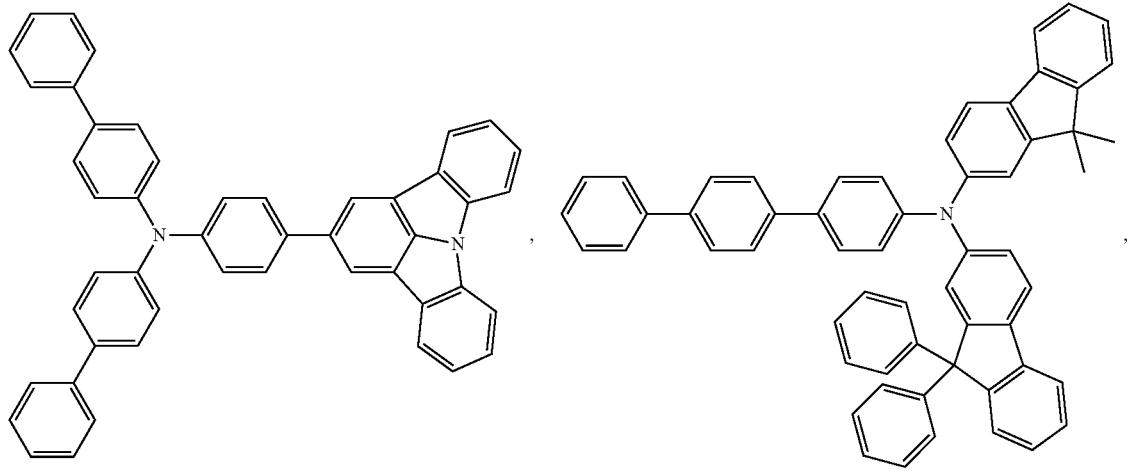
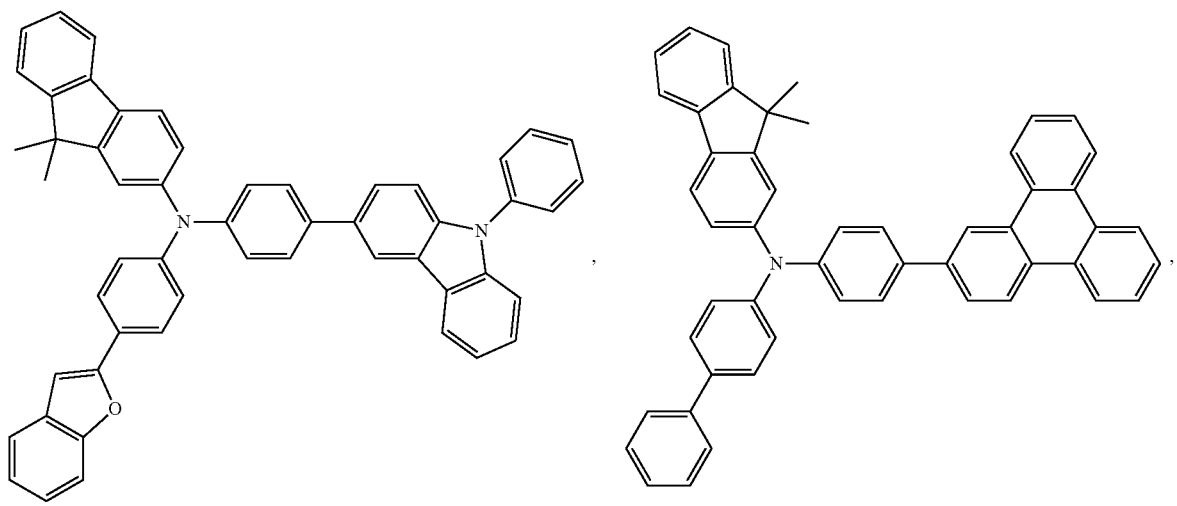
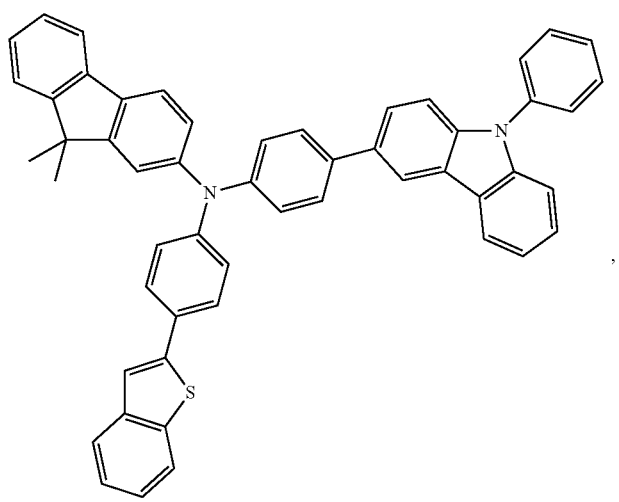

-continued
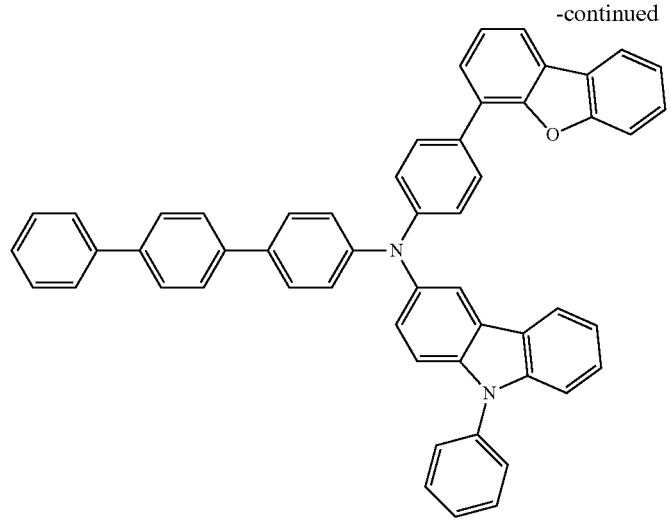
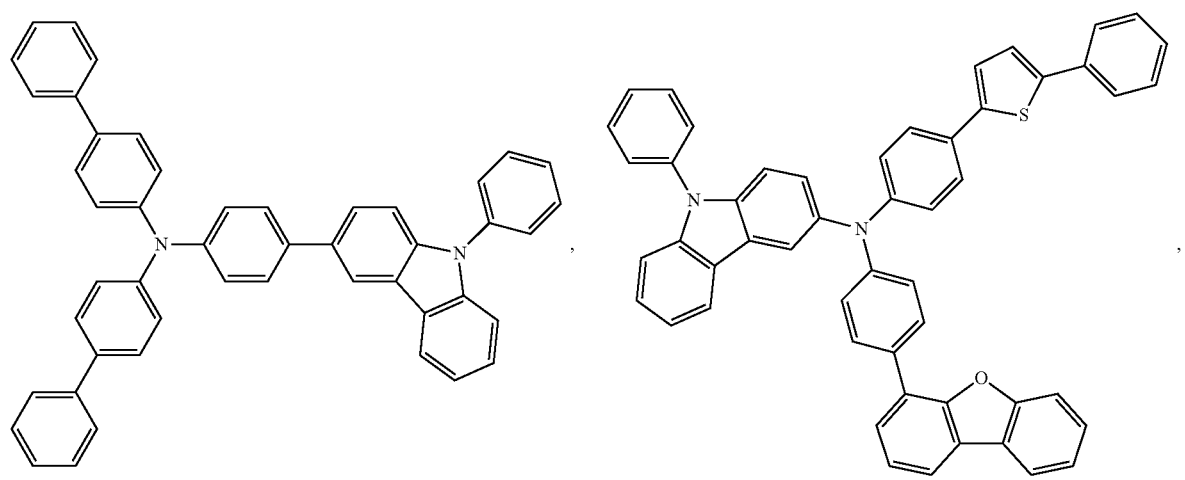
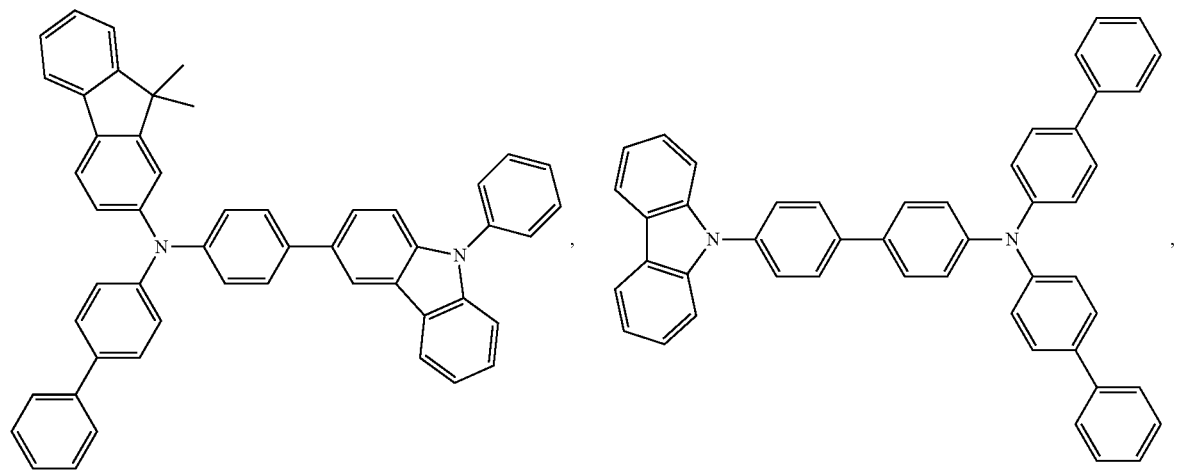

-continued
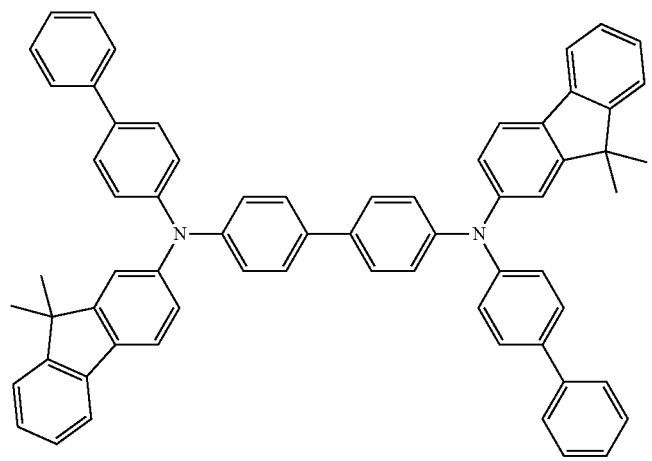
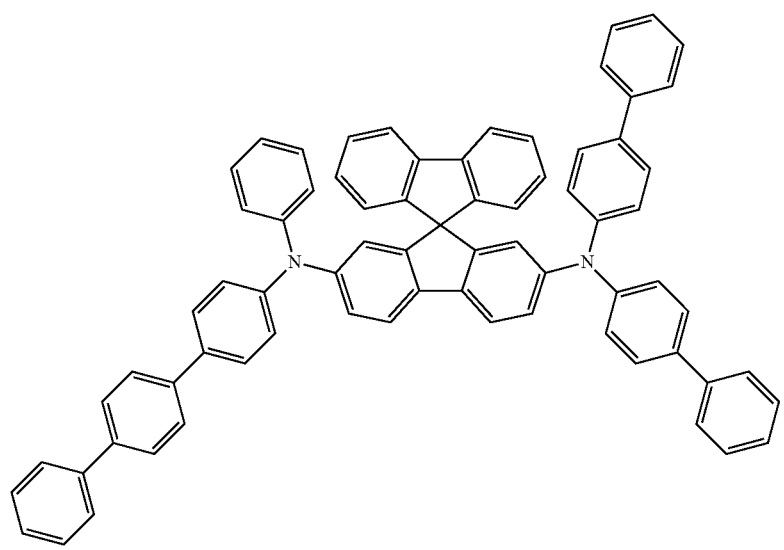
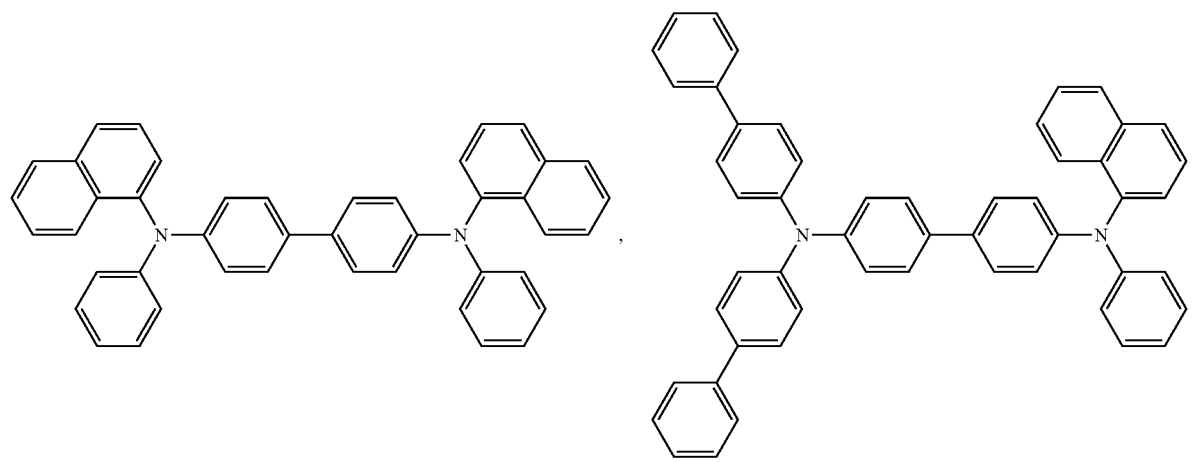

391
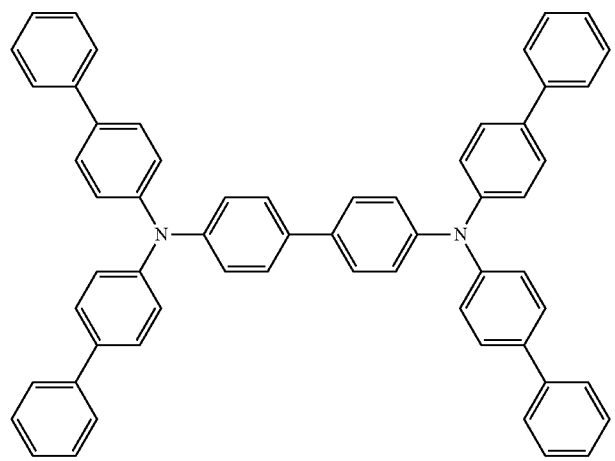
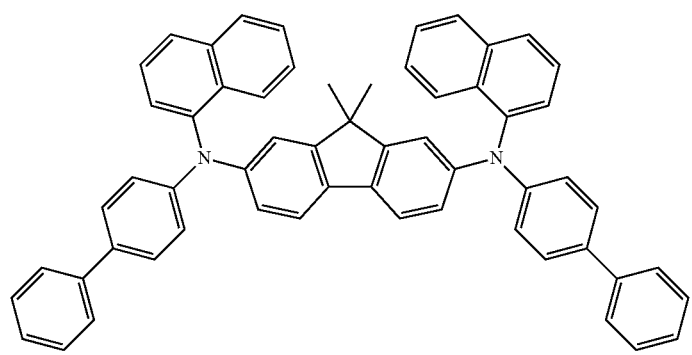
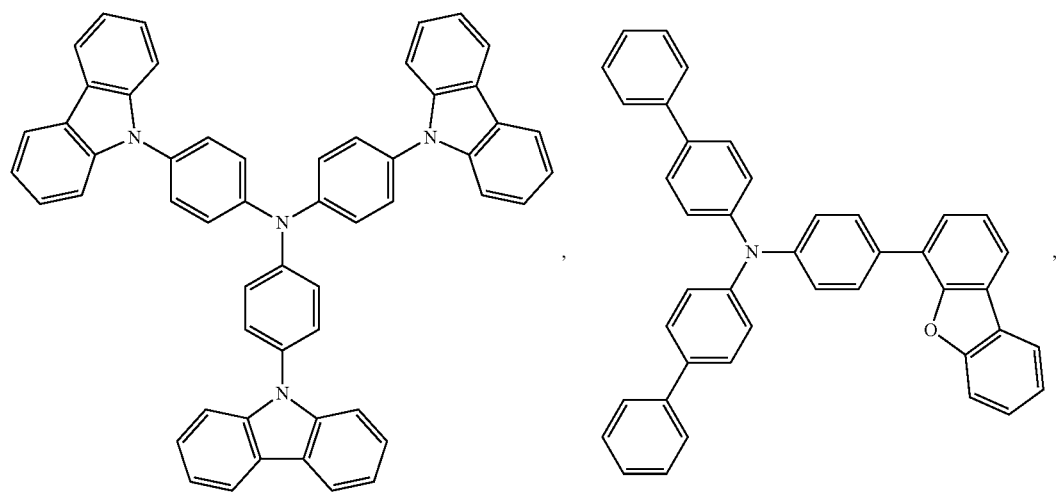
392
-continued

-continued

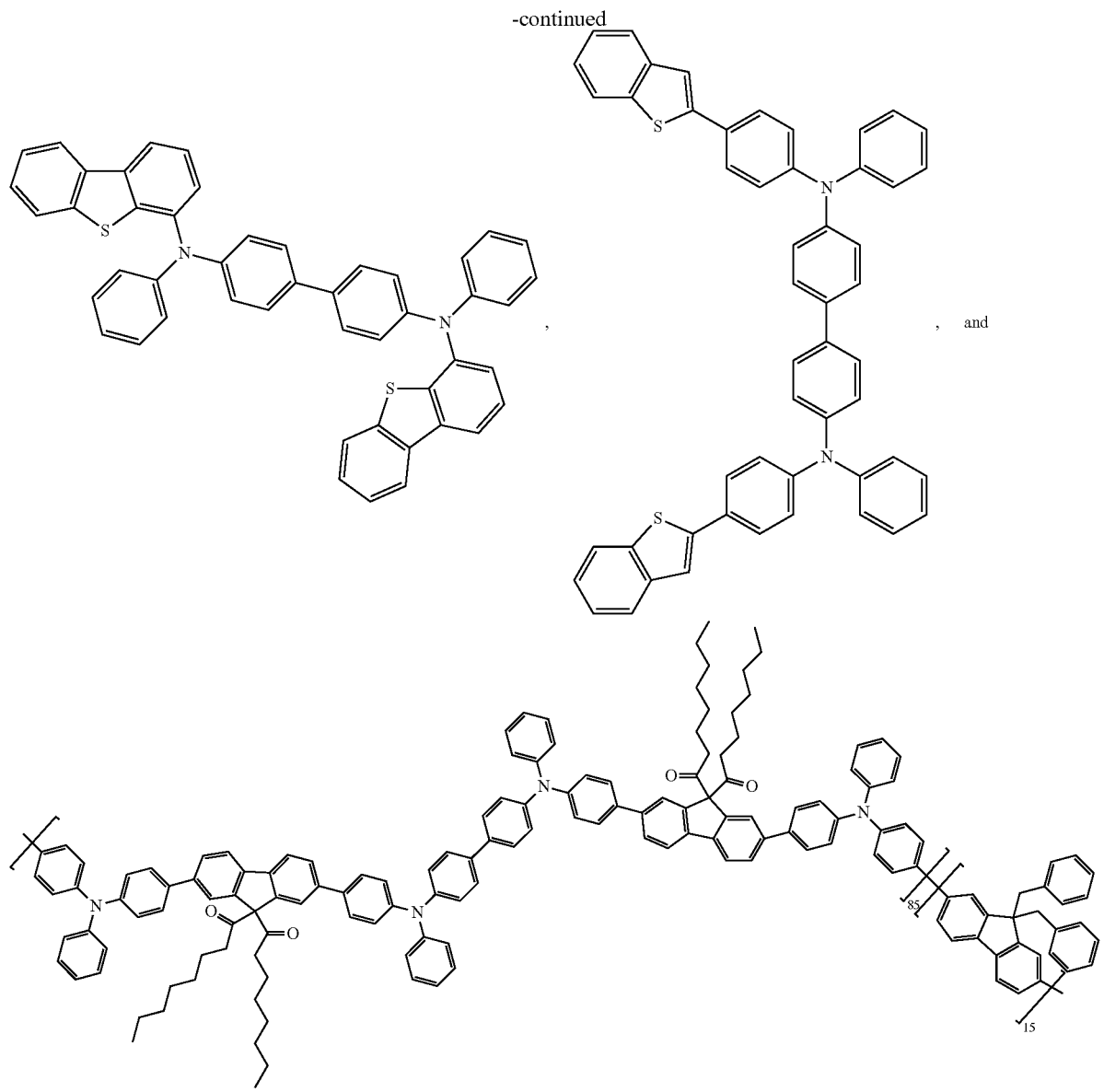

c) EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

d) Hosts:

The light emitting layer of the organic EL device of the present disclosure preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

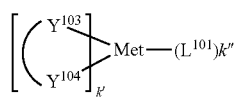

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

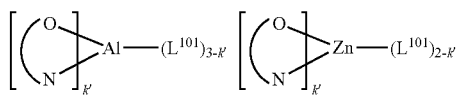

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

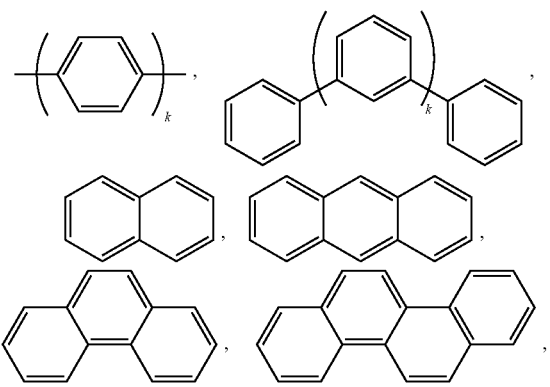

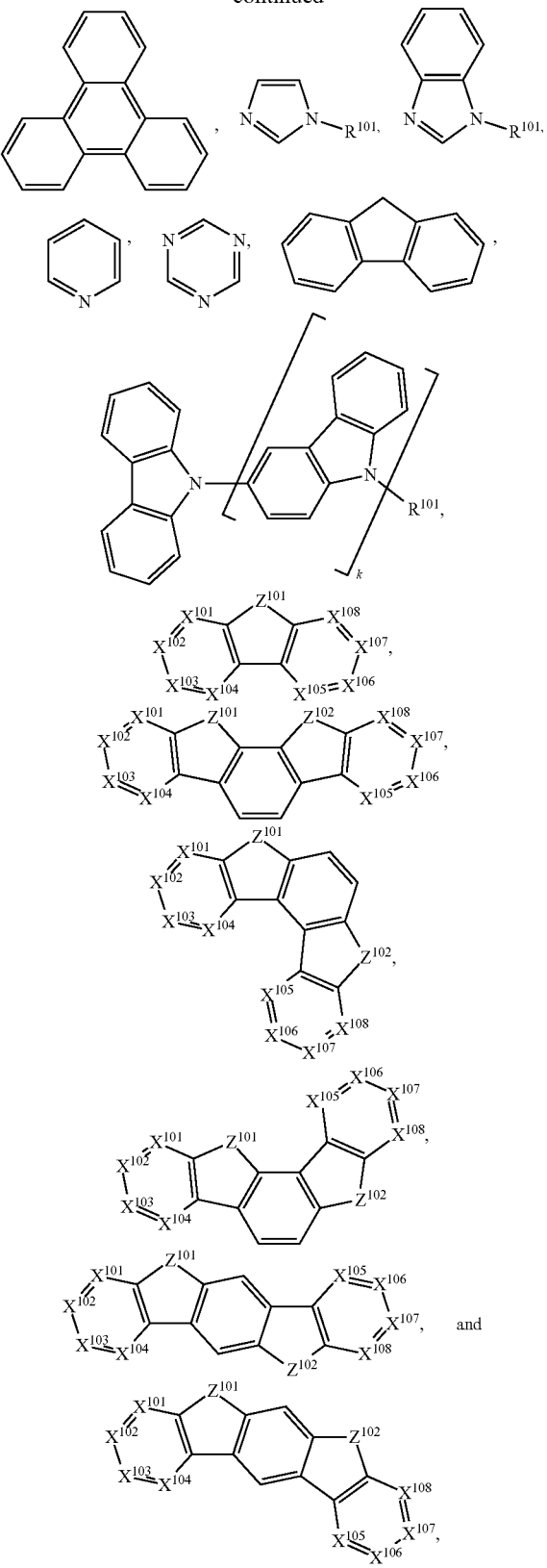

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, US7154114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803,

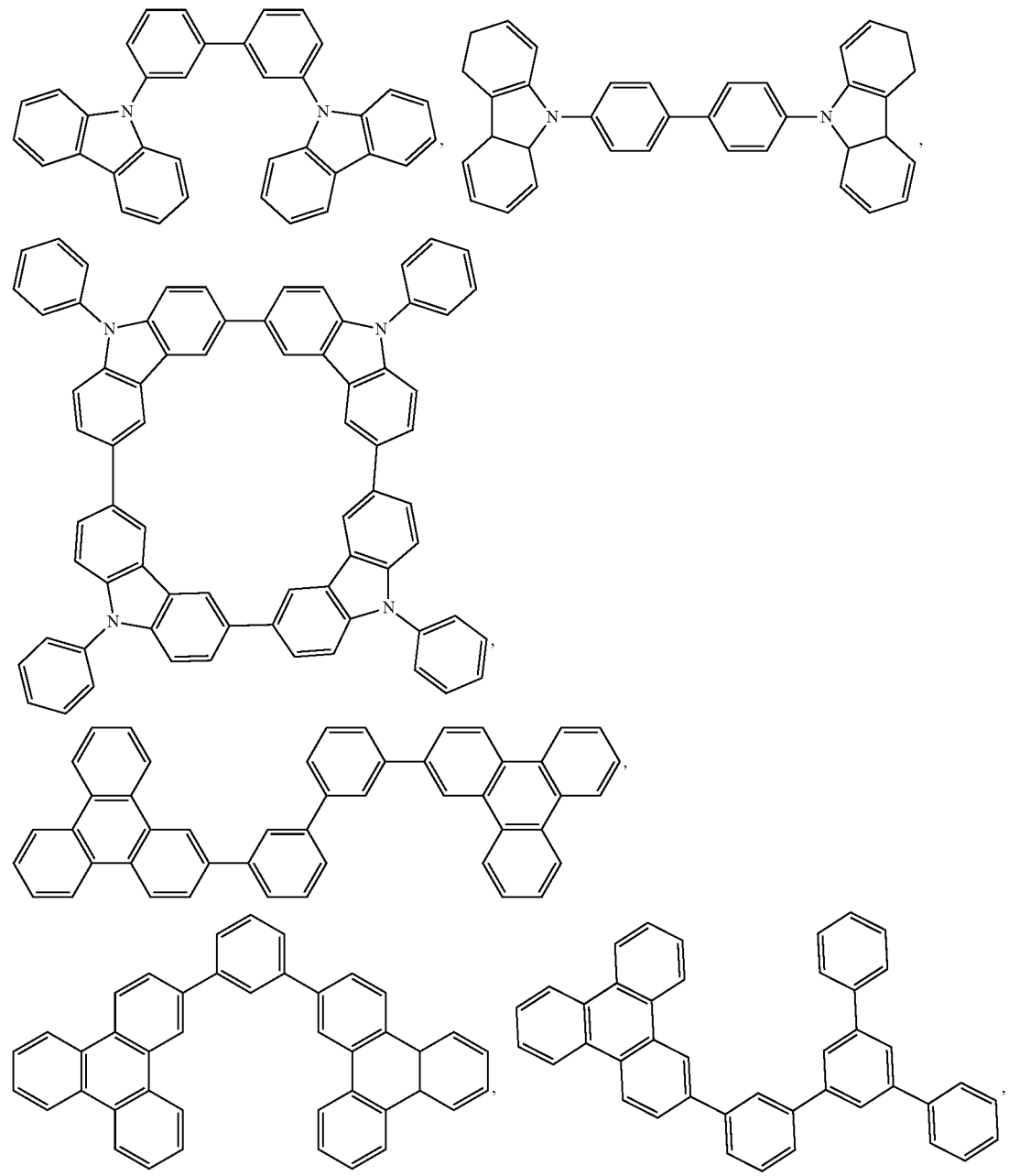

399                                    400
-continued
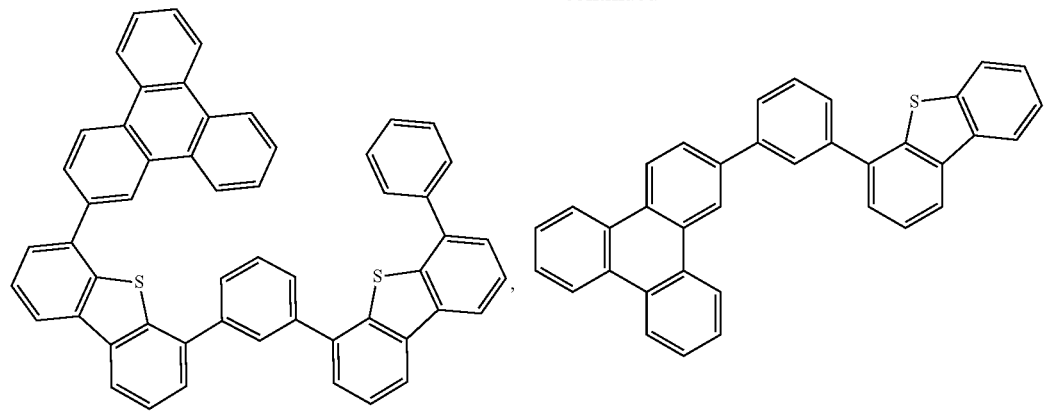
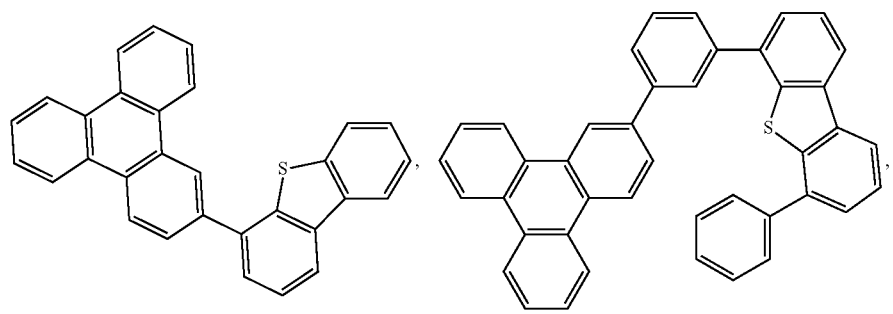
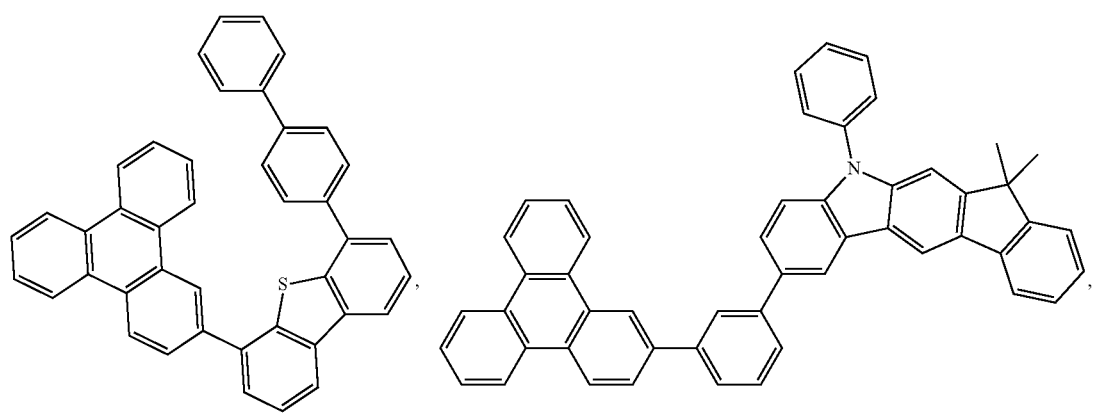
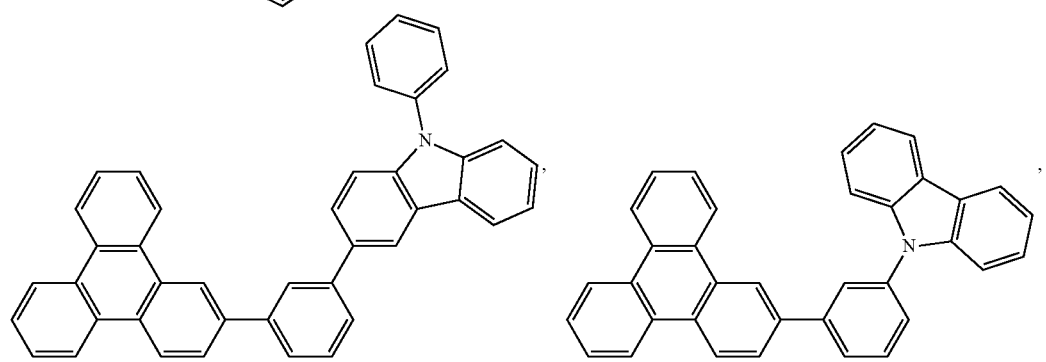

-continued
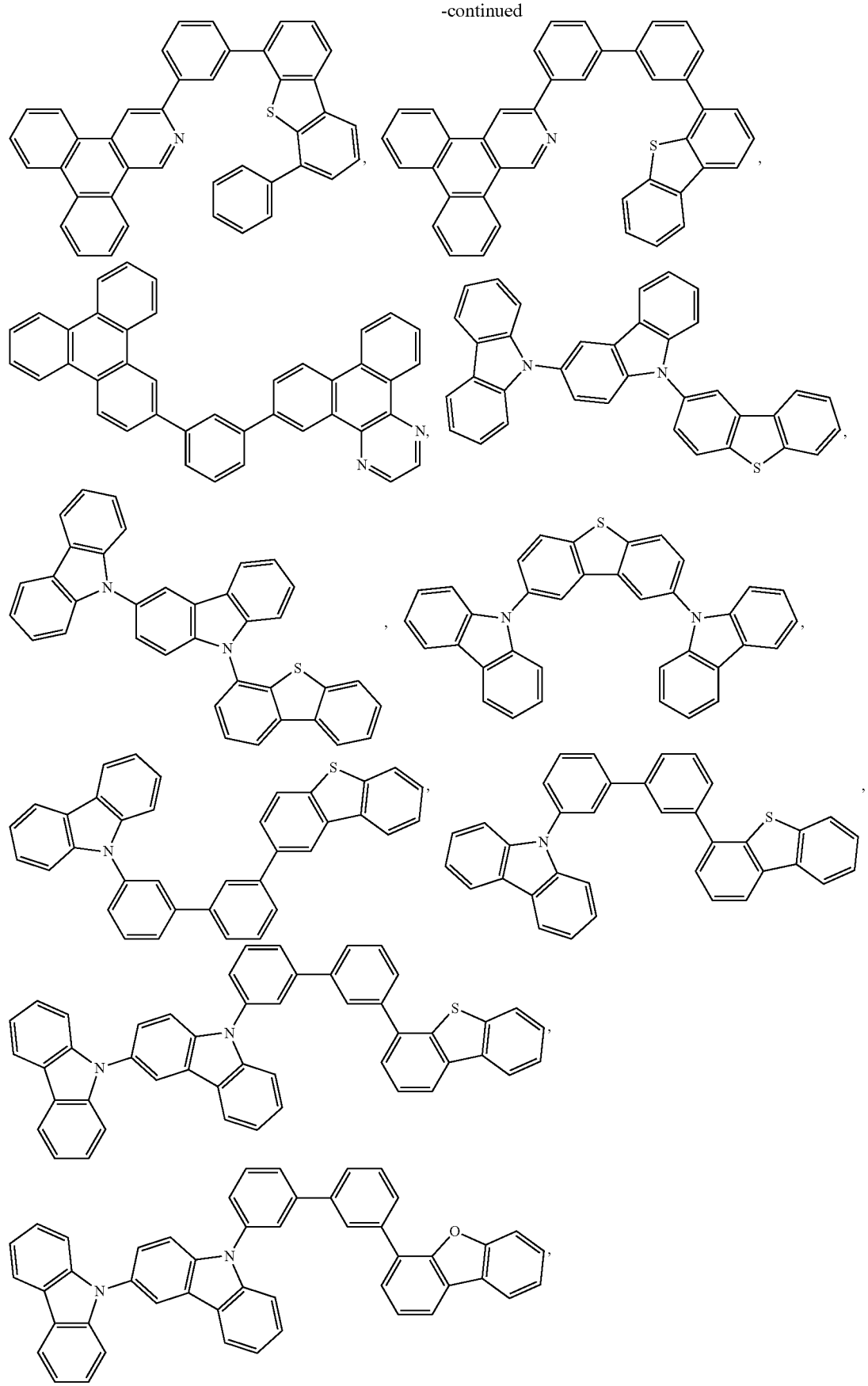

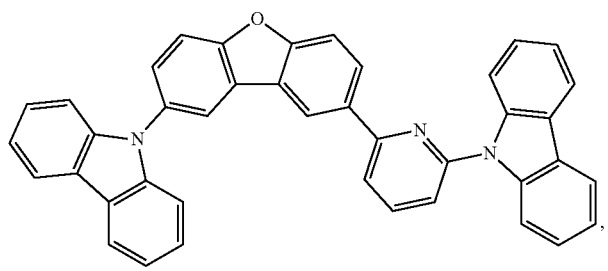
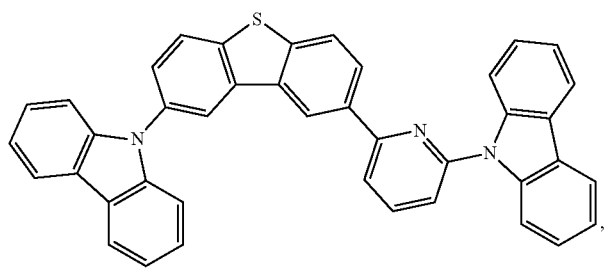
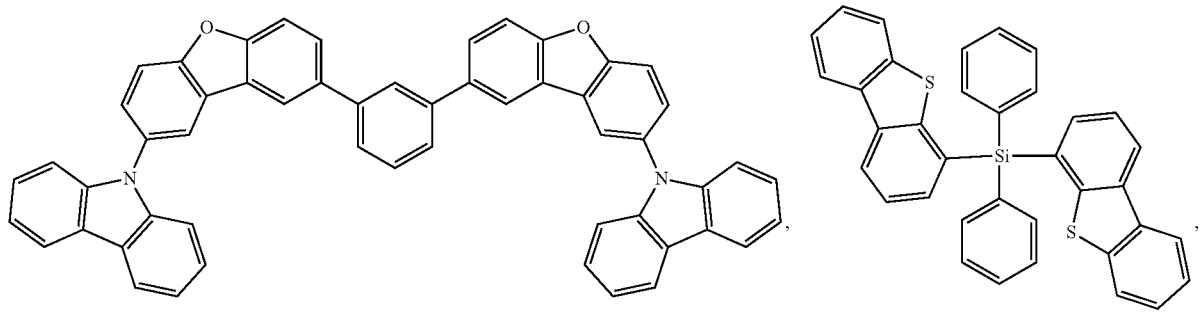
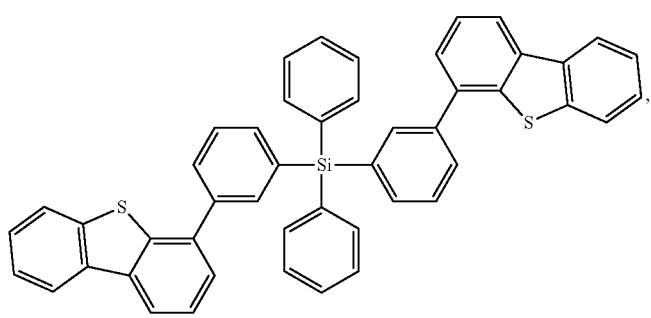
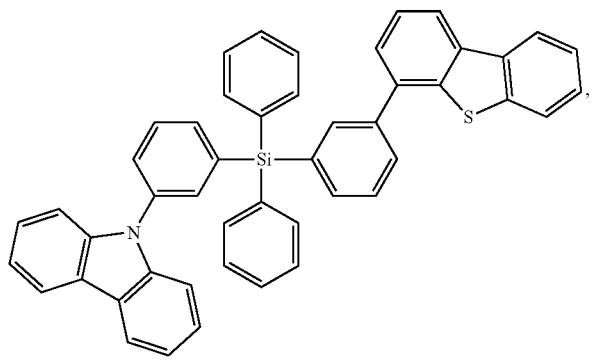

405
-continued
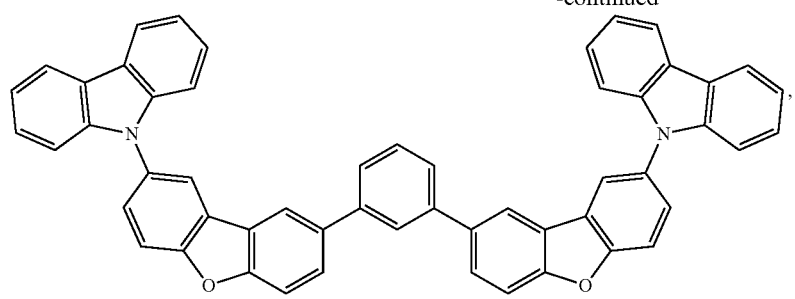
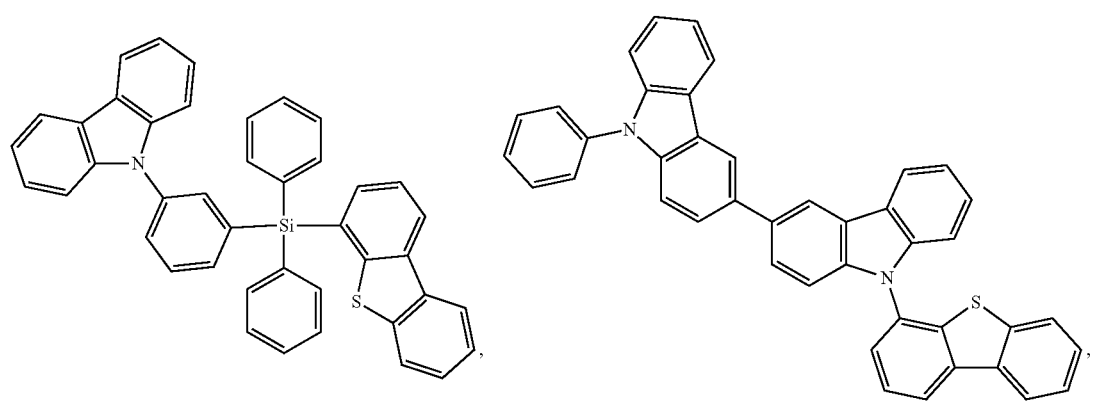
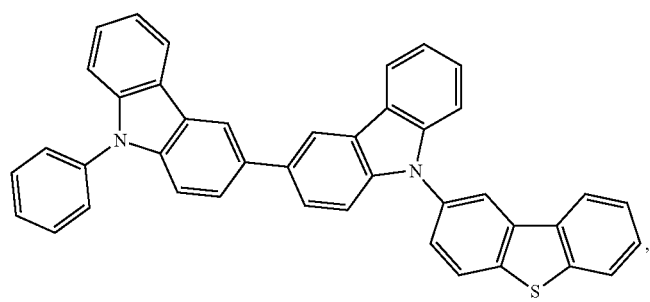
406
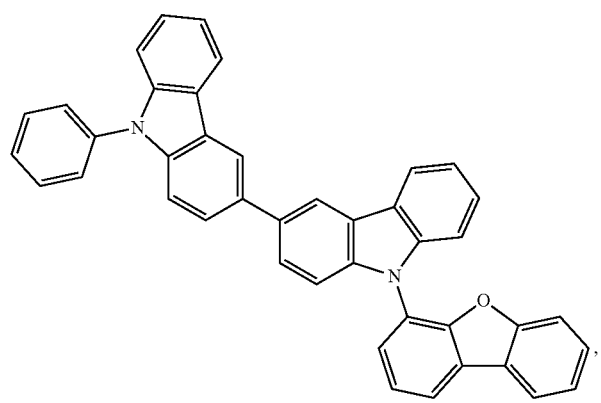

-continued
| 407 | 408 |
|---|---|
| 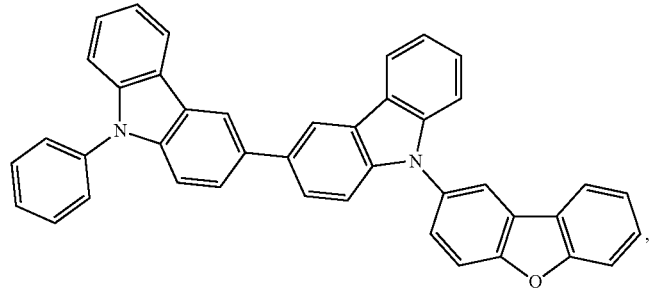 | 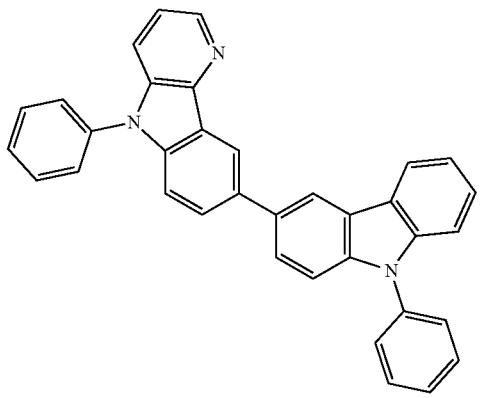 |
| 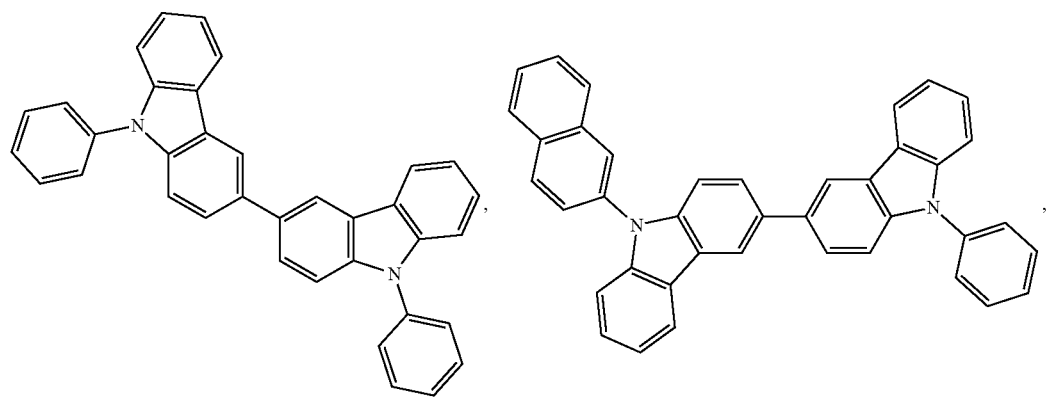 | 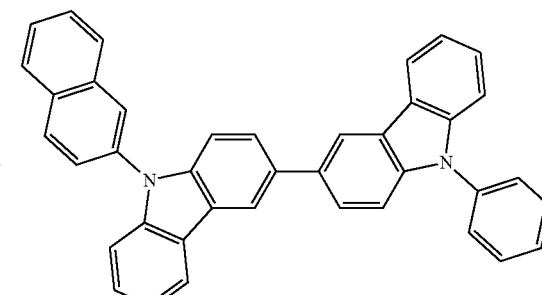 |
| 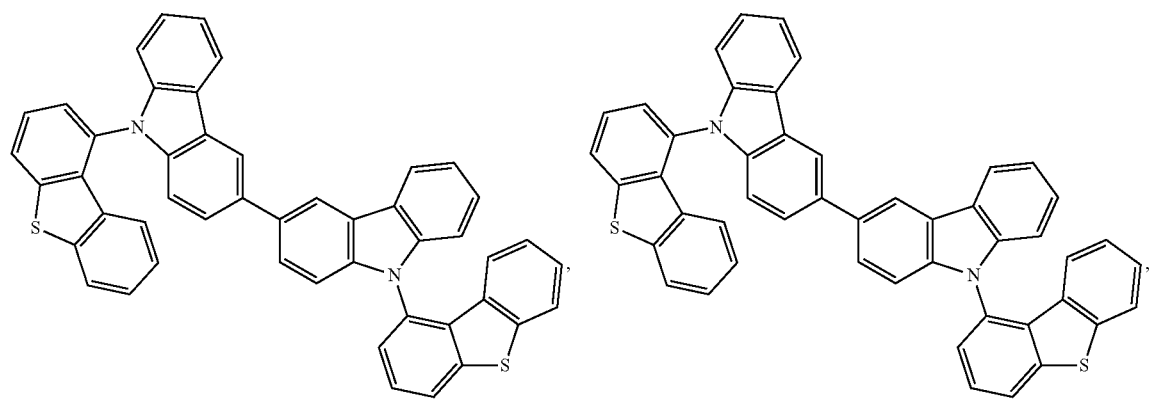 | 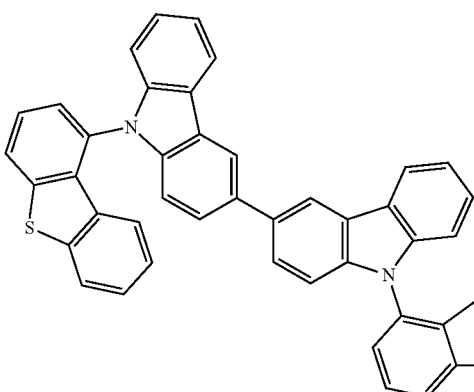 |
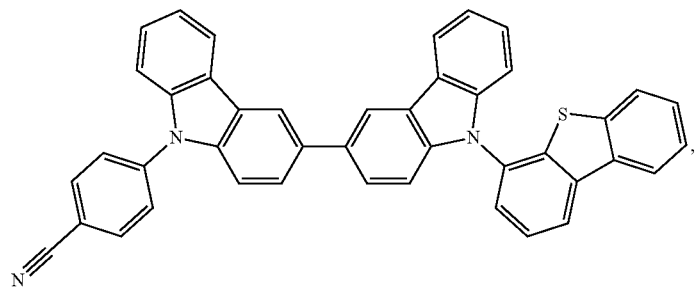

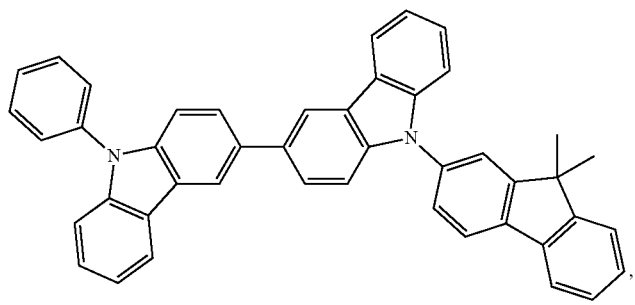
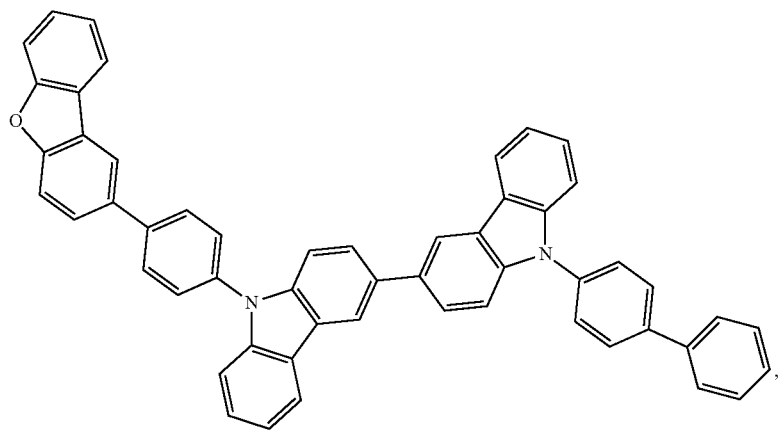
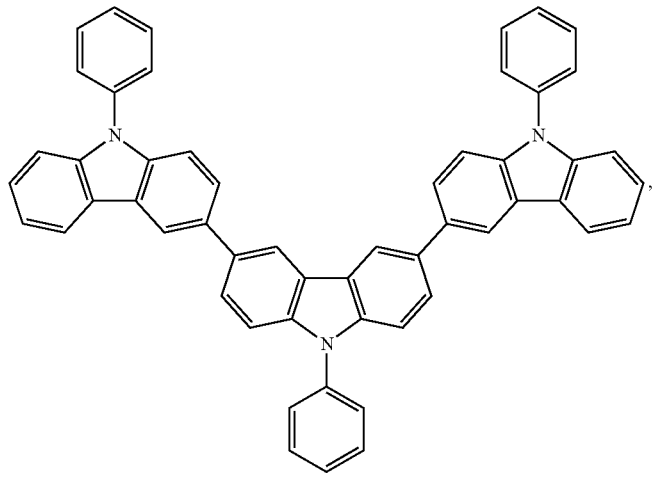
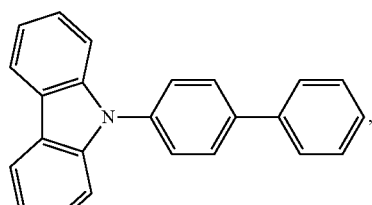
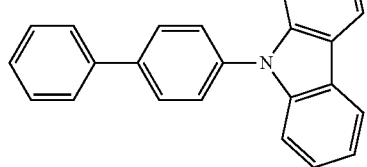

411
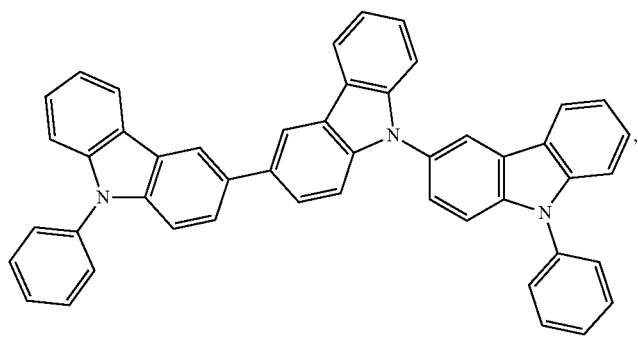
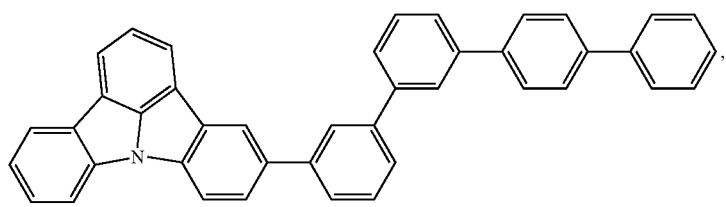
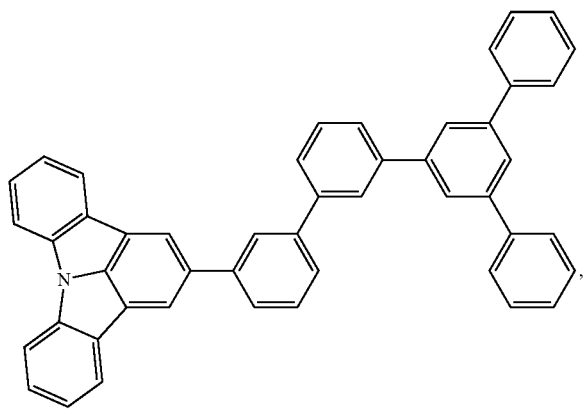
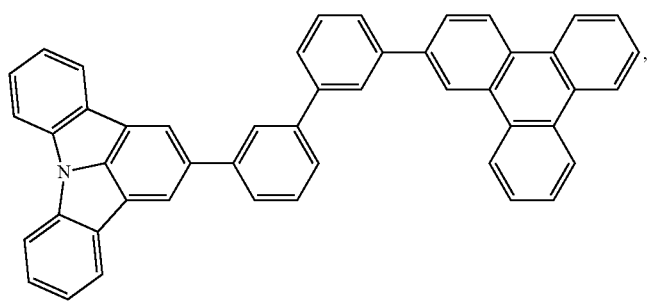
412
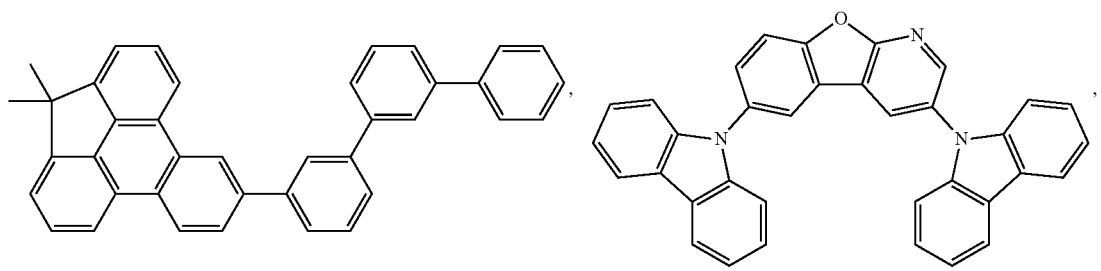

-continued
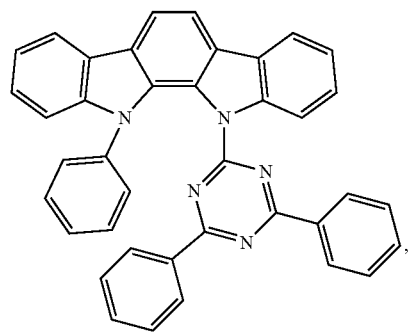
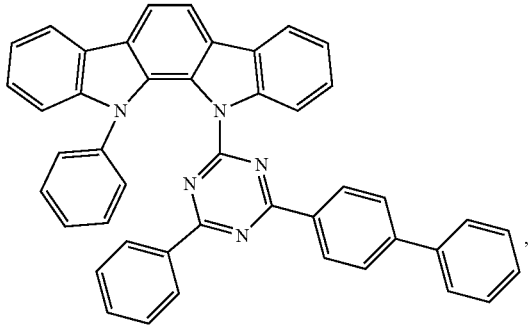
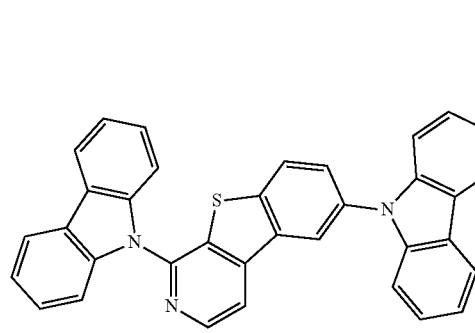
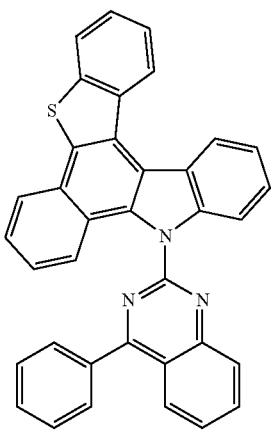
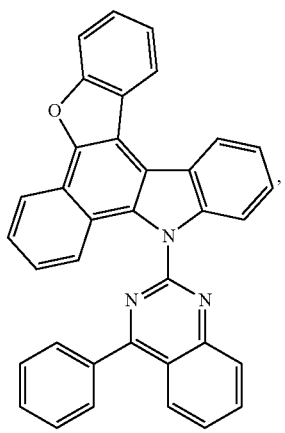
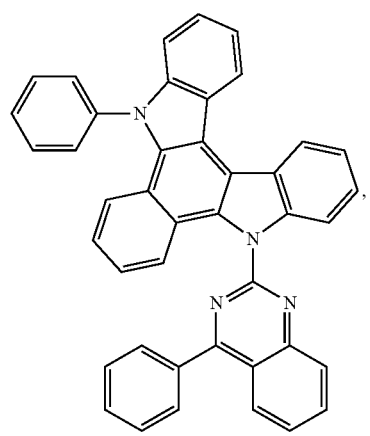
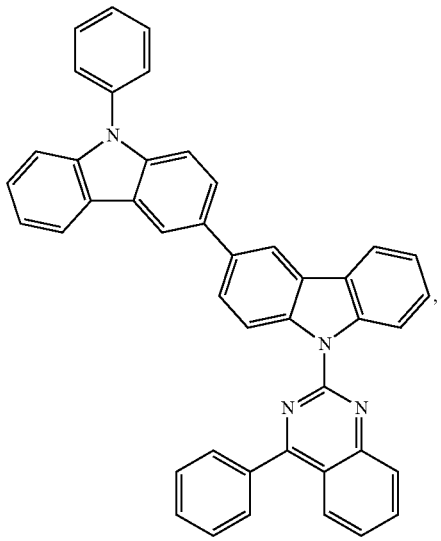
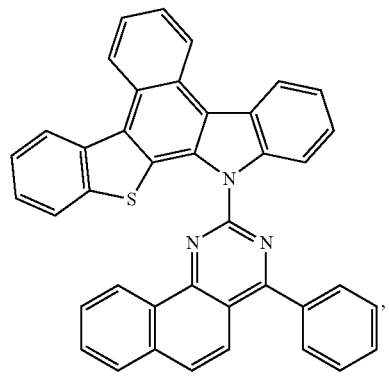
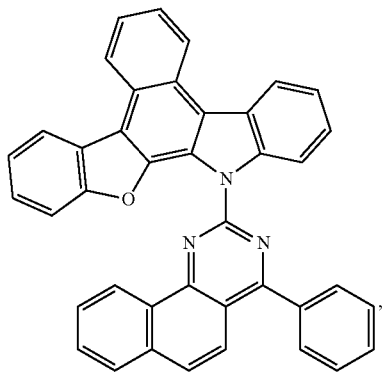

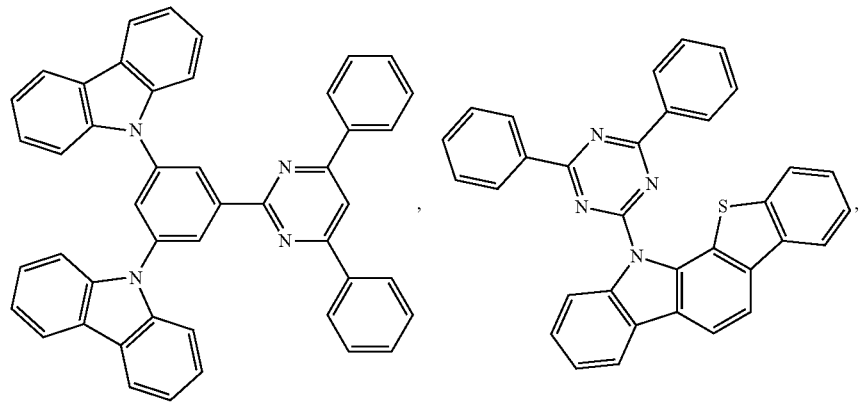
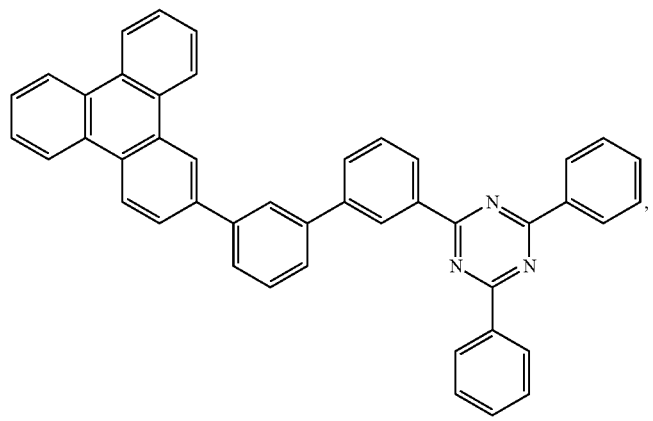
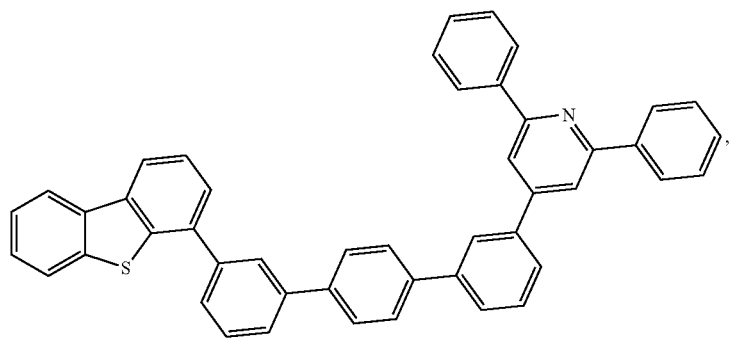
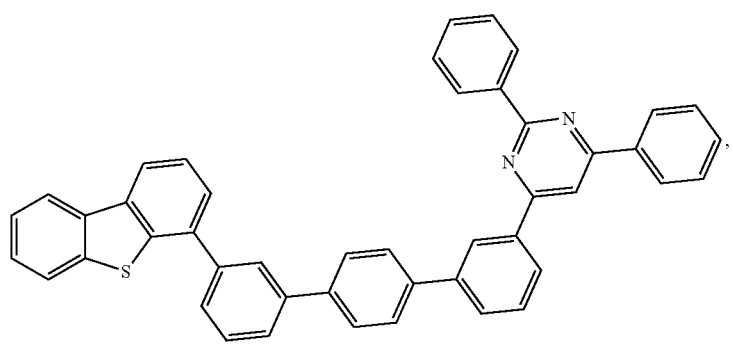

-continued
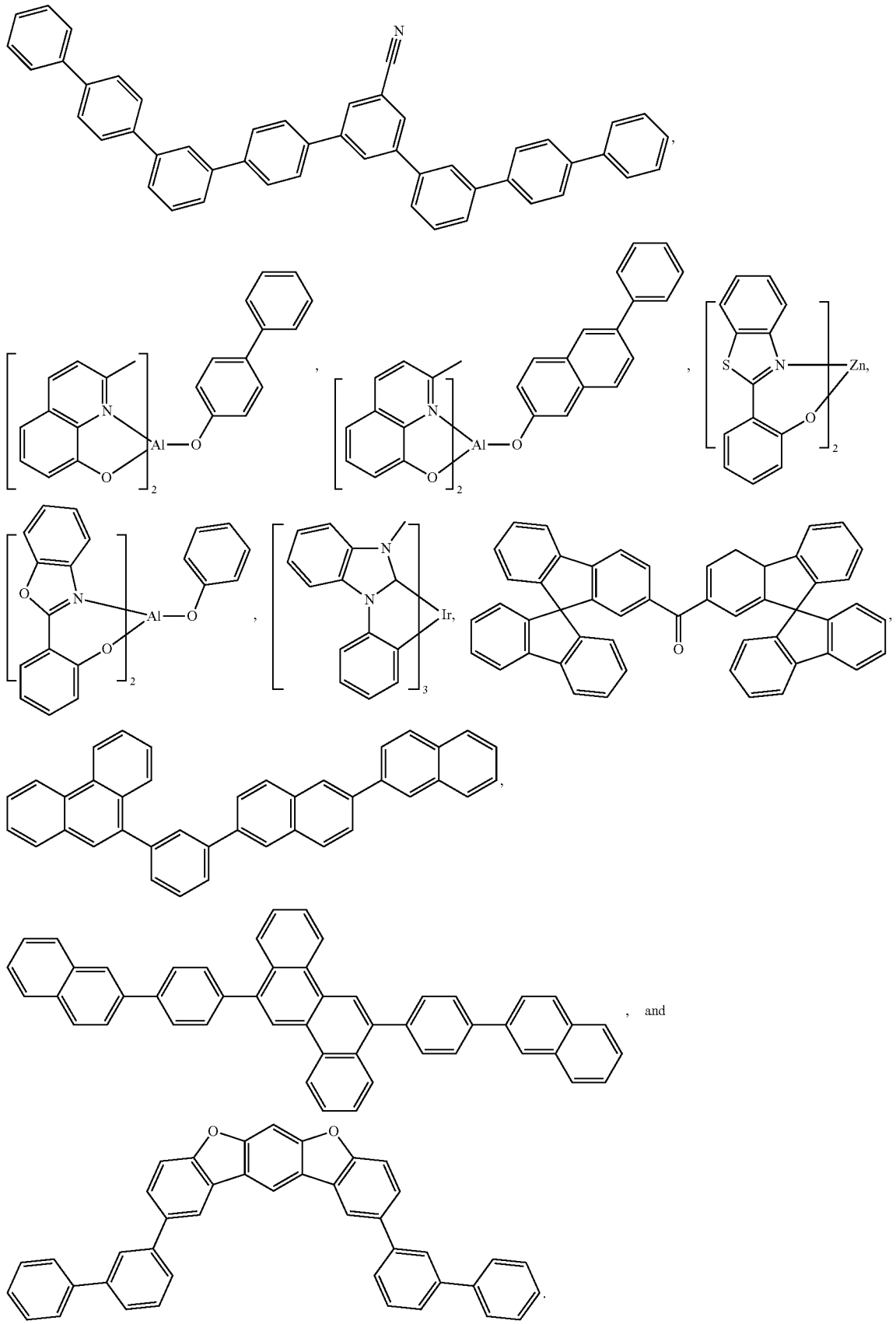

e) Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, US06699599, U.S. Pat. No. 06,916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

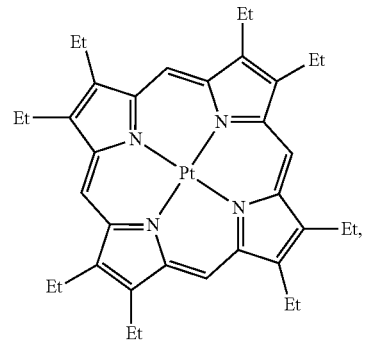

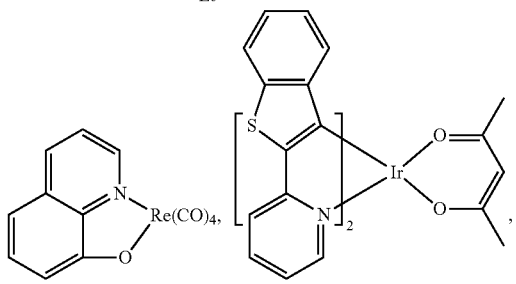

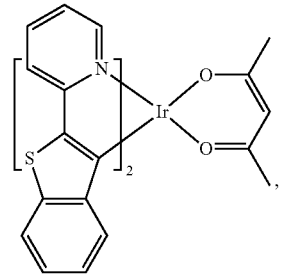

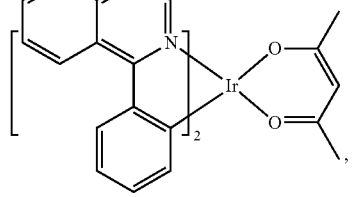

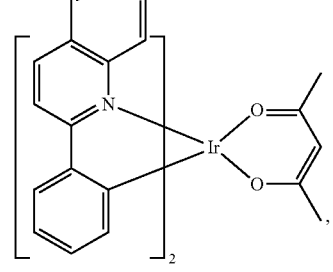

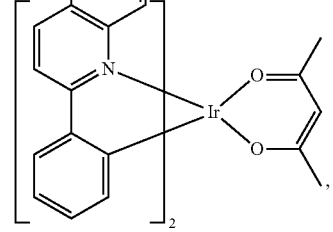

421
-continued
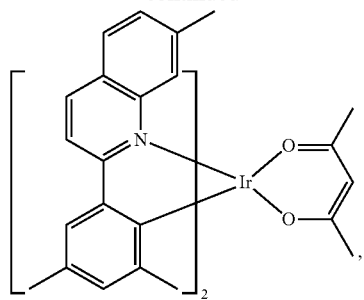
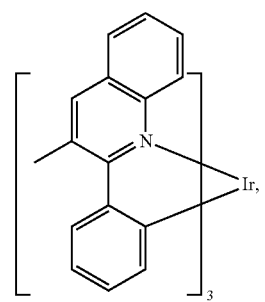
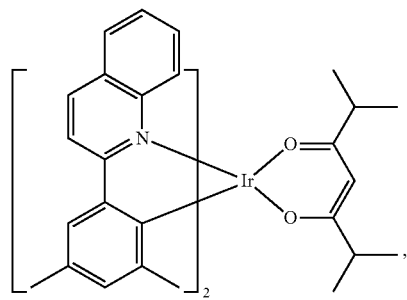
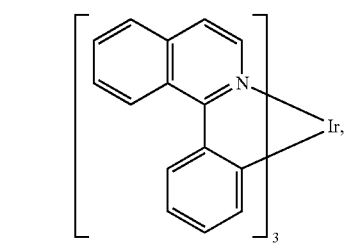
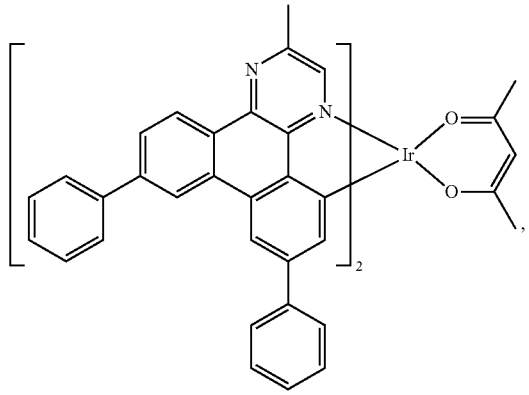
422
-continued
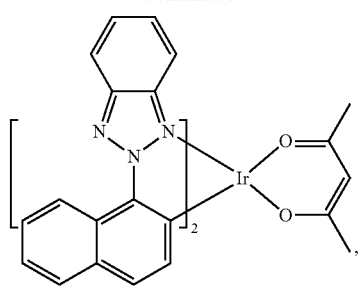
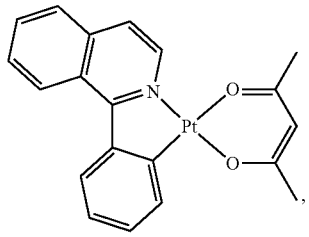
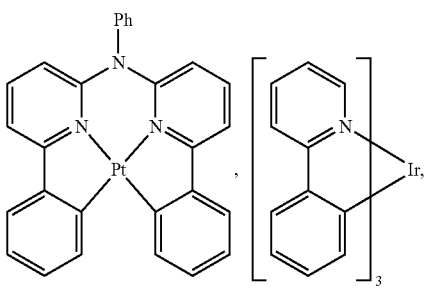
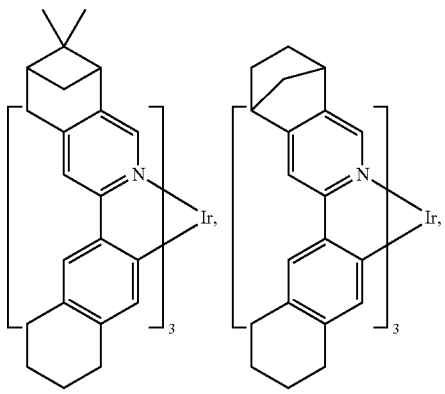
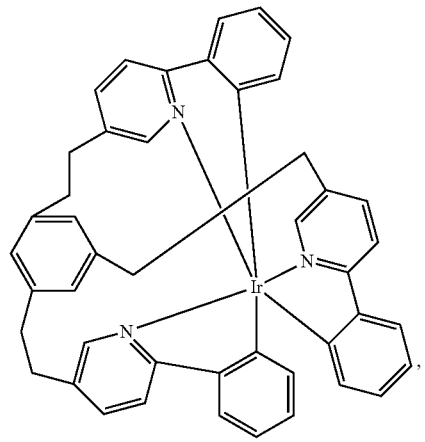

423
-continued
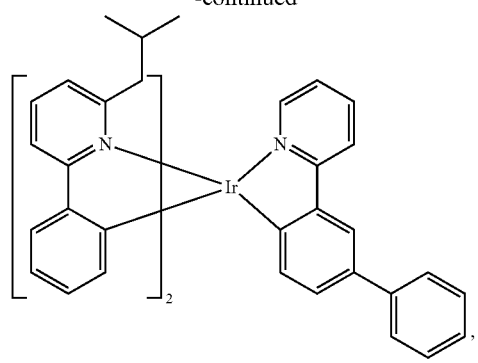
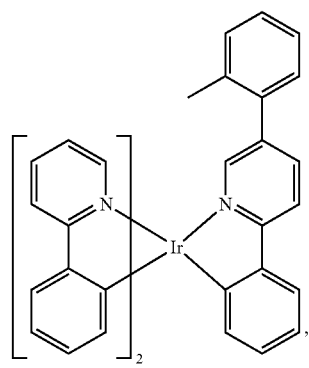
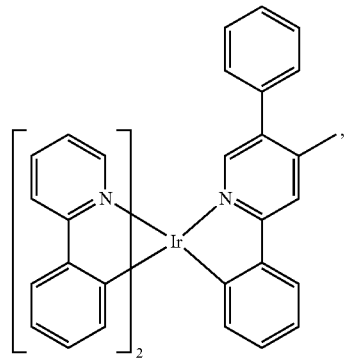
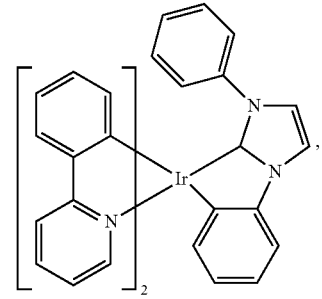
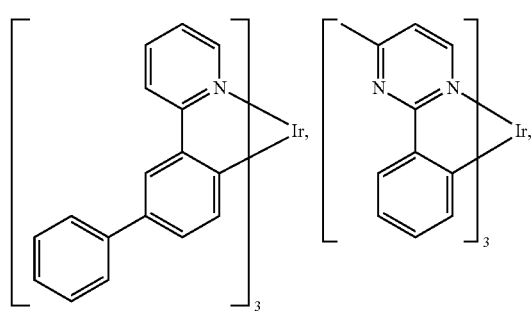
424
-continued
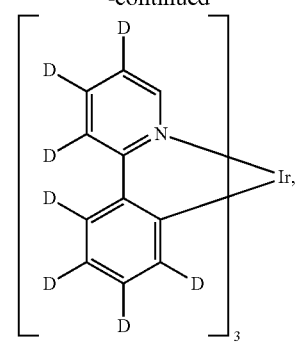
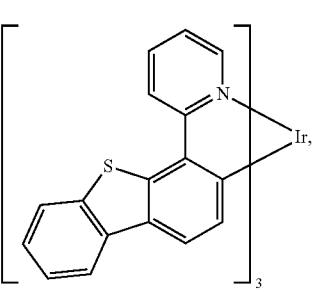
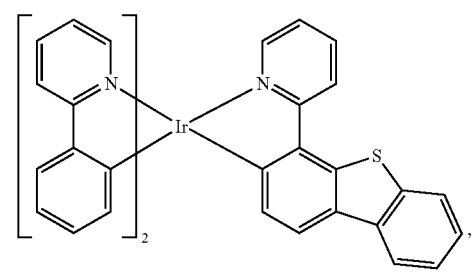
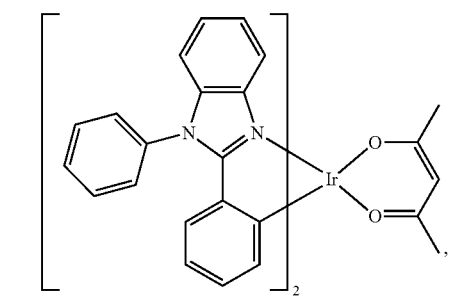
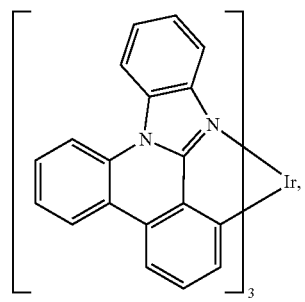

425
-continued
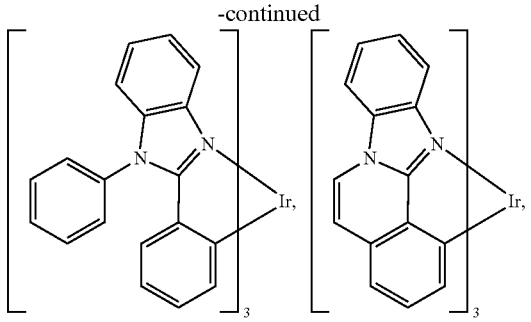
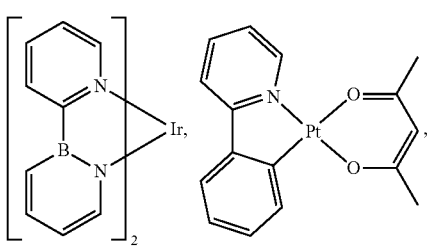
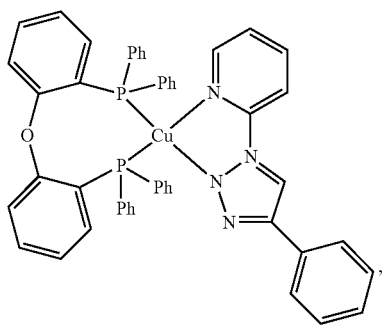
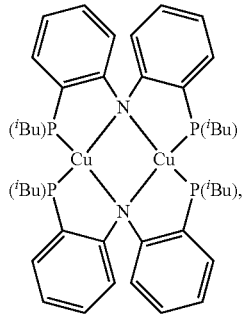
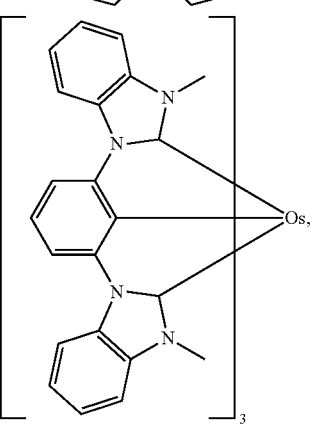
426
-continued
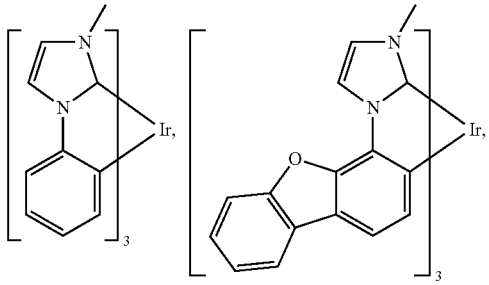
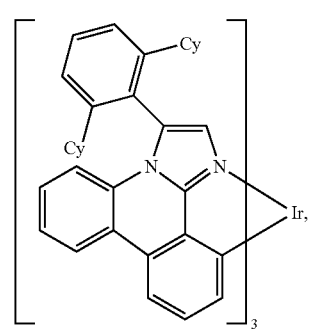
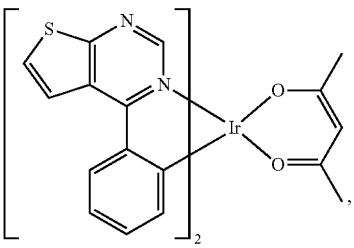
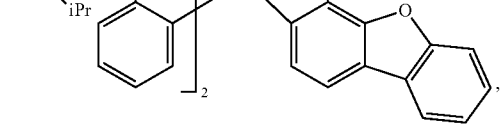
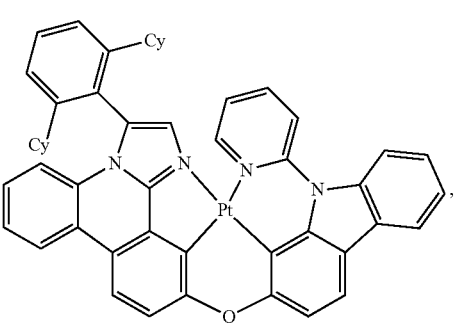

427 -continued
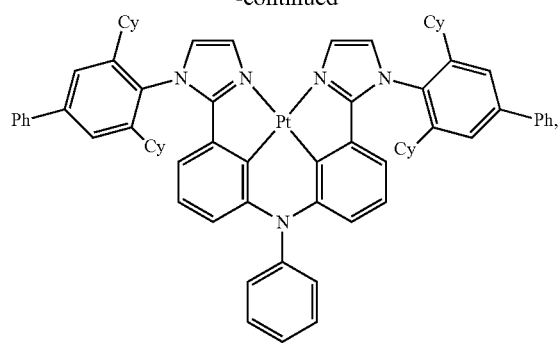
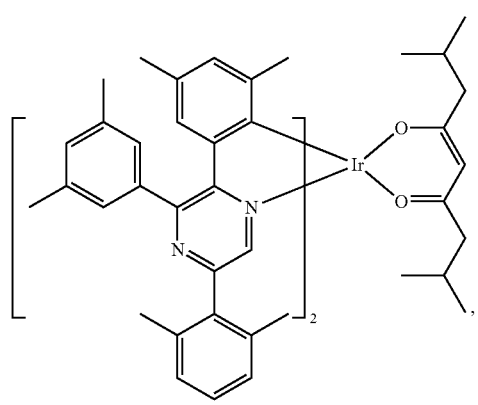
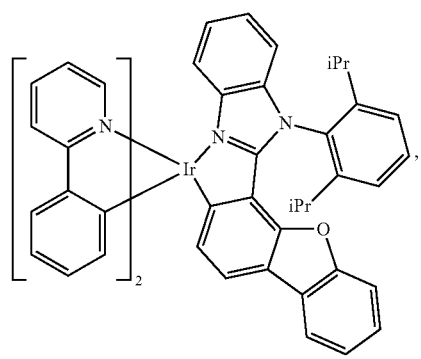
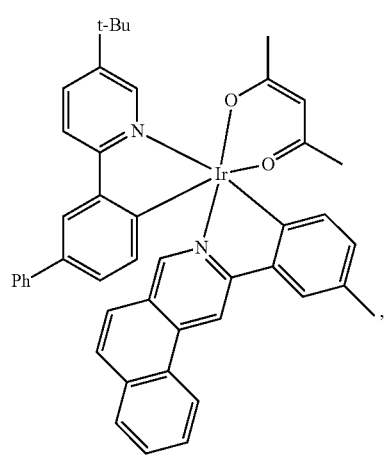
428 -continued
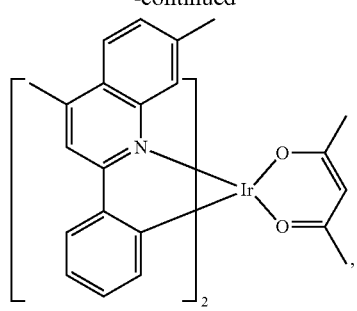
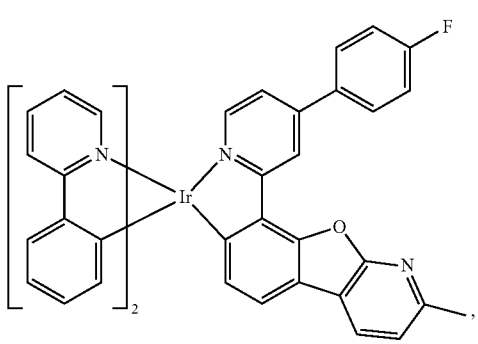
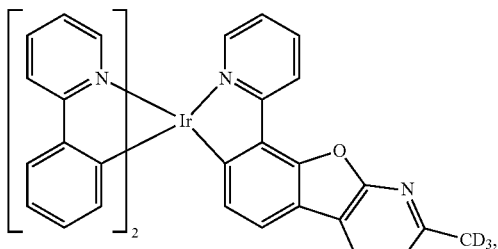
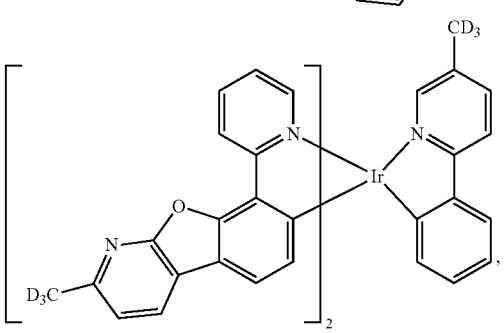
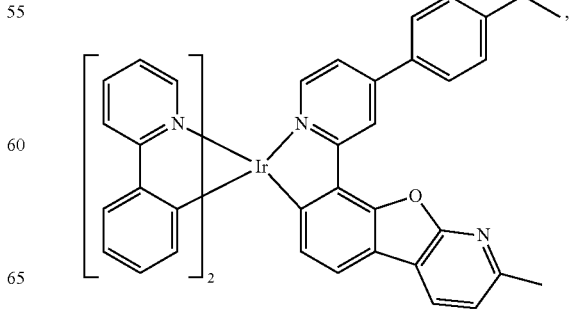

429
-continued
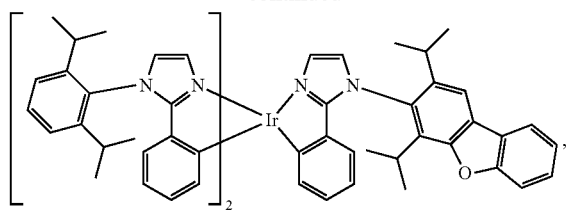
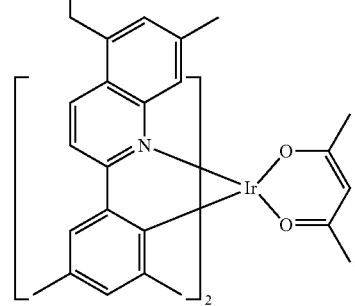
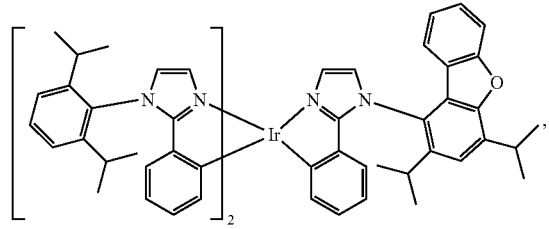
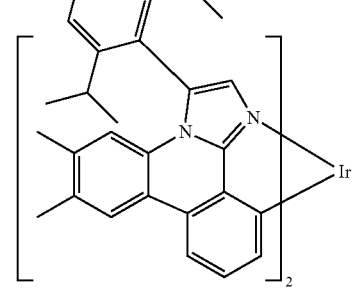
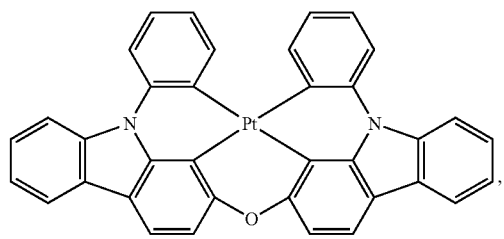
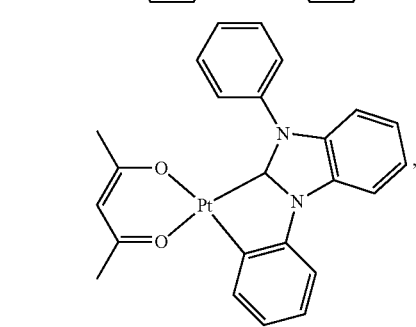
430
-continued
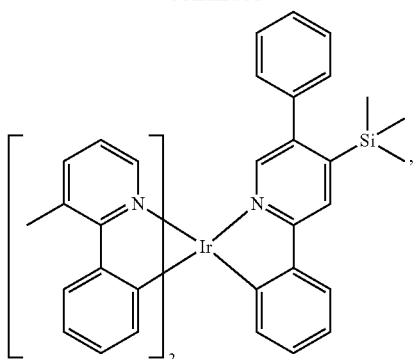
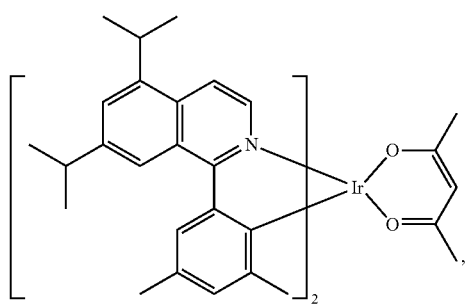
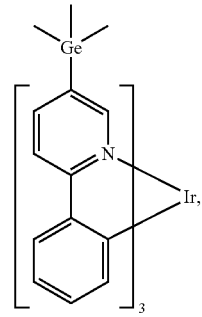
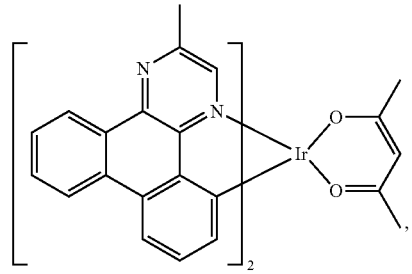
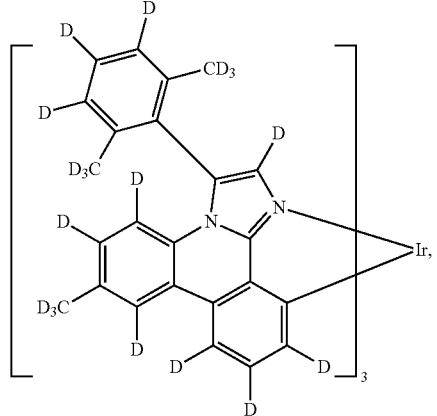

431
-continued
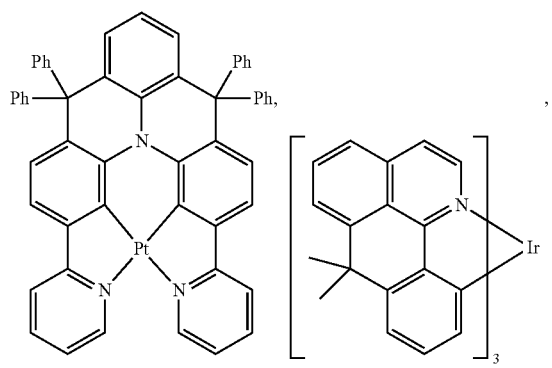
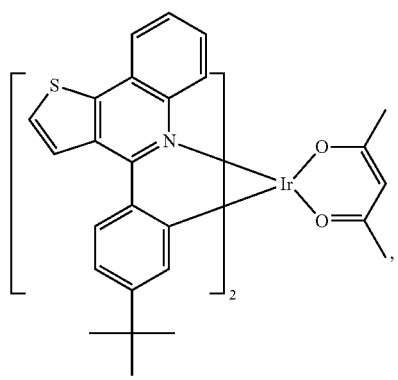
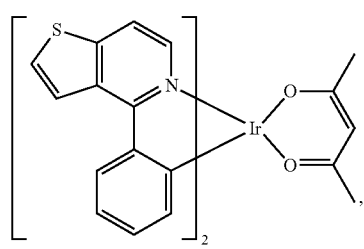
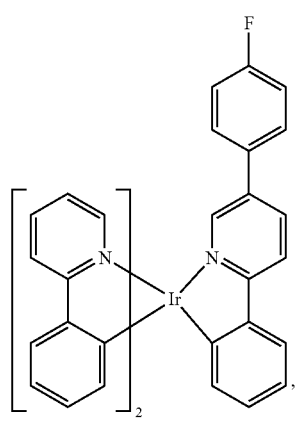
432
-continued
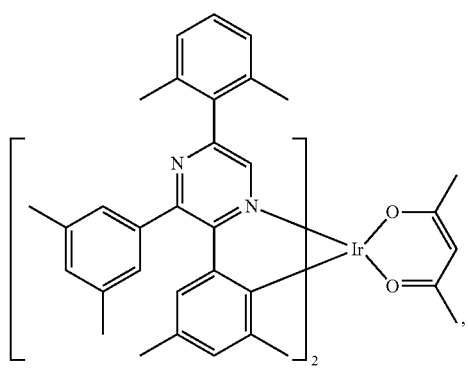
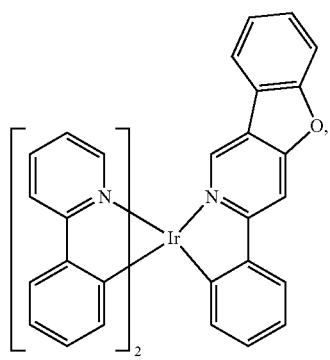
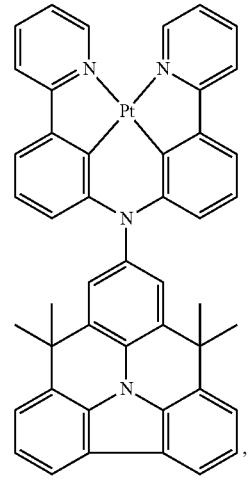
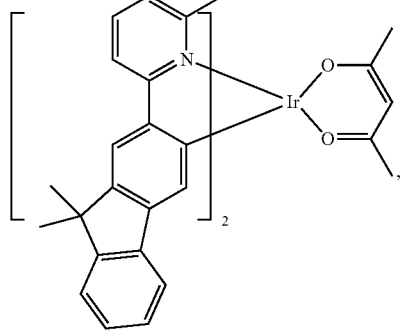

433
-continued
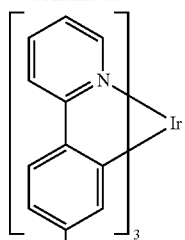
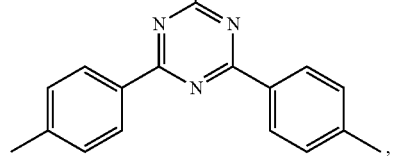
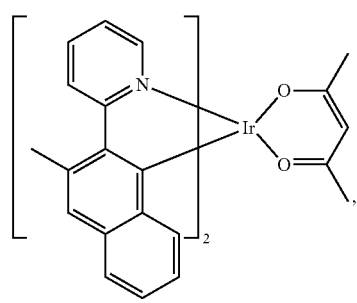
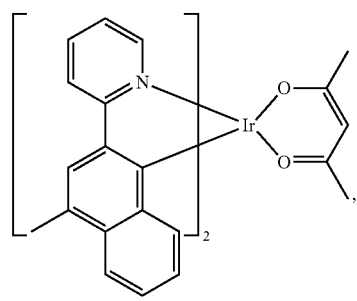
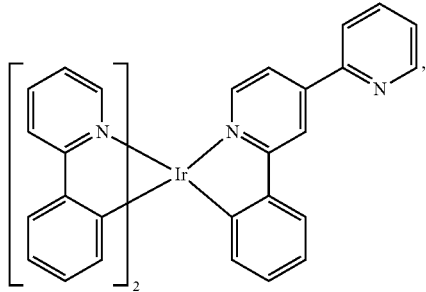
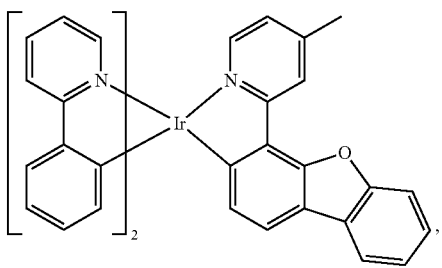
434
-continued
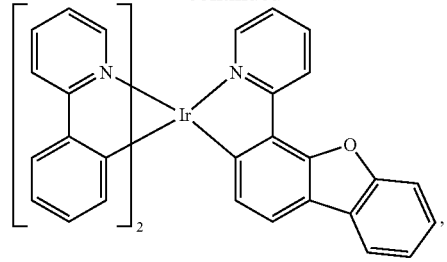
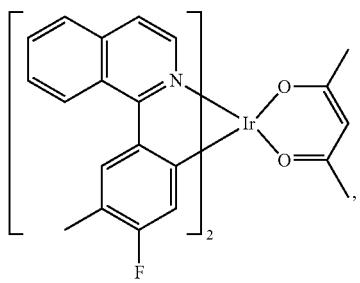
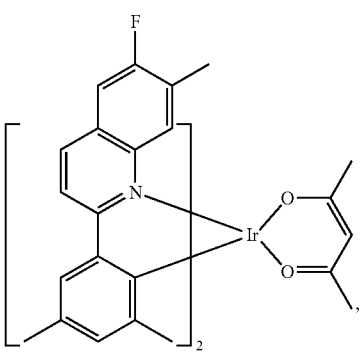
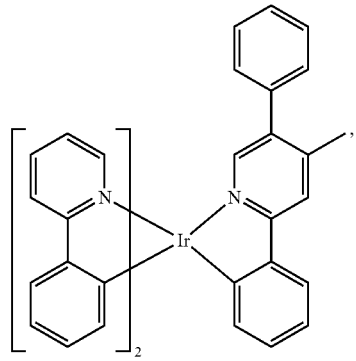
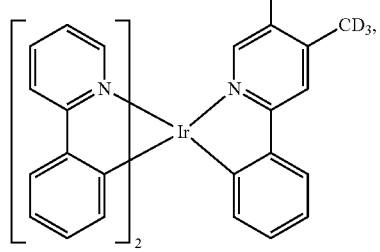

-continued
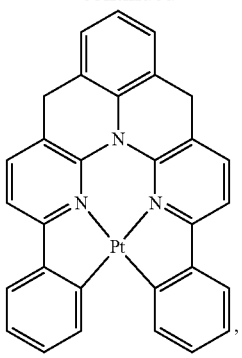
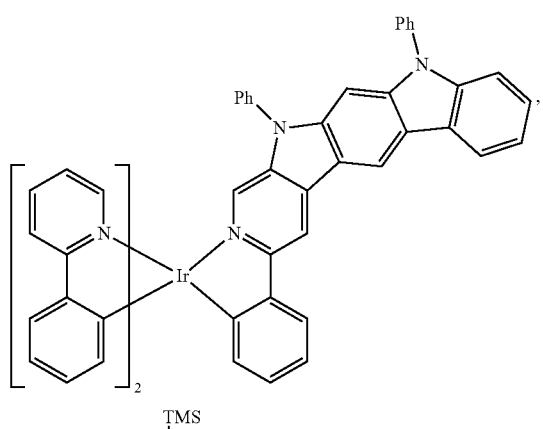
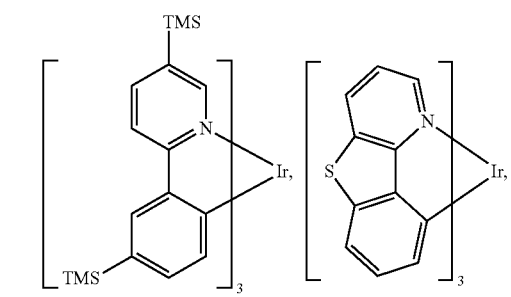
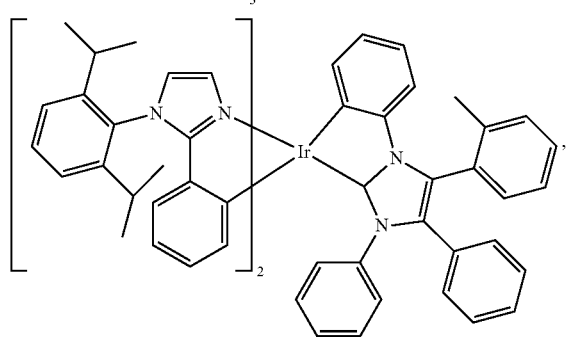
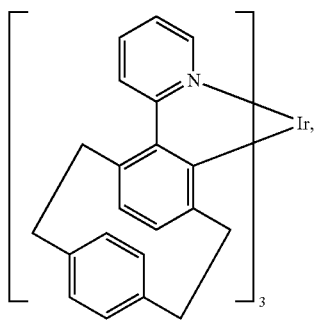
-continued
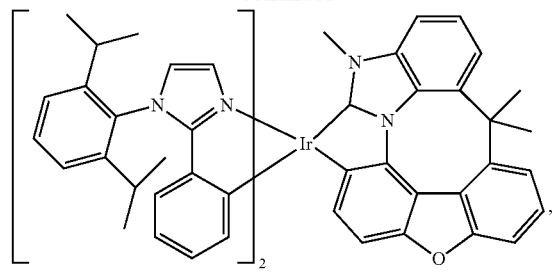
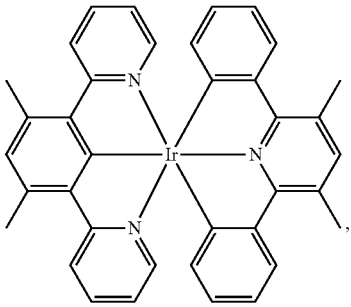
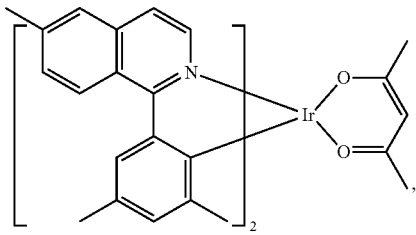
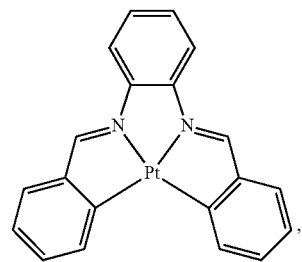
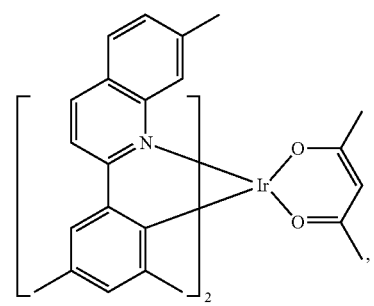
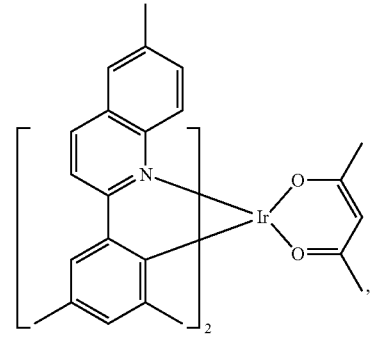

437
-continued
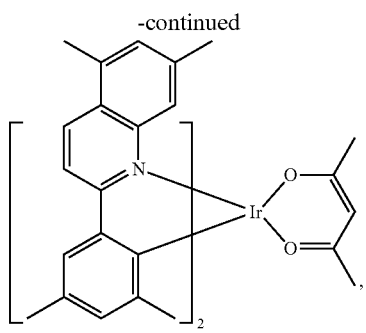
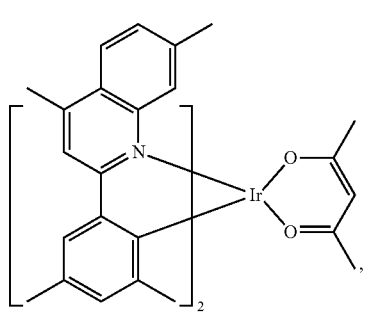
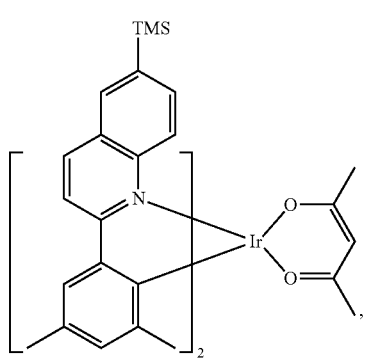
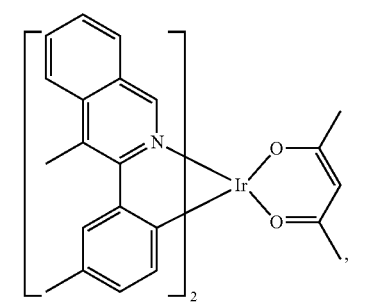
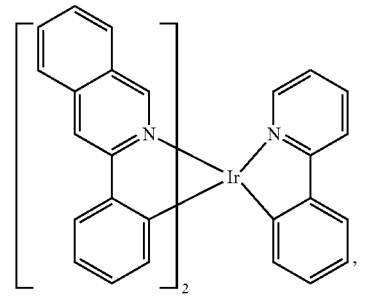
438
-continued
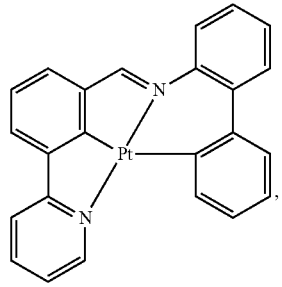
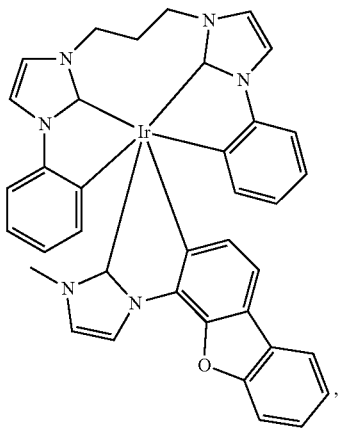
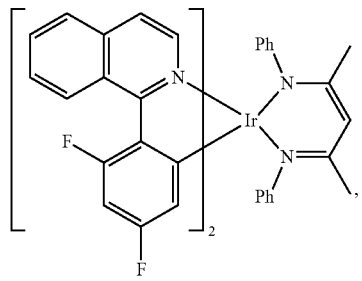

-continued
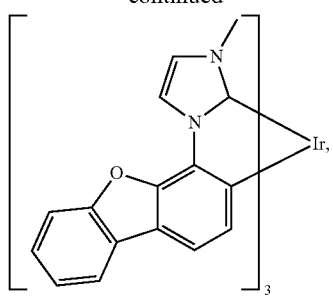
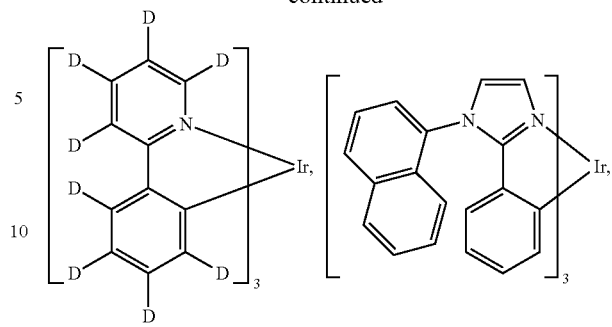
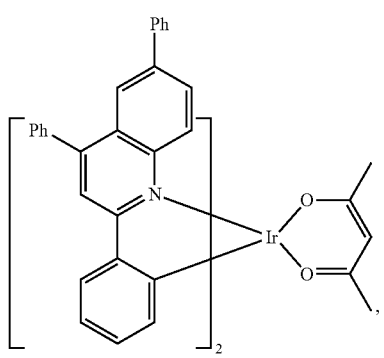
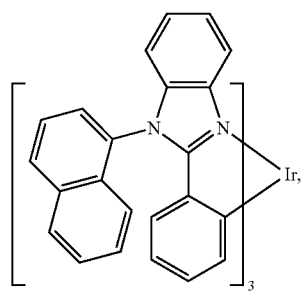
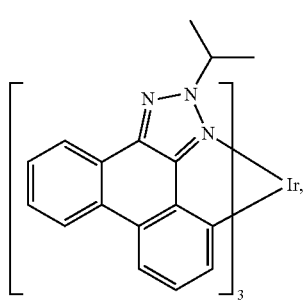
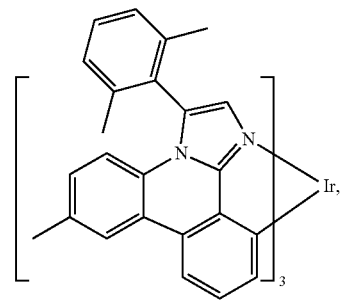
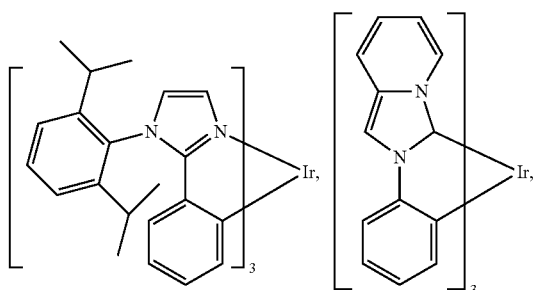
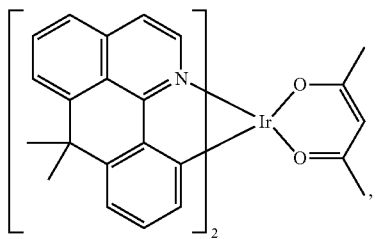
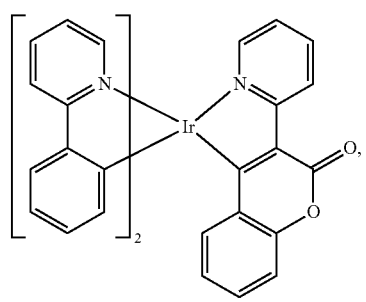
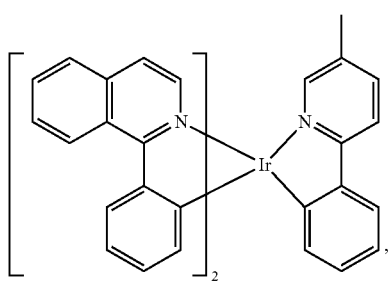

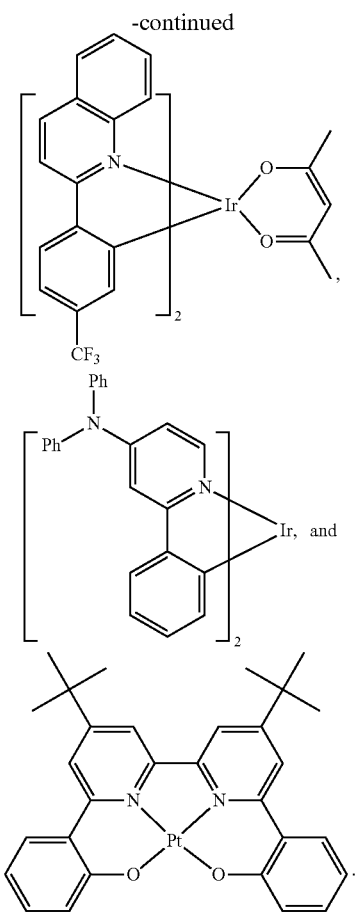

f) HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

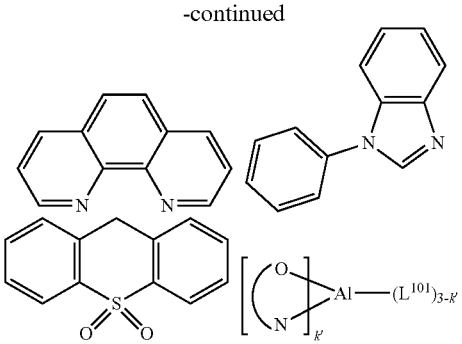

wherein k is an integer from 1 to 20; $L^{101}$ is another ligand, k' is an integer from 1 to 3.

g) ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

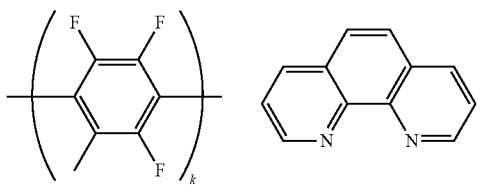

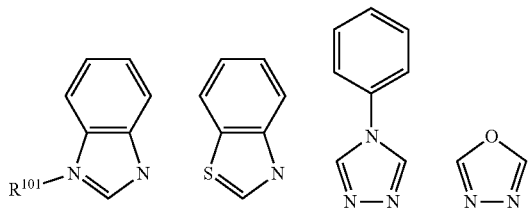

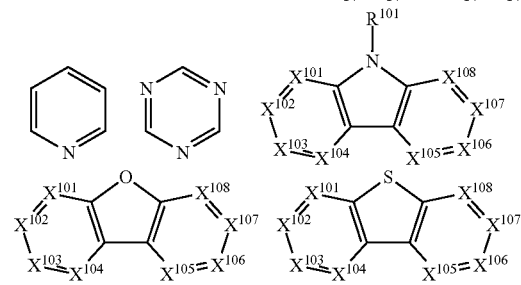

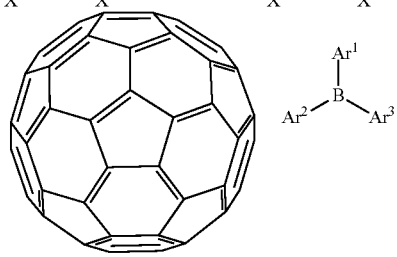

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

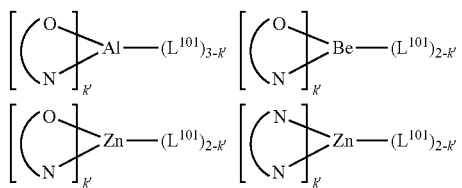

wherein (O—N) or (N—N) is a bidentate ligand, having metal coordinated to atoms O, N or N, N; is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

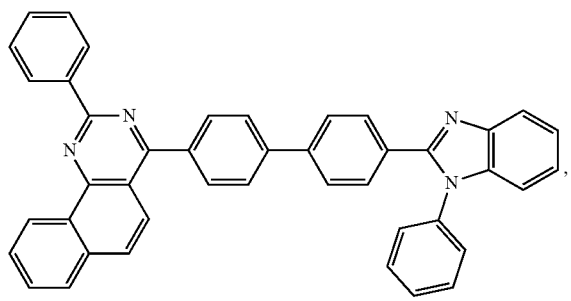

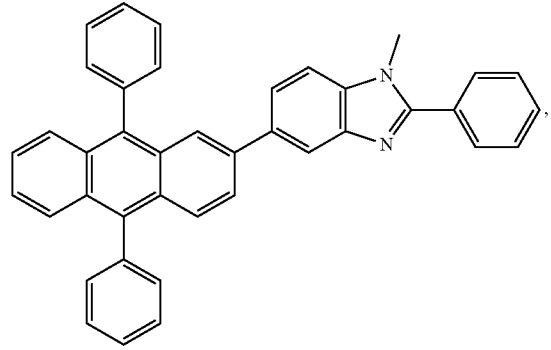

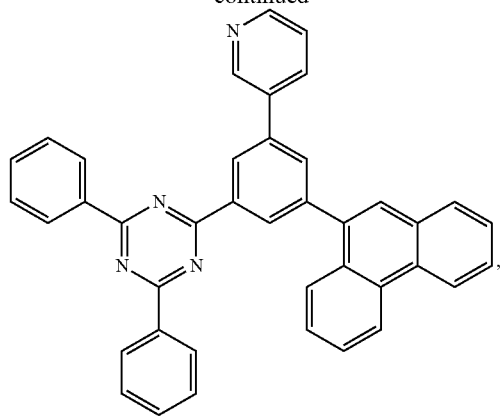

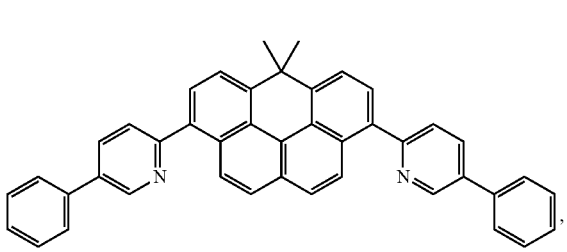

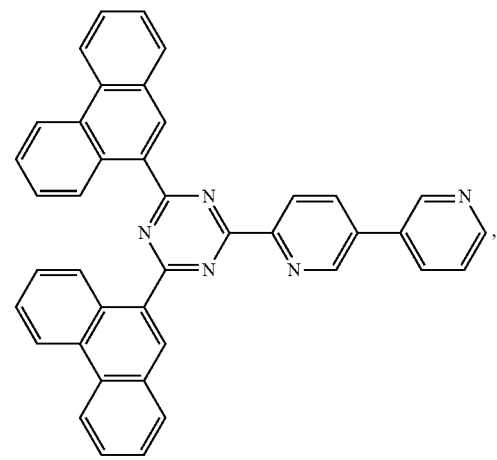

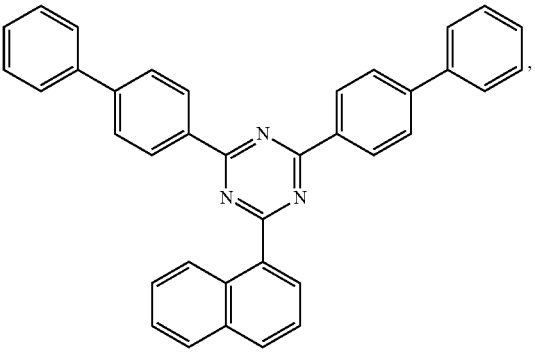

445
-continued
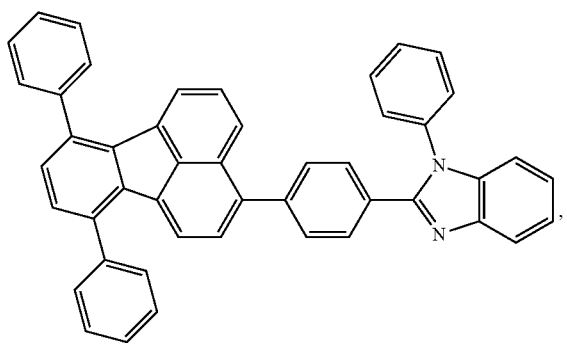
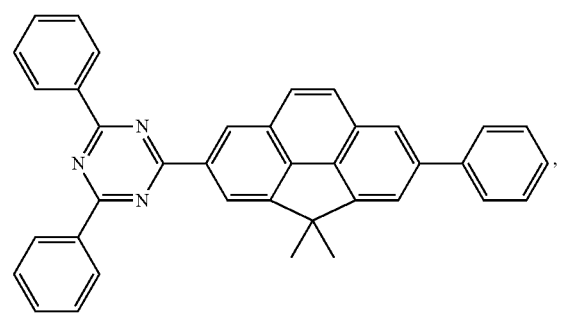
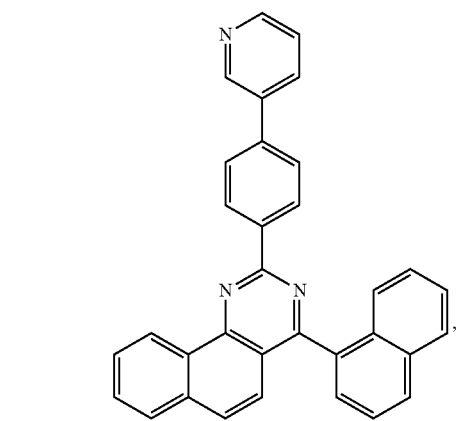
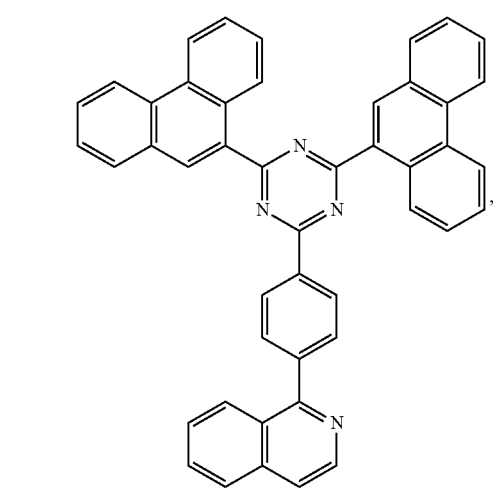
446
-continued
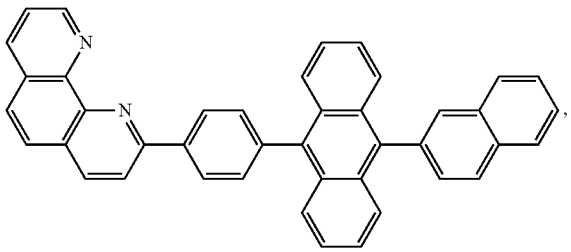
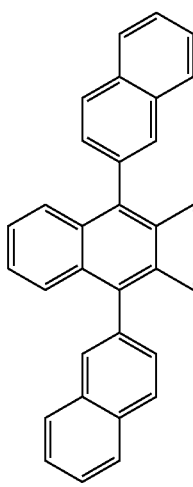
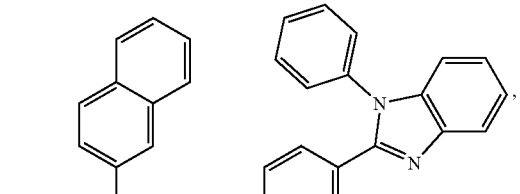
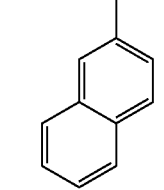
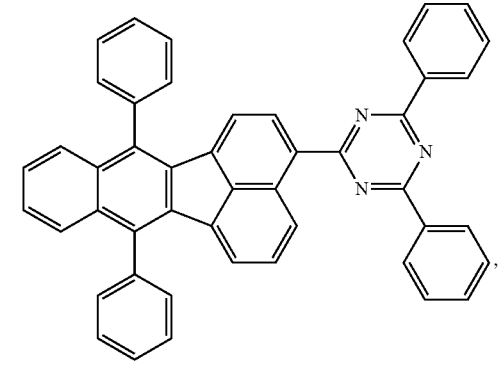

447
-continued
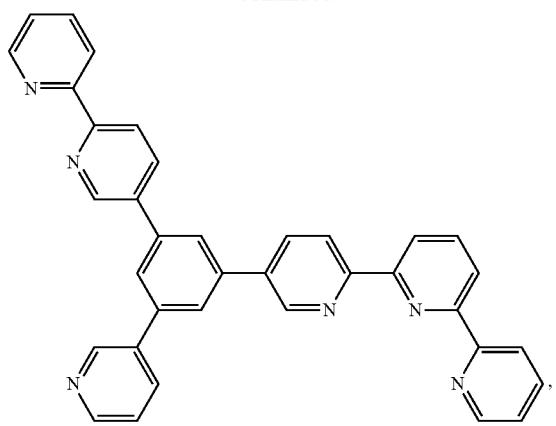
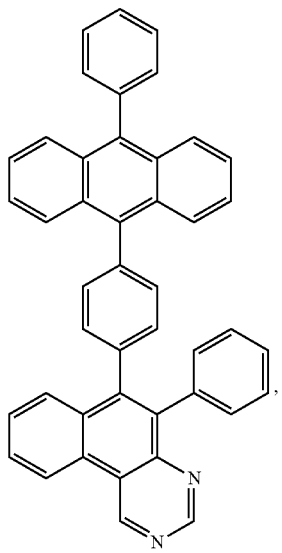
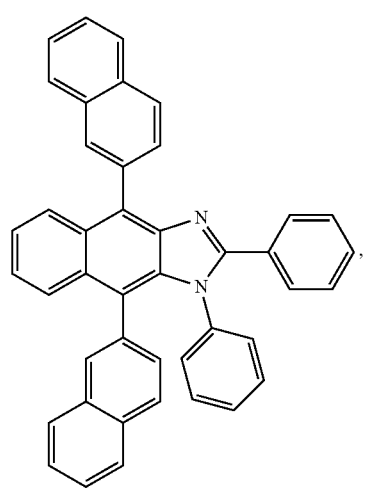
448
-continued
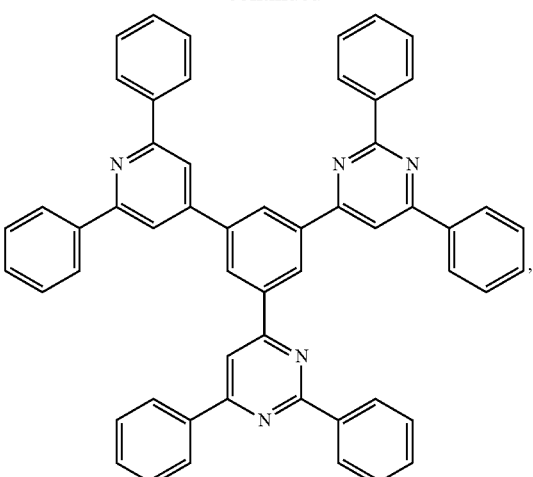
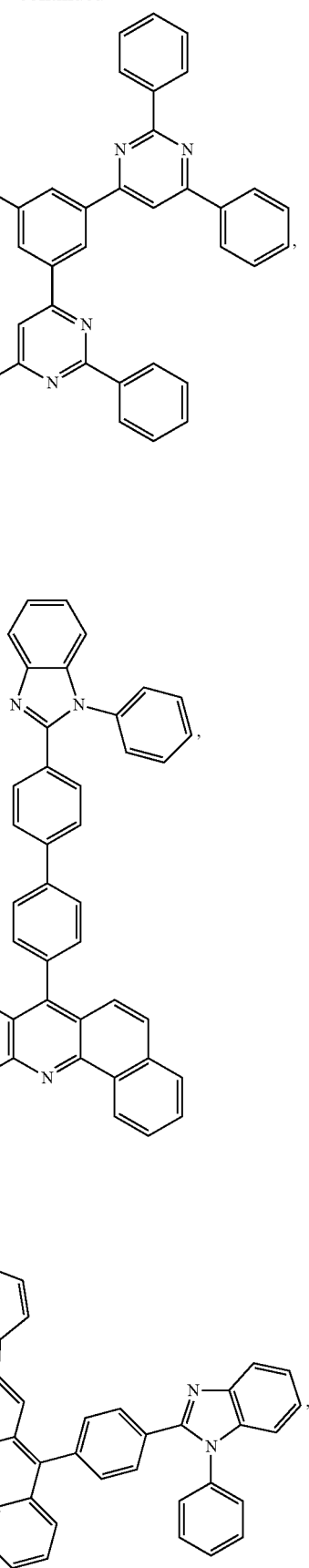

449
-continued
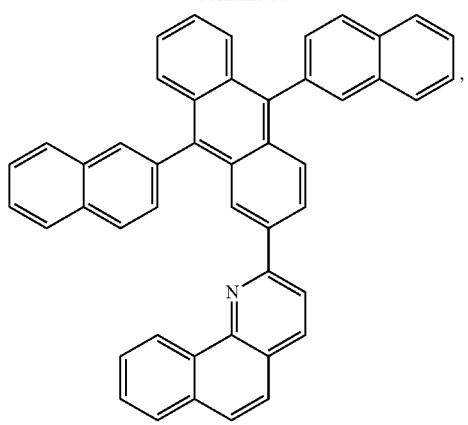
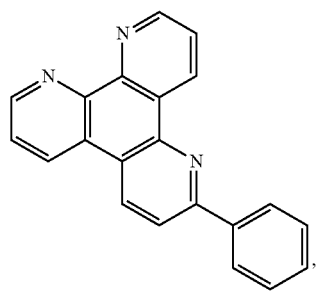
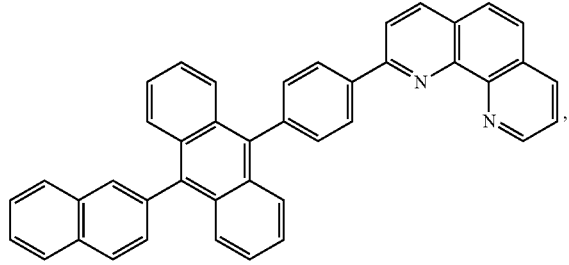
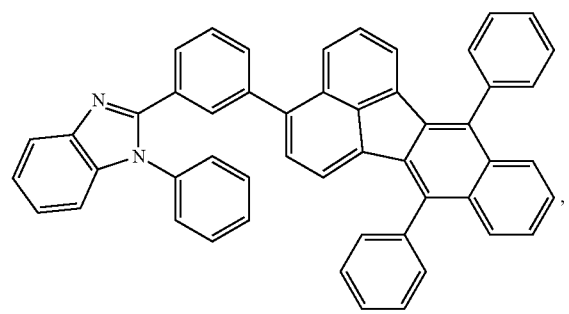
450
-continued
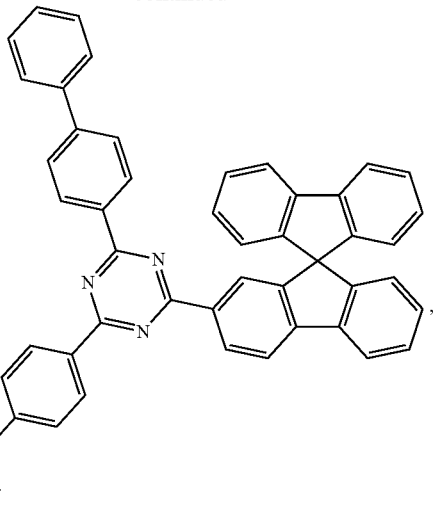
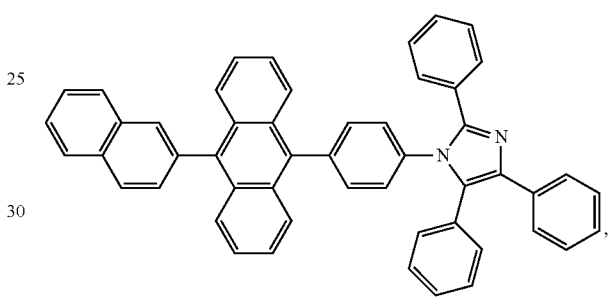
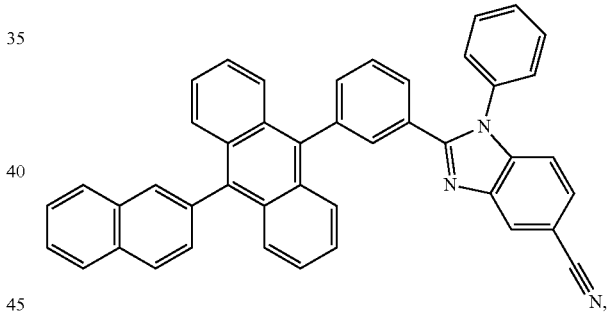
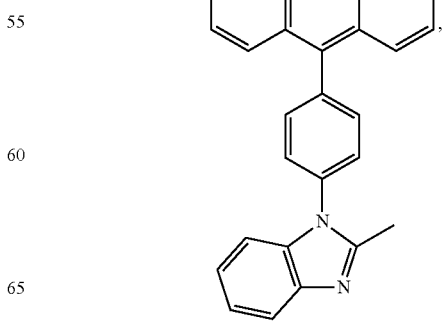

-continued

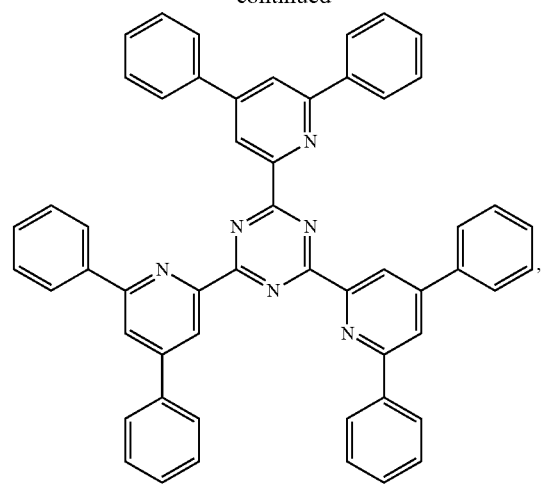

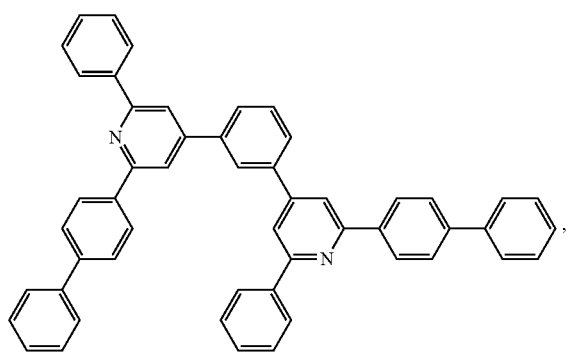

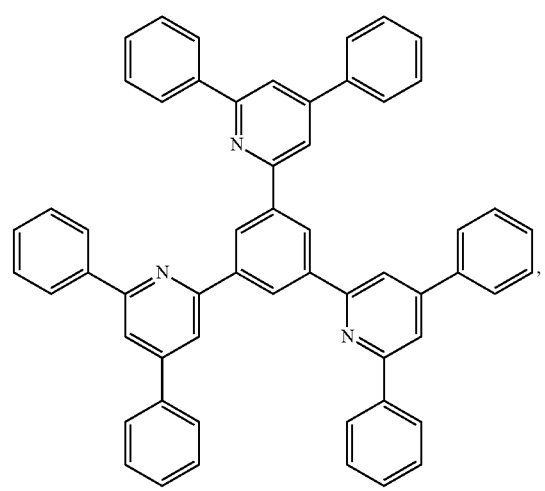

-continued

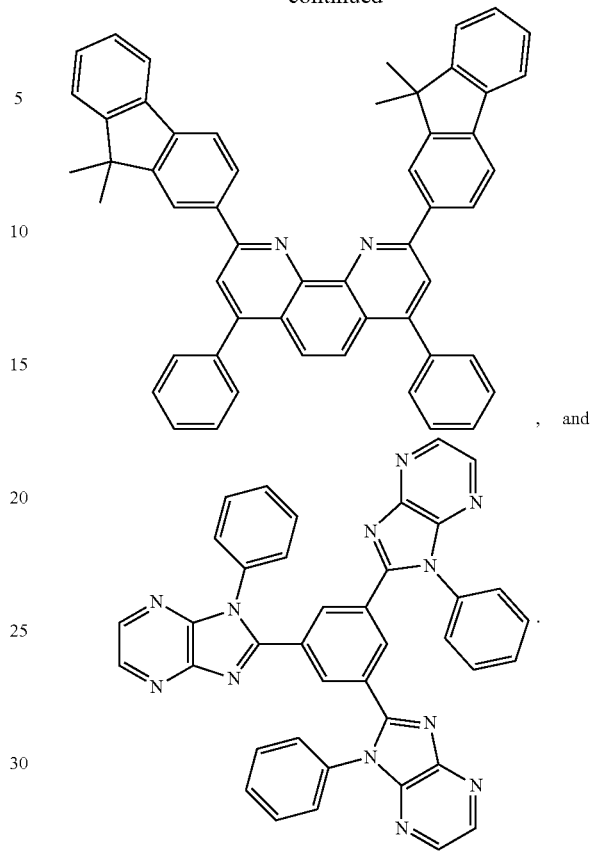

h) Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

It is understood that the various embodiments described herein are by way of example only and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

E. Experimental Data

Synthesis of Compound 1

Synthesis of 4-(2,6-diisopropylphenyl)-1-(1-ethoxyethyl)-1H-pyrazole

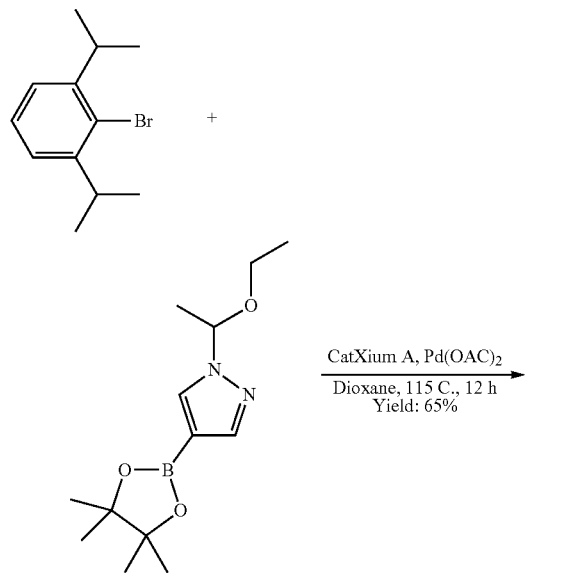

A 1000 mL round-bottom-flask was charged with potassium carbonate (15.58 g, 113 mmol) and water (120 ml) and sparged with argon for 5 minutes. Dioxane (240 ml), 1-(1-ethoxyethyl)-4-(4,4,5,5-tetramethyl-1,3,2-dioxaborolan-2-yl)-1H-pyrazole (10.00 g, 37.6 mmol), and 2-bromo-1,3-diisopropylbenzene (9.97 g, 41.3 mmol) were added to the solution and was degassed for 15 minutes, then a pre-mixed and degassed solution (15 min) of palladium(II) acetate (0.211 g, 0.939 mmol) and di((3S,5S,7S)-adamantan-1-yl)(butyl) phosphane (0.808 g, 2.254 mmol) in Dioxane (20 ml) was added. The reaction mixture was heated to 110° C. overnight, under argon. After cooling to room temperature, the layers were separated, the aqueous layer was extracted with EtOAc (2×200 mL). The organic layers were combined, dried over $Na_2SO_4$, and concentrated under reduced pressure. The crude product was purified on a 330 g ISCO gold silica gel column, with 0-30% EtOAc/Hexane to obtain an amber semi-solid 4-(2,6-diisopropylphenyl)-1-(1-ethoxyethyl)-1H-pyrazole (65% Yield).

Synthesis of 4-(2,6-diisopropylphenyl)-1H-pyrazole

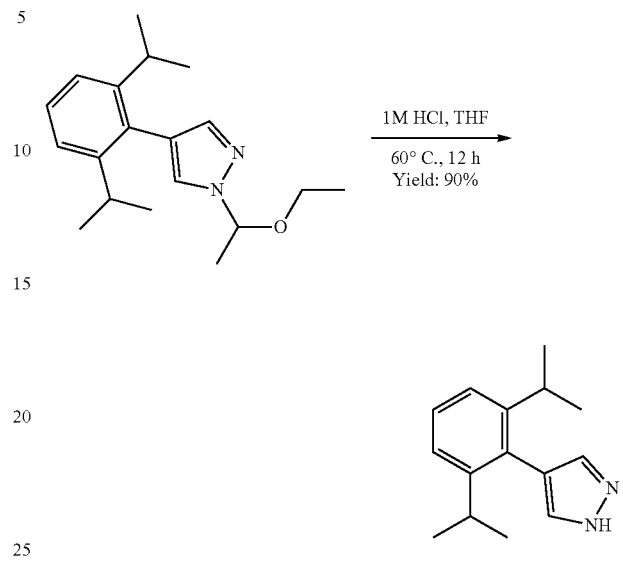

A 500 mL round-bottom-flask was charged with 4-(2,6-diisopropylphenyl)-1-(1-ethoxyethyl)-1H-pyrazole (18.3 g, 60.9 mmol) and dissolved in THF (162 ml) then hydrochloric acid (aq) (187 ml, 187 mmol) was added, the reaction mixture was stirred at 50° C. for 22 hours. The reaction was monitored by liquid chromatography (LC), and upon complete consumption of starting material the reaction mixture was allowed to cool to room temperature and neutralized with solid $Na_2CO_3$. The layers were separated, and the aqueous layer was extracted with EtOAc (2*200 mL). The organic layers were combined, washed with brine (200 mL), dried over $Na_2SO_4$, and concentrated under reduced pressure. The crude product was chromatographed on a 220 g Gold silica gel column, with 0-40% EtOAc/hexane to obtain a very light yellow solid, 4-(2,6-diisopropylphenyl)-1H-pyrazole (90% Yield).

Synthesis of 1-(3-bromo-4-fluorophenyl)-4-(2,6-diisopropylphenyl)-1H-pyrazole

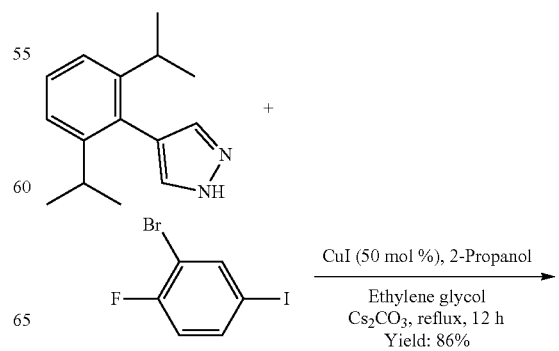

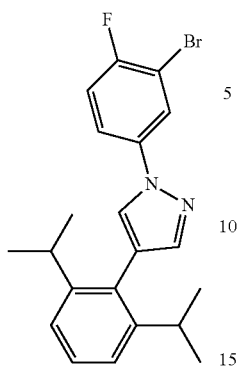

A 250 mL round-bottom-flask was charged with 4-(2,6-diisopropylphenyl)-1H-pyrazole (6.91 g, 30.3 mmol) 2-bromo-1-fluoro-4-iodobenzene (10.02 g, 33.3 mmol) in 2-Propanol (80 ml) with copper(I) iodide (3.17 g, 16.64 mmol) Cs$_2$CO$_3$ (32.5 g, 100 mmol). The reaction mixture was sparged with argon for 10 minutes, then heated to 100° C. for overnight. The reaction was monitored by LC, upon complete consumption of starting material the reaction mixture was quenched with water, the layers were separated and solids were filtered through a fritted funnel to access the crude product 1-(3-bromo-4-fluorophenyl)-4-(2,6-diisopropylphenyl)-1H-pyrazole with 86% yield.

Synthesis of 4-(2,6-diisopropylphenyl)-1-(4-fluoro-3-(4,4,5,5-tetramethyl-1,3,2-dioxaborolan-2-yl) phenyl)-1H-pyrazole

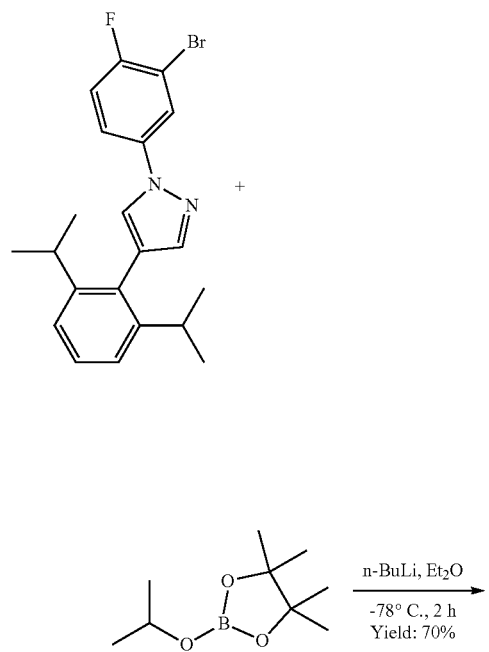

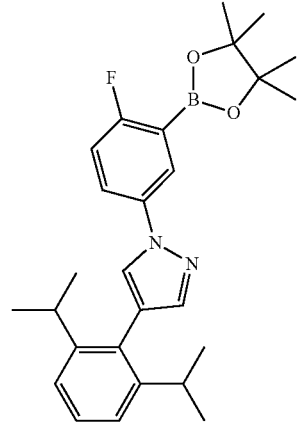

A stirred solution of 1-(3-bromo-4-fluorophenyl)-4-(2,6-diisopropylphenyl)-1H-pyrazole (4.00 g, 9.97 mmol) in dry Et$_2$O (49.8 ml) under argon atmosphere was cooled to −78° C. n-Butyllithium (4.98 ml, 11.96 mmol, 2.4 M) was added dropwise over 5 minutes and allowed to stir for 60 minutes at the same temperature. 2-isopropoxy-4,4,5,5-tetramethyl-1,3,2-dioxaborolane (2.040 g, 10.96 mmol) was added in one portion and the reaction was stirred at −78° C. for 20 minutes then allowed to warm to room temperature and continued stirring for 30 minutes. The reaction was monitored by LC, upon complete consumption of starting material the reaction mixture was quenched with saturated ammonium chloride solution and extracted with ethyl acetate (2×200 mL). The combined organic layers were dried over Na$_2$SO$_4$ followed by concentration under reduced pressure, the crude reaction mixture was subjected to trituration with hexane at −20° C. to obtain solid as product, 4-(2,6-diisopropylphenyl)-1-(4-fluoro-3-(4,4,5,5-tetramethyl-1,3,2-dioxaborolan-2-yl) phenyl)-1H-pyrazole with 70% yield.

Synthesis of 1,1'-(6,6"-difluoro-3',6'-dimethoxy-[1,1',2',1"-terphenyl]-3,3"-diyl)bis(4-(2,6-diisopropylphenyl)-1H-pyrazole)

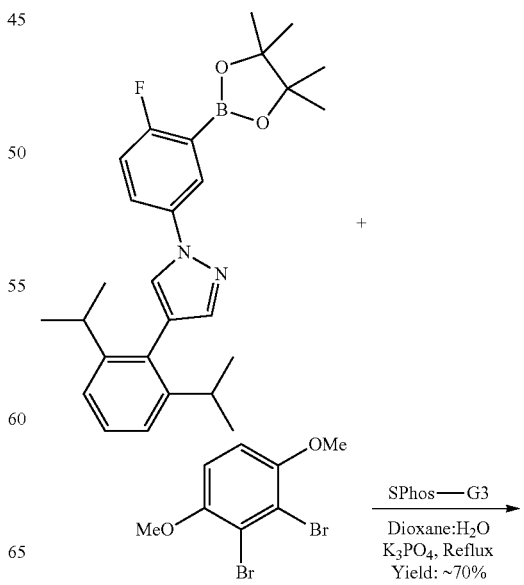

457

-continued

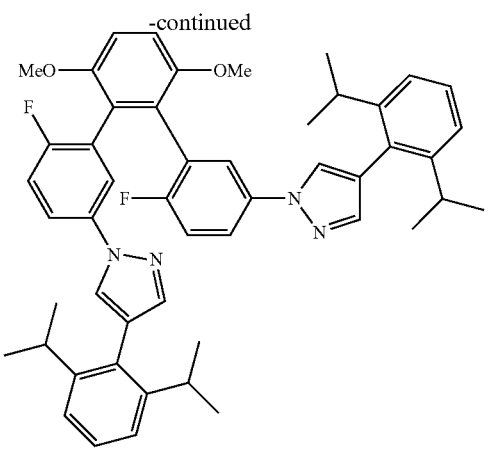

458

-continued

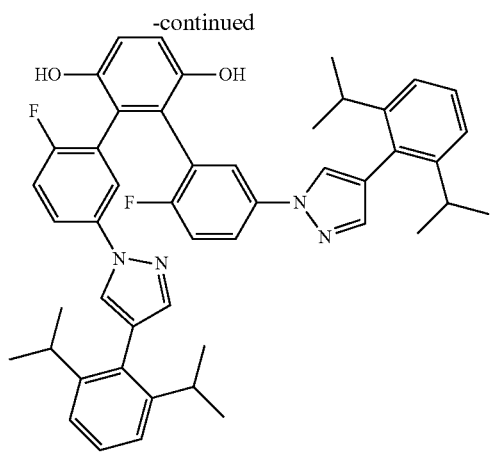

A Solution of 2,3-dibromo-1,4-dimethoxybenzene (2.50 g, 8.45 mmol), and 4-(2,6-diisopropylphenyl)-1-(4-fluoro-3-(4,4,5,5-tetramethyl-1,3,2-dioxaborolan-2-yl)phenyl)-1H-pyrazole (7.95 g, 17.74 mmol), potassium phosphate monohydrate (5.84 g, 25.3 mmol), in DME (77 mL) and water (7.6 mL) under argon atmosphere was equipped with a reflux condenser. The reaction mixture was argon bubbled for 10 minutes, then SPhos-3 (0.659 g, 0.845 mmol) was added and argon bubbling continued for 5 more minutes. The reaction mixture was heated to reflux 100° C. for 12 hours. The reaction was monitored by LC, upon complete consumption of starting material the reaction mixture was cooled to room temperature and water (50 mL) was added and extracted with ethyl acetate several times. combined organics were dried over MgSO$_4$ and concentrated under vacuum to yield gummy solid. The crude mixture was treated with hexane and vigorously stirred for 4 hours to access five flowing solid. The solid product was then filtered using funnel and dried in vacuo to afford pure off-white solid 1,1'-(6,6"-difluoro-3',6'-dimethoxy-[1,1':2',1"-terphenyl]-3,3"-diyl)bis(4-(2,6-diisopropylphenyl)-1H-pyrazole) (5.21 g, 6.69 mmol, 79% yield).

Synthesis of 5,5"-bis(4-(2,6-diisopropylphenyl)-1H-pyrazol-1-yl)-2,2"-difluoro-[1,1':2',1"-terphenyl]-3',6'-diol A 250 mL RBF was charged with 1,1'-(6,6"-difluoro-3',6'-dimethoxy[1,1':2',1"-terphenyl]-3,3"-diyl)bis(4-(2,6-diisopropylphenyl)-1H-pyrazole) (5.1 g, 6.55 mmol) and dissolved in dichloromethane (35 mL) under argon atmosphere then cooled to 0° C. Then Boron tribromide (1.547 ml, 16.37 mmol) was added at 0° C. and the resulting mixture was stirred at room temperature for about 2-4 hours until complete consumption of the starting material by LC. The reaction mixture was slowly cooled to 0° C., and quenched with methanol (5 ml) and concentrated in vacuo. The gummy residue was slowly quenched with water (100 mL) and the crude gummy mixture was stirred vigorously to precipitate solids, the solids were filtered and the slurry was washed with water (2×50 mL) to afford pure product 5,5"-bis(4-(2,6-diisopropylphenyl)-1H-pyrazol-1-yl)-2,2"-difluoro-[1,1':2',1"-terphenyl]-3',6'-diol (4.1 g, 5.46 mmol, 83% yield).

Synthesis of Ligand 1

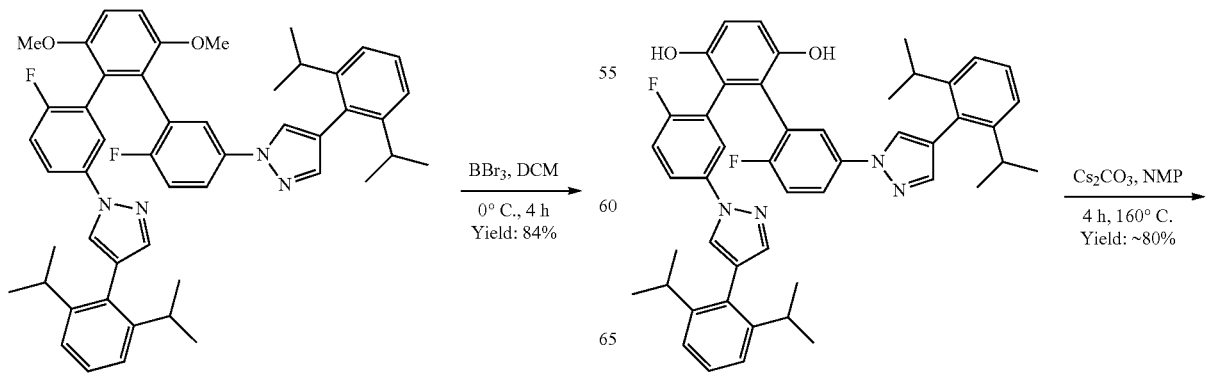

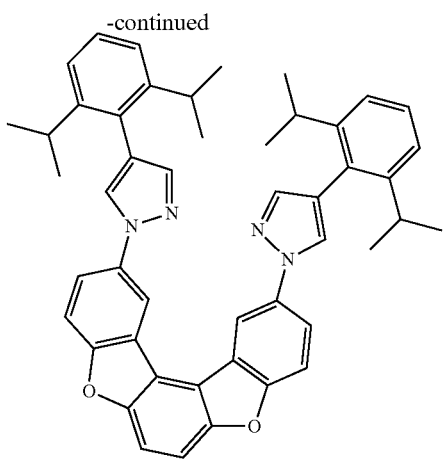

A 250 mL round-bottom-flask was charged with 5,5"-bis(4-(2,6-diisopropylphenyl)-1H-pyrazol-1-yl)-2,2"-difluoro-[1,1':2',1"-terphenyl]-3',6'-diol (5.60 g, 7.46 mmol) was dissolved in NMP (75 mL), under argon atmosphere. Then cesium carbonate (7.29 g, 22.37 mmol) was added, and the resulting mixture was stirred at 160° C. for about 2-4 hours until the complete consumption of the starting material was monitored by LC. Then reaction mixture was cooled to room temperature and quenched with water (50 mL) to precipitate out solids and the slurry was stirred for 1 hour, the solids were filtered and washed with water (2×100 mL) to afford the crude Ligand 1, which was purified by column chromatography (3.2 g, 5.6 mmol, 54% yield).

Synthesis of Compound 1

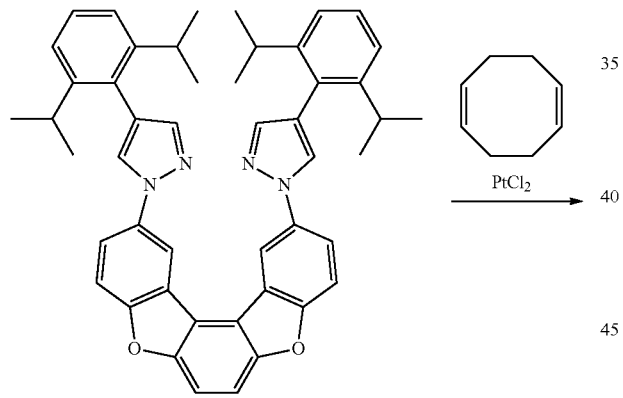

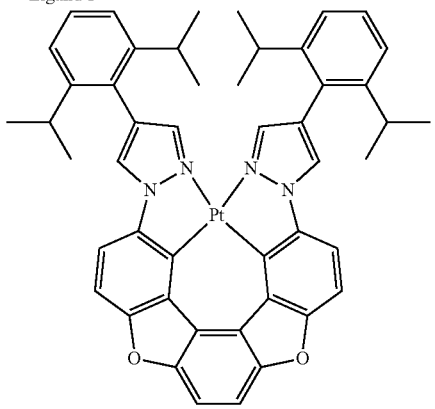

Compound 1

A mixture of Ligand 1 (50.8 mg, 0.071 mmol) and Pt(COD)Cl$_2$ (26.7 mg, 0.071 mmol) in a Schlenk tube was vacuumed and back-filled with nitrogen. 1,2-dichlorobenzene (2 ml) was added and refluxed for 2 weeks. The crude reaction mixture was coated on Celite and chromatographed on silica (DCM/Hep=1/1) yielding the product Compound 1 (15 mg, 23% yield).

Synthesis of Compound 2

Synthesis of (2-fluoro-5-(pyridin-2-yl) phenyl) Boronic Acid

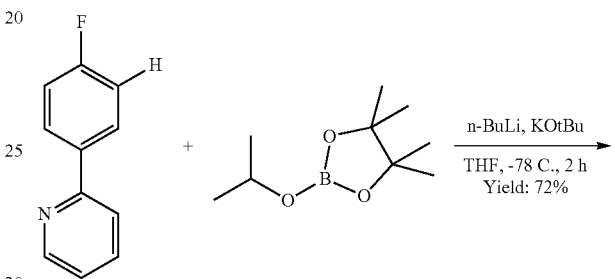

To a stirred solution of 2-(4-fluorophenyl)pyridine (5.000 g, 28.9 mmol) in dry THF (144 mL) under argon atmosphere was added potassium 2-methylpropan-2-olate (3.56 g, 31.8 mmol) and the reaction mixture was cooled to −78° C. n-Butyllithium (13.23 ml, 31.8 mmol, 2.4 M) was added dropwise over 5 minutes and allowed to stir for 60 minutes at the same temperature. 2-isopropoxy-4,4,5,5-tetramethyl-1,3,2-dioxaborolane (8.06 g, 43.3 mmol) was added in one portion and the reaction was stirred at −78° C. for 20 minutes. The reaction was monitored by LCMS, after complete consumption of the starting material the reaction was quenched with saturated ammonium chloride solution and extracted with ethyl acetate (2×200 mL). The organic layers were combined and dried over Na$_2$SO$_4$ followed by concentration under reduced pressure to afford crude product (2-fluoro-5-(pyridin-2-yl) phenyl) boronic acid with 72% yield.

461
Synthesis of 2,2'-(6,6"-difluoro-3',6'-dimethoxy-[1,1':2',1"-terphenyl]-3,3"-diyl) dipyridine

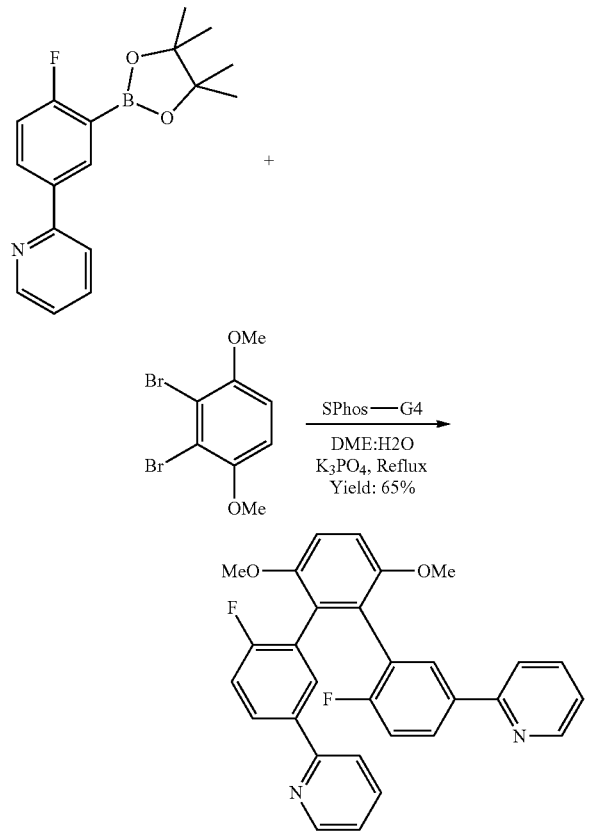

A Solution of 2,3-dibromo-1,4-dimethoxybenzene (5.000 g, 16.89 mmol), and (2-fluoro-5-(pyridin-2-yl)phenyl)boronic acid (8.43 g, 38.9 mmol), potassium carbonate (8.17 g, 59.1 mmol), in DME (77 mL) and water (7.6 mL) under argon atmosphere with a reflux condenser. The reaction mixture was argon bubbled for 10 minutes, then SPhos-4 (1.341 g, 1.689 mmol) was added and continued bubbling argon for 5 more minutes. The reaction mixture was heated to reflux 100° C. for 12 hours. The reaction was monitored by LCMS and after complete consumption of starting material, the reaction mixture was cooled to room temperature and water (50 mL) was added and extracted with ethyl acetate several times. The combined organics were dried over MgSO₄ and concentrated in vacuo to yield a gummy solid. The crude product was treated with hexane and vigorously stirred for 4 hours to access free flow solid. The solid product was then filtered using funnel and dried under vacuum to afford pure off-white solid 2,2'-(6,6"-difluoro-3',6'-dimethoxy-[1,1':2',1"-terphenyl]-3,3"-diyl)dipyridine. (12.2 g, 40.7 mmol, 65% yield).

462
Synthesis of 2,2"-difluoro-5,5"-di(pyridin-2-yl)-[1,1':2',1"-terphenyl]-3',6'-diol

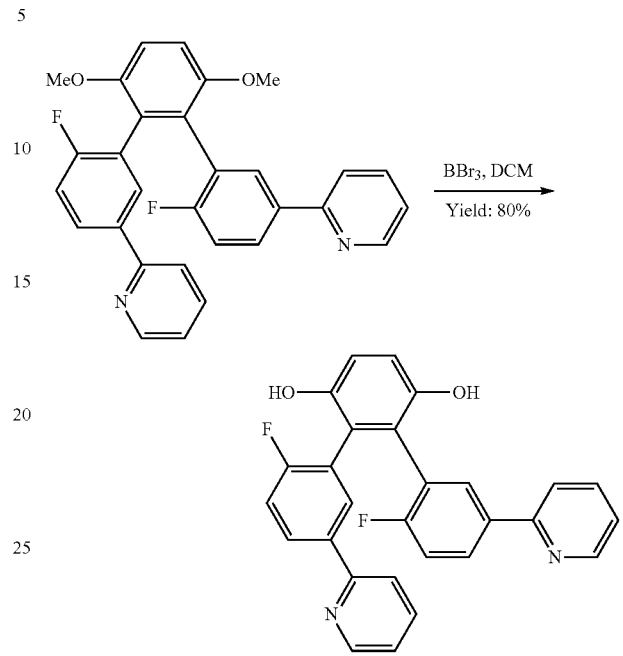

A 500 mL round-bottom-flask was charged with 2,2'-(6,6"-difluoro-3',6'-dimethoxy-[1,1':2',1"-terphenyl]-3,3"-diyl) dipyridine (6.500 g, 13.53 mmol) and dissolved in dichloromethane (68 mL) under argon atmosphere then cooled to 0° C. Then Boron tribromide (3.20 ml, 33.8 mmol) was added at 0° C. and the resulting mixture was stirred at room temperature for about 2-4 hours until the starting material was completely consumed as monitored by LC. The reaction mixture was slowly cooled to 0° C. and quenched with methanol (5 ml) then concentrated in vacuo. The gummy residue was slowly quenched with water (100 mL) and the crude gummy mixture was stirred vigorously to precipitate solids, filter the solids and slurry wash with water (2*50 mL) to afford pure product 2,2"-difluoro-5,5"-di(pyridin-2-yl)-[1,1':2',1"-terphenyl]-3',6'-diol (7.00 g, 15.47 mmol, 80% yield).

Synthesis of Benzo[1,2-b:4,3-b']bisbenzofuran-2,11-2-pyridine (Ligand 2)

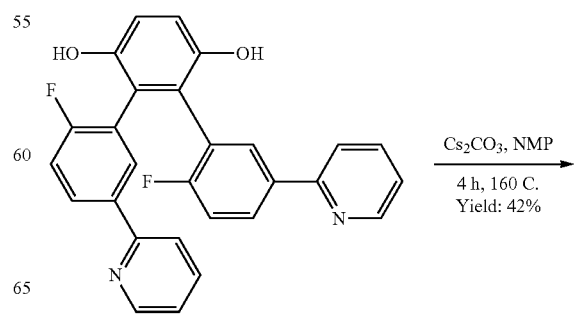

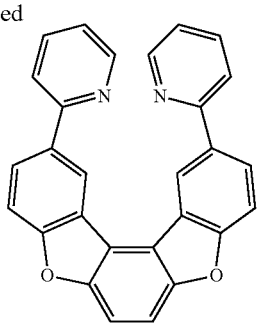

A 250 mL RBF was charged with 2,2"-difluoro-5,5"-di(pyridin-2-yl)-[1,1':2',1"-terphenyl]-3',6'-diol (7.00 g, 15.47 mmol) dissolved in NMP (77 ml), under argon atmosphere. Then cesium carbonate (15.12 g, 46.4 mmol) was added, and the resulting mixture was stirred at 160° C. for about 2-4 h until the complete consumption of the starting material by LC. Then reaction mixture was cooled to room temperature and quenched with water (50 mL) to precipitate grey colored solids, which were filtered and washed with water (2×100 mL) to afford the crude product. The wet solid was dried under vacuum for 1 hour, then performed slurry wash with methanol (2×50 mL), trituration with diethyl ether, trituration DMF, trituration with hot diethyl ether, and charcoal treatment in DCM to access the product Benzo[1,2-b:4,3-b']bisbenzofuran-2,11-2-pyridine (Ligand 2) (2.86 g, 6.96 mmol, 45% yield).

Synthesis of Compound 2

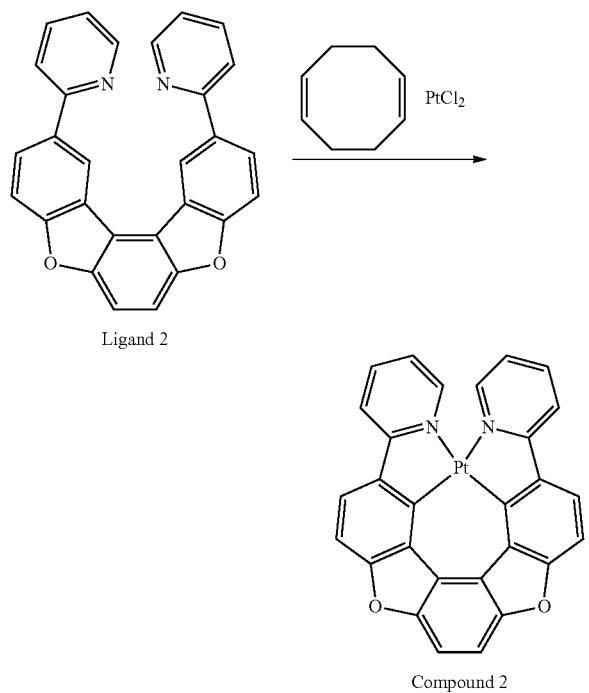

A mixture of Ligand 2 (100 mg, 0.242 mmol) and Pt(COD)Cl₂ (91 mg, 0.242 mmol) in a Schlenk tube was vacuumed and back-filled with nitrogen. 1,2-dichlorobenzene (2 ml) was added and refluxed for 2 weeks. The reaction mixture was cooled down, coated on celite, and chromatographed on silica (DCM/Hep=2/1) to obtain the product Compound 2 (7 mg, 4.8% yield).

The emission spectra of Compounds 1 and 2 in a solution of 2-methyl tetrahydrofuran were collected on a Horiba Fluorolog-3 spectrophotometer at both room temperature (RT) and in frozen glass at 77K. The peak wavelengths (λmax) and the full width at half maximum (FWHM) of each of the compounds are given in Table 1. In general, the FWHM for a phosphorescent emitter complex is greater than 60 nm. It has been a long-sought goal to achieve the narrow FWHM. The narrower FWHM, the better color purity for the display application. As a background information, the ideal line shape is a single wavelength (single line). As can be seen here, the current inventive compounds can reach a single digit of FWHM, this is remarkably unexpected and is a breakthrough in OLED industry. Compound 2 has much larger FWHM at room temperature. Without being bound by any theory, this is probably due the higher metal to ligand charge transfer in the room temperature.

TABLE 1

| | λmax (RT) | FWHM (RT) | λmax (77K) | FWHM (77K) |
|---|---|---|---|---|
| Compound 1 | 462 | 6 | 459 | 4 |
| Compound 2 | 497 | 50 | 488 | 8 |

What is claimed is:
1. A compound having a fragment with at least five rings fused next to each other consecutively wherein the fragment is a ligand $L_A$ of Formula I;

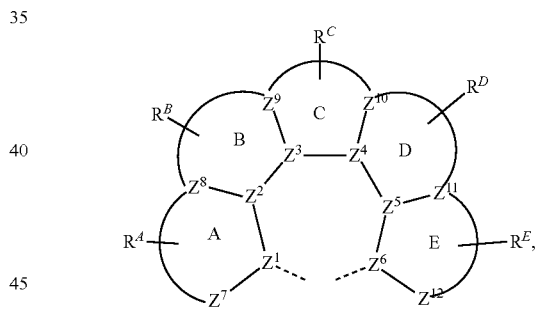

wherein:
  rings A, B, C, D, and E are each independently a 5-membered or 6-membered carbocyclic or heterocyclic ring;
  $Z^1$-$Z^{12}$ are each independently C or N;
  $R^A$, $R^B$, $R^C$, $R^D$, and $R^E$ each independently represents zero, mono, or up to a maximum allowed substitutions to its associated ring;
  if an $R^A$, $R^B$, $R^C$, $R^D$, or $R^E$ represents no substitution, then said $R^A$, $R^B$, $R^C$, $R^D$, or $R^E$ is hydrogen;
  if $R^A$, $R^B$, $R^C$, $R^D$, or $R^E$ represents a substituent, then each $R^A$, $R^B$, $R^C$, $R^D$, and $R^E$ is independently a substituent selected from the group consisting of deuterium, halide, alkyl, cycloalkyl, fluorinated alkyl, heteroalkyl, arylalkyl, alkoxy, aryloxy, amino, silyl, boryl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
  two substituents can be joined or fused together to form a ring;

wherein the ligand $L_A$ is complexed to a metal M at $Z^1$ and $Z^6$;

wherein the metal M is selected from the group consisting of Ir, Rh, Re, Ru, Os, Pt, Pd, Au, Ag, and Cu;

wherein M can be coordinated to other ligands; and wherein the ligand $L_A$ can be linked with other ligands to form a tridentate, tetradentate, pentadentate, or hexadentate ligand.

2. The compound of claim 1, wherein the at least five rings comprises two 5-membered rings and three 6-membered rings.

3. The compound of claim 1, wherein the at least five rings comprises five aromatic rings.

4. The compound of claim 1, wherein $R^A$, $R^B$, $R^C$, $R^D$, and $R^E$ are each independently selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, and combinations thereof.

5. The compound of claim 1, wherein M is Ir, Pt or Pd.

6. The compound of claim 1, wherein the ligand $L_A$ is linked with other ligands to form a tetradentate ligand.

7. The compound of claim 1, wherein ring A, ring C, and ring E are 6-membered rings, and ring B and ring D are 5-membered rings;

ring A, ring C, and ring E are 5-membered rings, and ring B and ring D are 6-membered rings;

ring A and ring E are 5-membered rings, and ring B, ring C, and ring D are 6-membered rings;

ring A and ring E are 6-membered rings, and ring B, ring C, and ring D are 5-membered rings; or ring A, ring B, ring D, and ring E are 5-membered rings, and ring C is a 6-membered ring.

8. The compound of claim 1, wherein $Z^1$-$Z^{12}$ are C.

9. The compound of claim 1, wherein at least one of $Z^1$-$Z^{12}$ is N.

10. A compound having a fragment with at least five rings fused next to each other consecutively wherein the fragment is a ligand $L_A$ having a formula selected from the group consisting of:

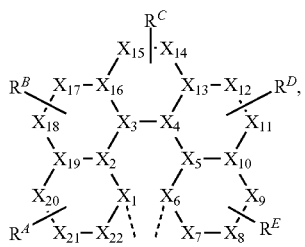

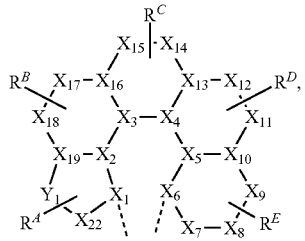

-continued

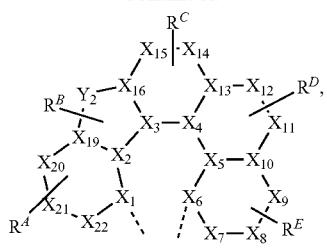

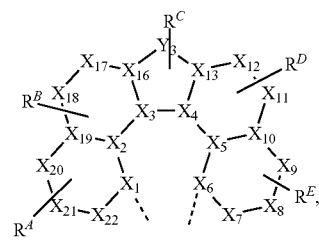

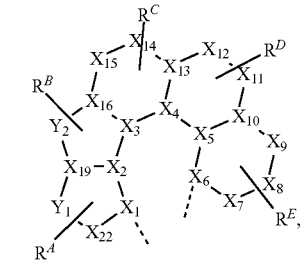

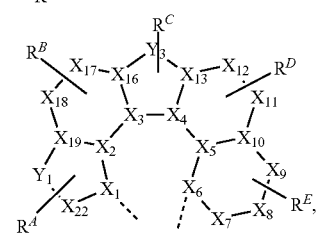

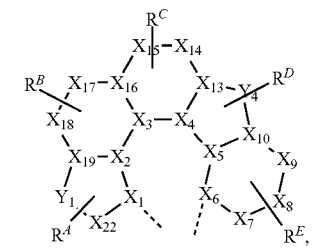

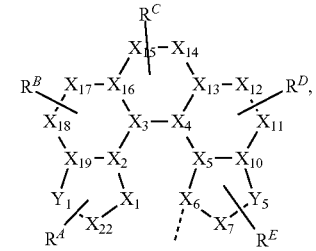

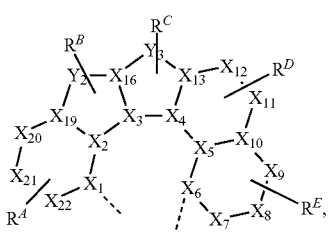

-continued

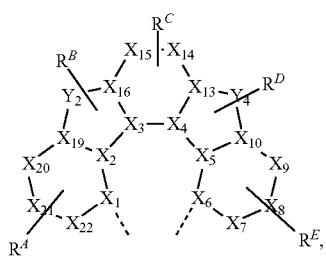

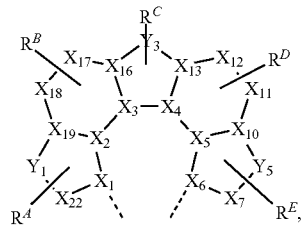

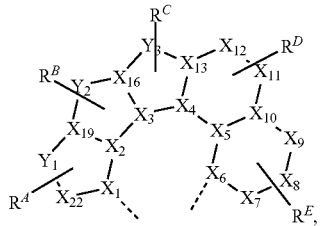

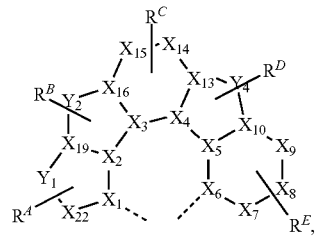

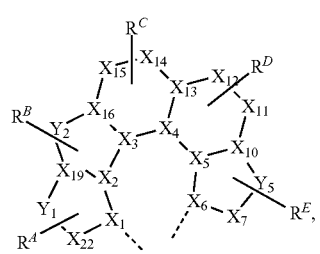

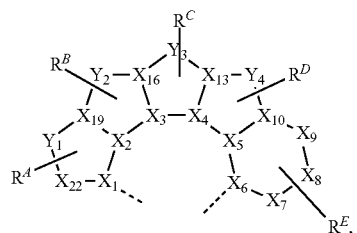

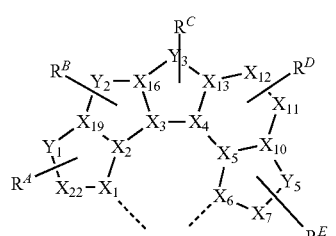

-continued

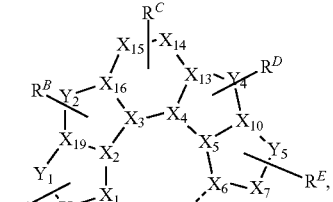

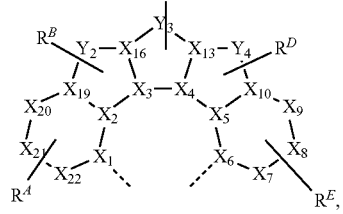

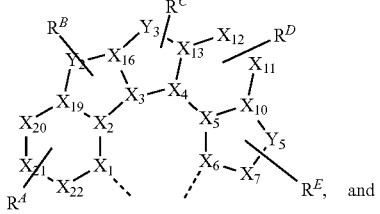

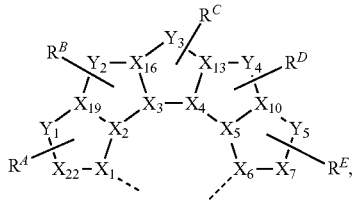

wherein each $X_1$-$X_2$ is independently selected from the group consisting of C and N; wherein no more than two N atoms are bonded to one another;

$R^A$, $R^B$, $R^C$, $R^D$, and $R^E$ each independently represents zero, mono, or up to a maximum allowed substitutions to its associated ring;

if an $R^A$, $R^B$, $R^C$, $R^D$, or $R^E$ represents no substitution, then said $R^A$, $R^B$, $R^C$, $R^D$, or $R^E$ is hydrogen;

if $R^A$, $R^B$, $R^C$, $R^D$, or $R^E$ represents a substituent, then each $R^A$, $R^B$, $R^C$, $R^D$, and $R^E$ is independently a substituent selected from the group consisting of deuterium, halide, alkyl, cycloalkyl, fluorinated alkyl, heteroalkyl, arylalkyl, alkoxy, aryloxy, amino, silyl, boryl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein each $Y_1$-$Y_5$ is selected from the group consisting of O, S, Se, NR, CRR', SiRR', GeRR', and BR; and wherein R and R' are independently selected from the group consisting of hydrogen, deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, and combinations thereof;

two substituents can be joined or fused together to form a ring;

wherein the dashed lines represent coordination to a metal M;

wherein the metal M is selected from the group consisting of Ir, Rh, Re, Ru, Os, Pt, Pd, Au, Ag, and Cu;

wherein M can be coordinated to other ligands; and wherein the ligand $L_A$ can be linked with other ligands to form a tridentate, tetradentate, pentadentate, or hexadentate ligand.
11. The compound of claim 10, wherein the ligand $L_A$ is selected from the group consisting of the following compounds:
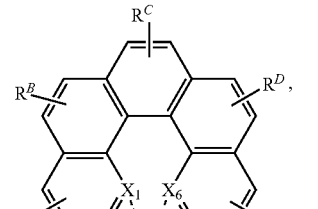
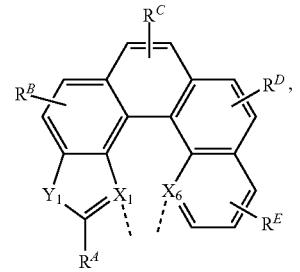
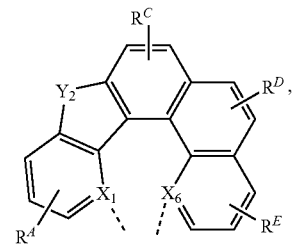
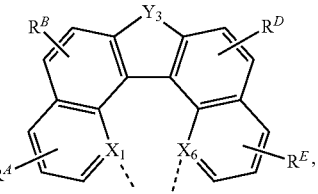
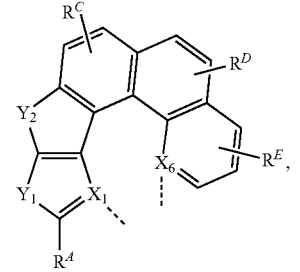
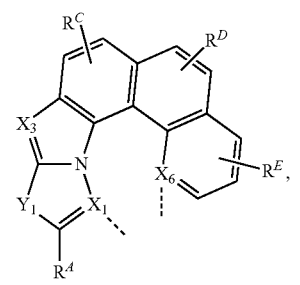
-continued
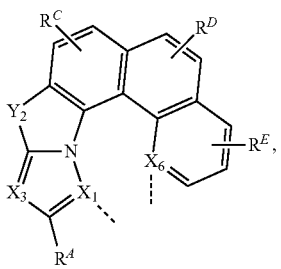
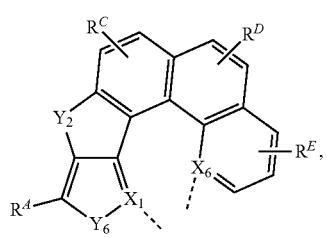
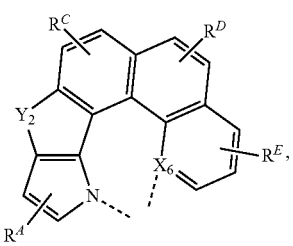
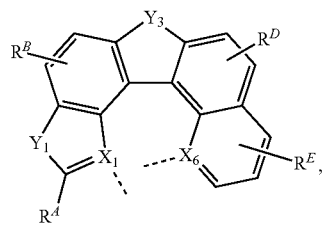
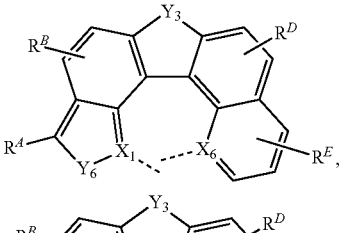
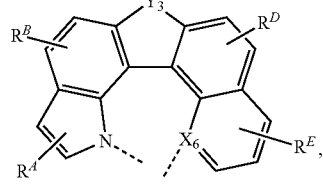
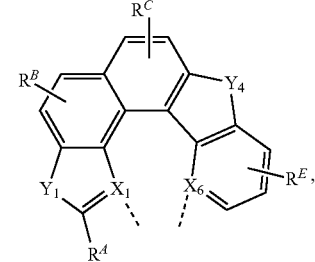

-continued
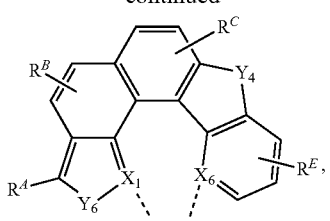
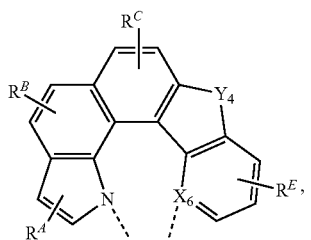
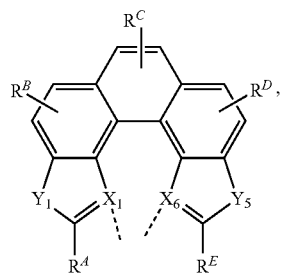
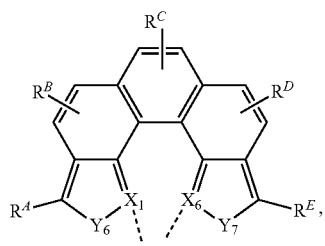
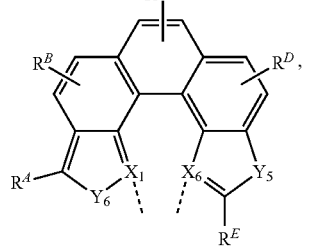
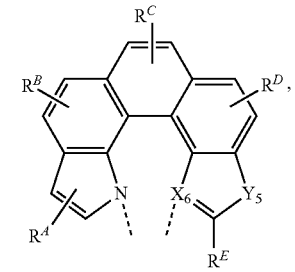
-continued
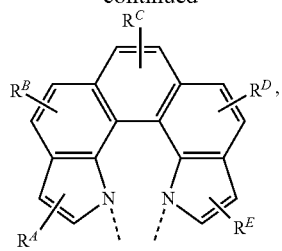
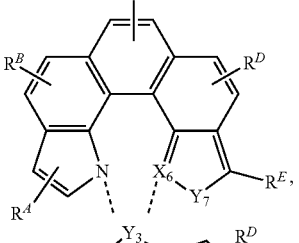
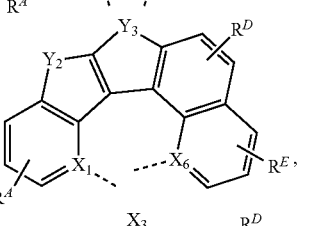
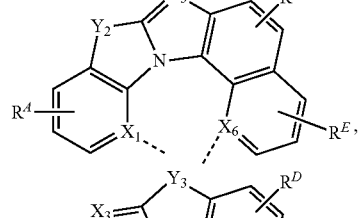
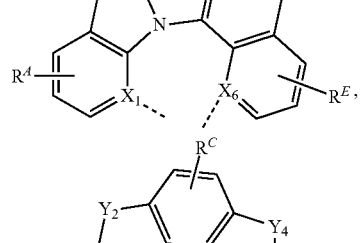
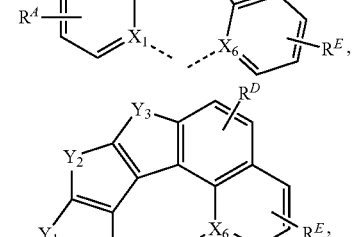
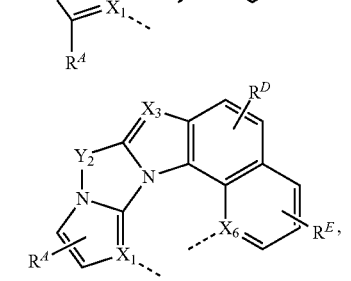

-continued
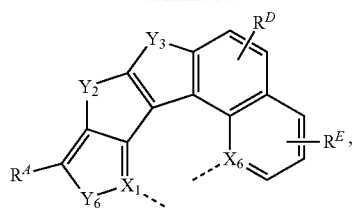
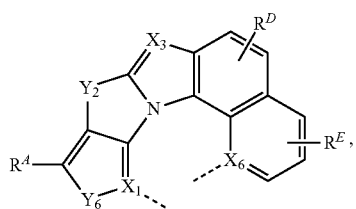
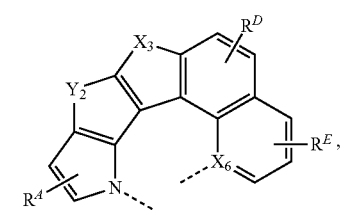
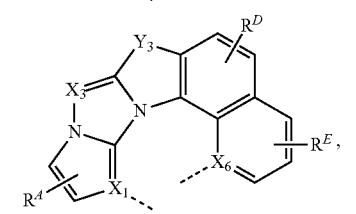
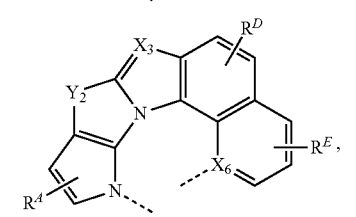
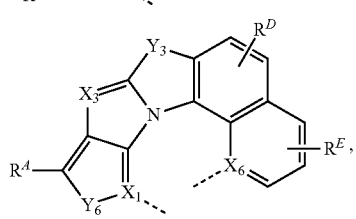
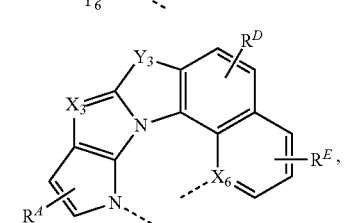
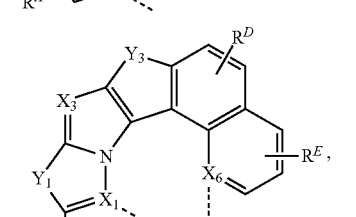
-continued
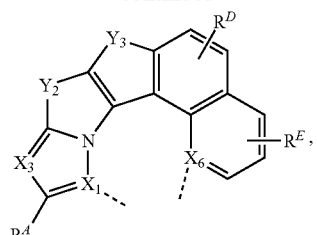
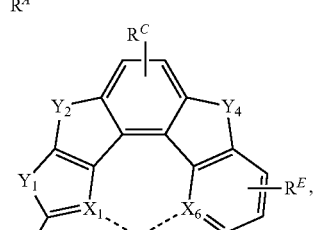
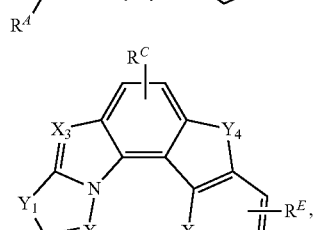
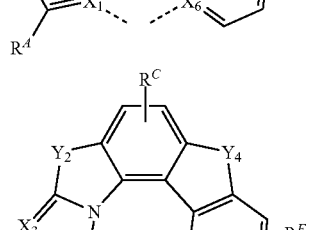
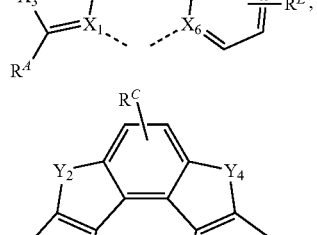
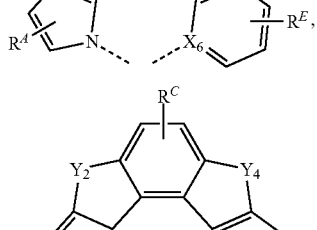
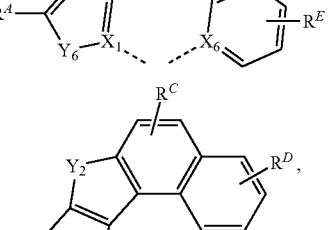
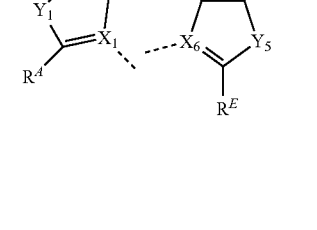

475
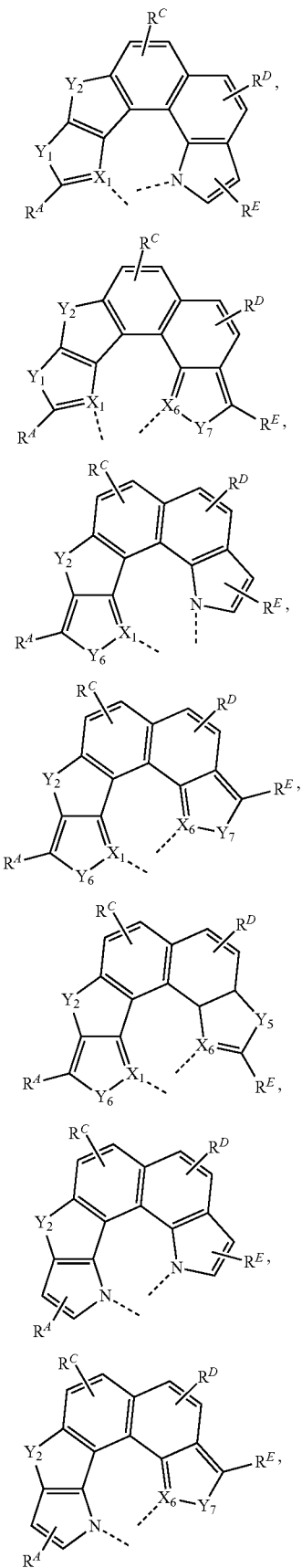
476
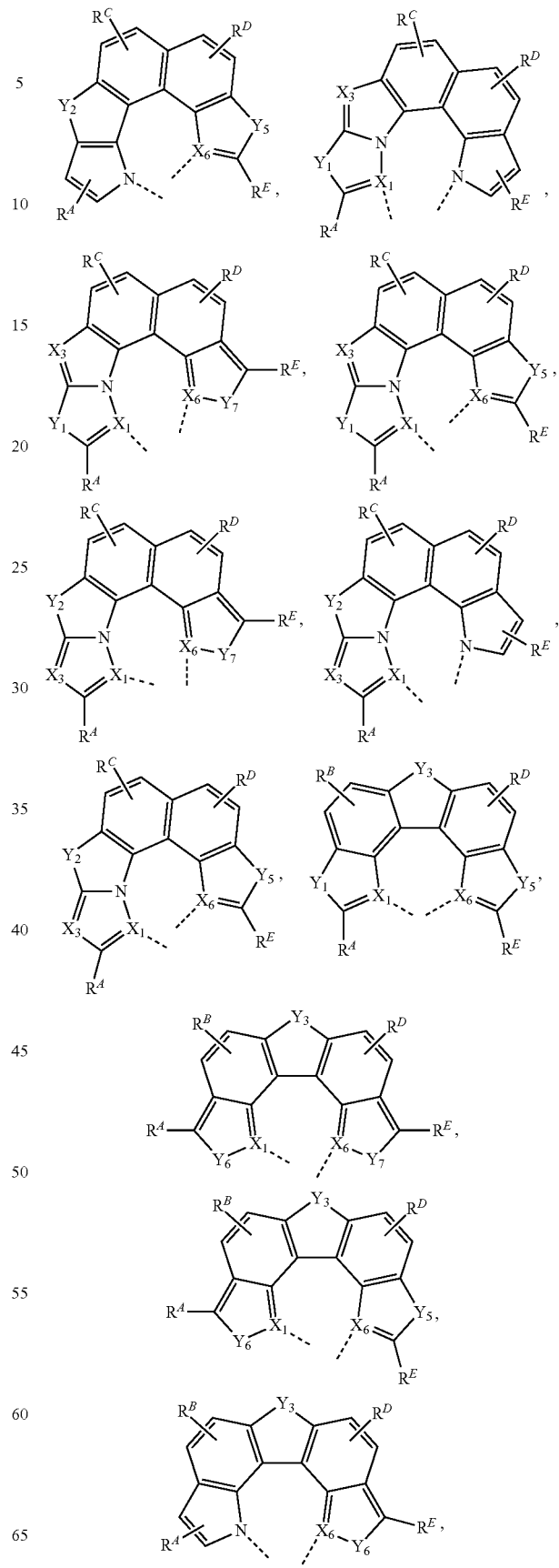

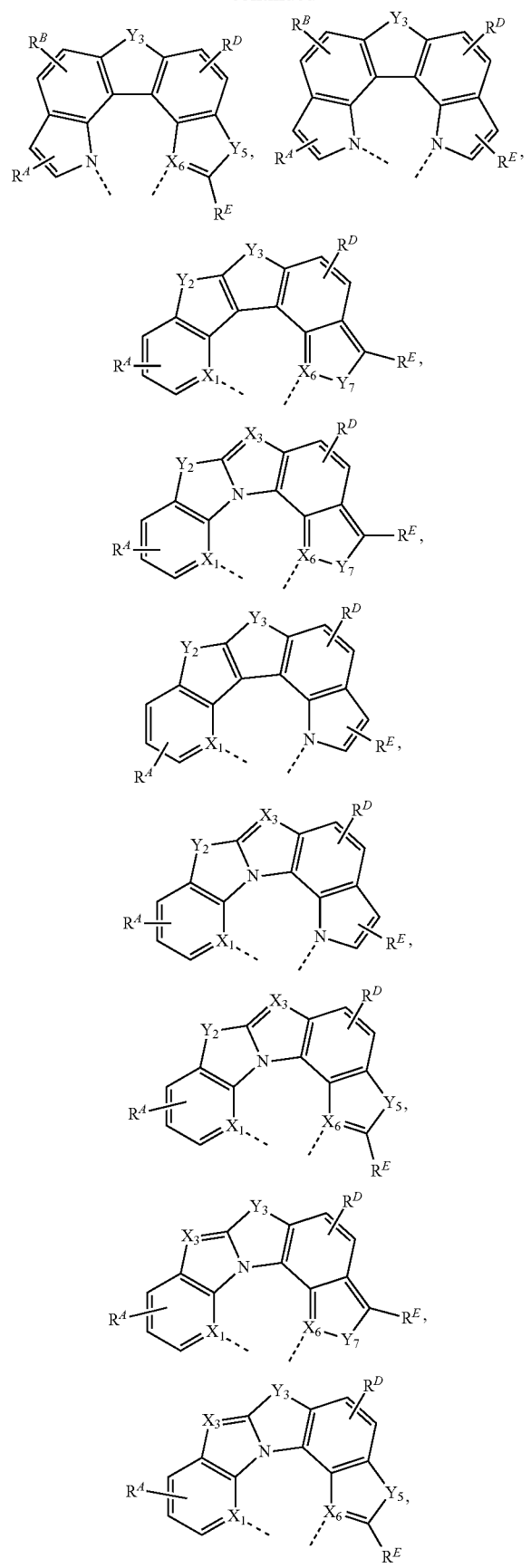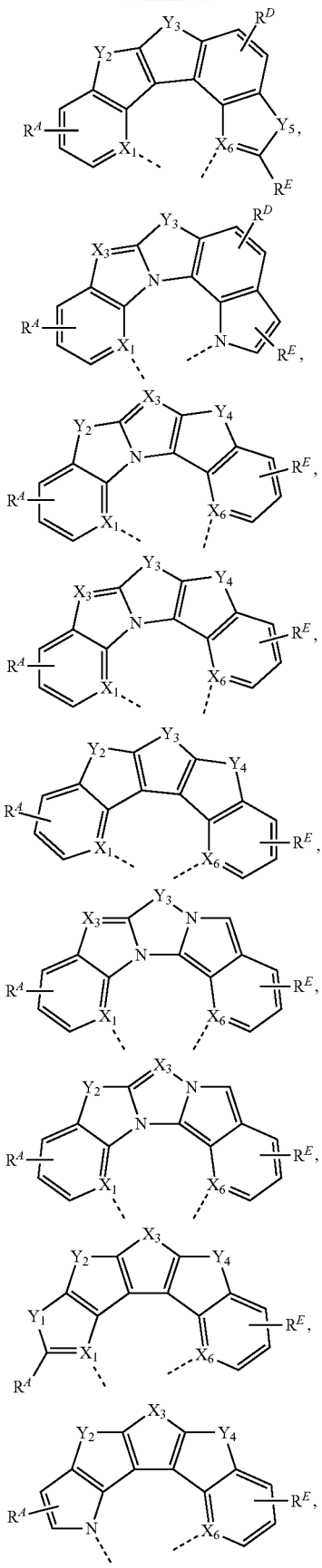

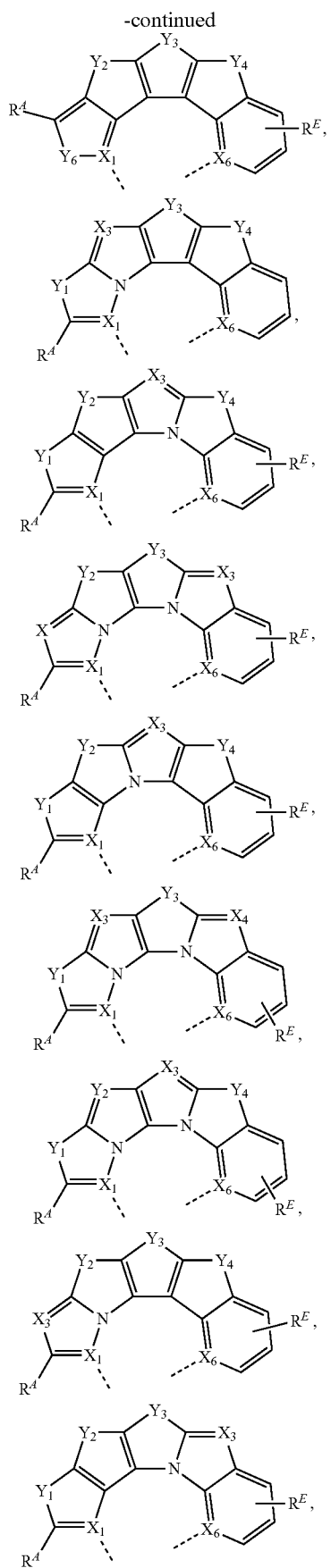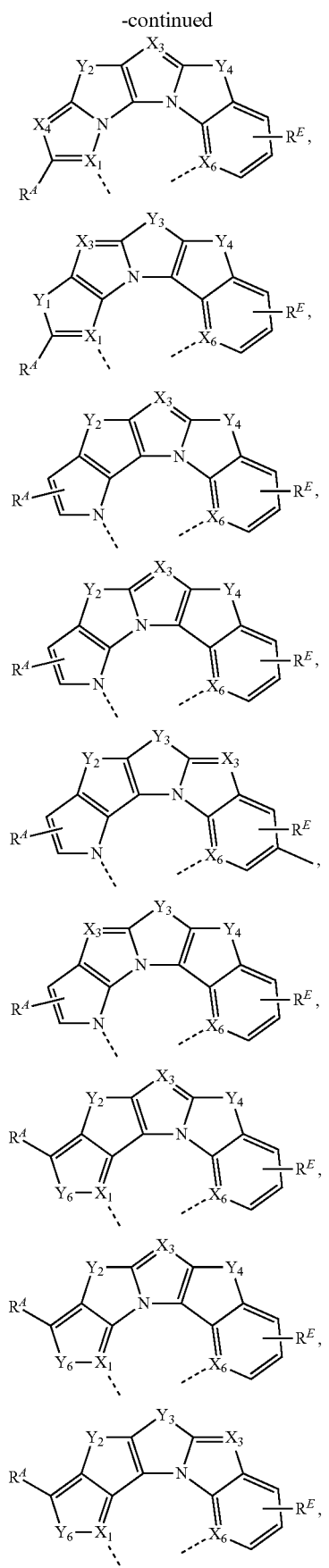

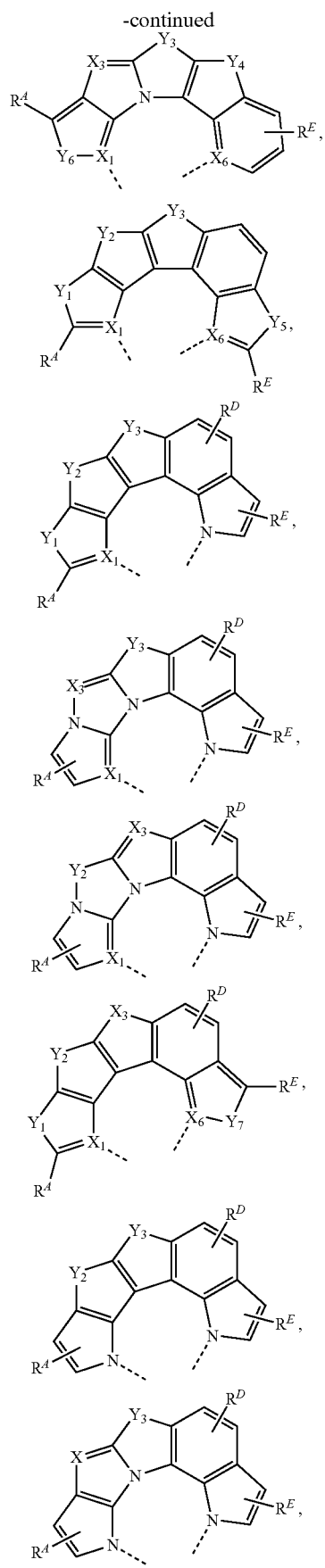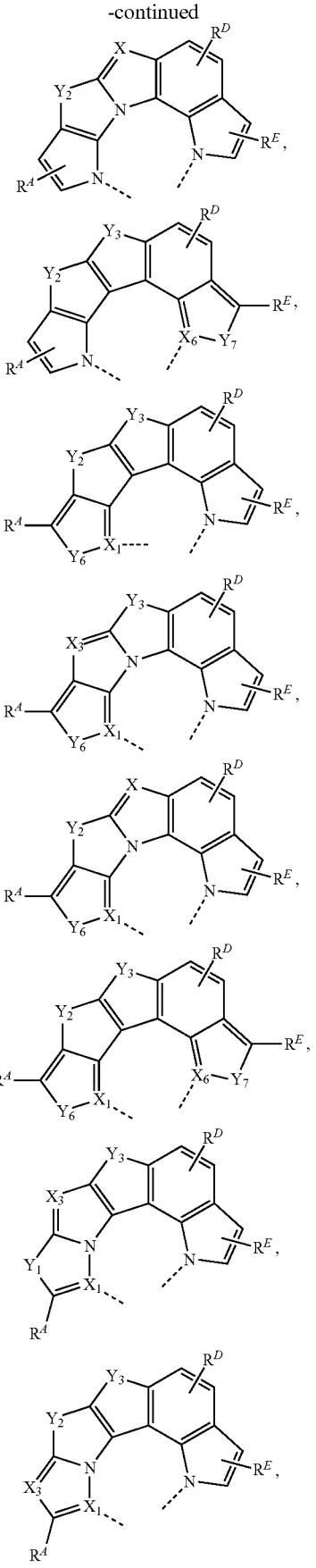

-continued
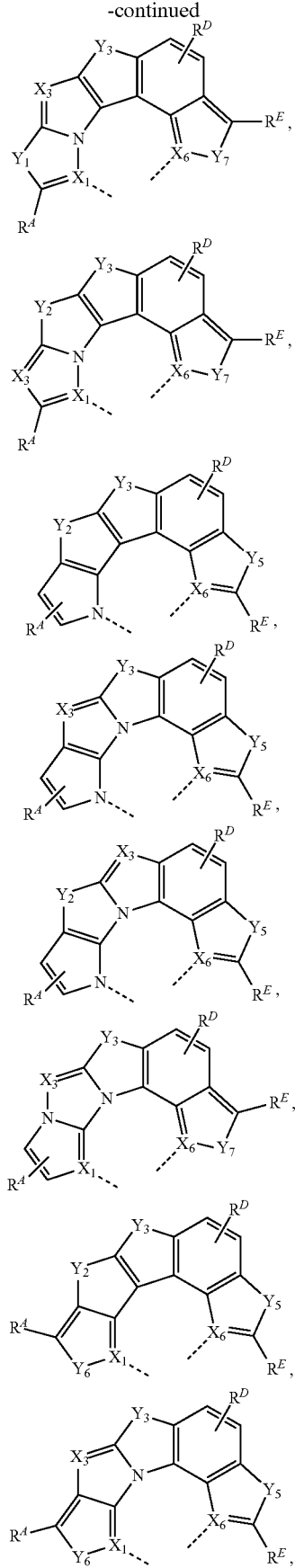
-continued
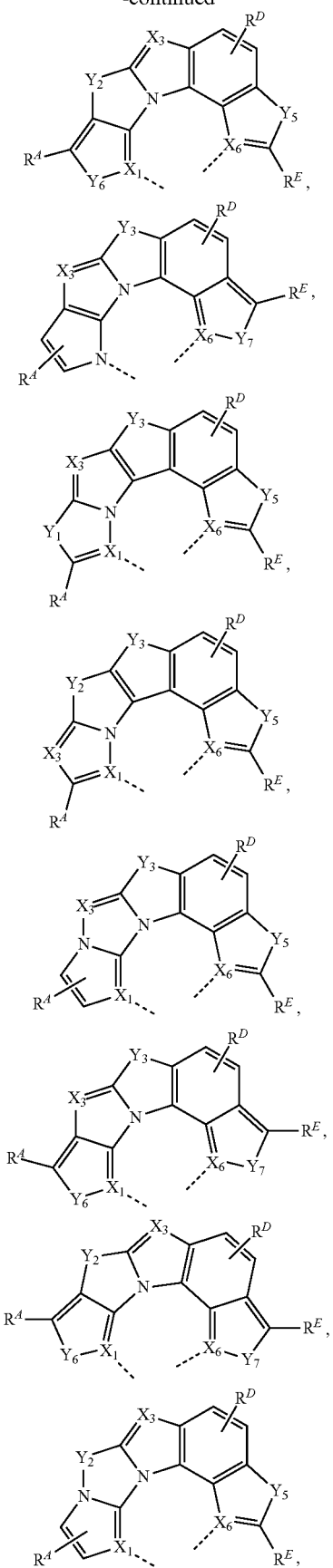

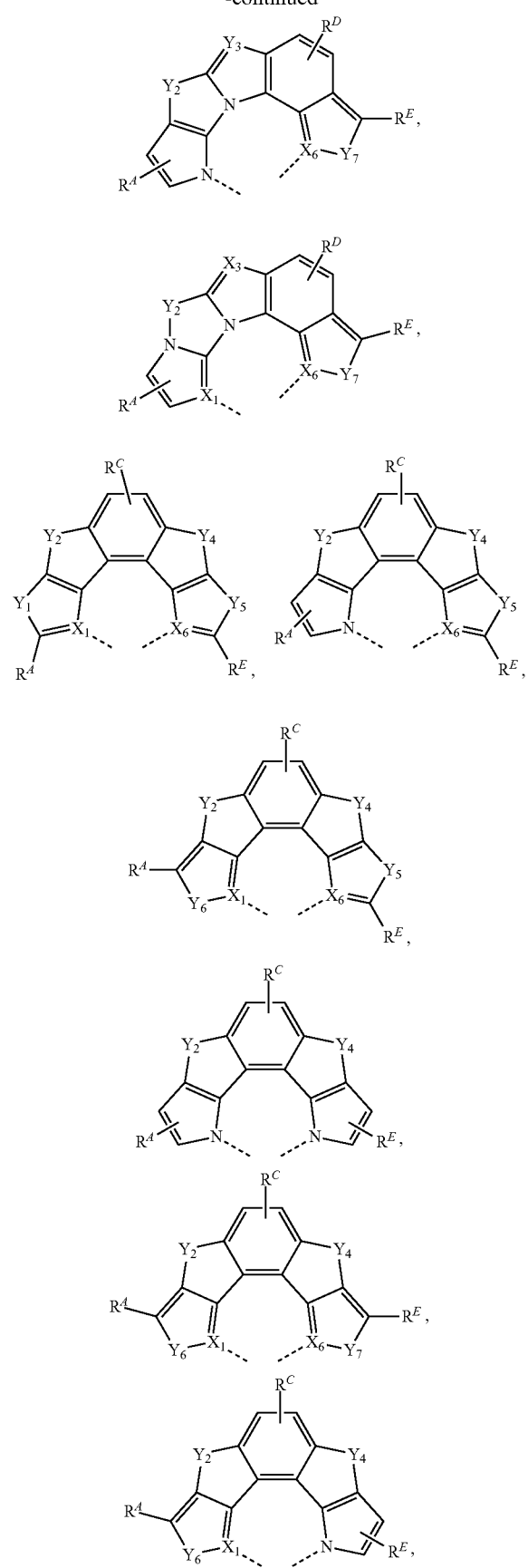
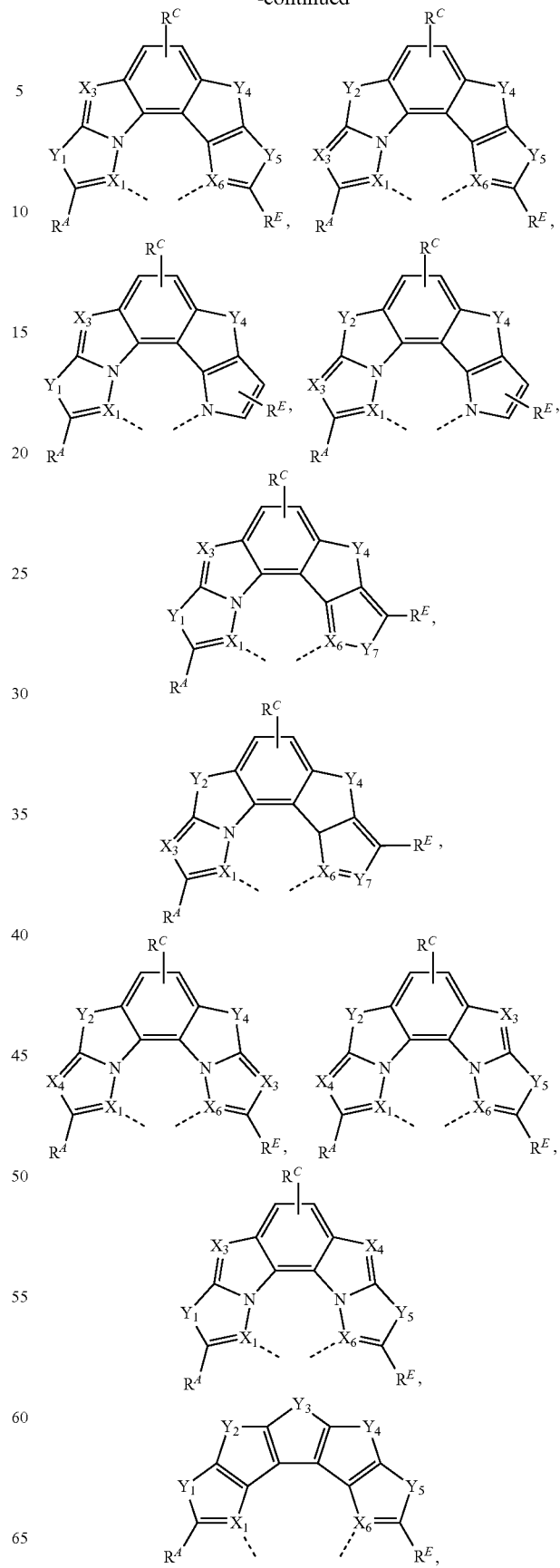

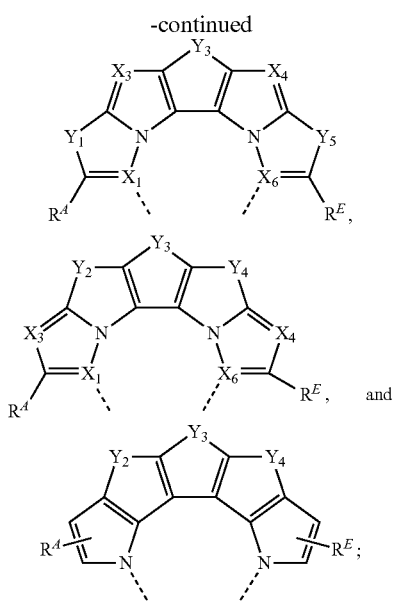

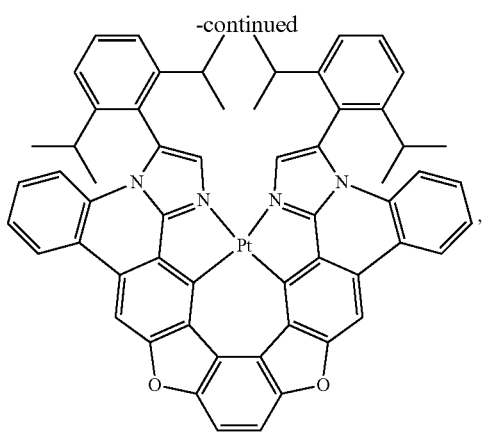

wherein each $X_1$-$X_6$ is independently selected from the group consisting of C and N; wherein no more than two N atoms are bond to one another; wherein each $Y_1$-$Y_7$ is selected from the group consisting of O, S, Se, NR, CRR', SiRR', GeRR', and BR; and wherein R and R' are each independently selected from the group consisting of hydrogen, deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, and combinations thereof.

12. The compound of claim 1, wherein the compound is selected from the group consisting of:

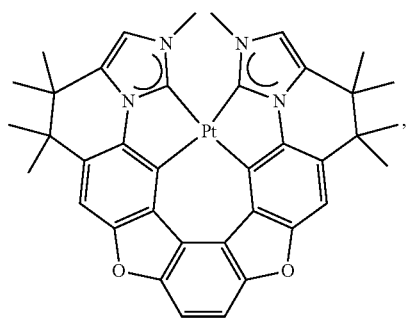

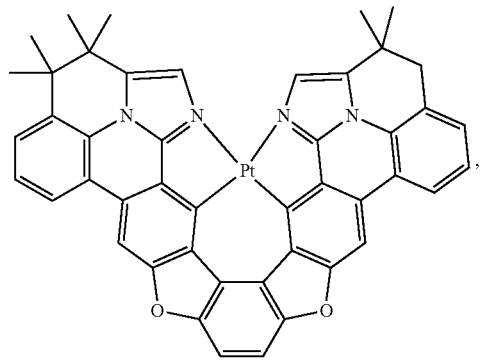

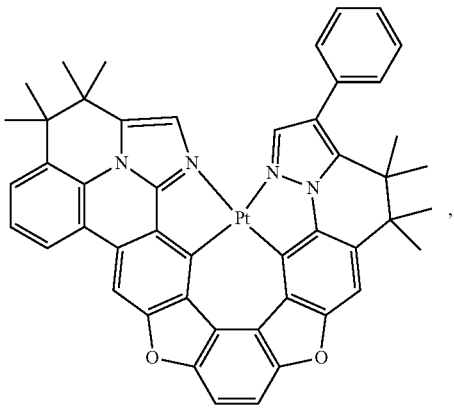

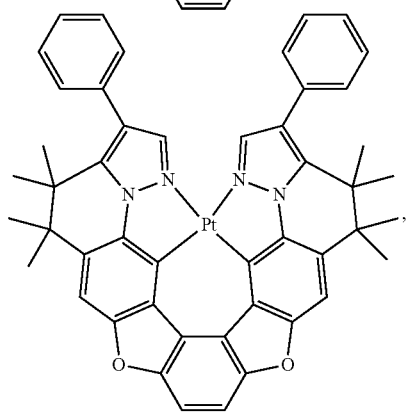

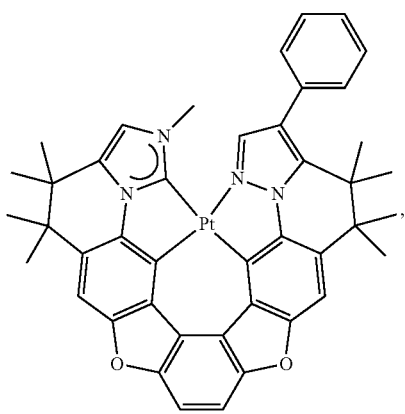

| 489 -continued | 490 -continued |
|---|---|
| 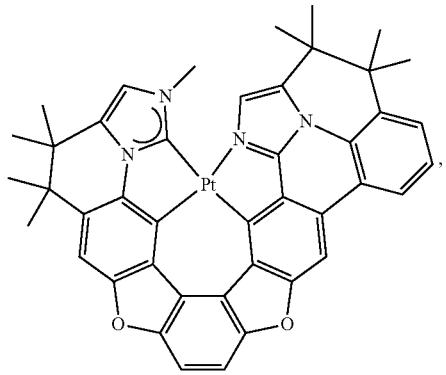 | 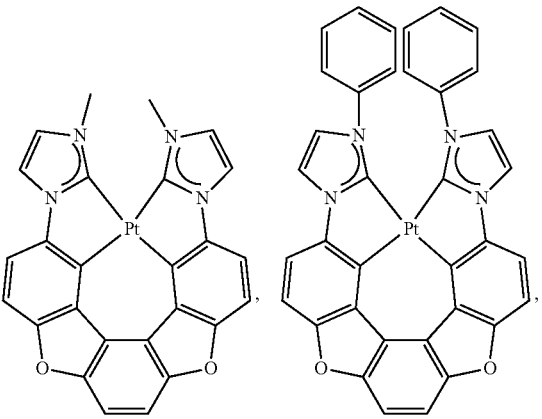 |
| 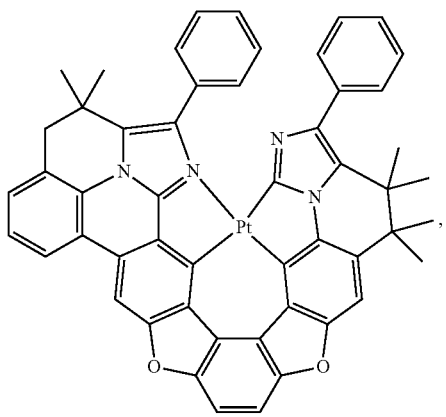 | 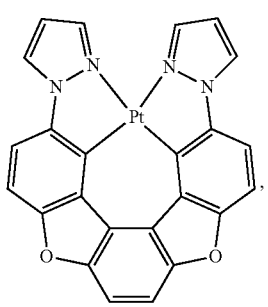 |
| 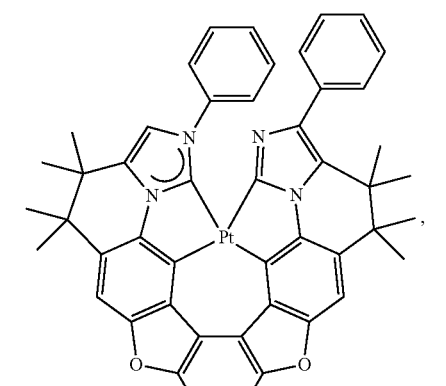 | 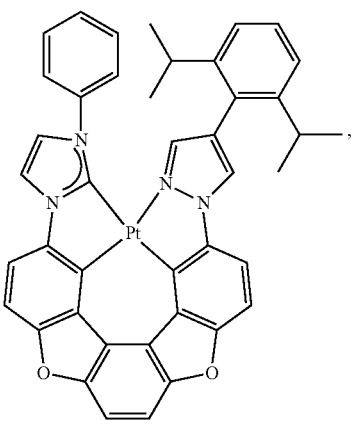 |
| 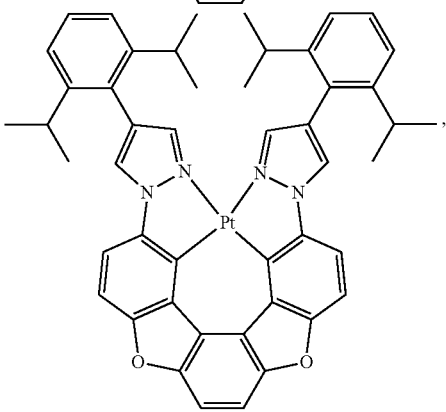 | 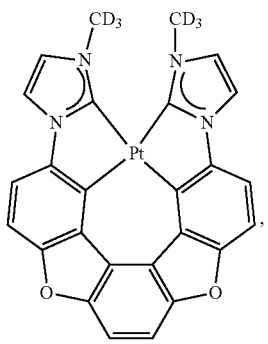 |

491 -continued
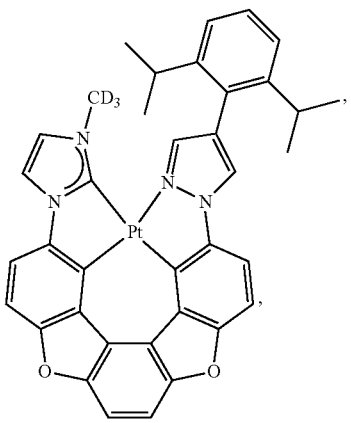
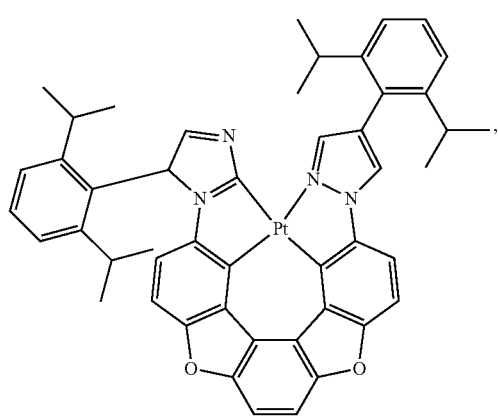
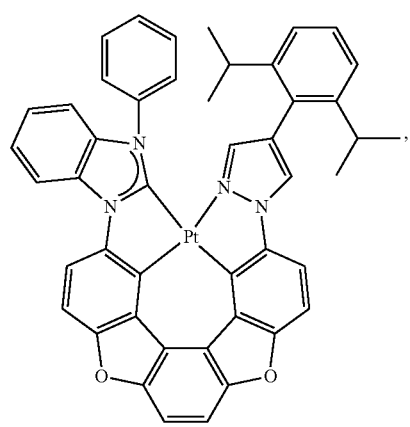
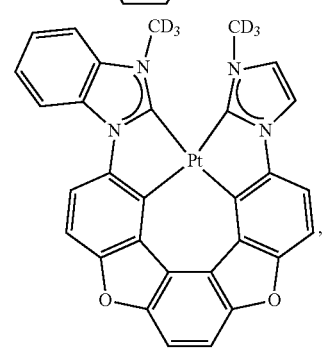
492 -continued
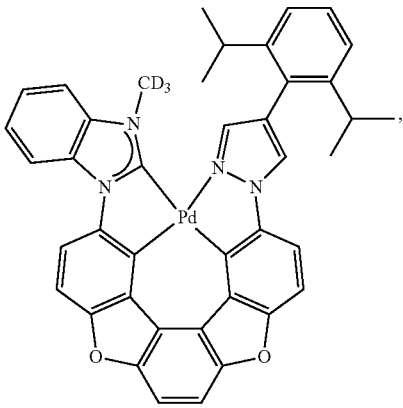
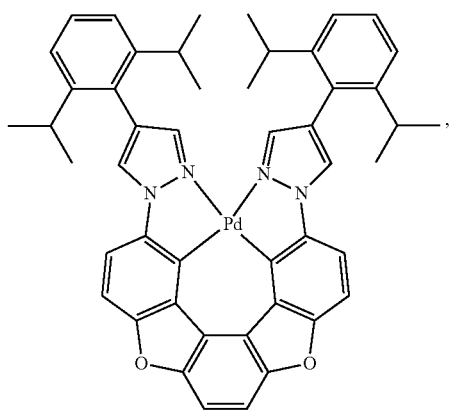
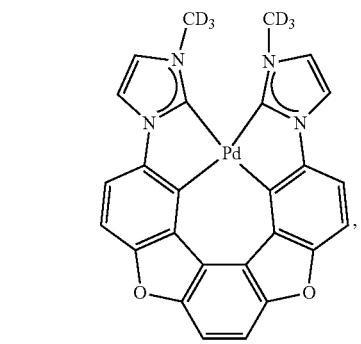
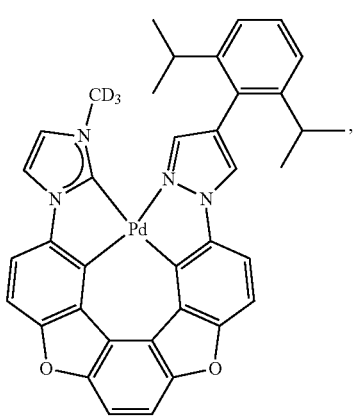

493
-continued
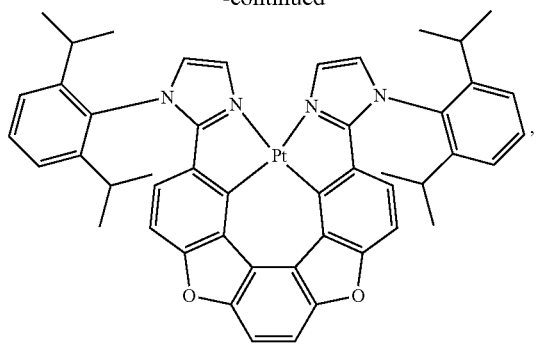
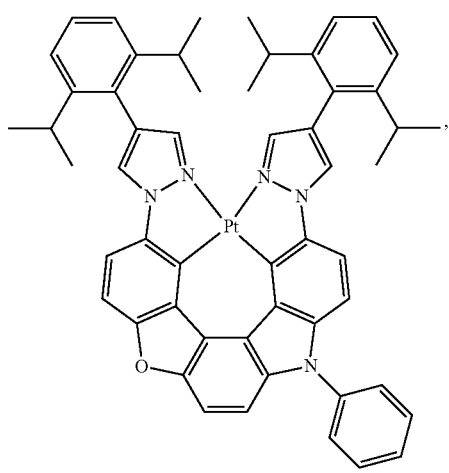
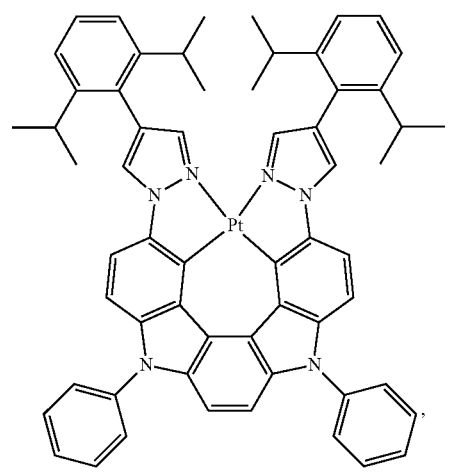
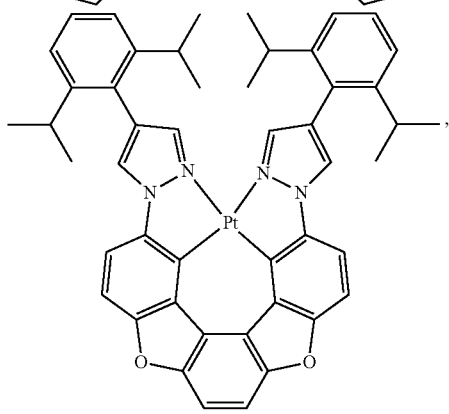
494
-continued
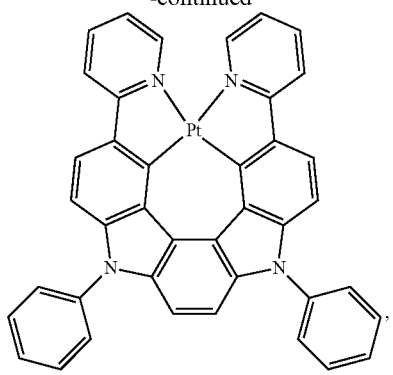
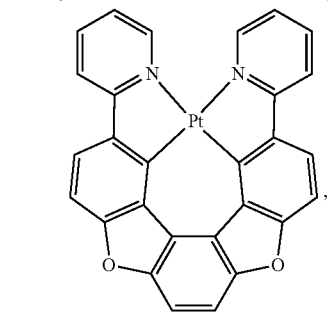
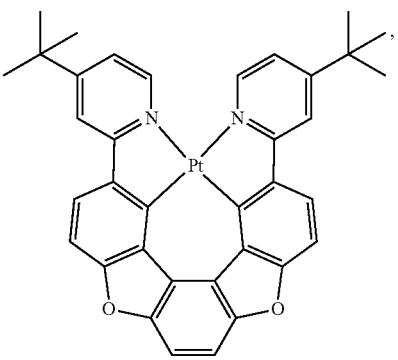
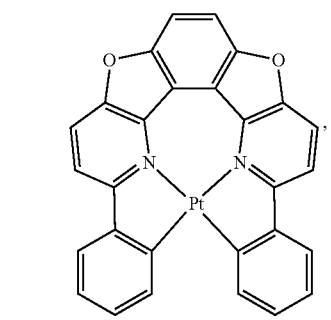
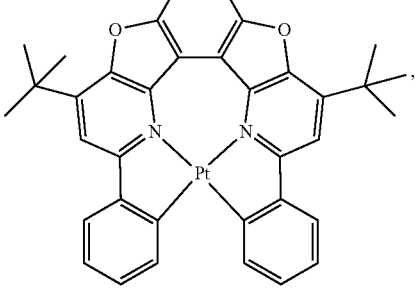

495
-continued

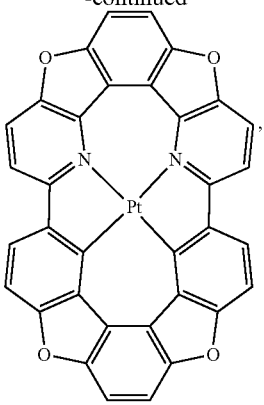

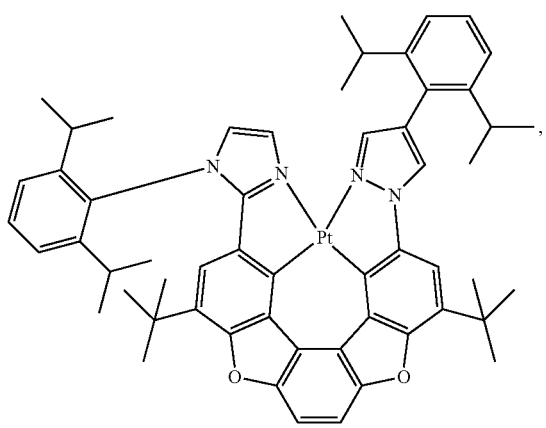

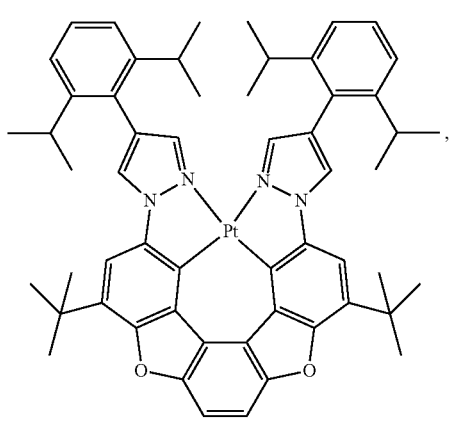

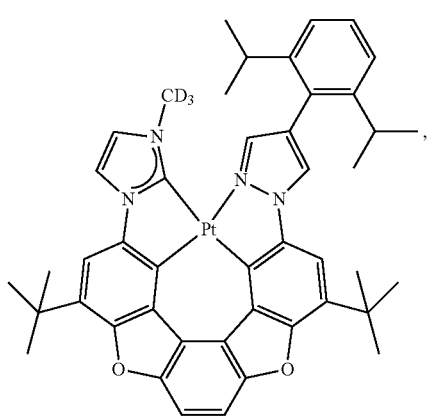

496
-continued

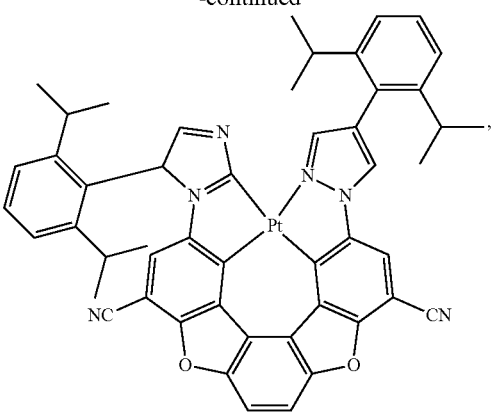

13. The compound of claim 1, wherein the compound emits light upon photoexcitation at room temperature; wherein the emitted light has an emission spectrum characterized by a peak emission wavelength $\lambda_{max}$ when measured at a concentration of 0.1 mM in a solution of 2-methyl tetrahydrofuran; and wherein the full width at half maximum of the emission at $\lambda_{max}$ that is equal to or less than 20 nm.

14. An organic light emitting device (OLED) comprising:
an anode;
a cathode; and
an organic layer disposed between the anode and the cathode, wherein the organic layer comprises a compound having a fragment with at least five rings fused next to each other consecutively wherein the fragment is a ligand $L_A$ of Formula I;

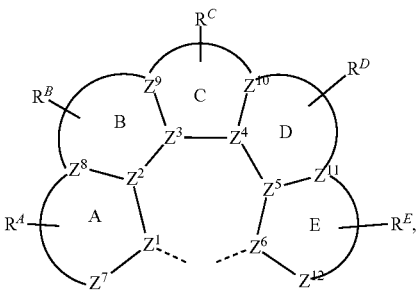

wherein:
rings A, B, C, D, and E are each independently a 5-membered or 6-membered carbocyclic or heterocyclic ring;
$Z^1$-$Z^{12}$ are each independently C or N;
$R^A$, $R^B$, $R^C$, $R^D$, and $R^E$ each independently represents zero, mono, or up to a maximum allowed substitutions to its associated ring;
if an $R^A$, $R^B$, $R^C$, $R^D$, or $R^E$ represents no substitution, then said $R^A$, $R^B$, $R^C$, $R^D$, or $R^E$ is hydrogen;
if $R^A$, $R^B$, $R^C$, $R^D$, or $R^E$ represents a substituent, then each $R^A$, $R^B$, $R^C$, $R^D$, and $R^E$ is independently a substituent selected from the group consisting of deuterium, halide, alkyl, cycloalkyl, fluorinated alkyl, heteroalkyl, arylalkyl, alkoxy, aryloxy, amino, silyl, boryl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
two substituents can be joined or fused together to form a ring;
wherein the ligand $L_A$ is complexed to a metal M at $Z^1$ and $Z^6$;
wherein the metal M is selected from the group consisting of Ir, Rh, Re, Ru, Os, Pt, Pd, Au, Ag, and Cu;
wherein M can be coordinated to other ligands; and
wherein the ligand $L_A$ can be linked with other ligands to form a tridentate, tetradentate, pentadentate, or hexadentate ligand.

15. The OLED of claim 14, wherein the organic layer further comprises a host, wherein host comprises at least one chemical group selected from the group consisting of metal complex, triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

16. A consumer product comprising an organic light-emitting device (OLED) comprising:
an anode;
a cathode; and
an organic layer disposed between the anode and the cathode, wherein the organic layer comprises a compound according to claim 1.

17. An organic light emitting device (OLED) comprising:
an anode;
a cathode; and
an organic layer disposed between the anode and the cathode, wherein the organic layer comprises the compound of claim 10.

* * * * *

UNITED STATES PATENT AND TRADEMARK OFFICE
CERTIFICATE OF CORRECTION

PATENT NO. : 11,925,105 B2
APPLICATION NO. : 16/988003
DATED : March 5, 2024
INVENTOR(S) : Tyler Fleetham, Hsiao-Fan Chen and Jerald Feldman Page 1 of 5

It is certified that error appears in the above-identified patent and that said Letters Patent is hereby corrected as shown below:

In the Claims

In Claim 12, Column 488, Lines 18-34, please delete the compound

"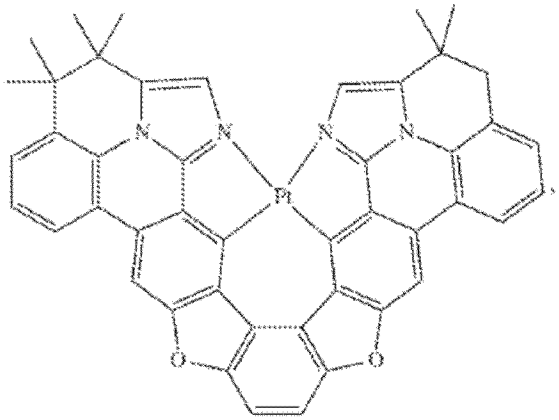" and insert

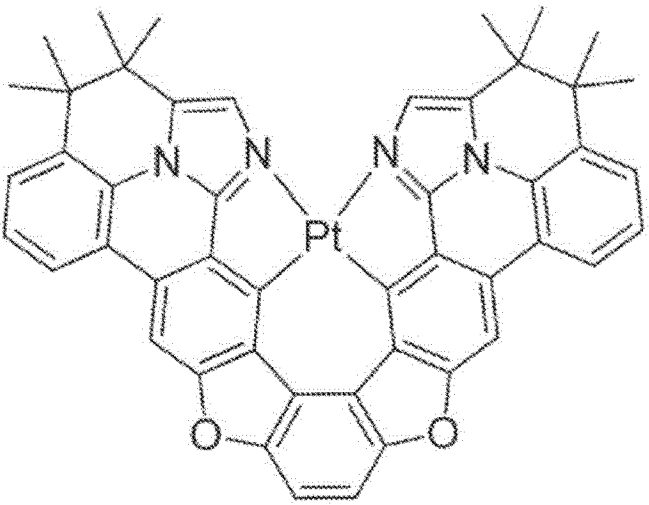

-- --

Signed and Sealed this
Twentieth Day of August, 2024

Katherine Kelly Vidal
*Director of the United States Patent and Trademark Office*

In Claim 12, Column 491, Lines 20-37, please delete the compound
" 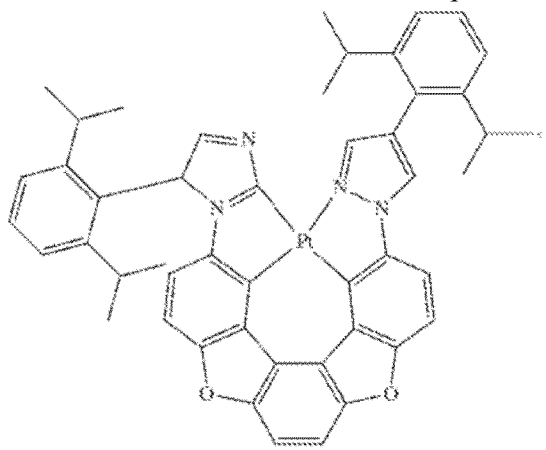 " and insert
-- 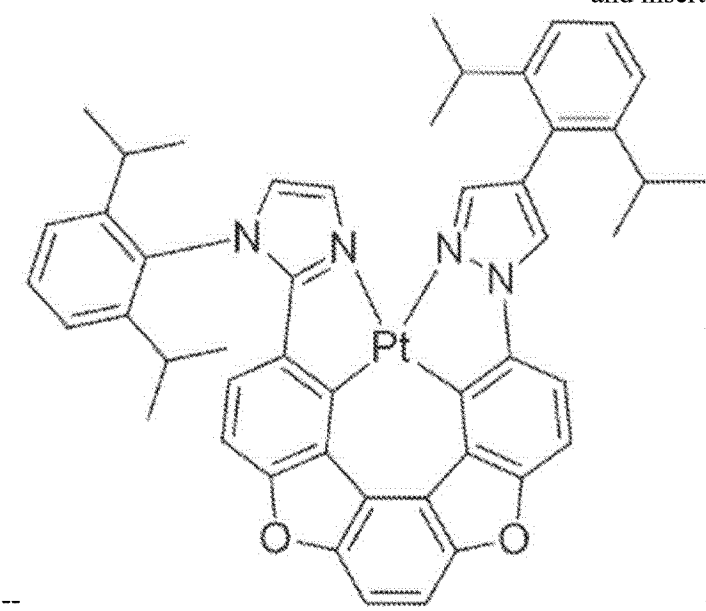 --
In Claim 12, Column 492, Lines 1-17, please delete the compound
" 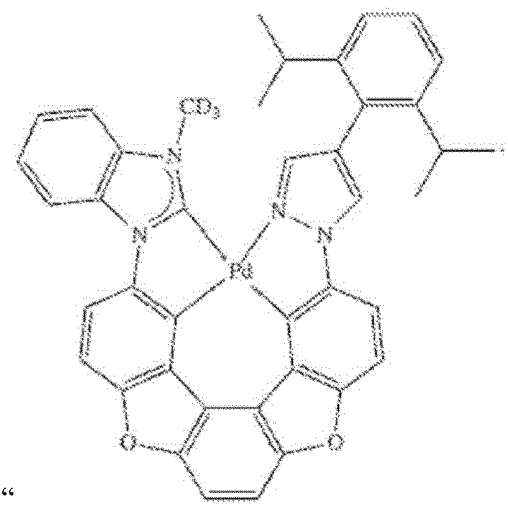 " and insert -- 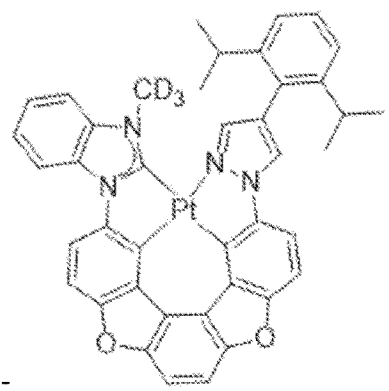 --

CERTIFICATE OF CORRECTION (continued)
U.S. Pat. No. 11,925,105 B2

In Claim 12, Column 493, Lines 52-67, please delete the compound

"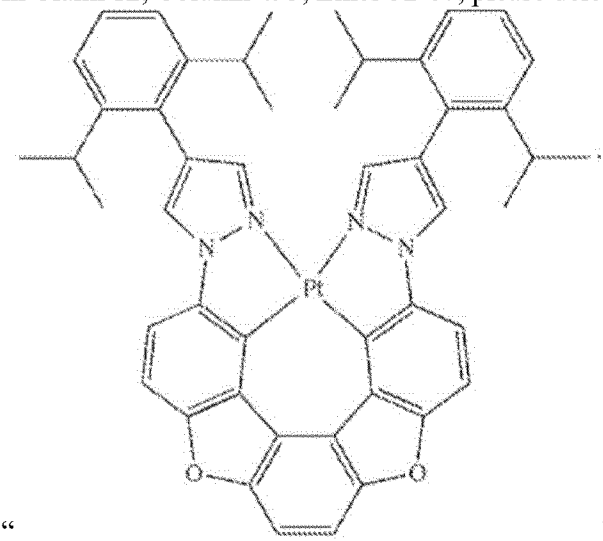" and insert

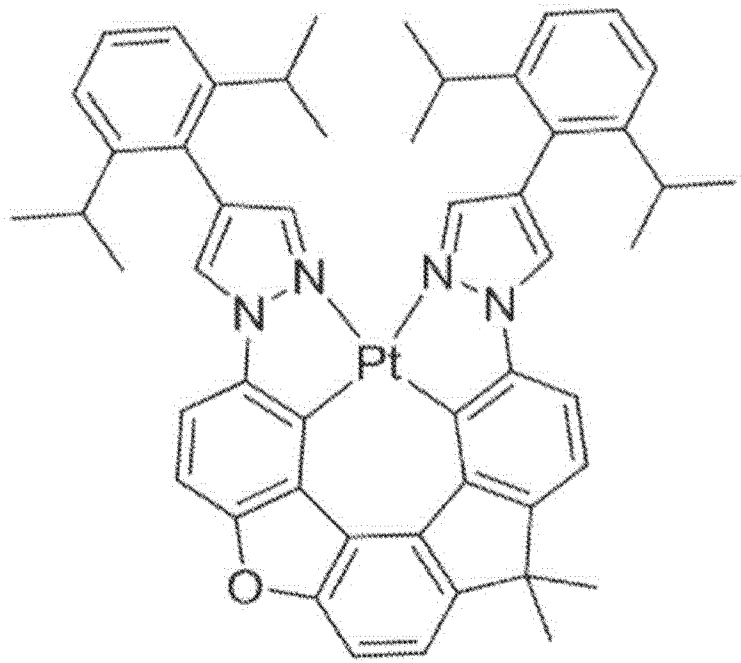

--                                                                                --

CERTIFICATE OF CORRECTION (continued)
U.S. Pat. No. 11,925,105 B2

In Claim 12, Column 496, Lines 1-17, please delete the compound

" 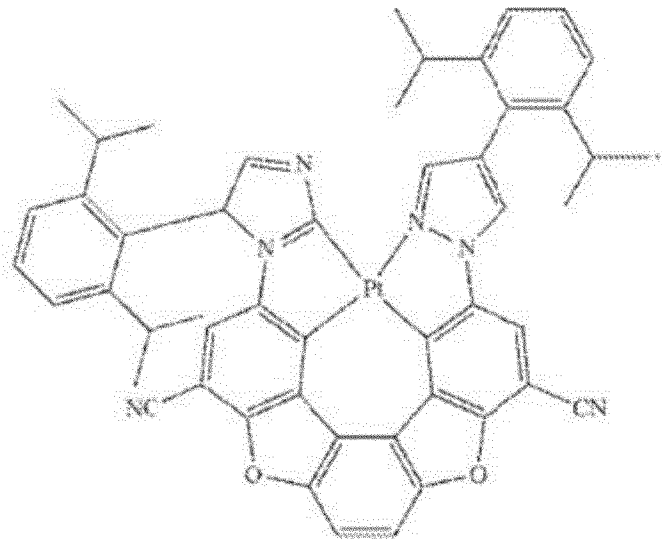 " and insert

-- 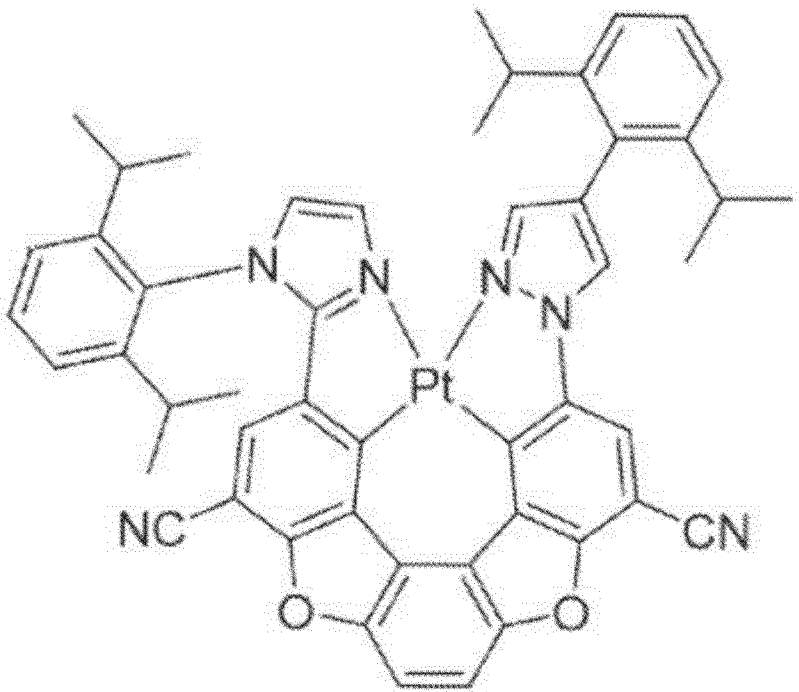 --

CERTIFICATE OF CORRECTION (continued)
U.S. Pat. No. 11,925,105 B2

In Claim 12, Column 496, Lines 34-50, please delete the compound

" 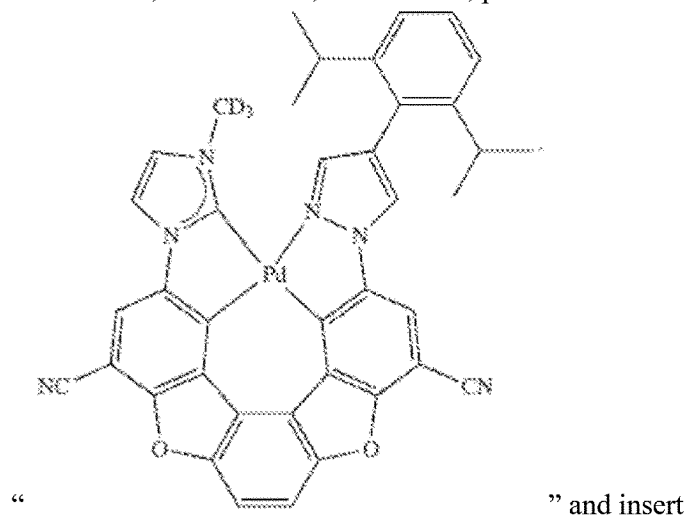 " and insert

-- 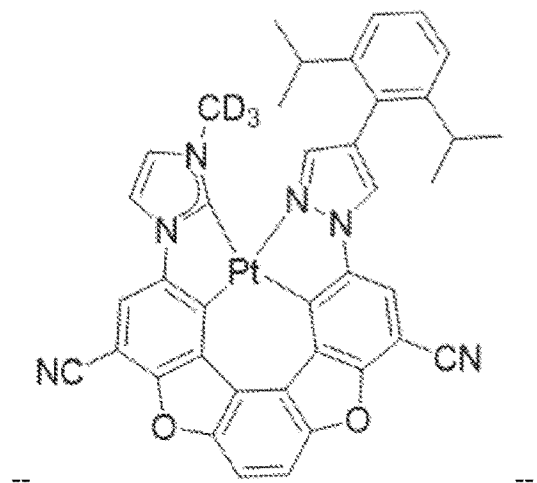 --